US012492188B2

(12) United States Patent
Yoon et al.

(10) Patent No.: US 12,492,188 B2
(45) Date of Patent: Dec. 9, 2025

(54) 1H-BENZO[D]IMIDAZOLE DERIVATIVES AS TLR9 INHIBITORS FOR THE TREATMENT OF FIBROSIS

(71) Applicant: BRISTOL-MYERS SQUIBB COMPANY, Princeton, NJ (US)

(72) Inventors: David S. Yoon, Ambler, PA (US); Alicia Regueiro-Ren, New Hope, PA (US); Michael Mandler, Lawrenceville, NJ (US); Shoshana L. Posy, Highland Park, NJ (US); Chunjian Liu, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 527 days.

(21) Appl. No.: 18/041,719

(22) PCT Filed: Aug. 18, 2021

(86) PCT No.: PCT/US2021/046421
§ 371 (c)(1),
(2) Date: Feb. 15, 2023

(87) PCT Pub. No.: WO2022/040260
PCT Pub. Date: Feb. 24, 2022

(65) Prior Publication Data

US 2023/0295122 A1 Sep. 21, 2023

Related U.S. Application Data

(60) Provisional application No. 63/067,587, filed on Aug. 19, 2020.

(51) Int. Cl.

| | |
|---|---|
| ***C07D 401/14*** | (2006.01) |
| ***C07D 235/18*** | (2006.01) |
| ***C07D 401/10*** | (2006.01) |
| ***C07D 401/12*** | (2006.01) |
| ***C07D 403/10*** | (2006.01) |
| ***C07D 405/12*** | (2006.01) |
| ***C07D 405/14*** | (2006.01) |
| ***C07D 413/14*** | (2006.01) |
| ***C07D 417/14*** | (2006.01) |
| ***C07D 451/02*** | (2006.01) |
| ***C07D 451/04*** | (2006.01) |
| ***C07D 471/04*** | (2006.01) |
| ***C07D 487/04*** | (2006.01) |
| ***C07D 487/10*** | (2006.01) |
| ***C07D 519/00*** | (2006.01) |

(52) U.S. Cl.
CPC ......... *C07D 401/14* (2013.01); *C07D 235/18* (2013.01); *C07D 401/10* (2013.01); *C07D 401/12* (2013.01); *C07D 403/10* (2013.01); *C07D 405/12* (2013.01); *C07D 405/14* (2013.01); *C07D 413/14* (2013.01); *C07D 417/14* (2013.01); *C07D 451/02* (2013.01); *C07D 451/04* (2013.01); *C07D 471/04* (2013.01); *C07D 487/04* (2013.01); *C07D 487/10* (2013.01); *C07D 519/00* (2013.01)

(58) Field of Classification Search
CPC .. C07D 401/14; C07D 235/18; C07D 401/10; C07D 401/12; C07D 403/10; C07D 405/12; C07D 405/14; C07D 413/14; C07D 417/14; C07D 451/02; C07D 451/04; C07D 471/04; C07D 487/04; C07D 487/10; C07D 519/00; A61P 1/16; A61P 1/18; A61P 11/00; A61P 13/12; A61P 43/00; A61K 31/4545
See application file for complete search history.

(56) References Cited

U.S. PATENT DOCUMENTS 9,271,500 B2 3/2016 Takahashi et al.
10,071,079 B2 9/2018 Dyckman et al.
(Continued)

FOREIGN PATENT DOCUMENTS

EP 2738172 A1 6/2014
WO WO 2006/076009 A2 * 7/2006 ......... A61K 31/5377
(Continued)

OTHER PUBLICATIONS

RN1339045-31-6, Database Registry Online, "1,2-Benzenediamine, 4-[6-[4-(dimethylamino)-1-piperidinyl]-1H-benzimidazol-2-yl]-", 2011, 3pgs.

(Continued)

*Primary Examiner* — Joseph K Mckane
*Assistant Examiner* — David M Shim
(74) *Attorney, Agent, or Firm* — Gary Greenblatt

(57) ABSTRACT

The present invention relates to 1H-benzo[d]imidazole derivatives of formula (I) or a salt thereof. The present compounds are inhibitors of TLR9 and useful in treating preventing, or slowing fibrotic diseases, such as e.g. liver fibrosis, renal fibrosis, biliary fibrosis or pancreatic fibrosis, non-alcoholic steatohepatitis (NASH), non-alcoholic fatty liver disease (NAFLD), chronic kidney disease, diabetic kidney disease, primary sclerosing cholangitis (PSC) or primary biliary cirrhosis (PBC), or idiopathic pulmonary fibrosis (IPF).

(I)

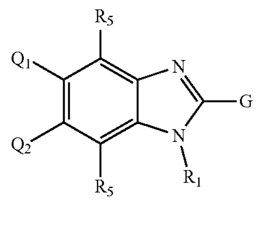

12 Claims, No Drawings

(56) References Cited

U.S. PATENT DOCUMENTS

| | | | |
|---|---|---|---|
| 10,478,424 B2 | 11/2019 | Dyckman et al. |
| 10,544,143 B2 | 1/2020 | Dyckman et al. |
| 10,660,877 B2 | 5/2020 | Dyckman et al. |
| 10,730,877 B2 | 8/2020 | Dyckman et al. |
| 10,912,766 B2 | 2/2021 | Dyckman et al. |
| 11,053,244 B1 | 7/2021 | Dyckman et al. |
| 11,130,756 B2 | 9/2021 | Dyckman et al. |
| 11,180,474 B2 | 11/2021 | Dyckman et al. |
| 11,299,501 B2 | 4/2022 | Dyckman et al. |
| 11,306,092 B2 | 4/2022 | Dyckman et al. |
| 11,420,958 B2 | 8/2022 | Dyckman et al. |
| 11,420,973 B2 | 8/2022 | Dyckman et al. |
| 11,427,580 B2 | 8/2022 | Dyckman et al. |
| 11,447,466 B2 | 9/2022 | Dyckman et al. |
| 2006/0235037 A1 | 10/2006 | Purandare et al. |
| 2009/0247504 A1 | 10/2009 | Churcher et al. |
| 2011/0275631 A1 | 11/2011 | Abeywardane et al. |
| 2013/0158049 A1 | 6/2013 | Alam et al. |
| 2013/0158066 A1 | 6/2013 | Alam et al. |
| 2017/0008885 A1 | 1/2017 | Koul et al. |
| 2020/0308172 A1 | 10/2020 | Dyckman et al. |
| 2021/0070751 A1 | 3/2021 | Dyckman et al. |
| 2021/0253593 A1 | 8/2021 | Dyckman et al. |

FOREIGN PATENT DOCUMENTS

| | | |
|---|---|---|
| WO | 2007115306 A2 | 10/2007 |
| WO | 2013092467 A1 | 6/2013 |
| WO | 2013150416 A1 | 10/2013 |
| WO | 2013156431 A1 | 10/2013 |
| WO | 2015088045 A1 | 6/2015 |
| WO | 2017100594 A1 | 6/2017 |
| WO | 2018089695 A1 | 5/2018 |
| WO | 2019008072 A1 | 1/2019 |
| WO | 2019125977 A1 | 6/2019 |
| WO | 2019126082 A1 | 6/2019 |
| WO | 2019126253 A1 | 6/2019 |
| WO | 2019136147 A1 | 7/2019 |
| WO | 2020033520 A1 | 2/2020 |

OTHER PUBLICATIONS

Zimmermann, Kurt, et al., "Balancing oral exposure with Cyp3A4 inhibition in benzimidazole-based IFG-IR inhibitors", Bioorganic & Medicinal Chemistry Letters, 2008, 18, pp. 4075-4080.

Chattopadhyay, S. et al . . . , "Tyrosine phosphorylation in Toll-like Receptor signaling", Cytokine & Growth Factor Reviews, 25 (2014) 533-541.

Huestis, et al., Org Lett 11(6) 1357-1360 (2009).

International Preliminary Report on Patentability for PCT/US2021/046421 issued Feb. 16, 2023.

Kawai, Taro, et al., "The role of pattern-recognition receptors in innate immunity: update on Toll-like receptors"; Nature Immunology, 2010, vol. 11, No. 5, pp. 373-384.

Lamphier, M. et al., "Novel Small Molecule Inhibitors of TLR7 and TLR9: Mechanism of Action and Efficacy in Vivo", Mol Pharmacol, 2014, 85:429-440.

Patra, Mahesh Chandra, et al., "Recent Progress in the Development of Toll-like Receptor (TLR) antagonists", Exp. Opin. On Therapeutic Patents, 2016, vol. 26, No. 6, 719-730.

Roy, et al., "Design and developmen of benzoxazole derivatives with toll-like receptor 9 antagonism", Eur J Med Chem, 2017, vol. 134, 334-347.

Sims, et al., "The IL-1 Family: Regulators of Immunity", Nature Rev. Immunol., 2010, 10, 89-102.

Thwaites et al., Frontier in Immunology 5 1-8 (2014).

* cited by examiner

1H-BENZO[D]IMIDAZOLE DERIVATIVES AS TLR9 INHIBITORS FOR THE TREATMENT OF FIBROSIS

CROSS REFERENCE

This application is a national phase application under 35 U.S.C. § 371 of International Patent Application No. PCT/US2021/046421, filed Aug. 18, 2021, which claims priority to U.S. Provisional Application Ser. 63/067,587, filed Aug. 19, 2020, the contents of which are specifically incorporated fully herein by reference.

DESCRIPTION

The present invention generally relates to substituted benzimidazole compounds useful as inhibitors of signaling through Toll-like receptor 9 (TLR9). Provided herein are substituted benzimidazole compounds, compositions comprising such compounds, and methods of their use. The invention further pertains to pharmaceutical compositions containing at least one compound according to the invention that are useful for the treatment or prophylaxis of fibrotic diseases and other diseases, disorders, and conditions for which a TLR9 inhibitor is indicated.

Toll-like receptors (TLRs) are transmembrane proteins having the ability to initiate an inflammatory response upon recognition of pattern-associated molecular patterns (PAMPs) or microbe-associated molecular patterns (MAMPs). A total of 10 human TLRs have been identified and can be located in the cell surface or, as in the case of TLR7, 8 and 9, in the endolysosomes. TLR9 recognizes unmethylated single-stranded DNA containing cytosine-phosphate-guanine (CpG) motifs that are typically found in bacterial and mitochondrial DNA (mtDNA). TLR9 may contribute to fibrogenesis by promoting inflammation via the MyD88-dependent signalling pathway that ultimately mediates activation of IL-6, IFN-α, IL-1β, and TNF-α among others cytokines. (Barton G M, Kagan J C (2009) *Nat. Rev. Immunol.* 9(8), 535-42; Li X, Jiang S, Tapping R I (2010), *Cytokine* 49(1), 1-9).

TLR9 levels are higher in lung biopsies of rapid idiopathic pulmonary fibrosis (IPF) progressors than in the healthy or stable IPF progressors (Sci. Transl. Med. 2010, 2(57):57ra82). Circulating mtDNA, the ligand for TLR9 has recently been identified as a mechanism-based prognostic biomarker of IPF (Am J. Resp. and Crit. Care Med. 2017, 196(12), 1502). In addition, it has been observed that TLR9 is up-regulated in human and murine non-alcoholic steatohepatitis (NASH) (Clin. Sci. 2017, 131(16), 2145), while hepatocyte mitochondrial DNA drives NASH via activation of TLR9 (J. Clin. Inv. 2016, 126(3), 859. Accordingly, inhibitors/antagonists of TLR9 are predicted to have efficacy as novel therapeutic agents to treat fibrotic diseases.

TLR9 inhibition has been recognized as a potential route to therapies for fibrotic diseases including idiopathic pulmonary fibrosis (Trujillo et al. *Sci. Transl. Med.* 2010, 2(57):57ra82; Yoshizaki et al. *Ann Rheum Dis.* 2016 October; 75(10):1858-65), non-alcoholic steatohepatitis (Garcia-Martinez et al. *J Clin Invest* 2016 126: 859-864; Gabele et al. *Biochem Biophys Res Commun.* 2008; 376:271-276), hepatic injury (Shaker et al. *Biochem Pharmacol.* 2016. 112:90-101; Hoeque et al. *J. Immun.* 2013, 190:4297-304), and scleroderma (systemic sclerosis or SSc) (Yoshizaki et al. *Ann Rheum Dis.* 2016 October; 75(10):1858-65); as well as heart failure (Oka et al. *Nature* 485, *pages* 251-255(2012)), and hypertension (McCarthy et al. *Cardiovascular Research,* 2015, *Pages* 119-130).

There remains a need for compounds useful as inhibitors of TLR9. Additionally, there remains a need for compounds useful as inhibitors of TLR9 that have selectivity over TLR7 or TLR8.

In view of the conditions that may benefit by treatment involving modulation of Toll-like receptors, it is immediately apparent that new compounds capable of inhibiting TLR9 and methods of using these compounds could provide substantial therapeutic benefits to a wide variety of patients.

Applicants have found potent compounds that have activity as TLR9 inhibitors. Further, applicants have found compounds that have activity as TLR9 inhibitors and are selective over TLR7 or TLR8. These compounds are provided to be useful as pharmaceuticals with desirable stability, bioavailability, therapeutic index, and toxicity values that are important to their drugability.

SUMMARY OF THE INVENTION

The present invention relates to a new class of substituted benzimidazole compounds found to be effective inhibitors of signaling through TLR9. These compounds are provided to be useful as pharmaceuticals with desirable stability, bioavailability, therapeutic index, and toxicity values that are important to their drugability.

The present invention provides compounds of Formula (I) that are useful as inhibitors of signaling through TLR9 and are useful for the treatment of fibrotic diseases, or stereoisomers, N-oxides, tautomers, pharmaceutically acceptable salts, solvates or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of Toll-like receptor 9 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating fibrotic diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method of treating a disease or disorder associated with TLR9 activity, the method comprising administering to a mammal in need thereof, at least one of the compounds of Formula (I) or salts, solvates, and prodrugs thereof.

The present invention also provides processes and intermediates for making the compounds of Formula (I) including salts, solvates, and prodrugs thereof.

The present invention also provides at least one of the compounds of Formula (I) or salts, solvates, and prodrugs thereof, for use in therapy.

The present invention also provides the use of at least one of the compounds of Formula (I) or salts, solvates, and prodrugs thereof, for the manufacture of a medicament for the treatment of prophylaxis of TLR9 related conditions, such as fibrotic diseases, allergic diseases, autoimmune diseases, and inflammatory diseases.

The compound of Formula (I) and compositions comprising the compounds of Formula (I) may be used in treating, preventing, or curing various TLR9 related conditions. Pharmaceutical compositions comprising these compounds are useful for treating, preventing, or slowing the progression of diseases or disorders in a variety of therapeutic areas, such as fibrotic diseases, allergic diseases, autoimmune diseases, and inflammatory diseases.

These and other features of the invention will be set forth in expanded form as the disclosure continues.

DETAILED DESCRIPTION

The first aspect of the present invention provides at least one compound of Formula (I):

(I)

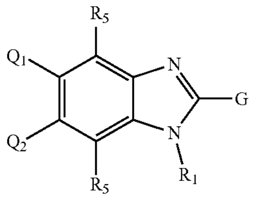

or stereoisomers, tautomer, solvates or salts thereof, wherein:

one of $Q_1$ and $Q_2$ is A and the other of $Q_1$ and $Q_2$ is $R_5$;

G is:

(i) phenyl substituted with 1 to 2 substituents independently selected from F, Cl, Br, —CN, $C_{1-3}$ alkyl, $C_{1-2}$ fluoroalkyl, $C_{1-3}$ alkoxy, $C_{1-2}$ fluoroalkoxy, $C_{3-6}$ cycloalkyl, $—NR_xR_x$, $—C(O)NR_yR_y$, $—S(O)_2(C_{1-3}$ alkyl), $—S(O)_2$(phenyl), $—S(O)_2NR_xR_x$, $—NR_xS(O)_2$ ($C_{1-3}$ alkyl), $—S(O)(NH)NR_xR_x$, and $—P(O)(OCH_2CH_3)_2$;

((ii)

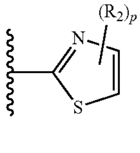
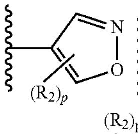
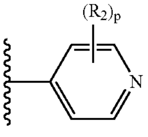
or
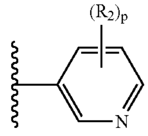
;

(iii)

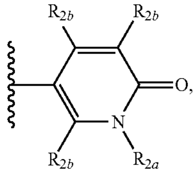
,
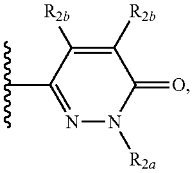
,
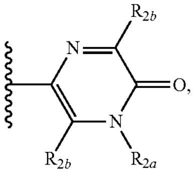
, or
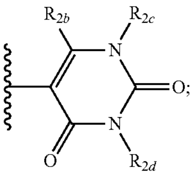
;

-continued (iv)

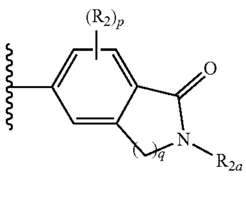
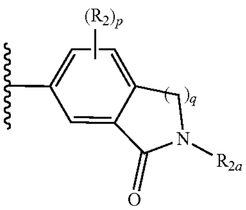
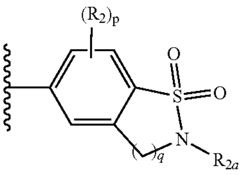
or
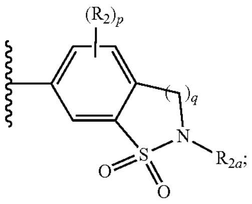
;

(v) a 9-membered heterocyclic ring selected from:

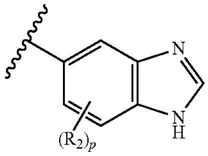
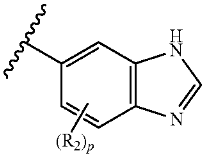
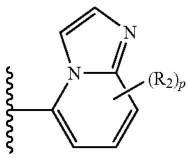
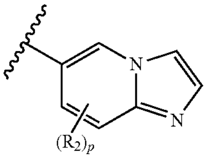
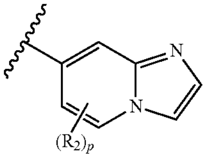
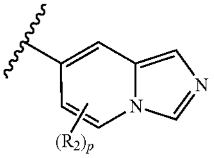
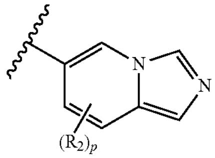
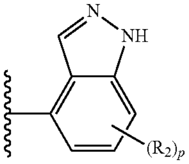
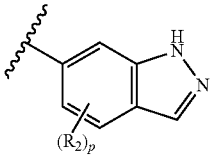
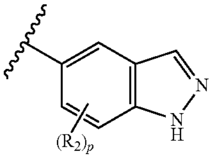
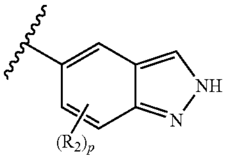
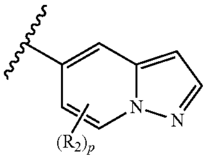
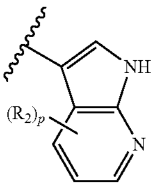
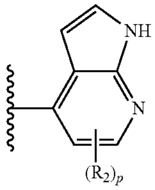
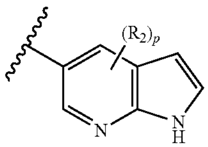

-continued
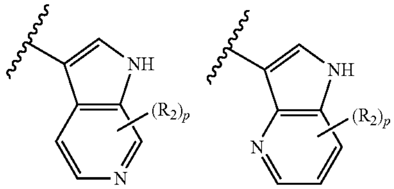
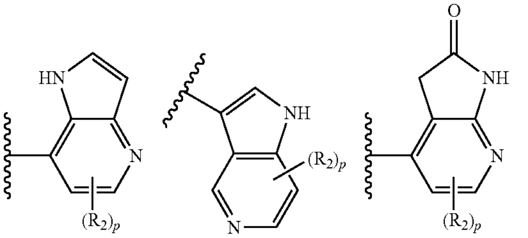
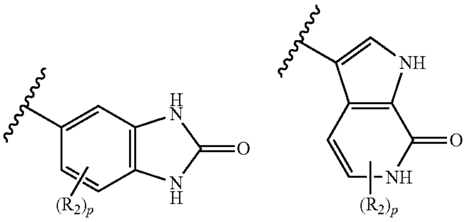
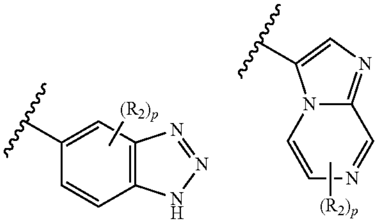
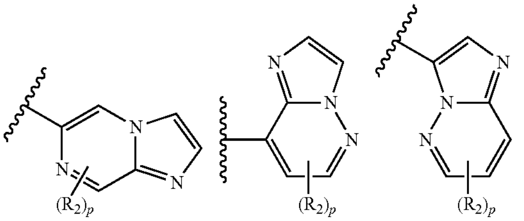
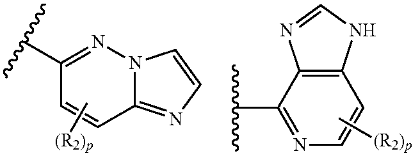
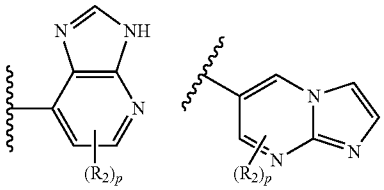
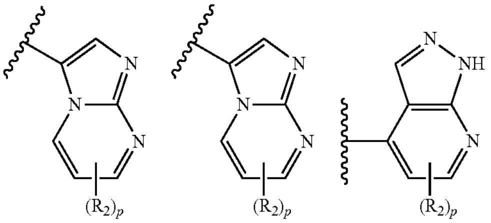
-continued
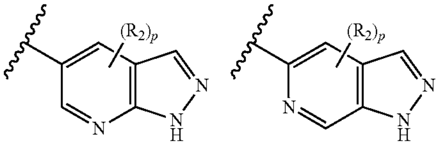
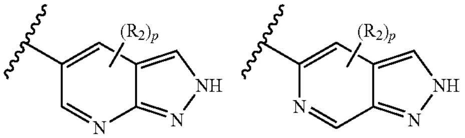
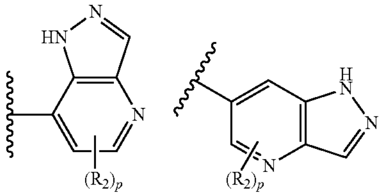
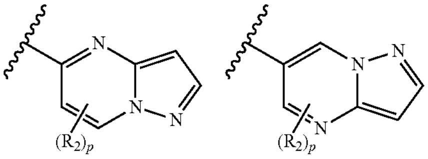
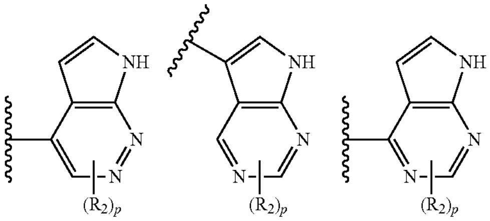
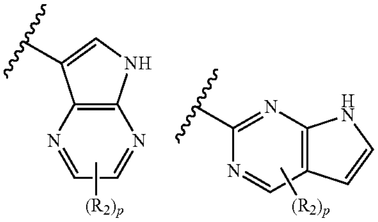
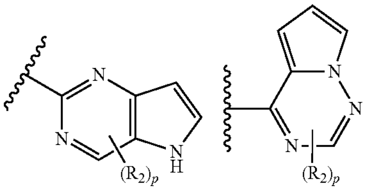
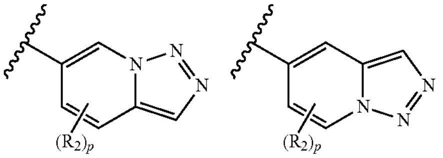
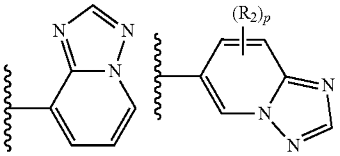

-continued
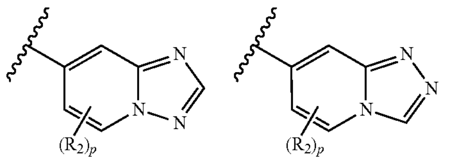
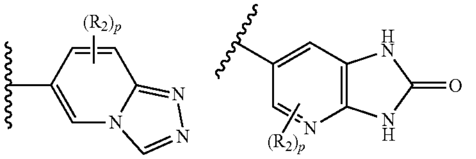
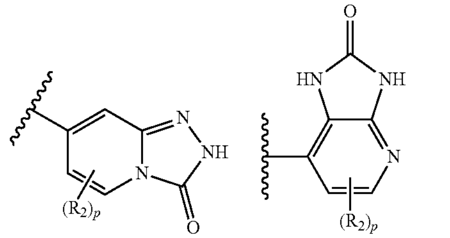
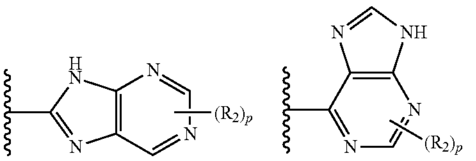
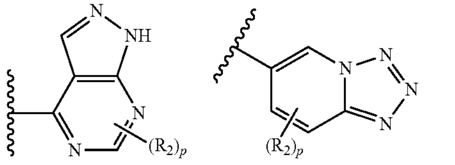
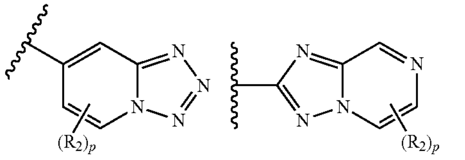
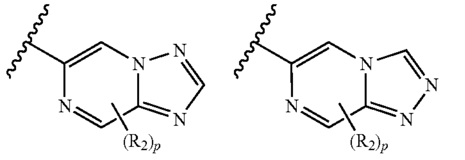
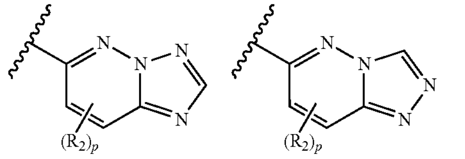
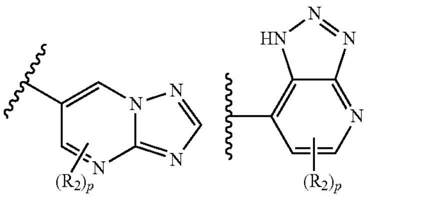
-continued
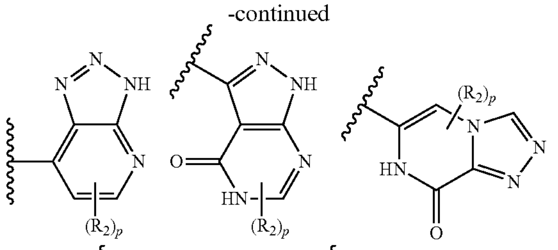
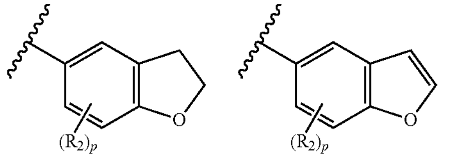
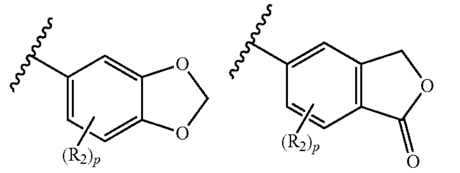
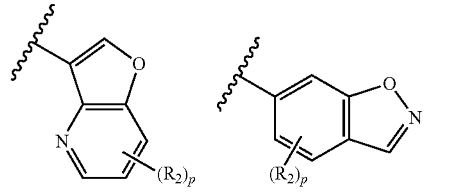
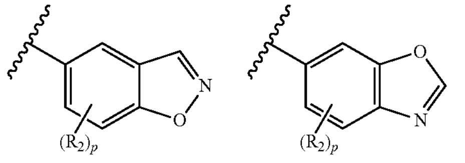
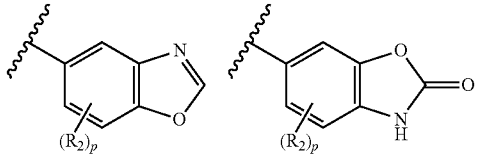
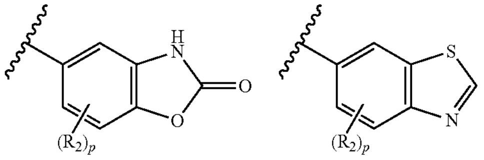
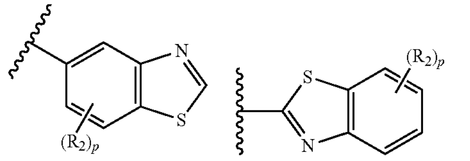
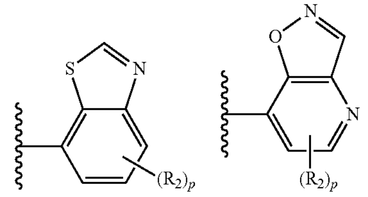
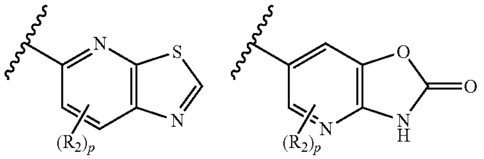

-continued

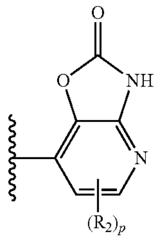

and

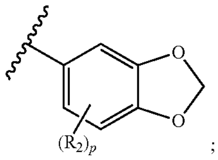

;

or (vi) 10-membered heterocyclic ring selected from:

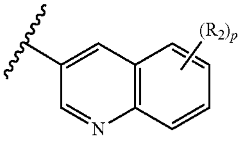

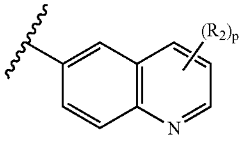

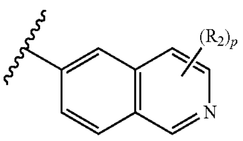

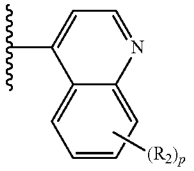

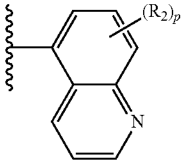

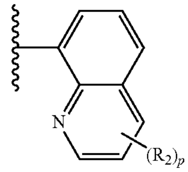

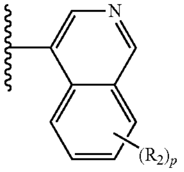

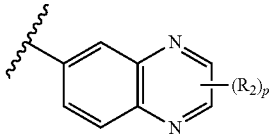

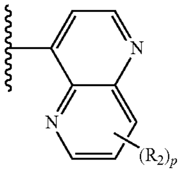

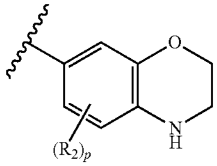

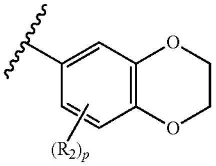

and

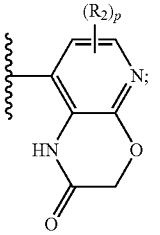

A is piperidinyl, phenyl, pyridinyl, pyrimidinyl, 6-azabicyclo[3.2.1]octanyl, or azabicyclo[3.2.1]octanyl, each substituted with -L-$R_4$ and zero to 3 $R_{4b}$;

L is a bond, —$(CR_xR_x)_{1-2}$—, —O—, or —C(O)$(CR_xR_x)_{0-2}$—;

$R_1$ is hydrogen, $C_{1-3}$ alkyl, $C_{1-2}$ fluoroalkyl, or $C_{3-4}$ cycloalkyl;

each $R_2$ is independently halo, —CN, —OH, —$NO_2$, $C_{1-4}$ alkyl, $C_{1-2}$ fluoroalkyl, $C_{1-2}$ cyanoalkyl, $C_{1-3}$ hydroxyalkyl, $C_{1-3}$ aminoalkyl, —$O(CH_2)_{1-2}OH$, —$(CH_2)_{0-4}O$ ($C_{1-4}$ alkyl), $C_{1-3}$ fluoroalkoxy, —$(CH_2)_{1-4}O(C_{1-3}$ alkyl), —$O(CH_2)_{1-2}OC(O)(C_{1-3}$ alkyl), —$O(CH_2)_{1-2}NR_xR_x$, —C(O)O($C_{1-3}$ alkyl), —$(CH_2)_{0-2}C(O)NR_yR_y$, —C(O)$NR_x(C_{1-5}$ hydroxyalkyl), —C(O)$NR_x(C_{2-6}$ alkoxyalkyl), —C(O)$NR_x(C_{3-6}$ cycloalkyl), —$NR_yR_y$, —$NR_y(C_{1-3}$ fluoroalkyl), —$NR_y(C_{1-4}$ hydroxyalkyl), —$NR_xCH_2$(phenyl), —$NR_xS(O)_2(C_{3-6}$ cycloalkyl), —$NR_xC(O)(C_{1-3}$ alkyl), —$NR_xCH_2(C_{3-6}$ cycloalkyl), —$S(O)_2(C_{1-3}$ alkyl), —$S(O)_2N(C_{1-3}$ alkyl$)_2$, —S(O)(NH)N($C_{1-3}$ alkyl$)_2$, —$(CH_2)_{0-2}(C_{3-6}$ cycloalkyl), —$(CH_2)_{0-2}$(phenyl), morpholinyl, dioxothiomorpholinyl, dimethyl pyrazolyl, methylpiperidinyl, methylpiperazinyl, amino-oxadiazolyl, imidazolyl, triazolyl, or —C(O)(thiazolyl);

$R_{2a}$ is $C_{1-6}$ alkyl, $C_{1-3}$ fluoroalkyl, $C_{1-6}$ hydroxyalkyl, $C_{1-3}$ aminoalkyl, —$(CH_2)_{0-4}O(C_{1-3}$ alkyl), $C_{3-6}$ cycloalkyl, —$(CH_2)_{1-3}C(O)NR_xR_x$, —$CH_2(C_{3-6}$ cycloalkyl), —$CH_2$(phenyl), tetrahydrofuranyl, tetrahydropyranyl, or phenyl;

each $R_{2b}$ is independently hydrogen, halo, —CN, —$NR_xR_x$, $C_{1-6}$ alkyl, $C_{1-3}$ fluoroalkyl, $C_{1-3}$ hydroxyalkyl, $C_{1-3}$ fluoroalkoxy, —$(CH_2)_{0-2}O(C_{1-3}$ alkyl), —$(CH_2)_{0-3}C(O)NR_xR_x$, —$(CH_2)_{1-3}(C_{3-6}$ cycloalkyl), —C(O)O($C_{1-3}$ alkyl), —C(O)$NR_x(C_{1-3}$ alkyl), —$CR_x$═$CR_xR_x$, or —$CR_x$═CH($C_{3-6}$ cycloalkyl);

$R_{2c}$ is $R_{2a}$ or $R_{2b}$;

$R_{2d}$ is $R_{2a}$ or $R_{2b}$; provided that one of $R_{2c}$ and $R_{2d}$ is $R_{2a}$, and the other of $R_{2c}$ and $R_{2d}$ is $R_{2b}$;

$R_4$ is:

(i) —$N(CH_3)_2$;

(ii) pyrrolidinyl, piperidinyl, piperazinyl, or pyridinyl, each substituted with zero to 2 $R_{4a}$; or (iii)

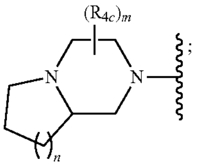

;

each $R_{4a}$ is independently $C_{1-6}$ alkyl, $C_{1-3}$ fluoroalkyl, —$(CH_2)_{1-2}O(C_{1-2}$ alkyl), $C_{3-6}$ cycloalkyl, —$CH_2(C_{3-6}$ cycloalkyl), —$CH_2$(oxetanyl), —C(O)($C_{1-4}$ alkyl), —C(O)($C_{3-6}$ cycloalkyl), —C(O)(phenyl), —C(O)$CH_2(C_{3-6}$ cycloalkyl), —C(O)$CH_2$(phenyl), —C(O)O($C_{1-4}$ alkyl), —$NR_x(C_{1-3}$ alkyl), —$NR_x(C_{3-6}$ cycloalkyl), azetidinyl, oxetanyl, tetrahydropyranyl, pyrrolidinyl, phenyl, or piperidinyl substituted with zero to 2 substituents selected from —OH or —$CH_3$;

$R_{4b}$ is F, Cl, or —$CH_3$;

each $R_{4c}$ is independently $C_{1-6}$ alkyl, $C_{1-3}$ fluoroalkyl, —$CH_2(C_{3-6}$ cycloalkyl), —C(O)($C_{1-4}$ alkyl), —C(O)(phenyl), —C(O)$CH_2$(phenyl), —C(O)$OCH_2CH_3$, or $C_{3-6}$ cycloalkyl;

each $R_5$ is independently hydrogen, F, Cl, $C_{1-2}$ alkyl, $C_{1-2}$ fluoroalkyl, or cyclopropyl;

each $R_x$ is independently hydrogen or —$CH_3$;

each $R_y$ is independently hydrogen or $C_{1-6}$ alkyl;

m is zero, 1, or 2;

n is zero, 1, or 2;

p is zero, 1, 2, 3, or 4; and q is 1 or 2.

The second aspect of the present invention provides at least one compound of Formula (I):

(I)
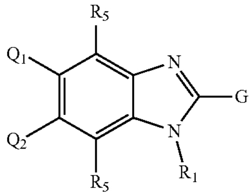
or a salt thereof, wherein:
one of $Q_1$ and $Q_2$ is A and the other of $Q_1$ and $Q_2$ is $R_5$;
G is:
(i) phenyl substituted with 1 to 2 substituents independently selected from F, Cl, Br, $C_{1-2}$ alkoxy, $C_{1-2}$ fluoroalkoxy, $C_{3-4}$ cycloalkyl —C(O)$NR_yR_y$, —$S(O)_2CH_3$, —$S(O)_2$(phenyl), —$S(O)_2NR_xR_x$, and —S(O)(NH)$NR_xR_x$;
((ii)
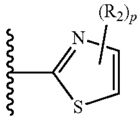
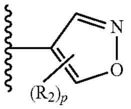
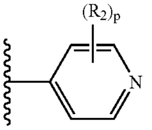
or
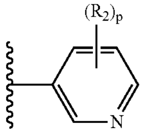
;
(iii)
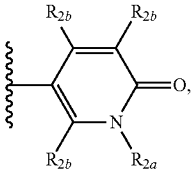
,
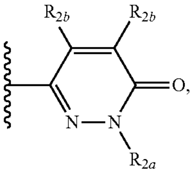
,
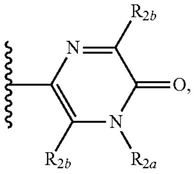
or
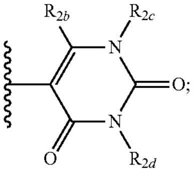
;
(iv)
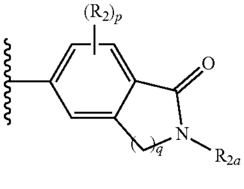
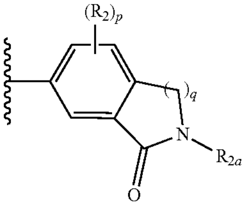
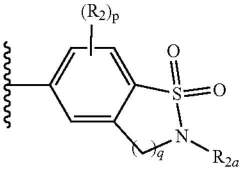
or
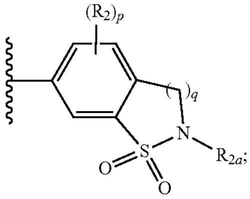
;
(v) a 9-membered heterocyclic ring selected from:
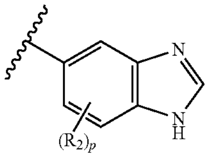
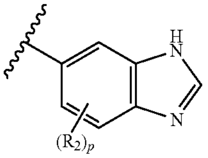
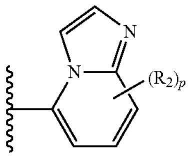
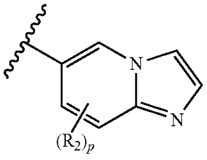
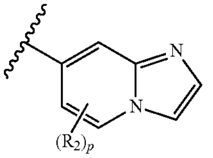
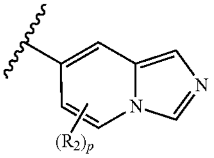
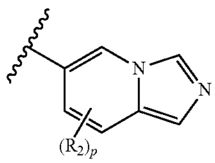
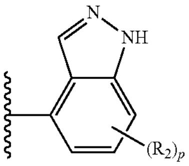
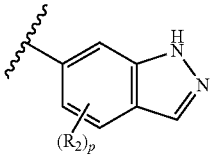
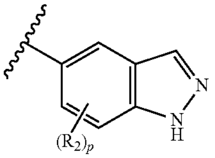
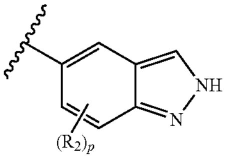
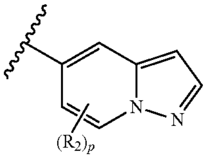
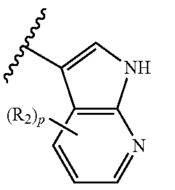
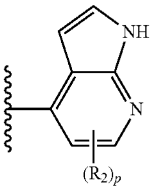
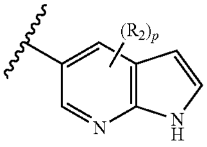
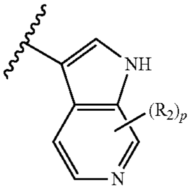
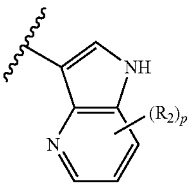
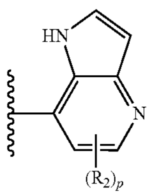
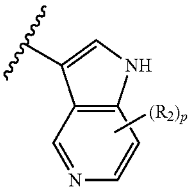
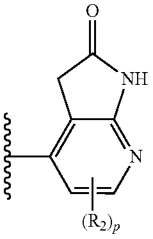

-continued
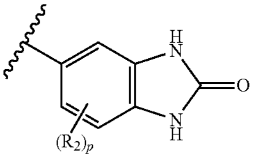
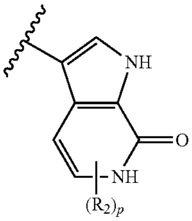
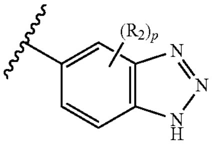
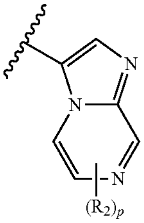
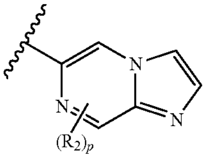
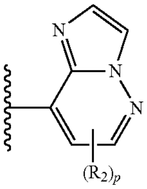
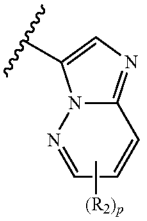
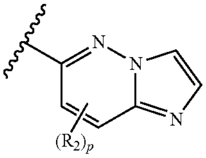
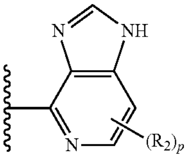
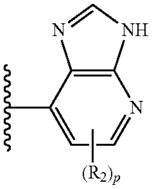
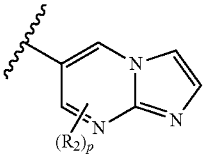
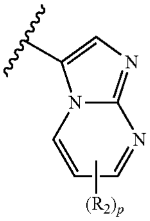
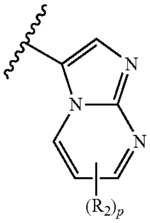
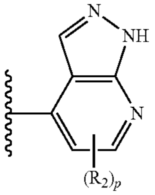
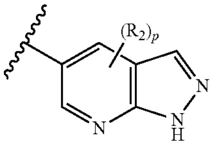
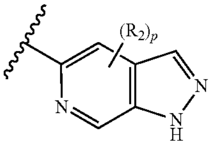
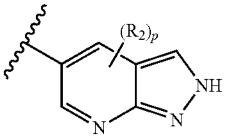
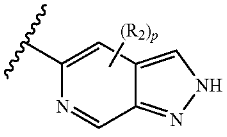
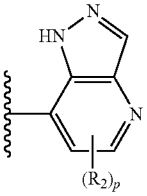
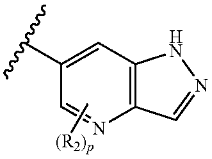
-continued
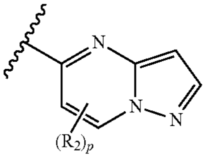
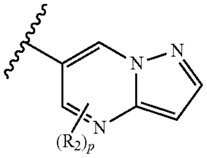
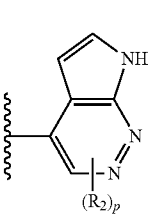
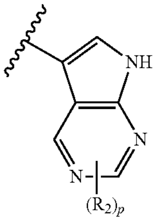
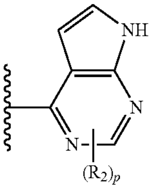
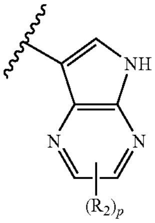
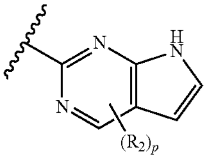
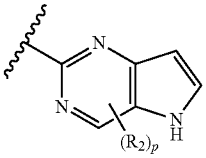
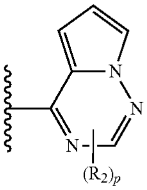
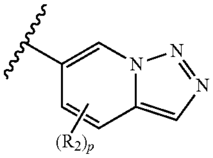
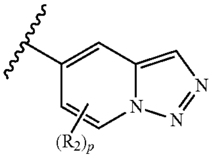
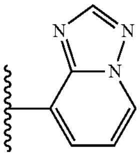
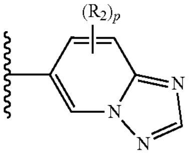
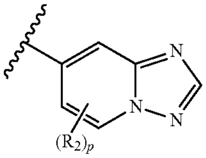
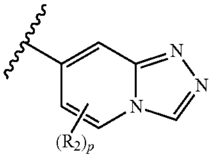
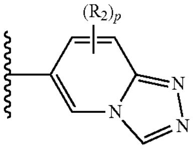
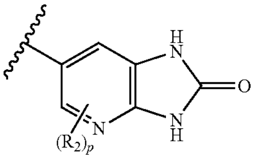
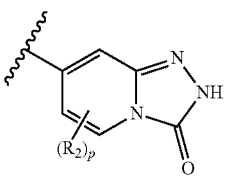
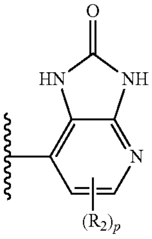

-continued
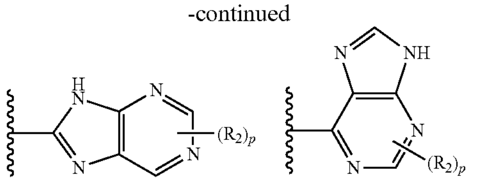
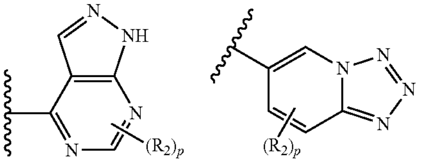
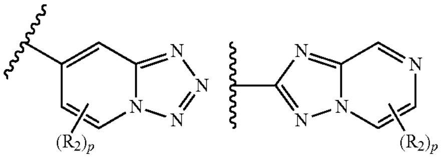
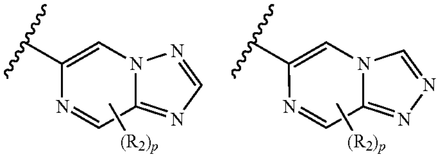
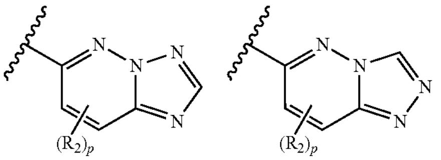
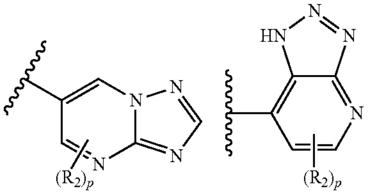
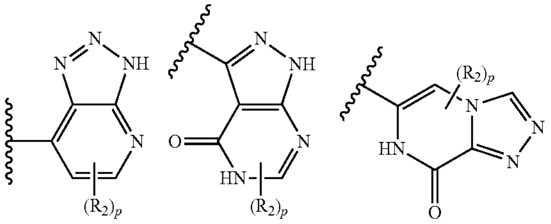
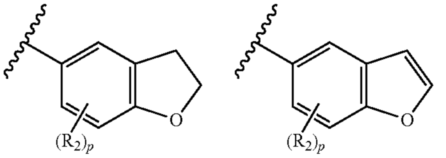
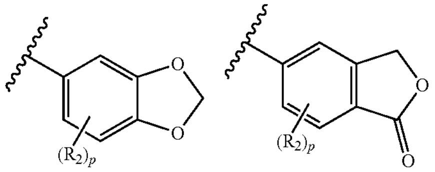
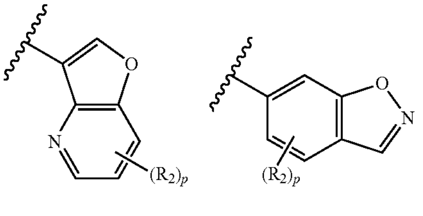
-continued
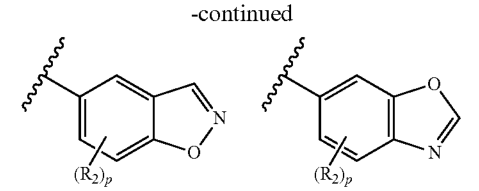
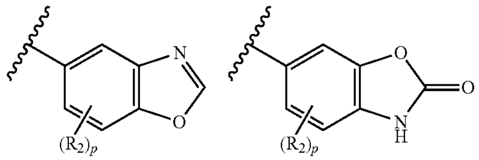
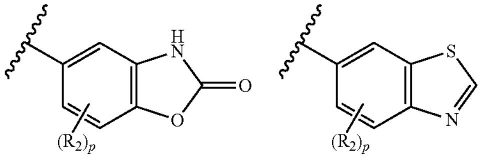
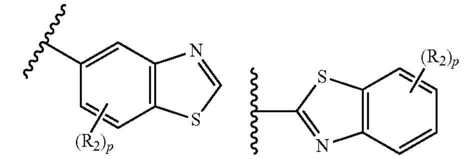
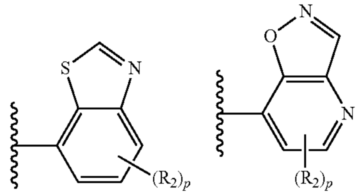
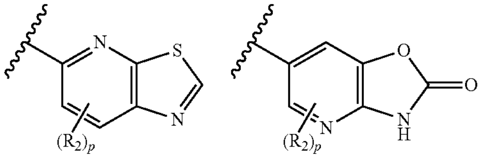
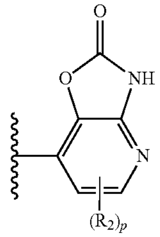
and
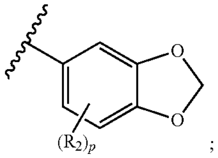
;
(vi) 10-membered heterocyclic ring selected from:
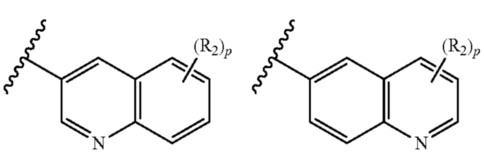
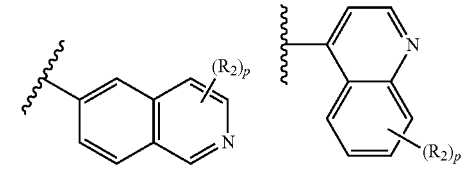

-continued

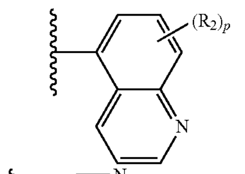
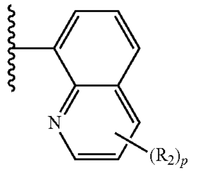
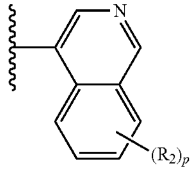
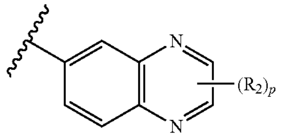
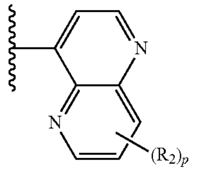
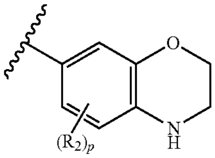
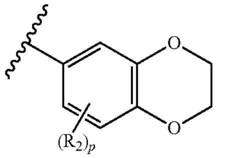
and
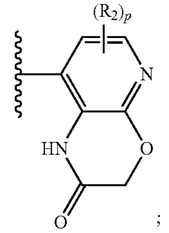
;

A is piperidinyl, phenyl, pyridinyl, pyrimidinyl, 6-azabicyclo[3.2.1]octanyl, or azabicyclo[3.2.1]octanyl, each substituted with -L-$R_4$ and zero to 1 $R_{4b}$;

L is a bond, —$CR_xR_x$— or —$C(O)(CR_xR_x)_{0-2}$—;

$R_1$ is hydrogen, $C_{1-3}$ alkyl, $C_{1-2}$ fluoroalkyl, or $C_{3-4}$ cycloalkyl;

each $R_2$ is independently halo, —CN, —OH, —$NO_2$, $C_{1-4}$ alkyl, $C_{1-2}$ fluoroalkyl, $C_{1-2}$ cyanoalkyl, $C_{1-3}$ hydroxyalkyl, $C_{1-3}$ aminoalkyl, —$O(CH_2)_{1-2}OH$, —$(CH_2)_{0-4}O$($C_{1-4}$ alkyl), $C_{1-3}$ fluoroalkoxy, —$(CH_2)_{1-4}O$($C_{1-3}$ alkyl), —$O(CH_2)_{1-2}OC(O)$($C_{1-3}$ alkyl), —$O(CH_2)_{1-2}NR_xR_x$, —C(O)O($C_{1-3}$ alkyl), —$(CH_2)_{0-2}C(O)NR_yR_y$, —$C(O)NR_x$($C_{1-5}$ hydroxyalkyl), —$C(O)NR_x$($C_{2-6}$ alkoxyalkyl), —$C(O)NR_x$($C_{3-6}$ cycloalkyl), —$NR_yR_y$, —$NR_y$($C_{1-3}$ fluoroalkyl), —$NR_y$($C_{1-4}$ hydroxyalkyl), —$NR_xCH_2$(phenyl), —$NR_xS(O)_2$($C_{3-6}$ cycloalkyl), —$NR_xC(O)$($C_{1-3}$ alkyl), —$NR_xCH_2$($C_{3-6}$ cycloalkyl), —$S(O)_2$($C_{1-3}$ alkyl), —$S(O)_2N$($C_{1-3}$ alkyl$)_2$, —S(O)(NH)N($C_{1-3}$ alkyl$)_2$, —$(CH_2)_{0-2}$($C_{3-6}$ cycloalkyl), —$(CH_2)_{0-2}$(phenyl), morpholinyl, dioxothiomorpholinyl, dimethyl pyrazolyl, methylpiperidinyl, methylpiperazinyl, amino-oxadiazolyl, imidazolyl, triazolyl, or —C(O)(thiazolyl);

$R_{2a}$ is $C_{1-6}$ alkyl, $C_{1-3}$ fluoroalkyl, $C_{1-6}$ hydroxyalkyl, $C_{1-3}$ aminoalkyl, —$(CH_2)_{0-4}O$($C_{1-3}$ alkyl), $C_{3-6}$ cycloalkyl, —$(CH_2)_{1-3}C(O)NR_xR_x$, —$CH_2$($C_{3-6}$ cycloalkyl), —$CH_2$(phenyl), tetrahydrofuranyl, tetrahydropyranyl, or phenyl;

each $R_{2b}$ is independently hydrogen, halo, —CN, —$NR_xR_x$, $C_{1-6}$ alkyl, $C_{1-3}$ fluoroalkyl, $C_{1-3}$ hydroxyalkyl, $C_{1-3}$ fluoroalkoxy, —$(CH_2)_{0-2}O$($C_{1-3}$ alkyl), —$(CH_2)_{0-3}C(O)NR_xR_x$, —$(CH_2)_{1-3}$($C_{3-6}$ cycloalkyl), —C(O)O($C_{1-3}$ alkyl), —$C(O)NR_x$($C_{1-3}$ alkyl), —$CR_x$=$CR_xR_x$, or —$CR_x$=CH($C_{3-6}$ cycloalkyl);

$R_{2c}$ is $R_{2a}$ or $R_{2b}$;

$R_{2d}$ is $R_{2a}$ or $R_{2b}$; provided that one of $R_{2c}$ and $R_{2d}$ is $R_{2a}$, and the other of $R_{2c}$ and $R_{2d}$ is $R_{2b}$;

$R_4$ is:

(i) —$N(CH_3)_2$;

(ii) pyrrolidinyl, piperidinyl, piperazinyl, pyridinyl, azaspiro[3.3]heptanyl, or azabicyclo[3.2.1]octanyl, each substituted with zero to 2 $R_{4a}$; or (iii)

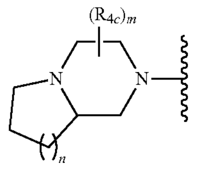

each $R_{4a}$ is independently $C_{1-6}$ alkyl, $C_{1-3}$ fluoroalkyl, $C_{3-6}$ cycloalkyl, —$CH_2$($C_{3-6}$ cycloalkyl), —C(O)($C_{1-4}$ alkyl), —C(O)($C_{3-6}$ cycloalkyl), —C(O)(phenyl), —$C(O)CH_2$($C_{3-6}$ cycloalkyl), —$C(O)CH_2$(phenyl), or —C(O)O($C_{1-4}$ alkyl);

$R_{4b}$ is F, Cl, or —$CH_3$;

each $R_{4c}$ is independently $C_{1-6}$ alkyl, $C_{1-3}$ fluoroalkyl, —$CH_2$($C_{3-6}$ cycloalkyl), —C(O)($C_{1-4}$ alkyl), —C(O)(phenyl), —$C(O)CH_2$(phenyl), —$C(O)OCH_2CH_3$, or $C_{3-6}$ cycloalkyl;

each $R_5$ is independently hydrogen, F, Cl, $C_{1-2}$ alkyl, $C_{1-2}$ fluoroalkyl, or cyclopropyl; each $R_x$ is independently hydrogen or —$CH_3$;

each $R_y$ is independently hydrogen or $C_{1-6}$ alkyl;

m is zero, 1, or 2;

n is zero, 1, or 2;

p is zero, 1, 2, 3, or 4; and q is 1 or 2.

In one embodiment, a compound of Formula (I) or stereoisomers, tautomers, solvates or salts thereof is provided wherein $Q_1$ is $R_5$ and $Q_2$ is A. Compounds of this embodiment have the structure of Formula (II):

(II)

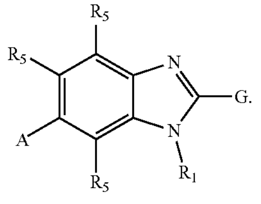

In one embodiment, a compound of Formula (I) or stereoisomers, tautomer, solvates or salts thereof is provided wherein $Q_1$ is A and $Q_2$ is $R_5$. Compounds of this embodiment have the structure of Formula (III):

(III)

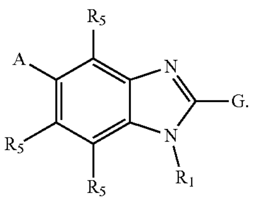

In one embodiment, a compound of Formula (I) or stereoisomers, tautomer, solvates or salts thereof is provided wherein G is phenyl substituted with 1 to 2 substituents independently selected from F, Cl, Br, —CN, $C_{1-3}$ alkyl, $C_{1-2}$ fluoroalkyl, $C_{1-3}$ alkoxy, $C_{1-2}$ fluoroalkoxy, $C_{3-6}$ cycloalkyl, —$NR_xR_x$, —C(O)$NR_yR_y$, —$S(O)_2(C_{1-3}$ alkyl), —$S(O)_2$(phenyl), —$S(O)_2NR_xR_x$, —$NR_xS(O)_2(C_{1-3}$ alkyl), —S(O)(NH)$NR_xR_x$, and —P(O)$(OCH_2CH_3)_2$.

In one embodiment, a compound of Formula (I) or stereoisomers, tautomer, solvates or salts thereof is provided wherein G is phenyl substituted with 1 to 2 substituents independently selected from F, Cl, Br, —CN, —$CH_3$, —$OCH_3$, —$OCHF_2$, —$OCF_3$, cyclopropyl, —C(O)$NR_yR_y$, —$N(CH_3)_2$, —$S(O)_2CH_3$, —$S(O)_2$(phenyl), —$S(O)_2NR_xR_x$, —$NHS(O)_2CH_3$, —S(O)(NH)$NR_xR_x$, and —P(O)$(OCH_2CH_3)_2$.

In one embodiment, a compound of Formula (I) or stereoisomers, tautomer, solvates or salts thereof is provided wherein G is phenyl substituted with 1 to 2 substituents independently selected from F, Cl, Br, —CN, —$CH_3$, —$OCH_3$, —$OCHF_2$, —$OCF_3$, cyclopropyl, —C(O)$NR_yR_y$, —$N(CH_3)_2$, —$S(O)_2CH_3$, —$S(O)_2$(phenyl), —$S(O)_2NR_xR_x$, —$NHS(O)_2CH_3$, —S(O)(NH)$NR_xR_x$, and —P(O)$(OCH_2CH_3)_2$.

In one embodiment, a compound of Formula (I) or stereoisomers, tautomer, solvates or salts thereof is provided wherein G is phenyl substituted with zero to 2 substituents independently selected from F, Cl, Br, —CN, —$CH_3$, —$OCH_3$, —$OCHF_2$, —$OCF_3$, cyclopropyl, —$N(CH_3)_2$, —$S(O)_2CH_3$, —$S(O)_2$(phenyl), —$NHS(O)_2CH_3$, and —P(O)$(OCH_2CH_3)_2$.

In one embodiment, a compound of Formula (I) or stereoisomers, tautomer, solvates or salts thereof is provided wherein G is phenyl substituted with 1 to 2 substituents independently selected from —$OCH_3$, —$S(O)_2CH_3$, or —$S(O)_2$(phenyl). Included in this embodiment are compounds in which G is phenyl substituted with 1 to 2 substituents selected from —$OCH_3$. Also included in this embodiment are compounds in which G is phenyl substituted with —$S(O)_2CH_3$.

In one embodiment, a compound of Formula (I) or stereoisomers, tautomer, solvates or salts thereof is provided wherein G is phenyl substituted with 1 to 2 substituents independently selected from F, Cl, Br, —$OCH_3$, —$OCHF_2$, —$OCF_3$, cyclopropyl, —C(O)$NR_yR_y$, —$S(O)_2CH_3$, —$S(O)_2$ (phenyl), —$S(O)_2NR_xR_x$, and —S(O)(NH)$NR_xR_x$. Included in this embodiment are compounds in which G is phenyl substituted with 1 to 2 substituents independently selected from —$OCH_3$, —$S(O)_2CH_3$, —$S(O)_2N(CH_3)_2$, and —S(O)(NH)$N(CH_3)_2$. Also included in this embodiment are compounds in which G is phenyl substituted with 1 to 2 substituents independently selected from —$OCH_3$ and —$S(O)_2CH_3$. Additionally, included in this embodiment are compounds in which G is:

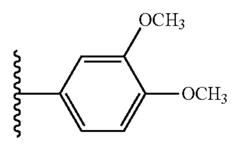

or

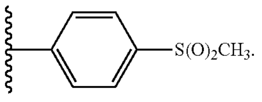

In one embodiment, a compound of Formula (I) or stereoisomers, tautomer, solvates or salts thereof is provided wherein G is

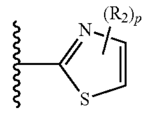

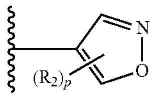

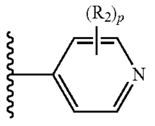

or

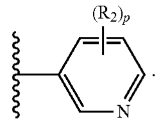

Included in this embodiment are compounds in which each $R_2$ is independently F, Cl, Br, —CN, —OH, —$CH_3$, —$CH_2CH_3$, —$CF_3$, —$CH_2OH$, —$C(CH_3)_2OH$, —$CH_2NH_2$, —$OCH_3$, —$OCH_2CH_3$, —$OCH(CH_3)_2$, —$OCH_2CH_2OCH_3$, —$OCH_2CH_2N(CH_3)_2$, —$OCHF_2$, —C(O)$OCH_3$, —C(O)$NH_2$, —C(O)NH($CH_2CH_3$), —C(O)(thiazolyl), —$NH_2$, —NH($CH_3$), —NH($CH_2CH_3$), —$N(CH_3)_2$, —NHC(O)$CH_3$, —NHC(O)$C(CH_3)_3$, —NH($CH_2$-cyclopropyl), cyclopropyl, methylpiperidinyl, methylpiperazinyl, amino-oxadiazolyl, imidazolyl, or triazolyl. Also included in this embodiment are compounds in which each $R_2$ is independently F, Cl, —CN, —$CH_3$, —$OCH_3$, —$NH_2$, or cyclopropyl. Additionally, included in this embodiment are compounds in which p is 2; one $R_2$ is —$CH_3$; and the other $R_2$ is F, Cl, —CN, —$CH_3$, —$OCH_3$, —$NH_2$, or cyclopropyl.

In one embodiment, a compound of Formula (I) or stereoisomers, tautomer, solvates or salts thereof is provided wherein G is a 9-membered heterocyclic ring selected from:

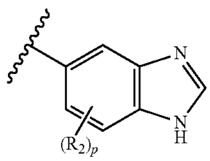

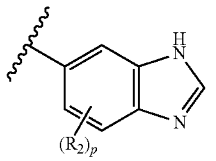

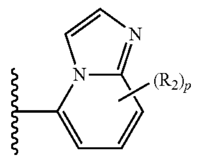

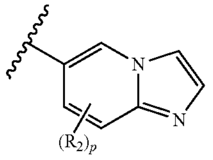

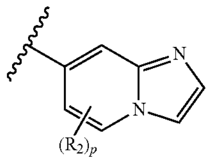

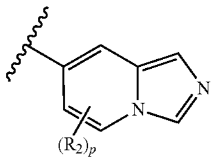

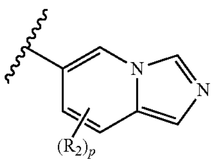

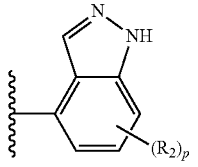

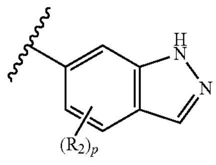

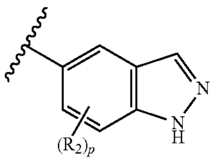

-continued
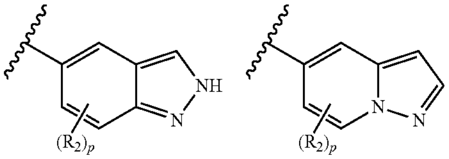
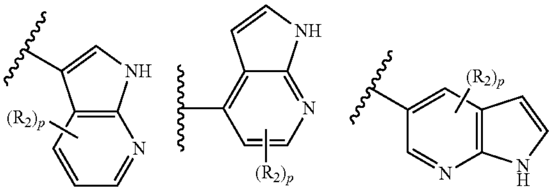
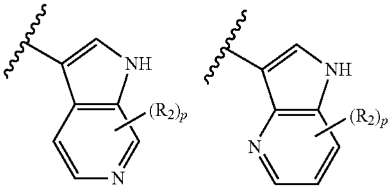
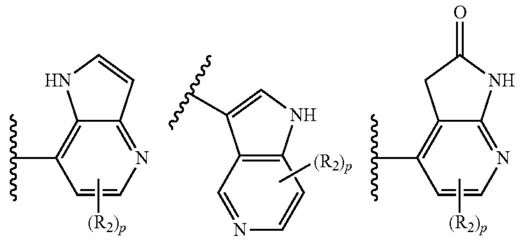
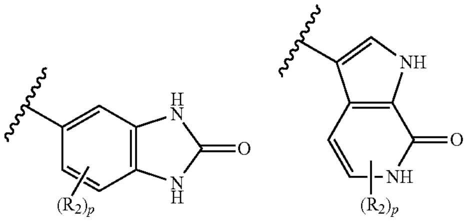
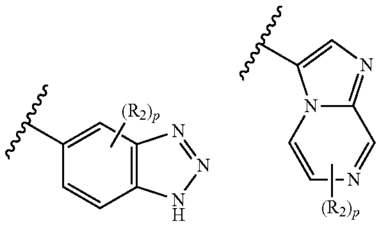
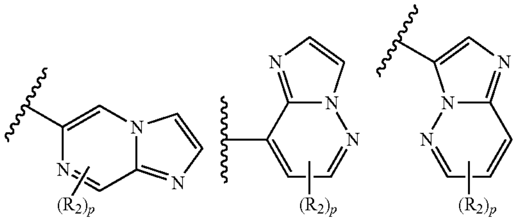
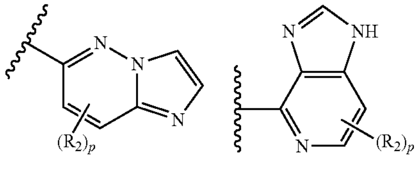
-continued
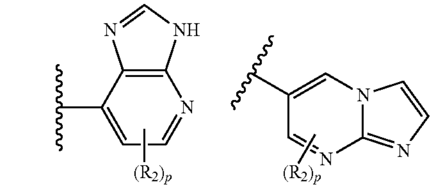
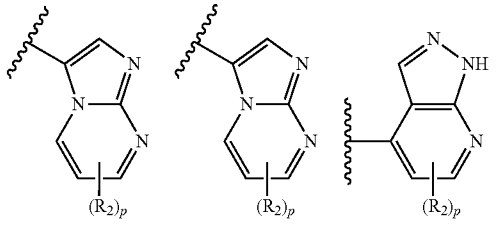
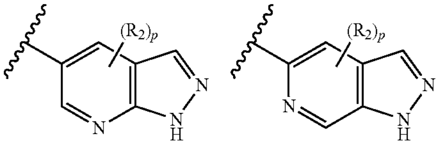
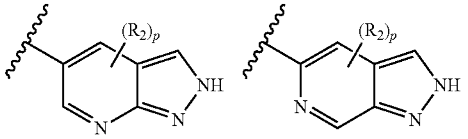
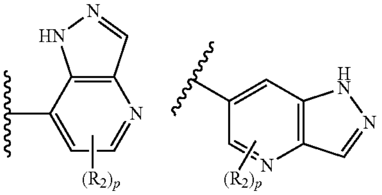
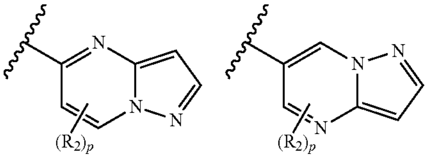
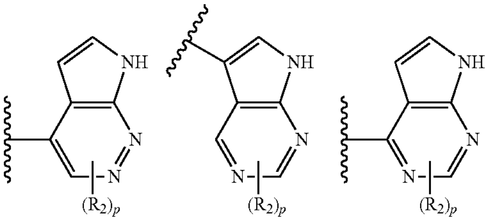
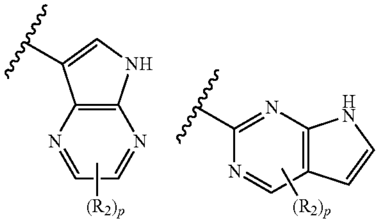
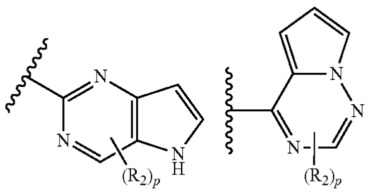

-continued
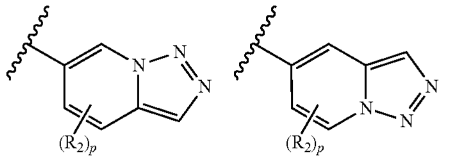
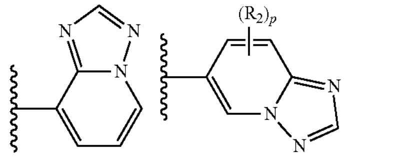
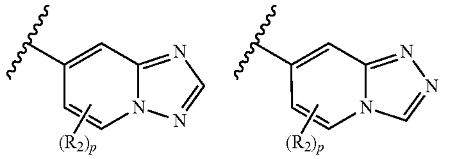
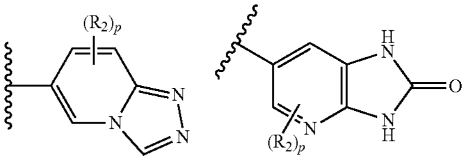
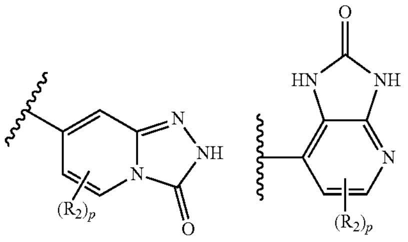
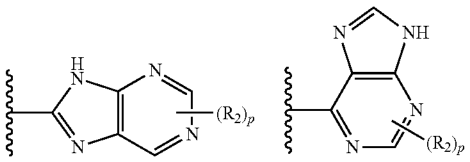
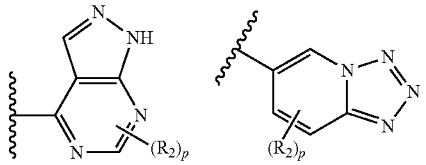
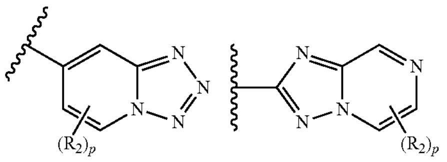
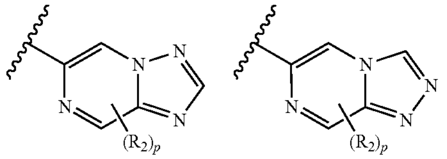
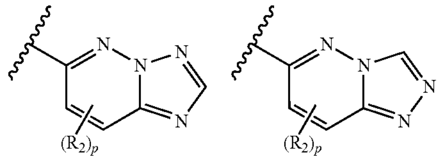
-continued
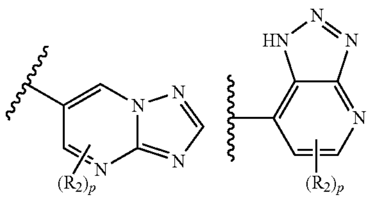
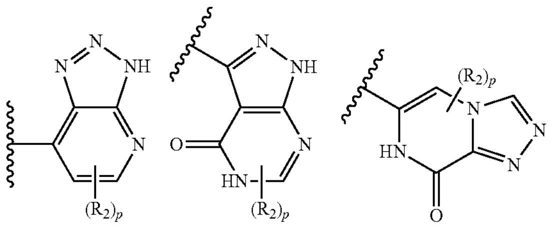
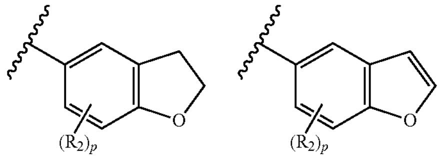
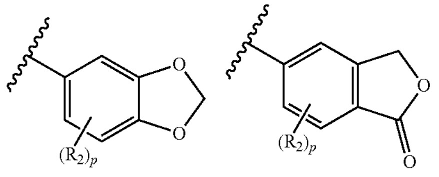
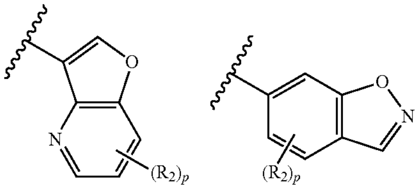
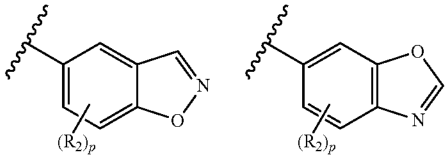
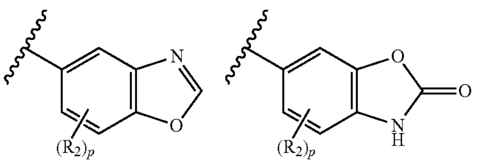
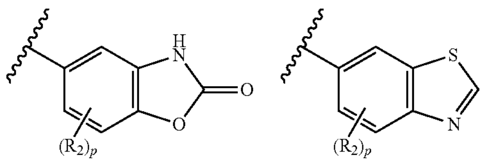
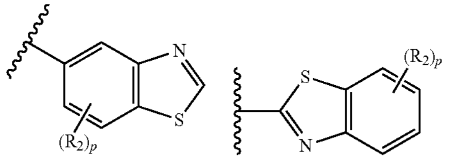

-continued

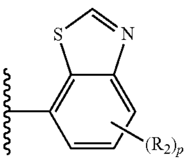 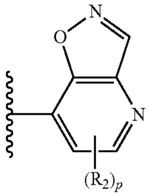

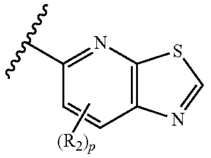 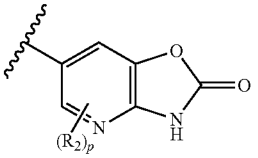

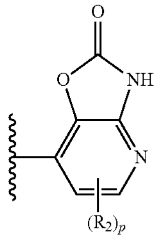 and 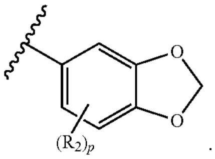 .

Included in this embodiment are compounds in which G is:

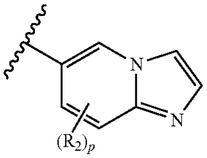 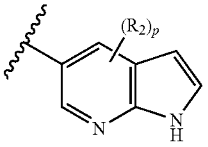

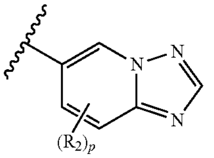 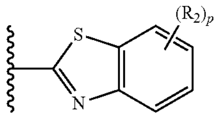

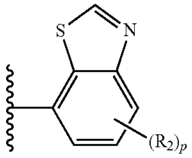 and 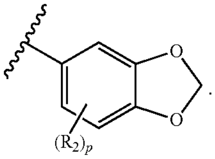 .

In one embodiment, a compound of Formula (I) or stereoisomers, tautomer, solvates or salts thereof is provided wherein G is a 10-membered heterocyclic ring selected from:

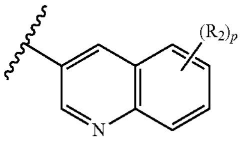 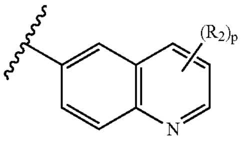

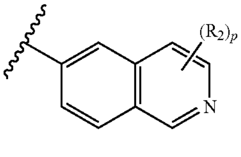 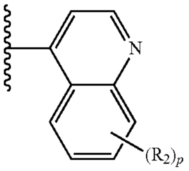

-continued

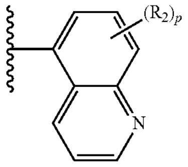 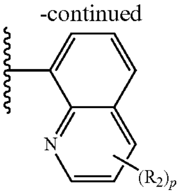 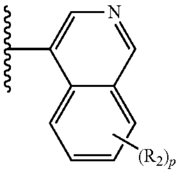

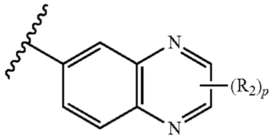 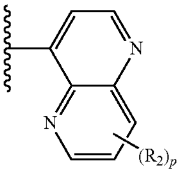

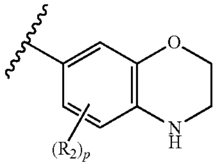 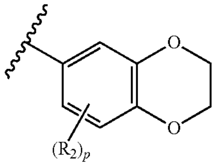 and

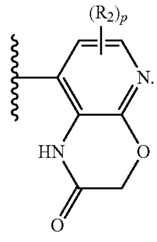

Included in this embodiment are compounds in which G is:

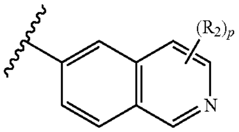 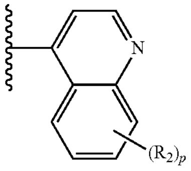

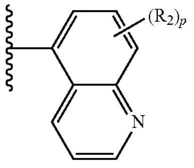 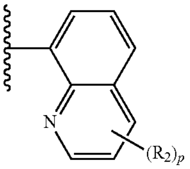 and

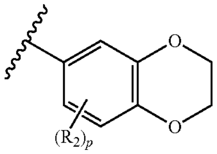 .

In one embodiment, a compound of Formula (I) or stereoisomers, tautomer, solvates or salts thereof is provided wherein G is:

(i) phenyl substituted with 1 to 2 substituents independently selected from F, Cl, Br, $-OCH_3$, $-OCHF_2$, $-OCF_3$, cyclopropyl, $-S(O)_2CH_3$, or $-S(O)_2$(phenyl);

(ii)

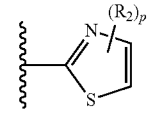

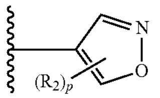

or

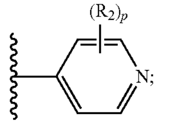

(iii) a 9-membered heterocyclic ring selected from:

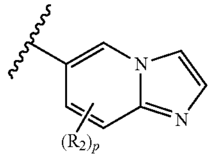

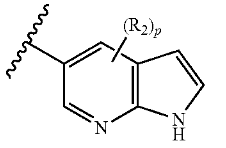

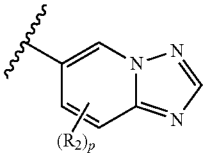

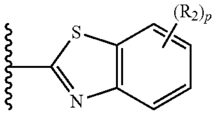

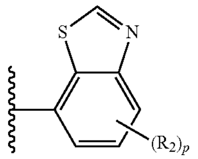

and

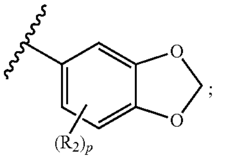

or (iv) 10-membered heterocyclic ring selected from:

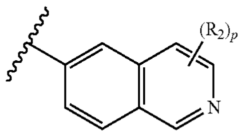

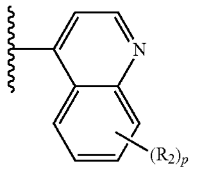

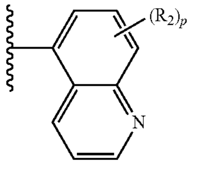

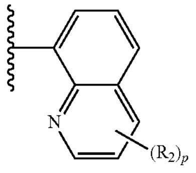

and

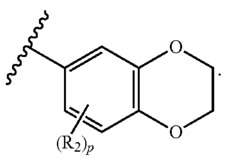

Included in this embodiment are compounds in which each $R_2$ is independently F, Cl, —$CH_3$, —$CH_2CH_3$, —$CH_2OH$, —$CH_2CH_2OH$, —$CH_2CN$, —$OCH_3$, —$CH_2OCH_3$, or —$CH_2CH_2S(O)_2CH_3$. Also included in this embodiment are compounds in which each $R_2$ is independently F, —$CH_3$, or —$OCH_3$.

In one embodiment, a compound of Formula (I) or stereoisomers, tautomer, solvates or salts thereof is provided wherein p is zero, 1, 2, or 3. Included in this embodiment are compounds in which p is 1 or 2.

In one embodiment, a compound of Formula (I) or stereoisomers, tautomer, solvates or salts thereof is provided wherein A is piperidinyl, phenyl, pyridinyl, pyrimidinyl, 6-azabicyclo[3.2.1]octanyl, or azabicyclo[3.2.1]octanyl, each substituted with -L-$R_4$ and zero to 1 $R_{4b}$.

In one embodiment, a compound of Formula (I) or stereoisomers, tautomer, solvates or salts thereof is provided wherein A is piperidinyl, phenyl, pyridinyl, 6-azabicyclo[3.2.1]octanyl, or azabicyclo[3.2.1]octanyl, each substituted with -L-$R_4$ and zero to 3 $R_{4b}$. Included in this embodiment are compounds in which A is piperidinyl, phenyl, pyridinyl, pyrimidinyl, or azabicyclo[3.2.1]octanyl, each substituted with -L-$R_4$ and zero to 2 $R_{4b}$.

In one embodiment, a compound of Formula (I) or stereoisomers, tautomer, solvates or salts thereof is provided wherein A is piperidinyl, phenyl, or pyridinyl, each substituted with -L-$R_4$ and zero to 1 $R_{4b}$. Included in this embodiment are compounds in which A is piperidinyl or phenyl, each substituted with -L-$R_4$ and zero to 1 $R_{4b}$. Also, included in this embodiment are compounds in which A is phenyl or pyridinyl, each substituted with -L-$R_4$ and zero to 1 $R_{4b}$.

In one embodiment, a compound of Formula (I) or stereoisomers, tautomer, solvates or salts thereof is provided wherein A is piperidinyl, phenyl, pyridinyl, or pyrimidinyl, each substituted with -L-$R_4$ and zero to 1 $R_{4b}$; and L is a bond. Included in this embodiment are compounds in which A is piperidinyl, phenyl, or pyridinyl, each substituted with -L-$R_4$ and zero to 1 $R_{4b}$; and L is a bond.

In one embodiment, a compound of Formula (I) or stereoisomers, tautomer, solvates or salts thereof is provided wherein L is a bond, —$CH_2$—, —$CH_2CH_2$—, —O—, or —$C(O)(CH_2)_{0\text{-}2}$—. Included in this embodiment are compounds in which L is a bond, —$CH_2$—, —$CH_2CH_2$—, or —O—.

In one embodiment, a compound of Formula (I) or stereoisomers, tautomer, solvates or salts thereof is provided wherein L is a bond.

In one embodiment, a compound of Formula (I) or stereoisomers, tautomer, solvates or salts thereof is provided wherein L is a —$(CR_xR_x)_{1\text{-}2}$—.

In one embodiment, a compound of Formula (I) or stereoisomers, tautomer, solvates or salts thereof is provided wherein L is —$CR_xR_x$—. Included in this embodiment are compounds in which L is —$CH_2$—.

In one embodiment, a compound of Formula (I) or stereoisomers, tautomer, solvates or salts thereof is provided wherein L is —$CR_xR_x$—. Included in this embodiment are compounds in which L is —$CH_2CH_2$—.

In one embodiment, a compound of Formula (I) or stereoisomers, tautomer, solvates or salts thereof is provided wherein L is —O—.

In one embodiment, a compound of Formula (I) or stereoisomers, tautomer, solvates or salts thereof is provided wherein L is —$C(O)(CR_xR_x)_{0\text{-}2}$—. Included in this embodiment are compounds in which L is —$C(O)(CH_2)_{0\text{-}2}$—. Also included in this embodiment are compounds in which L is —$C(O)(CH_2)_{0\text{-}1}$—. Additionally, included in this embodiment are compounds in which L is —C(O)—.

In one embodiment, a compound of Formula (I) or stereoisomers, tautomer, solvates or salts thereof is provided wherein L is —$CR_xR_x$— or —$C(O)(CR_xR_x)_{0\text{-}2}$—. Included in this embodiment are compounds in which L is —$CR_xR_x$— or —$C(O)(CR_xR_x)_{0\text{-}1}$—. Also included in this embodiment are compounds in which L is —$CR_xR_x$— or —C(O)—. Additionally, included in this embodiment are compounds in which each $R_x$ is hydrogen.

In one embodiment, a compound of Formula (I) or stereoisomers, tautomer, solvates or salts thereof is provided wherein L is a bond, —$CH_2$— or —$C(O)(CH_2)_{0-2}$—. Included in this embodiment are compounds in which L is a bond or —C(O)—.

In one embodiment, a compound of Formula (I) or stereoisomers, tautomer, solvates or salts thereof is provided wherein $R_4$ is —$N(CH_3)_2$.

In one embodiment, a compound of Formula (I) or stereoisomers, tautomer, solvates or salts thereof is provided wherein $R_4$ is pyrrolidinyl, piperidinyl, piperazinyl, azepanyl, diazepanyl, pyridinyl, azaspiro[3.3]heptanyl, azabicyclo[3.2.1]octanyl, diazaspiro[3.3]heptanyl, or hexahydropyrrolo[3,4-c]pyrrolyl, each substituted with zero to 2 $R_{4a}$.

In one embodiment, a compound of Formula (I) or stereoisomers, tautomer, solvates or salts thereof is provided wherein $R_4$ is pyrrolidinyl, piperidinyl, piperazinyl, pyridinyl, azaspiro[3.3]heptanyl, or azabicyclo[3.2.1]octanyl, each substituted with zero to 2 $R_{4a}$. Included in this embodiment are compounds in which $R_4$ is pyrrolidinyl, piperidinyl, piperazinyl, or pyridinyl. Also included in this embodiment are compounds in which $R_4$ is piperidinyl, piperazinyl, or pyridinyl.

In one embodiment, a compound of Formula (I) or stereoisomers, tautomer, solvates or salts thereof is provided wherein $R_4$ is

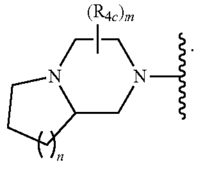

Included in this embodiment are compounds in which n is 1 or 2. Also included in this embodiment are compounds in which n is 1. Additionally, included in this embodiment are compounds in which n is 2.

In one embodiment, a compound of Formula (I) or stereoisomers, tautomer, solvates or salts thereof is provided wherein $R_4$ is pyrrolidinyl, piperidinyl, piperazinyl, or pyridinyl, each substituted with zero to 2 $R_{4a}$; or

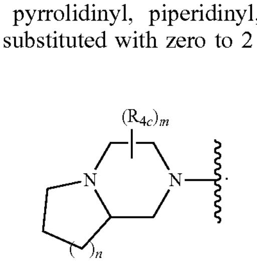

In one embodiment, a compound of Formula (I) or stereoisomers, tautomer, solvates or salts thereof is provided wherein $R_{4a}$ is independently —$CH_3$, —$CH_2CH_3$, —$CH(CH_3)_2$, —$CH_2CH(CH_3)_2$, —$CH_2CH_2OCH_3$, —$C(O)CH(CH_3)_2$, cyclopropyl, cyclobutyl, —$CH_2$(cyclopropyl), —$CH_2$(cyclobutyl), —$CH_2$(oxetanyl), —$N(CH_3)_2$, —$N(CH_3)(CH_2CH_3)$, —$N(CH_3)$(cyclopropyl), azetidinyl, oxetanyl, tetrahydropyranyl, pyrrolidinyl, phenyl, or piperidinyl substituted with zero to 2 substituents selected from —OH or —$CH_3$.

In one embodiment, a compound of Formula (I) or stereoisomers, tautomer, solvates or salts thereof is provided wherein $R_{4b}$ is F or Cl. Included in this embodiment are compounds in which $R_{4b}$ is F.

In one embodiment, a compound of Formula (I) or stereoisomers, tautomer, solvates or salts thereof is provided wherein each $R_{4a}$ is independently $C_{1-6}$ alkyl, $C_{1-3}$ fluoroalkyl, —$(CH_2)_{1-2}OCH_3$, $C_{3-6}$ cycloalkyl, —$CH_2(C_{3-6}$ cycloalkyl), —$CH_2$(oxetanyl), —$C(O)(C_{1-4}$ alkyl), —C(O)($C_{3-6}$ cycloalkyl), —C(O)(phenyl), —$C(O)CH_2(C_{3-6}$ cycloalkyl), —$C(O)CH_2$(phenyl), —$C(O)O(C_{1-4}$ alkyl), —$NR_x(C_{1-3}$ alkyl), —$NR_x$(cyclopropyl), azetidinyl, oxetanyl, tetrahydropyranyl, pyrrolidinyl, phenyl, or piperidinyl substituted with zero to 2 substituents selected from —OH or —$CH_3$.

In one embodiment, a compound of Formula (I) or stereoisomers, tautomer, solvates or salts thereof is provided wherein each $R_{4c}$ is independently $C_{1-4}$ alkyl, $C_{1-2}$ fluoroalkyl, —$CH_2(C_{3-6}$ cycloalkyl), —$C(O)(C_{1-3}$ alkyl), —C(O)(phenyl), —$C(O)CH_2$(phenyl), —$C(O)OCH_2CH_3$, or $C_{3-6}$ cycloalkyl. Included in this embodiment are compounds in which each $R_{4c}$ is independently $C_{1-3}$ alkyl, $C_{1-2}$ fluoroalkyl, —$CH_2(C_{3-4}$ cycloalkyl), —$C(O)(C_{1-2}$ alkyl), —C(O)(phenyl), —$C(O)CH_2$(phenyl), —$C(O)OCH_2CH_3$, or $C_{3-4}$ cycloalkyl.

In one embodiment, a compound of Formula (I) or stereoisomers, tautomer, solvates or salts thereof is provided wherein $R_1$ is hydrogen, $C_{1-2}$ alkyl, —$CH_2F$, —$CHF_2$, —$CF_3$, or $C_{3-4}$ cycloalkyl. Included in this embodiment are compounds in which $R_1$ is hydrogen, —$CH_3$, —$CF_3$, or cyclopropyl. Also included in this embodiment are compounds in which $R_1$ is hydrogen or —$CH_3$.

In one embodiment, a compound of Formula (I) or stereoisomers, tautomer, solvates or salts thereof is provided wherein $R_1$ is hydrogen, —$CH_3$, —$CH_2CH_3$, —$CH(CH_3)_2$, —$CH_2CHF_2$, or cyclopropyl.

In one embodiment, a compound of Formula (I) or stereoisomers, tautomer, solvates or salts thereof is provided wherein each $R_2$ is independently F, Cl, —CN, —OH, $C_{1-3}$ alkyl, $C_{1-2}$ fluoroalkyl, $C_{1-2}$ cyanoalkyl, $C_{1-3}$ hydroxyalkyl, $C_{1-2}$ aminoalkyl, —$(CH_2)_{0-2}O(C_{1-3}$ alkyl), $C_{3-6}$ cycloalkyl, —$NR_xR_x$, —$(CH_2)_{0-2}C(O)NR_xR_x$, —$CH_2(C_{3-6}$ cycloalkyl), —$CH_2$(phenyl), or phenyl. Included in this embodiment are compounds in which each $R_2$ is independently Cl, —$CH_3$, —$CH_2CH_3$, —$CH_2OH$, —$CH_2CH_2OH$, —$CH_2CN$, —$OCH_3$, —$CH_2OCH_3$, or —$CH_2CH_2S(O)_2CH_3$. Also, included in this embodiment are compounds in which each $R_2$ is independently Cl, —$CH_3$, —$CH_2OH$, or —$OCH_3$.

In one embodiment, a compound of Formula (I) or stereoisomers, tautomer, solvates or salts thereof is provided wherein $R_{2a}$ is $C_{1-4}$ alkyl, $C_{1-2}$ fluoroalkyl, $C_{1-4}$ hydroxyalkyl, —$(CH_2)_{1-3}OCH_3$, $C_{3-6}$ cycloalkyl, —$CH_2C(O)NR_xR_x$, —$CH_2(C_{3-6}$ cycloalkyl), —$CH_2$(phenyl), tetrahydrofuranyl, or phenyl; and each $R_{2b}$ is independently H, F, Cl, —CN, —$NR_xR_x$, $C_{1-6}$ alkyl, $C_{1-2}$ fluoroalkyl, $C_{1-3}$ hydroxyalkyl, —$(CH_2)_{0-2}O(C_{1-2}$ alkyl), —$(CH_2)_{0-2}C(O)NR_xR_x$, —$(CH_2)_{1-3}$(cyclopropyl), —$C(O)O(C_{1-2}$ alkyl), —$C(O)NR_x(C_{1-3}$ alkyl), —$CR_x$=$CH_2$, or —CH=CH($C_{3-6}$ cycloalkyl). Also included in this embodiment are compounds in which $R_{2a}$ is —$CH_3$; and each $R_{2b}$ is independently H, $C_1$, or —$CH_3$.

In one embodiment, a compound of Formula (I) or stereoisomers, tautomer, solvates or salts thereof is provided wherein each $R_5$ is independently hydrogen, F, Cl, —$CH_3$, —$CHF_2$, —$CF_3$, or cyclopropyl. Included in this embodiment are compounds in which each $R_5$ is independently hydrogen, F, Cl, —$CH_3$, —$CF_3$, or cyclopropyl. Also included are compounds in which each $R_5$ is hydrogen —$CH_3$, or —$CF_3$.

In one embodiment, a compound of Formula (I) or stereoisomers, tautomer, solvates or salts thereof, wherein:

G is:

(i) phenyl substituted with 1 to 2 substituents independently selected from F, Cl, Br, —CN, —$CH_3$, —$OCH_3$, —$OCHF_2$, —$OCF_3$, cyclopropyl, —C(O)$NR_yR_y$, —$N(CH_3)_2$, —$S(O)_2CH_3$, —$S(O)_2$(phenyl), —$S(O)_2NR_xR_x$, —$NHS(O)_2CH_3$, —S(O)(NH)$NR_xR_x$, and —$P(O)(OCH_2CH_3)_2$;

(ii)

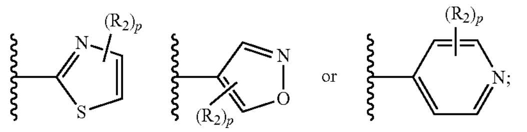

or (iii)

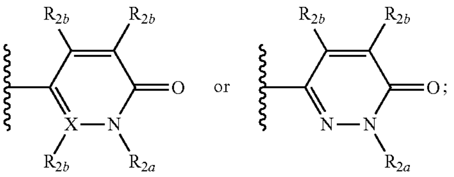

or (iv)

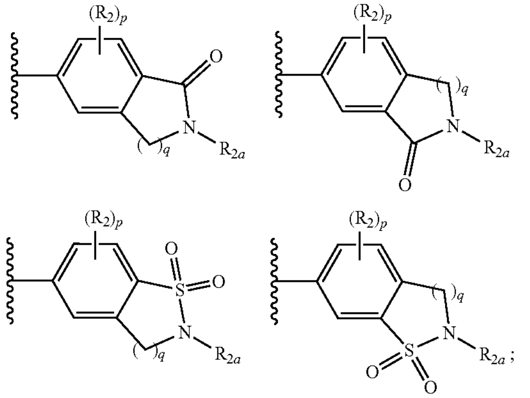

(v) a 9-membered heterocyclic ring selected from:

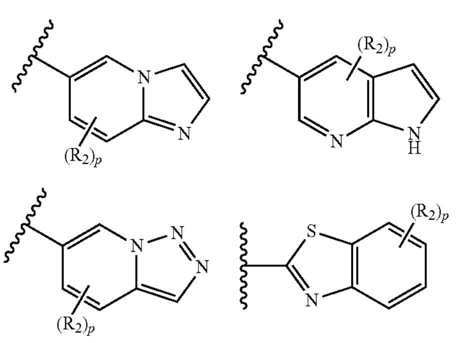

-continued

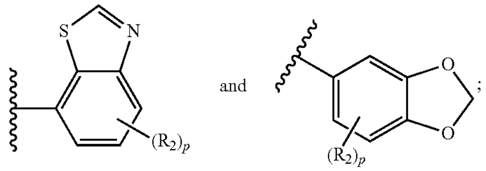

and or (vi) 10-membered heterocyclic ring selected from:

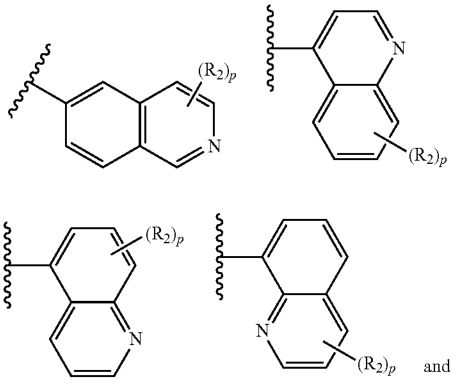

and

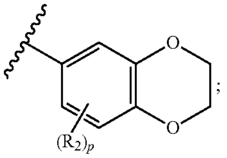

A is piperidinyl, phenyl, pyridinyl, pyrimidinyl, or azabicyclo[3.2.1]octanyl, each substituted with -L-$R_4$ and zero to 2 $R_{4b}$;

L is a bond, —$CH_2$—, —$CH_2CH_2$—, —O—, or —C(O)$(CH_2)_{0-2}$—;

$R_1$ is hydrogen, $C_{1-3}$ alkyl, or $C_{1-2}$ fluoroalkyl;

each $R_2$ is independently F, Cl, —CN, —OH, $C_{1-3}$ alkyl, $C_{1-2}$ fluoroalkyl, $C_{1-2}$ cyanoalkyl, $C_{1-3}$ hydroxyalkyl, $C_{1-2}$ aminoalkyl, —$(CH_2)_{0-2}O(C_{1-3}$ alkyl), $C_{3-6}$ cycloalkyl, —$NR_xR_x$, —$(CH_2)_{0-2}C(O)NR_xR_x$, —$CH_2(C_{3-6}$ cycloalkyl), —$CH_2$(phenyl), or phenyl;

$R_{2a}$ is $C_{1-4}$ alkyl, $C_{1-2}$ fluoroalkyl, $C_{1-4}$ hydroxyalkyl, —$(CH_2)_{1-3}OCH_3$, $C_{3-6}$ cycloalkyl, —$CH_2C(O)NR_xR_x$, —$CH_2(C_{3-6}$ cycloalkyl), —$CH_2$(phenyl), tetrahydrofuranyl, or phenyl;

each $R_{2b}$ is independently hydrogen, F, Cl, —CN, —$NR_xR_x$, $C_{1-6}$ alkyl, $C_{1-2}$ fluoroalkyl, $C_{1-3}$ hydroxyalkyl, —$(CH_2)_{0-2}O(C_{1-2}$ alkyl), —$(CH_2)_{0-2}C(O)NR_xR_x$, —$(CH_2)_{1-3}$(cyclopropyl), —C(O)O($C_{1-2}$ alkyl), —C(O)$NR_x(C_{1-3}$ alkyl), —$CR_x$=$CH_2$, or —CH=CH($C_{3-6}$ cycloalkyl);

$R_4$ is:

(i) pyrrolidinyl, piperidinyl, piperazinyl, pyridinyl, azaspiro[3.3]heptanyl, or azabicyclo[3.2.1]octanyl, each substituted with zero to 2 $R_{4a}$; or (ii)

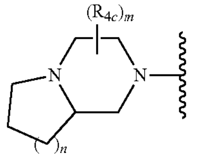

each $R_{4a}$ is independently $C_{1-6}$ alkyl, $C_{1-3}$ fluoroalkyl, $—(CH_2)_{1-2}OCH_3$, $C_{3-6}$ cycloalkyl, $—CH_2(C_{3-6}$ cycloalkyl), $—CH_2$(oxetanyl), $—C(O)(C_{1-4}$ alkyl), $—C(O)(C_{3-6}$ cycloalkyl), —C(O)(phenyl), $—C(O)CH_2(C_{3-6}$ cycloalkyl), $—C(O)CH_2$(phenyl), $—C(O)O(C_{1-4}$ alkyl), $—NR_x(C_{1-3}$ alkyl), $—NR_x$(cyclopropyl), azetidinyl, oxetanyl, tetrahydropyranyl, pyrrolidinyl, phenyl, or piperidinyl substituted with zero to 2 substituents selected from —OH or $—CH_3$;

$R_{4b}$ is F or $—CH_3$;

each $R_{4c}$ is independently $C_{1-6}$ alkyl, $C_{1-3}$ fluoroalkyl, $—CH_2(C_{3-6}$ cycloalkyl), $—C(O)(C_{1-4}$ alkyl), —C(O)(phenyl), $—C(O)CH_2$(phenyl), $—C(O)OCH_2CH_3$, or $C_{3-6}$ cycloalkyl; and each $R_5$ is independently hydrogen, F, Cl, $C_{1-2}$ alkyl, $C_{1-2}$ fluoroalkyl, or cyclopropyl.

In one embodiment, a compound of Formula (I) or stereoisomers, tautomer, solvates or salts thereof is provided wherein:

G is:

(i) phenyl substituted with zero to 2 substituents independently selected from F, Cl, Br, —CN, $—CH_3$, $—OCH_3$, $—OCHF_2$, $—OCF_3$, cyclopropyl, $—N(CH_3)_2$, $—S(O)_2CH_3$, $—S(O)_2$(phenyl), $—NHS(O)_2CH_3$, and $—P(O)(OCH_2CH_3)_2$;

(ii)

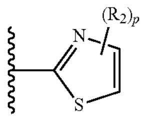 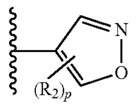 or 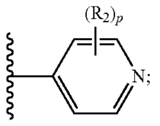

(iii) a 9-membered heterocyclic ring selected from:

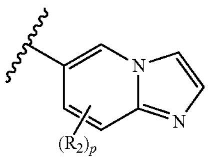 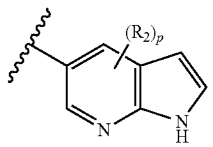

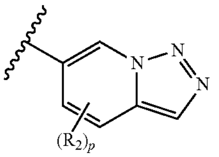 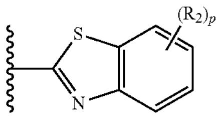

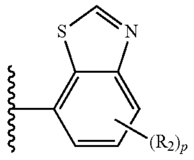 and 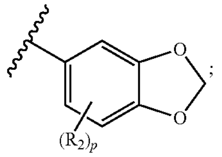

or (iv) 10-membered heterocyclic ring selected from:

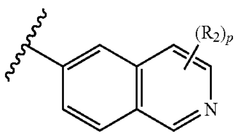 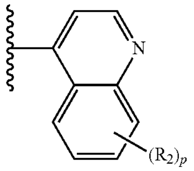

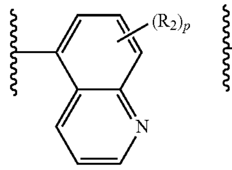 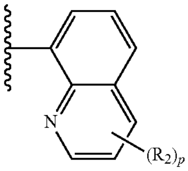 and

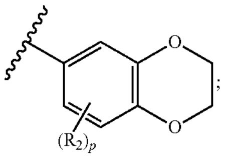

A is piperidinyl, phenyl, pyridinyl, or azabicyclo[3.2.1]octanyl, each substituted with $-L-R_4$ and zero to 2 $R_{4b}$;

L is a bond, $—CH_2—$, $—CH_2CH_2—$, or —O—;

$R_1$ is hydrogen, $—CH_3$, $—CH_2CH_3$, $—CH(CH_3)_2$, $—CH_2CHF_2$, or cyclopropyl;

each $R_2$ is independently F, $—CH_3$, or $—OCH_3$;

$R_4$ is pyrrolidinyl, piperidinyl, piperazinyl, azepanyl, diazepanyl, pyridinyl, azaspiro[3.3]heptanyl, azabicyclo[3.2.1]octanyl, diazaspiro[3.3]heptanyl, or hexahydropyrrolo[3,4-c]pyrrolyl, each substituted with zero to 2 $R_{4a}$;

$R_{4a}$ is independently $—CH_3$, $—CH_2CH_3$, $—CH(CH_3)_2$, $—CH_2CH(CH_3)_2$, $—CH_2CH_2OCH_3$, $—C(O)CH(CH_3)_2$, cyclopropyl, cyclobutyl, $—CH_2$(cyclopropyl), $—CH_2$(cyclobutyl), $—CH_2$(oxetanyl), $—N(CH_3)_2$, $—N(CH_3)(CH_2CH_3)$, $—N(CH_3)$(cyclopropyl), azetidinyl, oxetanyl, tetrahydropyranyl, pyrrolidinyl, phenyl, or piperidinyl substituted with zero to 2 substituents selected from —OH or $—CH_3$; and each $R_5$ is independently hydrogen, $—CH_3$, or $—CF_3$.

In one embodiment, a compound of Formula (I) or stereoisomers, tautomer, solvates or salts thereof is provided wherein:

G is:

(i) phenyl substituted with 1 to 2 substituents independently selected from F, Cl, Br, $—OCH_3$, $—OCHF_2$, $—OCF_3$, cyclopropyl, $—S(O)_2CH_3$, and $—S(O)_2$(phenyl);

(ii)

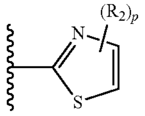 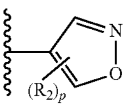 or 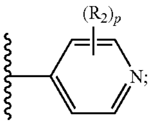

(iii) a 9-membered heterocyclic ring selected from:

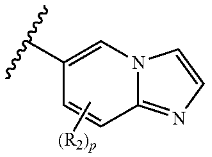

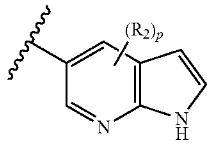

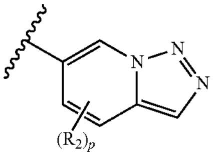

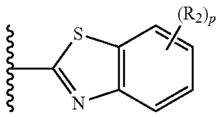

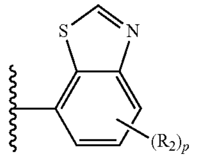

and

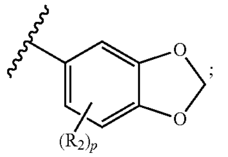

or (iv) 10-membered heterocyclic ring selected from:

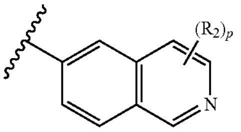

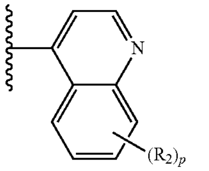

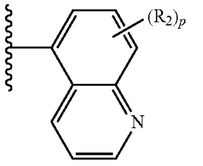

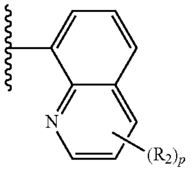

and

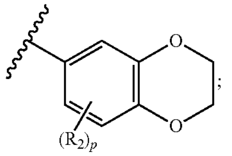

A is piperidinyl or azabicyclo[3.2.1]octanyl, each substituted with -L-$R_4$;

L is a bond;

$R_1$ is hydrogen, —$CH_3$, —$CH_2CH_3$, —$CH(CH_3)_2$, or —$CH_2CHF_2$;

each $R_2$ is independently F, —$CH_3$, or —$OCH_3$;

$R_4$ is piperidinyl, azaspiro[3.3]heptanyl, or azabicyclo[3.2.1]octanyl, each substituted with zero to 2 $R_{4a}$;

$R_{4a}$ is independently —$CH(CH_3)_2$, —$CH_2CH(CH_3)_2$, —$C(O)CH(CH_3)_2$, cyclopropyl, cyclobutyl, or —$CH_2$ (cyclopropyl); and each $R_5$ is independently hydrogen, —$CH_3$, or —$CF_3$.

In one embodiment, a compound of Formula (I) or stereoisomers, tautomer, solvates or salts thereof is provided wherein: $Q_1$ is A; $Q_2$ is $R_5$; G is dimethoxyphenyl; A is piperidinyl substituted with -L-$R_4$; L is a bond; $R_4$ is piperidinyl substituted with zero to 2 $R_{4a}$; $R_{4a}$ is independently —$CH(CH_3)_2$, —$CH_2CH(CH_3)_2$, or cyclopropyl; and each $R_5$ is independently hydrogen, —$CH_3$, or —$CF_3$.

One embodiment provides a compound of Formula (I) or stereoisomers, tautomer, solvates or salts thereof, wherein said compound is: 2-(3,4-dimethoxyphenyl)-5-(1'-isopropyl-[1,4'-bipiperidin]-4-yl)-1-methyl-1H-benzo[d]imidazole (5); 2-(3,4-dimethoxyphenyl)-1-isopropyl-5-(1'-isopropyl-[1,4'-bipiperidin]-4-yl)-1H-benzo[d]imidazole (6); 1-(2,2-difluoroethyl)-2-(3,4-dimethoxyphenyl)-5-(1'-isopropyl-[1,4'-bipiperidin]-4-yl)-1H-benzo[d]imidazole (7); 2-(3,4-dimethoxyphenyl)-1-ethyl-5-(1'-isopropyl-[1,4'-bipiperidin]-4-yl)-1H-benzo[d]imidazole (9); 2-(3,4-dimethoxyphenyl)-5-(1'-isopropyl-[1,4'-bipiperidin]-4-yl)-6-(trifluoromethyl)-1H-benzo[d]imidazole (10); 2-(3,4-dimethoxyphenyl)-5-(1'-isobutyl-[1,4'-bipiperidin]-4-yl)-1-methyl-1H-benzo[d]imidazole (34); 5-(1'-cyclopropyl-[1,4'-bipiperidin]-4-yl)-2-(3,4-dimethoxyphenyl)-1-methyl-1H-benzo[d]imidazole (35); 2-(3,4-dimethoxyphenyl)-5-(1'-isobutyl-[1,4'-bipiperidin]-4-yl)-1-isopropyl-1H-benzo[d]imidazole (36); 5-(1'-cyclopropyl-[1,4'-bipiperidin]-4-yl)-2-(3,4-dimethoxyphenyl)-1-isopropyl-1H-benzo[d]imidazole (37); 1-(2,2-difluoroethyl)-2-(3,4-dimethoxyphenyl)-5-(1'-isobutyl-[1,4'-bipiperidin]-4-yl)-1H-benzo[d]imidazole (38); 5-(1'-cyclopropyl-[1,4'-bipiperidin]-4-yl)-1-(2,2-difluoroethyl)-2-(3,4-dimethoxyphenyl)-1H-benzo[d]imidazole (39); 2-(3,4-dimethoxyphenyl)-1-ethyl-5-(1'-isobutyl-[1,4'-bipiperidin]-4-yl)-1H-benzo[d]imidazole (41); 2-(3,4-dimethoxyphenyl)-5-(1'-isobutyl-[1,4'-bipiperidin]-4-yl)-6-(trifluoromethyl)-1H-benzo[d]imidazole (42); 4-fluoro-5-(1'-isopropyl-[1,4'-bipiperidin]-4-yl)-1-methyl-2-(4-(methylsulfonyl)phenyl)-1H-benzo[d]imidazole (88); 4-fluoro-5-(1-(8-isopropyl-8-azabicyclo[3.2.1]octan-3-yl) piperidin-4-yl)-1-methyl-2-(4-(methylsulfonyl)phenyl)-1H-benzo[d]imidazole (89-90); 7-fluoro-5-(1'-isopropyl-[1,4'-bipiperidin]-4-yl)-1-methyl-2-(4-(methylsulfonyl)phenyl)-1H-benzo[d]imidazole (91); 7-fluoro-5-(1-(8-isopropyl-8-azabicyclo[3.2.1]octan-3-yl) piperidin-4-yl)-1-methyl-2-(4-(methylsulfonyl)phenyl)-1H-benzo[d]imidazole (92-93); 6-fluoro-5-(1'-isopropyl-[1,4'-bipiperidin]-4-yl)-1-methyl-2-(4-(methylsulfonyl)phenyl)-1H-benzo[d]imidazole (99); 6-fluoro-5-(1-(8-isopropyl-8-azabicyclo[3.2.1]octan-3-yl) piperidin-4-yl)-1-methyl-2-(4-(methylsulfonyl)phenyl)-1H-benzo[d]imidazole (100-101); 4-fluoro-5-(1'-isobutyl-[1,4'-bipiperidin]-4-yl)-1-methyl-2-(4-(methylsulfonyl)phenyl)-1H-benzo[d]imidazole (184); 5-(1'-cyclopropyl-[1,4'-bipiperidin]-4-yl)-4-fluoro-1-methyl-2-(4-(methylsulfonyl) phenyl)-1H-benzo[d]imidazole (185); 4-fluoro-1-methyl-2-(4-(methylsulfonyl)phenyl)-5-(1'-(oxetan-3-yl)-[1,4'-bipiperidin]-4-yl)-1H-benzo[d]imidazole (186); 4-fluoro-1-methyl-2-(4-(methylsulfonyl)phenyl)-5-(1'-(tetrahydro-2H-pyran-4-yl)-[1,4'-bipiperidin]-4-yl)-1H-benzo[d]imidazole (187); 4-fluoro-5-(1'-(2-methoxyethyl)-[1,4'-bipiperidin]-4-yl)-1-methyl-2-(4-(methylsulfonyl) phenyl)-1H-benzo[d]imidazole (188); 4-fluoro-5-(1-(8-isobutyl-8-azabicyclo[3.2.1]octan-3-yl) piperidin-4-yl)-1-methyl-2-(4-(methylsulfonyl)phenyl)-1H-benzo[d]imidazole (189-190); 5-(1-(8-(cyclopropylmethyl)-8-azabicyclo[3.2.1]octan-3-yl) piperidin-4-yl)-4-fluoro-1-methyl-2-(4-(methylsulfonyl) phenyl)-1H-benzo[d]imidazole (191-192); 4-fluoro-1-methyl-2-(4-(methylsulfonyl)phenyl)-5-(1-(8-(oxetan-3-ylmethyl)-8-azabicyclo[3.2.1]octan-3-yl)piperidin-4-yl)-1H-benzo[d]imidazole (193-194); 4-fluoro-1-methyl-2-(4-(methylsulfonyl)phenyl)-5-(1-(8-(oxetan-3-yl)-8-azabicyclo[3.2.1]octan-3-yl)piperidin-4-yl)-1H-benzo[d]imidazole (195-196); 4-fluoro-1-methyl-2-(4-(methylsulfonyl)phenyl)-5-(1-(8-(tetrahydro-2H-pyran-4-yl)-8-azabicyclo[3.2.1]octan-3-yl)piperidin-4-yl)-1H-benzo[d]imidazole (197-198); 4-fluoro-5-(1-(8-(2-methoxyethyl)-8-azabicyclo[3.2.1]octan-3-yl)piperidin-4-yl)-1-methyl-2-(4-(methylsulfonyl)phenyl)-1H-benzo[d]imidazole (199-200); 7-fluoro-5-(1'-isobutyl-[1,4'-bipiperidin]-4-yl)-1-methyl-2-(4-(methylsulfonyl)phenyl)-1H-benzo[d]imidazole (201);

5-(1'-cyclopropyl-[1,4'-bipiperidin]-4-yl)-7-fluoro-1-methyl-2-(4-(methylsulfonyl)phenyl)-1H-benzo[d]imidazole (202); 5-(1'-(cyclopropylmethyl)-[1,4'-bipiperidin]-4-yl)-7-fluoro-1-methyl-2-(4-(methylsulfonyl)phenyl)-1H-benzo[d]imidazole (203); 7-fluoro-1-methyl-2-(4-(methylsulfonyl)phenyl)-5-(1'-(oxetan-3-ylmethyl)-[1,4'-bipiperidin]-4-yl)-1H-benzo[d]imidazole (204); 5-(1'-cyclobutyl-[1,4'-bipiperidin]-4-yl)-7-fluoro-1-methyl-2-(4-(methylsulfonyl)phenyl)-1H-benzo[d]imidazole (205); 7-fluoro-1-methyl-2-(4-(methylsulfonyl)phenyl)-5-(1'-(oxetan-3-yl)-[1,4'-bipiperidin]-4-yl)-1H-benzo[d]imidazole (206); 7-fluoro-1-methyl-2-(4-(methylsulfonyl)phenyl)-5-(1'-(tetrahydro-2H-pyran-4-yl)-[1,4'-bipiperidin]-4-yl)-1H-benzo[d]imidazole (207); 7-fluoro-5-(1'-(2-methoxyethyl)-[1,4'-bipiperidin]-4-yl)-1-methyl-2-(4-(methylsulfonyl) phenyl)-1H-benzo[d]imidazole (208); 7-fluoro-5-(1-(8-isobutyl-8-azabicyclo[3.2.1]octan-3-yl) piperidin-4-yl)-1-methyl-2-(4-(methylsulfonyl)phenyl)-1H-benzo[d]imidazole (209-210); 7-fluoro-1-methyl-2-(4-(methylsulfonyl)phenyl)-5-(1-(8-(tetrahydro-2H-pyran-4-yl)-8-azabicyclo[3.2.1]octan-3-yl) piperidin-4-yl)-1H-benzo[d]imidazole (211-212); 7-fluoro-1-methyl-2-(4-(methylsulfonyl)phenyl)-5-(1-(8-(oxetan-3-yl)-8-azabicyclo[3.2.1]octan-3-yl)piperidin-4-yl)-1H-benzo[d]imidazole (213-214); 5-(1-(8-cyclobutyl-8-azabicyclo[3.2.1]octan-3-yl)piperidin-4-yl)-7-fluoro-1-methyl-2-(4-(methylsulfonyl) phenyl)-1H-benzo[d]imidazole (215-216); 5-(1-(8-(cyclopropylmethyl)-8-azabicyclo[3.2.1]octan-3-yl) piperidin-4-yl)-7-fluoro-1-methyl-2-(4-(methylsulfonyl) phenyl)-1H-benzo[d]imidazole (217-218); 6-fluoro-5-(1'-isobutyl-[1,4'-bipiperidin]-4-yl)-1-methyl-2-(4-(methylsulfonyl)phenyl)-1H-benzo[d]imidazole (240); 5-(1'-cyclopropyl-[1,4'-bipiperidin]-4-yl)-6-fluoro-1-methyl-2-(4-(methylsulfonyl) phenyl)-1H-benzo[d]imidazole (241); 5-(1'-(cyclopropylmethyl)-[1,4'-bipiperidin]-4-yl)-6-fluoro-1-methyl-2-(4-(methylsulfonyl)phenyl)-1H-benzo[d] imidazole (242); 5-(1'-cyclobutyl-[1,4'-bipiperidin]-4-yl)-6-fluoro-1-methyl-2-(4-(methylsulfonyl)phenyl)-1H-benzo[d] imidazole (243); 6-fluoro-1-methyl-2-(4-(methylsulfonyl) phenyl)-5-(1'-(oxetan-3-yl)-[1,4'-bipiperidin]-4-yl)-1H-benzo[d]imidazole (244); 6-fluoro-1-methyl-2-(4-(methylsulfonyl) phenyl)-5-(1'-(tetrahydro-2H-pyran-4-yl)-[1,4'-bipiperidin]-4-yl)-1H-benzo[d]imidazole (245); 6-fluoro-5-(1'-(2-methoxyethyl)-[1,4'-bipiperidin]-4-yl)-1-methyl-2-(4-(methylsulfonyl)phenyl)-1H-benzo[d]imidazole (246); 6-fluoro-5-(1-(8-isobutyl-8-azabicyclo[3.2.1]octan-3-yl)piperidin-4-yl)-1-methyl-2-(4-(methylsulfonyl) phenyl)-1H-benzo[d]imidazole (247-248); 5-(1-(8-(cyclopropylmethyl)-8-azabicyclo[3.2.1]octan-3-yl) piperidin-4-yl)-6-fluoro-1-methyl-2-(4-(methylsulfonyl) phenyl)-1H-benzo[d]imidazole (249-250); 5-(1-(8-cyclobutyl-8-azabicyclo[3.2.1]octan-3-yl)piperidin-4-yl)-6-fluoro-1-methyl-2-(4-(methylsulfonyl)phenyl)-1H-benzo[d] imidazole (251-252); 6-fluoro-1-methyl-2-(4-(methylsulfonyl)phenyl)-5-(1-(8-(oxetan-3-yl)-8-azabicyclo [3.2.1]octan-3-yl)piperidin-4-yl)-1H-benzo[d]imidazole (253-254); 6-fluoro-1-methyl-2-(4-(methylsulfonyl)phenyl)-5-(1-(8-(tetrahydro-2H-pyran-4-yl)-8-azabicyclo [3.2.1]octan-3-yl)piperidin-4-yl)-1H-benzo[d]imidazole (255-256); or 6-fluoro-5-(1-(8-(2-methoxyethyl)-8-azabicyclo[3.2.1]octan-3-yl) piperidin-4-yl)-1-methyl-2-(4-(methylsulfonyl)phenyl)-1H-benzo[d]imidazole (257-258).

One embodiment provides a compound of Formula (I) or stereoisomers, tautomer, solvates or salts thereof, wherein said compound is: 2-(3,4-dimethoxyphenyl)-6-(1'-isopropyl-[1,4'-bipiperidin]-4-yl)-1-methyl-1H-benzo[d]imidazole (1); 2-(3,4-dimethoxyphenyl)-6-(1'-isopropyl-[1,4'-bipiperidin]-4-yl)-1H-benzo[d]imidazole (2); 2-(3,4-dimethoxyphenyl)-1-isopropyl-6-(1'-isopropyl-[1,4'-bipiperidin]-4-yl)-1H-benzo[d]imidazole (3); 1-(2,2-difluoroethyl)-2-(3,4-dimethoxyphenyl)-6-(1'-isopropyl-[1,4'-bipiperidin]-4-yl)-1H-benzo[d]imidazole (4); 2-(3,4-dimethoxyphenyl)-1-ethyl-6-(1'-isopropyl-[1,4'-bipiperidin]-4-yl)-1H-benzo[d]imidazole (8); 2-(3,4-dimethoxyphenyl)-6-(1'-isopropyl-[1,4'-bipiperidin]-4-yl)-4-methyl-1H-benzo[d]imidazole (11); 2-(3,4-dimethoxyphenyl)-6-(1-(2-isopropyl-2-azaspiro[3.3] heptan-6-yl)piperidin-4-yl)-4-methyl-1H-benzo[d] imidazole (12); 6-([1,4'-bipiperidin]-4-yl)-2-(3,4-dimethoxyphenyl)-4-methyl-1H-benzo[d]imidazole tris(2,2,2-trifluoroacetate) (13); 1-(4-(2-(3,4-dimethoxyphenyl)-4-methyl-1H-benzo[d]imidazol-6-yl)-[1,4'-bipiperidin]-1'-yl)-2-methylpropan-1-one (14); 2-(3,4-dimethoxyphenyl)-6-(1'-isobutyl-[1,4'-bipiperidin]-4-yl)-1,4-dimethyl-1H-benzo[d] imidazole tris(2,2,2-trifluoroacetate) (15); 2-(3,4-dimethoxyphenyl)-6-(1-(2-isopropyl-2-azaspiro[3.3] heptan-6-yl)piperidin-4-yl)-1,4-dimethyl-1H-benzo[d] imidazole tris(2,2,2-trifluoroacetate) (16); 2-(3,4-dimethoxyphenyl)-6-(1-(8-isobutyl-8-azabicyclo[3.2.1] octan-3-yl)piperidin-4-yl)-1,4-dimethyl-1H-benzo[d] imidazole (17-18); 2-(3,4-dimethoxyphenyl)-6-(1-(8-isobutyl-8-azabicyclo[3.2.1]octan-3-yl)piperidin-4-yl)-4-methyl-1H-benzo[d]imidazole (19-20); 2-(3,4-dimethoxyphenyl)-6-(8-(1-isopropylpiperidin-4-yl)-8-azabicyclo[3.2.1]octan-3-yl)-1,4-dimethyl-1H-benzo[d] imidazole (21); 6-(1'-isopropyl-[1,4'-bipiperidin]-4-yl)-1,4-dimethyl-2-(4-(methylsulfonyl)phenyl)-1H-benzo[d] imidazole (22); 2-(3-fluoro-4-methoxyphenyl)-6-(1'-isopropyl-[1,4'-bipiperidin]-4-yl)-1,4-dimethyl-1H-benzo [d]imidazole (23); 2-(3-fluoro-4-methoxyphenyl)-6-(1'-isopropyl-[1,4'-bipiperidin]-4-yl)-4-methyl-1H-benzo[d] imidazole (24); 2-(imidazo[1,2-a]pyridin-6-yl)-6-(1'-isobutyl-[1,4'-bipiperidin]-4-yl)-4-methyl-1H-benzo[d] imidazole (25); 2-(3,4-dimethoxyphenyl)-6-(1'-isobutyl-[1,4'-bipiperidin]-4-yl)-1-methyl-1H-benzo[d]imidazole (26); 6-(1'-cyclopropyl-[1,4'-bipiperidin]-4-yl)-2-(3,4-dimethoxyphenyl)-1-methyl-1H-benzo[d]imidazole (27); 2-(3,4-dimethoxyphenyl)-6-(1'-isobutyl-[1,4'-bipiperidin]-4-yl)-1H-benzo[d]imidazole (28); 6-(1'-cyclopropyl-[1,4'-bipiperidin]-4-yl)-2-(3,4-dimethoxyphenyl)-1H-benzo[d] imidazole (29); 2-(3,4-dimethoxyphenyl)-6-(1'-isobutyl-[1,4'-bipiperidin]-4-yl)-1-isopropyl-1H-benzo[d]imidazole (30); 6-(1'-cyclopropyl-[1,4'-bipiperidin]-4-yl)-2-(3,4-dimethoxyphenyl)-1-isopropyl-1H-benzo[d]imidazole (31); 1-(2,2-difluoroethyl)-2-(3,4-dimethoxyphenyl)-6-(1'-isobutyl-[1,4'-bipiperidin]-4-yl)-1H-benzo[d]imidazole (32); 6-(1'-cyclopropyl-[1,4'-bipiperidin]-4-yl)-1-(2,2-difluoroethyl)-2-(3,4-dimethoxyphenyl)-1H-benzo[d]imidazole (33); 2-(3,4-dimethoxyphenyl)-1-ethyl-6-(1'-isobutyl-[1,4'-bipiperidin]-4-yl)-1H-benzo[d]imidazole (40); 2-(3,4-dimethoxyphenyl)-6-(1'-isobutyl-[1,4'-bipiperidin]-4-yl)-4-methyl-1H-benzo[d]imidazole tris(2,2,2-trifluoroacetate) (43); 6-(1'-cyclopropyl-[1,4'-bipiperidin]-4-yl)-2-(3,4-dimethoxyphenyl)-4-methyl-1H-benzo[d]imidazole (44); 2-(3,4-dimethoxyphenyl)-6-(1'-isopropyl-[1,4'-bipiperidin]-4-yl)-1,4-dimethyl-1H-benzo[d]imidazole (45); 6-(1'-cyclopropyl-[1,4'-bipiperidin]-4-yl)-2-(3,4-dimethoxyphenyl)-1,4-dimethyl-1H-benzo[d]imidazole tris (2,2,2-trifluoroacetate) (46); 2-(3,4-dimethoxyphenyl)-6-(1-(2-isobutyl-2-azaspiro[3.3]heptan-6-yl)piperidin-4-yl)-1,4-dimethyl-1H-benzo[d]imidazole tris(2,2,2-trifluoroacetate) (47); 6-(1-(2-(cyclopropylmethyl)-2-azaspiro[3.3]heptan-6-yl) piperidin-4-yl)-2-(3,4-dimethoxyphenyl)-1,4-dimethyl-1H-benzo[d]imidazole (48); 6-(1-(2-cyclobutyl-2-azaspiro

[3.3]heptan-6-yl)piperidin-4-yl)-2-(3,4-dimethoxyphenyl)-1,4-dimethyl-1H-benzo[d]imidazole (49); 2-(3,4-dimethoxyphenyl)-6-(8-(1-isobutylpiperidin-4-yl)-8-azabicyclo[3.2.1]octan-3-yl)-1,4-dimethyl-1H-benzo[d]imidazole (50); 6-(8-(1-cyclopropylpiperidin-4-yl)-8-azabicyclo[3.2.1]octan-3-yl)-2-(3,4-dimethoxyphenyl)-1,4-dimethyl-1H-benzo[d]imidazole (51); 6-(1'-isobutyl-[1,4'-bipiperidin]-4-yl)-1,4-dimethyl-2-(4-(methylsulfonyl)phenyl)-1H-benzo[d]imidazole (52); 6-(1'-cyclopropyl-[1,4'-bipiperidin]-4-yl)-1,4-dimethyl-2-(4-(methylsulfonyl)phenyl)-1H-benzo[d]imidazole (53); 2-(3-fluoro-4-methoxyphenyl)-6-(1'-isobutyl-[1,4'-bipiperidin]-4-yl)-1,4-dimethyl-1H-benzo[d]imidazole (54); 6-(1'-cyclopropyl-[1,4'-bipiperidin]-4-yl)-2-(3-fluoro-4-methoxyphenyl)-1,4-dimethyl-1H-benzo[d]imidazole (55); 2-(3-fluoro-4-methoxyphenyl)-6-(1'-isobutyl-[1,4'-bipiperidin]-4-yl)-4-methyl-1H-benzo[d]imidazole (56); 6-(1'-cyclopropyl-[1,4'-bipiperidin]-4-yl)-2-(3-fluoro-4-methoxyphenyl)-4-methyl-1H-benzo[d]imidazole (57); 6-(1'-isobutyl-[1,4'-bipiperidin]-4-yl)-4-methyl-2-(4-(methylsulfonyl)phenyl)-1H-benzo[d]imidazole tris(2,2,2-trifluoroacetate) (58); 4-(6-(1'-isobutyl-[1,4'-bipiperidin]-4-yl)-4-methyl-1H-benzo[d]imidazol-2-yl)quinoline (59); 2-(2,6-dimethylpyridin-4-yl)-6-(1'-isobutyl-[1,4'-bipiperidin]-4-yl)-4-methyl-1H-benzo[d]imidazole (60); 6-(6-(1'-isobutyl-[1,4'-bipiperidin]-4-yl)-4-methyl-1H-benzo[d]imidazol-2-yl)-8-methoxy-[1,2,4]triazolo[1,5-a]pyridine tris(2,2,2-trifluoroacetate) (61); 2-(2,3-dihydrobenzo[b][1,4]dioxin-6-yl)-6-(1'-isobutyl-[1,4'-bipiperidin]-4-yl)-4-methyl-1H-benzo[d]imidazole (62); 6-(1'-isobutyl-[1,4'-bipiperidin]-4-yl)-4-methyl-2-(4-(trifluoromethoxy)phenyl)-1H-benzo[d]imidazole (63); 2-(3-chloro-4-methoxyphenyl)-6-(1'-isobutyl-[1,4'-bipiperidin]-4-yl)-4-methyl-1H-benzo[d]imidazole (64); 2-(2,2-difluorobenzo[d][1,3]dioxol-5-yl)-6-(1'-isobutyl-[1,4'-bipiperidin]-4-yl)-4-methyl-1H-benzo[d]imidazole tris(2,2,2-trifluoroacetate) (65); 2-(3-fluoro-4-(methylsulfonyl)phenyl)-6-(1'-isobutyl-[1,4'-bipiperidin]-4-yl)-4-methyl-1H-benzo[d]imidazole (66); 2-(3-bromo-4-(methylsulfonyl)phenyl)-6-(1'-isobutyl-[1,4'-bipiperidin]-4-yl)-4-methyl-1H-benzo[d]imidazole (67); 2-(4-cyclopropylphenyl)-6-(1'-isobutyl-[1,4'-bipiperidin]-4-yl)-4-methyl-1H-benzo[d]imidazole (68); 2-(4-(difluoromethoxy)-3-fluorophenyl)-6-(1'-isobutyl-[1,4'-bipiperidin]-4-yl)-4-methyl-1H-benzo[d]imidazole tris(2,2,2-trifluoroacetate) (69); 2-(6-(1'-isobutyl-[1,4'-bipiperidin]-4-yl)-4-methyl-1H-benzo[d]imidazol-2-yl)benzo[d]thiazole tris(2,2,2-trifluoroacetate) (70); 4-(6-(1'-isobutyl-[1,4'-bipiperidin]-4-yl)-4-methyl-1H-benzo[d]imidazol-2-yl)-3,5-dimethylisoxazole (71); 5-(6-(1'-isobutyl-[1,4'-bipiperidin]-4-yl)-4-methyl-1H-benzo[d]imidazol-2-yl)quinoline tris(2,2,2-trifluoroacetate) (72); 2-(3-chloro-4-(trifluoromethoxy)phenyl)-6-(1'-isobutyl-[1,4'-bipiperidin]-4-yl)-4-methyl-1H-benzo[d]imidazole tris(2,2,2-trifluoroacetate) (73); 6-(6-(1'-isobutyl-[1,4'-bipiperidin]-4-yl)-4-methyl-1H-benzo[d]imidazol-2-yl)isoquinoline (74); 6-(1'-isobutyl-[1,4'-bipiperidin]-4-yl)-4-methyl-2-(4-(phenylsulfonyl)phenyl)-1H-benzo[d]imidazole tris(2,2,2-trifluoroacetate) (75); 2-(3-(difluoromethoxy)phenyl)-6-(1'-isobutyl-[1,4'-bipiperidin]-4-yl)-4-methyl-1H-benzo[d]imidazole (76); 7-(6-(1'-isobutyl-[1,4'-bipiperidin]-4-yl)-4-methyl-1H-benzo[d]imidazol-2-yl)benzo[d]thiazole (77); 2-(4-(difluoromethoxy)phenyl)-6-(1'-isobutyl-[1,4'-bipiperidin]-4-yl)-4-methyl-1H-benzo[d]imidazole (78); 2-(6-(1'-isobutyl-[1,4'-bipiperidin]-4-yl)-4-methyl-1H-benzo[d]imidazol-2-yl)thiazole (79); 6-(1'-isobutyl-[1,4'-bipiperidin]-4-yl)-4-methyl-2-(2-(trifluoromethoxy)phenyl)-1H-benzo[d]imidazole tris(2,2,2-trifluoroacetate) (80); 6-(1'-isobutyl-[1,4'-bipiperidin]-4-yl)-4-methyl-2-(1H-pyrrolo[2,3-b]pyridin-5-yl)-1H-benzo[d]imidazole (81); 8-(6-(1'-isobutyl-[1,4'-bipiperidin]-4-yl)-4-methyl-1H-benzo[d]imidazol-2-yl)quinoline (82); 2-(3,4-dimethoxyphenyl)-4-fluoro-6-(1'-isopropyl-[1,4'-bipiperidin]-4-yl)-1H-benzo[d]imidazole (83); 6-(1-(8-isopropyl-8-azabicyclo[3.2.1]octan-3-yl)piperidin-4-yl)-1,4-dimethyl-2-(4-(methylsulfonyl)phenyl)-1H-benzo[d]imidazole (84-85); 6-(4-(4-isopropylpiperazin-1-yl)phenyl)-1,4-dimethyl-2-(4-(methylsulfonyl)phenyl)-1H-benzo[d]imidazole (86); 7-fluoro-6-(1'-isopropyl-[1,4'-bipiperidin]-4-yl)-2-(4-(methylsulfonyl)phenyl)-1H-benzo[d]imidazole (87); 7-fluoro-6-(1-(8-isopropyl-8-azabicyclo[3.2.1]octan-3-yl)piperidin-4-yl)-2-(4-(methylsulfonyl)phenyl)-1H-benzo[d]imidazole (94-95); 5-fluoro-6-(1'-isopropyl-[1,4'-bipiperidin]-4-yl)-1-methyl-2-(4-(methylsulfonyl)phenyl)-1H-benzo[d]imidazole (96); 5-fluoro-6-(1-(8-isopropyl-8-azabicyclo[3.2.1]octan-3-yl)piperidin-4-yl)-1-methyl-2-(4-(methylsulfonyl) phenyl)-1H-benzo[d]imidazole (97-98); 7-fluoro-6-(1'-isopropyl-[1,4'-bipiperidin]-4-yl)-1-methyl-2-(4-(methylsulfonyl)phenyl)-1H-benzo[d]imidazole (102); 7-fluoro-6-(1-(8-isopropyl-8-azabicyclo[3.2.1]octan-3-yl)piperidin-4-yl)-1-methyl-2-(4-(methylsulfonyl) phenyl)-1H-benzo[d]imidazole (103-104); 4-fluoro-6-(1'-isopropyl-[1,4'-bipiperidin]-4-yl)-1-methyl-2-(4-(methylsulfonyl)phenyl)-1H-benzo[d]imidazole (105); 4-fluoro-6-(1-(8-isopropyl-8-azabicyclo[3.2.1]octan-3-yl)piperidin-4-yl)-1-methyl-2-(4-(methylsulfonyl)phenyl)-1H-benzo[d]imidazole (106-107); 4-fluoro-1-methyl-2-(4-(methylsulfonyl)phenyl)-6-(1-(1-(oxetan-3-yl)azepan-4-yl)piperidin-4-yl)-1H-benzo[d]imidazole (108-109); 6-(1-(1-cyclobutylazepan-4-yl)piperidin-4-yl)-1,4-dimethyl-2-(4-(methylsulfonyl)phenyl)-1H-benzo[d]imidazole (110-111); 4-(6-(1'-isopropyl-[1,4'-bipiperidin]-4-yl)-1,4-dimethyl-1H-benzo[d]imidazol-2-yl)benzenesulfonamide (112); 7-fluoro-6-(1-(1-isopropylazepan-4-yl)piperidin-4-yl)-1-methyl-2-(4-(methylsulfonyl)phenyl)-1H-benzo[d]imidazole (113-114); 1-cyclopropyl-4-fluoro-6-(1'-isopropyl-[1,4'-bipiperidin]-4-yl)-2-(4-(methylsulfonyl)phenyl)-1H-benzo[d]imidazole (115); 1-cyclopropyl-4-fluoro-6-(1-(8-isopropyl-8-azabicyclo[3.2.1]octan-3-yl)piperidin-4-yl)-2-(4-(methylsulfonyl)phenyl)-1H-benzo[d]imidazole (116-117); 6-(1-(8-isobutyl-8-azabicyclo[3.2.1]octan-3-yl)piperidin-4-yl)-1,4-dimethyl-2-(4-(methylsulfonyl)phenyl)-1H-benzo[d]imidazole (118); 6-(1'-isopropyl-[1,4'-bipiperidin]-4-yl)-1,7-dimethyl-2-(4-(methylsulfonyl)phenyl)-1H-benzo[d]imidazole (119); 6-(1'-isopropyl-[1,4'-bipiperidin]-4-yl)-1,5-dimethyl-2-(4-(methylsulfonyl)phenyl)-1H-benzo[d]imidazole (120); 6-(1-(8-isobutyl-8-azabicyclo[3.2.1]octan-3-yl)piperidin-4-yl)-4-methyl-2-(4-(methylsulfonyl)phenyl)-1H-benzo[d]imidazole (121); 2-(3-fluoro-4-(methylsulfonyl)phenyl)-6-(1'-isopropyl-[1,4'-bipiperidin]-4-yl)-1,4-dimethyl-1H-benzo[d]imidazole (122); 6-(1-(8-cyclobutyl-8-azabicyclo[3.2.1]octan-3-yl)piperidin-4-yl)-2-(3-fluoro-4-(methylsulfonyl)phenyl)-1,4-dimethyl-1H-benzo[d]imidazole (123-124); 6-(6-(1'-isopropyl-[1,4'-bipiperidin]-4-yl)-1,4-dimethyl-1H-benzo[d]imidazol-2-yl)-8-methoxy-[1,2,4]triazolo[1,5-a]pyridine (125); 6-(6-(1-(8-isobutyl-8-azabicyclo[3.2.1]octan-3-yl)piperidin-4-yl)-1,4-dimethyl-1H-benzo[d]imidazol-2-yl)-8-methoxy-[1,2,4]triazolo[1,5-a]pyridine (126); 2-(3,4-dimethoxyphenyl)-4-fluoro-6-(1'-isobutyl-[1,4'-bipiperidin]-4-yl)-1H-benzo[d]imidazole (127); 6-(1'-cyclopropyl-[1,4'-bipiperidin]-4-yl)-2-(3,4-dimethoxyphenyl)-4-fluoro-1H-benzo[d]imidazole (128); 2-(3,4-dimethoxyphenyl)-5-fluoro-6-(1'-isopropyl-[1,4'-bipiperidin]-4-yl)-1H-benzo[d]imidazole (129); 2-(3,4-dimethoxyphenyl)-5-fluoro-6-(1'-isobutyl-[1,4'-bipiperidin]-4-yl)-1H-benzo[d]imidazole (130); 6-(1'-cyclopropyl-[1,4'-bipiperidin]-4-yl)-2-(3,4-dimethoxyphenyl)-5-fluoro-1H-benzo[d]imidazole (131); 2-(3,4-dimethoxyphenyl)-7-fluoro-6-(1'-isopropyl-[1,4'-bipiperidin]-4-yl)-1H-benzo[d]imidazole (132); 2-(3,4-dimethoxyphenyl)-7-fluoro-6-(1'-isobutyl-[1,4'-bipiperidin]-4-yl)-1H-benzo[d]imidazole (133); 6-(1-(1-isopropylazepan-4-yl)piperidin-4-yl)-1,4-dimethyl-2-(4-(methylsulfonyl)phenyl)-1H-benzo[d]imidazole (134); 6-(1-(1-cyclobutylazepan-4-yl)piperidin-4-yl)-1,4-dimethyl-2-(4-(methylsulfonyl)phenyl)-1H-benzo[d]imidazole (135); 6-(1-(1-isobutylazepan-4-yl)piperidin-4-yl)-1,4-dimethyl-2-(4-(methylsulfonyl) phenyl)-1H-benzo[d]imidazole (136); 6-(1-(1-(cyclopropylmethyl)azepan-4-yl)piperidin-4-yl)-1,4-dimethyl-2-(4-(methylsulfonyl)phenyl)-1H-benzo[d]imidazole (137); 6-(1-(1-(cyclobutylmethyl)azepan-4-yl)piperidin-4-yl)-1,4-dimethyl-2-(4-(methylsulfonyl) phenyl)-1H-benzo[d]imidazole (138); 6-(1-(2-isopropyl-2-azaspiro[3.3]heptan-6-yl)piperidin-4-yl)-1,4-dimethyl-2-(4-(methylsulfonyl)phenyl)-1H-benzo[d]imidazole (139); 6-(1-(2-cyclobutyl-2-azaspiro[3.3]heptan-6-yl)piperidin-4-yl)-1,4-dimethyl-2-(4-(methylsulfonyl)phenyl)-1H-benzo[d]imidazole (140); 6-(1-(2-isobutyl-2-azaspiro[3.3]heptan-6-yl)piperidin-4-yl)-1,4-dimethyl-2-(4-(methylsulfonyl) phenyl)-1H-benzo[d]imidazole (141); 6-(1-(2-(cyclopropylmethyl)-2-azaspiro[3.3]heptan-6-yl) piperidin-4-yl)-1,4-dimethyl-2-(4-(methylsulfonyl)phenyl)-1H-benzo[d]imidazole (142); 6-(1-(2-(cyclobutylmethyl)-2-azaspiro[3.3]heptan-6-yl)piperidin-4-yl)-1,4-dimethyl-2-(4-(methylsulfonyl)phenyl)-1H-benzo[d]imidazole (143); 2-(3,4-dimethoxyphenyl)-6-(1-(8-isopropyl-8-azabicyclo[3.2.1]octan-3-yl)piperidin-4-yl)-1,4-dimethyl-1H-benzo[d]imidazole (144-145); 6-(1-(8-cyclobutyl-8-azabicyclo[3.2.1]octan-3-yl) piperidin-4-yl)-2-(3,4-dimethoxyphenyl)-1,4-dimethyl-1H-benzo[d]imidazole (146-147); 6-(1-(8-(cyclopropylmethyl)-8-azabicyclo[3.2.1]octan-3-yl) piperidin-4-yl)-2-(3,4-dimethoxyphenyl)-1,4-dimethyl-1H-benzo[d]imidazole (148-149); 6-(1-(8-(cyclobutylmethyl)-8-azabicyclo[3.2.1]octan-3-yl)piperidin-4-yl)-2-(3,4-dimethoxyphenyl)-1,4-dimethyl-1H-benzo[d]imidazole (150-151); 6-(1-(8-cyclobutyl-8-azabicyclo[3.2.1]octan-3-yl)piperidin-4-yl)-1,4-dimethyl-2-(4-(methylsulfonyl)phenyl)-1H-benzo[d]imidazole (152-153); 6-(1-(8-(cyclopropylmethyl)-8-azabicyclo[3.2.1]octan-3-yl)piperidin-4-yl)-1,4-dimethyl-2-(4-(methylsulfonyl)phenyl)-1H-benzo[d]imidazole (154-155); 6-(1-(8-(cyclobutylmethyl)-8-azabicyclo[3.2.1]octan-3-yl)piperidin-4-yl)-1,4-dimethyl-2-(4-(methylsulfonyl)phenyl)-1H-benzo[d]imidazole (156-157); 1,4-dimethyl-2-(4-(methylsulfonyl)phenyl)-6-(1-(8-(oxetan-3-yl)-8-azabicyclo[3.2.1]octan-3-yl) piperidin-4-yl)-1H-benzo[d]imidazole (158-159); 1,4-dimethyl-2-(4-(methylsulfonyl) phenyl)-6-(1-(8-(tetrahydro-2H-pyran-4-yl)-8-azabicyclo[3.2.1]octan-3-yl)piperidin-4-yl)-1H-benzo[d]imidazole (160-161); 6-(1-(8-(2-methoxyethyl)-8-azabicyclo[3.2.1]octan-3-yl) piperidin-4-yl)-1,4-dimethyl-2-(4-(methylsulfonyl)phenyl)-1H-benzo[d]imidazole (162-163); 2-(3,4-dimethoxyphenyl)-1,4-dimethyl-6-(1-(8-(oxetan-3-yl)-8-azabicyclo[3.2.1]octan-3-yl)piperidin-4-yl)-1H-benzo[d]imidazole (164-165); 2-(3,4-dimethoxyphenyl)-1,4-dimethyl-6-(1-(8-(tetrahydro-2H-pyran-4-yl)-8-azabicyclo[3.2.1]octan-3-yl)piperidin-4-yl)-1H-benzo[d]imidazole (166-167); 2-(3,4-dimethoxyphenyl)-6-(1-(8-(2-methoxyethyl)-8-azabicyclo[3.2.1]octan-3-yl)piperidin-4-yl)-1,4-dimethyl-1H-benzo[d]imidazole (168-169); 6-(4-(4-isobutylpiperazin-1-yl) phenyl)-1,4-dimethyl-2-(4-(methylsulfonyl)phenyl)-1H-benzo[d]imidazole (170); 6-(4-(4-(cyclopropylmethyl)piperazin-1-yl)phenyl)-1,4-dimethyl-2-(4-(methylsulfonyl) phenyl)-1H-benzo[d]imidazole (171); 6-(4-(4-(cyclobutylmethyl)piperazin-1-yl)phenyl)-1,4-dimethyl-2-(4-(methylsulfonyl)phenyl)-1H-benzo[d]imidazole (172); 6-(4-(4-(2-methoxyethyl)piperazin-1-yl)phenyl)-1,4-dimethyl-2-(4-(methylsulfonyl)phenyl)-1H-benzo[d]imidazole (173); 6-(4-(4-cyclobutylpiperazin-1-yl)phenyl)-1,4-dimethyl-2-(4-(methylsulfonyl)phenyl)-1H-benzo[d]imidazole (174); 6-(1'-cyclopropyl-[1,4'-bipiperidin]-4-yl)-2-(3,4-dimethoxyphenyl)-7-fluoro-1H-benzo[d]imidazole (175); 1,4-dimethyl-2-(4-(methylsulfonyl)phenyl)-6-(4-(4-(tetrahydro-2H-pyran-4-yl)piperazin-1-yl)phenyl)-1H-benzo[d]imidazole (176); 7-fluoro-6-(1'-isobutyl-[1,4'-bipiperidin]-4-yl)-2-(4-(methylsulfonyl)phenyl)-1H-benzo[d]imidazole (177); 6-(1'-cyclopropyl-[1,4'-bipiperidin]-4-yl)-7-fluoro-2-(4-(methylsulfonyl)phenyl)-1H-benzo[d]imidazole (178); 6-(1'-(cyclopropylmethyl)-[1,4'-bipiperidin]-4-yl)-7-fluoro-2-(4-(methylsulfonyl)phenyl)-1H-benzo[d]imidazole (179); 6-(1'-cyclobutyl-[1,4'-bipiperidin]-4-yl)-7-fluoro-2-(4-(methylsulfonyl)phenyl)-1H-benzo[d]imidazole (180); 7-fluoro-2-(4-(methylsulfonyl) phenyl)-6-(1'-(oxetan-3-yl)-[1,4'-bipiperidin]-4-yl)-1H-benzo[d]imidazole (181); 7-fluoro-2-(4-(methylsulfonyl)phenyl)-6-(1'-(tetrahydro-2H-pyran-4-yl)-[1,4'-bipiperidin]-4-yl)-1H-benzo[d]imidazole (182); 7-fluoro-2-(4-(methylsulfonyl)phenyl)-6-(1'-(oxetan-3-ylmethyl)-[1,4'-bipiperidin]-4-yl)-1H-benzo[d]imidazole (183); 7-fluoro-6-(1-(8-isobutyl-8-azabicyclo[3.2.1]octan-3-yl)piperidin-4-yl)-2-(4-(methylsulfonyl) phenyl)-1H-benzo[d]imidazole (219-220); 5-fluoro-6-(1'-isobutyl-[1,4'-bipiperidin]-4-yl)-1-methyl-2-(4-(methylsulfonyl)phenyl)-1H-benzo[d]imidazole (221); 6-(1'-cyclopropyl-[1,4'-bipiperidin]-4-yl)-5-fluoro-1-methyl-2-(4-(methylsulfonyl)phenyl)-1H-benzo[d]imidazole (222); 6-(1'-cyclobutyl-[1,4'-bipiperidin]-4-yl)-5-fluoro-1-methyl-2-(4-(methylsulfonyl) phenyl)-1H-benzo[d]imidazole (223); 6-(1'-(cyclopropylmethyl)-[1,4'-bipiperidin]-4-yl)-5-fluoro-1-methyl-2-(4-(methylsulfonyl) phenyl)-1H-benzo[d]imidazole (224); 5-fluoro-1-methyl-2-(4-(methylsulfonyl)phenyl)-6-(1'-(oxetan-3-yl)-[1,4'-bipiperidin]-4-yl)-1H-benzo[d]imidazole (225); 5-fluoro-1-methyl-2-(4-(methylsulfonyl)phenyl)-6-(1'-(tetrahydro-2H-pyran-4-yl)-[1,4'-bipiperidin]-4-yl)-1H-benzo[d]imidazole (226); 5-fluoro-6-(1'-(2-methoxyethyl)-[1,4'-bipiperidin]-4-yl)-1-methyl-2-(4-(methylsulfonyl) phenyl)-1H-benzo[d]imidazole (227); 5-fluoro-6-(1-(8-isobutyl-8-azabicyclo[3.2.1]octan-3-yl) piperidin-4-yl)-1-methyl-2-(4-(methylsulfonyl)phenyl)-1H-benzo[d]imidazole (228-229); 6-(1-(8-(cyclopropylmethyl)-8-azabicyclo[3.2.1]octan-3-yl) piperidin-4-yl)-5-fluoro-1-methyl-2-(4-(methylsulfonyl) phenyl)-1H-benzo[d]imidazole (230-231); 6-(1-(8-cyclobutyl-8-azabicyclo[3.2.1]octan-3-yl)piperidin-4-yl)-5-fluoro-1-methyl-2-(4-(methylsulfonyl)phenyl)-1H-benzo[d]imidazole (232-233); 5-fluoro-1-methyl-2-(4-(methylsulfonyl)phenyl)-6-(1-(8-(oxetan-3-yl)-8-azabicyclo[3.2.1]octan-3-yl)piperidin-4-yl)-1H-benzo[d]imidazole (234-235); 5-fluoro-1-methyl-2-(4-(methylsulfonyl)phenyl)-6-(1-(8-(tetrahydro-2H-pyran-4-yl)-8-azabicyclo[3.2.1]octan-3-yl) piperidin-4-yl)-1H-benzo[d]imidazole (236-237); 5-fluoro-6-(1-(8-(2-methoxyethyl)-8-azabicyclo[3.2.1]octan-3-yl)piperidin-4-yl)-1-methyl-2-(4-(methylsulfonyl)phenyl)-1H-benzo[d]imidazole (238-239); 7-fluoro-6-(1'-isobutyl-[1,4'-bipiperidin]-4-yl)-1-methyl-2-(4-(methylsulfonyl)phenyl)-1H-benzo[d]imidazole (259); 6-(1'-cyclopropyl-[1,4'-bipiperidin]-4-yl)-7-fluoro-1-methyl-2-(4-(methylsulfonyl)phenyl)-1H-benzo[d]imidazole (260); 6-(1'-(cyclopropylmethyl)-[1,4'-bipiperidin]-4-yl)-7-fluoro-1-methyl-2-(4-(methylsulfonyl)phenyl)-1H-benzo[d]imidazole (261); 6-(1'-cyclobutyl-[1,4'-bipiperidin]-4-yl)-7-fluoro-1-methyl-2-(4-(methylsulfonyl)

phenyl)-1H-benzo[d]imidazole (262); 7-fluoro-1-methyl-2-(4-(methylsulfonyl)phenyl)-6-(1'-(oxetan-3-yl)-[1,4'-bipiperidin]-4-yl)-1H-benzo[d]imidazole (263); 7-fluoro-1-methyl-2-(4-(methylsulfonyl)phenyl)-6-(1'-(tetrahydro-2H-pyran-4-yl)-[1,4'-bipiperidin]-4-yl)-1H-benzo[d]imidazole (264); 7-fluoro-6-(1'-(2-methoxyethyl)-[1,4'-bipiperidin]-4-yl)-1-methyl-2-(4-(methylsulfonyl) phenyl)-1H-benzo[d]imidazole (265); 7-fluoro-6-(1-(8-isobutyl-8-azabicyclo[3.2.1]octan-3-yl) piperidin-4-yl)-1-methyl-2-(4-(methylsulfonyl)phenyl)-1H-benzo[d]imidazole (266-267); 6-(1-(8-(cyclopropylmethyl)-8-azabicyclo[3.2.1]octan-3-yl) piperidin-4-yl)-7-fluoro-1-methyl-2-(4-(methylsulfonyl) phenyl)-1H-benzo[d]imidazole (268-269); 6-(1-(8-cyclobutyl-8-azabicyclo[3.2.1]octan-3-yl)piperidin-4-yl)-7-fluoro-1-methyl-2-(4-(methylsulfonyl)phenyl)-1H-benzo[d] imidazole (270-271); 7-fluoro-1-methyl-2-(4-(methylsulfonyl)phenyl)-6-(1-(8-(oxetan-3-yl)-8-azabicyclo[3.2.1]octan-3-yl)piperidin-4-yl)-1H-benzo[d]imidazole (272-273); 7-fluoro-1-methyl-2-(4-(methylsulfonyl)phenyl)-6-(1-(8-(tetrahydro-2H-pyran-4-yl)-8-azabicyclo[3.2.1]octan-3-yl) piperidin-4-yl)-1H-benzo[d]imidazole (274-275); 7-fluoro-6-(1-(8-(2-methoxyethyl)-8-azabicyclo[3.2.1]octan-3-yl)piperidin-4-yl)-1-methyl-2-(4-(methylsulfonyl)phenyl)-1H-benzo[d]imidazole (276-277); 4-fluoro-6-(1'-isobutyl-[1,4'-bipiperidin]-4-yl)-1-methyl-2-(4-(methylsulfonyl)phenyl)-1H-benzo[d]imidazole (278); 4-fluoro-1-methyl-2-(4-(methylsulfonyl)phenyl)-6-(1'-(oxetan-3-yl)-[1,4'-bipiperidin]-4-yl)-1H-benzo[d]imidazole (279); 4-fluoro-1-methyl-2-(4-(methylsulfonyl)phenyl)-6-(1'-(tetrahydro-2H-pyran-4-yl)-[1,4'-bipiperidin]-4-yl)-1H-benzo[d]imidazole (280); 4-fluoro-6-(1'-(2-methoxyethyl)-[1,4'-bipiperidin]-4-yl)-1-methyl-2-(4-(methylsulfonyl) phenyl)-1H-benzo[d]imidazole (281); 6-(1-(8-(cyclopropylmethyl)-8-azabicyclo[3.2.1]octan-3-yl) piperidin-4-yl)-4-fluoro-1-methyl-2-(4-(methylsulfonyl) phenyl)-1H-benzo[d]imidazole (282-283); 4-fluoro-6-(1-(8-isobutyl-8-azabicyclo[3.2.1]octan-3-yl) piperidin-4-yl)-1-methyl-2-(4-(methylsulfonyl)phenyl)-1H-benzo[d]imidazole (284-285); 4-fluoro-1-methyl-2-(4-(methylsulfonyl) phenyl)-6-(1-(8-(oxetan-3-yl)-8-azabicyclo[3.2.1]octan-3-yl)piperidin-4-yl)-1H-benzo[d]imidazole (286-287); 4-fluoro-1-methyl-2-(4-(methylsulfonyl)phenyl)-6-(1-(8-(tetrahydro-2H-pyran-4-yl)-8-azabicyclo[3.2.1]octan-3-yl) piperidin-4-yl)-1H-benzo[d]imidazole (288-289); 4-fluoro-6-(1-(8-(2-methoxyethyl)-8-azabicyclo[3.2.1]octan-3-yl) piperidin-4-yl)-1-methyl-2-(4-(methylsulfonyl)phenyl)-1H-benzo[d]imidazole (290-291); 6-(1-(8-cyclobutyl-8-azabicyclo[3.2.1]octan-3-yl)piperidin-4-yl)-4-fluoro-1-methyl-2-(4-(methylsulfonyl) phenyl)-1H-benzo[d]imidazole (292-293); 4-fluoro-6-(1-(1-isopropylazepan-4-yl) piperidin-4-yl)-1-methyl-2-(4-(methylsulfonyl)phenyl)-1H-benzo[d] imidazole (294-295); 4-fluoro-6-(1-(1-isobutylazepan-4-yl) piperidin-4-yl)-1-methyl-2-(4-(methylsulfonyl) phenyl)-1H-benzo[d]imidazole (296-297); 6-(1-(1-(cyclopropylmethyl)azepan-4-yl) piperidin-4-yl)-4-fluoro-1-methyl-2-(4-(methylsulfonyl)phenyl)-1H-benzo[d] imidazole (298-299); 4-fluoro-1-methyl-2-(4-(methylsulfonyl)phenyl)-6-(1-(1-(tetrahydro-2H-pyran-4-yl)azepan-4-yl)piperidin-4-yl)-1H-benzo[d]imidazole (300-301); 4-fluoro-6-(1-(1-(2-methoxyethyl)azepan-4-yl) piperidin-4-yl)-1-methyl-2-(4-(methylsulfonyl)phenyl)-1H-benzo[d]imidazole (302-303); 1,4-dimethyl-2-(4-(methylsulfonyl)phenyl)-6-(1-(1-(oxetan-3-yl) azepan-4-yl) piperidin-4-yl)-1H-benzo[d]imidazole (304-305); 1,4-dimethyl-2-(4-(methylsulfonyl)phenyl)-6-(1-(1-(tetrahydro-2H-pyran-4-yl)azepan-4-yl)piperidin-4-yl)-1H-benzo[d] imidazole (306-307); 6-(1-(1-(2-methoxyethyl)azepan-4-yl) piperidin-4-yl)-1,4-dimethyl-2-(4-(methylsulfonyl)phenyl)-1H-benzo[d]imidazole (308-309); 7-fluoro-6-(1-(1-isobutylazepan-4-yl)piperidin-4-yl)-1-methyl-2-(4-(methylsulfonyl) phenyl)-1H-benzo[d]imidazole (310-311); 6-(1-(1-cyclobutylazepan-4-yl)piperidin-4-yl)-7-fluoro-1-methyl-2-(4-(methylsulfonyl)phenyl)-1H-benzo[d]imidazole (312-313); 7-fluoro-1-methyl-2-(4-(methylsulfonyl) phenyl)-6-(1-(1-(oxetan-3-yl)azepan-4-yl) piperidin-4-yl)-1H-benzo[d]imidazole (314-315); 7-fluoro-1-methyl-2-(4-(methylsulfonyl)phenyl)-6-(1-(1-(tetrahydro-2H-pyran-4-yl)azepan-4-yl)piperidin-4-yl)-1H-benzo[d]imidazole (316-317); 1,4-dimethyl-2-(4-(methylsulfonyl)phenyl)-6-(1'-phenyl-[1,4'-bipiperidin]-4-yl)-1H-benzo[d]imidazole (318); 1-cyclopropyl-4-fluoro-6-(1'-isobutyl-[1,4'-bipiperidin]-4-yl)-2-(4-(methylsulfonyl)phenyl)-1H-benzo[d]imidazole (319); 1-cyclopropyl-6-(1'-(cyclopropylmethyl)-[1,4'-bipiperidin]-4-yl)-4-fluoro-2-(4-(methylsulfonyl) phenyl)-1H-benzo[d]imidazole (320); 1-cyclopropyl-4-fluoro-2-(4-(methylsulfonyl)phenyl)-6-(1'-(tetrahydro-2H-pyran-4-yl)-[1,4'-bipiperidin]-4-yl)-1H-benzo[d]imidazole (321); 1-cyclopropyl-4-fluoro-6-(1-(8-isobutyl-8-azabicyclo[3.2.1]octan-3-yl)piperidin-4-yl)-2-(4-(methylsulfonyl) phenyl)-1H-benzo[d]imidazole (322-323); 1-cyclopropyl-6-(1-(8-(cyclopropylmethyl)-8-azabicyclo[3.2.1]octan-3-yl) piperidin-4-yl)-4-fluoro-2-(4-(methylsulfonyl)phenyl)-1H-benzo[d]imidazole (324-325); 6-(1-(8-cyclobutyl-8-azabicyclo[3.2.1]octan-3-yl) piperidin-4-yl)-1-cyclopropyl-4-fluoro-2-(4-(methylsulfonyl)phenyl)-1H-benzo[d] imidazole (326-327); 1-cyclopropyl-4-fluoro-2-(4-(methylsulfonyl)phenyl)-6-(1-(8-(tetrahydro-2H-pyran-4-yl)-8-azabicyclo[3.2.1]octan-3-yl) piperidin-4-yl)-1H-benzo[d]imidazole (328-329); 6-(1'-isobutyl-[1,4'-bipiperidin]-4-yl)-1,7-dimethyl-2-(4-(methylsulfonyl) phenyl)-1H-benzo[d]imidazole (330); 6-(1'-isobutyl-[1,4'-bipiperidin]-4-yl)-1,5-dimethyl-2-(4-(methylsulfonyl) phenyl)-1H-benzo[d]imidazole (331); 6-(1-(8-isopropyl-8-azabicyclo[3.2.1]octan-3-yl)piperidin-4-yl)-4-methyl-2-(4-(methylsulfonyl) phenyl)-1H-benzo[d]imidazole (332-333); 6-(1-(8-cyclobutyl-8-azabicyclo[3.2.1]octan-3-yl)piperidin-4-yl)-4-methyl-2-(4-(methylsulfonyl)phenyl)-1H-benzo[d] imidazole (334); 6-(1-(8-(cyclopropylmethyl)-8-azabicyclo[3.2.1]octan-3-yl) piperidin-4-yl)-4-methyl-2-(4-(methylsulfonyl)phenyl)-1H-benzo[d]imidazole (335-336); 6-(1'-cyclobutyl-[1,4'-bipiperidin]-4-yl)-2-(3-fluoro-4-(methylsulfonyl)phenyl)-1,4-dimethyl-1H-benzo[d]imidazole (337); 6-(1'-(cyclopropylmethyl)-[1,4'-bipiperidin]-4-yl)-2-(3-fluoro-4-(methylsulfonyl)phenyl)-1,4-dimethyl-1H-benzo[d]imidazole (338); 6-(1'-cyclopropyl-[1,4'-bipiperidin]-4-yl)-2-(3-fluoro-4-(methylsulfonyl)phenyl)-1,4-dimethyl-1H-benzo[d]imidazole (339); 6-(1-(8-(cyclopropylmethyl)-8-azabicyclo[3.2.1]octan-3-yl) piperidin-4-yl)-2-(3-fluoro-4-(methylsulfonyl)phenyl)-1,4-dimethyl-1H-benzo[d]imidazole (340-341); 2-(3-fluoro-4-(methylsulfonyl)phenyl)-6-(1-(8-isobutyl-8-azabicyclo[3.2.1]octan-3-yl)piperidin-4-yl)-1,4-dimethyl-1H-benzo[d] imidazole (342); 2-(3-fluoro-4-(methylsulfonyl)phenyl)-6-(1'-isobutyl-[1,4'-bipiperidin]-4-yl)-1,4-dimethyl-1H-benzo[d]imidazole (343); 2-(3-fluoro-4-(methylsulfonyl)phenyl)-6-(1-(8-isopropyl-8-azabicyclo[3.2.1]octan-3-yl)piperidin-4-yl)-1,4-dimethyl-1H-benzo[d]imidazole (344); 6-(1-(8-cyclopropyl-8-azabicyclo[3.2.1]octan-3-yl)piperidin-4-yl)-2-(3-fluoro-4-(methylsulfonyl)phenyl)-1,4-dimethyl-1H-benzo[d]imidazole (345); 2-(3-fluoro-4-(methylsulfonyl) phenyl)-6-(1-(8-isobutyl-8-azabicyclo[3.2.1]octan-3-yl) piperidin-4-yl)-4-methyl-1H-benzo[d]imidazole (346); 6-(1-(8-cyclopropyl-8-azabicyclo[3.2.1]octan-3-yl) piperidin-4-yl)-2-(3-fluoro-4-(methylsulfonyl)phenyl)-4-methyl- 1H-benzo[d]imidazole (347); 2-(3-fluoro-4-(methylsulfonyl)phenyl)-6-(1-(8-isopropyl-8-azabicyclo[3.2.1]octan-3-yl)piperidin-4-yl)-4-methyl-1H-benzo[d]imidazole (348); 6-(1-(8-cyclobutyl-8-azabicyclo[3.2.1]octan-3-yl)piperidin-4-yl)-2-(3-fluoro-4-(methylsulfonyl)phenyl)-4-methyl-1H-benzo[d]imidazole (349-350); 6-(1-(8-(cyclopropylmethyl)-8-azabicyclo[3.2.1]octan-3-yl)piperidin-4-yl)-2-(3-fluoro-4-(methylsulfonyl)phenyl)-4-methyl-1H-benzo[d]imidazole (351-352); 6-(6-(1'-isobutyl-[1,4'-bipiperidin]-4-yl)-1,4-dimethyl-1H-benzo[d]imidazol-2-yl)-8-methoxy-[1,2,4]triazolo[1,5-a]pyridine (353); 6-(6-(1-(8-cyclopropyl-8-azabicyclo[3.2.1]octan-3-yl)piperidin-4-yl)-1,4-dimethyl-1H-benzo[d]imidazol-2-yl)-8-methoxy-[1,2,4]triazolo[1,5-a]pyridine (354); 6-(6-(1-(8-cyclobutyl-8-azabicyclo[3.2.1]octan-3-yl)piperidin-4-yl)-1,4-dimethyl-1H-benzo[d]imidazol-2-yl)-8-methoxy-[1,2,4]triazolo[1,5-a]pyridine (355-356); 6-(6-(1-(8-isopropyl-8-azabicyclo[3.2.1]octan-3-yl)piperidin-4-yl)-1,4-dimethyl-1H-benzo[d]imidazol-2-yl)-8-methoxy-[1,2,4]triazolo[1,5-a]pyridine (357); 6-(6-(1-(8-(cyclopropylmethyl)-8-azabicyclo[3.2.1]octan-3-yl)piperidin-4-yl)-1,4-dimethyl-1H-benzo[d]imidazol-2-yl)-8-methoxy-[1,2,4]triazolo[1,5-a]pyridine (358); 6-(6-(1-(8-isobutyl-8-azabicyclo[3.2.1]octan-3-yl)piperidin-4-yl)-4-methyl-1H-benzo[d]imidazol-2-yl)-8-methoxy-[1,2,4]triazolo[1,5-a]pyridine (359); 6-(6-(1-(8-cyclopropyl-8-azabicyclo[3.2.1]octan-3-yl)piperidin-4-yl)-4-methyl-1H-benzo[d]imidazol-2-yl)-8-methoxy-[1,2,4]triazolo[1,5-a]pyridine (360); 6-(6-(1-(8-cyclobutyl-8-azabicyclo[3.2.1]octan-3-yl)piperidin-4-yl)-4-methyl-1H-benzo[d]imidazol-2-yl)-8-methoxy-[1,2,4]triazolo[1,5-a]pyridine (361); 6-(6-(1-(8-isopropyl-8-azabicyclo[3.2.1]octan-3-yl)piperidin-4-yl)-4-methyl-1H-benzo[d]imidazol-2-yl)-8-methoxy-[1,2,4]triazolo[1,5-a]pyridine (362); 1,4-dimethyl-6-(4-(1-methylpiperidin-4-yl) phenyl)-2-(4-(methylsulfonyl)phenyl)-1H-benzo[d]imidazole (363); 1,4-dimethyl-2-(4-(methylsulfonyl)phenyl)-6-(4-(1-(tetrahydro-2H-pyran-4-yl)piperidin-4-yl)phenyl)-1H-benzo[d]imidazole (364); 6-(6-(1-isopropylpiperidin-4-yl)pyridin-3-yl)-1,4-dimethyl-2-(4-(methylsulfonyl)phenyl)-1H-benzo[d]imidazole (365); 1-(4-(1,4-dimethyl-2-(4-(methylsulfonyl)phenyl)-1H-benzo[d]imidazol-6-yl)phenethyl)-4-methylpiperidin-4-ol (366); 1,4-dimethyl-2-(4-(methylsulfonyl)phenyl)-6-(4-(4-(pyrrolidin-1-yl)piperidin-1-yl) phenyl)-1H-benzo[d]imidazole (367); 1-(4-(1,4-dimethyl-2-(4-(methylsulfonyl)phenyl)-1H-benzo[d]imidazol-6-yl)phenyl)-N,N-dimethylpiperidin-4-amine (368); 1,4-dimethyl-2-(4-(methylsulfonyl)phenyl)-6-(4-((4-(pyrrolidin-1-yl)piperidin-1-yl)methyl)phenyl)-1H-benzo[d]imidazole (369); 1,4-dimethyl-6-(4-((6-methyl-2,6-diazaspiro[3.3]heptan-2-yl)methyl)phenyl)-2-(4-(methylsulfonyl)phenyl)-1H-benzo[d]imidazole (370); 6-(4-((6-isobutyl-2,6-diazaspiro[3.3]heptan-2-yl)methyl) phenyl)-1,4-dimethyl-2-(4-(methylsulfonyl)phenyl)-1H-benzo[d]imidazole (371); 1-cyclopropyl-4-methyl-2-(4-(methylsulfonyl)phenyl)-6-(4-((4-(pyrrolidin-1-yl) piperidin-1-yl)methyl)phenyl)-1H-benzo[d]imidazole (372); N,N-dimethyl-1-(4-(1-methyl-2-phenyl-1H-benzo[d]imidazol-6-yl)benzyl)piperidin-4-amine (374); N,N-dimethyl-1-(4-(1-methyl-2-(4-(methylsulfonyl)phenyl)-1H-benzo[d]imidazol-6-yl)benzyl)piperidin-4-amine (375); 1-(4-(2-(4-methoxyphenyl)-1-methyl-1H-benzo[d]imidazol-6-yl)benzyl)-N,N-dimethylpiperidin-4-amine (376); 1-(4-(2-(3-fluorophenyl)-1-methyl-1H-benzo[d]imidazol-6-yl)benzyl)-N,N-dimethylpiperidin-4-amine (377); 1-(4-(2-(4-fluorophenyl)-1-methyl-1H-benzo[d]imidazol-6-yl)benzyl)-N,N-dimethylpiperidin-4-amine (378); N,N-dimethyl-1-(4-(1-methyl-2-(2-(methylsulfonyl)phenyl)-1H-benzo[d]imidazol-6-yl)benzyl)piperidin-4-amine (379); 1-(4-(2-(2-fluoro-4-(methylsulfonyl)phenyl)-1-methyl-1H-benzo[d]imidazol-6-yl)benzyl)-N,N-dimethylpiperidin-4-amine (380); 1-(4-(2-(3,5-difluorophenyl)-1-methyl-1H-benzo[d]imidazol-6-yl)benzyl)-N,N-dimethylpiperidin-4-amine (381); 1-(4-(2-(3,4-difluorophenyl)-1-methyl-1H-benzo[d]imidazol-6-yl)benzyl)-N,N-dimethylpiperidin-4-amine (382); 4-(6-(4-((4-(dimethylamino)piperidin-1-yl)methyl)phenyl)-1-methyl-1H-benzo[d]imidazol-2-yl)benzonitrile (383); N,N-dimethyl-1-(4-(1-methyl-2-(3-(methylsulfonyl)phenyl)-1H-benzo[d]imidazol-6-yl)benzyl)piperidin-4-amine (384); 1-(4-(1,4-dimethyl-2-(4-(methylsulfonyl)phenyl)-1H-benzo[d]imidazol-6-yl)benzyl)-N,N-dimethylpiperidin-4-amine (385); 1-(4-(1,4-dimethyl-2-(4-(methylsulfonyl)phenyl)-1H-benzo[d]imidazol-6-yl)phenyl)-N-ethyl-N-methylpiperidin-4-amine (386); 6-(3-fluoro-4-((4-(pyrrolidin-1-yl)piperidin-1-yl)methyl)phenyl)-1,4-dimethyl-2-(4-(methylsulfonyl) phenyl)-1H-benzo[d]imidazole (387); 6-(3-fluoro-4-((cis-5-methylhexahydropyrrolo[3,4-c]pyrrol-2(1H)-yl)methyl)phenyl)-1,4-dimethyl-2-(4-(methylsulfonyl)phenyl)-1H-benzo[d]imidazole (388); 6-(4-((4-ethyl-1,4-diazepan-1-yl)methyl)-3-fluorophenyl)-1,4-dimethyl-2-(4-(methylsulfonyl)phenyl)-1H-benzo[d]imidazole (389); 1-(4-(1,4-dimethyl-2-(4-(methylsulfonyl)phenyl)-1H-benzo[d]imidazol-6-yl)-2-fluorobenzyl)-N,N-dimethylpiperidin-4-amine (390); 6-(3,5-difluoro-4-((4-(pyrrolidin-1-yl)piperidin-1-yl)methyl)phenyl)-1,4-dimethyl-2-(4-(methylsulfonyl)phenyl)-1H-benzo[d]imidazole (391); 1-(4-(1,4-dimethyl-2-(4-(methylsulfonyl)phenyl)-1H-benzo[d]imidazol-6-yl)-2,6-difluorobenzyl)-N,N-dimethylpiperidin-4-amine (392); N-cyclopropyl-1-(4-(1,4-dimethyl-2-(4-(methylsulfonyl)phenyl)-1H-benzo[d]imidazol-6-yl)benzyl)-N-methylpiperidin-4-amine (393); N-cyclopropyl-1-(4-(1,4-dimethyl-2-(4-(methylsulfonyl) phenyl)-1H-benzo[d]imidazol-6-yl)-2-fluorobenzyl)-N-methylpiperidin-4-amine (394); 1,4-dimethyl-2-(4-(methylsulfonyl)phenyl)-6-(4-(pyrrolidin-1-ylmethyl)phenyl)-1H-benzo[d]imidazole (395); 6-(4-((cis-5-isobutylhexahydropyrrolo[3,4-c]pyrrol-2(1H)-yl)methyl)phenyl)-1,4-dimethyl-2-(4-(methylsulfonyl)phenyl)-1H-benzo[d]imidazole (396); 6-(4-((cis-5-isopropylhexahydropyrrolo[3,4-c]pyrrol-2(1H)-yl)methyl)phenyl)-1,4-dimethyl-2-(4-(methylsulfonyl)phenyl)-1H-benzo[d]imidazole (397); 1,4-dimethyl-6-(4-((cis-5-methylhexahydropyrrolo[3,4-c]pyrrol-2(1H)-yl)methyl)phenyl)-2-(4-(methylsulfonyl)phenyl)-1H-benzo[d]imidazole (398); 6-(4-((6-isopropyl-2,6-diazaspiro[3.3]heptan-2-yl)methyl)phenyl)-1,4-dimethyl-2-(4-(methylsulfonyl)phenyl)-1H-benzo[d]imidazole (399); 1,4-dimethyl-6-(4-(1'-methyl-[1,4'-bipiperidin]-4-yl) phenyl)-2-(4-(methylsulfonyl)phenyl)-1H-benzo[d]imidazole (400); 6-(4-(1'-cyclopropyl-[1,4'-bipiperidin]-4-yl)phenyl)-1,4-dimethyl-2-(4-(methylsulfonyl)phenyl)-1H-benzo[d]imidazole (401); 6-(4-((4-(azetidin-1-yl)piperidin-1-yl)methyl)phenyl)-1,4-dimethyl-2-(4-(methylsulfonyl)phenyl)-1H-benzo[d]imidazole (402); 6-(4-((4-(azetidin-1-yl)piperidin-1-yl)methyl)-3-fluorophenyl)-1,4-dimethyl-2-(4-(methylsulfonyl)phenyl)-1H-benzo[d]imidazole (403); 6-(3-fluoro-4-((6-isopropyl-2,6-diazaspiro[3.3]heptan-2-yl)methyl)phenyl)-1,4-dimethyl-2-(4-(methylsulfonyl)phenyl)-1H-benzo[d]imidazole (404); 6-(3-fluoro-5-((4-(pyrrolidin-1-yl)piperidin-1-yl)methyl)phenyl)-1,4-dimethyl-2-(4-(methylsulfonyl)phenyl)-1H-benzo[d]imidazole (405); 6-(3-((4-(azetidin-1-yl)piperidin-1-yl)methyl)-5-fluorophenyl)-1,4-dimethyl-2-(4-(methylsulfonyl)phenyl)-1H-benzo[d]imidazole (405); 1-cyclopropyl-4-methyl-2-(4-(methylsulfonyl)phenyl)-6-(3-((4-(pyrrolidin-1-yl)piperidin-1-yl)methyl)phenyl)-1H-benzo[d]imidazole (407); 1-cyclopropyl-4-fluoro-2-(4-(methylsulfonyl)phenyl)-6-(4-((4-(pyrrolidin-1-yl)piperidin-1-yl)methyl)phenyl)-1H-benzo[d]imidazole (408); 4-fluoro-1-methyl-2-(4-(methylsulfonyl) phenyl)-6-(4-((4-(pyrrolidin-1-yl)piperidin-1-yl)methyl)phenyl)-1H-benzo[d]imidazole (409); 1-cyclopropyl-4-fluoro-6-(4-((6-isopropyl-2,6-diazaspiro[3.3]heptan-2-yl)methyl) phenyl)-2-(4-(methylsulfonyl)phenyl)-1H-benzo[d]imidazole (410); 1-cyclopropyl-4-fluoro-6-(4-((6-isobutyl-2,6-diazaspiro[3.3]heptan-2-yl)methyl)phenyl)-2-(4-(methylsulfonyl)phenyl)-1H-benzo[d]imidazole (411); 1-cyclopropyl-4-fluoro-2-(4-(methylsulfonyl)phenyl)-6-(4-((6-(tetrahydro-2H-pyran-4-yl)-2,6-diazaspiro[3.3]heptan-2-yl)methyl)phenyl)-1H-benzo[d]imidazole (412); 6-(4-((4-isopropylpiperazin-1-yl)methyl)phenyl)-1,4-dimethyl-2-(4-(methylsulfonyl) phenyl)-1H-benzo[d]imidazole (413); 6-(4-((4-isobutylpiperazin-1-yl)methyl)phenyl)-1,4-dimethyl-2-(4-(methylsulfonyl) phenyl)-1H-benzo[d]imidazole (414); 1-cyclopropyl-7-fluoro-6-(1'-isobutyl-[1,4'-bipiperidin]-4-yl)-2-(4-(methylsulfonyl)phenyl)-1H-benzo[d]imidazole (415); 6-(4-((1-isopropylpiperidin-4-yl)oxy)phenyl)-1,4-dimethyl-2-(4-(methylsulfonyl) phenyl)-1H-benzo[d]imidazole (416); 6-(4-((1-isobutylpiperidin-4-yl)oxy)phenyl)-1,4-dimethyl-2-(4-(methylsulfonyl)phenyl)-1H-benzo[d]imidazole (417); 6-(1-((2,6-dimethylpyridin-4-yl)methyl)piperidin-4-yl)-1,4-dimethyl-2-(4-(methylsulfonyl)phenyl)-1H-benzo[d]imidazole (418); 1,4-dimethyl-6-(1-((6-methylpyridin-3-yl)methyl)piperidin-4-yl)-2-(4-(methylsulfonyl)phenyl)-1H-benzo[d]imidazole (419); diethyl(4-(6-(1'-isopropyl-[1,4'-bipiperidin]-4-yl)-1,4-dimethyl-1H-benzo[d]imidazol-2-yl)phenyl)phosphonate (420); diethyl(4-(6-(1'-isobutyl-[1,4'-bipiperidin]-4-yl)-1,4-dimethyl-1H-benzo[d]imidazol-2-yl)phenyl)phosphonate (421); diethyl(4-(6-(1'-cyclopropyl-[1,4'-bipiperidin]-4-yl)-1,4-dimethyl-1H-benzo[d]imidazol-2-yl)phenyl)phosphonate (422); 1-((4-(1-(115-ethyl)-2-(p-tolyl)-1H-benzo[d]imidazol-6-yl)phenyl)methyl)-N,N-dimethylpiperidin-4-amine (423); N-(4-(6-(4-((4-(dimethylamino)piperidin-1-yl) methyl) phenyl)-1-methyl-1H-benzo[d]imidazol-2-yl)phenyl)methanesulfonamide (424); 1-(4-(2-(4-(dimethylamino) phenyl)-1-methyl-1H-benzo[d]imidazol-6-yl)benzyl)-N,N-dimethylpiperidin-4-amine (425); 1-(4-(2-(4-(1H-imidazol-1-yl)phenyl)-1-methyl-1H-benzo[d]imidazol-6-yl)benzyl)-N,N-dimethylpiperidin-4-amine (426); or N-(3-(6-(4-((4-(dimethylamino)piperidin-1-yl)methyl)phenyl)-1-methyl-1H-benzo[d]imidazol-2-yl) phenyl)methanesulfonamide (427).

One embodiment provides compounds of the Formula (I) having TLR9 $IC_{50}$ values of ≤0.6 μM.

One embodiment provides compounds of the Formula (I) having TLR9 $IC_{50}$ values of ≤0.1 μM.

One embodiment provides compounds of the Formula (I) having TLR9 $IC_{50}$ values of ≤0.05 μM.

One embodiment provides compounds of the Formula (I) having TLR9 $IC_{50}$ values of ≤0.025 μM.

One embodiment provides compounds of the Formula (I) having TLR9 $IC_{50}$ values of ≤0.015 μM.

One embodiment provides compounds of the Formula (I) having TLR9 $IC_{50}$ values of ≤0.01 μM.

In another embodiment, the present invention provides a composition comprising at least one of the compounds of the present invention, or a stereoisomer, a tautomer, or a pharmaceutically acceptable salt or a solvate thereof.

In another embodiment, the present invention provides a pharmaceutical composition comprising a pharmaceutically acceptable carrier and at least one of the compounds of the present invention or a stereoisomer, a tautomer, or a pharmaceutically acceptable salt or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, or a pharmaceutically acceptable salt or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising one or more additional therapeutic agents.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

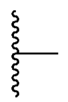

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "amino" refers to the group —$NH_2$.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The term "aminoalkyl" includes both branched and straight-chain saturated alkyl groups substituted with one or more amine groups. For example, "aminoalkyl" includes —$CH_2NH_2$, —$CH_2CH_2NH_2$, and $C_{1-4}$ aminoalkyl.

The term "hydroxyalkyl" includes both branched and straight-chain saturated alkyl groups substituted with one or more hydroxyl groups. For example, "hydroxyalkyl" includes —$CH_2OH$, —$CH_2CH_2OH$, and $C_1$14 hydroxyalkyl.

The term "aminoalkyl" includes both branched and straight-chain saturated alkyl groups substituted with one or more amine groups. For example, "aminoalkyl" includes —$CH_2NH_2$, —$CH_2CH_2NH_2$, and $C_{1-4}$ aminoalkyl.

The term "cyanoalkyl" includes both branched and straight-chain saturated alkyl groups substituted with one or more cyano groups. For example, "aminoalkyl" includes —$CH_2CN$, —$CH_2CH_2CN$, and $C_{1-4}$ cyanoalkyl.

The term "alkoxy," as used herein, refers to an alkyl group attached to the parent molecular moiety through an oxygen atom, for example, methoxy group (—$OCH_3$). For example, "$C_{1-3}$ alkoxy" denotes alkoxy groups with one to three carbon atoms.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The term "alkoxyalkyl," as used herein, refers to an alkoxy group attached through its oxygen atom to an alkyl group, which is attached to the parent molecular moiety through a carbon atom, for example, methoxymethyl group (—$CH_2OCH_3$). For example, "$C_{2-4}$ alkoxyalkyl" denotes alkoxyalkyl groups with two to four carbon atoms, such as —$CH_2OCH_3$, —$CH_2CH_2OCH_3$, —$CH_2OCH_2CH_3$, and —$CH_2CH_2OCH_2CH_3$.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in Rautio, J. et al., *Nature Review Drug Discovery,* 17, 559-587 (2018).

In addition, compounds of Formula (I), subsequent to their preparation, can be isolated and purified to obtain a composition containing an amount by weight equal to or greater than 99% of a compound of Formula (I), respectively ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor of TLR9, or effective to treat or prevent disorders associated with a fibrotic disease or disorder, dysregulation of bile acids, such as pathological fibrosis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl ($—CH_3$) also includes deuterated methyl groups such as $—CD_3$.

Utility

The compounds of the invention are useful for inhibiting the TLR9 receptor.

One embodiment provides a method for the treatment of a disease, disorder, or condition associated with dysregulation of bile acids in a patient in need of such treatment, and the method comprises administering a therapeutically effective amount of a compound of the present invention, or a stereoisomer, a tautomer, or a pharmaceutically acceptable salt or solvate thereof, to the patient.

One embodiment provides a method for the treatment of a disease, disorder, or condition associated with activity of the TLR9 receptor in a patient in need of such treatment comprising administering a therapeutically effective amount of a compound of the present invention, or a stereoisomer, a tautomer, or a pharmaceutically acceptable salt or solvate thereof, to the patient.

One embodiment provides a method for the treatment of the disease, disorder, or condition comprising administering to a patient in need of such treatment a therapeutically effective amount of at least one of the compounds of the present invention, alone, or, optionally, in combination with another compound of the present invention and/or at least one other type of therapeutic agent.

One embodiment provides a method for eliciting an TLR9 receptor agonizing effect in a patient comprising administering a therapeutically effective amount of a compound of the present invention, or a stereoisomer, a tautomer, or a pharmaceutically acceptable salt or solvate thereof, to the patient.

In some embodiments, the disease, disorder, or condition is associated with TLR9 dysfunction include pathological fibrosis, cancer, inflammatory disorders, metabolic, or cholestatic disorders.

In some embodiments, the disease, disorder, or condition is associated with fibrosis, including liver, biliary, renal, cardiac, dermal, ocular, and pancreatic fibrosis.

In other embodiments, the disease, disorder, or condition is associated with cell-proliferative disorders, such as cancer. In some embodiments, the cancer includes solid tumor growth or neoplasia. In other embodiments, the cancer includes tumor metastasis. In some embodiments, the cancer is of the liver, gall bladder, small intestine, large intestine, kidney, prostate, bladder, blood, bone, brain, breast, central nervous system, cervix, colon, endometrium, esophagus, genitalia, genitourinary tract, head, larynx, lung, muscle tissue, neck, oral or nasal mucosa, ovary, pancreas, skin, spleen, stomach, testicle, or thyroid. In other embodiments, the cancer is a carcinoma, sarcoma, lymphoma, leukemia, melanoma, mesothelioma, multiple myeloma, or seminoma.

Examples of diseases, disorders, or conditions associated with the activity of FXR that can be prevented, modulated, or treated according to the present invention include, but are not limited to, transplant injection, fibrotic disorders (e. g., liver fibrosis, kidney fibrosis), inflammatory disorders (e.g., acute hepatitis, chronic hepatitis, non-alcoholic steatohepatitis (NASH), irritable bowel syndrome (IBS), inflammatory bowel disease (IBD)), as well as cell-proliferative disorders (e.g., cancer, myeloma, fibroma, hepatocellular carcinoma, colorectal cancer, prostate cancer, leukemia, Kaposi's sarcoma, solid tumors).

The fibrotic disorders, inflammatory disorders, as well as cell-proliferative disorders that are suitable to be prevented or treated by the compounds of the present invention include, but are not limited to, non-alcoholic fatty liver disease (NAFLD), alcoholic or non-alcoholic steatohepatitis (NASH), acute hepatitis, chronic hepatitis, liver cirrhosis, primary biliary cirrhosis, primary sclerosing cholangitis, drug-induced hepatitis, biliary cirrhosis, portal hypertension, regenerative failure, liver hypofunction, hepatic blood flow disorder, nephropathy, irritable bowel syndrome (IBS), inflammatory bowel disease (IBD), abnormal pancreatic secretion, benign prostatic hyperplasia, neuropathic bladder disease, diabetic nephropathy, focal segmental glomerulosclerosis, IgA nephropathy, nephropathy induced by drugs or transplantation, autoimmune nephropathy, lupus nephritis, liver fibrosis, kidney fibrosis, chronic kidney disease (CKD), diabetic kidney disease (DKD), skin fibrosis, keloids, systemic sclerosis, scleroderma, virally-induced fibrosis, idiopathic pulmonary fibrosis (IPF), interstitial lung disease, non-specific interstitial pneumonia (NSIP), usual interstitial pneumonia (UIP), radiation-induced fibrosis, familial pulmonary fibrosis, airway fibrosis, chronic obstructive pulmonary disease (COPD), spinal cord tumor, hernia of intervertebral disk, spinal canal stenosis, heart failure, cardiac fibrosis, vascular fibrosis, perivascular fibrosis, foot-and-mouth disease, cancer, myeloma, fibroma, hepatocellular carcinoma, colorectal cancer, prostate cancer, leukemia, chronic lymphocytic leukemia, Kaposi's sarcoma, solid tumors, cerebral infarction, cerebral hemorrhage, neuropathic pain, peripheral neuropathy, age-related macular degeneration (AMD), glaucoma, ocular fibrosis, corneal scarring, diabetic retinopathy, proliferative vitreoretinopathy (PVR), cicatricial pemphigoid glaucoma filtration surgery scarring, Crohn's disease or systemic lupus erythematosus; keloid formation resulting from abnormal wound healing; fibrosis occurring after organ transplantation, myelofibrosis, and fibroids. In one embodiment, the present invention provides a method for the treatment of a fibrotic disorder, an inflammatory disorder, or a cell-proliferative disorder, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of a fibrotic disorder, an inflammatory disorder, or a cell-proliferative disorder thereof.

In another embodiment, the present invention also provides the use of a compound of the present invention for the manufacture of a medicament for the treatment of a fibrotic disorder, an inflammatory disorder, or a cell-proliferative disorder thereof.

In another embodiment, the present invention provides a method for the treatment of a fibrotic disorder, an inflammatory disorder, or a cell-proliferative disorder, comprising administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of a fibrotic disorder, an inflammatory disorder, or a cell-proliferative disorder.

The compounds of the present invention may be employed in combination with additional therapeutic agent (s), such as one or more anti-fibrotic and/or anti-inflammatory therapeutic agents.

In one embodiment, additional therapeutic agent(s) used in combined pharmaceutical compositions or combined methods or combined uses, are selected from one or more, preferably one to three, of the following therapeutic agents: TGFβ receptor inhibitors (for example, galunisertib), inhibitors of TGFβ synthesis (for example, pirfenidone), inhibitors of vascular endothelial growth factor (VEGF), platelet-derived growth factor (PDGF) and fibroblast growth factor (FGF) receptor kinases (for example, nintedanib), humanized anti-αvβ6 integrin monoclonal antibody (for example, 3G9), human recombinant pentraxin-2, recombinant human Serum Amyloid P, recombinant human antibody against TGFβ-1, -2, and -3, endothelin receptor antagonists (for example, macitentan), interferon gamma, c-Jun amino-terminal kinase (INK) inhibitor (for example, 4-[[9-[(3S)-tetrahydro-3-furanyl]-8-[(2,4,6-trifluorophenyl)amino]-9H-purin-2-yl]amino]-trans-cyclohexanol, 3-pentylbenzeneacetic acid (PBI-4050), tetra-substituted porphyrin derivative containing manganese (III), monoclonal antibody targeting eotaxin-2, interleukin-13 (IL-13) antibody (for example, lebrikizumab, tralokinumab), bispecific antibody targeting interleukin 4 (IL-4) and interleukin 13 (IL-13), NK1 tachykinin receptor agonist (for example, $Sar^9$, $Met(O_2)^{11}$-Substance P), Cintredekin Besudotox, human recombinant DNA-derived, IgG1 kappa monoclonal antibody to connective growth factor, and fully human IgG1 kappa antibody, selective for CC-chemokine ligand 2 (for example, carlumab, CCX140), antioxidants (for example, N-acetylcysteine), phosphodiesterase 5 (PDE5) inhibitors (for example, sildenafil), agents for treatment of obstructive airway diseases such as muscarinic antagonists (for example, tiotropium, ipratropium bromide), adrenergic β2 agonists (for example, salbutamol, salmeterol), corticosteroids (for example, triamcinolone, dexamethasone, fluticasone), immunosuppressive agents (for example, tacrolimus, rapamycin, pimecrolimus), and therapeutic agents useful for the treatment of fibrotic conditions, such as liver, biliary, and kidney fibrosis, Non-Alcoholic Fatty Liver Disease (NALFD), Non-Alcoholic Steato-Hepatitis (NASH), cardiac fibrosis, Idiopathic Pulmonary Fibrosis (IPF), and systemic sclerosis. The therapeutic agents useful for the treatment of such fibrotic conditions include, but are not limited to, FXR agonists (for example OCA, GS-9674, and LJN452), LOXL2 inhibitors (for example simtuzumab), LPA1 antagonists (for example, BMS-986020 and SAR 100842), PPAR modulators (for example, elafibrinor, pioglitazone, and saroglitazar, IVA337), SSAO/VAP-1 inhibitors (for example, PXS-4728A and SZE5302), ASK-1 inhibitors (for example GS-4997 or selonsertib), ACC inhibitors (for example, CP-640186 and NDI-010976 or GS-0976), FGF21 mimetics (for example, LY2405319 and BMS-986036), caspase inhibitors (for example, emricasan), NOX4 inhibitors (for example, GKT137831), MGAT2 inhibitor (for example, BMS-963272), αV integrin inhibitors (for example, abituzumab) and bile acid/fatty acid conjugates (for example aramchol). The FXR agonists of various embodiments of the present invention may also be used in combination with one or more therapeutic agents such as CCR2/5 inhibitors (for example, cenicriviroc), Galectin-3 inhibitors (for example, TD-139, GR-MD-02), leukotriene receptor antagonists (for example, tipelukast, montelukast), SGLT2 inhibitors (for example, dapagliflozin, remogliflozin), GLP-1 receptor agonists (for example, liraglutide and semaglutide), FAK inhibitors (for example, GSK-2256098), CB1 inverse agonists (for example, JD-5037), CB2 agonists (for example, APD-371 and JBT-101), autotaxin inhibitors (for example, GLPG1690), prolyl t-RNA synthetase inhibitors (for example, halofugenone), FPR2 agonists (for example, ZK-994), and THR agonists (for example, MGL:3196). In another embodiment, additional therapeutic agent(s) used in combined pharmaceutical compositions or combined methods or combined uses, are selected from one or more, preferably one to three, of immunooncology agents, such as Alemtuzumab, Atezolizumab, Ipilimumab, Nivolumab, Ofatumumab, Pembrolizumab, and Rituximab.

When the terms “TLR9-associated condition” or “TLR9-associated disease or disorder” are used herein, each is intended to encompass all of the conditions identified above as if repeated at length, as well as any other condition that is affected by inhibition of TLR9.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating TLR9-associated conditions.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A “pharmaceutically acceptable carrier” refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington: The Science and Practice of Pharmacy*, 22$^{nd}$ Edition (2013).

Compounds in accordance with Formula (I) can be administered by any means suitable for the condition to be treated, which can depend on the need for site-specific treatment or quantity of Formula (I) compound to be delivered.

The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one nontoxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, *arachis* oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and *arachis* oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular disorder, diuresis, and/or natriuresis. In another embodiment, the package insert states that the pharmaceutical composition can be used in combination (as defined previously) with a second therapeutic agent to treat cardiovascular disorder, diuresis, and/or natriuresis. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, or other written sheet that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic) on which the desired information has been formed (e.g., printed or applied).

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below.

The reactions and techniques described in this section are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

SCHEME 1

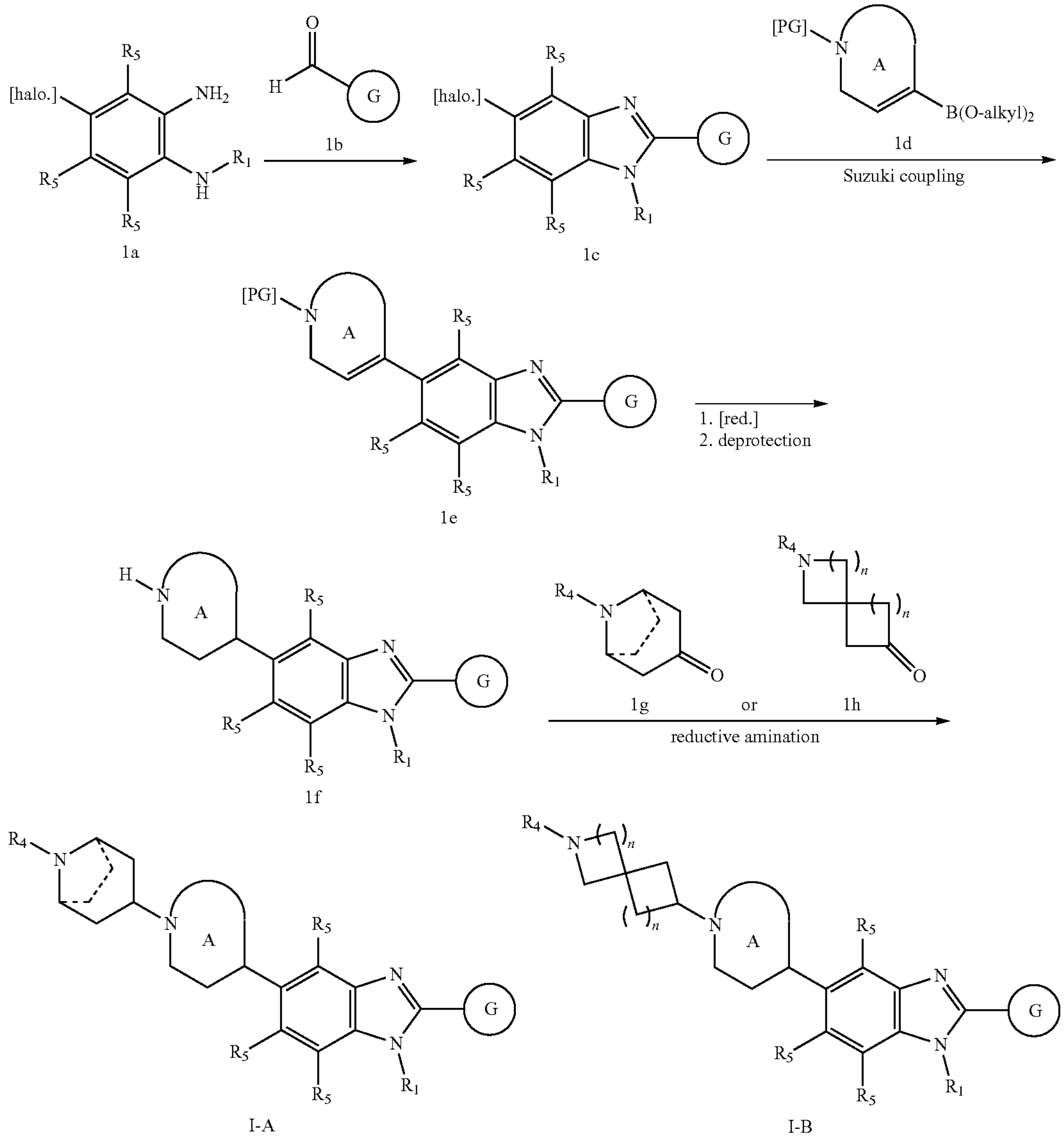

Scheme 1 describes the synthesis of compounds of Formula I-A and I-B, a subset of Formula I. The term "halo." in this scheme refers to any halogen that one of ordinary skill in the art would deem suitable to achieve the intended transformation. The term "PG" refers to any suitable amino protective group, such as alkyl carbamate, alkyl amide, or alkyl. Ring A as shown in Formula I-A and I-B is substituted at the 5-position of the 1H-benzo[d]imidazole ring, however, a person of ordinary skill can readily modify this synthetic scheme to install Ring A at the 6-position by using appropriate starting material.

Compound 1a can be reacted with aldehyde 1b, in any typical reaction solvent (e.g. EtOH, DMF, DMSO, NMP) with heating. The reaction can be conducted in the presence of base such as potassium carbonate or sodium bicarbonate, but is not necessary. Addition of additive sodium metabisulfite is not necessary but expedites the reaction. Compound 1c can be coupled with boronate ester Id under standard Suzuki coupling conditions. The resultant alkene can be reduced by catalytic hydrogenation using a catalyst such as Pd or Pt. Protective group PG can be removed by one of ordinary skill in the art using appropriate reagents and conditions. Reductive amination of amine if with ketone 1 g or 1 h, can be achieved with a reducing agent such as sodium triacetoxyborohydride or sodium cyanoborohydride, with or without an acid catalyst (i.e. AcOH), to furnish compounds of Formula I-A and I-B.

EXAMPLES

Compounds of the current invention and intermediates used in the preparation of compounds of the current invention can be prepared using procedures shown in the following examples and related procedures. The methods and conditions used in these examples, and the actual compounds prepared in these examples, are not meant to be limiting, but are meant to demonstrate how the compounds of the current invention can be prepared. Starting materials and reagents used in these examples, when not prepared by a procedure described herein, are generally either commercially available, or are reported in the chemical literature, or may be prepared by using procedures described in the chemical literature. The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather defined by the claims appended hereto.

In the examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being dried and concentrated).

Column chromatography was performed with pre-packed silica gel cartridges using an Isco medium pressure chromatography apparatus (Teledyne Corporation), eluting with the solvent or solvent mixture indicated. Preparative high performance liquid chromatography (HPLC) was performed using a reverse phase column (Waters Sunfire Cis, Waters Xbridge Cis, PHENOMENEX® Axia $C_{18}$, YMC S5 ODS or the like) of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chemical names were determined using ChemDraw Ultra, version 9.0.5 (CambridgeSoft). The following abbreviations are used:

ACN acetonitrile
AcOH acetic acid
aq. aqueous
brine saturated aqueous sodium chloride
DCE dichloroethane
DCM dichloromethane
DEA diethylamine
DMAP dimethylaminopyridine
DMF N,N-dimethylformamide
DMSO dimethyl sulfoxide
EtOAc ethyl acetate
FA formic acid
g gram(s)
h hour(s)
Hex hexanes
HPLC High Performance Liquid Chromatography
IPA isopropyl alcohol
LCMS Liquid Chromatography-Mass Spectroscopy
MeCN acetonitrile
MeOH methanol
NMP N-methylpyrrolidinone
Oxone potassium peroxymonosulfate
$Pd(dppf)Cl_2$ [1,1'-bis(diphenylphosphino)ferrocene]dichloropalladium(II)
pet ether petroleum ether
TEA triethylamine
TFA trifluoroacetic acid
THF tetrahydrofuran
XPhos-Pd-G3 (2-dicyclohexylphosphino-2',4',6'-triisopropyl-1,1'-biphenyl)[2-(2'-amino-1,1'-biphenyl)]palladium(II) methanesulfonate Preparation All reagents purchased from commercial sources were used without further purification unless otherwise noted. All reactions involving air or moisture sensitive reagents were performed under an inert atmosphere. Proton magnetic resonance spectra were recorded either on a Bruker 400 or a JEOL Eclipse 500 spectrometer.

Analytical LC/MS Methods

Method 1: Column: Waters XBridge C18, 2.1 mm×50 mm, 1.7 m particles; Mobile Phase A: 5:95 acetonitrile: water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm).

Method 2: Column: Waters XBridge C18, 2.1 mm×50 mm, 1.7 m particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm).

Method 3: Column: Waters Acquity BEH C18, 2.1×50 mm, 1.7 m particles; Mobile Phase A: 5:95 acetonitrile: water with 0.05% trifluoroacetic acid; Mobile Phase B: 95:5 acetonitrile:water with 0.05% trifluoroacetic acid; Temperature: 60° C.; Gradient: 2% B to 98% B over 1 min, then a 0.50 min hold at 98% B; Flow: 0.8 mL/min; Detection: MS and UV (220 nm).

Method 4: Column: Waters Acquity BEH C18, 2.1×50 mm, 1.7 m particles; Mobile Phase A: 5:95 acetonitrile: water with 0.05% trifluoroacetic acid; Mobile Phase B: 95:5 acetonitrile:water with 0.05% trifluoroacetic acid; Temperature: 50° C.; Gradient: 0% B to 100% B over 3 min, then a 0.50 min hold at 100% B; Flow: 1.0 mL/min; Detection: MS and UV (220, 254 nm).

Method 5: Column: Waters Acquity BEH C18, 2.1×50 mm, 1.7 m particles; Mobile Phase A: 5:95 acetonitrile: water with 10 mM $NH_4OAc$; Mobile Phase B: 95:5 acetonitrile: water with 10 mM $NH_4OAc$; Temperature: 50° C.; Gradient: 0% B to 100% B over 3 min, then a 0.50 min hold at 100% B; Flow: 1.0 mL/min; Detection: MS and UV (220 nm).

Method 6: Column: HALO C18, 3.0×30 mm, 2.7 m particles; Mobile Phase A: water with 0.05% trifluoroacetic acid; Mobile Phase B: acetonitrile with 0.05% trifluoroacetic acid; Temperature: 40° C.; Gradient: 5% B to 50% B over 2 min, 50% B to 100% B over 0.4 min, then a 0.40 min hold at 100% B; Flow: 1.5 mL/min; Detection: MS and UV (220 nm).

Method 7: Column: HALO C18, 3.0×30 mm, 2.0 m particles; Mobile Phase A: water with 0.1% formic acid; Mobile Phase B: acetonitrile with 0.05% formic acid; Temperature: 40° C.; Gradient: 5% B to 100% B over 1.2 min, then a 0.60 min hold at 100% B; Flow: 1.2 mL/min; Detection: MS and UV (220 nm).

Method 8: Column: HALO C18, 3.0×30 mm, 2.7 m particles; Mobile Phase A: water with 0.05% trifluoroacetic acid; Mobile Phase B: acetonitrile with 0.05% trifluoroacetic acid; Temperature: 40° C.; Gradient: 5% B to 100% B over 1.3 min, then a 0.50 min hold at 100% B; Flow: 1.5 mL/min; Detection: MS and UV (220 nm).

Method 9: Column: Shim-pack Scepter C18, 3.0 mm×33 mm, 3.0 m particles; Mobile Phase A: water with 5 mM ammonium bicarbonate; Mobile Phase B: acetonitrile; Temperature: 40° C.; Gradient: 50% B to 95% B over 2 min, then a 0.70 min hold at 95% B; Flow: 1.5 mL/min; Detection: MS and UV (220 nm).

Chiral Analytical Methods

SFC Method 1: Instrument: Shimadzu Nexera UC SFC; Column: Chiral OD, 4.6×100 mm, 5 micron; Mobile Phase: 70% $CO_2$/30% MeOH w/0.1% DEA; Flow Conditions: 2 mL/min; Detector Wavelength: 220 nm.

SFC Method 2: Instrument: Shimadzu Nexera UC SFC; Column: Chiral OD, 4.6×100 mm, 5 micron; Mobile Phase: 60% $CO_2$/40% MeOH—$NH_4OH$; Flow Conditions: 2 mL/min; Detector Wavelength: 220 nm.

SFC Method 3: Instrument: Shimadzu Nexera UC SFC; Column: Chiral OD, 4.6×100 mm, 5 micron; Mobile Phase: 65% $CO_2$/35% MeOH w/0.1% DEA; Flow Conditions: 2 mL/min; Detector Wavelength: 220 nm.

SFC Method 4: Instrument: Shimadzu Nexera UC SFC; Column: Chiral OD, 4.6×100 mm, 5 micron; Mobile Phase: 70% $CO_2$/30% IPA w/0.3% DEA/0.2% FA; Flow Conditions: 2 mL/min; Detector Wavelength: 220 nm.

SFC Method 5: Instrument: Shimadzu Nexera UC SFC; Column: Chiral OD, 4.6×100 mm, 5 micron; Mobile Phase: 60% $CO_2$/40% IPA w/0.3% DEA/0.2% FA; Flow Conditions: 2 mL/min; Detector Wavelength: 220 nm.

SFC Method 6: Instrument: Shimadzu Nexera UC SFC; Column: Chiral OD, 4.6×100 mm, 5 micron; Mobile Phase: 70% $CO_2$/30% IPA w/0.1% DEA/0.1% FA; Flow Conditions: 2 mL/min; Detector Wavelength: 220 nm.

SFC Method 7: Instrument: Shimadzu Nexera UC SFC; Column: Chiral OD, 4.6×100 mm, 5 micron; Mobile Phase: 60% $CO_2$/40% IPA w/0.5% DEA/0.3% FA; Flow Conditions: 2 mL/min; Detector Wavelength: 220 nm.

SFC Method 8: Instrument: Shimadzu Nexera UC SFC; Column: Chiral OD, 4.6×100 mm, 5 micron; Mobile Phase: 60% $CO_2$/40% MeOH w/0.2% DEA/0.2% FA; Flow Conditions: 2 mL/min; Detector Wavelength: 220 nm.

SFC Method 9: Instrument: Shimadzu Nexera UC SFC; Column: Chiral OD, 4.6×100 mm, 5 micron; Mobile Phase: 70% $CO_2$/30% IPA w/0.1% DEA; Flow Conditions: 2 mL/min; Detector Wavelength: 220 nm.

Preparative HPLC Methods

Prep Method 1: Column: XBridge C18, 200 mm×19 mm, 5-μm particles; Mobile Phase A: 5:95 acetonitrile: water with ammonium acetate; Mobile Phase B: 95:5 acetonitrile: water with ammonium acetate; Gradient: (variable; dependent on substrate) % B over 20 minutes, then a 0-minute hold at 100% B; Flow Rate: 20 mL/min; Column Temperature: 25° C. Fraction collection was triggered by MS and UV signals. Fractions containing the desired product were combined and dried via centrifugal evaporation.

Prep Method 2: Column: XBridge C18, 200 mm×19 mm, 5-μm particles; Mobile Phase A: 5:95 acetonitrile: water with 0.05% trifluoroacetic acid; Mobile Phase B: 95:5 acetonitrile: water with 0.05% trifluoroacetic acid; Gradient: (variable; dependent on substrate) % B over 20 minutes, then a 0-minute hold at 100% B; Flow Rate: 20 mL/min; Column Temperature: 25° C. Fraction collection was triggered by MS and UV signals. Fractions containing the desired product were combined and dried via centrifugal evaporation.

Prep Method 3: Column: XBridge Prep C18 OBD Column, 19×150 mm 5 m; Mobile Phase A: Water (10 mmol/L $NH_4HCO_3$), Mobile Phase B: ACN; Flow rate: 20 mL/min; Gradient: (variable; dependent on substrate); 254/210 nm. Fractions containing the desired product were combined and dried via centrifugal evaporation.

Prep Method 4: Column: Luna 5u C18, 100 mm×21 mm. 5-μm particles; Solvent A: 90% $H_2O$-10% methanol-0.1% TFA; Solvent B: 10% methanol-90% $H_2O$ 0.1% TFA. Flow rate: 20 mL/min. Gradient Time: 15 minutes. Start B: variable; dependent on substrate); Final B: 100%. Fractions containing the desired product were combined and dried via centrifugal evaporation.

Example 1

2-(3,4-dimethoxyphenyl)-6-(1'-isopropyl-[1,4'-bipiperidin]-4-yl)-1-methyl-1H-benzo[d]imidazole (1)

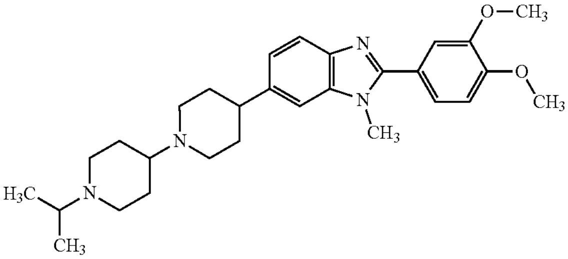

Step A. Intermediate 1A. Preparation of 5-bromo-N-methyl-2-nitroaniline (1A)

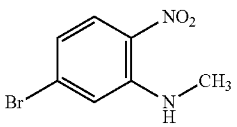

To a 1 L round bottomed flask were added 4-bromo-2-fluoro-1-nitrobenzene (16 g, 73 mmol) and DCM (400 mL). To this mixture was added methylamine (2.0 M solution in THF) (88 mL, 180 mmol). Upon addition of amine, the solution rapidly changed from a pale yellow to a bright orange solution. The reaction mixture was stirred at room temperature under a closed system. After 18 h, the reaction mixture was filtered through a plug of $SiO_2$ (250 g), with 2:1 Hex:EtOAc as eluent. The filtrate was concentrated and dried in vacuo to afford the title compound (16 g, 69 mmol, 95% yield) as a yellow solid. $^1H$ NMR (500 MHz, METHANOL-$d_4$) δ 8.05 (d, J=9.1 Hz, 1H), 7.18 (d, J=1.9 Hz, 1H), 6.85-6.78 (m, 1H), 3.02 (s, 3H). Analytical LC/MS (Method 3): Observed Mass: 232.9; Retention Time: 0.97 min.

Step B. Intermediate 1B. Preparation of 5-bromo-$N^1$-methylbenzene-1,2-diamine (1B)

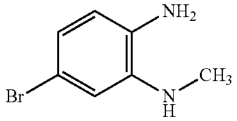

To a solution of Intermediate 1A (16 g, 69 mmol) in MeOH (200 mL) was added tin(II) chloride dihydrate (48 g, 210 mmol). The reaction mixture was stirred at reflux. After 3 h, the reaction mixture was cooled and carefully poured into ice cold 20% NaOH solution (500 mL). The aqueous suspension was partitioned into EtOAc (500 mL), upon which a fine white precipitate formed. The suspension was filtered and the layers were separated. The aqueous phase was extracted with EtOAc (250 mL), the organic phase was combined, washed with brine, dried over $MgSO_4$, filtered and concentrated. The residue was purified by flash column chromatography (330 g silica gel cartridge; A=Hex, B=EtOAc; 30 min grad.; 0% B to 100% B; flow rate=120 mL/min). The fractions corresponding to product were combined, concentrated and dried in vacuo to afford the title compound (12 g, 60 mmol, 87% yield) as a dark oil. $^1H$ NMR (500 MHz, METHANOL-$d_4$) δ 6.66-6.62 (m, 2H), 6.60-6.57 (m, 1H), 2.81 (s, 3H). Analytical LC/MS (Method 3): Observed Mass: 200.9; Retention Time: 0.60 min.

Step C. Intermediate 1C. Preparation of 6-bromo-2-(3,4-dimethoxyphenyl)-1-methyl-1H-benzo[d]imidazole (1C)

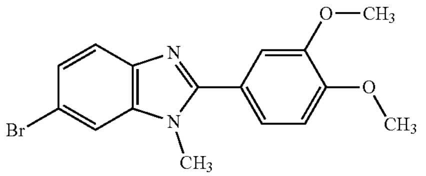

To a 40 mL vial were added Intermediate 1B (0.75 g, 3.7 mmol), 3,4-dimethoxybenzaldehyde (0.74 g, 4.4 mmol) and MeOH (5 mL). The vial was capped and the mixture was stirred at 60° C. After 18 h, the reaction mixture was cooled, diluted with water (100 mL) and extracted with EtOAc (2×50 mL). The organic phase was combined, washed with brine, dried over $MgSO_4$, filtered and concentrated. The residue was purified by flash column chromatography (80 g silica gel cartridge; A=Hex, B=EtOAc; 30 min grad.; 0% B to 100% B; flow rate=60 mL/min). The fractions corresponding to product were combined, concentrated and dried in vacuo to afford the title compound (0.31 g, 0.89 mmol, 24% yield) as a yellow solid. $^1H$ NMR (500 MHz, METHANOL-$d_4$) δ 7.79-7.77 (m, 1H), 7.61-7.57 (m, 1H), 7.45-7.42 (m, 1H), 7.41-7.39 (m, 1H), 7.38-7.35 (m, 1H), 7.19-7.15 (m, 1H), 3.95 (s, 3H), 3.94 (s, 3H), 3.90 (s, 3H). Analytical LC/MS (Method 3): Observed Mass: 346.9; Retention Time: 0.68 min.

Step D. Intermediate 1D. Preparation of tert-butyl 4-(2-(3,4-dimethoxyphenyl)-1-methyl-1H-benzo[d]imidazol-6-yl)-3,6-dihydropyridine-1(2H)-carboxylate (1D)

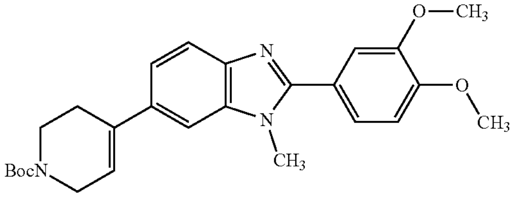

To a 40 mL vial were added Intermediate 1C (0.31 g, 0.89 mmol), tert-butyl 4-(4,4,5,5-tetramethyl-1,3,2-dioxaborolan-2-yl)-3,6-dihydropyridine-1(2H)-carboxylate (0.33 g, 1.1 mmol), followed by 1,4-dioxane (10 mL) and potassium phosphate tribasic (0.57 g, 2.7 mmol) dissolved in water (1 mL). The vial was purged with $N_2$, then 1,1'-bis(diphenylphosphino)ferrocene-palladium(II)dichloride dichloromethane complex (0.036 g, 0.045 mmol) was added. The vial was purged again with $N_2$, and the reaction stirred at 75° C. After 18 h, the reaction mixture was cooled and the mixture was partitioned into water (30 mL) and ethyl acetate (30 mL). The layers were separated, the aqueous phase was extracted with EtOAc (20 mL), the organic phase was combined, washed with brine, dried over $MgSO_4$, filtered and concentrated. The residue was purified by flash column chromatography (80 g silica gel cartridge; A=Hex, B=EtOAc; 20 min grad.; 0% B to 100% B; flow rate=60 mL/min). The fractions corresponding to product were combined, concentrated and dried in vacuo to afford the title compound (0.37 g, 0.82 mmol, 92% yield) as a pale yellow solid. $^1H$ NMR (500 MHz, METHANOL-$d_4$) δ 7.65-7.60 (m, 1H), 7.59-7.55 (m, 1H), 7.47-7.42 (m, 1H), 7.41-7.39 (m, 1H), 7.38-7.35 (m, 1H), 7.20-7.15 (m, 1H), 6.24-6.14 (m, 1H), 4.16-4.10 (m, 2H), 3.95 (s, 6H), 3.94-3.91 (m, 3H), 3.75-3.66 (m, 2H), 2.70-2.65 (m, 2H), 1.53 (s, 9H). Analytical LC/MS (Method 3): Observed Mass: 450.2; Retention Time: 0.91 min.

Step E. Intermediate 1E. Preparation of tert-butyl 4-(2-(3,4-dimethoxyphenyl)-1-methyl-1H-benzo[d]imidazol-6-yl)piperidine-1-carboxylate (1E)

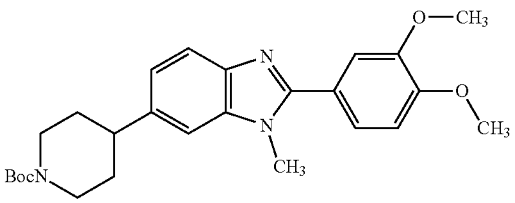

To a 100 mL pear shaped flask were added Intermediate 1D (0.37 g, 0.82 mmol) and MeOH (20 mL). The vessel was evacuated and purged with $N_2$, then Pd—C (10% wt.) (0.088 g, 0.082 mmol) was added and the reaction mixture was stirred under hydrogen at 1 atm. After 2.5 h, the catalyst was filtered and the filtrate was concentrated. The product was dried in vacuo to afford the title compound (0.34 g, 0.75 mmol, 91% yield) as a pale yellow solid. $^1$H NMR (500 MHz, METHANOL-$d_4$) δ 7.60 (s, 1H), 7.44-7.42 (m, 1H), 7.41-7.38 (m, 1H), 7.38-7.34 (m, 1H), 7.25-7.21 (m, 1H), 7.19-7.15 (m, 1H), 4.32-4.24 (m, 2H), 3.95 (s, 6H), 3.91 (s, 3H), 2.99-2.88 (m, 3H), 1.97-1.90 (m, 2H), 1.79-1.69 (m, 2H), 1.52 (s, 9H). Analytical LC/MS (Method 3): Observed Mass: 452.2; Retention Time: 0.81 min.

Step F. Intermediate 1F. Preparation of 2-(3,4-dimethoxyphenyl)-1-methyl-6-(piperidin-4-yl)-1H-benzo[d]imidazole bis(2,2,2-trifluoroacetate)

(1F)

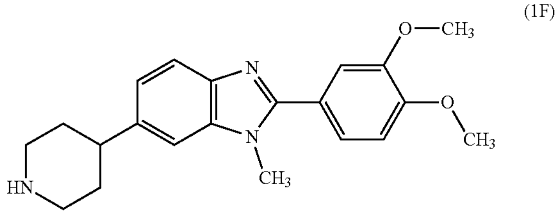 [SMILES: COc1ccc(-c2nc3ccc(C4CCNCC4)cc3n2C)cc1OC]

To a 100 mL pear shaped flask were added Intermediate 1E (0.34 g, 0.75 mmol), DCM (8 mL), and TFA (2 mL). After stirring 15 min, the solvent was concentrated, the residue was co-evaporated with toluene (2×), and the product was dried in vacuo to afford the title compound (0.41 g, 0.71 mmol, 95% yield) as a pale yellow solid. $^1$H NMR (500 MHz, METHANOL-$d_4$) δ 7.87-7.84 (m, 1H), 7.83-7.80 (m, 1H), 7.65-7.62 (m, 1H), 7.56-7.52 (m, 1H), 7.50-7.46 (m, 1H), 7.34-7.31 (m, 1H), 4.15 (s, 3H), 4.00 (s, 3H), 3.98 (s, 3H), 3.63-3.57 (m, 2H), 3.29-3.19 (m, 3H), 2.28-2.18 (m, 2H), 2.14-2.00 (m, 2H). Analytical LC/MS (Method 3): Observed Mass: 352.1; Retention Time: 0.51 min.

Step G. Example 1

To a 40 mL vial were added Intermediate 1F (50 mg, 0.086 mmol), 1-isopropylpiperidin-4-one (61 mg, 0.43 mmol), AcOH (5.7 mg, 0.095 mmol), magnesium sulfate (220 mg, 1.8 mmol), and DMF (2 mL). The reaction mixture was stirred for 20 min, then sodium triacetoxyborohydride (91 mg, 0.43 mmol) was added and the reaction mixture was stirred. After 18 h, the reaction mixture was filtered and the filter cake was washed with 10% IPA/chloroform (20 mL). The filtrate was washed with 10% aqueous NaOH (10 mL), brine, dried over $MgSO_4$, filtered and concentrated. The crude material was purified via preparative HPLC (Prep Method 1) to afford the title compound (13 mg, 0.027 mmol, 31% yield). $^1$H NMR (500 MHz, DMSO-$d_6$) δ 7.55 (d, J=8.2 Hz, 1H), 7.45 (s, 1H), 7.41-7.35 (m, 2H), 7.14 (dd, J=8.2, 4.0 Hz, 2H), 3.90-3.83 (m, 9H), 3.04-2.97 (m, 2H), 2.89-2.80 (m, 2H), 2.72-2.57 (m, 2H), 2.31-2.24 (m, 2H), 2.24-2.18 (m, 1H), 2.15-2.03 (m, 2H), 1.86-1.80 (m, 2H), 1.80-1.71 (m, 4H), 1.50-1.39 (m, 2H), 0.97 (d, J=6.4 Hz, 6H). TLR9 $IC_{50}$ (nM)=56. Analytical LC/MS (Method 1): Purity: 96.9%; Observed Mass: 477.18; Retention Time: 0.61 min. (Method 2): Purity: 100%; Observed Mass: 476.96; Retention Time: 1.26 min.

Example 2

2-(3,4-dimethoxyphenyl)-6-(1'-isopropyl-[1,4'-bipiperidin]-4-yl)-1H-benzo[d]imidazole (2)

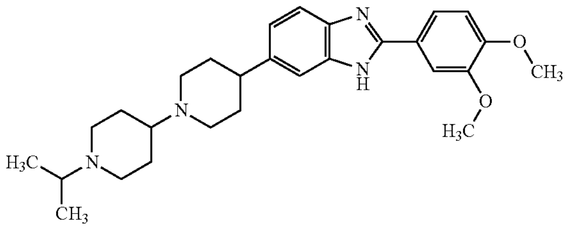

Step A. Intermediate 2A. Preparation of 6-bromo-2-(3,4-dimethoxyphenyl)-1H-benzo[d]imidazole (2A)

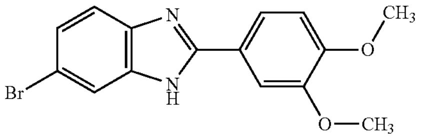

Intermediate 2A was synthesized according to methods described for the preparation of Intermediate 1C, using 4-bromobenzene-1,2-diamine (6 g, 32 mmol) as starting material to afford the title compound (3.7 g, 11 mmol, 34% yield) as an off white solid. $^1$H NMR (500 MHz, METHANOL-$d_4$) δ 7.77-7.71 (m, 1H), 7.70-7.65 (m, 1H), 7.59-7.44 (m, 2H), 7.41-7.34 (m, 1H), 7.17-7.10 (m, 1H), 4.00-3.95 (m, 3H), 3.93 (s, 3H). Analytical LC/MS (Method 1): Observed Mass: 335.2; Retention Time: 0.65 min.

Step B. Intermediate 2B. Preparation of tert-butyl 4-(2-(3,4-dimethoxyphenyl)-1H-benzo[d]imidazol-6-yl)-3,6-dihydropyridine-1(2H)-carboxylate (2B)

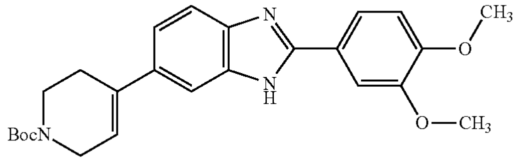

Intermediate 2B was synthesized according to methods described for the preparation of Intermediate 1D, using Intermediate 2A (1.2 g, 3.6 mmol) as starting material to afford the title compound (1.4 g, 3.2 mmol, 89% yield) as a pale yellow solid. $^1$H NMR (500 MHz, METHANOL-$d_4$) δ 7.75 (d, J=2.2 Hz, 1H), 7.71-7.66 (m, 1H), 7.65-7.50 (m, 2H), 7.41-7.37 (m, 1H), 7.13 (d, J=8.5 Hz, 1H), 6.19-6.09 (m, 1H), 4.16-4.09 (m, 2H), 3.98 (s, 3H), 3.93 (s, 3H), 3.75-3.67 (m, 2H), 2.70-2.58 (m, 2H), 1.53 (s, 9H). Analytical LC/MS (Method 3): Observed Mass: 436.3; Retention Time: 0.81 min.

Step C. Intermediate 2C. Preparation of tert-butyl 4-(2-(3,4-dimethoxyphenyl)-1H-benzo[d]imidazol-6-yl)piperidine-1-carboxylate (2C)

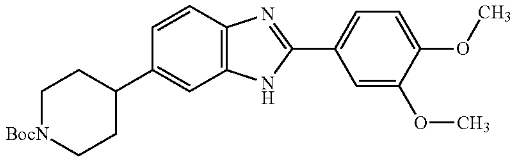

Intermediate 2C was synthesized according to methods described for the preparation of Intermediate IE, using Intermediate 2B (1.4 g, 3.2 mmol) as starting material to afford the title compound (0.98 g, 2.1 mmol, 69% yield) as an off white solid. $^1$H NMR (500 MHz, METHANOL-$d_4$) δ 7.76-7.73 (m, 1H), 7.70-7.65 (m, 1H), 7.57-7.49 (m, 1H), 7.48-7.40 (m, 1H), 7.19-7.16 (m, 1H), 7.14-7.10 (m, 1H), 4.30-4.22 (m, 2H), 4.00-3.97 (m, 3H), 3.95-3.92 (m, 3H), 2.99-2.81 (m, 3H), 1.97-1.88 (m, 2H), 1.76-1.63 (m, 2H), 1.53-1.49 (m, 9H). Analytical LC/MS (Method 3): Observed Mass: 438.2; Retention Time: 0.81 min.

Step D. Intermediate 2D. Preparation of 2-(3,4-dimethoxyphenyl)-6-(piperidin-4-yl)-1H-benzo[d]imidazole dihydrochloride (2D)

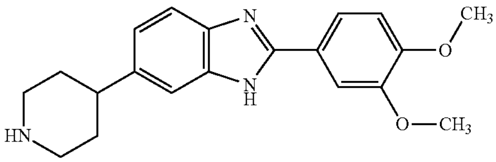

To a 100 mL pear shaped flask were added Intermediate 4C (430 mg, 0.98 mmol) and a minimal amount of MeOH. To this mixture was added 4 M HCl in dioxane (20 mL) and the reaction mixture was stirred. After 15 min, the solvent was concentrated, and the residue was co-evaporated with toluene. The product was dried in vacuo to afford the title compound (400 mg, 0.97 mmol, 99% yield) as an off white solid. $^1$H NMR (500 MHz, METHANOL-$d_4$) δ 7.81-7.74 (m, 3H), 7.71-7.67 (m, 1H), 7.56-7.51 (m, 1H), 7.31-7.27 (m, 1H), 4.02 (s, 3H), 4.00 (s, 3H), 3.63-3.55 (m, 2H), 3.28-3.18 (m, 3H), 2.24-2.17 (m, 2H), 2.12-2.01 (m, 2H). Analytical LC/MS (Method 3): Observed Mass: 338.3; Retention Time: 0.58 min.

Step E. Example 2

To a 40 mL vial were added Intermediate 2D (60 mg, 0.15 mmol), 1-isopropylpiperidin-4-one (110 mg, 0.78 mmol), AcOH (11 mg, 0.18 mmol), magnesium sulfate (220 mg, 1.8 mmol), and DMF (2 mL). The reaction mixture was stirred for 20 min, then sodium triacetoxyborohydride (170 mg, 0.80 mmol) was added and the reaction mixture was stirred. After 18 h, the reaction mixture was filtered and the filter cake was washed with 10% IPA/chloroform (20 mL). The filtrate was washed with 10% aqueous NaOH (10 mL), brine, dried over $MgSO_4$, filtered and concentrated. The crude material was purified via preparative HPLC (Prep Method 1) to afford the title compound (37 mg, 0.080 mmol, 53% yield). $^1$H NMR (500 MHz, DMSO-$d_6$) δ 7.75 (s, 1H), 7.74-7.70 (m, 1H), 7.55-7.45 (m, 1H), 7.44-7.31 (m, 1H), 7.14-7.11 (m, 1H), 7.11-7.05 (m, 1H), 3.89 (s, 3H), 3.84 (s, 3H), 3.53-3.41 (m, 1H), 3.06-2.98 (m, 2H), 2.96-2.87 (m, 2H), 2.83-2.71 (m, 1H), 2.66-2.58 (m, 1H), 2.38-2.28 (m, 3H), 2.26-2.16 (m, 2H), 1.86-1.78 (m, 3H), 1.75-1.66 (m, 2H), 1.56-1.45 (m, 2H), 1.03-0.98 (m, 6H). TLR9 $IC_{50}$ (nM)=120. Analytical LC/MS (Method 1): Purity: 98%; Observed Mass: 463.03; Retention Time: 0.97 min. (Method 2): Purity: 100%; Observed Mass: 463.16; Retention Time: 1.23 min.

Example 3

2-(3,4-dimethoxyphenyl)-1-isopropyl-6-(1'-isopropyl-[1,4'-bipiperidin]-4-yl)-1H-benzo[d]imidazole (3)

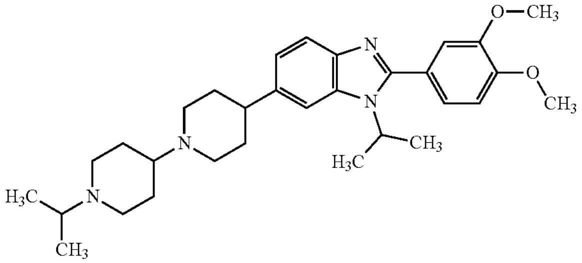

Step A. Intermediate 3A. Preparation of 5-bromo-N-isopropyl-2-nitroaniline (3A)

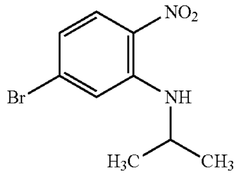

Intermediate 3A was synthesized according to methods described for the preparation of Intermediate 1A, using 4-bromo-2-fluoro-1-nitrobenzene (1.0 g, 4.5 mmol) as starting material, and substituting propan-2-amine (0.67 g, 11 mmol) where appropriate to afford the title compound (1.1 g, 4.2 mmol, 93% yield) as a yellow solid. $^1$H NMR (500 MHz, METHANOL-$d_4$) δ 8.06-8.03 (m, 1H), 7.25-7.19 (m, 1H), 6.84-6.78 (m, 1H), 3.98-3.87 (m, 1H), 1.35-1.33 (m, 6H). Analytical LC/MS (Method 3): Observed Mass: 259.1; Retention Time: 1.07 min.

Step B. Intermediate 3B. Preparation of tert-butyl 4-(3-(isopropylamino)-4-nitrophenyl)-3,6-dihydropyridine-1(2H)-carboxylate

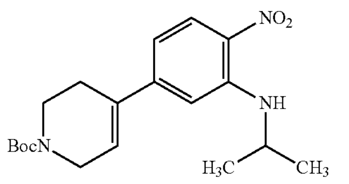

(3B)

To a 40 mL vial were added Intermediate 3A (1.1 g, 4.2 mmol), tert-butyl 4-(4,4,5,5-tetramethyl-1,3,2-dioxaborolan-2-yl)-3,6-dihydropyridine-1(2H)-carboxylate (1.7 g, 5.5 mmol), followed by 1,4-dioxane (10 mL) and potassium phosphate tribasic (2.9 g, 14 mmol) dissolved in water (2 mL). The vessel degassed with $N_2$, 1,1'-bis(diphenylphosphino)ferrocene-palladium(II)dichloride dichloromethane complex (0.19 g, 0.23 mmol) was added, the vial capped and the reaction mixture was stirred at 75° C. After 18 h, the reaction mixture was cooled, diluted with water (100 mL) and extracted with EtOAc (2×50 mL). The organic phase was combined, washed with brine, dried over $MgSO_4$, filtered and concentrated. The residue was purified by flash column chromatography (80 g silica gel cartridge; A=Hex, B=EtOAc; 30 min grad.; 0% B to 100% B; flow rate=60 mL/min). The fractions corresponding to product were combined, concentrated and dried in vacuo to afford the title compound (1.4 g, 3.9 mmol, 93% yield) as a yellow solid. $^1H$ NMR (500 MHz, METHANOL-$d_4$) δ 8.13-8.08 (m, 1H), 6.97-6.93 (m, 1H), 6.81-6.75 (m, 1H), 6.36-6.29 (m, 1H), 4.17-4.08 (m, 2H), 3.70-3.63 (m, 2H), 2.59-2.51 (m, 2H), 1.52 (s, 9H), 1.38-1.34 (m, 6H) (one proton obscured). Analytical LC/MS (Method 3): Observed Mass: 362.2; Retention Time: 1.16 min.

Step C. Intermediate 3C. Preparation of tert-butyl 4-(4-amino-3-(isopropylamino) phenyl)piperidine-1-carboxylate

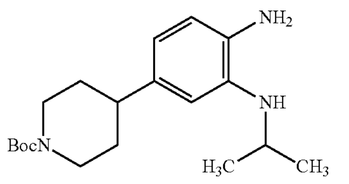

(3C)

To a 100 mL round bottomed flask were added Intermediate 3B (1.4 g, 3.9 mmol) and MeOH (50 mL). The vessel was evacuated and purged with $N_2$ (2×), then Pd—C (10% wt.) (0.42 g, 0.39 mmol) was added. The reaction mixture was stirred under hydrogen at 1 atm. After 18 h, the reaction mixture was filtered, the filtrate concentrated and the product was dried in vacuo to afford the title compound (1.3 g, 3.9 mmol, 100% yield) as a pale yellow solid. $^1H$ NMR (500 MHz, METHANOL-$d_4$) δ 6.70-6.67 (m, 1H), 6.56-6.52 (m, 1H), 6.48-6.44 (m, 1H), 4.24-4.14 (m, 2H), 3.68-3.57 (m, 1H), 2.93-2.77 (m, 2H), 2.63-2.53 (m, 1H), 1.83-1.75 (m, 2H), 1.59-1.51 (m, 2H), 1.50 (s, 9H), 1.23 (d, J=6.3 Hz, 6H). Analytical LC/MS (Method 3): Observed Mass: 334.3; Retention Time: 0.76 min.

Step D. Intermediate 3D. Preparation of tert-butyl 4-(2-(3,4-dimethoxyphenyl)-1-isopropyl-1H-benzo[d]imidazol-6-yl)piperidine-1-carboxylate (3D)

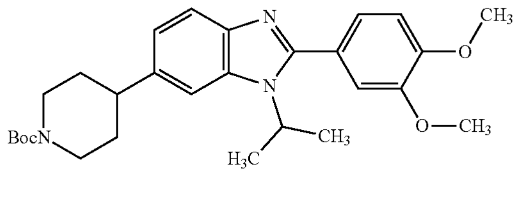

To a 40 mL vial were added Intermediate 3C (0.57 g, 1.7 mmol) and NMP (7 mL). To this mixture was added sodium metabisulfite (0.49 g, 2.6 mmol), followed by 3,4-dimethoxybenzaldehyde (0.33 g, 2.0 mmol). The reaction mixture was heated to 70° C. and stirred. After 24 h, the reaction mixture was cooled, diluted with water (100 mL) and extracted with EtOAc (50 mL). The organic phase was washed with water (50 mL) and the combined aqueous phase was extracted with EtOAc (20 mL). The organic phase was combined, washed with brine, dried over $MgSO_4$, filtered and concentrated. The residue was purified by flash column chromatography (80 g silica gel cartridge; A=Hex, B=EtOAc; 30 min grad.; 0% B to 100% B; flow rate=60 mL/min). The fractions corresponding to product were combined, concentrated and dried in vacuo to afford the title compound (0.77 g, 1.6 mmol, 94% yield) as a light yellow solid. $^1H$ NMR (500 MHz, METHANOL-$d_4$) δ 7.63-7.59 (m, 2H), 7.24 (d, J=1.9 Hz, 1H), 7.23-7.20 (m, 2H), 7.17 (s, 1H), 4.31-4.24 (m, 2H), 3.95 (s, 3H), 3.93 (s, 3H), 3.01-2.86 (m, 3H), 1.96-1.90 (m, 2H), 1.78-1.70 (m, 2H), 1.69 (s, 3H), 1.68 (s, 3H), 1.52 (s, 9H) (one proton obscured). Analytical LC/MS (Method 3): Observed Mass: 480.5; Retention Time: 0.85 min.

Step E. Intermediate 3E. Preparation of 2-(3,4-dimethoxyphenyl)-1-isopropyl-6-(piperidin-4-yl)-1H-benzo[d]imidazole dihydrochloride (3E)

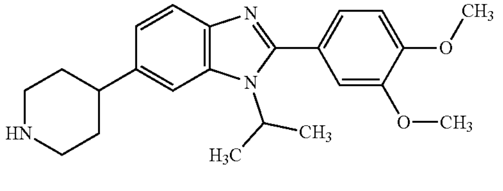

To a 100 mL pear shaped flask were added Intermediate 3D (0.77 g, 1.6 mmol) and a minimal amount of MeOH. To this mixture was added 4 M HCl in dioxane (20 mL) and the reaction mixture was stirred. After 2 h, the solvent was concentrated, and the residue was co-evaporated with toluene. The product was dried in vacuo to afford the title compound (0.68 g, 1.5 mmol, 94% yield) as an off white solid. $^1H$ NMR (500 MHz, METHANOL-$d_4$) δ 8.04 (s, 1H), 7.86-7.83 (m, 1H), 7.67-7.64 (m, 1H), 7.45-7.42 (m, 1H), 7.41-7.39 (m, 1H), 7.33-7.30 (m, 1H), 4.01-3.99 (m, 3H), 3.98-3.95 (m, 3H), 3.63-3.58 (m, 2H), 3.31-3.20 (m, 4H), 2.25-2.18 (m, 2H), 2.16-2.08 (m, 2H), 1.84 (s, 3H), 1.83 (s, 3H). Analytical LC/MS (Method 3): Observed Mass: 380.4; Retention Time: 0.57 min.

Step F. Example 3

To a 40 mL vial were added Intermediate 3E (65 mg, 0.14 mmol), 1-isopropylpiperidin-4-one (110 mg, 0.78 mmol), AcOH (11 mg, 0.18 mmol), magnesium sulfate (220 mg, 1.8 mmol), and DMF (2 mL). The reaction mixture was stirred for 20 min, then sodium triacetoxyborohydride (170 mg, 0.80 mmol) was added and the reaction mixture was stirred. After 18 h, the reaction mixture was filtered and the filter cake was washed with 10% IPA/chloroform (20 mL). The filtrate was washed with 10% aqueous NaOH (10 mL), brine, dried over $MgSO_4$, filtered and concentrated. The crude material was purified via preparative HPLC (Prep Method 1) to afford the title compound (61 mg, 0.12 mmol, 86% yield). $^1$H NMR (500 MHz, DMSO-$d_6$) δ 7.60-7.54 (m, 2H), 7.15 (br d, J=2.4 Hz, 4H), 4.82-4.71 (m, 1H), 3.85 (s, 3H), 3.83 (s, 3H), 3.58-3.44 (m, 4H), 3.09-2.93 (m, 3H), 2.74-2.62 (m, 1H), 2.43-2.21 (m, 4H), 1.88-1.80 (m, 3H), 1.80-1.70 (m, 2H), 1.59 (d, J=6.9 Hz, 6H), 1.57-1.46 (m, 2H), 1.03 (s, 3H), 1.02 (s, 3H). TLR9 $IC_{50}$ (nM)=170. Analytical LC/MS (Method 1): Purity: 90.4%; Observed Mass: 505.02; Retention Time: 1.00 min. (Method 2) Purity: 90.8%; Observed Mass: 504.96; Retention Time: 1.37 min.

Example 4

1-(2,2-difluoroethyl)-2-(3,4-dimethoxyphenyl)-6-(1'-isopropyl-[1,4'-bipiperidin]-4-yl)-1H-benzo[d]imidazole (4)

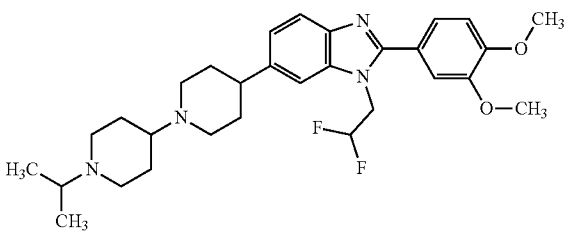

Step A. Intermediate 4A. Preparation of 5-bromo-N-(2,2-difluoroethyl)-2-nitroaniline (4A)

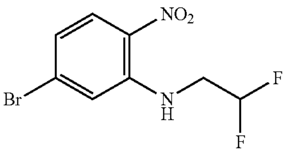

To a 40 mL vial were added 4-bromo-2-fluoro-1-nitrobenzene (1.0 g, 4.6 mmol), and MeCN (20 mL). To this mixture was added 2,2-difluoroethan-1-amine (0.92 g, 12 mmol), the vial was capped and the reaction mixture was stirred at 80° C. After 18 h, the reaction mixture was cooled, the solvent concentrated and the residue was purified by flash column chromatography (120 g silica gel cartridge; A=Hex, B=EtOAc; 35 min grad.; 0% B to 100% B; flow rate=80 mL/min). The fractions corresponding to product were combined, concentrated and dried in vacuo to afford the title compound (1.2 g, 4.3 mmol, 93% yield) as a yellow solid. $^1$H NMR (400 MHz, METHANOL-$d_4$) δ 8.10-8.05 (m, 1H), 7.39-7.34 (m, 1H), 6.95-6.87 (m, 1H), 6.29-5.93 (m, 1H), 3.92-3.79 (m, 2H). Analytical LC/MS (Method 3): Observed Mass: 281.1; Retention Time: 0.98 min.

Step B. Intermediate 4B. Preparation of tert-butyl 4-(3-((2,2-difluoroethyl)amino)-4-nitrophenyl)-3,6-dihydropyridine-1(2H)-carboxylate (4B)

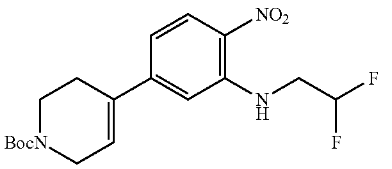

Intermediate 4B was synthesized according to methods described for the preparation of Intermediate 3B, using Intermediate 4A (1.2 g, 4.3 mmol) as starting material to afford the title compound (1.6 g, 4.2 mmol, 98% yield) as a yellow solid. $^1$H NMR (400 MHz, METHANOL-$d_4$) δ 8.18 (d, J=2.2 Hz, 1H), 7.70 (s, 1H), 7.15 (d, J=9.0 Hz, 1H), 6.25-5.94 (m, 1H), 6.13 (br s, 1H), 4.14-4.05 (m, 2H), 3.93-3.81 (m, 2H), 3.70-3.62 (m, 2H), 2.57-2.48 (m, 2H), 1.51 (s, 9H). Analytical LC/MS (Method 3): Observed Mass: 328.3 (–tBu); Retention Time: 1.07 min.

Step C. Intermediate 4C. Preparation of tert-butyl 4-(4-amino-3-((2,2-difluoroethyl) amino)phenyl) piperidine-1-carboxylate (4C)

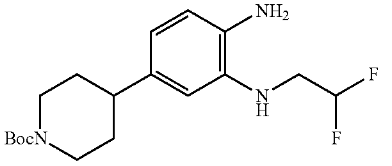

Intermediate 4C was synthesized according to methods described for the preparation of Intermediate 3C, using Intermediate 4B (1.6 g, 4.2 mmol) as starting material to afford the title compound (1.5 g, 4.2 mmol, 100% yield) as a pale yellow solid. $^1$H NMR (500 MHz, METHANOL-$d_4$) δ 6.83-6.77 (m, 2H), 6.76-6.73 (m, 1H), 6.15-5.89 (m, 1H), 4.24-4.16 (m, 2H), 3.59-3.48 (m, 2H), 3.34-3.32 (m, 2H), 2.93-2.77 (m, 2H), 2.65-2.55 (m, 1H), 1.85-1.75 (m, 2H), 1.51-1.49 (m, 9H). Analytical LC/MS (Method 3): Observed Mass: 300.3 (–tBu); Retention Time: 0.81 min.

Step D. Intermediate 4D. Preparation of tert-butyl 4-(1-(2,2-difluoroethyl)-2-(3,4-dimethoxyphenyl)-1H-benzo[d]imidazol-6-yl)piperidine-1-carboxylate (4D)

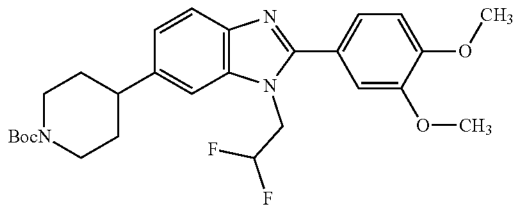

Intermediate 4D was synthesized according to methods described for the preparation of Intermediate 3D, using Intermediate 4C (1.5 g, 4.2 mmol) as starting material to afford the title compound (1.5 g, 3.0 mmol, 71% yield). $^{1}H$ NMR (500 MHz, METHANOL-$d_4$) δ 7.61-7.55 (m, 2H), 7.34-7.28 (m, 3H), 7.20-7.15 (m, 1H), 6.41-6.13 (m, 1H), 4.77-4.67 (m, 2H), 4.30-4.23 (m, 2H), 3.95 (s, 3H), 3.93 (s, 3H), 3.02-2.86 (m, 3H), 1.99-1.89 (m, 2H), 1.76-1.64 (m, 2H), 1.52 (s, 9H). Analytical LC/MS (Method 3): Observed Mass: 502.4; Retention Time: 0.85 min.

Step E. Intermediate 4E. Preparation of 1-(2,2-difluoroethyl)-2-(3,4-dimethoxyphenyl)-6-(piperidin-4-yl)-1H-benzo[d]imidazole dihydrochloride (4E)

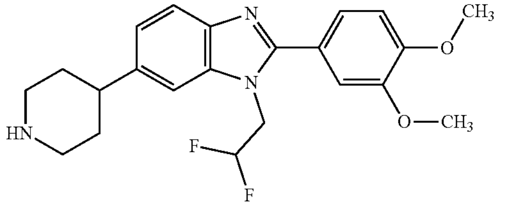

Intermediate 4E was synthesized according to methods described for the preparation of Intermediate 3E, using Intermediate 4D (1.4 g, 2.8 mmol) as starting material to afford the title compound (1.4 g, 2.7 mmol, 96% yield) as a tan solid. 1H NMR (500 MHz, METHANOL-$d_4$) δ 8.01-7.96 (m, 1H), 7.81-7.78 (m, 1H), 7.70-7.65 (m, 1H), 7.52-7.49 (m, 1H), 7.47-7.45 (m, 1H), 7.34-7.29 (m, 1H), 6.60-6.32 (m, 1H), 5.10-5.00 (m, 2H), 4.00 (s, 3H), 3.97 (s, 3H), 3.63-3.54 (m, 2H), 3.24 (br d, J=3.0 Hz, 3H), 2.25-2.18 (m, 2H), 2.15-2.02 (m, 2H). Analytical LC/MS (Method 3): Observed Mass: 402.3; Retention Time: 0.56 min.

Step F. Example 4

To a 40 mL vial were added Intermediate 4E (65 mg, 0.14 mmol), 1-isopropylpiperidin-4-one (110 mg, 0.78 mmol), AcOH (11 mg, 0.18 mmol), magnesium sulfate (220 mg, 1.8 mmol), and DMF (2 mL). The reaction mixture was stirred for 20 min, then sodium triacetoxyborohydride (170 mg, 0.80 mmol) was added and the reaction mixture was stirred. After 18 h, the reaction mixture was filtered and the filter cake was washed with 10% IPA/chloroform (20 mL). The filtrate was washed with 10% aqueous NaOH (10 mL), brine, dried over $MgSO_4$, filtered and concentrated. The crude material was purified via preparative HPLC (Prep Method 1) to afford the title compound (63 mg, 0.12 mmol, 86% yield). $^{1}H$ NMR (500 MHz, DMSO-$d_6$) δ 7.59 (br d, J=8.2 Hz, 1H), 7.53 (s, 1H), 7.29 (s, 2H), 7.24-7.11 (m, 2H), 6.56-6.29 (m, 1H), 4.81-4.71 (m, 2H), 3.86 (s, 3H), 3.84 (s, 3H), 3.06-2.99 (m, 2H), 2.97-2.88 (m, 2H), 2.85-2.76 (m, 1H), 2.69-2.60 (m, 1H), 2.40-2.30 (m, 3H), 2.29-2.19 (m, 2H), 1.88-1.78 (m, 4H), 1.78-1.68 (m, 2H), 1.57-1.46 (m, 2H), 1.02 (br d, J=6.7 Hz, 6H). TLR9 $IC_{50}$ (nM)=250. Analytical LC/MS (Method 1): Purity: 98.7%; Observed Mass: 527.24; Retention Time: 1.00 min. (Method 2): Purity: 98.8%; Observed Mass: 527.25; Retention Time: 1.36 min.

Example 5

2-(3,4-dimethoxyphenyl)-5-(1'-isopropyl-[1,4'-bipiperidin]-4-yl)-1-methyl-1H-benzo[d]imidazole (5)

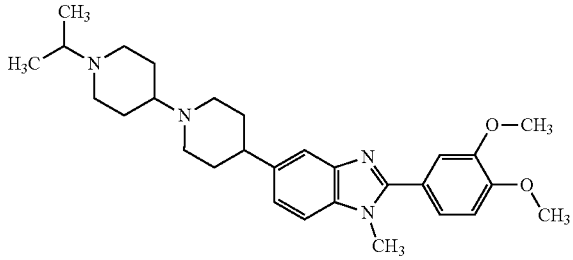

Step A. Intermediate 5A. Preparation of 4-bromo-N-methyl-2-nitroaniline (5A)

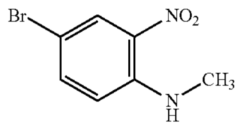

Intermediate 5A was synthesized according to methods described for the preparation of Intermediate 1A, using 4-bromo-1-fluoro-2-nitrobenzene (11 g, 50 mmol) as starting material to afford the title compound (11 g, 48 mmol, 96% yield) as a yellow solid. $^{1}H$ NMR (500 MHz, CHLOROFORM-d) δ 8.35 (d, J=2.5 Hz, 1H), 8.12-7.98 (m, 1H), 7.55 (dd, J=9.1, 2.2 Hz, 1H), 6.78 (d, J=9.1 Hz, 1H), 3.07-3.02 (m, 3H). Analytical LC/MS (Method 3): Observed Mass: 230.8; Retention Time: 0.97 min.

Step B. Intermediate 5B. Preparation of 4-bromo-$N^1$-methylbenzene-1,2-diamine (5B)

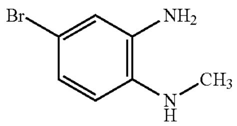

Intermediate 5B was synthesized according to methods described for the preparation of Intermediate 1B, using Intermediate 5A (16 g, 69 mmol) as starting material to afford the title compound (6.5 g, 32 mmol, 46% yield) as a pale yellow solid. $^1$H NMR (500 MHz, CHLOROFORM-d) δ 6.99-6.94 (m, 1H), 6.87-6.84 (m, 1H), 6.56-6.48 (m, 1H), 3.44-3.30 (m, 2H), 2.86 (s, 3H). Analytical LC/MS (Method 3): Observed Mass: 200.8; Retention Time: 0.56 min.

Step C. Intermediate 5C. Preparation of 5-bromo-2-(3,4-dimethoxyphenyl)-1-methyl-1H-benzo[d]imidazole (5C)

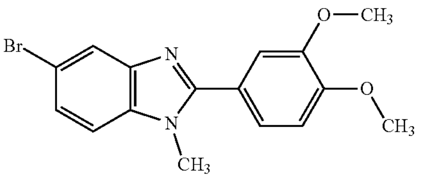

Intermediate 5C was synthesized according to methods described for the preparation of Intermediate 1C, using Intermediate 5B (0.75 g, 3.7 mmol) as starting material to afford the title compound (0.62 g, 1.8 mmol, 49% yield) as a yellow solid. 1H NMR (500 MHz, METHANOL-$d_4$) δ 7.25-7.23 (m, 1H), 7.06-7.03 (m, 1H), 6.99-6.95 (m, 1H), 6.74-6.70 (m, 1H), 6.56-6.53 (m, 1H), 6.30-6.25 (m, 1H), 3.87 (s, 3H), 3.85 (s, 3H), 2.54 (s, 3H). Analytical LC/MS (Method 3): Observed Mass: 348.9; Retention Time: 0.67 min.

Step D. Intermediate 5D. Preparation of tert-butyl 4-(2-(3,4-dimethoxyphenyl)-1-methyl-1H-benzo[d]imidazol-5-yl)-3,6-dihydropyridine-1(2H)-carboxylate (5D)

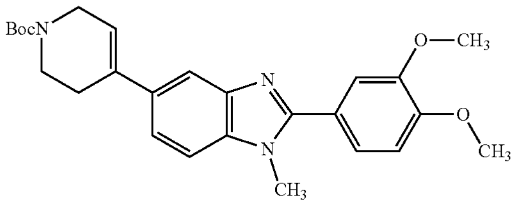

Intermediate 5D was synthesized according to methods described for the preparation of Intermediate 1D, using Intermediate 5C (0.62 g, 1.8 mmol) as starting material to afford the title compound (0.38 g, 0.85 mmol, 47% yield) as a pale yellow solid. $^1$H NMR (500 MHz, METHANOL-$d_4$) δ 7.70 (d, J=0.8 Hz, 1H), 7.54-7.46 (m, 2H), 7.40 (s, 1H), 7.39-7.35 (m, 1H), 7.19-7.16 (m, 1H), 6.17-6.10 (m, 1H), 4.16-4.08 (m, 2H), 3.95 (s, 6H), 3.92 (s, 3H), 3.74-3.67 (m, 2H), 2.68-2.61 (m, 2H), 1.53 (s, 9H). Analytical LC/MS (Method 3): Observed Mass: 450.2; Retention Time: 0.82 min.

Step E. Intermediate 5E. Preparation of tert-butyl 4-(2-(3,4-dimethoxyphenyl)-1-methyl-1H-benzo[d]imidazol-5-yl)piperidine-1-carboxylate (5E)

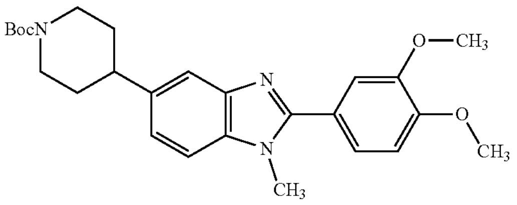

Intermediate 5E was synthesized according to methods described for the preparation of Intermediate 1E, using Intermediate 5D (0.38 g, 0.85 mmol) as starting material to afford the title compound (0.33 g, 0.73 mmol, 86% yield) as a pale yellow semisolid. $^1$H NMR (500 MHz, METHANOL-$d_4$) δ 7.55-7.53 (m, 1H), 7.50-7.47 (m, 1H), 7.40-7.38 (m, 1H), 7.37-7.34 (m, 1H), 7.28-7.25 (m, 1H), 7.18-7.15 (m, 1H), 4.29-4.23 (m, 2H), 3.94 (s, 6H), 3.90 (s, 3H), 3.00-2.84 (m, 3H), 1.95-1.88 (m, 2H), 1.75-1.65 (m, 2H), 1.52 (s, 9H). Analytical LC/MS (Method 3): Observed Mass: 452.2; Retention Time: 0.81 min.

Step F. Intermediate 5F. Preparation of 2-(3,4-dimethoxyphenyl)-1-methyl-5-(piperidin-4-yl)-1H-benzo[d]imidazole bis(2,2,2-trifluoroacetate)

(5F)

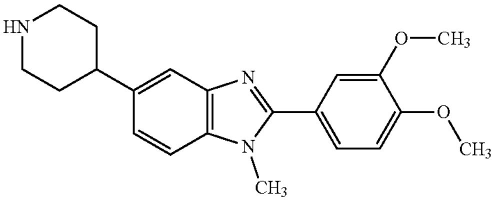

Intermediate 5F was synthesized according to the general methods described for the preparation of Intermediate 1F, using Intermediate 5E (0.33 g, 0.73 mmol) as starting material to afford the title compound (0.42 g, 0.72 mmol, 99% yield) as a pale yellow solid. $^1$H NMR (500 MHz, METHANOL-$d_4$) δ 7.95-7.91 (m, 1H), 7.74-7.71 (m, 1H), 7.67-7.62 (m, 1H), 7.57-7.53 (m, 1H), 7.51-7.46 (m, 1H), 7.34-7.30 (m, 1H), 4.13 (s, 3H), 4.00 (s, 3H), 3.99 (s, 3H), 3.63-3.55 (m, 2H), 3.28-3.18 (m, 3H), 2.25-2.18 (m, 2H), 2.10-1.99 (m, 2H). Analytical LC/MS (Method 3): Observed Mass: 352.1; Retention Time: 0.54 min.

Step G. Example 5

To a 40 mL vial were added Intermediate 5F (50 mg, 0.086 mmol), 1-isopropylpiperidin-4-one (61 mg, 0.43 mmol), AcOH (5.7 mg, 0.095 mmol), magnesium sulfate (220 mg, 1.8 mmol), and DMF (2 mL). The reaction mixture was stirred for 20 min, then sodium triacetoxyborohydride (91 mg, 0.43 mmol) was added and the reaction mixture was stirred. After 18 h, the reaction mixture was filtered and the filter cake was washed with 10% IPA/chloroform (20 mL). The filtrate was washed with 10% aqueous NaOH (10 mL), brine, dried over $MgSO_4$, filtered and concentrated. The crude material was purified via preparative HPLC (Prep Method 1) to afford the title compound (17 mg, 0.036 mmol, 42% yield). $^1H$ NMR (500 MHz, DMSO-$d_6$) δ 7.55-7.47 (m, 2H), 7.41-7.36 (m, 2H), 7.22-7.18 (m, 1H), 7.17-7.13 (m, 1H), 3.86 (br d, J=1.5 Hz, 6H), 3.61-3.53 (m, 1H), 3.25-3.14 (m, 3H), 2.81-2.61 (m, 4H), 2.40-2.31 (m, 1H), 2.05-1.97 (m, 2H), 1.95-1.88 (m, 2H), 1.85-1.65 (m, 5H), 1.15 (br d, J=6.1 Hz, 6H) (4 protons obscured). TLR9 $IC_{50}$ (nM)=250. Analytical LC/MS (Method 1): Purity: 99%; Observed Mass: 477.12; Retention Time: 0.92 min. (Method 2): Purity: 100%; Observed Mass: 477.13; Retention Time: 1.32 min.

Example 6

2-(3,4-dimethoxyphenyl)-1-isopropyl-5-(1'-isopropyl-[1,4'-bipiperidin]-4-yl)-1H-benzo[d]imidazole (6)

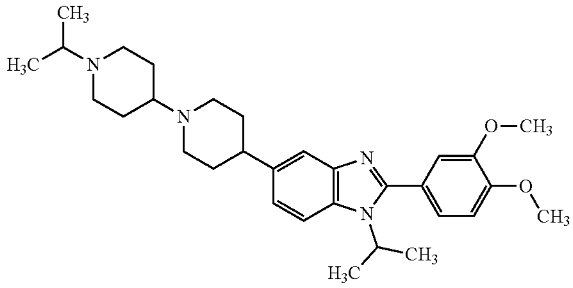

Step A. Intermediate 6A. Preparation of 4-bromo-N-isopropyl-2-nitroaniline (6A)

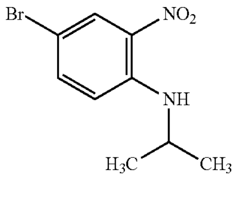

Intermediate 6A was synthesized according to methods described for the preparation of Intermediate 1A, using 4-bromo-1-fluoro-2-nitrobenzene (1.0 g, 4.5 mmol) as starting material, and substituting propan-2-amine (0.67 g, 11 mmol) where appropriate to afford the title compound (1.1 g, 4.2 mmol, 93% yield) as a yellow solid. $^1H$ NMR (500 MHz, METHANOL-$d_4$) δ 8.26-8.23 (m, 1H), 7.60-7.55 (m, 1H), 7.04-6.98 (m, 1H), 3.35-3.31 (m, 1H), 1.34 (s, 3H), 1.33 (s, 3H). Analytical LC/MS (Method 3): Observed Mass: 259.1; Retention Time: 1.08 min.

Step B. Intermediate 6B. Preparation of tert-butyl 4-(4-(isopropylamino)-3-nitrophenyl)-3,6-dihydropyridine-1(2H)-carboxylate (6B)

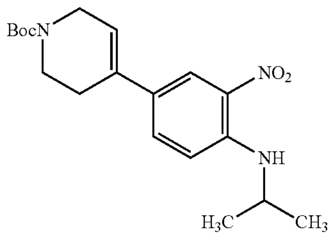

Intermediate 6B was synthesized according to methods described for the preparation of Intermediate 3B, using Intermediate 6A (1.1 g, 4.2 mmol) as starting material to afford the title compound (1.2 g, 3.3 mmol, 79% yield) as a yellow solid. 1H NMR (500 MHz, METHANOL-$d_4$) δ 8.17-8.14 (m, 1H), 7.72-7.67 (m, 1H), 7.08-7.03 (m, 1H), 6.14-6.07 (m, 1H), 4.11-4.04 (m, 2H), 4.04-3.91 (m, 1H), 3.69-3.63 (m, 2H), 2.55-2.49 (m, 2H), 1.51 (s, 9H), 1.36-1.35 (m, 3H), 1.35-1.34 (m, 3H). Analytical LC/MS (Method 3): Observed Mass: 362.2; Retention Time: 1.17 min.

Step C. Intermediate 6C. Preparation of tert-butyl 4-(3-amino-4-(isopropylamino) phenyl)piperidine-1-carboxylate (6C)

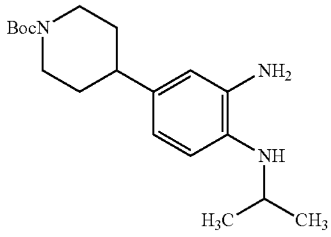

Intermediate 6C was synthesized according to methods described for the preparation of Intermediate 3C, using Intermediate 6B (1.2 g, 3.3 mmol) as starting material to afford the title compound (1.1 g, 3.3 mmol, 100% yield) as a pale yellow solid. $^1H$ NMR (500 MHz, METHANOL-$d_4$) δ 6.66-6.64 (m, 1H), 6.64-6.61 (m, 1H), 6.60-6.56 (m, 1H), 4.25-4.14 (m, 2H), 3.62-3.53 (m, 1H), 2.95-2.77 (m, 2H), 2.61-2.50 (m, 1H), 1.81-1.75 (m, 2H), 1.59-1.51 (m, 2H), 1.49 (s, 9H), 1.23-1.22 (m, 3H), 1.22-1.20 (m, 3H). Analytical LC/MS (Method 3): Observed Mass: 334.3; Retention Time: 0.76 min.

Step D. Intermediate 6D. Preparation of tert-butyl 4-(2-(3,4-dimethoxyphenyl)-1-isopropyl-1H-benzo[d]imidazol-5-yl)piperidine-1-carboxylate (6D)

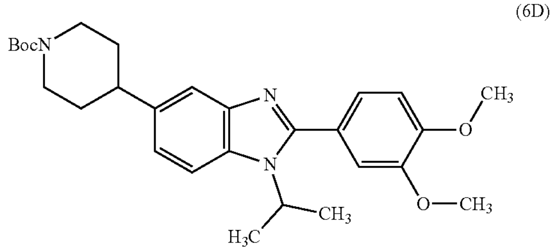 [SMILES: COc1ccc(-c2nc3cc(C4CCN(C(=O)OC(C)(C)C)CC4)ccc3n2C(C)C)cc1OC]

Intermediate 6D was synthesized according to methods described for the preparation of Intermediate 3D, using Intermediate 6C (0.53 g, 1.6 mmol) as starting material to afford the title compound (0.62 g, 1.3 mmol, 81% yield) as a light yellow solid. $^{1}H$ NMR (500 MHz, METHANOL-$d_4$) δ 7.74-7.70 (m, 1H), 7.55-7.52 (m, 1H), 7.25-7.20 (m, 3H), 7.19-7.15 (m, 1H), 4.29-4.23 (m, 2H), 3.95 (s, 3H), 3.93 (s, 3H), 3.02-2.83 (m, 3H), 1.95-1.88 (m, 2H), 1.75-1.69 (m, 1H), 1.68 (s, 3H), 1.67 (s, 3H), 1.51 (s, 9H) (two protons obscured). Analytical LC/MS (Method 3): Observed Mass: 480.4; Retention Time: 0.85 min.

Step E. Intermediate 6E. Preparation of 2-(3,4-dimethoxyphenyl)-1-isopropyl-5-(piperidin-4-yl)-1H-benzo[d]imidazole dihydrochloride (6E)

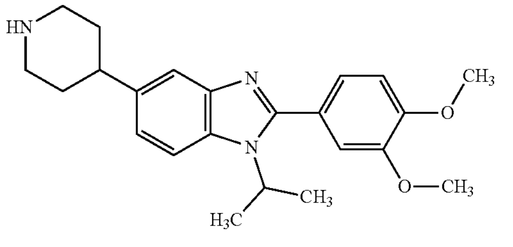

Intermediate 6E was synthesized according to methods described for the preparation of Intermediate 3E, using Intermediate 6D (0.62 g, 1.3 mmol) as starting material to afford the title compound (0.59 g, 1.3 mmol, 100% yield) as an off white solid. $^{1}H$ NMR (500 MHz, METHANOL-$d_4$) δ 8.17-8.13 (m, 1H), 7.77-7.73 (m, 1H), 7.64-7.59 (m, 1H), 7.43-7.40 (m, 1H), 7.40-7.37 (m, 1H), 7.33-7.29 (m, 1H), 5.12-5.05 (m, 1H), 4.00 (s, 3H), 3.97 (s, 3H), 3.62-3.56 (m, 2H), 3.27-3.18 (m, 3H), 2.25-2.18 (m, 2H), 2.10-2.00 (m, 2H), 1.81 (s, 3H), 1.80 (s, 3H). Analytical LC/MS (Method 3): Observed Mass: 380.4; Retention Time: 0.59 min.

Step F. Example 6

To a 40 mL vial were added Intermediate 6E (65 mg, 0.14 mmol), 1-isopropylpiperidin-4-one (110 mg, 0.78 mmol), AcOH (11 mg, 0.18 mmol), magnesium sulfate (220 mg, 1.8 mmol), and DMF (2 mL). The reaction mixture was stirred for 20 min, then sodium triacetoxyborohydride (170 mg, 0.80 mmol) was added and the reaction mixture was stirred. After 18 h, the reaction mixture was filtered and the filter cake was washed with 10% IPA/chloroform (20 mL). The filtrate was washed with 10% aqueous NaOH (10 mL), brine, dried over $MgSO_4$, filtered and concentrated. The crude material was purified via preparative HPLC (Prep Method 1) to afford the title compound (61 mg, 0.12 mmol, 86% yield). $^{1}H$ NMR (500 MHz, DMSO-$d_6$) δ 7.69 (d, J=8.5 Hz, 1H), 7.49 (s, 1H), 7.19-7.17 (m, 1H), 7.17-7.12 (m, 3H), 4.80-4.72 (m, 1H), 3.85 (s, 3H), 3.83 (s, 3H), 3.04-2.97 (m, 2H), 2.91-2.84 (m, 2H), 2.75-2.67 (m, 1H), 2.63-2.57 (m, 1H), 2.34-2.22 (m, 3H), 2.19-2.10 (m, 2H), 1.80 (br s, 4H), 1.75-1.66 (m, 2H), 1.58 (s, 3H), 1.57 (s, 3H), 1.51-1.42 (m, 2H), 0.99 (s, 3H), 0.98 (s, 3H). TLR9 $IC_{50}$ (nM)=190. Analytical LC/MS (Method 1): Purity: 98.6%; Observed Mass: 505.33; Retention Time: 1.05 min. (Method 2): Purity: 98.7%; Observed Mass: 505.02; Retention Time: 1.47 min.

Example 7

1-(2,2-difluoroethyl)-2-(3,4-dimethoxyphenyl)-5-(1'-isopropyl-[1,4'-bipiperidin]-4-yl)-1H-benzo[d]imidazole (7)

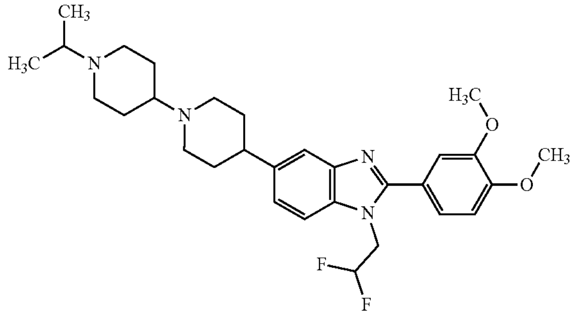

Step A. Intermediate 7A. Preparation of 4-bromo-N-(2,2-difluoroethyl)-2-nitroaniline (7A)

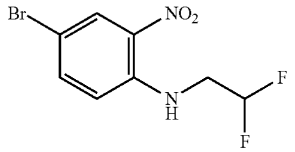

Intermediate 7A was synthesized according to methods described for the preparation of Intermediate 4A, using 4-bromo-1-fluoro-2-nitrobenzene (1.0 g, 4.6 mmol) as starting material to afford the title compound (1.3 g, 4.6 mmol, 100% yield) as a yellow solid. $^{1}H$ NMR (400 MHz, METHANOL-$d_4$) δ 8.30-8.25 (m, 1H), 7.66-7.59 (m, 1H), 7.17-7.08 (m, 1H), 6.27-5.93 (m, 1H), 3.91-3.78 (m, 2H). Analytical LC/MS (Method 3): Observed Mass: 281.2; Retention Time: 0.98 min.

Step B. Intermediate 7B. Preparation of tert-butyl 4-(4-((2,2-difluoroethyl)amino)-3-nitrophenyl)-3,6-dihydropyridine-1(2H)-carboxylate (7B)

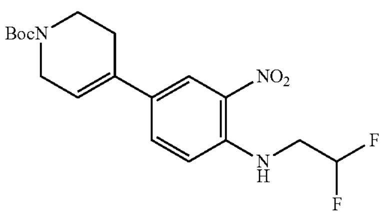

Intermediate 7B was synthesized according to methods described for the preparation of Intermediate 3B, using Intermediate 7A (1.3 g, 4.6 mmol) as starting material to afford the title compound (1.7 g, 4.4 mmol, 100% yield) as a yellow solid. 1H NMR (500 MHz, METHANOL-$d_4$) δ 8.20-8.16 (m, 1H), 7.71 (dd, J=8.9, 2.3 Hz, 1H), 7.18-7.12 (m, 1H), 6.23-5.97 (m, 1H), 6.13 (br s, 1H), 4.14-4.05 (m, 2H), 3.92-3.83 (m, 2H), 3.70-3.64 (m, 2H), 2.57-2.49 (m, 2H), 1.51 (s, 9H). Analytical LC/MS (Method 3): Observed Mass: 328.2 (−tBu); Retention Time: 1.07 min.

Step C. Intermediate 7C. Preparation of tert-butyl 4-(3-amino-4-((2,2-difluoroethyl) amino)phenyl) piperidine-1-carboxylate (7C)

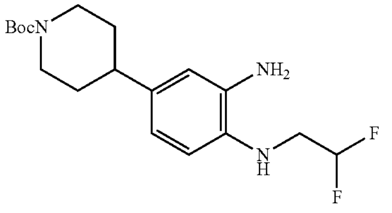

Intermediate 7C was synthesized according to methods described for the preparation of Intermediate 3C, using Intermediate 7B (1.7 g, 4.4 mmol) as starting material to afford the title compound (1.5 g, 4.2 mmol, 95% yield) as a pale yellow solid. $^1$H NMR (500 MHz, METHANOL-$d_4$) δ 6.80-6.77 (m, 1H), 6.77-6.75 (m, 1H), 6.74-6.72 (m, 1H), 6.14-5.88 (m, 1H), 4.25-4.15 (m, 2H), 3.58-3.47 (m, 2H), 2.96-2.77 (m, 2H), 2.64-2.51 (m, 1H), 1.82-1.74 (m, 2H), 1.62-1.51 (m, 2H), 1.49 (s, 9H). Analytical LC/MS (Method 3): Observed Mass: 300.3 (−tBu); Retention Time: 0.81 min.

Step D. Intermediate 7D. Preparation of tert-butyl 4-(1-(2,2-difluoroethyl)-2-(3,4-dimethoxyphenyl)-1H-benzo[d]imidazol-5-yl)piperidine-1-carboxylate (7D)

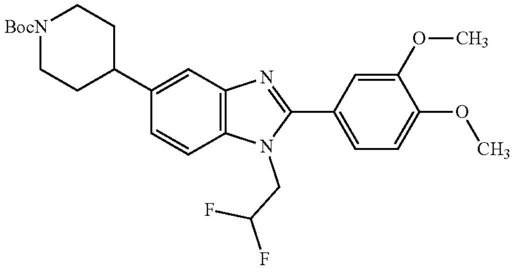

Intermediate 7D was synthesized according to methods described for the preparation of Intermediate 3D, using Intermediate 7C (1.5 g, 4.2 mmol) as starting material to afford the title compound (1.7 g, 3.4 mmol, 81% yield) as a light yellow solid. $^1$H NMR (500 MHz, METHANOL-$d_4$) δ 7.60-7.58 (m, 1H), 7.57-7.56 (m, 1H), 7.34-7.29 (m, 3H), 7.19-7.16 (m, 1H), 6.39-6.14 (m, 1H), 4.77-4.67 (m, 2H), 4.31-4.23 (m, 2H), 3.95 (s, 3H), 3.93 (s, 3H), 3.05-2.84 (m, 3H), 1.97-1.89 (m, 2H), 1.76-1.65 (m, 2H), 1.52 (s, 9H). Analytical LC/MS (Method 3): Observed Mass: 502.4; Retention Time: 0.85 min.

Step E. Intermediate 7E. Preparation of 1-(2,2-difluoroethyl)-2-(3,4-dimethoxyphenyl)-5-(piperidin-4-yl)-1H-benzo[d]imidazole dihydrochloride (7E)

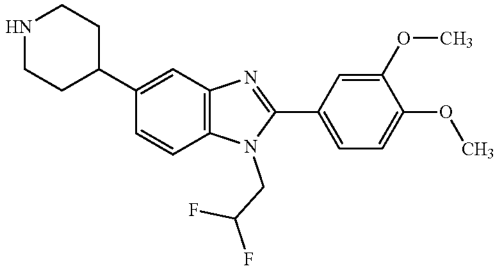

Intermediate 7E was synthesized according to methods described for the preparation of Intermediate 3E, using Intermediate 7D (1.7 g, 3.4 mmol) as starting material to afford the title compound (1.5 g, 3.2 mmol, 94% yield) as a tan solid. 1H NMR (500 MHz, METHANOL-$d_4$) δ 8.05-7.98 (m, 1H), 7.82 (s, 1H), 7.73-7.66 (m, 1H), 7.55-7.51 (m, 1H), 7.48 (d, J=2.2 Hz, 1H), 7.33 (d, J=8.5 Hz, 1H), 6.60-6.33 (m, 1H), 5.13-5.02 (m, 2H), 4.00 (s, 3H), 3.98 (s, 3H), 3.63-3.56 (m, 2H), 3.30-3.21 (m, 3H), 2.27-2.18 (m, 2H), 2.17-2.05 (m, 2H). Analytical LC/MS (Method 3): Observed Mass: 402.3; Retention Time: 0.56 min.

Step G. Example 7

To a 40 mL vial were added Intermediate 7E (65 mg, 0.14 mmol), 1-isopropylpiperidin-4-one (110 mg, 0.78 mmol), AcOH (11 mg, 0.18 mmol), magnesium sulfate (220 mg, 1.8 mmol), and DMF (2 mL). The reaction mixture was stirred for 20 min, then sodium triacetoxyborohydride (170 mg, 0.80 mmol) was added and the reaction mixture was stirred. After 18 h, the reaction mixture was filtered and the filter cake was washed with 10% IPA/chloroform (20 mL). The filtrate was washed with 10% aqueous NaOH (10 mL), brine, dried over $MgSO_4$, filtered and concentrated. The crude material was purified via preparative HPLC (Prep Method 1) to afford the title compound (58 mg, 0.11 mmol, 79% yield). $^1H$ NMR (500 MHz, DMSO-$d_6$) δ 7.57 (br d, J=8.1 Hz, 1H), 7.51 (s, 1H), 7.30-7.25 (m, 2H), 7.20 (d, J=8.5 Hz, 1H), 7.14 (s, 1H), 6.53-6.25 (m, 1H), 4.79-4.68 (m, 2H), 3.84 (s, 3H), 3.82 (s, 3H), 3.03-2.93 (m, 2H), 2.87-2.79 (m, 2H), 2.71-2.56 (m, 2H), 2.33-2.16 (m, 3H), 2.14-2.03 (m, 2H), 1.84-1.63 (m, 6H), 1.49-1.37 (m, 2H), 0.96 (s, 3H), 0.95 (s, 3H). TLR9 $IC_{50}$ (nM)=280. Analytical LC/MS (Method 1): Purity: 100%; Observed Mass: 527.04; Retention Time: 1.02 min. (Method 2): Purity: 100%; Observed Mass: 527.30; Retention Time: 1.45 min.

Examples 8 and 9

2-(3,4-dimethoxyphenyl)-1-ethyl-6-(1'-isopropyl-[1,4'-bipiperidin]-4-yl)-1H-benzo[d]imidazole (8) and 2-(3,4-dimethoxyphenyl)-1-ethyl-5-(1'-isopropyl-[1,4'-bipiperidin]-4-yl)-1H-benzo[d]imidazole (9)

(8)

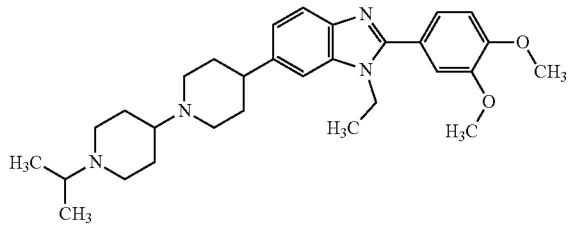

(9)

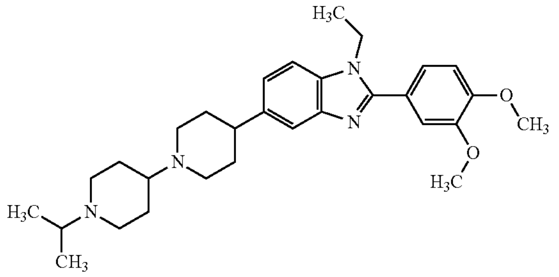

Step A. Intermediate 8A. Preparation of tert-butyl 4-(2-(3,4-dimethoxyphenyl)-1-ethyl-1H-benzo[d]imidazol-6-yl)piperidine-1-carboxylate (Regioisomeric Mixture)

(8A)

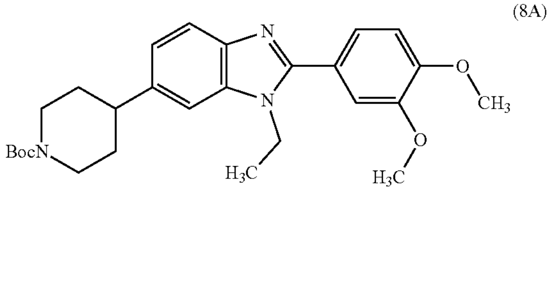 [SMILES: CCn1c(-c2ccc(OC)c(OC)c2)nc2ccc(C3CCN(C(=O)OC(C)(C)C)CC3)cc21]

To a 250 mL round bottomed flask were added Intermediate 2C (0.53 g, 1.2 mmol) and THE (20 mL). The reaction mixture was cooled to 0° C., then NaH (60% dispersion in mineral oil) (0.24 g, 6.1 mmol) was added. After stirring 10 min at the above temperature, iodoethane (0.95 g, 6.1 mmol) was added and the reaction mixture was allowed to reach room temperature. After stirring 18 h, the reaction was quenched with water (200 mL) and extracted with EtOAc (2×100 mL). The organic phase was combined, washed with brine, dried over $MgSO_4$, filtered and concentrated. The residue was purified by flash column chromatography (80 g silica gel cartridge; A=Hex, B=EtOAc; 30 min grad.; 0% B to 100% B; flow rate=60 mL/min). The fractions corresponding to product were combined, concentrated and dried in vacuo to afford the title compound (0.56 g, 1.2 mmol, 100% yield) as a colorless oil. $^1H$ NMR (500 MHz, METHANOL-$d_4$) δ 7.64-7.44 (m, 2H), 7.34-7.28 (m, 2H), 7.28-7.21 (m, 1H), 7.20-7.15 (m, 1H), 4.41-4.32 (m, 2H), 4.31-4.22 (m, 2H), 4.17-4.08 (m, 1H), 3.94 (d, J=5.0 Hz, 6H), 3.02-2.83 (m, 2H), 1.99-1.86 (m, 2H), 1.80-1.66 (m, 2H), 1.54-1.49 (m, 9H), 1.47-1.40 (m, 3H). Analytical LC/MS (Method 3): Observed Mass: 466.5; Retention Time: 0.82 min.

Step B. Intermediate 8B. Preparation of 2-(3,4-dimethoxyphenyl)-1-ethyl-6-(piperidin-4-yl)-1H-benzo[d]imidazole dihydrochloride (Regioisomeric Mixture)

(8B)

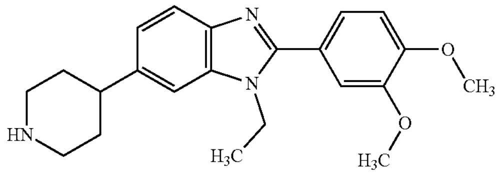

To a 250 mL round bottomed flask were added Intermediate 8A (0.56 g, 1.2 mmol) and 4 M HCl in dioxane (20 mL). After stirring 2 h, the solvent was concentrated and the residue was co-evaporated with toluene. The product was dried in vacuo to afford the title compound (0.53 g, 1.2 mmol, 100% yield) as a pale yellow solid. $^1H$ NMR (500 MHz, METHANOL-$d_4$) δ 8.02-7.76 (m, 2H), 7.69-7.64 (m, 1H), 7.53-7.49 (m, 1H), 7.47-7.44 (m, 1H), 7.35-7.31 (m, 1H), 4.67-4.58 (m, 2H), 4.01 (s, 3H), 3.98 (s, 3H), 3.63-3.57 (m, 2H), 3.29-3.20 (m, 3H), 2.26-2.16 (m, 2H), 2.15-2.02 (m, 2H), 1.65-1.57 (m, 3H). Analytical LC/MS (Method 3): Observed Mass: 366.4; Retention Time: 0.57 min.

Step C. Examples 8 and 9

To a 40 mL vial were added Intermediate 8B (regioisomeric mixture) (120 mg, 0.27 mmol), 1-isopropylpiperidin-4-one (200 mg, 1.4 mmol), AcOH (18 mg, 0.30 mmol), magnesium sulfate (220 mg, 1.8 mmol) and DMF (2 mL). The reaction mixture was stirred for 20 min, then sodium triacetoxyborohydride (300 mg, 1.4 mmol) was added and the reaction mixture was stirred. After 18 h, the reaction mixture was filtered and the filter cake was washed with 10% IPA/chloroform (20 mL). The filtrate was washed with 10% aqueous NaOH (10 mL), brine, dried over $MgSO_4$, filtered and concentrated. The crude material was purified via preparative HPLC (Prep Method 1) to afford the regioisomeric mixture of products (98 mg, 0.20 mmol, 74% yield). The mixture of regioisomers was separated by chiral SFC chromatography under the following conditions: Column: Chiral OD, 30×250 mm, 5 micron; Flow Rate: 100 mL/min; Oven Temperature: 40° C.; BPR Setting: 120 bar; UV wavelength: 220 nm; Mobile Phase: 75% $CO_2$/25% MeOH w/0.1% DEA (isocratic); Injection: 300 μL of 98 mg/3 mL MeOH.

Example 8 (24 mg, 0.049 mmol, 18% yield) was isolated as the $1^{st}$ eluting regioisomer. $^1$H NMR (500 MHz, DMSO-$d_6$) δ 7.78-7.74 (m, 1H), 7.73-7.67 (m, 1H), 7.43-7.35 (m, 3H), 7.28-7.22 (m, 1H), 4.47-4.37 (m, 2H), 3.89 (s, 3H), 3.86 (s, 3H), 3.69-3.47 (m, 2H), 3.26-3.02 (m, 5H), 2.42-2.31 (m, 2H), 2.21-2.13 (m, 2H), 2.13-1.96 (m, 4H), 1.43 (t, J=7.2 Hz, 3H), 1.27 (br d, J=6.7 Hz, 6H) (4 protons obscured). TLR9 $IC_{50}$ (nM)=210. Analytical LC/MS (Method 1): Purity: 100%; Observed Mass: 491.15; Retention Time: 0.98 min. (Method 2): Purity: 100%; Observed Mass: 490.90; Retention Time: 1.26 min.

Example 9 (24 mg, 0.049 mmol, 18% yield) was isolated as the $2^{nd}$ eluting regioisomer. $^1$H NMR (500 MHz, DMSO-$d_6$) δ 7.55-7.48 (m, 2H), 7.31-7.26 (m, 2H), 7.21-7.16 (m, 1H), 7.16-7.12 (m, 1H), 4.32-4.24 (m, 2H), 3.85 (s, 3H), 3.84 (s, 3H), 3.06-3.00 (m, 2H), 2.98-2.91 (m, 2H), 2.85-2.75 (m, 1H), 2.68-2.58 (m, 1H), 2.40-2.30 (m, 3H), 2.29-2.20 (m, 2H), 1.87-1.80 (m, 4H), 1.78-1.67 (m, 2H), 1.58-1.46 (m, 2H), 1.34 (s, 3H), 1.03-0.98 (m, 6H). TLR9 $IC_{50}$ (nM)=250. Analytical LC/MS (Method 1): Purity: 99.3%; Observed Mass: 491.00; Retention Time: 1.00 min. (Method 2): Purity: 96.4%; Observed Mass: 491.35; Retention Time: 1.63 min.

Example 10

2-(3,4-dimethoxyphenyl)-5-(1'-isopropyl-[1,4'-bipiperidin]-4-yl)-6-(trifluoromethyl)-1H-benzo[d]imidazole (10)

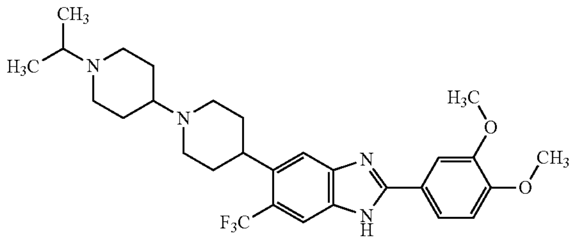

Step A. Intermediate 10A. Preparation of 4-bromo-5-(trifluoromethyl)benzene-1,2-diamine

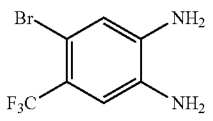

To a 200 mL pear shaped flask were added 4-bromo-2-nitro-5-(trifluoromethyl) aniline (2.0 g, 7.0 mmol), MeOH (100 mL), and tin(II) chloride dihydrate (7.0 g, 31 mmol). The reaction mixture was stirred at reflux. After 18 h, the reaction mixture was cooled, partitioned into 10% KOH (400 mL) and extracted with EtOAc (2×). The organic phase was combined washed with brine, dried over $MgSO_4$, filtered and concentrated. The residue was purified by flash column chromatography (120 g silica gel cartridge; A=Hex, B=EtOAc; 30 min grad.; 0% B to 100% B; flow rate=80 mL/min). The fractions corresponding to product were combined, concentrated and dried in vacuo to afford the title compound (1.7 g, 6.7 mmol, 96% yield) as a pale yellow solid. $^1$H NMR (500 MHz, METHANOL-$d_4$) δ 7.03-6.99 (m, 1H), 6.95-6.92 (m, 1H). Analytical LC/MS (Method 3): Observed Mass: 257.0; Retention Time: 0.79 min.

Step B. Intermediate 10B. Preparation of 5-bromo-2-(3,4-dimethoxyphenyl)-6-(trifluoromethyl)-1H-benzo[d]imidazole 2,2,2-trifluoroacetate (10B)

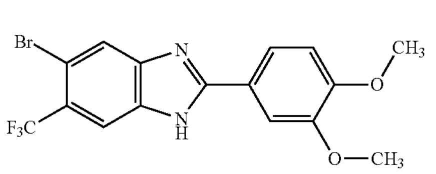

To a 250 mL round bottomed flask were added Intermediate 10A (1.7 g, 6.7 mmol), MeOH (100 mL), followed by 3,4-dimethoxybenzaldehyde (1.2 g, 7.2 mmol). The reaction mixture was stirred at reflux. After 72 h, the reaction mixture was cooled, the solvent concentrated and the residue was purified by flash column chromatography (120 g silica gel cartridge; A=Hex, B=EtOAc; 30 min grad.; 0% B to 100% B; flow rate=60 mL/min). The fractions corresponding to product were combined, concentrated and dried in vacuo. The product was further purified by flash column chromatography (300 g reverse phase C18 GOLD silica gel cartridge; A=water:MeCN:TFA 90:10:0.05%, B=water:MeCN:TFA 10:90:0.05%; 40 min grad.; 10% B to 100% B; flow rate=120 mL/min). Fractions containing product were combined, the solvent concentrated, and the product was dried in vacuo to afford the title compound (1.8 g, 3.5 mmol, 52% yield) as a tan solid. $^1$H NMR (500 MHz, METHANOL-$d_4$) δ 8.07-8.04 (m, 2H), 7.78-7.74 (m, 2H), 7.24-7.20 (m, 1H), 4.00 (s, 3H), 3.97 (s, 3H). Analytical LC/MS (Method 3): Observed Mass: 403.0; Retention Time: 0.88 min.

Step C. Intermediate 10C. Preparation of tert-butyl 4-(2-(3,4-dimethoxyphenyl)-6-(trifluoromethyl)-1H-benzo[d]imidazol-5-yl)-3,6-dihydropyridine-1(2H)-carboxylate (10C)

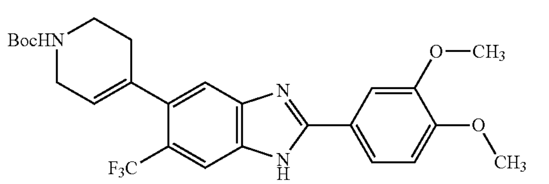

To a 40 mL vial were added Intermediate 10B (0.98 g, 1.9 mmol), tert-butyl 4-(4,4,5,5-tetramethyl-1,3,2-dioxaborolan-2-yl)-3,6-dihydropyridine-1(2H)-carboxylate (0.69 g, 2.2 mmol), followed by 1,4-dioxane (10 mL) and potassium phosphate tribasic (1.2 g, 5.7 mmol) dissolved in water (2 mL). The vessel degassed with $N_2$, then 1,1'-bis(diphenylphosphino)ferrocene-palladium(II)dichloride dichloromethane complex (0.076 g, 0.093 mmol) was added. The vial was blanketed with $N_2$, capped and stirred at 75° C. After 18 h, the reaction mixture was cooled, the mixture was diluted with water (200 mL) and extracted with EtOAc (2×100 mL). The organic phase was combined, washed with brine, dried over $MgSO_4$, filtered and concentrated. The residue was purified by flash column chromatography (120 g silica gel cartridge; A=Hex, B=EtOAc; 20 min grad.; 0% B to 100% B; hold for 10 min then; A=DCM, B=MeOH; 30 min grad.; 0% B to 10% B; flow rate=120 mL/min). The fractions corresponding to product were combined, concentrated and dried in vacuo to afford the title compound (0.69 g, 1.4 mmol, 74% yield) as a pale yellow solid. $^1H$ NMR (500 MHz, METHANOL-$d_4$) δ 7.96-7.89 (m, 1H), 7.79-7.76 (m, 1H), 7.75-7.71 (m, 1H), 7.49-7.42 (m, 1H), 7.18-7.13 (m, 1H), 5.75-5.62 (m, 1H), 4.11-4.04 (m, 2H), 3.99 (s, 3H), 3.95 (s, 3H), 3.72-3.64 (m, 2H), 2.48-2.42 (m, 2H), 1.56-1.52 (m, 9H). Analytical LC/MS (Method 3): Observed Mass: 504.2; Retention Time: 0.91 min.

Step D. Intermediate 10D. Preparation of 2-(3,4-dimethoxyphenyl)-5-(1,2,3,6-tetrahydropyridin-4-yl)-6-(trifluoromethyl)-1H-benzo[d]imidazole dihydrochloride (10D)

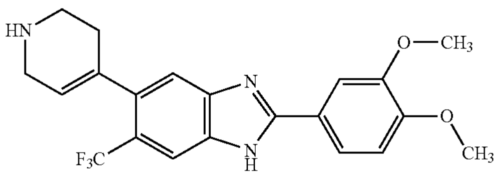

To a 100 mL pear shaped flask were added Intermediate 10C (0.69 g, 1.4 mmol) and 4 M HCl in dioxane (10 mL). After stirring 15 min, the solvent was concentrated and the residue was co-evaporated with toluene (2×). The product was dried in vacuo to afford the title compound (0.62 g, 1.3 mmol, 93% yield) as a pale yellow solid. $^1H$ NMR (500 MHz, METHANOL-$d_4$) δ 8.18-8.15 (m, 1H), 7.89-7.85 (m, 1H), 7.84-7.80 (m, 2H), 7.35-7.31 (m, 1H), 5.89-5.83 (m, 1H), 4.05-4.03 (m, 3H), 4.03-4.00 (m, 3H), 3.93-3.90 (m, 2H), 3.56-3.51 (m, 2H), 2.80-2.73 (m, 2H). Analytical LC/MS (Method 3): Observed Mass: 404.4; Retention Time: 0.57 min.

Step E. Intermediate 10E. Preparation of 2-(3,4-dimethoxyphenyl)-5-(piperidin-4-yl)-6-(trifluoromethyl)-1H-benzo[d]imidazole dihydrochloride (10E)

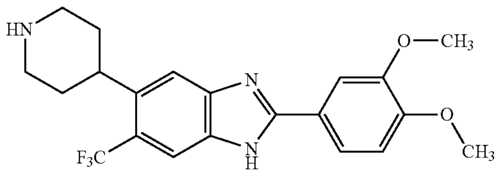

To a 250 mL round bottomed flask were added Intermediate 10D (0.62 g, 1.3 mmol), and MeOH (40 mL). The vessel was evacuated and purged with $N_2$, then platinum(IV) oxide (120 mg, 0.53 mmol) was added and the reaction mixture was stirred under hydrogen at 1 atm. After 18 h, the catalyst was filtered, the filtrate was concentrated and the product was dried in vacuo to afford the title compound (0.56 g, 1.2 mmol, 92% yield) as a pale yellow solid. $^1H$ NMR (400 MHz, METHANOL-$d_4$) δ 8.11-8.09 (m, 1H), 7.99-7.97 (m, 1H), 7.86-7.82 (m, 1H), 7.82-7.79 (m, 1H), 7.32-7.28 (m, 1H), 4.03 (s, 3H), 4.00 (s, 3H), 3.72-3.66 (m, 1H), 3.64-3.57 (m, 2H), 3.30-3.20 (m, 2H), 2.16 (br s, 4H). Analytical LC/MS (Method 3): Observed Mass: 406.2; Retention Time: 0.61 min.

Step F. Example 10

To a 40 mL vial were added Intermediate 10E (62 mg, 0.13 mmol), 1-isopropylpiperidin-4-one (92 mg, 0.65 mmol), AcOH (8.6 mg, 0.14 mmol), magnesium sulfate (220 mg, 1.8 mmol), and DMF (2 mL). The reaction mixture was stirred for 20 min, then sodium triacetoxyborohydride (140 mg, 0.66 mmol) was added and the reaction mixture was stirred. After 18 h, the reaction mixture was filtered and the filter cake was washed with 10% IPA/chloroform (20 mL). The filtrate was washed with 10% aqueous NaOH (10 mL), brine, dried over $MgSO_4$, filtered and concentrated. The crude material was purified via preparative HPLC (Prep Method 1) to afford the title compound (40 mg, 0.075 mmol, 58% yield). $^1H$ NMR (500 MHz, DMSO-$d_6$) δ 7.91-7.84 (m, 1H), 7.80-7.74 (m, 2H), 7.73-7.67 (m, 1H), 7.20-7.14 (m, 1H), 3.90 (s, 3H), 3.86 (s, 3H), 3.64-3.51 (m, 1H), 3.19-3.03 (m, 6H), 2.97-2.85 (m, 2H), 2.39-2.31 (m, 2H), 1.88-1.75 (m, 5H), 1.71-1.58 (m, 2H), 1.12 (br d, J=5.8 Hz, 6H) (one proton obscured). TLR9 $IC_{50}$ (nM)=240. Analytical LC/MS (Method 1): Purity: 98.7%; Observed Mass: 531.31; Retention Time: 1.03 min. (Method 2): Purity: 100%; Observed Mass: 531.04; Retention Time: 1.52 min.

Example 11

2-(3,4-dimethoxyphenyl)-6-(1'-isopropyl-[1,4'-bipiperidin]-4-yl)-4-methyl-1H-benzo[d]imidazole (11)

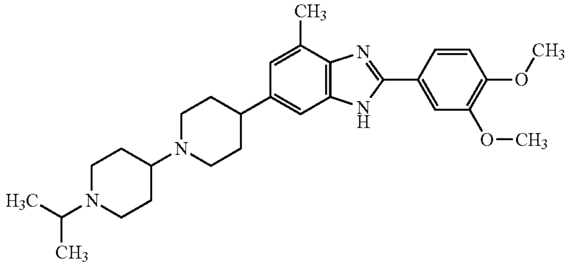

Step A. Intermediate 11A. Preparation of 6-bromo-2-(3,4-dimethoxyphenyl)-4-methyl-1H-benzo[d]imidazole (11A)

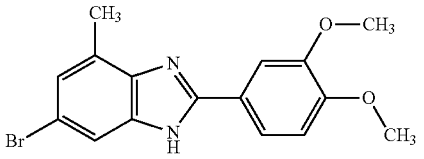

To a 500 mL pear shaped flask were added 5-bromo-3-methylbenzene-1,2-diamine (6.0 g, 30 mmol) and NMP (120 mL). To this mixture was added sodium metabisulfite (8.6 g, 45 mmol), followed by 3,4-dimethoxybenzaldehyde (6.0 g, 36 mmol). The reaction mixture was heated to 70° C. and stirred under $N_2$. After 18 h, the reaction mixture was cooled, diluted with water (500 mL) and extracted with EtOAc (250 mL). The organic phase was washed with water (100 mL) and the combined aqueous phase was extracted with EtOAc (100 mL). The organic phase was combined, washed with brine, dried over $MgSO_4$, filtered and concentrated. The residue was purified by flash column chromatography (220 g silica gel cartridge; A=Hex, B=EtOAc; 30 min grad.; 0% B to 100% B; flow rate=120 mL/min). The fractions corresponding to desired product were combined, concentrated and dried in vacuo to afford the title compound (8.0 g, 23 mmol, 77% yield) as a light yellow solid. $^1$H NMR (500 MHz, METHANOL-$d_4$) δ 7.81-7.77 (m, 1H), 7.75-7.70 (m, 1H), 7.59-7.54 (m, 1H), 7.21-7.17 (m, 1H), 7.15-7.11 (m, 1H), 4.03-3.97 (m, 3H), 3.96-3.92 (m, 3H), 2.68-2.57 (m, 3H). Analytical LC/MS (Method 3): Observed Mass: 349.2; Retention Time: 0.72 min.

Step B. Intermediate 111B. Preparation of tert-butyl 4-(2-(3,4-dimethoxyphenyl)-4-methyl-1H-benzo[d]imidazol-6-yl)-3,6-dihydropyridine-1(2H)-carboxylate (11B)

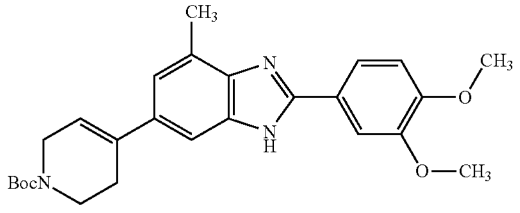

To a 200 mL pear shaped flask were added Intermediate 11A (3.2 g, 9.2 mmol), tert-butyl 4-(4,4,5,5-tetramethyl-1,3,2-dioxaborolan-2-yl)-3,6-dihydropyridine-1(2H)-carboxylate (3.4 g, 11 mmol), followed by 1,4-dioxane (40 mL) and potassium phosphate tribasic (5.9 g, 28 mmol) dissolved in water (10 mL). The vessel evacuated and purged with $N_2$, then 1,1'-bis(diphenylphosphino)ferrocene-palladium(II)dichloride dichloromethane complex (0.38 g, 0.46 mmol) was added. The vessel was evacuated and purged again and stirred at 75° C. After 18 h, the reaction mixture was cooled, diluted with water (200 mL) and extracted with EtOAc (2×100 mL). The organic phase was combined, washed with brine, dried over $MgSO_4$, filtered and concentrated. The residue was purified by flash column chromatography (220 g silica gel cartridge; A=Hex, B=EtOAc; 30 min grad.; 0% B to 100% B; flow rate=80 mL/min). The fractions corresponding to desired product were combined, concentrated and dried in vacuo to afford the title compound (4.0 g, 8.9 mmol, 97% yield) as a light yellow solid. $^1$H NMR (400 MHz, METHANOL-$d_4$) δ 7.81-7.78 (m, 1H), 7.75-7.70 (m, 1H), 7.45-7.42 (m, 1H), 7.20-7.17 (m, 1H), 7.15-7.11 (m, 1H), 6.17-6.05 (m, 1H), 4.15-4.08 (m, 2H), 3.99 (s, 3H), 3.94 (s, 3H), 3.72-3.67 (m, 2H), 2.67-2.60 (m, 2H), 2.64 (s, 3H), 1.53 (s, 9H). Analytical LC/MS (Method 3): Observed Mass: 450.4; Retention Time: 0.83 min.

Step C. Intermediate 11C. Preparation of tert-butyl 4-(2-(3,4-dimethoxyphenyl)-4-methyl-1H-benzo[d]imidazol-6-yl)piperidine-1-carboxylate (11C)

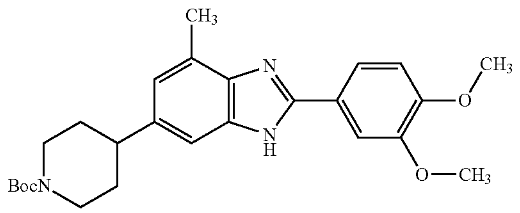

To a 250 mL round bottomed flask were added Intermediate 11B (4.0 g, 8.8 mmol) and MeOH (50 mL). The vessel was evacuated and purged with $N_2$, then Pd—C (10% wt.) (0.94 g, 0.88 mmol) was added and reaction mixture was stirred under hydrogen at 1 atm. After 18 h, the catalyst was filtered and the filtrate concentrated. The product was dried in vacuo to afford the title compound (3.8 g, 8.4 mmol, 95% yield) as a pale yellow solid. $^1$H NMR (500 MHz, METHANOL-$d_4$) δ 7.81-7.78 (m, 1H), 7.74-7.68 (m, 1H), 7.30-7.22 (m, 1H), 7.15-7.11 (m, 1H), 6.98-6.94 (m, 1H), 4.29-4.22 (m, 2H), 3.99 (s, 3H), 3.93 (s, 3H), 3.80-3.72 (m, 1H), 2.86-2.77 (m, 1H), 2.65-2.59 (m, 3H), 1.93-1.86 (m, 2H), 1.73-1.61 (m, 3H), 1.52 (s, 9H). Analytical LC/MS (Method 3): Observed Mass: 452.5; Retention Time: 0.83 min.

Step D. Intermediate 11D. Preparation of 2-(3,4-dimethoxyphenyl)-4-methyl-6-(piperidin-4-yl)-1H-benzo[d]imidazole bis(2,2,2-trifluoroacetate)

(11D)

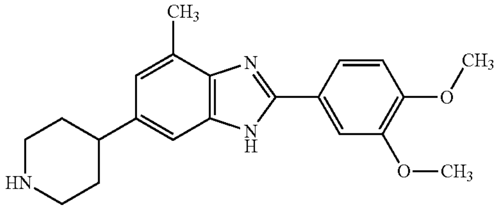

To a 500 mL pear shaped flask were added Intermediate 11C (3.8 g, 8.4 mmol), DCM (50 mL), and TFA (50 mL). After stirring 2 h, the solvent was concentrated and the residue was co-evaporated with toluene. The product was dried in vacuo to afford the title compound (4.8 g, 8.3 mmol, 99% yield) as a pale yellow solid. $^1$H NMR (500 MHz, METHANOL-$d_4$) δ 7.85-7.82 (m, 1H), 7.81-7.80 (m, 1H), 7.51-7.48 (m, 1H), 7.35-7.33 (m, 1H), 7.31-7.28 (m, 1H), 4.02 (s, 3H), 4.00 (s, 3H), 3.61-3.54 (m, 2H), 3.24-3.18 (m, 3H), 2.73 (s, 3H), 2.22-2.15 (m, 2H), 2.07-1.98 (m, 2H). Analytical LC/MS (Method 3): Observed Mass: 352.4; Retention Time: 0.53 min.

Step E. Example 11

To a 40 mL vial were added Intermediate 11D (81 mg, 0.14 mmol), 1-isopropylpiperidin-4-one (110 mg, 0.78 mmol), AcOH (11 mg, 0.18 mmol), magnesium sulfate (220 mg, 1.8 mmol), and DMF (2 mL). The reaction mixture was stirred for 20 min, then sodium triacetoxyborohydride (170 mg, 0.80 mmol) was added and the reaction mixture was stirred. After 18 h, the reaction mixture was filtered and the filter cake was washed with 10% IPA/chloroform (20 mL). The filtrate was washed with 10% aqueous NaOH (10 mL), brine, dried over $MgSO_4$, filtered and concentrated. The crude material was purified via preparative HPLC (Prep Method 1) to afford the title compound (52 mg, 0.11 mmol, 79% yield). $^1$H NMR (500 MHz, DMSO-$d_6$) δ 7.80-7.72 (m, 2H), 7.22-7.16 (m, 1H), 7.14-7.09 (m, 1H), 6.89-6.86 (m, 1H), 3.89 (s, 3H), 3.84 (s, 3H), 3.04-2.97 (m, 2H), 2.92-2.86 (m, 2H), 2.78-2.70 (m, 1H), 2.54 (s, 3H), 2.34-2.25 (m, 3H), 2.21-2.13 (m, 2H), 1.85-1.75 (m, 5H), 1.74-1.64 (m, 2H), 1.53-1.43 (m, 2H), 0.99 (d, J=6.7 Hz, 6H). TLR9 $IC_{50}$ (nM)=33. Analytical LC/MS (Method 1): Purity: 98.6%; Observed Mass: 477.16; Retention Time: 1.00 min. (Method 2): Purity: 100%; Observed Mass: 477.18; Retention Time: 1.26 min.

Example 12

2-(3,4-dimethoxyphenyl)-6-(1-(2-isopropyl-2-azaspiro[3.3]heptan-6-yl)piperidin-4-yl)-4-methyl-1H-benzo[d]imidazole (12)

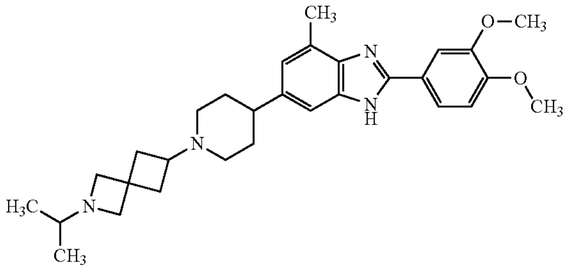

Step A. Intermediate 12A. Preparation of 6-(1-(2-azaspiro[3.3]heptan-6-yl)piperidin-4-yl)-2-(3,4-dimethoxyphenyl)-4-methyl-1H-benzo[d]imidazole trihydrochloride (12A)

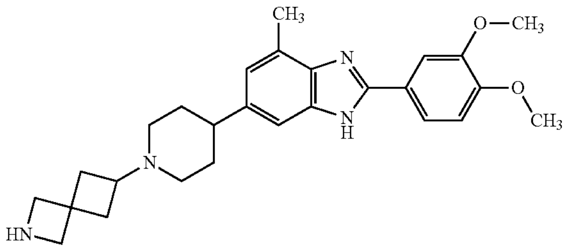

To a 40 mL vial were added Intermediate 11D (140 mg, 0.24 mmol), tert-butyl 6-oxo-2-azaspiro[3.3]heptane-2-carboxylate (150 mg, 0.71 mmol), AcOH (16 mg, 0.26 mmol), magnesium sulfate (220 mg, 1.8 mmol), and DMF (2 mL). The reaction mixture was stirred for 20 min, then sodium triacetoxyborohydride (150 mg, 0.71 mmol) was added and the reaction mixture was stirred. After 18 h, the reaction mixture was filtered and the filtrate was concentrated. The residue was purified by flash column chromatography (40 g silica gel cartridge; A=DCM, B=MeOH; 30 min grad.; 0% B to 30% B; flow rate=40 mL/min). The fractions corresponding to product were combined and concentrated. The resultant residue was dissolved in 4 M HCl in dioxane (20 mL) and stirred. After 15 min, the solvent was concentrated and the residue was co-evaporated with toluene. The product was dried in vacuo to afford the title compound (100 mg, 0.180 mmol, 75% yield) as an off white solid. $^1$H NMR (500 MHz, METHANOL-$d_4$) δ 7.84-7.80 (m, 2H), 7.53-7.49 (m, 1H), 7.37-7.33 (m, 1H), 7.30-7.27 (m, 1H), 4.03 (s, 3H), 4.00 (s, 3H), 3.78-3.74 (m, 4H), 3.71-3.67 (m, 7H), 3.63-3.59 (m, 4H), 2.84-2.79 (m, 3H), 2.74-2.71 (m, 3H). Analytical LC/MS (Method 3): Observed Mass: 447.5; Retention Time: 0.50 min.

Step B. Example 12

To a 40 mL vial were added Intermediate 12A (100 mg, 0.18 mmol), propan-2-one (52 mg, 0.90 mmol), AcOH (12 mg, 0.20 mmol), magnesium sulfate (220 mg, 1.8 mmol), and DMF (2 mL). The reaction mixture was stirred for 5 min, then sodium triacetoxyborohydride (190 mg, 0.90 mmol) was added and the reaction mixture was stirred. After 18 h, the reaction mixture was filtered and the filter cake was washed with 10% IPA/chloroform (20 mL). The filtrate was washed with 10% aqueous NaOH (10 mL), brine, dried over $MgSO_4$, filtered and concentrated. The crude material was purified via preparative HPLC (Prep Method 1) to afford the title compound (37 mg, 0.076 mmol, 42% yield). $^1H$ NMR (500 MHz, DMSO-$d_6$) δ 7.80-7.71 (m, 2H), 7.24-7.14 (m, 1H), 7.14-7.08 (m, 1H), 6.89-6.84 (m, 1H), 3.88 (s, 3H), 3.83 (s, 3H), 3.62-3.55 (m, 2H), 3.32-3.26 (m, 1H), 3.19-3.14 (m, 1H), 2.91-2.85 (m, 2H), 2.61-2.57 (m, 1H), 2.53 (s, 3H), 2.44-2.36 (m, 1H), 2.22-2.15 (m, 2H), 1.84-1.74 (m, 4H), 1.70-1.61 (m, 2H), 0.89-0.84 (m, 6H) (three protons obscured). TLR9 $IC_{50}$ (nM)=60. Analytical LC/MS (Method 1): Purity: 100%; Observed Mass: 489.29; Retention Time: 1.01 min. (Method 2): Purity: 100%; Observed Mass: 488.96; Retention Time: 1.21 min.

Example 13

6-([1,4'-bipiperidin]-4-yl)-2-(3,4-dimethoxyphenyl)-4-methyl-1H-benzo[d]imidazole tris(2,2,2-trifluoroacetate)

(13)

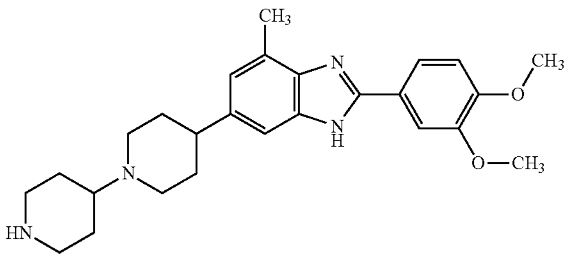

To a 40 mL vial were added Intermediate 11D (1.0 g, 1.7 mmol), tert-butyl 4-oxopiperidine-1-carboxylate (1.0 g, 5.0 mmol), AcOH (110 mg, 1.8 mmol), magnesium sulfate (3.0 g, 25 mmol), and DMF (10 mL). The reaction mixture was stirred for 20 min, then sodium triacetoxyborohydride (1.1 g, 5.2 mmol) was added and the reaction mixture was stirred. After 18 h, the reaction mixture was filtered, the filter cake was washed with DCM/MeOH and the filtrate was concentrated. The remaining DMF solution was loaded onto a Celite cartridge and purified by flash column chromatography (275 g reverse phase C18 GOLD silica gel cartridge; A=water:MeCN:TFA 90:10:0.05%, B=water:MeCN:TFA 10:90:0.05%; 20 min grad.; 0% B to 100% B; flow rate=120 mL/min). The fractions corresponding to product were combined and the solvent was concentrated. The resultant residue was dissolved in a minimal amount of MeOH, then 4 M HCl in dioxane (30 mL) was added and the reaction mixture was stirred. After 2 h, the solvent was concentrated and the residue was co-evaporated with toluene. The crude product was purified by preparative HPLC (Prep Method 2) to afford the title compound (0.42 g, 0.54 mmol, 32% yield) as a tan solid. $^1H$ NMR (500 MHz, DMSO-$d_6$) δ 7.84-7.72 (m, 2H), 7.29-7.17 (m, 1H), 7.16-7.11 (m, 1H), 6.91-6.87 (m, 1H), 3.91 (s, 3H), 3.86 (s, 3H), 3.51-3.43 (m, 1H), 3.22-3.14 (m, 2H), 3.04-2.94 (m, 2H), 2.74-2.65 (m, 2H), 2.57-2.55 (m, 3H), 2.50-2.45 (m, 1H), 2.35-2.26 (m, 2H), 1.87-1.79 (m, 4H), 1.75-1.65 (m, 2H), 1.59-1.49 (m, 2H). TLR9 $IC_{50}$ (nM)=620. Analytical LC/MS (Method 1): Purity: 99.3%; Observed Mass: 435.31; Retention Time: 0.92 min. (Method 2): Purity: 100%; Observed Mass: 435.15; Retention Time: 1.2 min.

Example 14

1-(4-(2-(3,4-dimethoxyphenyl)-4-methyl-1H-benzo[d]imidazol-6-yl)-[1,4'-bipiperidin]-1'-yl)-2-methylpropan-1-one (14)

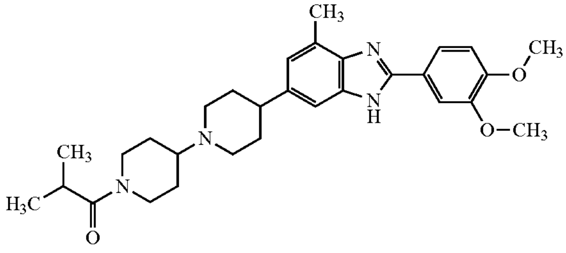

To a 40 mL vial were added Example 13 (85 mg, 0.11 mmol), isobutyric acid (11 mg, 0.12 mmol), TEA (56 mg, 0.55 mmol), DMAP (13 mg, 0.11 mmol), and DMF (2 mL). To this mixture was added EDC (42 mg, 0.22 mmol), the vial was capped and the reaction mixture was stirred. After 4 d, the reaction mixture was diluted with water (20 mL), saturated with solid NaCl, and extracted with EtOAc (5×10 mL). The organic phase was combined, dried over $MgSO_4$, filtered and concentrated. The crude product was purified by preparative HPLC (Prep Method 1) to afford the title compound (31 mg, 0.061 mmol, 55% yield). $^1H$ NMR (500 MHz, DMSO-$d_6$) δ 7.81-7.76 (m, 1H), 7.75-7.68 (m, 1H), 7.14-7.09 (m, 1H), 7.28-7.08 (m, 1H), 6.89-6.85 (m, 1H), 4.48-4.40 (m, 1H), 4.03-3.95 (m, 1H), 3.88 (s, 3H), 3.83 (s, 3H), 3.03-2.94 (m, 3H), 2.91-2.83 (m, 1H), 2.53 (s, 3H), 2.34-2.24 (m, 2H), 1.87-1.75 (m, 4H), 1.72-1.61 (m, 2H), 1.41-1.32 (m, 1H), 1.31-1.20 (m, 1H), 1.03-0.94 (m, 6H) (three protons obscured). TLR9 $IC_{50}$ (nM)=510. Analytical LC/MS (Method 1): Purity: 100%; Observed Mass: 505.17; Retention Time: 1.08 min. (Method 2): Purity: 100%; Observed Mass: 505.22; Retention Time: 1.29 min.

Example 15

2-(3,4-dimethoxyphenyl)-6-(1'-isobutyl-[1,4'-bipiperidin]-4-yl)-1,4-dimethyl-1H-benzo[d]imidazole tris(2,2,2-trifluoroacetate)

(15)

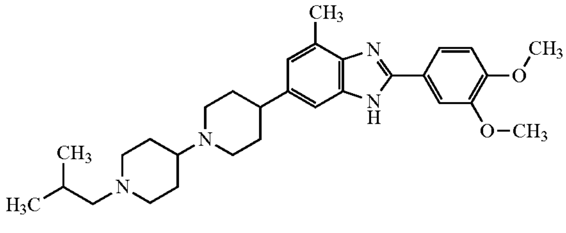

Step A. Intermediate 15A. Preparation of 5-bromo-N,3-dimethyl-2-nitroaniline (15A)

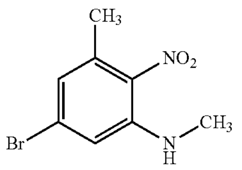

Intermediate 15A was synthesized according to methods described for the preparation of Intermediate 1A, using 5-bromo-1-fluoro-3-methyl-2-nitrobenzene (1.0 g, 4.3 mmol) as starting material to afford the title compound (1.0 g, 4.1 mmol, 95% yield) as a yellow solid. $^1$H NMR (400 MHz, METHANOL-$d_4$) δ 6.94-6.89 (m, 1H), 6.75-6.73 (m, 1H), 2.89 (s, 3H), 2.38 (s, 3H). Analytical LC/MS (Method 3): Observed Mass: 247.1; Retention Time: 1.03 min.

Step B. Intermediate 15B. Preparation of tert-butyl 4-(3-methyl-5-(methylamino)-4-nitrophenyl)-3,6-dihydropyridine-1(2H)-carboxylate (15B)

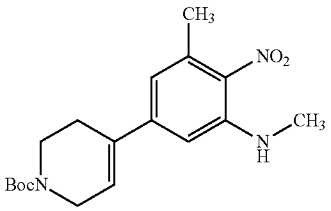

Intermediate 15B was synthesized according to methods described for the preparation of Intermediate 3B, using Intermediate 15A (1.0 g, 4.1 mmol) as starting material to afford the title compound (1.4 g, 4.0 mmol, 98% yield) as a yellow solid. 1H NMR (500 MHz, METHANOL-$d_4$) δ 6.74-6.70 (m, 1H), 6.68-6.65 (m, 1H), 6.28-6.22 (m, 1H), 4.15-4.06 (m, 2H), 3.70-3.61 (m, 2H), 2.95 (s, 3H), 2.58-2.51 (m, 2H), 2.45 (s, 3H), 1.51 (s, 9H). Analytical LC/MS (Method 3): Observed Mass: 348.3; Retention Time: 1.12 min.

Step C. Intermediate 15C. Preparation of tert-butyl 4-(4-amino-3-methyl-5-(methylamino)phenyl)piperidine-1-carboxylate (15C)

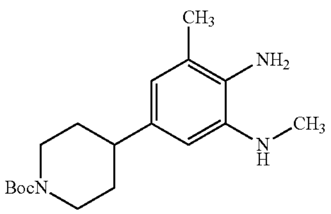

Intermediate 15C was synthesized according to methods described for the preparation of Intermediate 3C, using Intermediate 15B (1.4 g, 4.0 mmol) as starting material to afford the title compound (1.2 g, 3.8 mmol, 95% yield) as a pale yellow solid. $^1$H NMR (500 MHz, METHANOL-$d_4$) δ 6.43-6.37 (m, 2H), 4.25-4.15 (m, 2H), 2.92-2.78 (m, 2H), 2.83 (s, 3H) 2.62-2.51 (m, 1H), 2.18 (s, 3H), 1.82-1.75 (m, 2H), 1.59-1.53 (m, 2H), 1.50 (s, 9H). Analytical LC/MS (Method 3): Observed Mass: 320.4; Retention Time: 0.75 min.

Step D. Intermediate 15D. Preparation of tert-butyl 4-(2-(3,4-dimethoxyphenyl)-1,4-dimethyl-1H-benzo[d]imidazol-6-yl)piperidine-1-carboxylate (15D)

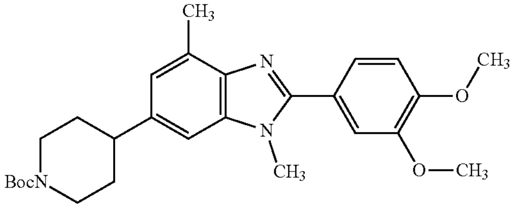

Intermediate 15D was synthesized according to methods described for the preparation of Intermediate 3D, using Intermediate 15C (1.2 g, 3.8 mmol, 95% yield) as starting material to afford the title compound (1.7 g, 3.7 mmol, 97% yield) as a pale yellow semisolid. $^1$H NMR (500 MHz, METHANOL-$d_4$) δ 7.40-7.38 (m, 1H), 7.35-7.32 (m, 1H), 7.24-7.22 (m, 1H), 7.19-7.15 (m, 1H), 7.03-7.01 (m, 1H), 4.32-4.21 (m, 2H), 3.97-3.93 (m, 6H), 3.86 (s, 3H), 2.99-2.83 (m, 3H), 2.62 (s, 3H), 1.95-1.89 (m, 2H), 1.77-1.67 (m, 2H), 1.52 (s, 9H). Analytical LC/MS (Method 3): Observed Mass: 466.4; Retention Time: 0.83 min.

Step E. Intermediate 15E. Preparation of 2-(3,4-dimethoxyphenyl)-1,4-dimethyl-6-(piperidin-4-yl)-1H-benzo[d]imidazole dihydrochloride (15E)

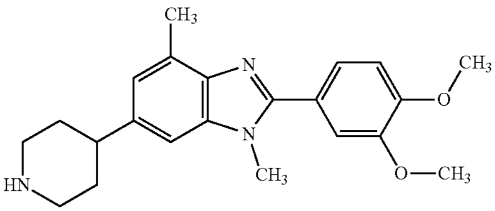

Intermediate 15E was synthesized according to methods described for the preparation of Intermediate 3E, using Intermediate 15D (1.7 g, 3.7 mmol) as starting material to afford the title compound (1.4 g, 3.2 mmol, 86% yield) as a light tan solid. $^1$H NMR (500 MHz, METHANOL-$d_4$) δ 7.67 (s, 1H), 7.55-7.52 (m, 1H), 7.50 (s, 1H), 7.44-7.41 (m, 1H), 7.34-7.30 (m, 1H), 4.11 (s, 3H), 4.01-4.00 (m, 3H), 3.99-3.98 (m, 3H), 3.62-3.56 (m, 2H), 3.27-3.20 (m, 2H), 3.20-3.14 (m, 1H), 2.71 (s, 3H), 2.23-2.17 (m, 2H), 2.14-2.04 (m, 2H). Analytical LC/MS (Method 3): Observed Mass: 366.3; Retention Time: 0.53 min.

Step F. Example 15

To a 40 mL vial were added Intermediate 15E (70 mg, 0.16 mmol), 1-isobutylpiperidin-4-one (120 mg, 0.77 mmol), AcOH (11 mg, 0.18 mmol), magnesium sulfate (220 mg, 1.8 mmol), and DMF (2 mL). The reaction mixture was stirred for 20 min, then sodium triacetoxyborohydride (170 mg, 0.8 mmol) was added and the reaction mixture was stirred. After 18 h, the reaction mixture was filtered and the filter cake was washed with 10% IPA/chloroform (20 mL). The filtrate was washed with 10% aqueous NaOH (10 mL), brine, dried over $MgSO_4$, filtered and concentrated. The crude material was purified via preparative HPLC (Prep Method 2) to afford the title compound (85 mg, 0.10 mmol, 63% yield). $^1$H NMR (500 MHz, DMSO-$d_6$) δ 7.56-7.52 (m, 1H), 7.51-7.48 (m, 1H), 7.47 (s, 1H), 7.27 (s, 1H), 7.25-7.21 (m, 1H), 3.96 (s, 3H), 3.90 (s, 3H), 3.87 (s, 3H), 3.73-3.56 (m, 1H), 3.25-3.16 (m, 1H), 3.13-2.90 (m, 4H), 2.61 (s, 3H), 2.38-2.25 (m, 2H), 2.21-1.99 (m, 7H), 0.97 (d, J=6.6 Hz, 6H) (6 protons obscured). TLR9 $IC_{50}$ (nM)=19. Analytical LC/MS (Method 1): Purity: 100%; Observed Mass: 505.09; Retention Time: 0.99 min. (Method 2): Purity: 99.5%; Observed Mass: 505.90; Retention Time: 1.6 min.

Example 16

2-(3,4-dimethoxyphenyl)-6-(1-(2-isopropyl-2-azaspiro[3.3]heptan-6-yl)piperidin-4-yl)-1,4-dimethyl-1H-benzo[d]imidazole tris(2,2,2-trifluoroacetate)

(16)

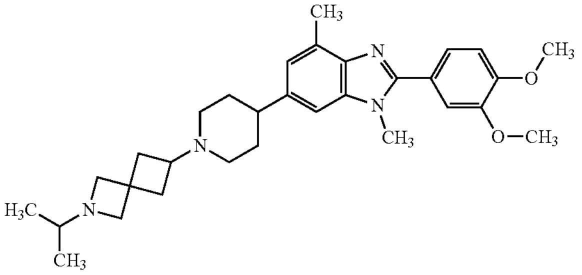

Step A. Intermediate 16A. Preparation of 6-(1-(2-azaspiro[3.3]heptan-6-yl)piperidin-4-yl)-2-(3,4-dimethoxyphenyl)-1,4-dimethyl-1H-benzo[d]imidazole trihydrochloride (16A)

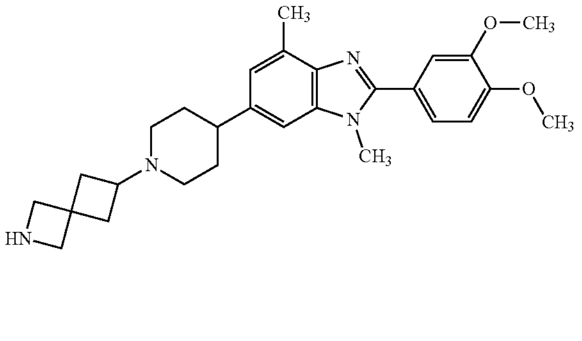

To a 40 mL vial were added Intermediate 15E (0.50 g, 1.1 mmol), tert-butyl 6-oxo-2-azaspiro[3.3]heptane-2-carboxylate (0.70 g, 3.3 mmol), AcOH (0.078 g, 1.3 mmol), magnesium sulfate (1.9 g, 16 mmol), and DMF (10 mL). The reaction mixture was stirred for 20 min, then sodium triacetoxyborohydride (0.73 g, 3.4 mmol) was added and the reaction mixture was stirred. After 18 h, the reaction mixture was filtered, the filter cake was washed with DCM/MeOH and the filtrate was concentrated. The remaining DMF solution was loaded onto a Celite cartridge and purified by flash column chromatography (275 g reverse phase C18 GOLD silica gel cartridge; A=water:MeCN:TFA 90:10:0.05%, B=water:MeCN:TFA 10:90:0.05%; 20 min grad.; 10% B to 100% B; flow rate=125 mL/min). The fractions corresponding to product were combined and concentrated while maintaining the rotovap bath at 30° C. The resultant residue was dissolved in a minimal amount of MeOH, then further diluted with THE (20 mL). To this mixture was added 4 M HCl in dioxane (4 mL) and the reaction mixture was stirred. After 6 h, the solvent was concentrated while maintaining the rotovap bath at 30° C., the residue was co-evaporated with toluene and the product was dried in vacuo to afford the title compound (0.63 g, 1.1 mmol, 100% yield) as an off white solid. $^1$H NMR (500 MHz, METHANOL-$d_4$) δ 7.72-7.64 (m, 1H), 7.57-7.52 (m, 1H), 7.51-7.48 (m, 1H), 7.46-7.40 (m, 1H), 7.34-7.29 (m, 1H), 4.25-4.22 (m, 1H), 4.17-4.14 (m, 1H), 4.11 (s, 3H), 3.99 (s, 3H), 3.98 (s, 3H), 3.94-3.88 (m, 1H), 3.77-3.69 (m, 1H), 3.68-3.60 (m, 2H), 3.23-3.14 (m, 1H), 3.11-2.97 (m, 2H), 2.88-2.75 (m, 3H), 2.73-2.62 (m, 1H), 2.69 (s, 3H), 2.61-2.49 (m, 1H), 2.38-2.17 (m, 4H). Analytical LC/MS (Method 3): Observed Mass: 461.5; Retention Time: 0.56 min.

Step B. Example 16

To a 40 mL vial were added Intermediate 16A (50 mg, 0.088 mmol), propan-2-one (26 mg, 0.45 mmol), AcOH (6 mg, 0.10 mmol), magnesium sulfate (220 mg, 1.8 mmol), and DMF (2 mL). The reaction mixture was stirred for 20 min, then sodium triacetoxyborohydride (95 mg, 0.45 mmol) was added and the reaction mixture was stirred. After 18 h, the reaction mixture was filtered and the filter cake was washed with 10% IPA/chloroform (20 mL). The filtrate was washed with 10% aqueous NaOH (10 mL), brine, dried over $MgSO_4$, filtered and concentrated. The crude material was purified via preparative HPLC (Prep Method 2) to afford the title compound (27 mg, 0.032 mmol, 36% yield). $^1$H NMR (500 MHz, DMSO-$d_6$) δ 7.45-7.38 (m, 3H), 7.23-7.19 (m, 1H), 7.14-7.09 (m, 1H), 4.20-4.11 (m, 2H), 4.10-3.98 (m, 2H), 3.90 (s, 3H), 3.87 (s, 3H), 3.85 (s, 3H), 3.74-3.62 (m, 2H), 3.53-3.42 (m, 1H), 3.41-3.31 (m, 1H), 3.06-2.96 (m, 1H), 2.95-2.79 (m, 2H), 2.76-2.67 (m, 1H), 2.58-2.56 (m, 3H), 2.49-2.39 (m, 1H), 2.14-2.04 (m, 2H), 1.99-1.88 (m, 2H), 1.10 (d, J=6.4 Hz, 6H) (two protons obscured). TLR9 $IC_{50}$ (nM)=100. Analytical LC/MS (Method 1): Purity: 100%; Observed Mass: 503.16; Retention Time: 1.00 min. (Method 2): Purity: 99.2%; Observed Mass: 503.19; Retention Time: 1.38 min.

Examples 17 and 18

2-(3,4-dimethoxyphenyl)-6-(1-(8-isobutyl-8-azabicyclo[3.2.1]octan-3-yl)piperidin-4-yl)-1,4-dimethyl-1H-benzo[d]imidazole (17-18)

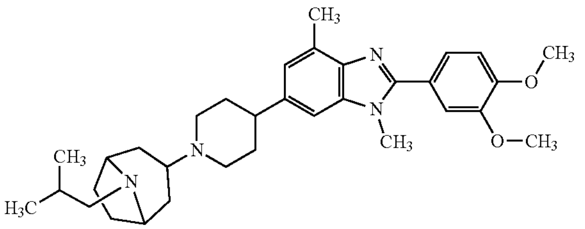

Step A. Intermediate 17A. Preparation of 6-(1-(8-azabicyclo[3.2.1]octan-3-yl)piperidin-4-yl)-2-(3,4-dimethoxyphenyl)-1,4-dimethyl-1H-benzo[d]imidazole trihydrochloride (17A)

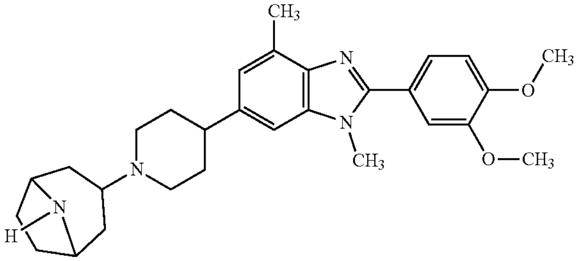

To a 40 mL vial were added Intermediate 15E (0.44 g, 1.0 mmol), DCE (1 mL), DME (1 mL), followed by tert-butyl 3-oxo-8-azabicyclo[3.2.1]octane-8-carboxylate (1.0 g, 4.4 mmol). To the resultant suspension was added titanium(IV) isopropoxide (1.5 g, 5.3 mmol), the vessel was flushed with $N_2$, capped, and the reaction mixture was stirred at 35° C. After 18 h, DMF (20 mL) was added and the reaction mixture was continued. After 3 h, the reaction mixture was cooled to −40° C., then sodium triacetoxyborohydride (0.89 g, 4.2 mmol) was added in portions. The reaction mixture was stirred at room temperature for 1 h, then partitioned into 10% NaOH (100 mL), and extracted with 10% IPA/$CHCl_3$ (3×50 mL). The organic phase was combined, dried over $MgSO_4$, filtered and concentrated. The residue was purified by flash column chromatography (100 g reverse phase C18 GOLD silica gel cartridge; A=water:MeCN:TFA 90:10:0.05%, B=water:MeCN:TFA 10:90:0.05%; 20 min grad.; 0% B to 100% B; flow rate=80 mL/min). The fractions containing product were combined and concentrated. The residue was dissolved in MeOH (10 mL) and 4 M HCl in dioxane (10 mL) and stirred. After 1 h, the solvent was concentrated and the product was dried in vacuo to afford the title compound (0.11 g, 0.19 mmol, 19% yield) as a colorless oil. Analytical LC/MS (Method 3): Observed Mass: 475.3; Retention Time: 0.68 min.

Step B. Examples 17 and 18

To a 40 mL vial were added Intermediate 17A (0.11 g, 0.19 mmol), isobutyraldehyde (65 mg, 0.90 mmol), AcOH (12 mg, 0.20 mmol), magnesium sulfate (220 mg, 1.8 mmol), and DMF (2 mL). The reaction mixture was stirred for 20 min, then sodium triacetoxyborohydride (120 mg, 0.57 mmol) was added and the reaction mixture was stirred. After 18 h, the reaction mixture was filtered and the filter cake was washed with 10% IPA/chloroform (20 mL). The filtrate was washed with 10% aqueous NaOH (10 mL), brine, dried over $MgSO_4$, filtered and concentrated. The crude isomeric mixture was purified via preparative HPLC with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 15% B, 15-70% B over 25 minutes, then a 0-minute hold at 100% B; Flow Rate: 20 mL/min; Column Temperature: 25° C. Fraction collection was triggered by MS signals. Fractions corresponding to the respective desired products were combined and dried via centrifugal evaporation.

Example 17 (35 mg, 0.066 mmol, 35% yield) was isolated as the $1^{st}$ eluting isomer. $^1H$ NMR (500 MHz, DMSO-$d_6$) δ 7.38-7.32 (m, 2H), 7.25-7.22 (m, 1H), 7.16-7.11 (m, 1H), 6.96-6.92 (m, 1H), 3.86 (s, 6H), 3.82 (s, 3H), 3.27-3.20 (m, 1H), 3.07-3.01 (m, 2H), 2.65-2.57 (m, 2H), 2.56 (s, 3H), 2.26-2.19 (m, 2H), 2.17-2.13 (m, 2H), 1.88-1.79 (m, 4H), 1.77-1.70 (m, 2H), 1.68-1.56 (m, 6H), 1.56-1.50 (m, 2H), 0.92-0.87 (m, 6H). TLR9 $IC_{50}$ (nM)=25. Analytical LC/MS (Method 1): Purity: 98%; Observed Mass: 531.02; Retention Time: 1.01 min. (Method 2): Purity: 100%; Observed Mass: 531.24; Retention Time: 1.59 min.

Example 18 (16 mg, 0.030 mmol, 16% yield) was isolated as the $2^{nd}$ eluting isomer. $^1H$ NMR (500 MHz, DMSO-$d_6$) δ 7.37 (s, 2H), 7.26-7.22 (m, 1H), 7.16-7.12 (m, 1H), 6.98-6.93 (m, 1H), 3.87 (s, 6H), 3.84 (s, 3H), 2.66-2.58 (m, 1H), 2.55 (s, 3H), 2.49-2.37 (m, 1H), 2.07-1.95 (m, 3H), 1.95-1.83 (m, 8H), 1.82-1.61 (m, 6H), 0.95-0.87 (m, 6H) (4 protons obscured). TLR9 $IC_{50}$ (nM)=29. Analytical LC/MS (Method 1): Purity: 100%; Observed Mass: 531.23; Retention Time: 1.06 min. (Method 2): Purity: 96.8%; Observed Mass: 530.90; Retention Time: 1.91 min.

Examples 19 and 20

2-(3,4-dimethoxyphenyl)-6-(1-(8-isobutyl-8-azabicyclo[3.2.1]octan-3-yl)piperidin-4-yl)-4-methyl-1H-benzo[d]imidazole (19-20)

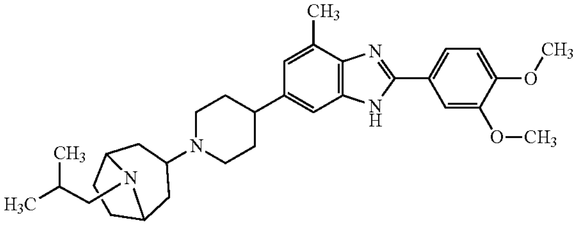

Step A. Intermediate 19A. Preparation of 6-(1-(8-azabicyclo[3.2.1]octan-3-yl)piperidin-4-yl)-2-(3,4-dimethoxyphenyl)-4-methyl-1H-benzo[d]imidazole dihydrochloride (19A)

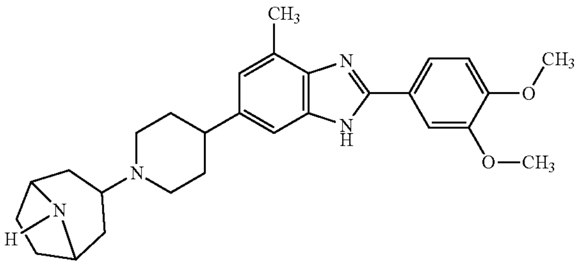

Intermediate 19A was synthesized according to the general methods described for the preparation of Intermediate 17A, using Intermediate 11D (640 mg, 1.1 mmol) as starting material to afford the title compound (120 mg, 0.22 mmol, 20% yield) as a colorless oil. Analytical LC/MS (Method 3): Observed Mass: 461.3; Retention Time: 0.67 min.

Step B. Preparation of Examples 19 and 20

Examples 19 and 20 were synthesized according to the general methods described for the preparation of Examples 17 and 18, using Intermediate 19A (120 mg, 0.22 mmol) as the starting material. The crude isomeric mixture was purified via preparative HPLC with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 11% B, 11-59% B over 20 minutes, then a 0-minute hold at 100% B; Flow Rate: 20 mL/min; Column Temperature: 25° C. Fraction collection was triggered by MS and UV signals. Fractions corresponding to the respective desired products were combined and dried via centrifugal evaporation.

Example 19 (46 mg, 0.089 mmol, 40% yield) was isolated as the 1$^{st}$ eluting isomer. $^1$H NMR (500 MHz, DMSO-$d_6$) δ 7.85-7.67 (m, 2H), 7.29-7.09 (m, 2H), 6.89-6.84 (m, 1H), 3.89 (s, 3H), 3.84 (s, 3H), 3.24-2.81 (m, 1H), 2.69-2.57 (m, 2H), 2.48-2.39 (m, 1H), 2.35-2.20 (m, 2H), 1.97-1.84 (m, 7H), 1.80-1.66 (m, 7H), 1.65-1.56 (m, 2H), 0.94-0.87 (m, 6H) (4 protons obscured). TLR9 $IC_{50}$ (nM)=28. Analytical LC/MS (Method 1): Purity: 100%; Observed Mass: 516.98; Retention Time: 1.05 min. (Method 2): Purity: 98.5%; Observed Mass: 516.97; Retention Time: 1.45 min.

Example 20 (41 mg, 0.079 mmol, 36% yield) was isolated as the 2$^{nd}$ eluting isomer. $^1$H NMR (500 MHz, DMSO-$d_6$) δ 7.85-7.68 (m, 2H), 7.32-7.10 (m, 2H), 6.91-6.85 (m, 1H), 3.88 (s, 3H), 3.84 (s, 3H), 3.77-3.55 (m, 1H), 3.53-3.45 (m, 2H), 3.20-3.15 (m, 1H), 2.55 (s, 5H), 2.49-2.46 (m, 1H), 2.34-2.12 (m, 3H), 2.09-2.00 (m, 3H), 1.96-1.88 (m, 4H), 1.80-1.65 (m, 2H), 0.99-0.91 (m, 6H) (4 protons obscured). TLR9 $IC_{50}$ (nM)=69. Analytical LC/MS (Method 1): Purity: 100%; Observed Mass: 517.38; Retention Time: 1.04 min. (Method 2): Purity: 99.3%; Observed Mass: 517.03; Retention Time: 1.63 min.

Example 21

2-(3,4-dimethoxyphenyl)-6-(8-(1-isopropylpiperidin-4-yl)-8-azabicyclo[3.2.1]octan-3-yl)-1,4-dimethyl-1H-benzo[d]imidazole (Isomeric Mixture)

(21)

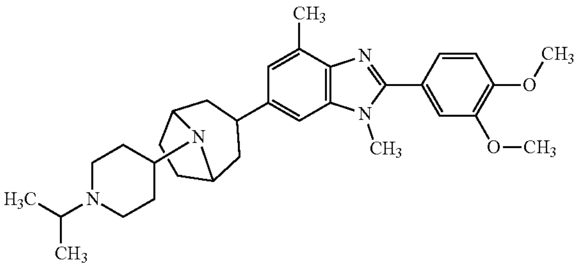

Step A. Intermediate 21A. Preparation of 5-bromo-$N^1$,3-dimethylbenzene-1,2-diamine (21A)

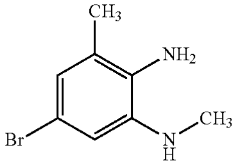

Intermediate 21A was synthesized according to methods described for the preparation of Intermediate 11, using Intermediate 15A (2.0 g, 8.2 mmol) as starting material to afford the title compound (1.6 g, 7.4 mmol, 90% yield) as a pale yellow solid. $^1$H NMR (500 MHz, METHANOL-$d_4$) δ 6.65-6.60 (m, 1H), 6.57-6.53 (m, 1H), 2.81 (s, 3H), 2.15 (s, 3H). Analytical LC/MS (Method 3): Observed Mass: 215.0; Retention Time: 0.67 min.

Step B. Intermediate 21B. Preparation of 6-bromo-2-(3,4-dimethoxyphenyl)-1,4-dimethyl-1H-benzo[d]imidazole (21B)

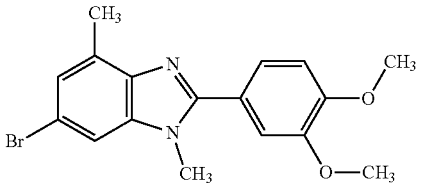

To a 40 mL vial were added Intermediate 21A (0.56 g, 2.6 mmol) and NMP (10 mL). To this mixture was added sodium metabisulfite (0.72 g, 3.8 mmol), followed by 3,4-dimethoxybenzaldehyde (0.52 g, 3.1 mmol). The mixture was stirred at 70° C. After 18 h, the reaction mixture was cooled, diluted with water (100 mL) and extracted with EtOAc (2×50 mL). The organic phase was combined, washed with brine, dried over $MgSO_4$, filtered and concentrated. The residue was purified by flash column chromatography (120 g silica gel cartridge; A=Hex, B=EtOAc; 30 min grad.; 0% B to 100% B; flow rate=80 mL/min). The fractions corresponding to product were combined, concentrated and dried in vacuo to afford the title compound (0.83 g, 2.3 mmol, 88% yield) as a light yellow solid. $^1H$ NMR (500 MHz, METHANOL-$d_4$) δ 7.61-7.58 (m, 1H), 7.41-7.38 (m, 1H), 7.37-7.33 (m, 1H), 7.27-7.24 (m, 1H), 7.21-7.15 (m, 1H), 3.97-3.94 (m, 6H), 3.87-3.84 (m, 3H), 2.64-2.61 (m, 3H). Analytical LC/MS (Method 3): Observed Mass: 363.0; Retention Time: 0.71 min.

Step C. Intermediate 21C. Preparation of tert-butyl 3-(2-(3,4-dimethoxyphenyl)-1,4-dimethyl-1H-benzo[d]imidazol-6-yl)-8-azabicyclo[3.2.1]oct-2-ene-8-carboxylate

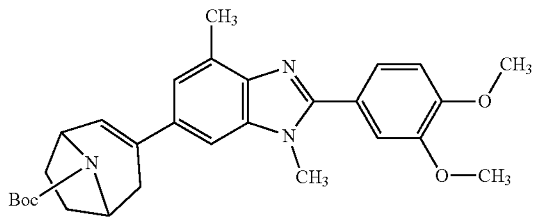 [SMILES: COc1ccc(-c2nc3c(C)cc(C4=CC5CCC(C4)N5C(=O)OC(C)(C)C)cc3n2C)cc1OC]

To a 40 mL vial were added Intermediate 21B (270 mg, 0.75 mmol), tert-butyl 3-(4,4,5,5-tetramethyl-1,3,2-dioxaborolan-2-yl)-8-azabicyclo[3.2.1]oct-2-ene-8-carboxylate (250 mg, 0.75 mmol), XPhos Pd G3 (63 mg, 0.075 mmol), 1,4-dioxane (15 mL), followed by potassium phosphate tribasic (550 mg, 2.6 mmol) dissolved in water (3 mL). The vessel was flushed with $N_2$, capped and the reaction mixture was stirred at 85° C. After 18 h, the reaction mixture was cooled, diluted with water (100 mL) and extracted with EtOAc (2×50 mL). The organic phase was combined, washed with brine, dried over $MgSO_4$, filtered and concentrated. The residue was purified by flash column chromatography (120 g silica gel cartridge; A=Hex, B=EtOAc; 30 min grad.; 0% B to 100% B; flow rate=80 mL/min). The fractions corresponding to product were combined, concentrated and dried in vacuo to afford the title compound (360 mg, 0.74 mmol, 99% yield) as a pale yellow solid. $^1H$ NMR (500 MHz, METHANOL-$d_4$) δ 7.42-7.38 (m, 1H), 7.38-7.32 (m, 2H), 7.23-7.20 (m, 1H), 7.19-7.15 (m, 1H), 6.56-6.51 (m, 1H), 4.56-4.47 (m, 2H), 3.95 (s, 6H), 3.90-3.86 (m, 3H), 3.25-3.11 (m, 1H), 2.63 (s, 3H), 2.51-2.39 (m, 1H), 2.35-2.21 (m, 1H), 2.10-2.04 (m, 2H), 1.88-1.76 (m, 1H), 1.49 (s, 9H). Analytical LC/MS (Method 3): Observed Mass: 490.4; Retention Time: 0.90 min.

Step D. Intermediate 21D. Preparation of 6-(8-azabicyclo[3.2.1]octan-3-yl)-2-(3,4-dimethoxyphenyl)-1,4-dimethyl-1H-benzo[d]imidazole dihydrochloride (21D)

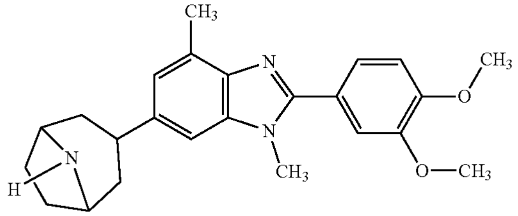

To a 100 mL pear shaped flask were added Intermediate 21C (360 mg, 0.74 mmol), and MeOH (30 mL). The vessel was evacuated and purged with $N_2$, then Pd—C (10% wt.) (78 mg, 0.074 mmol) was added and the reaction mixture was stirred under hydrogen at 1 atm. After 18 h, the catalyst was filtered and to the filtrate was added 4 M HCl in dioxane (30 mL). After 30 min, the solvent was concentrated, the residue was co-evaporated with toluene (2×) and the product was dried in vacuo to afford the title compound (300 mg, 0.65 mmol, 88% yield) as a tan solid. $^1H$ NMR (500 MHz, METHANOL-$d_4$) δ 7.88-7.73 (m, 1H), 7.59-7.47 (m, 3H), 7.34-7.30 (m, 1H), 4.23-4.14 (m, 2H), 4.14-4.09 (m, 3H), 4.00 (d, J=6.9 Hz, 6H), 3.79-3.59 (m, 3H), 3.52-3.37 (m, 1H), 2.73-2.68 (m, 3H), 2.68-2.37 (m, 2H), 2.14-2.05 (m, 2H), 2.00-1.92 (m, 1H). Analytical LC/MS (Method 3): Observed Mass: 392.3; Retention Time: 0.58 min.

Step E. Example 21

To a 40 mL vial were added Intermediate 21D (98 mg, 0.21 mmol), 1-isopropylpiperidin-4-one (140 mg, 1.0 mmol), AcOH (14 mg, 0.24 mmol), magnesium sulfate (220 mg, 1.8 mmol), and DMF (2 mL). The reaction mixture was stirred for 20 min, then sodium triacetoxyborohydride (210 mg, 1.0 mmol) was added and the reaction mixture was stirred. After 18 h, the reaction mixture was filtered and the filter cake was washed with 10% IPA/chloroform (20 mL). The filtrate was washed with 10% aqueous NaOH (10 mL), brine, dried over $MgSO_4$, filtered and concentrated. The crude material was purified via preparative HPLC (Prep Method 1) to afford the title compound (72 mg, 0.14 mmol, 67% yield). $^1H$ NMR (500 MHz, DMSO-$d_6$) δ 7.37-7.31 (m, 2H), 7.25-7.21 (m, 1H), 7.15-7.11 (m, 1H), 7.02-6.97 (m, 1H), 3.84 (s, 6H), 3.81 (s, 3H), 3.13-3.05 (m, 1H), 2.91-2.86 (m, 2H), 2.78-2.73 (m, 1H), 2.53 (s, 3H), 2.38-2.29 (m, 1H), 2.26-2.20 (m, 3H), 2.00-1.91 (m, 6H), 1.82-1.77 (m, 2H), 1.66-1.58 (m, 2H), 1.45-1.35 (m, 3H), 1.01-0.99 (m, 6H). TLR9 $IC_{50}$ (nM)=24. Analytical LC/MS (Method 1): Purity: 100%; Observed Mass: 517.08; Retention Time: 1.03 min. (Method 2): Purity: 100%; Observed Mass: 517.20; Retention Time: 1.43 min.

Example 22

6-(1'-isopropyl-[1,4'-bipiperidin]-4-yl)-1,4-dimethyl-2-(4-(methylsulfonyl)phenyl)-1H-benzo[d]imidazole (22)

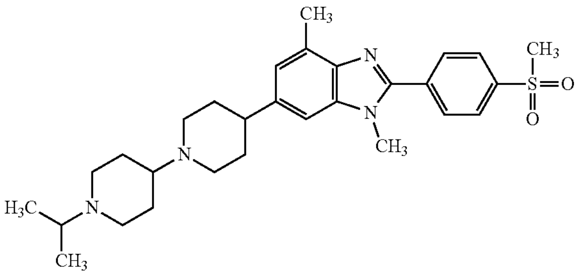

Step A. Intermediate 22A. Preparation of 6-bromo-1,4-dimethyl-2-(4-(methylsulfonyl)phenyl)-1H-benzo[d]imidazole (22A)

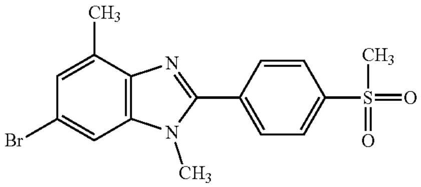

Intermediate 22A was synthesized according to methods described for the preparation of Intermediate 21B, using Intermediate 21A (200 mg, 0.93 mmol) as starting material and substituting 4-(methylsulfonyl)benzaldehyde (200 mg, 1.1 mmol) where appropriate to afford the title compound (350 mg, 0.92 mmol, 99% yield) as a light yellow solid. $^{1}H$ NMR (500 MHz, METHANOL-$d_4$) δ 8.22-8.18 (m, 2H), 8.11-8.07 (m, 2H), 7.69-7.65 (m, 1H), 7.34-7.29 (m, 1H), 3.90 (s, 3H), 3.24 (s, 3H), 2.67-2.64 (m, 3H). Analytical LC/MS (Method 3): Observed Mass: 381.1; Retention Time: 0.78 min.

Step B. Intermediate 22B. Preparation of tert-butyl 4-(1,4-dimethyl-2-(4-(methylsulfonyl)phenyl)-1H-benzo[d]imidazol-6-yl)-3,6-dihydropyridine-1(2H)-carboxylate (22B)

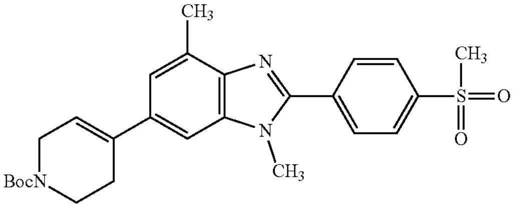

To a 40 mL vial were added Intermediate 22A (350 mg, 0.92 mmol), tert-butyl 4-(4,4,5,5-tetramethyl-1,3,2-dioxaborolan-2-yl)-3,6-dihydropyridine-1(2H)-carboxylate (340 mg, 1.1 mmol), XPhos Pd G3 (78 mg, 0.092 mmol), 1,4-dioxane (15 mL), followed by potassium phosphate tribasic (680 mg, 3.2 mmol) dissolved in water (3 mL). The vessel was flushed with $N_2$, capped and the reaction mixture was stirred at 85° C. After 18 h, the reaction mixture was cooled, diluted with water (100 mL) and extracted with EtOAc (2×50 mL). The organic phase was combined, washed with brine, dried over $MgSO_4$, filtered and concentrated. The residue was purified by flash column chromatography (80 g silica gel cartridge; A=Hex, B=EtOAc; 30 min grad.; 0% B to 100% B; flow rate=60 mL/min). The fractions corresponding to product were combined, concentrated and dried in vacuo to afford the title compound (400 mg, 0.83 mmol, 90% yield) as a pale yellow solid. $^{1}H$ NMR (500 MHz, METHANOL-$d_4$) δ 8.22-8.16 (m, 2H), 8.08 (br d, J=8.3 Hz, 2H), 7.45 (s, 1H), 7.29 (s, 1H), 6.23-6.17 (m, 1H), 4.18-4.08 (m, 2H), 3.92 (s, 3H), 3.76-3.64 (m, 2H), 3.27-3.21 (m, 3H), 2.69-2.64 (m, 2H), 2.66 (s, 3H), 1.53 (s, 9H). Analytical LC/MS (Method 3): Observed Mass: 482.3; Retention Time: 0.79 min.

Step C. Intermediate 22C. Preparation of 1,4-dimethyl-2-(4-(methylsulfonyl)phenyl)-6-(piperidin-4-yl)-1H-benzo[d]imidazole dihydrochloride (22C)

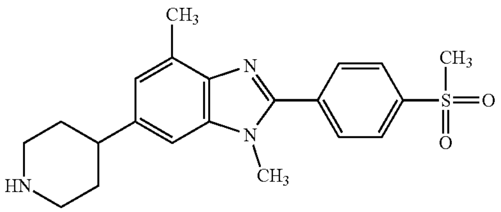

To a 100 mL pear shaped flask were added Intermediate 22B (400 mg, 0.83 mmol), and MeOH (30 mL). The vessel was evacuated and purged with $N_2$, then Pd—C (10% wt.) (88 mg, 0.083 mmol) was added and the reaction mixture was stirred under hydrogen at 1 atm. After 45 min, the reaction mixture was filtered and to the filtrate was added 4 M HCl in dioxane (30 mL). After stirring 30 min, the solvent was concentrated and the residue was co-evaporated with toluene (2×). The product was dried in vacuo to afford the title compound (370 mg, 0.81 mmol, 98% yield) as a tan solid. $^{1}H$ NMR (500 MHz, METHANOL-$d_4$) δ 8.38-8.33 (m, 2H), 8.23-8.19 (m, 2H), 7.74 (s, 1H), 7.70-7.47 (m, 1H), 4.14-4.11 (m, 3H), 3.99-3.93 (m, 1H), 3.79-3.66 (m, 1H), 3.63-3.56 (m, 2H), 3.29 (s, 3H), 3.27-3.17 (m, 2H), 3.04-2.95 (m, 1H), 2.77-2.72 (m, 3H), 2.27-2.06 (m, 2H). Analytical LC/MS (Method 3): Observed Mass: 384.2; Retention Time: 0.52 min.

Step D. Example 22

To a 40 mL vial were added Intermediate 22C (60 mg, 0.13 mmol), 1-isopropylpiperidin-4-one (92 mg, 0.65 mmol), AcOH (9.0 mg, 0.15 mmol), magnesium sulfate (220 mg, 1.8 mmol), and DMF (2 mL). The reaction mixture was stirred for 20 min, then sodium triacetoxyborohydride (140 mg, 0.66 mmol) was added and the reaction mixture was stirred. After 18 h, the reaction mixture was filtered and the filter cake was washed with 10% IPA/chloroform (20 mL). The filtrate was washed with 10% aqueous NaOH (10 mL), brine, dried over $MgSO_4$, filtered and concentrated. The crude material was purified via preparative HPLC (Prep Method 1) to afford the title compound (14 mg, 0.028 mmol, 22% yield). $^1$H NMR (500 MHz, DMSO-$d_6$) δ 8.16-8.09 (m, 4H), 7.33 (s, 1H), 7.01 (s, 1H), 3.90 (s, 3H), 3.03-2.96 (m, 2H), 2.88-2.82 (m, 2H), 2.72-2.64 (m, 1H), 2.63-2.58 (m, 1H), 2.56 (s, 3H), 2.31-2.19 (m, 3H), 2.14-2.05 (m, 2H), 1.94-1.89 (m, 1H), 1.85-1.71 (m, 6H), 1.49-1.39 (m, 2H), 0.97 (d, J=6.4 Hz, 6H) (two protons obscured). TLR9 $IC_{50}$ (nM)=7.6. Analytical LC/MS (Method 1): Purity: 100%; Observed Mass: 509.21; Retention Time: 0.86 min. (Method 2): Purity: 100%; Observed Mass: 509.22; Retention Time: 1.15 min.

Example 23

2-(3-fluoro-4-methoxyphenyl)-6-(1'-isopropyl-[1,4'-bipiperidin]-4-yl)-1,4-dimethyl-1H-benzo[d]imidazole (23)

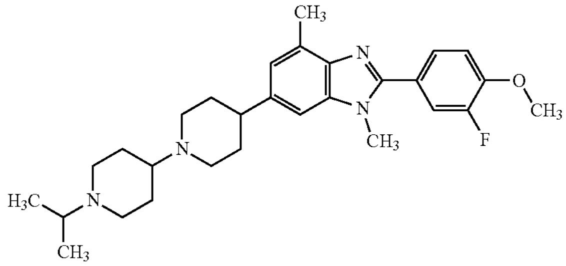

Step A. Intermediate 23A. Preparation of 6-bromo-2-(3-fluoro-4-methoxyphenyl)-1,4-dimethyl-1H-benzo[d]imidazole

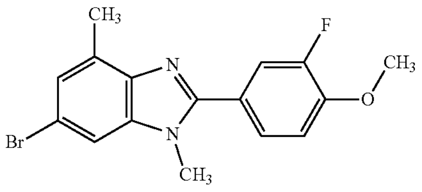 [SMILES: COc1ccc(-c2nc3c(C)cc(Br)cc3n2C)cc1F]

Intermediate 23A was synthesized according to methods described for the preparation of Intermediate 21B, using Intermediate 21A (200 mg, 0.93 mmol) as starting material and substituting 3-fluoro-4-methoxybenzaldehyde (170 mg, 1.1 mmol) where appropriate to afford the title compound (300 mg, 0.86 mmol, 92% yield) as a pale yellow solid. $^1$H NMR (500 MHz, METHANOL-$d_4$) δ 7.63-7.56 (m, 3H), 7.37-7.31 (m, 1H), 7.28-7.24 (m, 1H), 4.00 (s, 3H), 3.85 (s, 3H), 2.62 (s, 3H). Analytical LC/MS (Method 3): Observed Mass: 351.1; Retention Time: 0.79 min.

Step B. Intermediate 23B. Preparation of tert-butyl 4-(2-(3-fluoro-4-methoxyphenyl)-1,4-dimethyl-1H-benzo[d]imidazol-6-yl)-3,6-dihydropyridine-1(2H)-carboxylate (23B)

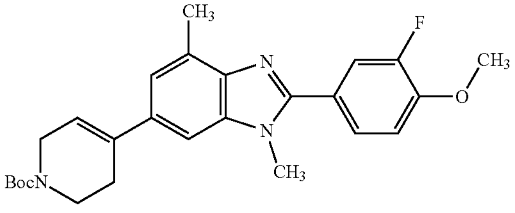

Intermediate 23B was synthesized according to methods described for the preparation of Intermediate 22B, using Intermediate 23A (350 mg, 1.0 mmol) as starting material to afford the title compound (0.45 g, 1.0 mmol, 100% yield) as a pale yellow solid. $^1$H NMR (500 MHz, METHANOL-$d_4$) δ 7.62-7.55 (m, 2H), 7.42-7.38 (m, 1H), 7.37-7.31 (m, 1H), 7.27-7.23 (m, 1H), 6.22-6.14 (m, 1H), 4.18-4.08 (m, 2H), 4.00 (s, 3H), 3.88 (s, 3H), 3.74-3.66 (m, 2H), 2.68-2.63 (m, 2H), 2.64 (s, 3H), 1.22 (s, 9H). Analytical LC/MS (Method 3): Observed Mass: 452.4; Retention Time: 0.90 min.

Step C. Intermediate 23C. Preparation of 2-(3-fluoro-4-methoxyphenyl)-1,4-dimethyl-6-(piperidin-4-yl)-1H-benzo[d]imidazole dihydrochloride (23C)

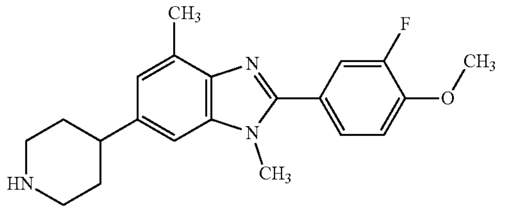

Intermediate 23C was synthesized according to methods described for the preparation of Intermediate 22C, using Intermediate 23B (0.45 g, 1.0 mmol) as starting material to afford the title compound (420 mg, 0.99 mmol, 99% yield) as a tan solid. $^1$H NMR (500 MHz, METHANOL-$d_4$) δ 7.81-7.75 (m, 2H), 7.71 (s, 1H), 7.54-7.48 (m, 1H), 7.46 (s, 1H), 4.11 (s, 3H), 4.07 (s, 3H), 3.61-3.56 (m, 2H), 3.28-3.16 (m, 3H), 2.71 (s, 3H), 2.25-2.16 (m, 2H), 2.16-2.03 (m, 2H). Analytical LC/MS (Method 3): Observed Mass: 354.3; Retention Time: 0.58 min.

Step D. Example 23

To a 40 mL vial were added Intermediate 23C (60 mg, 0.14 mmol), 1-isopropylpiperidin-4-one (100 mg, 0.71 mmol), AcOH (9.6 mg, 0.16 mmol), magnesium sulfate (220 mg, 1.8 mmol), and DMF (2 mL). The reaction mixture was stirred for 20 min, then sodium triacetoxyborohydride (150 mg, 0.71 mmol) was added and the reaction mixture was stirred. After 18 h, the reaction mixture was filtered and the filter cake was washed with 10% IPA/chloroform (20 mL). The filtrate was washed with 10% aqueous NaOH (10 mL), brine, dried over $MgSO_4$, filtered and concentrated. The crude material was purified via preparative HPLC (Prep Method 1) to afford the title compound (48 mg, 0.10 mmol, 71% yield). $^1$H NMR (500 MHz, DMSO-$d_6$) δ 7.73-7.67 (m, 1H), 7.66-7.60 (m, 1H), 7.40-7.33 (m, 1H), 7.29-7.23 (m, 1H), 6.99-6.93 (m, 1H), 3.95 (s, 3H), 3.84 (s, 3H), 3.41-3.26 (m, 2H), 3.06-2.99 (m, 2H), 2.96-2.87 (m, 2H), 2.82-2.72 (m, 1H), 2.63-2.58 (m, 1H), 2.33-2.27 (m, 2H), 2.25-2.16 (m, 2H), 1.85-1.75 (m, 5H), 1.56-1.42 (m, 2H), 1.00 (br d, J=6.4 Hz, 6H) (three protons obscured). TLR9 $IC_{50}$ (nM)= 160. Analytical LC/MS (Method 1): Purity: 99.2%; Observed Mass: 479.19; Retention Time: 0.98 min. (Method 2): Purity: 98.1%; Observed Mass: 479.19; Retention Time: 1.36 min.

Example 24

2-(3-fluoro-4-methoxyphenyl)-6-(1'-isopropyl-[1,4'-bipiperidin]-4-yl)-4-methyl-1H-benzo[d]imidazole (24)

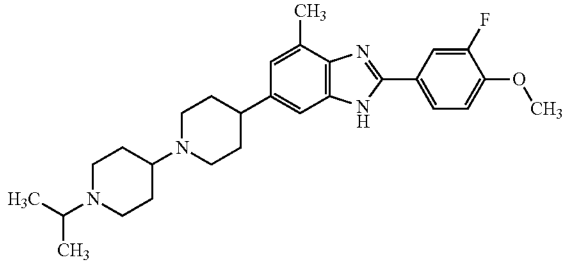

Step A. Intermediate 24A. Preparation of 6-bromo-2-(3-fluoro-4-methoxyphenyl)-4-methyl-1H-benzo[d]imidazole (24A)

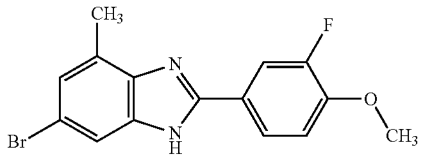

Intermediate 24A was synthesized according to the general procedures described for the preparation of Intermediate 11A, using 5-bromo-3-methylbenzene-1,2-diamine (340 mg, 1.7 mmol) as starting material and substituting 3-fluoro-4-methoxybenzaldehyde (320 mg, 2.1 mmol) where appropriate to afford the title compound (340 mg, 1.0 mmol, 59% yield) as a pale yellow solid. $^1$H NMR (500 MHz, METHANOL-$d_4$) δ 7.96-7.88 (m, 2H), 7.65-7.51 (m, 1H), 7.32-7.27 (m, 1H), 7.23-7.18 (m, 1H), 3.99 (s, 3H), 2.62 (s, 3H). Analytical LC/MS (Method 3): Observed Mass: 337.0; Retention Time: 0.79 min.

Step B. Intermediate 24B. Preparation of tert-butyl 4-(2-(3-fluoro-4-methoxyphenyl)-4-methyl-1H-benzo[d]imidazol-6-yl)-3,6-dihydropyridine-1(2H)-carboxylate (24B)

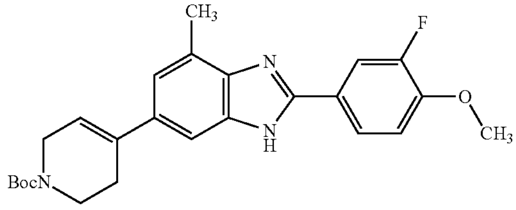

Intermediate 24B was synthesized according to the general procedures described for the preparation of Intermediate 111B, using Intermediate 24A (340 mg, 1.0 mmol) as starting material to provide the title compound (430 mg, 0.98 mmol, 98% yield) as a pale yellow solid. $^1$H NMR (500 MHz, METHANOL-$d_4$) δ 7.97-7.86 (m, 2H), 7.56-7.33 (m, 1H), 7.31-7.25 (m, 1H), 7.21-7.16 (m, 1H), 6.14-6.07 (m, 1H), 4.11 (br s, 2H), 3.98 (s, 3H), 3.72-3.65 (m, 2H), 2.65-2.59 (m, 5H), 1.53 (s, 9H). Analytical LC/MS (Method 3): Observed Mass: 438.4; Retention Time: 0.89 min.

Step C. Intermediate 24C. Preparation of 2-(3-fluoro-4-methoxyphenyl)-4-methyl-6-(piperidin-4-yl)-1H-benzo[d]imidazole dihydrochloride (24C)

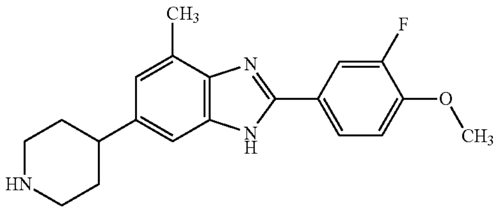

Intermediate 24C was synthesized according to the general procedures described for the preparation of Intermediate 11D (Steps C-D), using Intermediate 24B (430 mg, 0.98 mmol) as starting material to afford the title compound (260 mg, 0.63 mmol, 64% yield over two steps) as a tan solid. $^1$H NMR (500 MHz, METHANOL-$d_4$) δ 8.07-8.00 (m, 2H), 7.56-7.53 (m, 1H), 7.52-7.47 (m, 1H), 7.39-7.37 (m, 1H), 4.06 (s, 3H), 3.63-3.56 (m, 2H), 3.26-3.19 (m, 2H), 3.19-3.11 (m, 1H), 2.73 (s, 3H), 2.22-2.14 (m, 2H), 2.10-1.98 (m, 2H). Analytical LC/MS (Method 3): Observed Mass: 340.2; Retention Time: 0.59 min.

Step D. Example 24

To a 40 mL vial were added Intermediate 24C (62 mg, 0.15 mmol), 1-isopropylpiperidin-4-one (100 mg, 0.71 mmol), AcOH (9.6 mg, 0.16 mmol), magnesium sulfate (220 mg, 1.8 mmol), and DMF (2 mL). The reaction mixture was stirred for 20 min, then sodium triacetoxyborohydride (160 mg, 0.75 mmol) was added and the reaction mixture was stirred. After 18 h, the reaction mixture was filtered and the filter cake was washed with 10% IPA/chloroform (20 mL). The filtrate was washed with 10% aqueous NaOH (10 mL), brine, dried over $MgSO_4$, filtered and concentrated. The crude material was purified via preparative HPLC (Prep Method 1) to afford the title compound (60 mg, 0.13 mmol, 87% yield). $^1$H NMR (500 MHz, DMSO-$d_6$) δ 8.09-7.91 (m, 2H), 7.41-7.32 (m, 1H), 7.30-7.11 (m, 1H), 6.89 (br s, 1H), 3.94 (s, 3H), 3.06-2.99 (m, 2H), 2.98-2.90 (m, 2H), 2.89-2.76 (m, 1H), 2.56 (s, 3H), 2.41-2.19 (m, 5H), 1.87-1.78 (m, 5H), 1.74-1.65 (m, 2H), 1.57-1.46 (m, 2H), 1.02 (br d, J=6.4 Hz, 6H). TLR9 $IC_{50}$ (nM)=48. Analytical LC/MS (Method 1): Purity: 99.1%; Observed Mass: 464.93; Retention Time: 1.03 min. (Method 2): Purity: 100%; Observed Mass: 464.92; Retention Time: 1.34 min.

Example 25

2-(imidazo[1,2-a]pyridin-6-yl)-6-(1'-isobutyl-[1,4'-bipiperidin]-4-yl)-4-methyl-1H-benzo[d]imidazole (25)

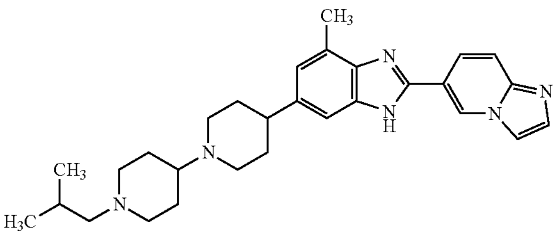

Step A. Intermediate 25A. Preparation of benzyl(4-bromo-2-methyl-6-nitrophenyl)carbamate

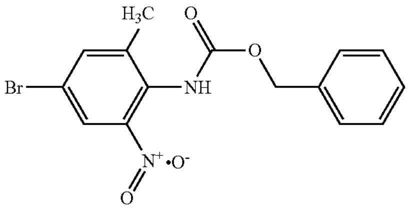

To a 500 mL pear shaped flask were added DCM (70 mL) and triphosgene (11 g, 37 mmol). To this mixture was dropwise added 4-bromo-2-methyl-6-nitroaniline (8.1 g, 35 mmol) dissolved in DCM (70 mL). After addition was complete, a solution of TEA (8.1 g, 80 mmol) dissolved in DCM (20 mL) was added dropwise. After stirring 2 h, the solvent was concentrated and the residue was purified by flash column chromatography (220 g silica gel cartridge; A=Hex, B=EtOAc; 30 min grad.; 0% B to 100% B; flow rate=120 mL/min). Fractions corresponding to the desired intermediate were combined and concentrated. The resultant residue was dissolved in THF (150 mL), then benzyl alcohol (7.9 g, 73 mmol) was added and the mixture was stirred at reflux. After 18 h, the reaction mixture was cooled, the solvent was concentrated and the residue was purified by flash column chromatography (220 g silica gel cartridge; A=Hex, B=EtOAc; 30 min grad.; 0% B to 100% B; flow rate=120 mL/min). Fractions corresponding to desired product were combined, concentrated and dried in vacuo to afford the title compound (12 g, 33 mmol, 94% yield) as a pale yellow solid. $^1$H NMR (500 MHz, CHLOROFORM-d) δ 8.02-7.98 (m, 1H), 7.67 (d, J=1.6 Hz, 1H), 7.66-7.55 (m, 1H), 7.42-7.35 (m, 5H), 5.21 (s, 2H), 2.36 (s, 3H).

Step B. Intermediate 25B. Preparation of tert-butyl 4-(4-(((benzyloxy)carbonyl)amino)-3-methyl-5-nitrophenyl)-3,6-dihydropyridine-1(2H)-carboxylate (25B)

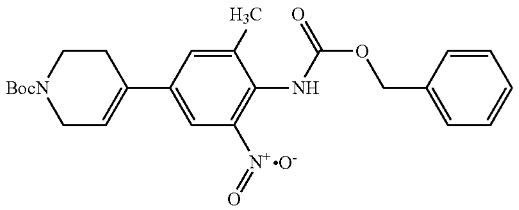

To a 500 mL pear shaped flask were added Intermediate 25A (12 g, 33 mmol), tert-butyl 4-(4,4,5,5-tetramethyl-1,3,2-dioxaborolan-2-yl)-3,6-dihydropyridine-1(2H)-carboxylate (11 g, 36 mmol), 1,4-dioxane (150 mL), followed by potassium phosphate tribasic (25 g, 120 mmol) dissolved in water (30 mL). The vessel was flushed with $N_2$, then 1,1'-bis(diphenylphosphino)ferrocene-palladium(II)dichloride dichloromethane complex (1.4 g, 1.7 mmol) was added and the reaction mixture was stirred at 85° C. After 18 h, the reaction mixture was cooled, diluted with water (400 mL) and extracted with EtOAc (2×200 mL). The organic phase was combined, washed with brine, dried over $MgSO_4$, filtered and concentrated. The residue was purified by flash column chromatography (330 g silica gel cartridge; A=Hex, B=EtOAc; 30 min grad.; 0% B to 100% B; flow rate=120 mL/min). Fractions corresponding to desired product were combined, concentrated and dried in vacuo to afford the title compound (15 g, 32 mmol, 97% yield) as a pale yellow solid. $^1$H NMR (500 MHz, METHANOL-$d_4$) δ 7.79-7.77 (m, 1H), 7.64-7.61 (m, 1H), 7.45-7.32 (m, 5H), 6.27-6.20 (m, 1H), 5.22-5.13 (m, 2H), 4.12-4.06 (m, 2H), 3.67-3.61 (m, 2H), 2.56-2.51 (m, 2H), 2.34 (s, 3H), 1.51 (s, 9H).

Step C. Intermediate 25C. Preparation of benzyl(4-(1-(1-isobutylpiperidin-4-yl)-1,2,3,6-tetrahydropyridin-4-yl)-2-methyl-6-nitrophenyl)carbamate bis(2,2,2-trifluoroacetate)

(25C)

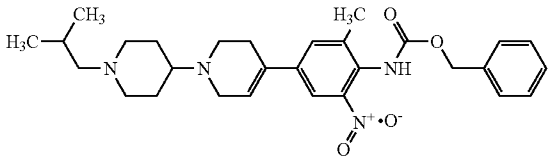

To a 500 mL pear shaped flask were added Intermediate 25B (15 g, 32 mmol), MeOH (30 mL) and 4 M HCl in dioxane (100 mL). After stirring 30 min, the solvent was concentrated and the residue was co-evaporated with toluene (2×). The resultant residue was dissolved in DMF (150 mL), and to this mixture was added 1-(2-methylpropyl)-4-piperidone (11 g, 71 mmol), $MgSO_4$ (60 g, 500 mmol), and AcOH (2.1 g, 35 mmol). After stirring for 10 min, sodium triacetoxyborohydride (21 g, 100 mmol) was added and the reaction mixture was stirred under $N_2$. After 18 h, the reaction mixture was filtered and the filter cake was washed with 10% IPA/$CHCl_3$. The filtrate was concentrated and the remaining DMF solution was loaded onto Celite cartridges and purified by flash column chromatography (3×275 g reverse phase C18 GOLD silica gel cartridge; A=water: MeCN:TFA 90:10:0.05%, B=water:MeCN:TFA 10:90: 0.05%; 20 min grad.; 10% B to 100% B; flow rate=120 mL/min). The fractions corresponding to product were combined, concentrated, the residue was co-evaporated with toluene (2×), and the product was dried in vacuo to afford the title compound (15 g, 20 mmol, 63% yield) as a tan solid. $^1H$ NMR (500 MHz, METHANOL-$d_4$) δ 7.88-7.86 (m, 1H), 7.72-7.69 (m, 1H), 7.46-7.31 (m, 5H), 6.34-6.29 (m, 1H), 5.27-5.13 (m, 2H), 4.06-3.96 (m, 2H), 3.87-3.73 (m, 2H), 3.67-3.51 (m, 3H), 3.17-3.05 (m, 2H), 3.05-2.99 (m, 2H), 2.96-2.90 (m, 2H), 2.53-2.42 (m, 2H), 2.38 (s, 3H), 2.29-2.15 (m, 3H), 1.10-1.06 (m, 6H). Analytical LC/MS (Method 3): Observed Mass: 507.3; Retention Time: 0.68 min.

Step D. Intermediate 25D. Preparation of 5-(1'-isobutyl-[1,4'-bipiperidin]-4-yl)-3-methylbenzene-1,2-diamine (25D)

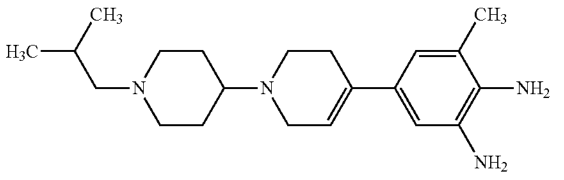

To a 2 L round bottomed flask were added Intermediate 25C (15 g, 20 mmol), and MeOH (500 mL). The vessel was evacuated and purged with $N_2$, then Pd—C (5% wt.) (2.7 g, 1.3 mmol) was added and the reaction mixture was stirred under hydrogen at 1 atm. After 18 h, the reaction mixture was filtered and to the filtrate was added Dowex 550A (OH) anion exchange resin (50 g) and stirred. After 2 h, the resin was filtered, and the filtrate was concentrated. The residue was dissolved in MeOH (500 mL), the vessel was evacuated and purged with $N_2$, then Pd—C (5% wt.) (2.7 g, 1.3 mmol) was added and the reaction mixture was stirred under hydrogen at 1 atm. After 18 h, the catalyst was filtered, the filtrate was concentrated and the product was dried in vacuo to afford the title compound (6.2 g, 18 mmol, 90% yield) as a tan solid. $^1H$ NMR (500 MHz, DMSO-$d_6$) δ 6.30-6.27 (m, 1H), 6.19-6.16 (m, 1H), 3.05-2.90 (m, 2H), 2.89-2.79 (m, 2H), 2.30-2.12 (m, 4H), 1.82 (br s, 2H), 1.71 (br s, 6H), 1.55-1.38 (m, 5H), 0.84 (d, J=6.6 Hz, 6H) (three protons obscured). Analytical LC/MS (Method 3): Observed Mass: 345.3; Retention Time: 0.58 min.

Step E. Example 25

To a 40 mL vial were added Intermediate 25D (52 mg, 0.15 mmol) and NMP (2 mL). To this mixture was added sodium metabisulfite (42 mg, 0.22 mmol), followed by imidazo[1,2-a]pyridine-6-carbaldehyde (22 mg, 0.15 mmol). The vial was capped and the reaction mixture was stirred at 70° C. After 20 h, the solution was filtered, and the filtrate was diluted with water (20 mL) and extracted with EtOAc (2×10 mL). The organic phase was combined, washed with brine, dried over $MgSO_4$, filtered and concentrated. The crude material was purified via preparative HPLC (Prep Method 1) to afford the title compound (42 mg, 0.089 mmol, 59% yield). $^1H$ NMR (500 MHz, DMSO-$d_6$) δ 9.44-9.30 (m, 1H), 8.15-8.08 (m, 1H), 8.07-7.92 (m, 1H), 7.77-7.71 (m, 1H), 7.70-7.64 (m, 1H), 7.33-7.15 (m, 1H), 6.96-6.88 (m, 1H), 3.02-2.94 (m, 2H), 2.89-2.80 (m, 2H), 2.56-2.54 (m, 3H), 2.31-2.17 (m, 3H), 2.03-1.96 (m, 2H), 1.86-1.63 (m, 9H), 1.52-1.40 (m, 2H), 0.84 (d, J=6.5 Hz, 6H) (one proton obscured). TLR9 $IC_{50}$ (nM)=160. Analytical LC/MS (Method 1): Purity: 95%; Observed Mass: 470.93; Retention Time: 0.86 min. (Method 2): Purity: 98.4%; Observed Mass: 469.17; Retention Time: 1.35 min.

The following Examples were prepared according to the general methods described elsewhere herein using appropriate starting materials, reagents and conditions.

| Ex. No. | Structure | Prep Method |
| --- | --- | --- |
| 26 | 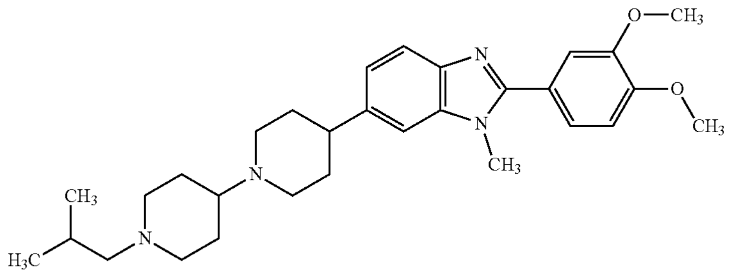 [SMILES: COc1ccc(-c2nc3ccc(C4CCN(C5CCN(CC(C)C)CC5)CC4)cc3n2C)cc1OC] | Ex. 1 Step G |

-continued
| Ex. No. | Structure | Prep Method |
|---|---|---|
| 27 | 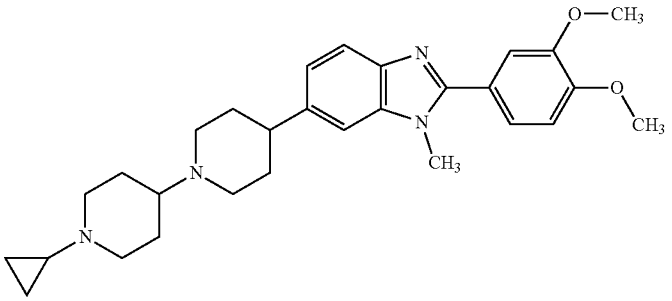 [SMILES: COc1ccc(-c2nc3ccc(C4CCN(C5CCN(C6CC6)CC5)CC4)cc3n2C)cc1OC] | Ex. 1 Step G |
| 28 | 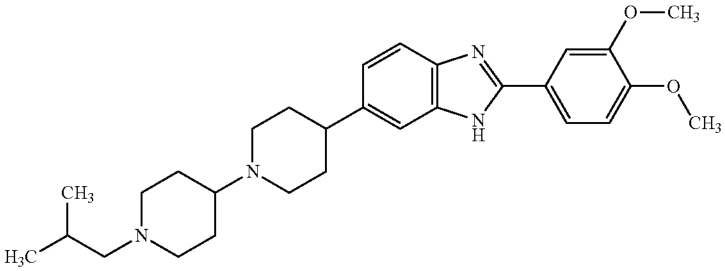 [SMILES: COc1ccc(-c2nc3ccc(C4CCN(C5CCN(CC(C)C)CC5)CC4)cc3[nH]2)cc1OC] | Ex. 2 Step E |
| 29 | 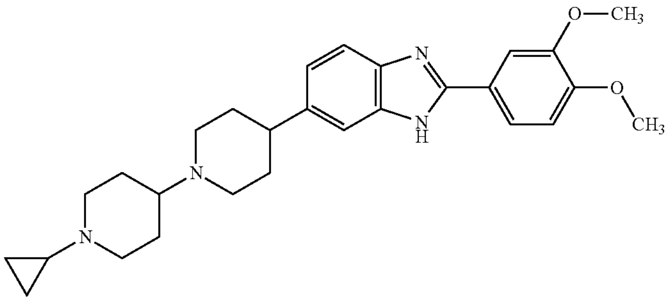 [SMILES: COc1ccc(-c2nc3ccc(C4CCN(C5CCN(C6CC6)CC5)CC4)cc3[nH]2)cc1OC] | Ex. 2 Step E |
| 30 | 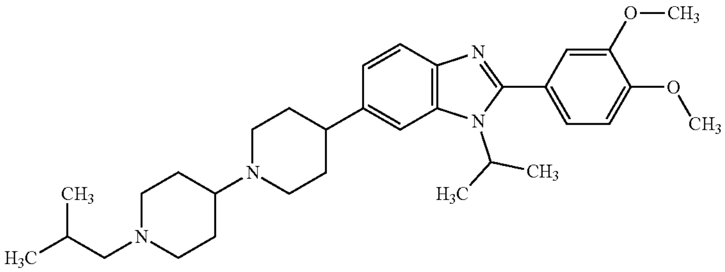 [SMILES: COc1ccc(-c2nc3ccc(C4CCN(C5CCN(CC(C)C)CC5)CC4)cc3n2C(C)C)cc1OC] | Ex. 3 Step F |
| 31 | 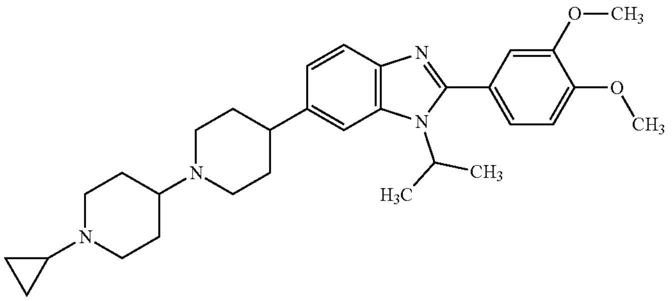 [SMILES: COc1ccc(-c2nc3ccc(C4CCN(C5CCN(C6CC6)CC5)CC4)cc3n2C(C)C)cc1OC] | Ex. 3 Step F |

-continued
| Ex. No. | Structure | Prep Method |
|---|---|---|
| 32 | 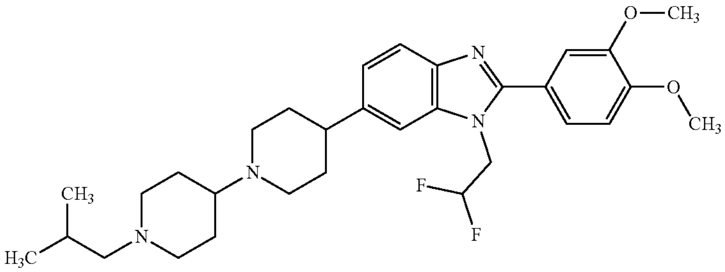 [SMILES: COc1ccc(-c2nc3ccc(C4CCN(C5CCN(CC(C)C)CC5)CC4)cc3n2CC(F)F)cc1OC] | Ex. 4 Step F |
| 33 | 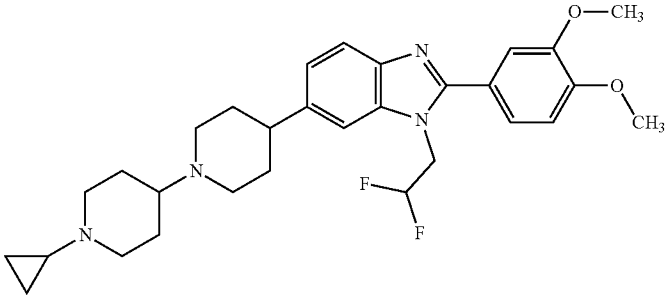 [SMILES: COc1ccc(-c2nc3ccc(C4CCN(C5CCN(C6CC6)CC5)CC4)cc3n2CC(F)F)cc1OC] | Ex. 4 Step F |
| 34 | 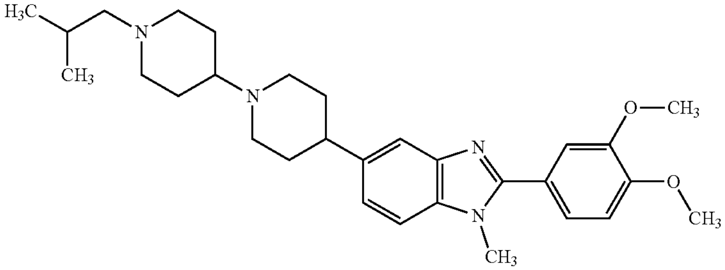 [SMILES: COc1ccc(-c2nc3cc(C4CCN(C5CCN(CC(C)C)CC5)CC4)ccc3n2C)cc1OC] | Ex. 5 Step G |
| 35 | 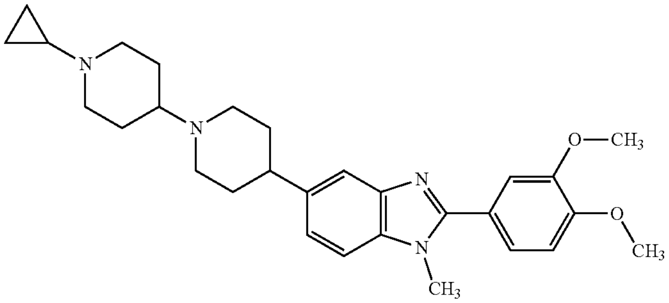 [SMILES: COc1ccc(-c2nc3cc(C4CCN(C5CCN(C6CC6)CC5)CC4)ccc3n2C)cc1OC] | Ex. 5 Step G |
| 36 | 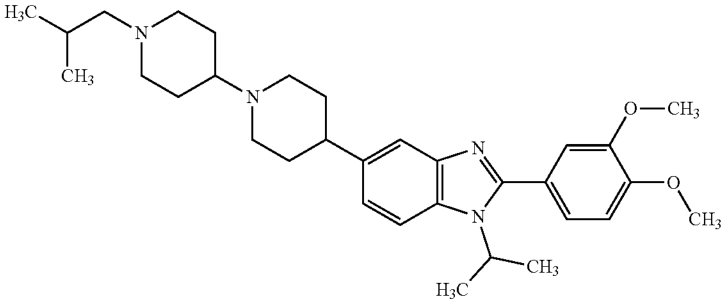 [SMILES: COc1ccc(-c2nc3cc(C4CCN(C5CCN(CC(C)C)CC5)CC4)ccc3n2C(C)C)cc1OC] | Ex. 6 Step F |

-continued
| Ex. No. | Structure | Prep Method |
|---|---|---|
| 37 | 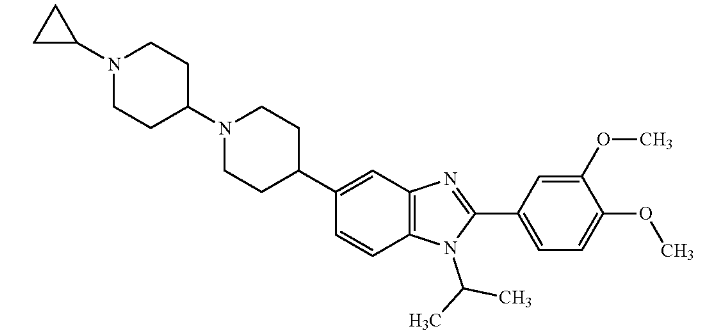 [SMILES: COc1ccc(-c2nc3cc(C4CCN(C5CCN(C6CC6)CC5)CC4)ccc3n2C(C)C)cc1OC] | Ex. 6 Step F |
| 38 | 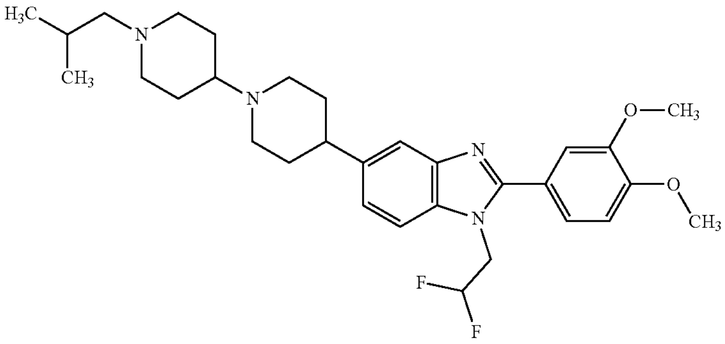 [SMILES: COc1ccc(-c2nc3cc(C4CCN(C5CCN(CC(C)C)CC5)CC4)ccc3n2CC(F)F)cc1OC] | Ex. 7 Step G |
| 39 | 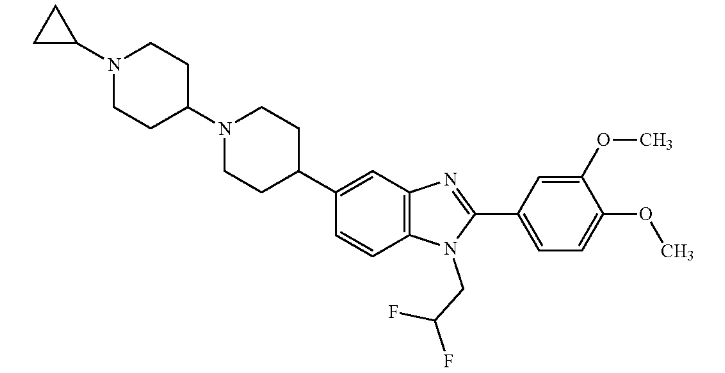 [SMILES: COc1ccc(-c2nc3cc(C4CCN(C5CCN(C6CC6)CC5)CC4)ccc3n2CC(F)F)cc1OC] | Ex. 7 Step G |
| 40 | 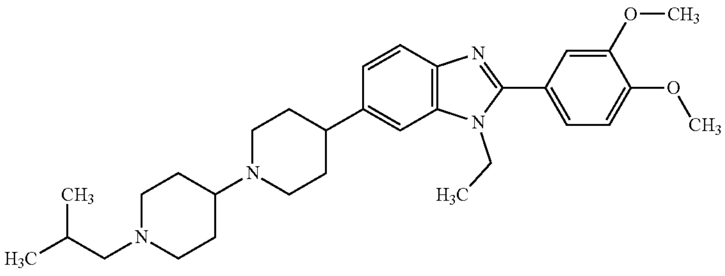 [SMILES: CCn1c(-c2ccc(OC)c(OC)c2)nc2ccc(C3CCN(C4CCN(CC(C)C)CC4)CC3)cc21] | Ex. 8-9 Step C |

-continued
| Ex. No. | Structure | Prep Method |
|---|---|---|
| 41 | 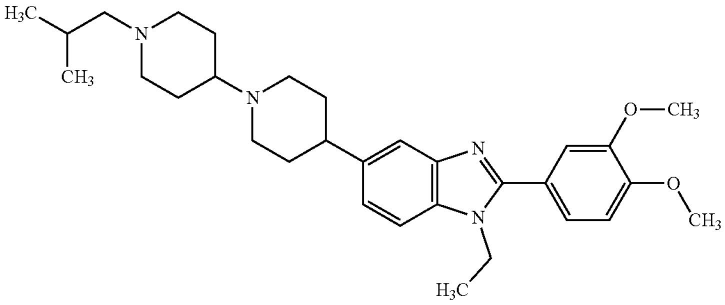 [SMILES: CCn1c(-c2ccc(OC)c(OC)c2)nc2cc(C3CCN(C4CCN(CC(C)C)CC4)CC3)ccc21] | Ex. 8-9 Step C |
| 42 | 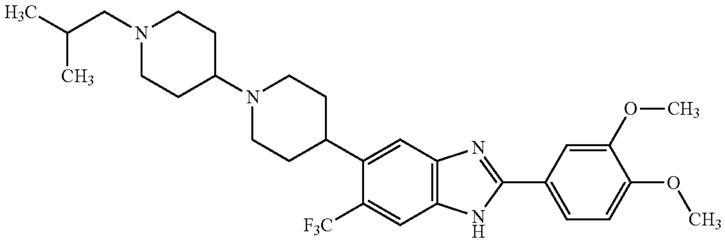 [SMILES: COc1ccc(-c2nc3cc(C4CCN(C5CCN(CC(C)C)CC5)CC4)c(C(F)(F)F)cc3[nH]2)cc1OC] | Ex. 10 Step F |
| 43 | 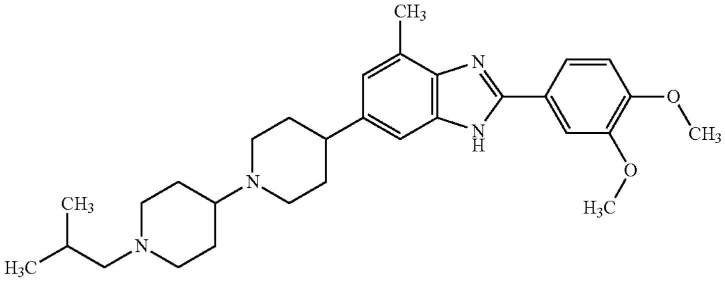 [SMILES: COc1ccc(-c2nc3c(C)cc(C4CCN(C5CCN(CC(C)C)CC5)CC4)cc3[nH]2)cc1OC] | Ex. 11 Step E |
| 44 | 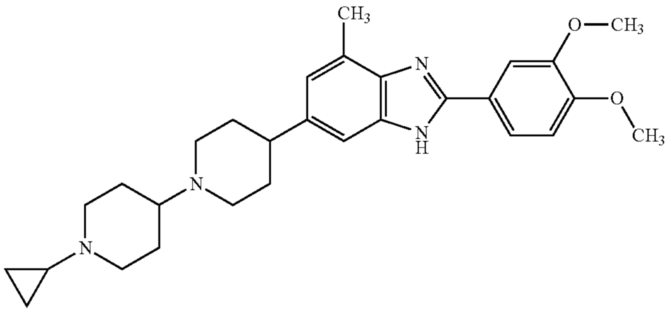 [SMILES: COc1ccc(-c2nc3c(C)cc(C4CCN(C5CCN(C6CC6)CC5)CC4)cc3[nH]2)cc1OC] | Ex. 11 Step E |
| 45 | 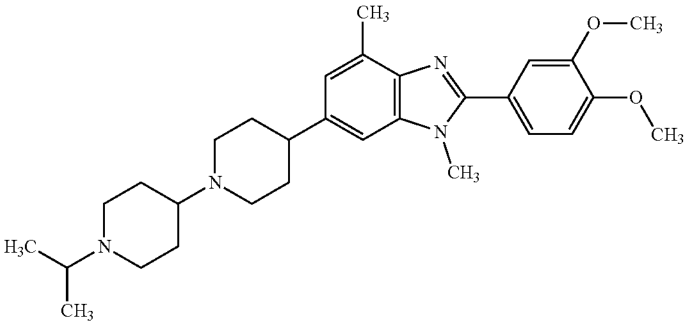 [SMILES: COc1ccc(-c2nc3c(C)cc(C4CCN(C5CCN(C(C)C)CC5)CC4)cc3n2C)cc1OC] | Ex. 15 Step F |

-continued
| Ex. No. | Structure | Prep Method |
|---|---|---|
| 46 | 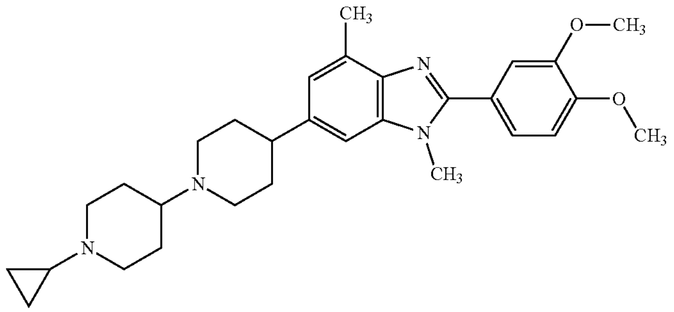 [SMILES: COc1ccc(-c2nc3c(C)cc(C4CCN(C5CCN(C6CC6)CC5)CC4)cc3n2C)cc1OC] | Ex. 15 Step F |
| 47 | 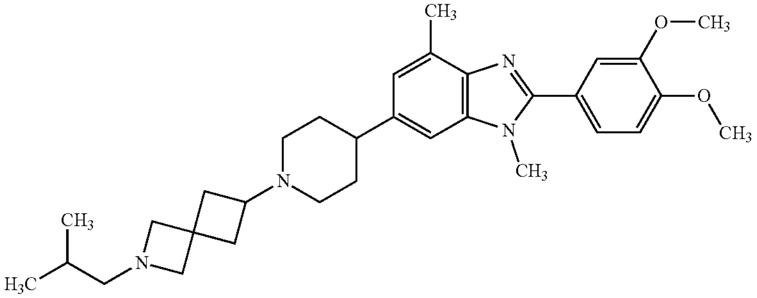 [SMILES: COc1ccc(-c2nc3c(C)cc(C4CCN(C5CC6(C5)CN(CC(C)C)C6)CC4)cc3n2C)cc1OC] | Ex. 16 Step B |
| 48 | 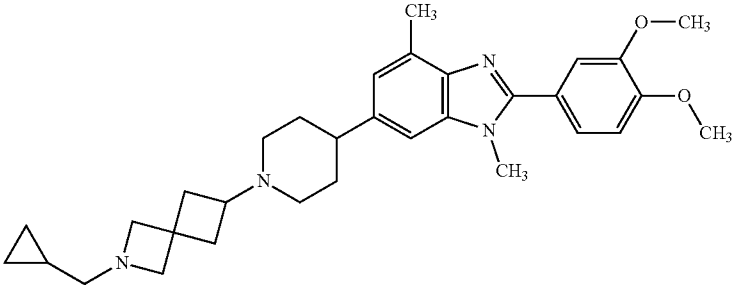 [SMILES: COc1ccc(-c2nc3c(C)cc(C4CCN(C5CC6(C5)CN(CC5CC5)C6)CC4)cc3n2C)cc1OC] | Ex. 16 Step B |
| 49 | 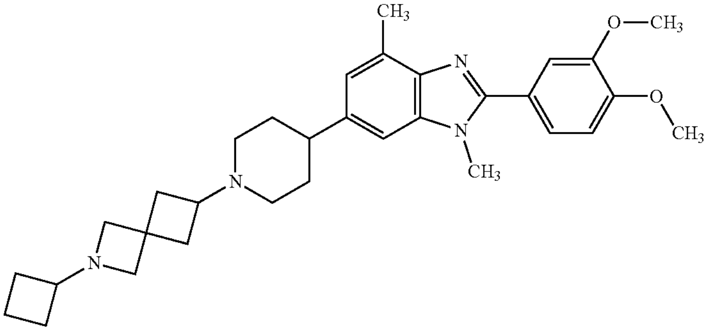 [SMILES: COc1ccc(-c2nc3c(C)cc(C4CCN(C5CC6(C5)CN(C5CCC5)C6)CC4)cc3n2C)cc1OC] | Ex. 16 Step B |
| 50 | 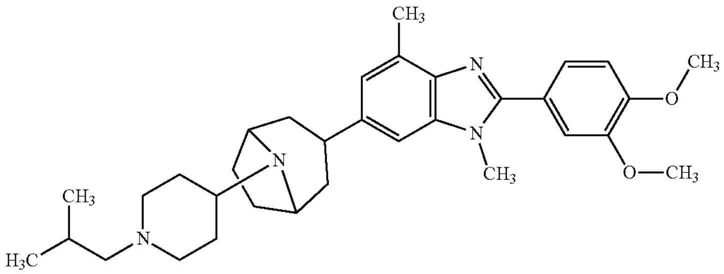 [SMILES: COc1ccc(-c2nc3c(C)cc(C4CC5CCC(C4)N5C4CCN(CC(C)C)CC4)cc3n2C)cc1OC] | Ex. 21 Step E |

-continued
| Ex. No. | Structure | Prep Method |
|---|---|---|
| 51 | 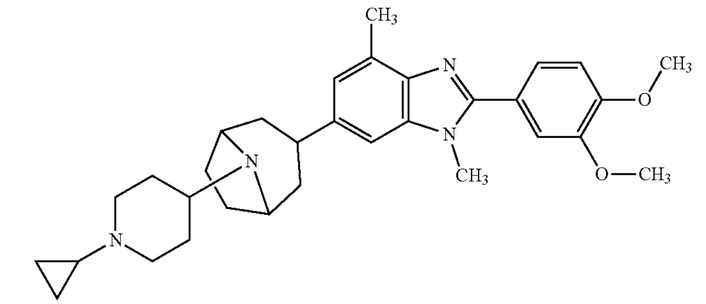 [SMILES: COc1ccc(-c2nc3c(C)cc(C4CC5CCC(C4)N5C4CCN(C5CC5)CC4)cc3n2C)cc1OC] | Ex. 21 Step E |
| 52 | 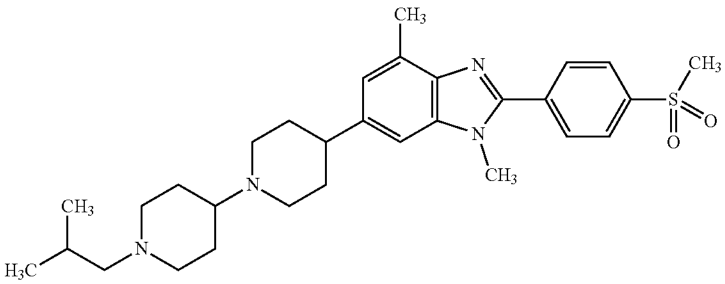 [SMILES: Cc1cc(C2CCN(C3CCN(CC(C)C)CC3)CC2)cc2c1nc(-c1ccc(S(C)(=O)=O)cc1)n2C] | Ex. 22 Step D |
| 53 | 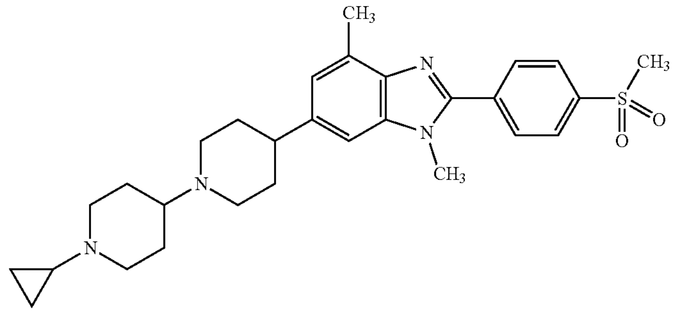 [SMILES: Cc1cc(C2CCN(C3CCN(C4CC4)CC3)CC2)cc2c1nc(-c1ccc(S(C)(=O)=O)cc1)n2C] | Ex. 22 Step D |
| 54 | 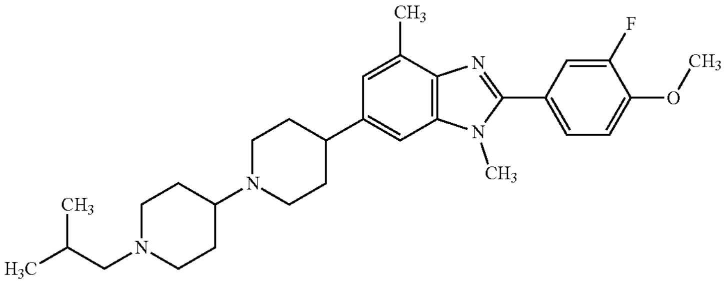 [SMILES: COc1ccc(-c2nc3c(C)cc(C4CCN(C5CCN(CC(C)C)CC5)CC4)cc3n2C)cc1F] | Ex. 23 Step D |
| 55 | 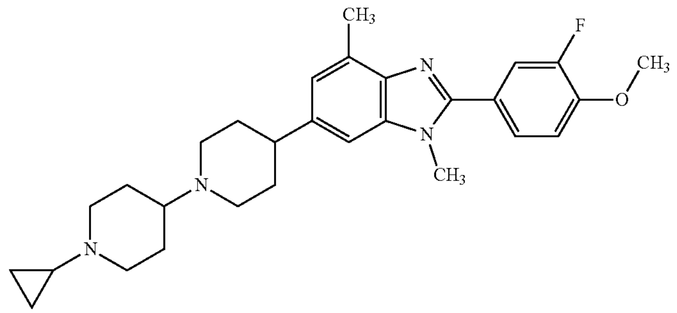 [SMILES: COc1ccc(-c2nc3c(C)cc(C4CCN(C5CCN(C6CC6)CC5)CC4)cc3n2C)cc1F] | Ex. 23 Step D |

-continued
| Ex. No. | Structure | Prep Method |
| --- | --- | --- |
| 56 | 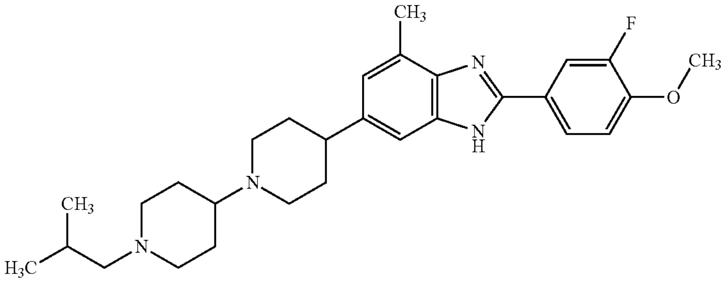 [SMILES: COc1ccc(-c2nc3c(C)cc(C4CCN(C5CCN(CC(C)C)CC5)CC4)cc3[nH]2)cc1F] | Ex. 24 Step D |
| 57 | 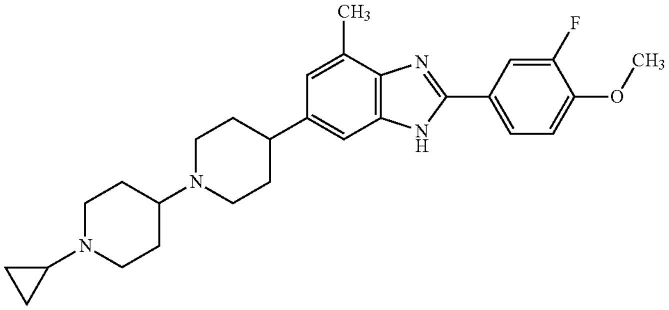 [SMILES: COc1ccc(-c2nc3c(C)cc(C4CCN(C5CCN(C6CC6)CC5)CC4)cc3[nH]2)cc1F] | Ex. 24 Step D |
| 58 | 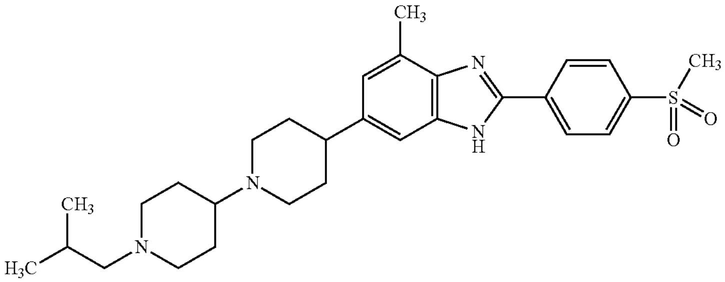 [SMILES: Cc1cc(C2CCN(C3CCN(CC(C)C)CC3)CC2)cc2[nH]c(-c3ccc(S(C)(=O)=O)cc3)nc12] | Ex. 25 Step E |
| 59 | 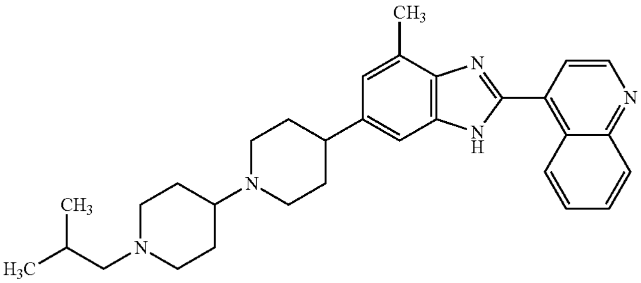 [SMILES: Cc1cc(C2CCN(C3CCN(CC(C)C)CC3)CC2)cc2[nH]c(-c3ccnc4ccccc34)nc12] | Ex. 25 Step E |
| 60 | 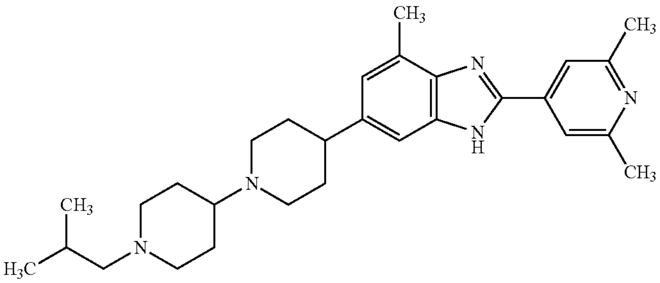 [SMILES: Cc1cc(-c2nc3c(C)cc(C4CCN(C5CCN(CC(C)C)CC5)CC4)cc3[nH]2)cc(C)n1] | Ex. 25 Step E |

-continued
| Ex. No. | Structure | Prep Method |
|---|---|---|
| 61 | 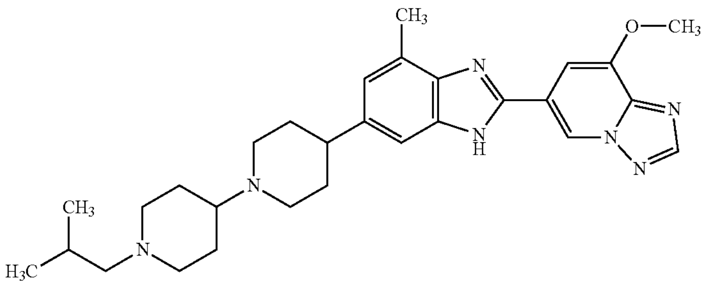 [SMILES: COc1cc(-c2nc3c(C)cc(C4CCN(C5CCN(CC(C)C)CC5)CC4)cc3[nH]2)cn2ncnc12] | Ex. 25 Step E |
| 62 | 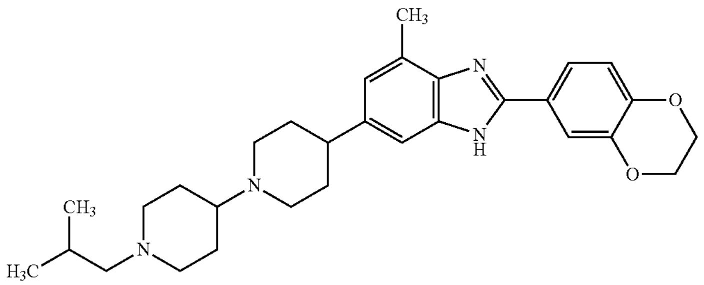 [SMILES: Cc1cc(C2CCN(C3CCN(CC(C)C)CC3)CC2)cc2[nH]c(-c3ccc4c(c3)OCCO4)nc12] | Ex. 25 Step E |
| 63 | 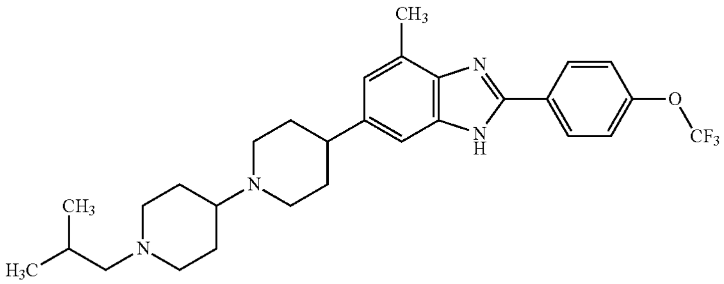 [SMILES: Cc1cc(C2CCN(C3CCN(CC(C)C)CC3)CC2)cc2[nH]c(-c3ccc(OC(F)(F)F)cc3)nc12] | Ex. 25 Step E |
| 64 | 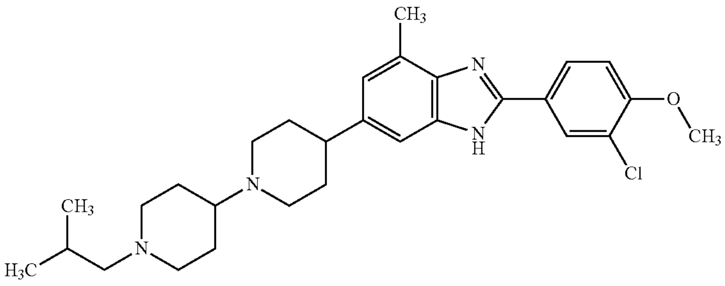 [SMILES: COc1ccc(-c2nc3c(C)cc(C4CCN(C5CCN(CC(C)C)CC5)CC4)cc3[nH]2)cc1Cl] | Ex. 25 Step E |
| 65 | 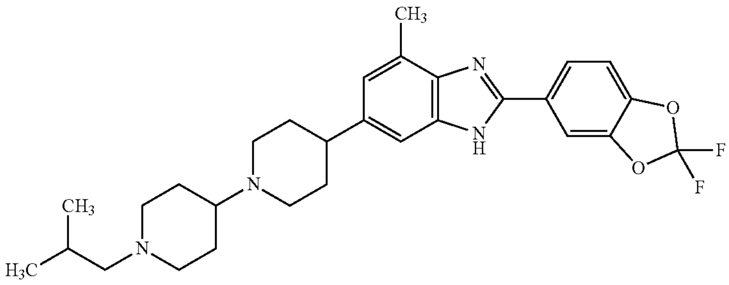 [SMILES: Cc1cc(C2CCN(C3CCN(CC(C)C)CC3)CC2)cc2[nH]c(-c3ccc4c(c3)OC(F)(F)O4)nc12] | Ex. 25 Step E |

-continued
| Ex. No. | Structure | Prep Method |
|---|---|---|
| 66 | 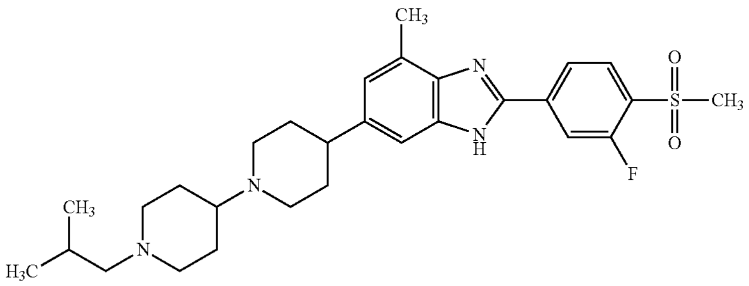 [SMILES: Cc1cc(C2CCN(C3CCN(CC(C)C)CC3)CC2)cc2[nH]c(-c3ccc(S(C)(=O)=O)c(F)c3)nc12] | Ex. 25 Step E |
| 67 | 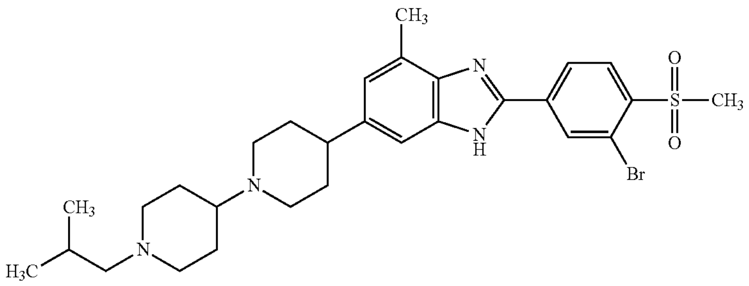 [SMILES: Cc1cc(C2CCN(C3CCN(CC(C)C)CC3)CC2)cc2[nH]c(-c3ccc(S(C)(=O)=O)c(Br)c3)nc12] | Ex. 25 Step E |
| 68 | 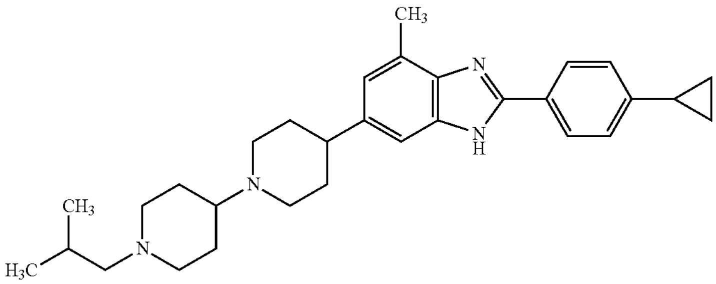 [SMILES: Cc1cc(C2CCN(C3CCN(CC(C)C)CC3)CC2)cc2[nH]c(-c3ccc(C4CC4)cc3)nc12] | Ex. 25 Step E |
| 69 | 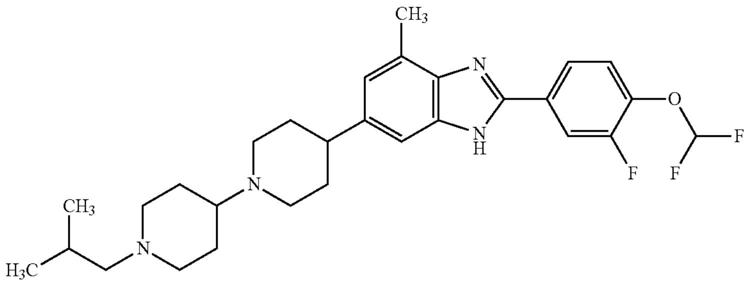 [SMILES: Cc1cc(C2CCN(C3CCN(CC(C)C)CC3)CC2)cc2[nH]c(-c3ccc(OC(F)F)c(F)c3)nc12] | Ex. 25 Step E |
| 70 | 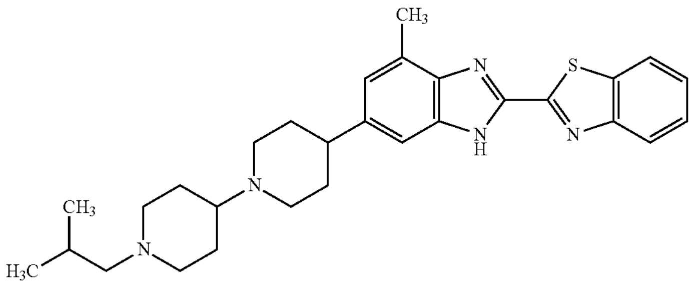 [SMILES: Cc1cc(C2CCN(C3CCN(CC(C)C)CC3)CC2)cc2[nH]c(-c3nc4ccccc4s3)nc12] | Ex. 25 Step E |

-continued
| Ex. No. | Structure | Prep Method |
|---|---|---|
| 71 | 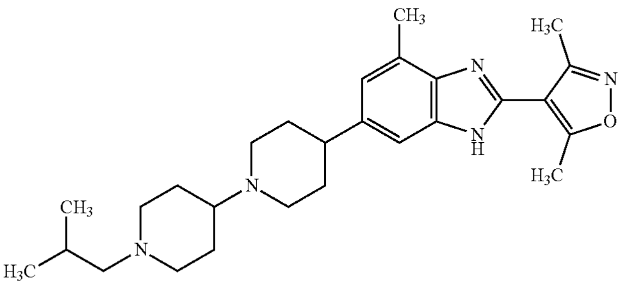 [SMILES: Cc1noc(C)c1-c1nc2c(C)cc(C3CCN(C4CCN(CC(C)C)CC4)CC3)cc2[nH]1] | Ex. 25 Step E |
| 72 | 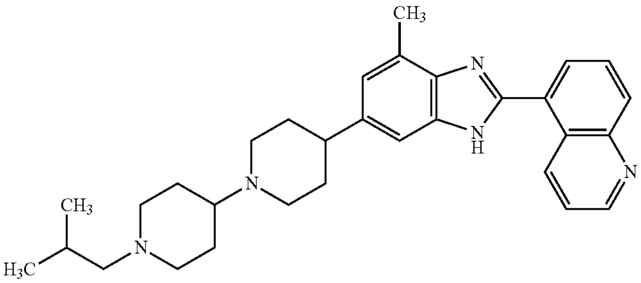 [SMILES: Cc1cc(C2CCN(C3CCN(CC(C)C)CC3)CC2)cc2[nH]c(-c3cccc4ncccc34)nc12] | Ex. 25 Step E |
| 73 | 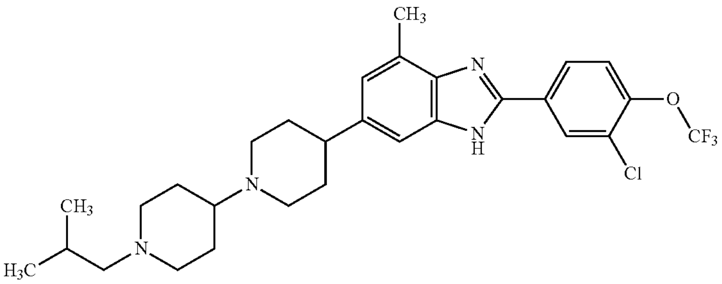 [SMILES: Cc1cc(C2CCN(C3CCN(CC(C)C)CC3)CC2)cc2[nH]c(-c3ccc(OC(F)(F)F)c(Cl)c3)nc12] | Ex. 25 Step E |
| 74 | 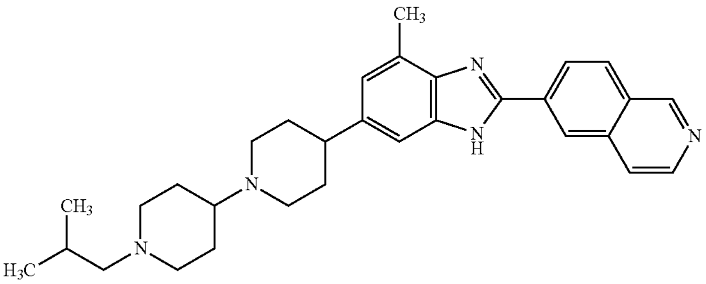 [SMILES: Cc1cc(C2CCN(C3CCN(CC(C)C)CC3)CC2)cc2[nH]c(-c3ccc4cnccc4c3)nc12] | Ex. 25 Step E |
| 75 | 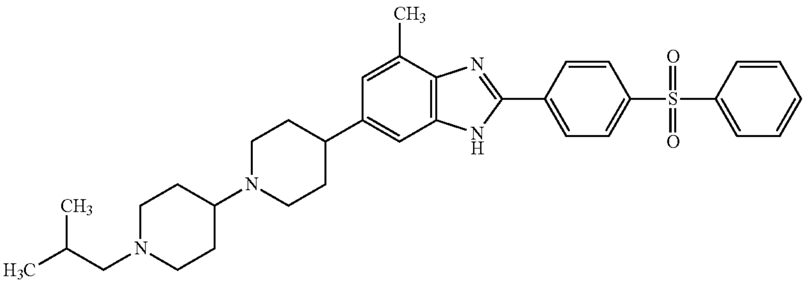 [SMILES: Cc1cc(C2CCN(C3CCN(CC(C)C)CC3)CC2)cc2[nH]c(-c3ccc(S(=O)(=O)c4ccccc4)cc3)nc12] | Ex. 25 Step E |

-continued
| Ex. No. | Structure | Prep Method |
|---|---|---|
| 76 | 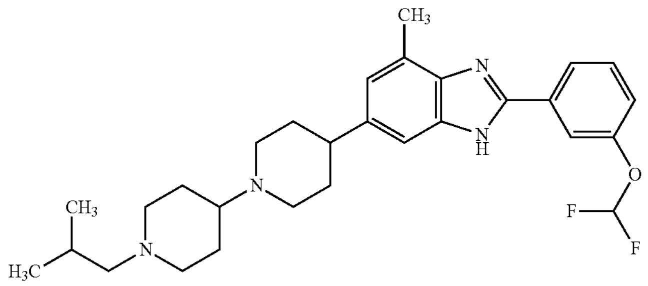 [SMILES: Cc1cc(C2CCN(C3CCN(CC(C)C)CC3)CC2)cc2[nH]c(-c3cccc(OC(F)F)c3)nc12] | Ex. 25 Step E |
| 77 | 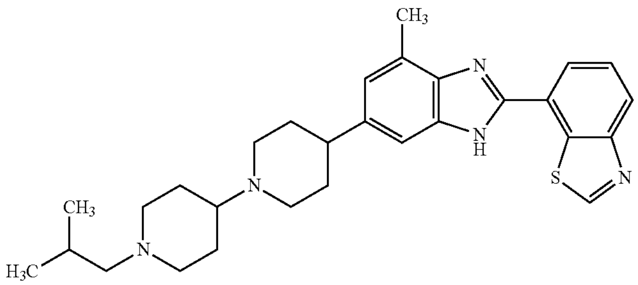 [SMILES: Cc1cc(C2CCN(C3CCN(CC(C)C)CC3)CC2)cc2[nH]c(-c3cccc4ncsc34)nc12] | Ex. 25 Step E |
| 78 | 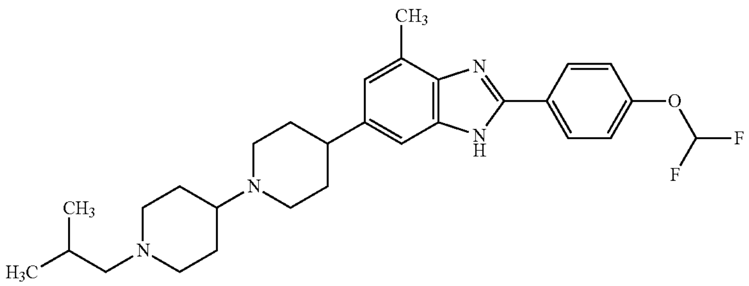 [SMILES: Cc1cc(C2CCN(C3CCN(CC(C)C)CC3)CC2)cc2[nH]c(-c3ccc(OC(F)F)cc3)nc12] | Ex. 25 Step E |
| 79 | 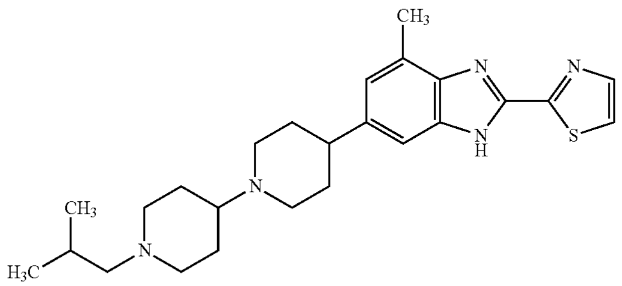 [SMILES: Cc1cc(C2CCN(C3CCN(CC(C)C)CC3)CC2)cc2[nH]c(-c3nccs3)nc12] | Ex. 25 Step E |
| 80 | 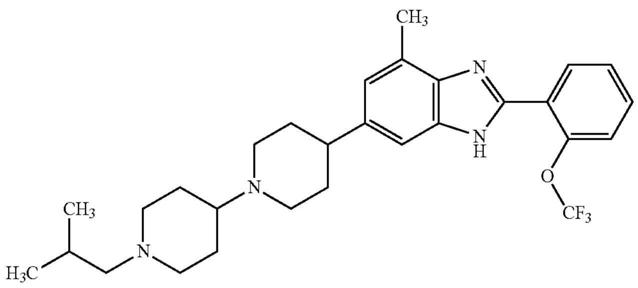 [SMILES: Cc1cc(C2CCN(C3CCN(CC(C)C)CC3)CC2)cc2[nH]c(-c3ccccc3OC(F)(F)F)nc12] | Ex. 25 Step E |

-continued

| Ex. No. | Structure | Prep Method |
|---|---|---|
| 81 | 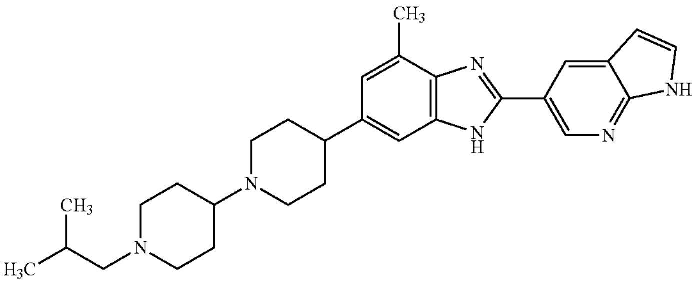 [SMILES: Cc1cc(C2CCN(C3CCN(CC(C)C)CC3)CC2)cc2[nH]c(-c3cnc4[nH]ccc4c3)nc12] | Ex. 25 Step E |
| 82 | 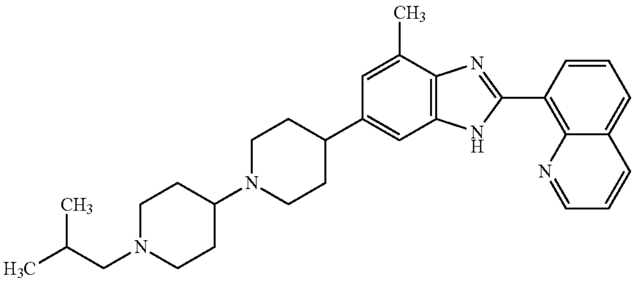 [SMILES: Cc1cc(C2CCN(C3CCN(CC(C)C)CC3)CC2)cc2[nH]c(-c3cccc4cccnc34)nc12] | Ex. 25 Step E |

| Ex. No. | Analytical LC/MS, Prep Method, Yield, and $^1H$ NMR |
|---|---|
| 26 | Analytical LC/MS (Method 1): Purity: 99.4%; Observed Mass: 491.33; Retention Time: 0.66 min. (Method 2): Purity: 98.7%; Observed Mass: 491.00; Retention Time: 1.44 min. Prep Method 1: 15 mg, 0.031 mmol, 36% yield; $^1H$ NMR (500 MHz, DMSO-$d_6$) δ 7.56 (d, J = 8.2 Hz, 1H), 7.45 (s, 1H), 7.41-7.36 (m, 2H), 7.14 (dd, J = 8.2, 3.7 Hz, 2H), 3.89-3.84 (m, 9H), 3.06-2.99 (m, 2H), 2.92-2.85 (m, 2H), 2.70-2.58 (m, 2H), 2.35-2.23 (m, 3H), 2.05-1.98 (m, 2H), 1.89-1.80 (m, 4H), 1.80-1.70 (m, 4H), 1.55-1.44 (m, 2H), 0.86 (d, J = 6.7 Hz, 6H). TLR9 $IC_{50}$ (nM) = 130 |
| 27 | Analytical LC/MS (Method 1): Purity: 95.6%; Observed Mass: 475.29; Retention Time: 0.94 min. (Method 2): Purity: 94.9%; Observed Mass: 474.95; Retention Time: 1.38 min. Prep Method 1: 31 mg, 0.065 mmol, 76% yield; $^1H$ NMR (500 MHz, DMSO-$d_6$) δ 7.31 (d, J = 8.2 Hz, 1H), 7.19 (s, 1H), 7.14 (s, 2H), 6.90 (br s, 2H), 3.66-3.56 (m, 9H), 2.85-2.71 (m, 3H), 2.46-2.37 (m, 1H), 2.20-2.06 (m, 3H), 1.95-1.87 (m, 2H), 1.63-1.47 (m, 6H), 1.39-1.30 (m, 1H), 1.26-1.12 (m, 2H), 0.20-0.13 (m, 2H), 0.07-0.01 (m, 2H) (one proton obscured). TLR9 $IC_{50}$ (nM) = 110 |
| 28 | Analytical LC/MS (Method 1): Purity: 98.9%; Observed Mass: 476.97; Retention Time: 1.00 min. (Method 2): Purity: 99.3%; Observed Mass: 476.98; Retention Time: 1.39 min. Prep Method 1: 26 mg, 0.055 mmol, 37% yield; $^1H$ NMR (500 MHz, DMSO-$d_6$) δ 7.76-7.73 (m, 1H), 7.72-7.68 (m, 1H), 7.53-7.48 (m, 1H), 7.44-7.39 (m, 1H), 7.15-7.08 (m, 2H), 3.88 (s, 3H), 3.84 (s, 3H), 3.21-3.15 (m, 2H), 3.00-2.93 (m, 2H), 2.76-2.64 (m, 2H), 2.11 (br s, 2H), 2.02-1.95 (m, 2H), 1.89-1.73 (m, 8H), 1.63-1.52 (m, 3H), 0.88-0.85 (m, 6H). TLR9 $IC_{50}$ (nM) = 19 |
| 29 | Analytical LC/MS (Method 1): Purity: 100%; Observed Mass: 460.95; Retention Time: 1.05 min. (Method 2): Purity: 100%; Observed Mass: 461.15; Retention Time: 1.32 min. Prep Method 1: 55 mg, 0.12 mmol, 80% yield; $^1H$ NMR (500 MHz, DMSO-$d_6$) δ 7.73 (br d, J = 0.9 Hz, 1H), 7.72-7.68 (m, 1H), 7.60-7.40 (m, 2H), 7.12 (br d, J = 8.2 Hz, 2H), 3.88 (s, 3H), 3.83 (s, 3H), 3.32-3.22 (m, 2H), 3.07-3.00 (m, 2H), 2.81-2.64 (m, 5H), 2.24-2.15 (m, 2H), 1.89-1.78 (m, 4H), 1.64-1.59 (m, 1H), 1.55-1.47 (m, 2H), 0.43 (br d, J = 4.6 Hz, 2H), 0.32 (br s, 2H) (one proton obscured). TLR9 $IC_{50}$ (nM) = 110 |
| 30 | Analytical LC/MS (Method 1): Purity: 98.9%; Observed Mass: 519.31; Retention Time: 1.03 min. (Method 2): Purity: 100%; Observed Mass: 519.00; Retention Time: 1.56 min. Prep Method 1: 51 mg, 0.098 mmol, 70% yield; $^1H$ NMR (500 MHz, DMSO-$d_6$) δ 7.63-7.56 (m, 2H), 7.20-7.12 (m, 4H), 4.83-4.72 (m, 1H), 3.86 (s, 3H), 3.83 (s, 3H), 3.60-3.52 (m, 1H), 3.38-3.26 (m, 1H), 3.10-2.97 (m, 2H), 2.94-2.60 (m, 4H), 2.29-2.03 (m, 4H), 2.02-1.79 (m, 7H), 1.72-1.63 (m, 2H), 1.61 (s, 3H), 1.59 (s, 3H), 0.89 (s, 3H), 0.88 (s, 3H).TLR9 $IC_{50}$ (nM) = 250 |
| 31 | Analytical LC/MS (Method 1): Purity: 99.5%; Observed Mass: 503.21; Retention Time: 1.01 min. (Method 2): Purity: 98.6%; Observed Mass: 502.97; Retention Time: 1.50 min. Prep Method 1: 60 mg, 0.12 mmol, 86% yield; $^1H$ |

-continued

| Ex. No. | Analytical LC/MS, Prep Method, Yield, and $^1$H NMR |
|---|---|
| | NMR (500 MHz, DMSO-$d_6$) δ 7.35-7.29 (m, 2H), 6.94-6.85 (m, 4H), 4.59-4.45 (m, 1H), 3.60 (s, 3H), 3.58 (s, 3H), 2.92-2.82 (m, 1H), 2.78-2.72 (m, 2H), 2.52-2.39 (m, 1H), 2.24-2.11 (m, 2H), 1.96-1.87 (m, 2H), 1.67-1.59 (m, 2H), 1.58-1.48 (m, 4H), 1.35 (s, 3H), 1.33 (s, 3H), 1.25-1.15 (m, 2H), 0.19-0.12 (m, 2H), 0.08-0.01 (m, 2H) (three protons obscured). TLR9 $IC_{50}$ (nM) = 750 |
| 32 | Analytical LC/MS (Method 1): Purity: 95.9%; Observed Mass: 540.98; Retention Time: 1.03 min. (Method 2): Purity: 92.9%; Observed Mass: 540.96; Retention Time: 1.55 min. Prep Method 1: 59 mg, 0.11 mmol, 79% yield; $^1$H NMR (500 MHz, DMSO-$d_6$) δ 7.63-7.56 (m, 1H), 7.54-7.49 (m, 1H), 7.32-7.26 (m, 2H), 7.24-7.12 (m, 2H), 6.56-6.29 (m, 1H), 4.81-4.70 (m, 2H), 3.86 (s, 3H), 3.84 (s, 3H), 3.05-2.95 (m, 2H), 2.91-2.82 (m, 2H), 2.64-2.55 (m, 1H), 2.33-2.19 (m, 3H), 2.03-1.98 (m, 2H), 1.87-1.78 (m, 4H), 1.78-1.65 (m, 5H), 1.54-1.42 (m, 2H), 0.86 (d, J = 6.4 Hz, 6H). TLR9 $IC_{50}$ (nM) = 210 |
| 33 | Analytical LC/MS (Method 1): Purity: 100%; Observed Mass: 525.02; Retention Time: 1.02 min. (Method 2): Purity: 100%; Observed Mass: 525.29; Retention Time: 1.53 min. Prep Method 1: 68 mg, 0.13 mmol, 93% yield; $^1$H NMR (500 MHz, DMSO-$d_6$) δ 7.61-7.56 (m, 1H), 7.54-7.50 (m, 1H), 7.31-7.26 (m, 2H), 7.24-7.19 (m, 1H), 7.17-7.12 (m, 1H), 6.41 (br s, 1H), 4.75 (br s, 2H), 3.86 (s, 3H), 3.83 (s, 3H), 3.11-2.93 (m, 4H), 2.70-2.60 (m, 1H), 2.46-2.31 (m, 3H), 2.21-2.10 (m, 2H), 1.89-1.81 (m, 2H), 1.80-1.67 (m, 4H), 1.61-1.55 (m, 1H), 1.49-1.38 (m, 2H), 0.45-0.37 (m, 2H), 0.29 (br s, 2H). TLR9 $IC_{50}$ (nM) = 680 |
| 34 | Analytical LC/MS (Method 1): Purity: 100%; Observed Mass: 490.96; Retention Time: 1.05 min. (Method 2): Purity: 100%; Observed Mass: 490.97; Retention Time: 1.50 min. Prep Method 1: 4.6 mg, 0.0094 mmol, 11% yield; $^1$H NMR (500 MHz, DMSO-$d_6$) δ 7.56-7.51 (m, 2H), 7.39 (s, 2H), 7.21-7.18 (m, 1H), 7.17-7.13 (m, 1H), 3.87 (s, 3H), 3.86 (d, J = 2.7 Hz, 6H), 3.50-3.36 (m, 1H), 3.14-3.00 (m, 2H), 2.99-2.83 (m, 2H), 2.33-2.09 (m, 3H), 2.02 (br s, 4H), 1.92 (br s, 2H), 1.88-1.78 (m, 2H), 1.76-1.66 (m, 2H), 0.89 (br d, J = 6.7 Hz, 6H) (three protons obscured). TLR9 $IC_{50}$ (nM) = 170 |
| 35 | Analytical LC/MS (Method 1): Purity: 100%; Observed Mass: 474.94; Retention Time: 0.97 min. (Method 2): Purity: 100%; Observed Mass: 475.24; Retention Time: 1.43 min. Prep Method 1: 28 mg, 0.059 mmol, 69% yield; $^1$H NMR (500 MHz, DMSO-$d_6$) δ 7.50 (br d, J = 4.9 Hz, 2H), 7.41-7.36 (m, 2H), 7.20-7.17 (m, 1H), 7.16-7.13 (m, 1H), 3.88-3.84 (m, 9H), 3.50-3.39 (m, 1H), 3.11-3.05 (m, 1H), 3.04-2.94 (m, 2H), 2.72-2.60 (m, 1H), 2.48-2.35 (m, 3H), 2.16 (br s, 2H), 1.84 (br s, 2H), 1.81-1.69 (m, 4H), 1.62-1.55 (m, 1H), 1.50-1.39 (m, 2H), 0.41 (br d, J = 4.6 Hz, 2H), 0.29 (br s, 2H). TLR9 $IC_{50}$ (nM) = 850 |
| 36 | Analytical LC/MS (Method 1): Purity: 98.3%; Observed Mass: 518.99; Retention Time: 1.06 min. (Method 2): Purity: 97%; Observed Mass: 519.08; Retention Time: 1.62 min. Prep Method 1: 62 mg, 0.12 mmol, 93% yield; $^1$H NMR (500 MHz, DMSO-d6) Shift 7.74-7.68 (m, 1H), 7.52-7.48 (m, 1H), 7.20-7.11 (m, 4H), 4.80-4.71 (m, 1H), 3.85 (s, 3H), 3.82 (s, 3H), 3.20-3.09 (m, 2H), 3.00-2.90 (m, 2H), 2.73-2.64 (m, 1H), 2.13-2.03 (m, 2H), 1.91 (s, 10H), 1.58 (s, 3H), 1.57 (s, 3H), 0.86 (s, 3H), 0.85 (s, 3H) (4 protons obscured). TLR9 $IC_{50}$ (nM) = 360 |
| 37 | Analytical LC/MS (Method 1): Purity: 99.3%; Observed Mass: 251.92; Retention Time: 1.07 min. (Method 2): Purity: 100%; Observed Mass: 503.20; Retention Time: 1.63 min. Prep Method 1: 47 mg, 0.093 mmol, 66% yield; $^1$H NMR (500 MHz, DMSO-d6) Shift 7.47-7.43 (m, 1H), 7.26-7.22 (m, 1H), 6.92 (s, 1H), 6.89 (s, 3H), 4.55-4.46 (m, 1H), 3.60 (s, 3H), 3.57 (s, 3H), 2.94-2.80 (m, 2H), 2.78-2.70 (m, 2H), 2.45-2.35 (m, 1H), 2.24-2.13 (m, 2H), 1.94-1.86 (m, 2H), 1.63-1.57 (m, 2H), 1.56-1.44 (m, 4H), 1.34-1.32 (m, 3H), 1.32-1.31 (m, 3H), 1.25-1.14 (m, 2H), 0.19-0.13 (m, 2H), 0.07-0.01 (m, 2H) (two protons obscured). TLR9 $IC_{50}$ (nM) = 390 |
| 38 | Analytical LC/MS (Method 1): Purity: 96.7%; Observed Mass: 540.99; Retention Time: 1.06 min. (Method 2): Purity: 100%; Observed Mass: 540.97; Retention Time: 1.61 min. Prep Method 1: 59 mg, 0.11 mmol, 79% yield; $^1$H NMR (500 MHz, DMSO-$d_6$) δ 7.59-7.54 (m, 1H), 7.51 (s, 1H), 7.26 (s, 2H), 7.22-7.18 (m, 1H), 7.16-7.11 (m, 1H), 6.51-6.25 (m, 1H), 4.81-4.67 (m, 2H), 3.84 (s, 3H), 3.81 (s, 3H), 3.01-2.95 (m, 2H), 2.88-2.81 (m, 2H), 2.64-2.56 (m, 1H), 2.30-2.18 (m, 3H), 2.04-1.95 (m, 2H), 1.84-1.77 (m, 4H), 1.76-1.66 (m, 5H), 1.53-1.39 (m, 2H), 0.84 (s, 3H), 0.83 (s, 3H). TLR9 $IC_{50}$ (nM) = 210 |
| 39 | Analytical LC/MS (Method 1): Purity: 97.8%; Observed Mass: 525.29; Retention Time: 1.02 min. Purity: 100%; Observed Mass: 524.94; Retention Time: 1.53 min. Prep Method 1: 68 mg, 0.13 mmol, 93% yield; $^1$H NMR (500 MHz, DMSO-$d_6$) δ 7.56 (s, 1H), 7.52 (s, 1H), 7.27 (s, 2H), 7.23-7.19 (m, 1H), 7.18-7.12 (m, 1H), 6.39 (br s, 1H), 4.74 (br s, 2H), 3.85 (s, 3H), 3.82 (s, 3H), 3.67-3.54 (m, 2H), 2.98 (br d, J = 7.9 Hz, 3H), 2.64-2.57 (m, 1H), 2.28 (br s, 3H), 2.18-2.09 (m, 2H), 1.84-1.78 (m, 2H), 1.76-1.64 (m, 3H), 1.59-1.53 (m, 1H), 1.47-1.33 (m, 2H), 0.44-0.36 (m, 2H), 0.29 (br d, J = 2.4 Hz, 2H). TLR9 $IC_{50}$ (nM) = 590 |
| 40 | Analytical LC/MS (Method 1): Purity: 100%; Observed Mass: 505.01; Retention Time: 1.00 min. (Method 2): Purity: 100%; Observed Mass: 505.18; Retention Time: 1.71 min. Prep Method 1: 17 mg, 0.034 mmol, 12% yield; $^1$H NMR (500 MHz, DMSO-$d_6$) δ 7.59-7.55 (m, 1H), 7.47-7.43 (m, 1H), 7.31-7.26 (m, 2H), 7.18-7.13 (m, 2H), 4.31 (br s, 2H), 3.84 (d, J = 6.4 Hz, 6H), 3.67-3.54 (m, 2H), 3.10-3.02 (m, 2H), 2.94-2.86 (m, 2H), 2.72-2.61 (m, 1H), 2.41-2.30 |

-continued

| Ex. No. | Analytical LC/MS, Prep Method, Yield, and $^1$H NMR |
|---|---|
| | (m, 3H), 2.08-2.00 (m, 2H), 1.93-1.82 (m, 3H), 1.81-1.68 (m, 4H), 1.57-1.45 (m, 2H), 1.34 (br t, J = 7.2 Hz, 3H), 0.85 (d, J = 6.4 Hz, 6H). TLR9 $IC_{50}$ (nM) = 150 |
| 41 | Analytical LC/MS (Method 1): Purity: 100%; Observed Mass: 504.98; Retention Time: 1.02 min. (Method 2): Purity: 99%; Observed Mass: 505.34; Retention Time: 1.77 min. Prep Method 1: 22 mg, 0.044 mmol, 16% yield; $^1$H NMR (500 MHz, DMSO-$d_6$) δ 7.55 (br d, J = 8.2 Hz, 1H), 7.54-7.50 (m, 1H), 7.31-7.27 (m, 2H), 7.21-7.17 (m, 1H), 7.17-7.13 (m, 1H), 4.34-4.27 (m, 2H), 3.87-3.82 (m, 4H), 3.66-3.54 (m, 3H), 3.32-3.24 (m, 1H), 3.05-2.96 (m, 2H), 2.83-2.62 (m, 4H), 2.21-2.11 (m, 2H), 2.11-2.00 (m, 2H), 1.99-1.88 (m, 4H), 1.87-1.74 (m, 3H), 1.69-1.57 (m, 2H), 1.34 (br t, J = 7.0 Hz, 3H), 0.87 (d, J = 6.4 Hz, 6H). TLR9 $IC_{50}$ (nM) = 400 |
| 42 | Analytical LC/MS (Method 1): Purity: 98.8%; Observed Mass: 546.10; Retention Time: 0.91 min. (Method 2): Purity: 100%; Observed Mass: 545.10; Retention Time: 1.95 min. Prep Method 1: 65 mg, 0.12 mmol, 92% yield; $^1$H NMR (500 MHz, DMSO-$d_6$) δ 7.97-7.91 (m, 1H), 7.76 (br s, 2H), 7.66-7.58 (m, 1H), 7.17-7.14 (m, 1H), 3.89 (s, 3H), 3.85 (s, 3H), 3.16-3.10 (m, 1H), 3.04-2.89 (m, 3H), 2.47-2.38 (m, 1H), 2.22-2.13 (m, 2H), 2.10-1.99 (m, 2H), 1.90-1.77 (m, 8H), 1.65-1.52 (m, 3H), 0.87 (d, J = 6.5 Hz, 6H) (one proton obscured). TLR9 $IC_{50}$ (nM) = 260 |
| 43 | Analytical LC/MS (Method 1): Purity: 100%; Observed Mass: 491.11; Retention Time: 0.98 min. (Method 2): Purity: 98.2%; Observed Mass: 491.10; Retention Time: 1.48 min. Prep Method 2: 80 mg, 0.096 mmol, 69% yield; $^1$H NMR (500 MHz, DMSO-$d_6$) δ 7.89 (br d, J = 8.4 Hz, 1H), 7.86 (s, 1H), 7.45 (s, 1H), 7.26 (d, J = 8.6 Hz, 1H), 7.18 (br s, 1H), 3.90-3.87 (m, 6H), 3.73-3.65 (m, 1H), 3.65-3.55 (m, 2H), 3.24-3.16 (m, 2H), 3.10-2.89 (m, 6H), 2.51 (br s, 3H), 2.37-2.26 (m, 2H), 2.16-2.03 (m, 8H), 0.97 (d, J = 6.6 Hz, 6H). TLR9 $IC_{50}$ (nM) = 9.8 |
| 44 | Analytical LC/MS (Method 1): Purity: 97.2%; Observed Mass: 475.29; Retention Time: 0.97 min. (Method 2): Purity: 97.5%; Observed Mass: 475.27; Retention Time: 1.39 min. Prep Method 1: 24 mg, 0.051 mmol, 36% yield; $^1$H NMR (500 MHz, DMSO-$d_6$) δ 7.86-7.69 (m, 2H), 7.17-7.07 (m, 2H), 6.89-6.85 (m, 1H), 3.89 (s, 3H), 3.84 (s, 3H), 3.65-3.47 (m, 2H), 3.02-2.94 (m, 4H), 2.54 (s, 3H), 2.33-2.24 (m, 2H), 2.17-2.08 (m, 2H), 1.82-1.76 (m, 2H), 1.75-1.62 (m, 4H), 1.59-1.53 (m, 1H), 1.45-1.35 (m, 2H), 0.42-0.37 (m, 2H), 0.30-0.26 (m, 2H). TLR9 $IC_{50}$ (nM) = 52 |
| 45 | Analytical LC/MS (Method 1): Purity: 98.9%; Observed Mass: 490.95; Retention Time: 0.95 min. (Method 2): Purity: 100%; Observed Mass: 490.94; Retention Time: 1.34 min. Prep Method 1: 17 mg, 0.035 mmol, 22% yield; $^1$H NMR (500 MHz, DMSO-$d_6$) δ 7.34 (s, 2H), 7.24-7.20 (m, 1H), 7.14-7.10 (m, 1H), 6.93 (s, 1H), 3.84 (s, 6H), 3.81 (s, 3H), 3.03-2.96 (m, 2H), 2.90-2.83 (m, 2H), 2.74-2.67 (m, 1H), 2.61-2.55 (m, 1H), 2.52 (s, 3H), 2.33-2.21 (m, 3H), 2.19-2.10 (m, 2H), 1.84-1.68 (m, 6H), 1.51-1.40 (m, 2H), 0.97 (d, J = 6.5 Hz, 6H). TLR9 $IC_{50}$ (nM) = 20 |
| 46 | Analytical LC/MS (Method 1): Purity: 100%; Observed Mass: 489.29; Retention Time: 1.03 min. (Method 2): Purity: 100%; Observed Mass: 488.96; Retention Time: 1.49 min. Prep Method 2: 100 mg, 0.12 mmol, 86% yield; $^1$H NMR (500 MHz, DMSO-$d_6$) δ 7.55-7.44 (m, 3H), 7.29-7.25 (m, 1H), 7.23-7.17 (m, 1H), 3.98-3.94 (m, 3H), 3.91 (s, 3H), 3.89 (s, 3H), 3.69-3.58 (m, 1H), 3.27-3.16 (m, 1H), 3.14-3.01 (m, 1H), 2.64-2.59 (m, 3H), 2.42-2.28 (m, 2H), 2.22-2.05 (m, 4H), 2.04-1.89 (m, 2H), 1.00-0.89 (m, 2H), 0.87-0.77 (m, 2H) (8 protons obscured). TLR9 $IC_{50}$ (nM) = 170 |
| 47 | Analytical LC/MS (Method 1): Purity: 100%; Observed Mass: 516.90; Retention Time: 1.04 min. (Method 2): Purity: 94.4%; Observed Mass: 516.90; Retention Time: 1.46 min. Prep Method 2: 30 mg, 0.013 mmol, 27% yield; $^1$H NMR (500 MHz, DMSO-$d_6$) δ 7.50-7.43 (m, 2H), 7.33-7.20 (m, 2H), 7.19-7.09 (m, 1H), 4.35-4.24 (m, 1H), 4.20-4.06 (m, 3H), 3.94 (s, 3H), 3.90 (s, 3H), 3.88 (s, 3H), 3.09-2.98 (m, 4H), 2.98-2.87 (m, 2H), 2.80-2.67 (m, 2H), 2.64-2.59 (m, 5H), 2.16-2.07 (m, 2H), 2.05-1.92 (m, 2H), 1.91-1.74 (m, 2H), 0.91 (d, J = 6.7 Hz, 6H) (one proton obscured). TLR9 $IC_{50}$ (nM) = 13 |
| 48 | Analytical LC/MS (Method 1): Purity: 100%; Observed Mass: 514.95; Retention Time: 1.02 min. (Method 2): Purity: 98.2%; Observed Mass: 515.02; Retention Time: 1.53 min. Prep Method 1: 31 mg, 0.060 mmol, 46% yield; $^1$H NMR (500 MHz, DMSO-$d_6$) δ 7.18-7.12 (m, 2H), 7.05-6.99 (m, 1H), 6.97-6.91 (m, 1H), 6.76-6.70 (m, 1H), 3.64 (s, 6H), 3.61 (s, 3H), 2.76-2.65 (m, 2H), 2.53-2.42 (m, 3H), 2.35 (s, 3H), 2.19-2.07 (m, 3H), 1.93-1.84 (m, 2H), 1.84-1.77 (m, 2H), 1.72-1.63 (m, 2H), 1.62-1.56 (m, 2H), 1.55-1.45 (m, 3H), 0.66-0.54 (m, 2H), 0.31-0.23 (m, 2H), 0.05--0.02 (m, 2H). TLR9 $IC_{50}$ (nM) = 19 |
| 49 | Analytical LC/MS (Method 3): Observed Mass: 515.5; Retention Time: 0.51 min. Prep Method 1: 9.8 mg, 0.019 mmol, 16% yield; $^1$H NMR (500 MHz, METHANOL-$d_4$) δ 7.39 (d, J = 1.9 Hz, 1H), 7.33 (dd, J = 8.4, 2.1 Hz, 1H), 7.23 (s, 1H), 7.17 (d, J = 8.3 Hz, 1H), 7.03 (s, 1H), 3.95 (s, 6H), 3.75-3.62 (m, 2H), 3.22-3.17 (m, 2H), 3.08-3.01 (m, 1H), 2.82-2.75 (m, 1H), 2.64-2.61 (m, 3H), 2.59-2.52 (m, 2H), 2.35-2.17 (m, 8H), 2.09-1.98 (m, 6H), 1.96-1.80 (m, 6H). TLR9 $IC_{50}$ (nM) = 65 |
| 50 | Analytical LC/MS (Method 1): Purity: 100%; Observed Mass: 531.01; Retention Time: 1.11 min. (Method 2): Purity: 100%; Observed Mass: 531.05; Retention Time: 1.6 min. Prep Method 1: 81 mg, 0.15 mmol, 71% yield; $^1$H NMR (500 MHz, DMSO-$d_6$) δ 7.36-7.30 (m, 2H), 7.24-7.20 (m, 1H), 7.14-7.10 |

-continued

| Ex. No. | Analytical LC/MS, Prep Method, Yield, and $^1$H NMR |
|---|---|
| | (m, 1H), 7.01-6.95 (m, 1H), 3.84 (s, 6H), 3.80 (s, 3H), 3.13-3.03 (m, 1H), 2.86-2.78 (m, 2H), 2.52 (s, 3H), 2.35-2.18 (m, 1H), 2.07-1.97 (m, 2H), 1.86 (br s, 9H), 1.80-1.67 (m, 3H), 1.62-1.55 (m, 1H), 1.49-1.31 (m, 2H), 0.84 (d, J = 6.6 Hz, 6H) (two protons obscured). TLR9 $IC_{50}$ (nM) = 23 |
| 51 | Analytical LC/MS (Method 1): Purity: 100%; Observed Mass: 514.95; Retention Time: 1.08 min. (Method 2): Purity: 100%; Observed Mass: 515.27; Retention Time: 1.48 min. Prep Method 1: 100 mg, 0.20 mmol, 95% yield; $^1$H NMR (500 MHz, DMSO-$d_6$) δ 7.38-7.32 (m, 2H), 7.27-7.23 (m, 1H), 7.16-7.13 (m, 1H), 7.01-6.98 (m, 1H), 3.86 (s, 6H), 3.83 (s, 3H), 3.64-3.51 (m, 3H), 3.18-3.04 (m, 1H), 3.01-2.92 (m, 2H), 2.55 (s, 3H), 2.40-2.28 (m, 1H), 2.24-2.15 (m, 2H), 1.99-1.87 (m, 4H), 1.87-1.75 (m, 2H), 1.66-1.55 (m, 3H), 1.52-1.45 (m, 1H), 1.40-1.26 (m, 2H), 0.45-0.37 (m, 2H), 0.34-0.27 (m, 2H). TLR9 $IC_{50}$ (nM) = 130 |
| 52 | Analytical LC/MS (Method 1): Purity: 98.1%; Observed Mass: 523.17; Retention Time: 0.94 min. (Method 2): Purity: 97.2%; Observed Mass: 523.16; Retention Time: 1.53 min. Prep Method 1: 32 mg, 0.061 mmol, 47% yield; $^1$H NMR (500 MHz, DMSO-$d_6$) δ 8.12 (d, J = 3.5 Hz, 4H), 7.31 (s, 1H), 7.00 (s, 1H), 3.90 (s, 3H), 3.00-2.92 (m, 1H), 2.76-2.66 (m, 1H), 2.65-2.58 (m, 1H), 2.56 (s, 3H), 2.49-2.40 (m, 1H), 2.18-2.04 (m, 2H), 1.84 (br d, J = 7.1 Hz, 9H), 1.65-1.51 (m, 2H), 0.87 (d, J = 6.6 Hz, 6H) (7 protons obscured). TLR9 $IC_{50}$ (nM) = 130 |
| 53 | Analytical LC/MS (Method 1): Purity: 95.9%; Observed Mass: 507.13; Retention Time: 0.90 min. (Method 2): Purity: 100%; Observed Mass: 507.14; Retention Time: 1.42 min. Prep Method 1: 17 mg, 0.033 mmol, 25% yield; $^1$H NMR (500 MHz, DMSO-$d_6$) δ 7.91-7.83 (m, 4H), 7.09-7.04 (m, 1H), 6.77-6.72 (m, 1H), 3.64 (s, 3H), 2.81-2.68 (m, 3H), 2.41-2.28 (m, 2H), 2.30 (s, 3H), 2.15-2.00 (m, 3H), 1.95-1.84 (m, 2H), 1.62-1.43 (m, 7H), 1.35-1.27 (m, 1H), 1.22-1.11 (m, 2H), 0.19-0.11 (m, 2H), 0.06-0.00 (m, 2H) (two protons obscured). TLR9 $IC_{50}$ (nM) = 420 |
| 54 | Analytical LC/MS (Method 1): Purity: 92.8%; Observed Mass: 493.25; Retention Time: 1.03 min. (Method 2): Purity: 99.3%; Observed Mass: 492.9; Retention Time: 1.58 min. Prep Method 1: 47 mg, 0.095 mmol, 68% yield; $^1$H NMR (500 MHz, DMSO-$d_6$) δ 7.72-7.67 (m, 1H), 7.65-7.61 (m, 1H), 7.38-7.32 (m, 1H), 7.27-7.22 (m, 1H), 6.98-6.93 (m, 1H), 3.94 (s, 3H), 3.84 (s, 3H), 3.08-2.96 (m, 2H), 2.83-2.68 (m, 2H), 2.54 (s, 5H), 2.23-2.09 (m, 2H), 2.07-1.71 (m, 9H), 1.71-1.57 (m, 2H), 0.88 (br d, J = 6.6 Hz, 6H) (two protons obscured). TLR9 $IC_{50}$ (nM) = 130 |
| 55 | Analytical LC/MS (Method 1): Purity: 98%; Observed Mass: 477.17; Retention Time: 0.98 min. (Method 2): Purity: 98.3%; Observed Mass: 477.17; Retention Time: 1.65 min. Prep Method 1: 36 mg, 0.076 mmol, 54% yield; $^1$H NMR (500 MHz, DMSO-$d_6$) δ 7.46-7.41 (m, 1H), 7.40-7.35 (m, 1H), 7.13-7.07 (m, 1H), 7.02-6.99 (m, 1H), 6.71-6.68 (m, 1H), 3.69 (s, 3H), 3.58 (s, 3H), 2.85-2.71 (m, 3H), 2.42-2.33 (m, 1H), 2.28 (s, 3H), 2.19-2.04 (m, 2H), 1.94-1.86 (m, 2H), 1.61-1.47 (m, 6H), 1.35-1.29 (m, 1H), 1.24-1.10 (m, 2H), 0.18-0.13 (m, 2H), 0.05-0.01 (m, 2H) (two protons obscured). TLR9 $IC_{50}$ (nM) = 140 |
| 56 | Analytical LC/MS (Method 1): Purity: 96.6%; Observed Mass: 479.26; Retention Time: 1.06 min. (Method 2): Purity: 98.9%; Observed Mass: 478.95; Retention Time: 1.50 min. Prep Method 1: 48 mg, 0.10 mmol, 67% yield; $^1$H NMR (500 MHz, DMSO-$d_6$) δ 8.09-7.91 (m, 2H), 7.40-7.32 (m, 1H), 7.29-7.10 (m, 1H), 6.92-6.86 (m, 1H), 3.94 (s, 3H), 3.02-2.95 (m, 2H), 2.90-2.83 (m, 2H), 2.56 (s, 3H), 2.31-2.19 (m, 3H), 2.04-1.98 (m, 2H), 1.87-1.61 (m, 9H), 1.52-1.41 (m, 2H), 0.86 (d, J = 6.4 Hz, 6H) (one proton obscured). TLR9 $IC_{50}$ (nM) = 50 |
| 57 | Analytical LC/MS (Method 1): Purity: 100%; Observed Mass: 463.15; Retention Time: 1.01 min. (Method 2): Purity: 100%; Observed Mass: 463.14; Retention Time: 1.41 min. Prep Method 1: 46 mg, 0.10 mmol, 67% yield; $^1$H NMR (500 MHz, DMSO-$d_6$) δ 8.11-7.90 (m, 2H), 7.39-7.32 (m, 1H), 7.31-7.10 (m, 1H), 6.92-6.86 (m, 1H), 3.94 (s, 3H), 3.03-2.96 (m, 3H), 2.54 (s, 3H), 2.36-2.27 (m, 3H), 2.18-2.11 (m, 2H), 1.85-1.63 (m, 6H), 1.60-1.55 (m, 1H), 1.48-1.35 (m, 2H), 0.45-0.38 (m, 2H), 0.33-0.25 (m, 2H) (two protons obscured). TLR9 $IC_{50}$ (nM) = 170 |
| 58 | Analytical LC/MS (Method 1): Purity: 100%; Observed Mass: 509.25; Retention Time: 0.98 min. (Method 2): Purity: 100%; Observed Mass: 509.27; Retention Time: 1.26 min. Prep Method 2: 19 mg, 0.022 mmol, 15% yield; $^1$H NMR (500 MHz, DMSO-$d_6$) δ 8.46-8.41 (m, 2H), 8.15-8.10 (m, 2H), 7.36-7.30 (m, 1H), 7.06-6.98 (m, 1H), 3.61-3.41 (m, 1H), 3.29 (s, 3H), 3.23-3.14 (m, 2H), 3.06-2.88 (m, 5H), 2.62-2.58 (m, 3H), 2.50-2.44 (m, 1H), 2.36-2.25 (m, 2H), 2.15-1.95 (m, 8H), 0.97 (br d, J = 6.6 Hz, 6H) (two protons obscured). TLR9 $IC_{50}$ (nM) = 47 |
| 59 | Analytical LC/MS (Method 1): Purity: 91.5%; Observed Mass: 482.31; Retention Time: 0.99 min. (Method 2): Purity: 92.8%; Observed Mass: 482.32; Retention Time: 1.35 min. Prep Method 1: 31 mg, 0.064 mmol, 43% yield; $^1$H NMR (500 MHz, DMSO-$d_6$) δ 9.40-9.19 (m, 1H), 9.13-9.05 (m, 1H), 8.18-8.10 (m, 1H), 8.06-7.94 (m, 1H), 7.91-7.82 (m, 1H), 7.79-7.71 (m, 1H), 7.50-7.22 (m, 1H), 7.08-6.96 (m, 1H), 3.13-3.04 (m, 1H), 2.96-2.84 (m, 2H), 2.70-2.56 (m, 4H), 2.49-2.34 (m, 3H), 2.08-2.01 (m, 2H), 1.91-1.84 (m, 3H), 1.83-1.69 (m, 5H), 1.58-1.47 (m, 2H), 0.90-0.81 (m, 6H) (two protons obscured). TLR9 $IC_{50}$ (nM) = 100 |

-continued

| Ex. No. | Analytical LC/MS, Prep Method, Yield, and $^1$H NMR |
|---|---|
| 60 | Analytical LC/MS (Method 1): Purity: 95.2%; Observed Mass: 460.25; Retention Time: 0.89 min. (Method 2): Purity: 100%; Observed Mass: 460.25; Retention Time: 1.35 min. Prep Method 1: 46 mg, 0.10 mmol, 68% yield; $^1$H NMR (500 MHz, DMSO-$d_6$) δ 7.86-7.71 (m, 2H), 7.40-7.15 (m, 1H), 7.00-6.91 (m, 1H), 3.06-2.98 (m, 2H), 2.92-2.84 (m, 2H), 2.57-2.55 (m, 6H), 2.54 (s, 3H), 2.34-2.25 (m, 3H), 2.05-2.00 (m, 2H), 1.88-1.66 (m, 10H), 1.53-1.44 (m, 2H), 0.87-0.85 (m, 6H). TLR9 $IC_{50}$ (nM) = 45 |
| 61 | Analytical LC/MS (Method 1): Purity: 100%; Observed Mass: 502.00; Retention Time: 1.06 min. (Method 2): Purity: 98.9%; Observed Mass: 502.27; Retention Time: 1.32 min. Prep Method 2: 15 mg, 0.018 mmol, 15% yield; $^1$H NMR (500 MHz, DMSO-$d_6$) δ 8.77 (s, 1H), 8.21-8.16 (m, 1H), 7.52-7.47 (m, 1H), 7.41-7.35 (m, 1H), 7.05-6.99 (m, 1H), 4.12 (s, 3H), 3.75-3.54 (m, 1H), 3.28-3.17 (m, 2H), 3.08-2.92 (m, 4H), 2.63 (s, 3H), 2.52 (br s, 3H), 2.38-2.27 (m, 2H), 2.23-1.98 (m, 7H), 0.99 (br d, J = 6.4 Hz, 6H) (two protons obscured). TLR9 $IC_{50}$ (nM) = 49 |
| 62 | Analytical LC/MS (Method 1): Purity: 95%; Observed Mass: 489.18; Retention Time: 1.04 min. (Method 2): Purity: 94.9%; Observed Mass: 489.33; Retention Time: 1.52 min. Prep Method 1: 12 mg, 0.025 mmol, 43% yield; $^1$H NMR (500 MHz, DMSO-$d_6$) δ 7.81-7.61 (m, 2H), 7.30-7.09 (m, 1H), 7.04-6.99 (m, 1H), 6.90-6.85 (m, 1H), 4.32 (s, 4H), 3.05-2.97 (m, 2H), 2.92-2.84 (m, 2H), 2.56 (s, 3H), 2.34-2.23 (m, 3H), 2.01 (s, 2H), 1.89-1.63 (m, 10H), 1.53-1.43 (m, 2H), 0.86 (d, J = 6.4 Hz, 6H). TLR9 $IC_{50}$ (nM) = 350 |
| 63 | Analytical LC/MS (Method 1): Purity: 100%; Observed Mass: 514.99; Retention Time: 1.21 min. (Method 2): Purity: 92%; Observed Mass: 515.37; Retention Time: 1.83 min. Prep Method 1: 4.7 mg, 0.0091 mmol, 16% yield; $^1$H NMR (500 MHz, DMSO-$d_6$) δ 8.41-8.21 (m, 2H), 7.62-7.49 (m, 2H), 7.30-7.19 (m, 1H), 7.00-6.86 (m, 1H), 3.04-2.95 (m, 2H), 2.91-2.83 (m, 2H), 2.56 (s, 3H), 2.30-2.19 (m, 3H), 2.03-1.98 (m, 2H), 1.87-1.77 (m, 5H), 1.77-1.63 (m, 5H), 1.53-1.42 (m, 2H), 0.86 (d, J = 6.4 Hz, 6H). TLR9 $IC_{50}$ (nM) = 200 |
| 64 | Analytical LC/MS (Method 1): Purity: 91.8%; Observed Mass: 495.23; Retention Time: 1.12 min. (Method 2): Purity: 91.6%; Observed Mass: 495.20; Retention Time: 1.65 min. Prep Method 1: 1.6 mg, 0.0032 mmol, 5.5% yield; $^1$H NMR (500 MHz, DMSO-$d_6$) δ 8.35-8.07 (m, 2H), 7.38-7.31 (m, 1H), 7.30-7.11 (m, 1H), 6.97-6.85 (m, 1H), 4.01-3.90 (m, 3H), 3.16-3.05 (m, 1H), 2.98-2.86 (m, 2H), 2.68-2.53 (m, 6H), 2.49-2.37 (m, 2H), 2.12-2.01 (m, 2H), 1.99-1.67 (m, 9H), 1.62-1.46 (m, 2H), 0.91-0.81 (m, 6H). TLR9 $IC_{50}$ (nM) = 91 |
| 65 | Analytical LC/MS (Method 1): Purity: 97.8%; Observed Mass: 511.12; Retention Time: 1.2 min. (Method 2): Purity: 100%; Observed Mass: 511.15; Retention Time: 1.79 min. Prep Method 2: 11 mg, 0.013 mmol, 22% yield; $^1$H NMR (500 MHz, DMSO-$d_6$) δ 8.18-8.12 (m, 1H), 8.10-8.04 (m, 1H), 7.65-7.60 (m, 1H), 7.29-7.24 (m, 1H), 6.99-6.91 (m, 1H), 3.73-3.62 (m, 1H), 3.62-3.48 (m, 2H), 3.24-3.12 (m, 1H), 3.06-2.89 (m, 4H), 2.57 (s, 3H), 2.49-2.40 (m, 1H), 2.36-2.24 (m, 2H), 2.17-1.91 (m, 8H), 0.97 (br d, J = 6.6 Hz, 6H) (two protons obscured). TLR9 $IC_{50}$ (nM) = 300 |
| 66 | Analytical LC/MS (Method 1): Purity: 94.5%; Observed Mass: 527.26; Retention Time: 1.05 min. (Method 2): Purity: 95.3%; Observed Mass: 527.29; Retention Time: 1.28 min. Prep Method 1: 25 mg, 0.047 mmol, 81% yield; $^1$H NMR (500 MHz, DMSO-$d_6$) δ 8.35-8.19 (m, 2H), 8.11-7.98 (m, 1H), 7.38-7.19 (m, 1H), 7.09-6.93 (m, 1H), 3.05-2.97 (m, 2H), 2.90-2.84 (m, 2H), 2.60-2.57 (m, 4H), 2.32-2.21 (m, 3H), 2.04-2.00 (m, 2H), 1.88-1.78 (m, 5H), 1.78-1.65 (m, 6H), 1.53-1.42 (m, 2H), 0.88-0.85 (m, 6H) (one proton obscured). TLR9 $IC_{50}$ (nM) = 69 |
| 67 | Analytical LC/MS (Method 1): Purity: 94%; Observed Mass: 586.93; Retention Time: 1.06 min. (Method 2): Purity: 98.2%; Observed Mass: 586.91; Retention Time: 1.52 min. Prep Method 1: 33 mg, 0.056 mmol, 97% yield; $^1$H NMR (500 MHz, DMSO-$d_6$) δ 8.77-8.60 (m, 1H), 8.51-8.34 (m, 1H), 8.28-8.17 (m, 1H), 7.41-7.17 (m, 1H), 7.06-6.92 (m, 1H), 3.53 (s, 3H), 3.14-3.03 (m, 1H), 2.96-2.85 (m, 2H), 2.68-2.56 (m, 4H), 2.55 (s, 3H), 2.47-2.32 (m, 2H), 2.08-2.03 (m, 1H), 1.96-1.66 (m, 9H), 1.58-1.44 (m, 2H), 0.85 (br d, J = 6.1 Hz, 6H). TLR9 $IC_{50}$ (nM) = 44 |
| 68 | Analytical LC/MS (Method 1): Purity: 100%; Observed Mass: 471.02; Retention Time: 1.17 min. (Method 2): Purity: 100%; Observed Mass: 470.97; Retention Time: 1.83 min. Prep Method 1: 6.1 mg, 0.013 mmol, 22% yield; $^1$H NMR (500 MHz, DMSO-$d_6$) δ 8.15-7.94 (m, 2H), 7.32-7.06 (m, 3H), 6.88 (s, 1H), 3.03-2.93 (m, 2H), 2.90-2.78 (m, 2H), 2.53 (s, 3H), 2.49-2.46 (m, 1H), 2.30-2.18 (m, 3H), 2.06-1.92 (m, 3H), 1.88-1.75 (m, 4H), 1.75-1.60 (m, 5H), 1.53-1.40 (m, 2H), 1.05-0.99 (m, 2H), 0.85 (d, J = 6.5 Hz, 6H), 0.79-0.73 (m, 2H). TLR9 $IC_{50}$ (nM) = 85 |
| 69 | Analytical LC/MS (Method 1): Purity: 100%; Observed Mass: 514.94; Retention Time: 1.14 min. (Method 2): Purity: 100%; Observed Mass: 515.37; Retention Time: 1.68 min. Prep Method 2: 15 mg, 0.018 mmol, 31% yield; $^1$H NMR (500 MHz, DMSO-$d_6$) δ 8.23-8.16 (m, 1H), 8.14-8.06 (m, 1H), 7.65-7.58 (m, 1H), 7.34-7.29 (m, 1H), 7.29-7.06 (m, 1H), 7.00 (s, 1H), 3.76-3.56 (m, 1H), 3.25-3.13 (m, 2H), 2.95 (br d, J = 6.7 Hz, 5H), 2.56 (s, 3H), 2.36-2.27 (m, 2H), 2.11 (br s, 7H), 0.98 (br d, J = 6.4 Hz, 6H) (4 protons obscured). TLR9 $IC_{50}$ (nM) = 240 |

-continued

| Ex. No. | Analytical LC/MS, Prep Method, Yield, and $^1H$ NMR |
|---|---|
| 70 | Analytical LC/MS (Method 1): Purity: 97.5%; Observed Mass: 488.15; Retention Time: 1.35 min. (Method 2): Purity: 99.2%; Observed Mass: 488.15; Retention Time: 1.73 min. Prep Method 2: 5.8 mg, 0.0070 mmol, 12% yield; $^1H$ NMR (500 MHz, DMSO-$d_6$) δ 8.26-8.21 (m, 1H), 8.19-8.12 (m, 1H), 7.68-7.61 (m, 1H), 7.61-7.54 (m, 1H), 7.39-7.24 (m, 1H), 7.06-6.97 (m, 1H), 3.78-3.54 (m, 1H), 3.29-3.10 (m, 1H), 3.09-2.86 (m, 2H), 2.62 (s, 3H), 2.42-2.22 (m, 2H), 2.21-1.89 (m, 7H), 0.98 (br d, J = 6.4 Hz, 6H) (8 protons obscured). TLR9 $IC_{50}$ (nM) = 210 |
| 71 | Analytical LC/MS (Method 1): Purity: 94.8%; Observed Mass: 450.01; Retention Time: 1.03 min. (Method 2): Purity: 100%; Observed Mass: 450.20; Retention Time: 1.47 min. Prep Method 1: 2.5 mg, 0.0056 mmol, 9.7% yield; $^1H$ NMR (500 MHz, DMSO-$d_6$) δ 7.34-7.25 (m, 1H), 6.97-6.90 (m, 1H), 3.49-3.45 (m, 1H), 3.08-2.84 (m, 3H), 2.66-2.61 (m, 3H), 2.56-2.53 (m, 9H), 2.48-2.42 (m, 3H), 2.37-2.20 (m, 3H), 2.19-1.87 (m, 8H), 0.97 (br d, J = 6.5 Hz, 6H). TLR9 $IC_{50}$ (nM) = 1800 |
| 72 | Analytical LC/MS (Method 1): Purity: 100%; Observed Mass: 481.96; Retention Time: 0.93 min. (Method 2): Purity: 100%; Observed Mass: 482.16; Retention Time: 1.39 min. Prep Method 2: 13 mg, 0.016 mmol, 28% yield; $^1H$ NMR (500 MHz, DMSO-$d_6$) δ 9.46-9.29 (m, 1H), 9.06 (br d, J = 2.4 Hz, 1H), 8.27 (d, J = 8.2 Hz, 1H), 8.18 (br d, J = 7.0 Hz, 1H), 8.01 (t, J = 7.9 Hz, 1H), 7.73 (dd, J = 8.7, 4.1 Hz, 1H), 7.41 (s, 1H), 7.08 (br s, 1H), 3.79-3.55 (m, 1H), 3.28-3.16 (m, 1H), 3.12-2.87 (m, 4H), 2.64 (s, 3H), 2.38-2.25 (m, 2H), 2.24-1.91 (m, 7H), 0.99 (br d, J = 6.7 Hz, 6H) (6 protons obscured). TLR9 $IC_{50}$ (nM) = 88 |
| 73 | Analytical LC/MS (Method 1): Purity: 99.2%; Observed Mass: 549.21; Retention Time: 1.31 min. (Method 2): Purity: 97.9%; Observed Mass: 549.28; Retention Time: 1.91 min. Prep Method 2: 9.0 mg, 0.010 mmol, 17% yield; $^1H$ NMR (500 MHz, DMSO-$d_6$) δ 8.48 (s, 1H), 8.36-8.23 (m, 1H), 7.84-7.72 (m, 1H), 7.29 (br s, 1H), 6.97 (s, 1H), 3.77-3.55 (m, 1H), 3.28-3.11 (m, 2H), 3.08-2.87 (m, 5H), 2.58 (s, 3H), 2.49-2.44 (m, 1H), 2.36-2.26 (m, 2H), 2.20-1.95 (m, 8H), 0.97 (br s, 6H) (two protons obscured). TLR9 $IC_{50}$ (nM) = 270 |
| 74 | Analytical LC/MS (Method 1): Purity: 100%; Observed Mass: 481.97; Retention Time: 0.96 min. (Method 2): Purity: 95.5%; Observed Mass: 481.98; Retention Time: 1.43 min. Prep Method 1: 18 mg, 0.038 mmol, 66% yield; $^1H$ NMR (500 MHz, DMSO-$d_6$) δ 9.45-9.35 (m, 1H), 8.85-8.71 (m, 1H), 8.63-8.57 (m, 1H), 8.56-8.45 (m, 1H), 8.32-8.26 (m, 1H), 8.00-7.91 (m, 1H), 7.41-7.20 (m, 1H), 7.03-6.94 (m, 1H), 3.26-3.09 (m, 1H), 2.95 (br d, J = 8.5 Hz, 2H), 2.79-2.65 (m, 1H), 2.61 (br d, J = 8.5 Hz, 3H), 2.14-2.06 (m, 2H), 1.93 (s, 9H), 1.64-1.51 (m, 2H), 0.88 (d, J = 6.4 Hz, 6H) (4 protons obscured) TLR9 $IC_{50}$ (nM) = 37 |
| 75 | Analytical LC/MS (Method 1): Purity: 100%; Observed Mass: 571.14; Retention Time: 1.24 min. (Method 2): Purity: 98.2%; Observed Mass: 571.37; Retention Time: 1.67 min. Prep Method 2: 13 mg, 0.014 mmol, 24% yield; $^1H$ NMR (500 MHz, DMSO-$d_6$) δ 8.43-8.38 (m, 2H), 8.19-8.12 (m, 2H), 8.06-7.99 (m, 2H), 7.77-7.71 (m, 1H), 7.71-7.63 (m, 2H), 7.31 (s, 1H), 6.99 (s, 1H), 3.74-3.49 (m, 1H), 3.29-3.12 (m, 2H), 3.08-2.88 (m, 4H), 2.60-2.57 (m, 3H), 2.37-2.22 (m, 2H), 2.18-1.92 (m, 7H), 1.00-0.96 (m, 6H) (5 protons obscured) TLR9 $IC_{50}$ (nM) = 63 |
| 76 | Analytical LC/MS (Method 1): Purity: 100%; Observed Mass: 496.98; Retention Time: 1.08 min. (Method 2): Purity: 100%; Observed Mass: 497.15; Retention Time: 1.64 min. Prep Method 1: 9.9 mg, 0.020 mmol, 34% yield; $^1H$ NMR (500 MHz, DMSO-$d_6$) δ 8.10-8.04 (m, 1H), 8.02-7.96 (m, 1H), 7.64-7.58 (m, 1H), 7.51-7.32 (m, 1H), 7.32-7.27 (m, 1H), 7.27-7.17 (m, 1H), 6.98-6.90 (m, 1H), 3.06-2.95 (m, 2H), 2.90-2.82 (m, 2H), 2.33-2.22 (m, 3H), 2.05-1.98 (m, 2H), 1.87-1.77 (m, 5H), 1.77-1.65 (m, 5H), 1.54-1.42 (m, 2H), 0.88-0.83 (m, 6H) (three protons obscured). TLR9 $IC_{50}$ (nM) = 260 |
| 77 | Analytical LC/MS (Method 1): Purity: 93.2%; Observed Mass: 487.90; Retention Time: 1.05 min. (Method 2): Purity: 93.8%; Observed Mass: 488.10; Retention Time: 1.43 min. Prep Method 1: 5.4 mg, 0.011 mmol, 19% yield; $^1H$ NMR (500 MHz, DMSO-$d_6$) δ 9.56-9.49 (m, 1H), 8.32-8.16 (m, 2H), 7.87-7.71 (m, 1H), 7.47-7.19 (m, 1H), 6.98 (br s, 1H), 3.04-2.98 (m, 2H), 2.90-2.83 (m, 2H), 2.53 (s, 3H), 2.33-2.23 (m, 3H), 2.05-1.98 (m, 2H), 1.85-1.79 (m, 4H), 1.77-1.66 (m, 6H), 1.52-1.42 (m, 2H), 0.87-0.84 (m, 6H). TLR9 $IC_{50}$ (nM) = 31 |
| 78 | Analytical LC/MS (Method 1): Purity: 96.9%; Observed Mass: 496.98; Retention Time: 1.07 min. (Method 2): Purity: 95.6%; Observed Mass: 497.28; Retention Time: 1.51 min. Prep Method 1: 27 mg, 0.055 mmol, 95% yield; $^1H$ NMR (500 MHz, DMSO-$d_6$) δ 8.31-8.17 (m, 2H), 7.38-7.34 (m, 2H), 7.22-7.14 (m, 1H), 6.94-6.88 (m, 1H), 3.49-3.39 (m, 1H), 3.15-2.68 (m, 3H), 2.58-2.55 (m, 3H), 2.31-2.06 (m, 2H), 2.06-1.96 (m, 4H), 1.95-1.78 (m, 4H), 1.78-1.62 (m, 2H), 0.88 (br d, J = 6.4 Hz, 6H) (6 protons obscured). TLR9 $IC_{50}$ (nM) = 270 |
| 79 | Analytical LC/MS (Method 1): Purity: 98.2%; Observed Mass: 438.20; Retention Time: 0.96 min. (Method 2): Purity: 99.5%; Observed Mass: 438.19; Retention Time: 1.42 min. Prep Method 1: 17 mg, 0.039 mmol, 67% yield; $^1H$ NMR (500 MHz, DMSO-$d_6$) δ 8.11-8.04 (m, 1H), 7.99-7.92 (m, 1H), 7.36-7.15 (m, 1H), 7.02-6.94 (m, 1H), 3.01 (br s, 2H), 2.88 (br d, J = 11.3 Hz, 2H), 2.57-2.56 (m, 4H), 2.27 (br d, J = 11.6 Hz, 3H), 2.05-1.99 (m, 2H), 1.90-1.78 (m, 4H), 1.78-1.62 (m, 5H), 1.55-1.43 (m, 2H), 0.90-0.83 (m, 6H). TLR9 $IC_{50}$ (nM) = 110 |

-continued

| Ex. No. | Analytical LC/MS, Prep Method, Yield, and $^1$H NMR |
|---|---|
| 80 | Analytical LC/MS (Method 1): Purity: 95.9%; Observed Mass: 515.15; Retention Time: 1.10 min. (Method 2): Purity: 98.5%; Observed Mass: 515.37; Retention Time: 1.68 min. Prep Method 2: 19 mg, 0.022 mmol, 38% yield; $^1$H NMR (500 MHz, DMSO-$d_6$) δ 8.09-8.03 (m, 1H), 7.74-7.69 (m, 1H), 7.66-7.59 (m, 2H), 7.35-7.30 (m, 1H), 7.03-6.96 (m, 1H), 3.76-3.56 (m, 1H), 3.27-3.15 (m, 1H), 3.11-2.90 (m, 4H), 2.59-2.53 (m, 6H), 2.36-2.26 (m, 2H), 2.19-1.96 (m, 7H), 1.01-0.96 (m, 6H) (three protons obscured). TLR9 $IC_{50}$ (nM) = 360 |
| 81 | Analytical LC/MS (Method 1): Purity: 97%; Observed Mass: 471.19; Retention Time: 0.91 min. (Method 2): Purity: 98%; Observed Mass: 471.02; Retention Time: 1.41 min. Prep Method 1: 22 mg, 0.046 mmol, 79% yield; $^1$H NMR (500 MHz, DMSO-$d_6$) δ 11.87 (br s, 1H), 9.12-8.97 (m, 1H), 8.78-8.63 (m, 1H), 7.62-7.52 (m, 1H), 7.34-7.12 (m, 1H), 6.94-6.84 (m, 1H), 6.65-6.55 (m, 1H), 3.14-3.03 (m, 1H), 2.96-2.84 (m, 2H), 2.55 (s, 5H), 2.41 (br s, 3H), 2.05 (br d, J = 7.2 Hz, 2H), 1.90-1.66 (m, 9H), 1.60-1.44 (m, 2H), 0.85 (d, J = 6.5 Hz, 6H). TLR9 $IC_{50}$ (nM) = 49 |
| 82 | Analytical LC/MS (Method 1): Purity: 96.8%; Observed Mass: 482.16; Retention Time: 0.98 min. (Method 2): Purity: 94.7%; Observed Mass: 482.01; Retention Time: 1.57 min. Prep Method 1: 20 mg, 0.042 mmol, 72% yield; $^1$H NMR (500 MHz, DMSO-$d_6$) δ 9.21-9.14 (m, 1H), 8.98-8.91 (m, 1H), 8.63-8.54 (m, 1H), 8.20-8.11 (m, 1H), 7.85-7.78 (m, 1H), 7.78-7.70 (m, 1H), 7.45-7.39 (m, 1H), 7.00-6.92 (m, 1H), 3.22-3.07 (m, 2H), 2.98-2.86 (m, 2H), 2.67-2.63 (m, 1H), 2.55 (s, 3H), 2.49-2.44 (m, 2H), 2.12-1.99 (m, 3H), 1.91 (s, 4H), 1.84-1.69 (m, 5H), 1.61-1.48 (m, 2H), 0.86 (br d, J = 6.8 Hz, 6H). TLR9 $IC_{50}$ (nM) = 32 |

Example 83

2-(3,4-dimethoxyphenyl)-4-fluoro-6-(1'-isopropyl-[1,4'-bipiperidin]-4-yl)-1H-benzo[d]imidazole (83)

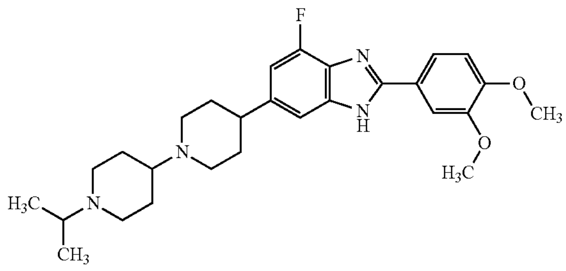

Step A. Intermediate 83A. Preparation of 2-(3,4-dimethoxyphenyl)-4-fluoro-6-(piperidin-4-yl)-1H-benzo[d]imidazole bis(2,2,2-trifluoroacetate)

(83A)

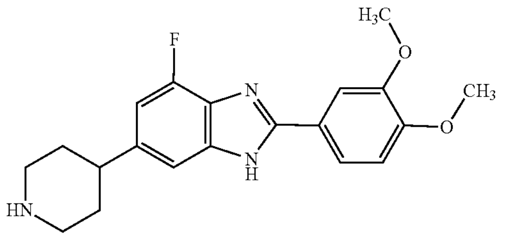

Intermediate 83A was synthesized according to the general procedures described for the preparation of Intermediate 11D (Steps A-D), using 5-bromo-3-fluorobenzene-1,2-diamine as starting material. $^1$H NMR (500 MHz, METHANOL-$d_4$) δ 7.78 (s, 2H), 7.42 (s, 1H), 7.22 (d, J=8.2 Hz, 1H), 7.20-7.16 (m, 1H), 4.01-3.99 (m, 3H), 3.98-3.96 (m, 3H), 3.60-3.53 (m, 2H), 3.24-3.18 (m, 2H), 3.16-3.10 (m, 1H), 2.23-2.17 (m, 2H), 2.05-1.94 (m, 2H). Analytical LC/MS (Method 4): Observed Mass: 356.1; Retention Time: 0.928 min.

Step B. Example 83

Example 83 was synthesized according to the general procedures described for the preparation of Example 11 (Step E), using Intermediate 83A (80 mg, 0.14 mmol) as starting material. The crude material was purified by preparative HPLC (Prep Method 1) to afford the title compound (49 mg, 0.10 mmol, 71% yield). $^1$H NMR (500 MHz, DMSO-$d_6$) δ 7.80-7.70 (m, 2H), 7.22-7.16 (m, 1H), 7.16-7.09 (m, 1H), 6.94-6.85 (m, 1H), 3.89 (s, 3H), 3.84 (s, 3H), 3.05-2.93 (m, 2H), 2.90-2.77 (m, 2H), 2.75-2.66 (m, 1H), 2.64-2.57 (m, 1H), 2.34-2.18 (m, 3H), 2.16-2.04 (m, 2H), 1.87-1.72 (m, 4H), 1.72-1.58 (m, 2H), 1.50-1.38 (m, 2H), 0.97 (d, J=6.7 Hz, 6H). Analytical LC/MS (Method 1): Purity: 96.9%; Observed Mass: 481.25; Retention Time: 0.98 min. (Method 2): Purity: 96.4%; Observed Mass: 481.27; Retention Time: 1.45 min. TLR9 $IC_{50}$ (nM)=210.

Examples 84 and 85

6-(1-(8-isopropyl-8-azabicyclo[3.2.1]octan-3-yl)piperidin-4-yl)-1,4-dimethyl-2-(4-(methylsulfonyl)phenyl)-1H-benzo[d]imidazole (84-85)

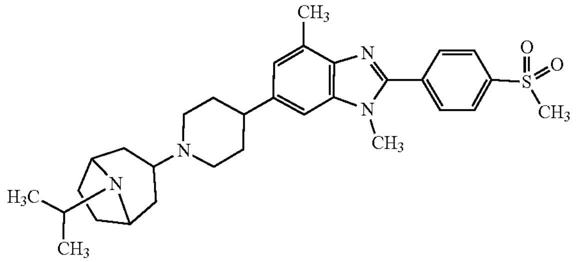

Step A. Intermediate 84A. Preparation of 6-(1-(8-azabicyclo[3.2.1]octan-3-yl)piperidin-4-yl)-1,4-dimethyl-2-(4-(methylsulfonyl)phenyl)-1H-benzo[d] imidazole dihydrochloride (84A)

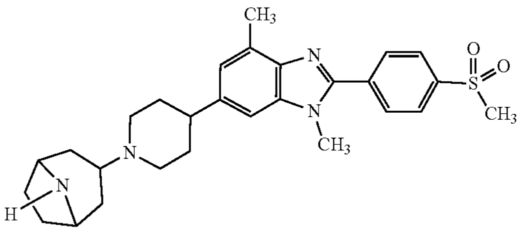

To a 250 mL round bottomed flask were added Intermediate 22C (1.0 g, 2.4 mmol), MeOH (50 mL) and DOWEX 550A anion exchange resin (10 g). The mixture was stirred for 15 min, the resin was filtered and the filtrate was concentrated. The resultant free amine was dissolved in DCE (15 ml) and DME (15 ml), then tert-butyl 3-oxo-8-azabicyclo[3.2.1]octane-8-carboxylate (2.2 g, 9.7 mmol) was added, followed by titanium(IV) isopropoxide (3.6 ml, 12 mmol). The reaction mixture was stirred at 40° C. under $N_2$. After 18 h, the mixture was cooled to room temperature, then sodium triacetoxyborohydride (2.0 g, 9.7 mmol) was added and the reaction was continued. After stirring 2 h, the reaction mixture was partitioned into 1 M KOH (sat. with solid NaCl) (150 mL) and 10% IPA/chloroform (150 mL). The layers were separated, the aqueous phase was extracted with 10% IPA/chloroform (75 mL), the organic phase was combined, washed with brine, dried over $MgSO_4$, filtered and concentrated. The residue was purified by flash column chromatography (120 g silica gel cartridge; A=DCM, B=MeOH; 30 min grad.; 0% B to 20% B; flow rate=80 mL/min.). Fractions corresponding to product were combined, concentrated and dried in vacuo. The resultant residue was dissolved in MeOH (20 mL) and 4 M HCl in dioxane (10 mL) and stirred. After 0.5 h, the solvent was concentrated and the residue was co-evaporated with toluene (2×). The product was dried in vacuo to afford the title compound (0.72 g, 1.3 mmol, 54% yield) as an off-white solid. $^1H$ NMR (500 MHz, METHANOL-$d_4$) δ 8.37-8.33 (m, 2H), 8.23-8.18 (m, 2H), 7.78-7.72 (m, 1H), 7.51-7.47 (m, 1H), 4.32-4.27 (m, 1H), 4.25-4.19 (m, 1H), 4.13-4.10 (m, 3H), 4.10-4.04 (m, 2H), 4.03-3.95 (m, 1H), 3.89-3.78 (m, 3H), 2.49-2.44 (m, 1H), 2.32-1.96 (m, 17H). Analytical LC/MS (Method 4): Observed Mass: 493.1; Retention Time: 0.827 min.

Step B. Examples 84 and 85

Examples 84 and 85 were synthesized according to the general procedures described for the preparation of Examples 17 and 18 (Step B), using Intermediate 84A (100 mg, 0.18 mmol) as starting material. The crude isomeric mixture was purified via preparative HPLC with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 10% B, 10-55% B over 25 minutes, then a 0-minute hold at 100% B; Flow Rate: 20 mL/min; Column Temperature: 25° C. Fraction collection was triggered by MS signals. Fractions corresponding to the respective desired products were combined and dried via centrifugal evaporation.

Example 84 (39 mg, 0.073 mmol, 41% yield) was isolated as the 1$^{st}$ eluting isomer. $^1H$ NMR (500 MHz, DMSO-$d_6$) δ 8.10 (s, 4H), 7.28 (s, 1H), 6.99 (s, 1H), 3.87 (s, 2H), 3.73-3.51 (m, 2H), 3.36-3.29 (m, 1H), 3.29 (s, 2H), 3.08-2.97 (m, 1H), 2.88-2.76 (m, 1H), 2.55 (s, 5H), 2.24-2.09 (m, 2H), 1.81 (s, 7H), 1.76-1.64 (m, 4H), 1.61-1.49 (m, 3H), 1.05 (br d, J=5.8 Hz, 6H). Analytical LC/MS (Method 1): Purity: 99.5%; Observed Mass: 535.00; Retention Time: 0.90 min. (Method 2): Purity: 100%; Observed Mass: 534.99; Retention Time: 1.24 min. TLR9 $IC_{50}$ (nM)=72.

Example 85 (5.5 mg, 0.010 mmol, 6% yield) was isolated as the 2$^{nd}$ eluting isomer. $^1H$ NMR (500 MHz, DMSO-$d_6$) δ 8.10 (s, 4H), 7.29 (s, 1H), 6.99 (s, 1H), 3.88 (s, 2H), 3.53 (s, 3H), 3.42-3.34 (m, 1H), 3.30 (s, 3H), 2.55 (s, 5H), 2.39-2.31 (m, 1H), 1.94-1.66 (m, 15H), 0.99 (d, J=6.1 Hz, 6H). Analytical LC/MS (Method 1): Purity: 95.6%; Observed Mass: 535.24; Retention Time: 1.01 min. (Method 2): Purity: 100%; Observed Mass: 535.23; Retention Time: 1.48 min. TLR9 $IC_{50}$ (nM)=110.

Example 86

6-(4-(4-isopropylpiperazin-1-yl)phenyl)-1,4-dimethyl-2-(4-(methylsulfonyl)phenyl)-1H-benzo[d] imidazole (86)

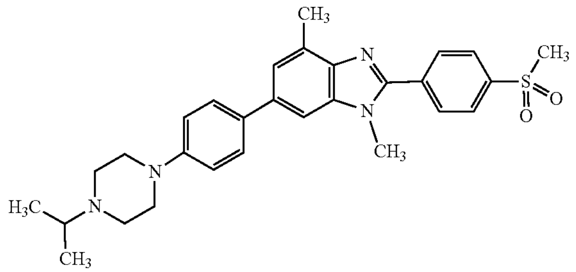

Step A. Intermediate 86A. Preparation of tert-butyl 4-(4-(1,4-dimethyl-2-(4-(methylsulfonyl)phenyl)-1H-benzo[d]imidazol-6-yl)phenyl)piperazine-1-carboxylate (86A)

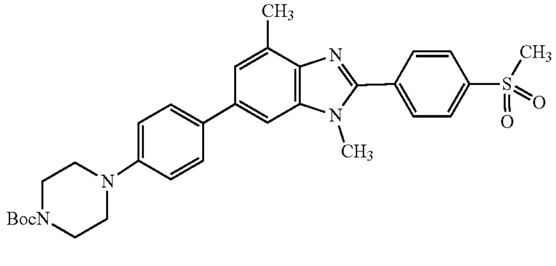

To a 40 mL vial were added Intermediate 22A (0.53 g, 1.4 mmol), tert-butyl 4-(4-(4,4,5,5-tetramethyl-1,3,2-dioxaborolan-2-yl)phenyl)piperazine-1-carboxylate (0.60 g, 1.5 mmol), XPhos Pd G3 (0.12 g, 0.14 mmol), 1,4-dioxane (10 mL), followed by potassium phosphate tribasic (1.0 g, 4.9 mmol) dissolved in water (3 mL). The vessel was flushed with $N_2$, capped, and the reaction mixture was stirred at 85° C. After 18 h, the reaction mixture was cooled, diluted with water (100 mL), and extracted with EtOAc (2×50 mL). The organic phase was combined, washed with brine, dried over $MgSO_4$, filtered and concentrated. The residue was purified by flash column chromatography (80 g silica gel cartridge; A=Hex, B=EtOAc; 30 min grad.; 0% B to 100% B; flow rate=60 mL/min). The fractions corresponding to product were combined, concentrated and dried in vacuo to afford the title compound (0.78 g, 1.4 mmol, 100% yield) as a pale yellow solid. 1H NMR (500 MHz, DMSO-$d_6$) δ 7.44-7.36 (m, 2H), 7.34-7.23 (m, 2H), 6.88-6.82 (m, 2H), 6.79-6.74 (m, 1H), 6.64-6.58 (m, 1H), 6.35-6.27 (m, 2H), 3.19-3.07 (m, 3H), 2.91-2.74 (m, 5H), 2.43 (s, 6H), 1.93-1.88 (m, 3H), 0.71 (s, 9H). Analytical LC/MS (Method 4): Observed Mass: 561.2; Retention Time: 1.777 min.

Step B. Intermediate 86B. Preparation of 1,4-dimethyl-2-(4-(methylsulfonyl)phenyl)-6-(4-(piperazin-1-yl)phenyl)-1H-benzo[d]imidazole dihydrochloride (86B)

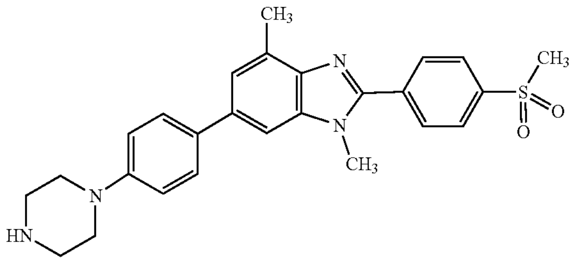

To a 100 mL pear shaped flask were added Intermediate 86A (0.78 g, 1.4 mmol), MeOH (10 mL), and 4 M HCl in dioxane (5 mL). After stirring 15 min, the solvent was concentrated and the residue was co-evaporated with toluene (2×), and the product was dried in vacuo to afford the title compound (0.74 g, 1.4 mmol, 100% yield) as a tan solid. $^1$H NMR (500 MHz, DMSO-$d_6$) δ 8.25 (s, 4H), 8.08-7.96 (m, 1H), 7.84-7.73 (m, 2H), 7.72-7.66 (m, 1H), 7.25-7.09 (m, 2H), 4.06 (s, 3H), 3.51-3.45 (m, 4H), 3.38 (s, 3H), 3.29-3.17 (m, 5H), 2.71 (s, 3H). Analytical LC/MS (Method 4): Observed Mass: 461.2; Retention Time: 0.94 min.

Step C. Example 86

To a 40 mL vial were added Intermediate 86B (70 mg, 0.13 mmol), propan-2-one (38 mg, 0.66 mmol), AcOH (8.3 μL, 0.14 mmol), magnesium sulfate (240 mg, 1.9 mmol), and DMF (2 mL). The reaction mixture was stirred for 10 min, then sodium triacetoxyborohydride (140 mg, 0.66 mmol) was added and the reaction mixture was stirred. After 18 h, the reaction mixture was diluted with 10% IPA/$CHCl_3$ (40 mL) and filtered. The filtrate was partitioned into 10% KOH sat. with solid NaCl (20 mL) and the layers were separated. The aqueous phase was extracted with 10% IPA/$CHCl_3$ (10 mL), the organic phase was combined, washed with brine, dried over $MgSO_4$, filtered and concentrated. The crude material was purified by preparative HPLC (Prep Method 1) to afford the title compound (27 mg, 0.054 mmol, 42% yield). $^1$H NMR (500 MHz, DMSO-$d_6$) δ 8.18-8.09 (m, 4H), 7.68-7.62 (m, 3H), 7.41-7.35 (m, 1H), 7.06-6.99 (m, 2H), 3.95 (s, 2H), 3.60-3.46 (m, 3H), 3.30 (s, 2H), 3.19 (br s, 3H), 2.71-2.64 (m, 1H), 2.61-2.57 (m, 2H), 2.51 (br s, 4H), 1.02 (d, J=6.4 Hz, 6H) (one proton obscured). Analytical LC/MS (Method 1): Purity: 91.6%; Observed Mass: 502.96; Retention Time: 1.13 min. (Method 2): Purity: 92.9%; Observed Mass: 502.96; Retention Time: 1.67 min. TLR9 $IC_{50}$ (nM)=300.

Example 87

7-fluoro-6-(1'-isopropyl-[1,4'-bipiperidin]-4-yl)-2-(4-(methylsulfonyl)phenyl)-1H-benzo[d]imidazole (87)

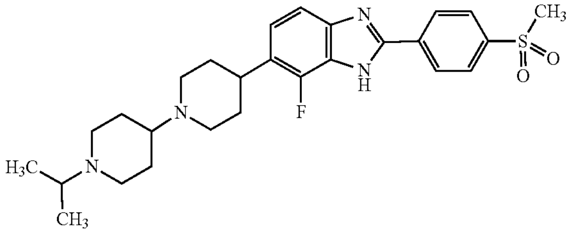

Step A. Intermediate 87A. Preparation of 7-fluoro-2-(4-(methylsulfonyl)phenyl)-6-(piperidin-4-yl)-1H-benzo[d]imidazole dihydrochloride (87A)

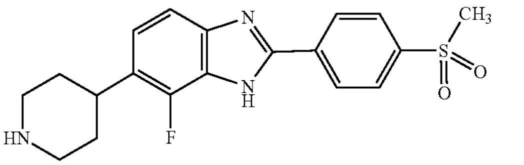

Intermediate 87A was synthesized according to the general procedures described for the preparation of Intermediate 11D (Steps A-D), using 4-bromo-3-fluorobenzene-1,2-diamine (1.4 g, 6.6 mmol) and 4-(methylsulfonyl)benzaldehyde (1.2 g, 6.6 mmol) as starting materials, and using HCl during Boc-deprotection (Step 11D), to afford the title compound (1.5 g, 3.4 mmol, 52% over 4 steps) as an off-white solid. $^1$H NMR (500 MHz, METHANOL-$d_4$) δ 8.43-8.38 (m, 2H), 8.32-8.28 (m, 2H), 7.70-7.65 (m, 1H), 7.59-7.54 (m, 1H), 3.63-3.56 (m, 2H), 3.56-3.46 (m, 1H), 3.39-3.36 (m, 2H), 3.29-3.24 (m, 3H), 2.21-2.12 (m, 4H). Analytical LC/MS (Method 4): Observed Mass: 373.9; Retention Time: 0.913 min.

Step B. Example 87

To a 40 mL vial were added Intermediate 87A (70 mg, 0.16 mmol), 1-isopropylpiperidin-4-one (110 mg, 0.78 mmol), AcOH (9.9 μL, 0.17 mmol), magnesium sulfate (280 mg, 2.4 mmol), and DMF (2 mL). The reaction mixture was stirred for 10 min, then sodium triacetoxyborohydride (170 mg, 0.78 mmol) was added and the reaction mixture was stirred. After 18 h, the reaction mixture was diluted with 10% IPA/$CHCl_3$ (40 mL) and filtered. The filtrate was partitioned into 10% KOH (sat. with solid NaCl) (20 mL) and the layers were separated. The aqueous phase was extracted with 10% IPA/$CHCl_3$ (10 mL), the organic phase was combined, washed with brine, dried over $MgSO_4$, filtered and concentrated. The crude material was purified by preparative HPLC (Prep Method 1) to afford the title compound (11 mg, 0.022 mmol, 14% yield). $^1$H NMR (500 MHz, DMSO-$d_6$) δ 8.45-8.37 (m, 2H), 8.13-8.07 (m, 2H), 7.44-7.35 (m, 1H), 7.25-7.16 (m, 1H), 3.31-3.24 (m, 2H), 3.03-2.97 (m, 2H), 2.96-2.83 (m, 3H), 2.78-2.66 (m, 2H), 2.35-2.22 (m, 3H), 2.21-2.09 (m, 2H), 1.95-1.86 (m, 2H), 1.82-1.72 (m, 5H), 1.52-1.42 (m, 2H), 0.98 (br d, J=6.5 Hz, 6H). Analytical LC/MS (Method 1): Purity: 98.5%; Observed Mass: 499.01; Retention Time: 0.98 min. (Method 2): Purity: 99.1%; Observed Mass: 498.94; Retention Time: 1.05 min. TLR9 $IC_{50}$ (nM)=950.

Example 88

4-fluoro-5-(1'-isopropyl-[1,4'-bipiperidin]-4-yl)-1-methyl-2-(4-(methylsulfonyl)phenyl)-1H-benzo[d]imidazole (88)

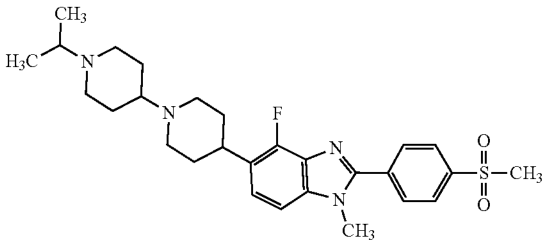

Step A. Intermediate 88A. Preparation of 4-bromo-3-fluoro-N-methyl-2-nitroaniline (88A)

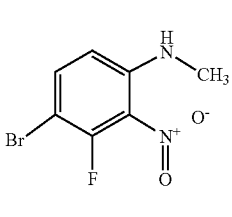

To a 250 mL round bottomed flask were added 4-bromo-3-fluoro-2-nitroaniline (1.0 g, 4.3 mmol), and DMF (30 mL). The reaction mixture was cooled to 0° C., then NaH (60% dispersion in mineral oil) (0.20 g, 5.1 mmol) was added. After stirring at the above temperature for 30 min, MeI (0.27 mL, 4.3 mmol) was added, the reaction mixture was allowed to slowly reach room temperature, and stirred under $N_2$. After 18 h, the reaction mixture was diluted with water (150 mL) and extracted with EtOAc (2×75 mL). The organic phase was combined, washed with brine, dried over $MgSO_4$, filtered and concentrated. The residue was purified by flash column chromatography (120 g silica gel cartridge; A=Hex, B=EtOAc; 30 min grad.; 0% B to 50% B; flow rate=80 mL/min). The fractions corresponding to product were combined, concentrated and dried in vacuo to afford the title compound (0.93 g, 3.7 mmol, 86% yield) as a yellow solid. $^1$H NMR (500 MHz, CHLOROFORM-d) δ 7.55-7.49 (m, 1H), 7.26-7.15 (m, 1H), 6.59-6.51 (m, 1H), 2.91 (s, 3H). Analytical LC/MS (Method 4): Observed Mass: 250.8; Retention Time: 1.766 min.

Step B. Intermediate 88B. Preparation of tert-butyl 4-(2-fluoro-4-(methylamino)-3-nitrophenyl)-3,6-dihydropyridine-1(2H)-carboxylate (88B)

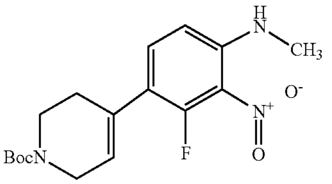

To a 40 mL vial were added Intermediate 88A (0.93 g, 3.7 mmol), tert-butyl 4-(4,4,5,5-tetramethyl-1,3,2-dioxaborolan-2-yl)-3,6-dihydropyridine-1(2H)-carboxylate (1.4 g, 4.5 mmol), XPhos Pd G3 (0.16 g, 0.19 mmol), 1,4-dioxane (10 mL), followed by potassium phosphate tribasic (2.8 g, 13 mmol) dissolved in water (3 mL). The vessel was flushed with $N_2$, capped, and the reaction mixture was stirred at 85° C. After 18 h, the reaction mixture was cooled, diluted with water (100 mL), and extracted with EtOAc (2×50 mL). The organic phase was combined, washed with brine, dried over $MgSO_4$, filtered and concentrated. The residue was purified by flash column chromatography (80 g silica gel cartridge; A=DCM, B=MeOH; 30 min grad.; 0% B to 15% B; flow rate=60 mL/min). The pure fractions were combined, concentrated and dried in vacuo to afford the title compound (1.3 g, 3.7 mmol, 100% yield) as a pale yellow solid. $^1$H NMR (500 MHz, CHLOROFORM-d) δ 7.32-7.29 (m, 1H), 7.03-6.95 (m, 1H), 6.62-6.54 (m, 1H), 5.90-5.84 (m, 1H), 4.11-4.06 (m, 2H), 3.67-3.59 (m, 2H), 3.04-2.98 (m, 2H), 2.94-2.87 (m, 3H), 1.52-1.52 (m, 9H). Analytical LC/MS (Method 4): Observed Mass: 251.8 (des-Boc); Retention Time: 2.276 min.

Step C. Intermediate 88C. Preparation of tert-butyl 4-(3-amino-2-fluoro-4-(methylamino)phenyl)piperidine-1-carboxylate (88C)

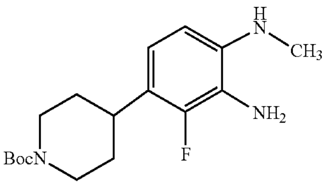

To a 100 mL hydrogenation vessel were added Intermediate 88B (1.3 g, 3.7 mmol), MeOH (30 mL), and 5% Pd—C (% wt. on carbon, wet) (0.79 g, 0.37 mmol). The vessel was purged with $N_2$ (3×) and stirred under $H_2$ at 50 psi. After 18 h, the catalyst was filtered and the filtrate was concentrated. The residue was purified by flash column chromatography (120 g silica gel cartridge; A=Hex, B=EtOAc; 30 min grad.; 0% B to 100% B; flow rate=80 mL/min). The fractions corresponding to product were combined, concentrated and dried in vacuo to afford the title compound (0.63 g, 2.0 mmol, 54% yield) as a pale yellow solid. $^1$H NMR (500 MHz, METHANOL-$d_4$) δ 6.59-6.53 (m, 1H), 6.38 (d, J=8.3 Hz, 1H), 4.25-4.16 (m, 2H), 2.96-2.86 (m, 2H), 2.84-2.80 (m, 3H), 1.84-1.74 (m, 2H), 1.67-1.55 (m, 2H), 1.50 (s, 9H) (one proton obscured). Analytical LC/MS (Method 4): Observed Mass: 267.9 (−tBu); Retention Time: 1.500 min.

Step D. Intermediate 88D. Preparation of tert-butyl 4-(4-fluoro-1-methyl-2-(4-(methylsulfonyl)phenyl)-1H-benzo[d]imidazol-5-yl)piperidine-1-carboxylate (88D)

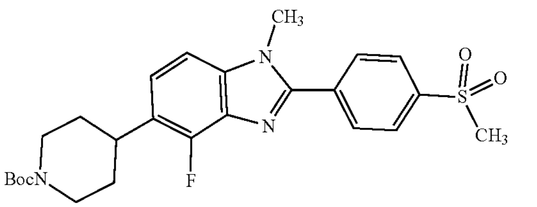

To a 250 mL round bottomed flask were added Intermediate 88C (0.63 g, 2.0 mmol) and NMP (15 mL). To this mixture was added sodium metabisulfite (0.56 g, 2.9 mmol), followed by 4-(methylsulfonyl)benzaldehyde (0.36 g, 2.0 mmol). The reaction mixture was heated to 70° C. and stirred under $N_2$. After 18 h, the reaction mixture was cooled, the mixture was diluted with water (100 mL) and the organic phase was extracted with EtOAc (2×50 mL), the combined extract was washed with brine, dried over $MgSO_4$, filtered and concentrated. The residue was purified by flash column chromatography (120 g silica gel cartridge; A=DCM, B=MeOH; 30 min grad.; 0% B to 15% B; flow rate=80 mL/min). The fractions corresponding to product were combined, concentrated and dried in vacuo (0.90 g, 1.8 mmol, 90% yield) as a pale yellow solid. $^1$H NMR (500 MHz, METHANOL-$d_4$) δ 8.22-8.17 (m, 2H), 8.13-8.07 (m, 2H), 7.43-7.39 (m, 1H), 7.35-7.29 (m, 1H), 4.32-4.22 (m, 2H), 3.95 (s, 3H), 3.35-3.32 (m, 5H), 3.26-3.22 (m, 3H), 1.89-1.82 (m, 2H), 1.52 (s, 9H). Analytical LC/MS (Method 4): Observed Mass: 488.1; Retention Time: 1.839 min.

Step E. Intermediate 88E. Preparation of 4-fluoro-1-methyl-2-(4-(methylsulfonyl) phenyl)-5-(piperidin-4-yl)-1H-benzo[d]imidazole hydrochloride (88E)

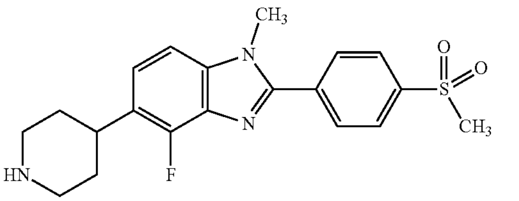

To a 100 mL pear shaped flask were added Intermediate 88D (0.90 g, 1.8 mmol), MeOH (20 mL), and 4 M HCl in dioxane (20 mL). After stirring 30 min, the solvent was concentrated and the residue was co-evaporated with toluene (2×), and the product was dried in vacuo to afford the title compound (0.76 g, 1.8 mmol, 100% yield) as a tan solid. $^1$H NMR (500 MHz, METHANOL-$d_4$) δ 8.39-8.32 (m, 2H), 8.24-8.19 (m, 2H), 7.88-7.81 (m, 1H), 7.74-7.67 (m, 1H), 4.17-4.09 (m, 3H), 3.63-3.57 (m, 2H), 3.56-3.44 (m, 2H), 3.29 (s, 3H), 2.90-2.81 (m, 1H), 2.42-2.35 (m, 1H), 2.22-2.13 (m, 3H). Analytical LC/MS (Method 4): Observed Mass: 387.9; Retention Time: 0.934 min.

Step F. Example 88

To a 40 mL vial were added Intermediate 88E (64 mg, 0.15 mmol), 1-isopropylpiperidin-4-one (110 mg, 0.76 mmol), AcOH (9.6 μL, 0.17 mmol), magnesium sulfate (280 mg, 2.3 mmol), and DMF (2 mL). The reaction mixture was stirred for 10 min, then sodium triacetoxyborohydride (160 mg, 0.76 mmol) was added and the reaction mixture was stirred. After 18 h, the reaction mixture was diluted with 10% IPA/$CHCl_3$ (40 mL) and filtered. The filtrate was partitioned into 10% KOH (sat. with solid NaCl) (20 mL) and the layers were separated. The aqueous phase was extracted with 10% IPA/$CHCl_3$ (10 mL), the organic phase was combined, washed with brine, dried over $MgSO_4$, filtered and concentrated. The crude material was purified by preparative HPLC (Prep Method 1) to afford the title compound (40 mg, 0.078 mmol, 52% yield). $^1$H NMR (500 MHz, DMSO-$d_6$) δ 8.18-8.10 (m, 4H), 7.49-7.42 (m, 1H), 7.33-7.25 (m, 1H), 3.96-3.87 (m, 3H), 3.50-3.48 (m, 6H), 3.05-2.98 (m, 2H), 2.96-2.88 (m, 2H), 2.40-2.27 (m, 3H), 2.27-2.13 (m, 2H), 1.85-1.73 (m, 5H), 1.55-1.42 (m, 2H), 1.00 (br d, J=6.2 Hz, 6H). Analytical LC/MS (Method 1): Purity: 98.3%; Observed Mass: 513.27; Retention Time: 0.96 min. (Method 2): Purity: 97.5%; Observed Mass: 512.99; Retention Time: 1.19 min. TLR9 $IC_{50}$ (nM)=360.

Examples 89 and 90

4-fluoro-5-(1-(8-isopropyl-8-azabicyclo[3.2.1]octan-3-yl)piperidin-4-yl)-1-methyl-2-(4-(methylsulfonyl) phenyl)-1H-benzo[d]imidazole (89-90)

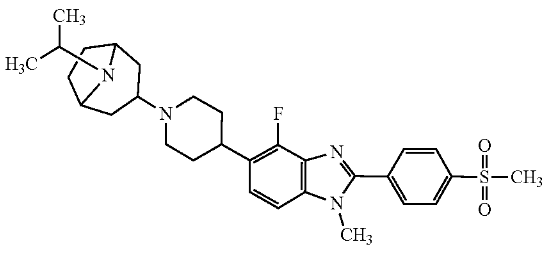

Step A. Intermediate 89A. Preparation of 5-(1-(8-azabicyclo[3.2.1]octan-3-yl)piperidin-4-yl)-4-fluoro-1-methyl-2-(4-(methylsulfonyl)phenyl)-1H-benzo[d]imidazole dihydrochloride (89A)

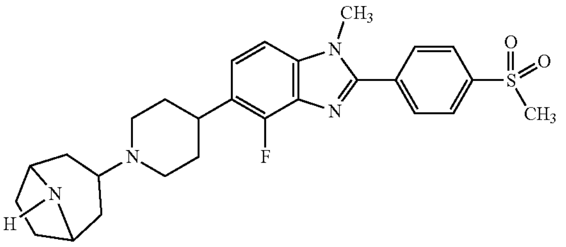

Intermediate 89A was synthesized according to the general procedures described for the preparation of Intermediate 84A, substituting Intermediate 88E (0.41 g, 0.98 mmol) where appropriate to afford the title compound (0.51 g, 0.90 mmol, 92% yield) as a light tan solid. $^1$H NMR (500 MHz, METHANOL-$d_4$) δ 8.30-8.24 (m, 2H), 8.19-8.13 (m, 2H), 7.64 (s, 1H), 7.58-7.51 (m, 1H), 4.32-4.20 (m, 3H), 4.12-4.03 (m, 6H), 3.86-3.79 (m, 2H), 3.78-3.74 (m, 1H), 3.72-3.66 (m, 3H), 3.64-3.58 (m, 1H), 3.50-3.43 (m, 2H), 3.30-3.25 (m, 5H), 2.41-2.38 (m, 3H). Analytical LC/MS (Method 4): Observed Mass: 497.2; Retention Time: 0.903 min.

Step B. Examples 89 and 90

Examples 89 and 90 were synthesized according to the general procedures described for the preparation of Examples 17 and 18 (Step B), using Intermediate 89A (75 mg, 0.13 mmol) as starting material. The crude isomeric mixture was purified via preparative HPLC with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 5% B, 5-55% B over 20 minutes, then a 0-minute hold at 100% B; Flow Rate: 20 mL/min; Column Temperature: 25° C. Fraction collection was triggered by MS signals. Fractions corresponding to the respective desired products were combined and dried via centrifugal evaporation.

Example 89 (14 mg, 0.026 mmol, 20% yield) was isolated as the 1$^{st}$ eluting isomer. $^1$H NMR (500 MHz, DMSO-$d_6$) δ 8.11 (s, 4H), 7.43 (d, J=8.6 Hz, 1H), 7.30-7.24 (m, 1H), 3.88 (s, 3H), 3.28 (s, 3H), 3.05-2.99 (m, 2H), 2.97-2.83 (m, 2H), 2.73-2.60 (m, 1H), 2.27-2.17 (m, 2H), 1.90-1.83 (m, 2H), 1.82-1.65 (m, 8H), 1.64-1.52 (m, 4H), 1.07 (br d, J=6.1 Hz, 6H). Analytical LC/MS (Method 1): Purity: 97.4%; Observed Mass: 539.27; Retention Time: 1.02 min. (Method 2): Purity: 97.4%; Observed Mass: 539.01; Retention Time: 1.3 min. TLR9 $IC_{50}$ (nM)=160.

Example 90 (7.3 mg, 0.014 mmol, 11% yield) was isolated as the 2$^{nd}$ eluting isomer. $^1$H NMR (500 MHz, DMSO-$d_6$) δ 8.14-8.10 (m, 4H), 7.46-7.42 (m, 1H), 7.31-7.24 (m, 1H), 3.92-3.88 (m, 3H), 3.68-3.54 (m, 5H), 3.28 (s, 4H), 2.00-1.90 (m, 4H), 1.89-1.81 (m, 5H), 1.81-1.70 (m, 6H), 1.14-1.02 (m, 6H). Analytical LC/MS (Method 1): Purity: 100%; Observed Mass: 539.01; Retention Time: 1.01 min. (Method 2): Purity: 100%; Observed Mass: 538.97; Retention Time: 1.50 min. TLR9 $IC_{50}$ (nM)=230.

Example 91

7-fluoro-5-(1'-isopropyl-[1,4'-bipiperidin]-4-yl)-1-methyl-2-(4-(methylsulfonyl)phenyl)-1H-benzo[d]imidazole (91)

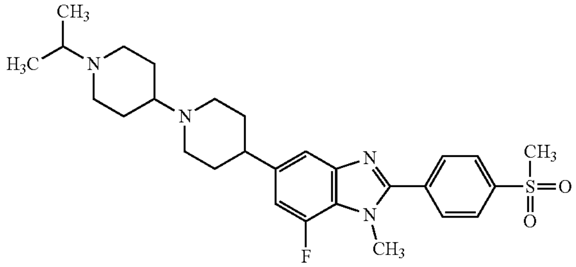

Step A. Intermediate 91A. Preparation of 7-fluoro-1-methyl-2-(4-(methylsulfonyl)phenyl)-5-(piperidin-4-yl)-1H-benzo[d]imidazole hydrochloride (91A)

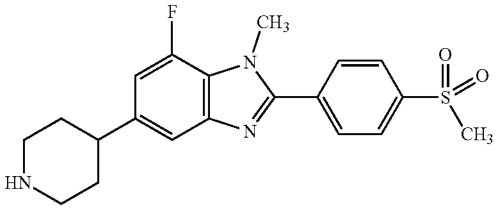

Intermediate 91A was synthesized according to the general procedures described for the preparation of Intermediate 88E (Steps A-E), using 4-bromo-2-fluoro-6-nitroaniline (3.0 g, 13 mmol) as starting material to afford the title compound (2.0 g, 4.8 mmol, 37% yield over 5 steps) as an off-white solid. $^1$H NMR (500 MHz, METHANOL-$d_4$) δ 8.36 (d, J=8.2 Hz, 2H), 8.21 (br d, J=8.3 Hz, 2H), 7.66 (s, 1H), 7.55-7.45 (m, 1H), 4.27-4.20 (m, 3H), 3.63-3.55 (m, 2H), 3.29 (s, 3H), 3.28-3.19 (m, 3H), 2.27-2.17 (m, 2H), 2.14-2.01 (m, 2H). Analytical LC/MS (Method 4): Observed Mass: 387.9; Retention Time: 0.969 min.

Step B. Example 91

Example 91 was synthesized according to the general procedures described for the preparation of Example 88 (Step F), using Intermediate 91A (60 mg, 0.14 mmol) as starting material. The crude material was purified by preparative HPLC (Prep Method 1) to afford the title compound (58 mg, 0.11 mmol, 85% yield). $^1$H NMR (500 MHz, DMSO-$d_6$) δ 8.17-8.05 (m, 4H), 7.43-7.36 (m, 1H), 7.11-7.01 (m, 1H), 4.00 (s, 3H), 3.55-3.50 (m, 2H), 3.32-3.29 (m, 2H), 3.05-2.99 (m, 2H), 2.98-2.90 (m, 2H), 2.87-2.78 (m, 1H), 2.69-2.58 (m, 1H), 2.39-2.22 (m, 4H), 1.83 (br s, 4H), 1.75-1.64 (m, 2H), 1.56-1.43 (m, 2H), 1.02 (d, J=6.6 Hz, 6H). Analytical LC/MS (Method 1): Purity: 97.5%; Observed Mass: 513.22; Retention Time: 0.95 min. (Method 2): Purity: 97.3%; Observed Mass: 513.42; Retention Time: 1.17 min. TLR9 $IC_{50}$ (nM)=100.

Examples 92 and 93

7-fluoro-5-(1-(8-isopropyl-8-azabicyclo[3.2.1]octan-3-yl)piperidin-4-yl)-1-methyl-2-(4-(methylsulfonyl)phenyl)-1H-benzo[d]imidazole (92-93)

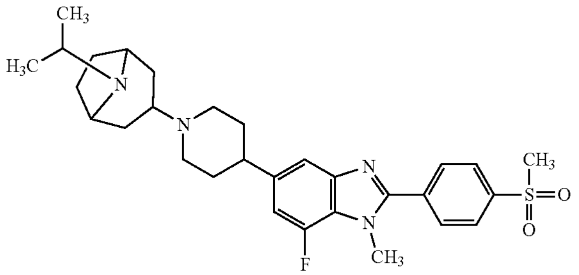

Step A. Intermediate 91A. Preparation of 5-(1-(8-azabicyclo[3.2.1]octan-3-yl)piperidin-4-yl)-7-fluoro-1-methyl-2-(4-(methylsulfonyl)phenyl)-1H-benzo[d]imidazole dihydrochloride (92A)

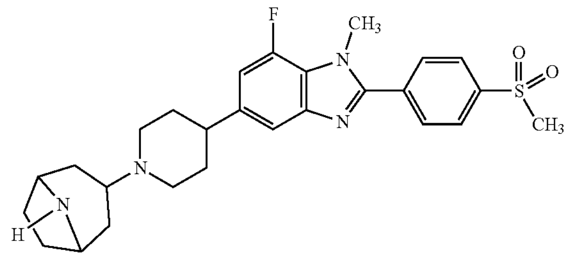

Intermediate 91A was synthesized according to the general procedures described for the preparation of Intermediate 84A, substituting Intermediate 91A (0.70 g, 1.6 mmol) where appropriate to afford the title compound (0.80 g, 1.4 mmol, 88% yield) as a tan solid. $^{1}H$ NMR (500 MHz, METHANOL-$d_4$) δ 8.35-8.30 (m, 2H), 8.20-8.16 (m, 2H), 7.64-7.59 (m, 1H), 7.48-7.40 (m, 1H), 4.30-4.25 (m, 2H), 4.24-4.19 (m, 4H), 4.11-4.02 (m, 4H), 3.83-3.74 (m, 3H), 3.72-3.64 (m, 2H), 3.62-3.58 (m, 1H), 2.40-2.33 (m, 3H), 2.20-2.10 (m, 7H). Analytical LC/MS (Method 4): Observed Mass: 497.2; Retention Time: 0.873 min.

Step B. Examples 92 and 93

Examples 92 and 93 were synthesized according to the general procedures described for the preparation of Examples 17 and 18 (Step B), using Intermediate 92A (58 mg, 0.10 mmol) as starting material. The crude isomeric mixture was purified via preparative HPLC with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 4% B, 4-55% B over 20 minutes, then a 0-minute hold at 100% B; Flow Rate: 20 mL/min; Column Temperature: 25° C. Fraction collection was triggered by MS signals. Fractions corresponding to the respective desired products were combined and dried via centrifugal evaporation.

Example 92 (13 mg, 0.026 mmol, 26% yield) was isolated as the $1^{st}$ eluting isomer. $^{1}H$ NMR (500 MHz, DMSO-$d_6$) δ 8.16-8.06 (m, 4H), 7.43-7.35 (m, 1H), 7.10-7.02 (m, 1H), 4.01 (s, 3H), 3.32 (s, 2H), 3.01 (br d, J=10.4 Hz, 2H), 2.93-2.81 (m, 1H), 2.74-2.57 (m, 2H), 2.55 (s, 3H), 2.29-2.14 (m, 2H), 1.90 (s, 3H), 1.88-1.78 (m, 3H), 1.76-1.60 (m, 4H), 1.59-1.49 (m, 2H), 1.08 (br d, J=6.1 Hz, 6H). Analytical LC/MS (Method 1): Purity: 98.3%; Observed Mass: 539.27; Retention Time: 1.29 min. (Method 2): Purity: 97.6%; Observed Mass: 538.99; Retention Time: 1.42 min. TLR9 $IC_{50}$ (nM)=110.

Example 93 (16 mg, 0.030 mmol, 30% yield) was isolated as the $2^{nd}$ eluting isomer. $^{1}H$ NMR (500 MHz, DMSO-$d_6$) δ 8.16-8.05 (m, 4H), 7.39 (s, 1H), 7.07 (br d, J=12.8 Hz, 1H), 4.00 (s, 3H), 3.68-3.50 (m, 3H), 3.31-3.25 (m, 4H), 2.85-2.75 (m, 1H), 2.67-2.57 (m, 1H), 2.52 (br s, 4H), 2.40-2.32 (m, 1H), 2.00-1.77 (m, 8H), 1.73-1.62 (m, 2H), 1.09 (br d, J=6.1 Hz, 6H). Analytical LC/MS (Method 1): Purity: 100%; Observed Mass: 538.93; Retention Time: 0.96 min. (Method 2): Purity: 98.5%; Observed Mass: 539.02; Retention Time: 1.59 min. TLR9 $IC_{50}$ (nM)=650.

Examples 94 and 95

7-fluoro-6-(1-(8-isopropyl-8-azabicyclo[3.2.1]octan-3-yl)piperidin-4-yl)-2-(4-(methylsulfonyl)phenyl)-1H-benzo[d]imidazole (94-95)

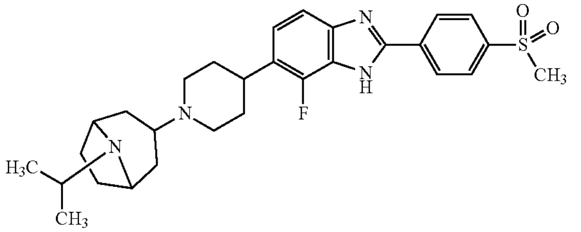

Step A. Intermediate 94A. Preparation of 6-(1-(8-azabicyclo[3.2.1]octan-3-yl)piperidin-4-yl)-7-fluoro-2-(4-(methylsulfonyl)phenyl)-1H-benzo[d]imidazole dihydrochloride (94A)

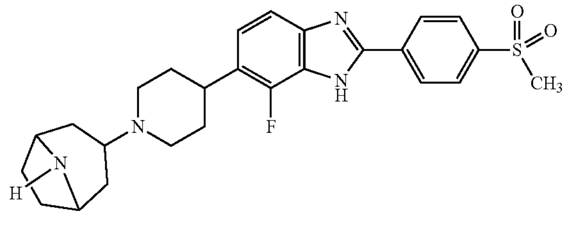

Intermediate 94A was synthesized according to the general procedures described for the preparation of Intermediate 84A, substituting Intermediate 87A (0.48 g, 1.3 mmol) where appropriate to afford the title compound (0.60 g, 1.1 mmol, 85% yield) as a tan solid. $^1$H NMR (500 MHz, METHANOL-$d_4$) δ 8.43-8.38 (m, 2H), 8.30-8.27 (m, 2H), 7.68-7.64 (m, 1H), 7.60-7.54 (m, 1H), 4.31-4.27 (m, 2H), 4.26-4.19 (m, 2H), 4.02-3.99 (m, 1H), 3.85-3.80 (m, 2H), 3.79-3.74 (m, 1H), 3.72-3.66 (m, 2H), 3.63-3.59 (m, 1H), 3.57 (s, 2H), 3.38-3.36 (m, 1H), 3.32-3.28 (m, 2H), 3.27-3.23 (m, 5H), 3.20-3.18 (m, 2H), 3.14-3.09 (m, 1H). Analytical LC/MS (Method 4): Observed Mass: 483.1; Retention Time: 0.824 min.

Step B. Examples 94 and 95

Examples 94 and 95 were synthesized according to the general procedures described for the preparation of Examples 17 and 18 (Step B), using Intermediate 94A (100 mg, 0.18 mmol) as starting material. The crude isomeric mixture was purified via preparative HPLC with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 5% B, 5-55% B over 20 minutes, then a 0-minute hold at 100% B; Flow Rate: 20 mL/min; Column Temperature: 25° C. Fraction collection was triggered by MS signals. Fractions corresponding to the respective desired products were combined and dried via centrifugal evaporation.

Example 94 (3.8 mg, 0.0072 mmol, 4% yield) was isolated as the 1$^{st}$ eluting isomer. $^1$H NMR (500 MHz, DMSO-$d_6$) δ 8.56-8.36 (m, 2H), 8.17-8.04 (m, 2H), 7.51-7.37 (m, 1H), 7.28-7.11 (m, 1H), 3.89-3.66 (m, 1H), 3.32-3.28 (m, 1H), 3.21-3.15 (m, 1H), 3.07-3.00 (m, 1H), 2.99-2.86 (m, 2H), 2.83-2.64 (m, 1H), 2.57-2.53 (m, 2H), 2.33-2.21 (m, 2H), 1.98-1.81 (m, 5H), 1.80-1.69 (m, 5H), 1.68-1.49 (m, 4H), 1.17-1.05 (m, 6H). Analytical LC/MS (Method 1): Purity: 97.9%; Observed Mass: 525.14; Retention Time: 0.98 min. (Method 2): Purity: 96.9%; Observed Mass: 525.19; Retention Time: 1.13 min. TLR9 $IC_{50}$ (nM) =73.

Example 95 (3.0 mg, 0.0057 mmol, 3% yield) was isolated as the 2$^{nd}$ eluting isomer. $^1$H NMR (500 MHz, DMSO-$d_6$) δ 8.49-8.38 (m, 2H), 8.15-8.07 (m, 2H), 7.45-7.36 (m, 1H), 7.24-7.17 (m, 1H), 3.91 (s, 1H), 3.82-3.66 (m, 1H), 3.55-3.46 (m, 1H), 3.29 (s, 1H), 2.99-2.87 (m, 1H), 2.74-2.62 (m, 1H), 2.57-2.53 (m, 2H), 2.51 (br s, 2H), 2.37 (br s, 1H), 1.97-1.72 (m, 13H), 1.05 (br d, J=6.1 Hz, 6H) (one proton obscured). Analytical LC/MS (Method 1): Purity: 96.4%; Observed Mass: 525.15; Retention Time: 0.98 min. (Method 2): Purity: 97.2%; Observed Mass: 525.18; Retention Time: 1.34 min. TLR9 $IC_{50}$ (nM)=29.

Example 96

5-fluoro-6-(1'-isopropyl-[1,4'-bipiperidin]-4-yl)-1-methyl-2-(4-(methylsulfonyl)phenyl)-1H-benzo[d]imidazole (96)

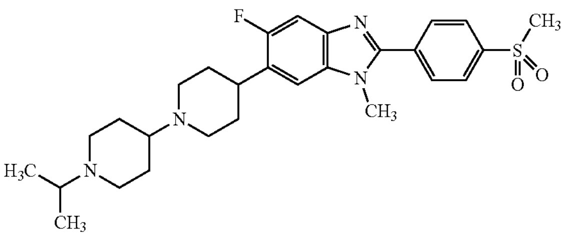

Step A. Intermediate 91A. Preparation of 5-fluoro-1-methyl-2-(4-(methylsulfonyl) phenyl)-6-(piperidin-4-yl)-1H-benzo[d]imidazole hydrochloride (96A)

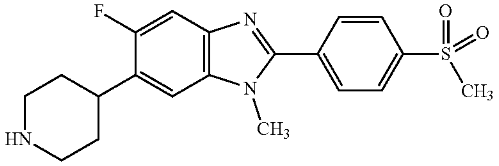

Intermediate 96A was synthesized according to the general procedures described for the preparation of Intermediate 88E (Steps B-E), using 5-bromo-4-fluoro-N-methyl-2-nitroaniline (1.1 g, 4.4 mmol) as starting material to afford the title compound (1.4 g, 3.3 mmol, 75% yield over 4 steps) as a tan solid. $^1$H NMR (500 MHz, METHANOL-$d_4$) δ 8.39-8.32 (m, 2H), 8.25-8.16 (m, 2H), 8.08-8.00 (m, 1H), 7.74-7.67 (m, 1H), 4.19 (s, 3H), 3.64-3.59 (m, 2H), 3.53-3.45 (m, 1H), 3.35-3.29 (m, 3H), 2.21 (br d, J=3.1 Hz, 4H), 2.05 (s, 2H). Analytical LC/MS (Method 4): Observed Mass: 387.9; Retention Time: 0.880 min.

Step B. Example 96

Example 96 was synthesized according to the general procedures described for the preparation of Example 88 (Step F), using Intermediate 96A (75 mg, 0.18 mmol) as starting material. The crude material was purified by preparative HPLC (Prep Method 2) to afford the title compound (24 mg, 0.032 mmol, 18% yield). $^1$H NMR (500 MHz, DMSO-$d_6$) δ 8.15-8.12 (m, 4H), 7.60-7.56 (m, 1H), 7.55-7.51 (m, 1H), 3.98-3.92 (m, 3H), 3.62-3.52 (m, 2H), 3.49-3.38 (m, 1H), 3.36-3.22 (m, 3H), 3.12-3.03 (m, 2H), 2.56-2.54 (m, 3H), 2.53-2.51 (m, 3H), 2.39-2.32 (m, 2H), 2.22-2.09 (m, 4H), 2.09-1.96 (m, 2H), 1.27 (br d, J=6.7 Hz, 6H). Analytical LC/MS (Method 1): Purity: 100%; Observed Mass: 512.95; Retention Time: 0.89 min. (Method 2): Purity: 100%; Observed Mass: 513.19; Retention Time: 1.23 min. TLR9 $IC_{50}$ (nM)=73.

Examples 97 and 98

5-fluoro-6-(1-(8-isopropyl-8-azabicyclo[3.2.1]octan-3-yl)piperidin-4-yl)-1-methyl-2-(4-(methylsulfonyl)phenyl)-1H-benzo[d]imidazole (97-98)

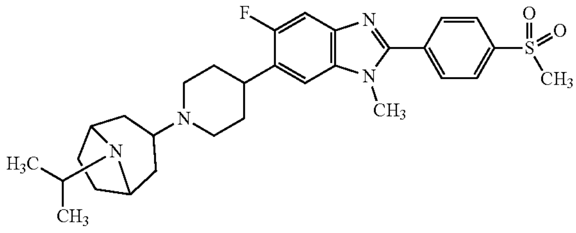

Step A. Intermediate 97A. Preparation of 6-(1-(8-azabicyclo[3.2.1]octan-3-yl)piperidin-4-yl)-5-fluoro-1-methyl-2-(4-(methylsulfonyl)phenyl)-1H-benzo[d]imidazole dihydrochloride (97A)

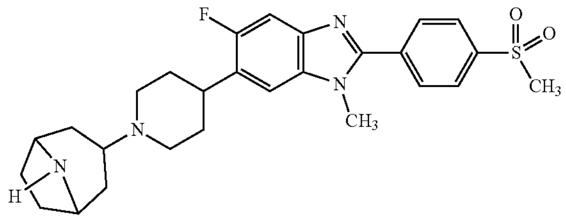

Intermediate 97A was synthesized according to the general procedures described for the preparation of Intermediate 84A, substituting Intermediate 96A (0.72 g, 1.7 mmol) where appropriate to afford the title compound (0.81 g, 1.4 mmol, 82% yield) as a tan solid. $^1$H NMR (500 MHz, METHANOL-$d_4$) δ 8.34-8.29 (m, 2H), 8.21-8.15 (m, 2H), 7.96-7.92 (m, 1H), 7.67-7.61 (m, 1H), 4.32-4.27 (m, 2H), 4.25-4.18 (m, 2H), 4.13-4.08 (m, 6H), 3.86-3.82 (m, 2H), 2.42-2.36 (m, 8H), 2.18-2.14 (m, 6H). Analytical LC/MS (Method 4): Observed Mass: 497.2; Retention Time: 0.627 min.

Step B. Examples 97 and 98

Examples 97 and 98 were synthesized according to the general procedures described for the preparation of Examples 17 and 18 (Step B), using Intermediate 97A (140 mg, 0.24 mmol) as starting material. The crude isomeric mixture was purified via preparative HPLC with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 0% B, 0-48% B over 20 minutes, then a 0-minute hold at 100% B; Flow Rate: 20 mL/min; Column Temperature: 25° C. Fraction collection was triggered by MS signals. Fractions corresponding to the respective desired products were combined and dried via centrifugal evaporation.

Example 97 (21 mg, 0.039 mmol, 16% yield) was isolated as the 1st eluting isomer. $^1$H NMR (500 MHz, DMSO-$d_6$) δ 8.11 (s, 4H), 7.58 (br d, J=6.7 Hz, 1H), 7.46 (d, J=11.0 Hz, 1H), 3.91 (s, 2H), 3.72-3.56 (m, 3H), 3.29 (s, 3H), 3.08-3.00 (m, 2H), 2.94-2.83 (m, 2H), 2.70 (br d, J=5.8 Hz, 1H), 2.31-2.18 (m, 2H), 1.90-1.80 (m, 8H), 1.66-1.53 (m, 4H), 1.09 (br d, J=6.1 Hz, 6H). Analytical LC/MS (Method 1): Purity: 97.2%; Observed Mass: 539.11; Retention Time: 0.89 min. (Method 2): Purity: 97.5%; Observed Mass: 538.95; Retention Time: 1.18 min. TLR9 $IC_{50}$ (nM)=79.

Example 98 (9.4 mg, 0.017 mmol, 7% yield) was isolated as the 2nd eluting isomer. $^1$H NMR (500 MHz, DMSO-$d_6$) δ 8.17-8.07 (m, 4H), 7.65-7.59 (m, 1H), 7.53-7.44 (m, 1H), 3.95 (s, 3H), 3.69-3.62 (m, 1H), 3.39-3.34 (m, 1H), 3.32 (s, 2H), 3.18 (s, 1H), 2.95-2.80 (m, 2H), 2.37 (br s, 1H), 2.08-1.93 (m, 6H), 1.92-1.77 (m, 10H), 1.12 (br d, J=6.1 Hz, 6H). Analytical LC/MS (Method 1): Purity: 97.6%; Observed Mass: 539.27; Retention Time: 1.37 min. (Method 2): Purity: 100%; Observed Mass: 539.29; Retention Time: 1.46 min. TLR9 $IC_{50}$ (nM)=10.

Example 99

6-fluoro-5-(1'-isopropyl-[1,4'-bipiperidin]-4-yl)-1-methyl-2-(4-(methylsulfonyl)phenyl)-1H-benzo[d]imidazole (99)

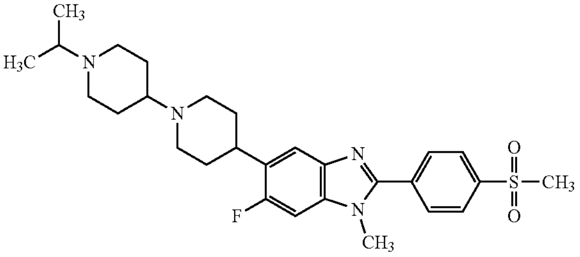

Step A. Intermediate 91A. Preparation of 6-fluoro-1-methyl-2-(4-(methylsulfonyl) phenyl)-5-(piperidin-4-yl)-1H-benzo[d]imidazole hydrochloride (99A)

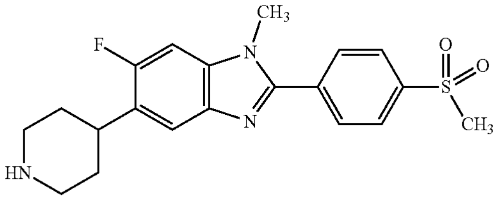

Intermediate 99A was synthesized according to the general procedures described for the preparation of Intermediate 88E (Steps A-E), using 4-bromo-5-fluoro-2-nitroaniline (3.0 g, 13 mmol) as starting material to afford the title compound (3.4 g, 8.0 mmol, 62% yield over 5 steps) as an off-white solid. $^1$H NMR (500 MHz, METHANOL-$d_4$) δ 8.38-8.33 (m, 2H), 8.23-8.19 (m, 2H), 7.94-7.89 (m, 1H), 7.89-7.86 (m, 1H), 4.11 (s, 3H), 3.63-3.57 (m, 2H), 3.53-3.44 (m, 2H), 3.34-3.32 (m, 1H), 3.28 (s, 5H), 2.23-2.19 (m, 2H). Analytical LC/MS (Method 4): Observed Mass: 387.9; Retention Time: 0.912 min.

Step B. Example 99

Example 99 was synthesized according to the general procedures described for the preparation of Example 88 (Step F), using Intermediate 99A (75 mg, 0.18 mmol) as starting material. The crude material was purified by preparative HPLC (Prep Method 1) to afford the title compound (59 mg, 0.12 mmol, 67% yield). $^1$H NMR (500 MHz, DMSO-$d_6$) δ 8.17-8.07 (m, 4H), 7.64-7.59 (m, 1H), 7.56-7.50 (m, 1H), 3.88 (s, 2H), 3.59-3.46 (m, 4H), 3.30 (s, 2H), 3.20-3.15 (m, 1H), 3.05-2.99 (m, 2H), 2.94-2.82 (m, 3H), 2.80-2.71 (m, 1H), 2.31 (br d, J=10.1 Hz, 2H), 2.24-2.13 (m, 2H), 1.83-1.72 (m, 4H), 1.51-1.44 (m, 2H), 1.02-0.92 (m, 6H). Analytical LC/MS (Method 1): Purity: 97%; Observed Mass: 513.25; Retention Time: 0.94 min. (Method 2): Purity: 96%; Observed Mass: 513.06; Retention Time: 1.29 min. TLR9 $IC_{50}$ (nM)=360.

Examples 100 and 101

6-fluoro-5-(1-(8-isopropyl-8-azabicyclo[3.2.1]octan-3-yl)piperidin-4-yl)-1-methyl-2-(4-(methylsulfonyl)phenyl)-1H-benzo[d]imidazole (100-101)

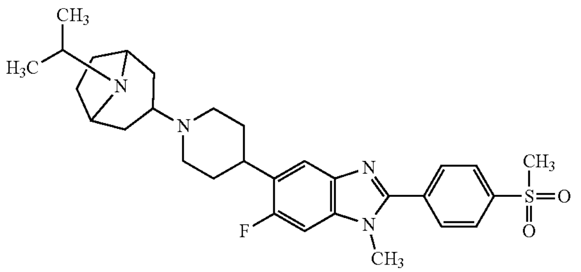

Step A. Intermediate 97A. Preparation of 5-(1-(8-azabicyclo[3.2.1]octan-3-yl)piperidin-4-yl)-6-fluoro-1-methyl-2-(4-(methylsulfonyl)phenyl)-1H-benzo[d]imidazole dihydrochloride (100A)

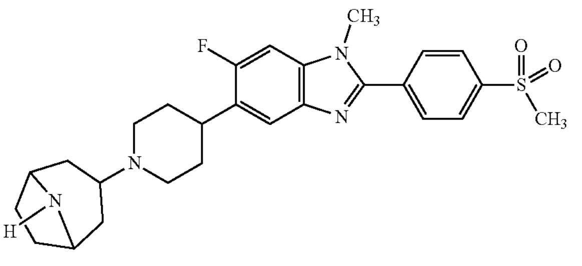

Intermediate 100A was synthesized according to the general procedures described for the preparation of Intermediate 84A, substituting Intermediate 99A (1.6 g, 3.8 mmol) where appropriate to afford the title compound (0.80 g, 1.4 mmol, 37% yield) as a tan solid. $^1$H NMR (500 MHz, METHANOL-$d_4$) δ 8.37-8.33 (m, 2H), 8.23-8.17 (m, 2H), 7.93-7.89 (m, 1H), 7.89-7.85 (m, 1H), 4.38-4.33 (m, 2H), 4.32-4.27 (m, 1H), 4.25-4.19 (m, 1H), 4.02-3.98 (m, 1H), 3.88-3.80 (m, 3H), 2.94 (br dd, J=17.3, 4.5 Hz, 3H), 2.61-2.58 (m, 1H), 2.57-2.54 (m, 1H), 2.50-2.42 (m, 1H), 2.41-2.31 (m, 4H), 2.31-2.23 (m, 6H), 2.07-2.03 (m, 2H). Analytical LC/MS (Method 4): Observed Mass: 497.0; Retention Time: 0.642 min.

Step B. Examples 100 and 101

Examples 100 and 101 were synthesized according to the general procedures described for the preparation of Examples 17 and 18 (Step B), using Intermediate 100A (110 mg, 0.20 mmol) as starting material. The crude isomeric mixture was purified via preparative HPLC with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 13% B, 13-55% B over 20 minutes, then a 0-minute hold at 100% B; Flow Rate: 20 mL/min; Column Temperature: 25° C. Fraction collection was triggered by MS signals. Fractions corresponding to the respective desired products were combined and dried via centrifugal evaporation.

Example 100 (12 mg, 0.022 mmol, 11% yield) was isolated as the $1^{st}$ eluting isomer. $^1$H NMR (500 MHz, DMSO-$d_6$) δ 8.16-8.08 (m, 4H), 7.63-7.59 (m, 1H), 7.57-7.49 (m, 1H), 3.89 (s, 3H), 3.31 (s, 2H), 3.01 (br d, J=11.0 Hz, 2H), 2.87-2.72 (m, 2H), 2.68-2.58 (m, 1H), 2.20 (br t, J=10.8 Hz, 2H), 1.86 (s, 3H), 1.78 (br s, 4H), 1.75-1.62 (m, 4H), 1.58-1.51 (m, 2H), 1.47-1.40 (m, 2H), 1.01 (d, J=6.1 Hz, 6H). Analytical LC/MS (Method 1): Purity: 98.3%; Observed Mass: 539.23; Retention Time: 0.93 min. (Method 2): Purity: 100%; Observed Mass: 538.98; Retention Time: 1.39 min. TLR9 $IC_{50}$ (nM)=62.

Example 101 (21 mg, 0.039 mmol, 20% yield) was isolated as the $2^{nd}$ eluting isomer. $^1$H NMR (500 MHz, DMSO-$d_6$) δ 8.16-8.07 (m, 4H), 7.64-7.59 (m, 1H), 7.58-7.51 (m, 1H), 3.89 (s, 3H), 3.31 (s, 3H), 2.89-2.79 (m, 1H), 2.72-2.61 (m, 1H), 2.42-2.32 (m, 1H), 1.97-1.69 (m, 17H), 1.04 (d, J=5.8 Hz, 6H) (one proton obscured). Analytical LC/MS (Method 1): Purity: 97.7%; Observed Mass: 539.26; Retention Time: 0.93 min. (Method 2): Purity: 96.4%; Observed Mass: 538.96; Retention Time: 1.43 min. TLR9 $IC_{50}$ (nM)=75.

Example 102

7-fluoro-6-(1'-isopropyl-[1,4'-bipiperidin]-4-yl)-1-methyl-2-(4-(methylsulfonyl)phenyl)-1H-benzo[d]imidazole (102)

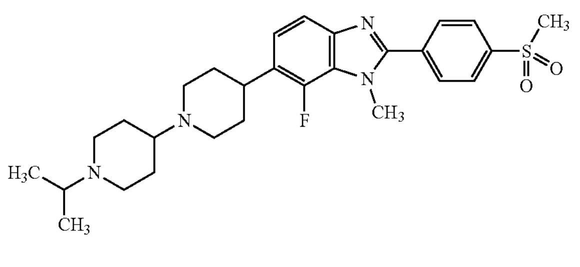

Step A. Intermediate 91A. Preparation of 7-fluoro-1-methyl-2-(4-(methylsulfonyl)phenyl)-6-(piperidin-4-yl)-1H-benzo[d]imidazole hydrochloride (102A)

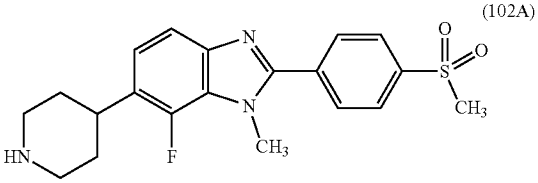 [SMILES: Cn1c(-c2ccc(S(C)(=O)=O)cc2)nc2ccc(C3CCNCC3)c(F)c21]

Intermediate 102A was synthesized according to the general procedures described for the preparation of Intermediate 88E (Steps A-E), using 3-bromo-2-fluoro-6-nitroaniline (1.2 g, 5.1 mmol) as starting material to afford the title compound (1.7 g, 4.0 mmol, 78% yield over 5 steps) as an off-white solid. $^1$H NMR (500 MHz, METHANOL-$d_4$) δ 8.22-8.17 (m, 2H), 8.11-8.05 (m, 2H), 7.67-7.62 (m, 1H), 7.43-7.40 (m, 1H), 4.29-4.18 (m, 2H), 3.92 (s, 3H), 3.88-3.82 (m, 2H), 3.81-3.75 (m, 1H), 3.23 (s, 3H), 2.10-1.96 (m, 3H), 1.86-1.82 (m, 1H). Analytical LC/MS (Method 4): Observed Mass: 387.9; Retention Time: 0.900 min.

Step B. Example 102

Example 102 was synthesized according to the general procedures described for the preparation of Example 88 (Step F), using Intermediate 102A (71 mg, 0.17 mmol) as starting material. The crude material was purified by preparative HPLC (Prep Method 1) to afford the title compound (30 mg, 0.059 mmol, 35% yield). $^1$H NMR (500 MHz, DMSO-$d_6$) δ 8.16-8.06 (m, 4H), 7.57 (d, J=8.5 Hz, 1H), 7.18 (br s, 1H), 4.03 (s, 3H), 3.67-3.46 (m, 4H), 3.42-3.33 (m, 1H), 3.31 (s, 4H), 3.11-3.01 (m, 2H), 2.53 (br d, J=18.9 Hz, 3H), 2.39-2.31 (m, 2H), 2.20-1.94 (m, 6H), 1.26 (br d, J=6.4 Hz, 6H). Analytical LC/MS (Method 1): Purity: 100%; Observed Mass: 512.97; Retention Time: 0.96 min. (Method 2): Purity: 98%; Observed Mass: 513.19; Retention Time: 1.20 min. TLR9 $IC_{50}$ (nM)=30.

Examples 103 and 104

7-fluoro-6-(1-(8-isopropyl-8-azabicyclo[3.2.1]octan-3-yl)piperidin-4-yl)-1-methyl-2-(4-(methylsulfonyl)phenyl)-1H-benzo[d]imidazole (103-104)

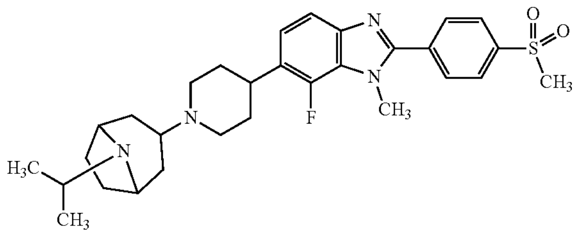

Step A. Intermediate 97A. Preparation of 6-(1-(8-azabicyclo[3.2.1]octan-3-yl)piperidin-4-yl)-7-fluoro-1-methyl-2-(4-(methylsulfonyl)phenyl)-1H-benzo[d]imidazole dihydrochloride (103A)

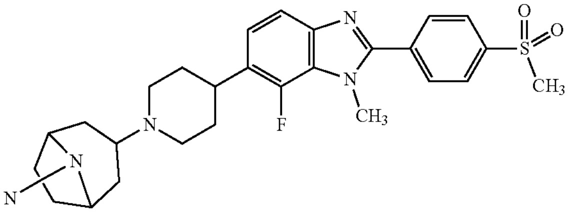

Intermediate 103A was synthesized according to the general procedures described for the preparation of Intermediate 84A, substituting Intermediate 102A (0.96 g, 2.3 mmol) where appropriate to afford the title compound (1.1 g, 1.9 mmol, 83% yield) as a tan solid. $^1$H NMR (500 MHz, METHANOL-$d_4$) δ 8.38-8.34 (m, 2H), 8.23-8.19 (m, 2H), 7.74-7.69 (m, 2H), 4.32-4.28 (m, 2H), 4.27-4.24 (m, 4H), 4.24-4.18 (m, 2H), 4.14-4.07 (m, 2H), 3.86-3.81 (m, 3H), 3.78-3.74 (m, 2H), 3.72-3.66 (m, 3H), 3.62-3.58 (m, 2H), 2.18-2.13 (m, 3H), 2.12-2.08 (m, 3H). Analytical LC/MS (Method 4): Observed Mass: 497.2; Retention Time: 0.892 min.

Step B. Examples 103 and 104

Examples 103 and 104 were synthesized according to the general procedures described for the preparation of Examples 17 and 18 (Step B), using Intermediate 103A (150 mg, 0.26 mmol) as starting material. The crude isomeric mixture was purified via preparative HPLC with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 6% B, 6-56% B over 20 minutes, then a 0-minute hold at 100% B; Flow Rate: 20 mL/min; Column Temperature: 25° C. Fraction collection was triggered by MS signals. Fractions corresponding to the respective desired products were combined and dried via centrifugal evaporation.

Example 103 (25 mg, 0.046 mmol, 18% yield) was isolated as the $1^{st}$ eluting isomer. $^1$H NMR (500 MHz, DMSO-$d_6$) δ 8.16-8.06 (m, 4H), 7.53-7.46 (m, 1H), 7.25-7.17 (m, 1H), 4.02 (br d, J=0.6 Hz, 3H), 3.77-3.68 (m, 1H), 3.54-3.38 (m, 2H), 3.31 (s, 2H), 3.06-2.88 (m, 2H), 2.83-2.72 (m, 1H), 2.71-2.59 (m, 1H), 2.44-2.34 (m, 1H), 2.27-2.17 (m, 1H), 2.15-2.02 (m, 2H), 1.96-1.72 (m, 8H), 1.71-1.62 (m, 1H), 1.59-1.51 (m, 1H), 1.51-1.43 (m, 1H), 1.02 (br d, J=6.1 Hz, 6H). Analytical LC/MS (Method 1): Purity: 99.1%; Observed Mass: 538.96; Retention Time: 1.33 min. (Method 2): Purity: 99.2%; Observed Mass: 539.01; Retention Time: 1.32 min. TLR9 $IC_{50}$ (nM)=54.

Example 104 (10 mg, 0.019 mmol, 7% yield) was isolated as the $2^{nd}$ eluting isomer. $^1$H NMR (500 MHz, DMSO-$d_6$) δ 8.19-8.04 (m, 4H), 7.50 (d, J=8.4 Hz, 1H), 7.21 (s, 1H), 4.02 (s, 3H), 3.43 (br s, 3H), 3.32 (s, 1H), 3.00-2.88 (m, 1H), 2.68-2.61 (m, 1H), 2.55-2.51 (m, 5H), 2.40-2.34 (m, 1H), 2.05-1.73 (m, 12H), 1.11 (br s, 6H). Analytical LC/MS (Method 1): Purity: 92.2%; Observed Mass: 539.16; Retention Time: 0.96 min. (Method 2): Purity: 94.9%; Observed Mass: 539.27; Retention Time: 1.39 min. TLR9 $IC_{50}$ (nM)=140.

Example 105

4-fluoro-6-(1'-isopropyl-[1,4'-bipiperidin]-4-yl)-1-methyl-2-(4-(methylsulfonyl)phenyl)-1H-benzo[d]imidazole (105)

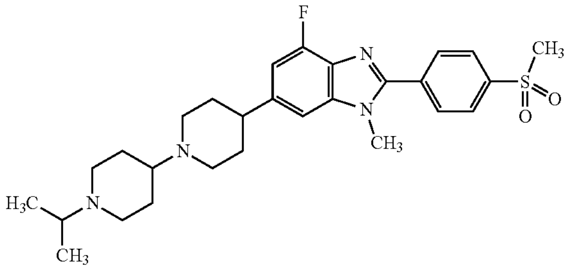

Step A. Intermediate 105A. Preparation of 5-bromo-3-fluoro-N-methyl-2-nitroaniline (105A)

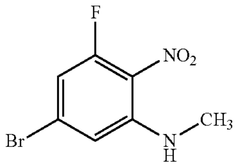

To a 250 mL round-bottom flask were added 5-bromo-1,3-difluoro-2-nitrobenzene (7.5 g, 32 mmol), THE (100 mL), followed by the batchwise addition of $Cs_2CO_3$ (12 g, 38 mmol). The mixture was cooled to 0° C., and methylamine (2.0 M in THF) (16 mL, 32 mmol) was added dropwise. The mixture was allowed to reach room temperature and stirred under $N_2$. After 18 h, the reaction mixture was diluted with water (500 mL), extracted with EtOAc (2×200 mL), the organic layers were combined, washed with brine, dried over $MgSO_4$, filtered and concentrated. The residue was purified by flash column chromatography (120 g silica gel cartridge; A=Hex, B=EtOAc; 30 min grad.; 0% B to 100% B; flow rate=80 mL/min). The fractions corresponding to product were combined, concentrated and dried in vacuo to afford the title compound (9.5 g, 31 mmol, 97% yield) as a yellow solid. $^1H$ NMR (500 MHz, METHANOL-$d_4$) δ 6.94-6.91 (m, 1H), 6.74-6.69 (m, 1H), 2.96-2.95 (m, 3H). Analytical LC/MS (Method 4): Observed Mass: 250.9; Retention Time: 1.878 min.

Step B. Intermediate 105B. Preparation of 4-fluoro-1-methyl-2-(4-(methylsulfonyl) phenyl)-6-(piperidin-4-yl)-1H-benzo[d]imidazole hydrochloride (105B)

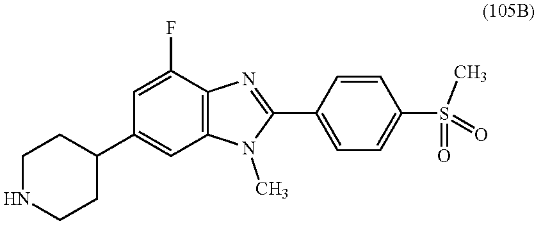 [SMILES: Cn1c(-c2ccc(S(C)(=O)=O)cc2)nc2c(F)cc(C3CCNCC3)cc21]

Intermediate 105B was synthesized according to the general procedures described for the preparation of Intermediate 88E (Steps B-E), using Intermediate 105A (3.9 g, 16 mmol) as starting material to afford the title compound (3.6 g, 8.5 mmol, 53% yield over 4 steps) as a tan solid. $^1H$ NMR (500 MHz, METHANOL-$d_4$) δ 8.34 (d, J=8.6 Hz, 2H), 8.21 (d, J=8.7 Hz, 2H), 7.80-7.76 (m, 1H), 7.50-7.46 (m, 1H), 4.17-4.12 (m, 3H), 3.63-3.57 (m, 2H), 3.30-3.28 (m, 3H), 3.27-3.20 (m, 3H), 2.28-2.19 (m, 2H), 2.15-2.05 (m, 2H). Analytical LC/MS (Method 4): Observed Mass: 388.0; Retention Time: 0.919 min.

Step C. Example 105

Example 105 was synthesized according to the general procedures described for the preparation of Example 88 (Step F), using Intermediate 105B (40 mg, 0.10 mmol) as starting material. The crude material was purified by preparative HPLC (Prep Method 1) to afford the title compound (36 mg, 0.070 mmol, 70% yield). $^1H$ NMR (500 MHz, DMSO-$d_6$) δ 8.19-8.07 (m, 4H), 7.43-7.37 (m, 1H), 7.07-6.99 (m, 1H), 3.92 (s, 3H), 3.46-3.36 (m, 1H), 3.32 (s, 1H), 3.22-3.13 (m, 1H), 3.03-2.96 (m, 2H), 2.90-2.81 (m, 2H), 2.75-2.61 (m, 2H), 2.27 (br s, 3H), 2.16-2.06 (m, 2H), 1.87-1.69 (m, 6H), 1.44 (br d, J=9.8 Hz, 2H), 0.97 (d, J=6.4 Hz, 6H). Analytical LC/MS (Method 1): Purity: 96.4%; Observed Mass: 513.37; Retention Time: 1.11 min. (Method 2): Purity: 98.9%; Observed Mass: 513.37; Retention Time: 1.25 min. TLR9 $IC_{50}$ (nM)=95.

Examples 106 and 107

4-fluoro-6-(1-(8-isopropyl-8-azabicyclo[3.2.1]octan-3-yl)piperidin-4-yl)-1-methyl-2-(4-(methylsulfonyl) phenyl)-1H-benzo[d]imidazole (106-107)

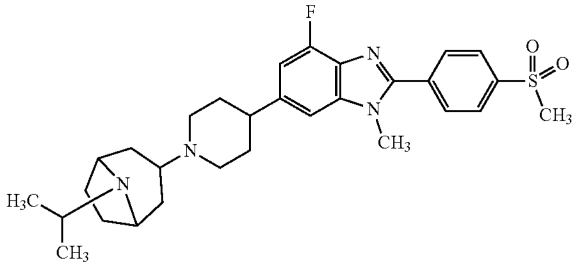

Step A. Intermediate 106A. Preparation of 6-(1-(8-azabicyclo[3.2.1]octan-3-yl) piperidin-4-yl)-4-fluoro-1-methyl-2-(4-(methylsulfonyl)phenyl)-1H-benzo[d]imidazole dihydrochloride (106A)

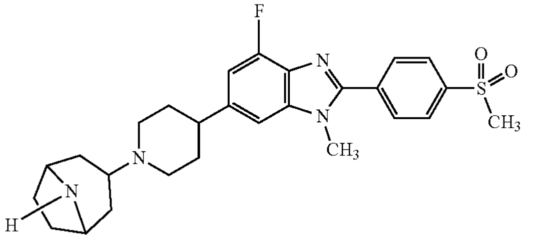

Intermediate 106A was synthesized according to the general procedures described for the preparation of Intermediate 84A, substituting Intermediate 105B (1.0 g, 2.4 mmol) where appropriate to afford the title compound (0.96 g, 1.7 mmol, 71% yield) as a tan solid. $^1$H NMR (500 MHz, METHANOL-$d_4$) δ 8.32-8.28 (m, 2H), 8.19-8.15 (m, 2H), 7.68-7.65 (m, 1H), 7.38-7.33 (m, 1H), 4.31-4.27 (m, 2H), 4.25-4.19 (m, 2H), 4.09 (br d, J=1.0 Hz, 9H), 3.85-3.80 (m, 2H), 2.49-2.42 (m, 2H), 2.18-2.11 (m, 9H). Analytical LC/MS (Method 4): Observed Mass: 497.2; Retention Time: 0.868 min.

Step B. Examples 106 and 107

Examples 106 and 107 were synthesized according to the general procedures described for the preparation of Examples 17 and 18 (Step B), using Intermediate 106A (140 mg, 0.25 mmol) as starting material. The crude isomeric mixture was purified via preparative HPLC with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 4% B, 4-44% B over 20 minutes, then a 0-minute hold at 100% B; Flow Rate: 20 mL/min; Column Temperature: 25° C. Fraction collection was triggered by MS signals. Fractions corresponding to the respective desired products were combined and dried via centrifugal evaporation.

Example 106 (11 mg, 0.020 mmol, 8% yield) was isolated as the 1$^{st}$ eluting isomer. $^1$H NMR (500 MHz, DMSO-$d_6$) δ 8.20-8.08 (m, 4H), 7.43-7.38 (m, 1H), 7.06-6.98 (m, 1H), 3.92 (s, 3H), 3.32 (s, 1H), 3.18 (s, 2H), 3.05-2.99 (m, 2H), 2.85-2.77 (m, 1H), 2.71-2.60 (m, 2H), 2.26-2.15 (m, 2H), 1.91 (s, 3H), 1.87-1.79 (m, 3H), 1.77-1.64 (m, 4H), 1.61-1.53 (m, 2H), 1.52-1.45 (m, 2H), 1.04 (d, J=6.1 Hz, 6H). Analytical LC/MS (Method 1): Purity: 95%; Observed Mass: 539.20; Retention Time: 1.13 min. (Method 2): Purity: 99%; Observed Mass: 539.20; Retention Time: 1.26 min. TLR9 $IC_{50}$ (nM)=390.

Example 107 (10 mg, 0.015 mmol, 6% yield) was isolated as the 2$^{nd}$ eluting isomer. $^1$H NMR (500 MHz, DMSO-$d_6$) δ 8.17-8.09 (m, 4H), 7.43-7.37 (m, 1H), 7.05-6.98 (m, 1H), 3.93 (s, 3H), 3.32 (s, 3H), 2.70-2.58 (m, 2H), 2.55-2.53 (m, 1H), 2.41-2.32 (m, 1H), 1.96-1.68 (m, 17H), 1.02 (d, J=5.8 Hz, 6H). Analytical LC/MS (Method 1): Purity: 100%; Observed Mass: 539.20; Retention Time: 1.37 min. (Method 2): Purity: 98%; Observed Mass: 539.20; Retention Time: 1.46 min. TLR9 $IC_{50}$ (nM)=270.

Examples 108 and 109

4-fluoro-1-methyl-2-(4-(methylsulfonyl)phenyl)-6-(1-(1-(oxetan-3-yl)azepan-4-yl) piperidin-4-yl)-1H-benzo[d]imidazole (108-109)

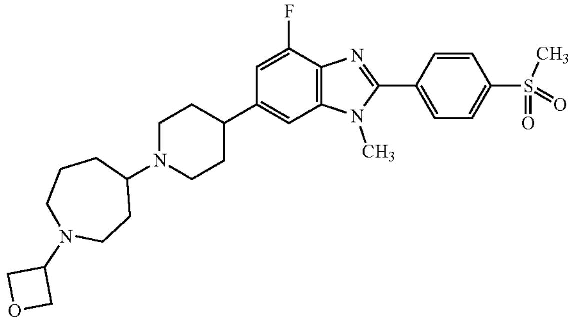

Step A. Intermediate 108A. Preparation of 6-(1-(azepan-4-yl)piperidin-4-yl)-4-fluoro-1-methyl-2-(4-(methylsulfonyl)phenyl)-1H-benzo[d]imidazole dihydrochloride (108A)

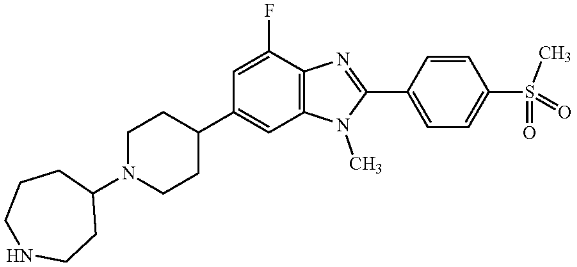

To a 40 mL vial were added Intermediate 105B (1.0 g, 2.4 mmol), tert-butyl 4-oxoazepane-1-carboxylate (2.5 g, 12 mmol), AcOH (0.15 mL, 2.6 mmol), magnesium sulfate (4.3 g, 35 mmol), and DMF (20 mL). The reaction mixture was stirred for 20 min, then sodium triacetoxyborohydride (2.5 g, 12 mmol) was added and the reaction mixture was stirred under $N_2$. After 18 h, the reaction mixture was diluted with 10% IPA/$CHCl_3$ (150 mL) and filtered. The filtrate was partitioned into 10% KOH (sat. with solid NaCl) (75 mL) and the layers were separated. The aqueous phase was extracted with 10% IPA/$CHCl_3$ (75 mL), the organic phase was combined, washed with brine, dried over $MgSO_4$, filtered and concentrated. The residue was purified by flash column chromatography (40 g silica gel cartridge; A=DCM, B=MeOH; 30 min grad.; 0% B to 20% B; flow rate=30 mL/min). The fractions corresponding to product were combined, concentrated and dried in vacuo. The resultant residue was dissolved in MeOH (40 mL), and 4 M HCl in dioxane (20 mL) and stirred. After 2 h, the solvent was concentrated and the residue was co-evaporated with toluene (2×), and the product was dried in vacuo to afford the title compound (1.3 g, 2.3 mmol, 96% yield) as a tan solid. $^1$H NMR (500 MHz, METHANOL-$d_4$) δ 8.35-8.31 (m, 2H), 8.23-8.19 (m, 2H), 7.82-7.76 (m, 1H), 7.51-7.45 (m, 1H), 4.14 (s, 3H), 3.75-3.53 (m, 5H), 3.50-3.46 (m, 2H), 3.24-3.20 (m, 4H), 3.18-3.14 (m, 3H), 2.66-2.58 (m, 1H), 2.52-2.26 (m, 7H), 2.24-2.16 (m, 1H). Analytical LC/MS (Method 4): Observed Mass: 485.2; Retention Time: 0.867 min.

Step B. Examples 108 and 109

To a 40 mL vial were added Intermediate 108A (150 mg, 0.27 mmol), oxetan-3-one (94 mg, 1.3 mmol), AcOH (0.016 mL, 0.29 mmol), magnesium sulfate (470 mg, 3.9 mmol), and DMF (2 mL). The reaction mixture was stirred for 20 min, then sodium triacetoxyborohydride (280 mg, 1.3 mmol) was added and the reaction mixture was stirred. After 18 h, the reaction mixture was diluted with 10% IPA/$CHCl_3$ (40 mL) and filtered. The filtrate was partitioned into 10% KOH (sat. with solid NaCl) (20 mL) and the layers were separated. The aqueous phase was extracted with 10% IPA/$CHCl_3$ (10 mL), the organic phase was combined, washed with brine, dried over $MgSO_4$, filtered and concentrated. The crude material was purified by preparative HPLC (Prep Method 1). The resultant racemic mixture was further purified by SFC-chiral chromatography with the following conditions: Instrument: Waters 100 Prep SFC; Column: Chiral AD, 30×250 mm. 5 micron; Mobile Phase: 70% $CO_2$/30% MeOH w/0.1% DEA; Flow Conditions: 100 mL/min.; Detector Wavelength: 220 nm; Injection Details: 300 μL, 100 mg dissolved in 3 mL MeOH. Fractions corresponding to the respective desired products were combined and dried via centrifugal evaporation.

Example 108 (13 mg, 0.024 mmol, 9% yield) was isolated as the 1$^{st}$ eluting enantiomer. $^1$H NMR (500 MHz, DMSO-$d_6$) δ 8.20-8.09 (m, 4H), 7.46-7.37 (m, 1H), 7.01 (d, J=12.2 Hz, 1H), 4.52 (s, 2H), 4.36 (s, 2H), 3.93 (s, 3H), 3.67-3.53 (m, 1H), 2.97-2.83 (m, 2H), 2.80-2.70 (m, 1H), 2.68-2.60 (m, 1H), 2.55 (s, 1H), 2.47-2.26 (m, 6H), 1.88-1.55 (m, 9H), 1.54-1.46 (m, 1H) (two protons obscured). Analytical LC/MS (Method 1): Purity: 95.3%; Observed Mass: 541.30; Retention Time: 1.02 min. (Method 2): Purity: 97.7%; Observed Mass: 541.30; Retention Time: 1.18 min. Chiral analytical (SFC Method 1): Purity: >95%; Retention Time: 17.28 min. TLR9 $IC_{50}$ (nM)=260.

Example 109 (13 mg, 0.024 mmol, 9% yield) was isolated as the 2$^{nd}$ eluting enantiomer. $^1$H NMR (500 MHz, DMSO-$d_6$) δ 8.22-8.07 (m, 4H), 7.40 (s, 1H), 7.02 (d, J=12.2 Hz, 1H), 4.52 (s, 2H), 4.36 (s, 2H), 3.93 (s, 3H), 3.66-3.54 (m, 1H), 3.37-3.27 (m, 1H), 2.98-2.87 (m, 1H), 2.81-2.72 (m, 1H), 2.70-2.60 (m, 1H), 2.55 (s, 1H), 2.49-2.25 (m, 6H), 1.94-1.57 (m, 9H), 1.55-1.45 (m, 1H) (two protons obscured). Analytical LC/MS (Method 1): Purity: 96.9%; Observed Mass: 541.3; Retention Time: 1.03 min. (Method 2): Purity: 99.3%; Observed Mass: 541.3; Retention Time: 1.18 min. Chiral analytical (SFC Method 1): Purity: >95%; Retention Time: 21.24 min. TLR9 $IC_{50}$ (nM)=90.

Examples 110 and 111

6-(1-(1-cyclobutylazepan-4-yl)piperidin-4-yl)-1,4-dimethyl-2-(4-(methylsulfonyl)phenyl)-1H-benzo[d]imidazole (110-111)

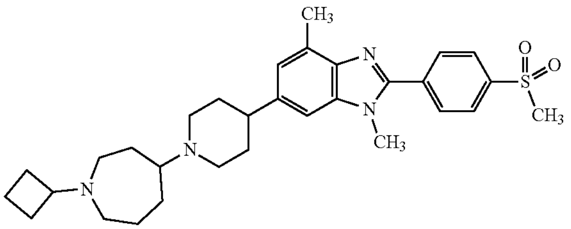

Example 135 (150 mg, 0.27 mmol) was further purified by SFC-chiral chromatography with the following conditions: Instrument: Waters 100 Prep SFC; Column: Chiral AD, 30×250 mm. 5 micron; Mobile Phase: 72% $CO_2$/28% IPA w/0.3% DEA/0.2% FA; Flow Conditions: 100 mL/min.; Detector Wavelength: 220 nm; Injection Details: 500 μL, 90 mg dissolved in 4 mL IPA. Fractions corresponding to the respective desired products were combined and dried via centrifugal evaporation.

Example 110 (14 mg, 0.026 mmol, 10% yield) was isolated as the 1$^{st}$ eluting enantiomer. $^1$H NMR (500 MHz, DMSO-$d_6$) δ 8.16-8.06 (m, 4H), 7.36-7.25 (m, 1H), 7.03-6.96 (m, 1H), 3.90 (s, 3H), 2.94-2.87 (m, 3H), 2.82-2.69 (m, 2H), 2.62-2.53 (m, 8H), 2.47-2.34 (m, 5H), 2.05-1.94 (m, 2H), 1.89-1.43 (m, 13H). Analytical LC/MS (Method 1): Purity: 97.5%; Observed Mass: 535.40; Retention Time: 0.89 min. (Method 2): Purity: 100%; Observed Mass: 535.40; Retention Time: 1.27 min. Chiral analytical (SFC Method 4): Purity: >99%; Retention Time: 35.0 min. TLR9 $IC_{50}$ (nM)=83.

Example 111 (5 mg, 0.0093 mmol, 3% yield) was isolated as the 2$^{nd}$ eluting enantiomer. $^1$H NMR (500 MHz, DMSO-$d_6$) δ 8.14-8.03 (m, 4H), 7.35-7.25 (m, 1H), 7.05-6.96 (m, 1H), 3.88 (br s, 3H), 3.53 (br d, J=3.7 Hz, 2H), 3.50-3.34 (m, 3H), 3.30 (br s, 2H), 2.85 (br d, J=7.9 Hz, 3H), 2.68 (br s, 1H), 2.48 (dt, J=9.1, 4.5 Hz, 1H), 2.42-2.24 (m, 5H), 2.01-1.90 (m, 2H), 1.89-1.39 (m, 14H). Analytical LC/MS (Method 1): Purity: 98.5%; Observed Mass: 535.20; Retention Time: 0.86 min. (Method 2): Purity: 97.7%; Observed Mass: 535.30; Retention Time: 1.19 min. Chiral analytical (SFC Method 4): Purity: >99%; Retention Time: 40.0 min. TLR9 $IC_{50}$ (nM)=24.

Example 112

4-(6-(1'-isopropyl-[1,4'-bipiperidin]-4-yl)-1,4-dimethyl-1H-benzo[d]imidazol-2-yl)benzenesulfonamide (112)

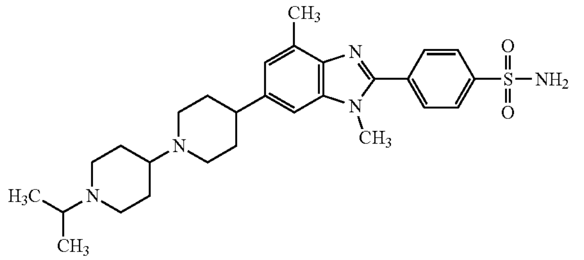

Step A. Intermediate 113A. Preparation of N-benzyl-5-bromo-N,3-dimethyl-2-nitroaniline (112A)

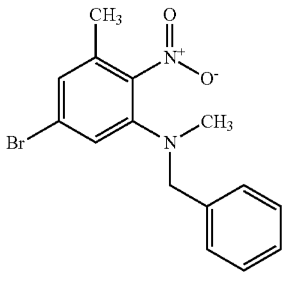

To a 100 mL pear shaped flask were added 5-bromo-1-fluoro-3-methyl-2-nitrobenzene (2.0 g, 8.6 mmol), $K_2CO_3$ (7.1 g, 51 mmol), DMF (15 mL), followed by N-methyl-1-phenylmethanamine (5.5 mL, 43 mmol). The reaction mixture was stirred at 100° C. for under $N_2$. After 24 h, the reaction mixture was cooled, diluted with water (150 mL) and extracted with EtOAc (2×75 mL). The organic phase was combined, washed with brine, dried over $MgSO_4$, filtered and concentrated. The residue was purified by flash column chromatography (120 g silica gel cartridge; A=Hex, B=EtOAc; 30 min grad.; 0% B to 100% B; flow rate=80 mL/min). The pure fractions were combined, concentrated and dried in vacuo to afford the title compound (2.8 g, 8.4 mmol, 98% yield) as a yellow solid. $^1$H NMR (500 MHz, CHLOROFORM-d) δ 7.37-7.31 (m, 2H), 7.30-7.22 (m, 3H), 7.15 (d, J=1.8 Hz, 1H), 7.09-7.03 (m, 1H), 4.14 (s, 2H), 2.68-2.62 (m, 3H), 2.32-2.24 (m, 3H). Analytical LC/MS (Method 4): Observed Mass: 336.9; Retention Time: 2.519 min.

Step B. Intermediate 112B. Preparation of tert-butyl 4-(3-(benzyl(methyl)amino)-5-methyl-4-nitrophenyl)-3,6-dihydropyridine-1(2H)-carboxylate (112B)

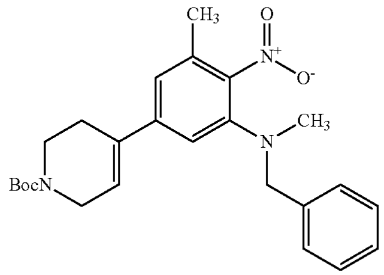

To a 100 mL pear shaped flask were added Intermediate 112A (3.1 g, 9.1 mmol), tert-butyl 4-(4,4,5,5-tetramethyl-1,3,2-dioxaborolan-2-yl)-3,6-dihydropyridine-1(2H)-carboxylate (3.4 g, 11 mmol), 1,4-dioxane (40 mL), followed by potassium phosphate tribasic (6.8 g, 32 mmol) dissolved in water (8 mL). The vessel was flushed with $N_2$, Pd(dppf)$Cl_2$·DCM complex (0.37 g, 0.46 mmol) was added, the vessel flushed again and stirred at 85° C. under $N_2$. After 18 h, the reaction mixture was cooled, diluted with water (100 mL) and extracted with EtOAc (2×50 mL). The organic phase was combined, washed with brine, dried over $MgSO_4$, filtered and concentrated. The residue was purified by flash column chromatography (120 g silica gel cartridge; A=Hex, B=EtOAc; 30 min grad.; 0% B to 100% B; flow rate=80 mL/min). The pure fractions were combined, concentrated and dried in vacuo to afford the title compound (3.8 g, 8.7 mmol, 96% yield) as a pale yellow solid. $^1$H NMR (500 MHz, METHANOL-$d_4$) δ 7.32-7.28 (m, 4H), 7.27-7.22 (m, 1H), 7.21-7.17 (m, 1H), 7.12-7.07 (m, 1H), 6.20-6.07 (m, 1H), 4.16-4.12 (m, 2H), 4.11-4.05 (m, 2H), 3.67-3.60 (m, 2H), 2.65 (s, 3H), 2.55-2.46 (m, 2H), 2.27 (s, 3H), 1.51 (s, 9H). Analytical LC/MS (Method 4): Observed Mass: 438.2; Retention Time: 2.722 min.

Step C. Intermediate 112C. Preparation of tert-butyl 4-(4-amino-3-methyl-5-(methylamino)phenyl)piperidine-1-carboxylate (112C)

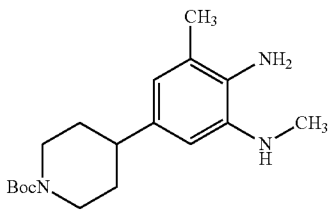

To a 250 mL pressure vessel was added Intermediate 112B (4.0 g, 9.1 mmol), MeOH (50 mL), and Pd—C (5% wt., wet) (2.0 g, 0.91 mmol). The vessel was evacuated and purged with $N_2$ (3×) and stirred under $H_2$ at 50 psi. After 18 h, the reaction mixture was filtered and the filtrate was concentrated. The product was dried in vacuo to afford the title compound (2.9 g, 9.0 mmol, 99% yield) as a tan semisolid. $^1$H NMR (500 MHz, METHANOL-$d_4$) δ 6.43-

6.43 (m, 1H), 6.45-6.40 (m, 1H), 4.26-4.16 (m, 2H), 2.84 (s, 2H), 2.63-2.52 (m, 1H), 2.18 (s, 3H), 1.86-1.75 (m, 2H), 1.63-1.53 (m, 3H), 1.50 (s, 9H), 1.47-1.36 (m, 2H). Analytical LC/MS (Method 4): Observed Mass: 264.0 (–tBu); Retention Time: 1.464 min.

Step D. Intermediate 112D. Preparation of tert-butyl 4-(1,4-dimethyl-2-(4-sulfamoylphenyl)-1H-benzo[d]imidazol-6-yl)piperidine-1-carboxylate (112D)

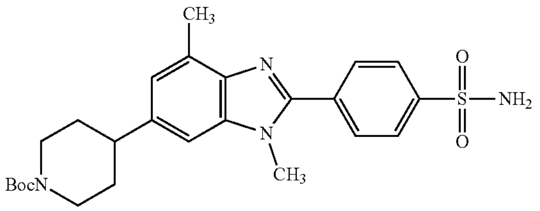

To a 40 mL vial were added Intermediate 112C (0.3 g, 0.94 mmol) and NMP (15 mL). To this mixture was added sodium metabisulfite (0.27 g, 1.4 mmol), followed by 4-formylbenzenesulfonamide (0.19 g, 1.0 mmol). The vessel was capped and the reaction mixture was stirred at 75° C. After 18 h, the reaction mixture was cooled, diluted with water (250 mL), and extracted with EtOAc (2×100 mL). The organic phase was combined, washed with brine, dried over $MgSO_4$, filtered and concentrated. The residue was purified by flash column chromatography (120 g silica gel cartridge; A=DCM, B=MeOH; 30 min grad.; 0% B to 15% B; flow rate=80 mL/min). The fractions corresponding to product were combined, concentrated and dried in vacuo to afford the title compound (0.44 g, 0.91 mmol, 97% yield) as a pale yellow solid. $^1H$ NMR (500 MHz, METHANOL-$d_4$) δ 8.14-8.09 (m, 2H), 8.00-7.95 (m, 2H), 7.32-7.26 (m, 1H), 7.10-7.02 (m, 1H), 4.30-4.23 (m, 2H), 3.89 (s, 3H), 3.01-2.86 (m, 3H), 2.64 (s, 3H), 1.96-1.89 (m, 2H), 1.79-1.67 (m, 2H), 1.51 (s, 9H). Analytical LC/MS (Method 4): Observed Mass: 485.2; Retention Time: 1.444 min.

Step E. Intermediate 112E. Preparation of 4-(1,4-dimethyl-6-(piperidin-4-yl)-1H-benzo[d]imidazol-2-yl)benzenesulfonamide hydrochloride (112E)

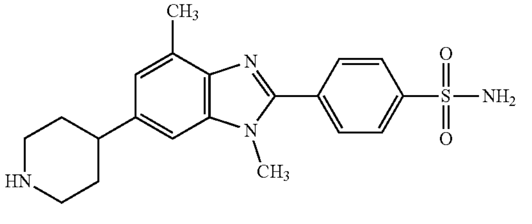

To a 100 mL pear shaped flask were added Intermediate 112D (0.44 g, 0.91 mmol), MeOH (10 mL), and 4 M HCl in dioxane (10 mL). The reaction mixture was stirred for 20 min, the solvent was concentrated and the residue was co-evaporated with toluene (2×). The product was dried in vacuo to afford the title compound (0.38 g, 0. mmol, 99% yield) as a tan solid. Analytical LC/MS (Method 4): Observed Mass: 385.1; Retention Time: 0.751 min.

Step F. Example 112

To a 40 mL vial were added Intermediate 112E (100 mg, 0.24 mmol), 1-isopropylpiperidin-4-one (170 mg, 1.2 mmol), AcOH (15 μL, 0.26 mmol), magnesium sulfate (580 mg, 4.8 mmol), and DMF (2 mL). The reaction mixture was stirred for 10 min, then sodium triacetoxyborohydride (250 mg, 1.2 mmol) was added and the reaction mixture was stirred. After 18 h, the reaction mixture was diluted with 10% IPA/$CHCl_3$ (40 mL) and filtered. The filtrate was partitioned into 10% KOH (sat. with solid NaCl) (20 mL) and the layers were separated. The aqueous phase was extracted with 10% IPA/$CHCl_3$ (10 mL), the organic phase was combined, washed with brine, dried over $MgSO_4$, filtered and concentrated. The crude material was purified by preparative HPLC (Prep Method 1) to afford the title compound to afford the title compound (51 mg, 0.10 mmol, 42% yield). $^1H$ NMR (500 MHz, DMSO-$d_6$) δ 8.06-7.96 (m, 4H), 7.32-7.27 (m, 1H), 7.02-6.95 (m, 1H), 3.06-2.98 (m, 2H), 2.95-2.87 (m, 2H), 2.83-2.74 (m, 1H), 2.67-2.57 (m, 1H), 2.38-2.26 (m, 3H), 2.25-2.18 (m, 2H), 1.92 (br s, 5H), 1.82 (br s, 6H), 1.56-1.44 (m, 2H), 1.00 (d, J=6.4 Hz, 6H) (three protons obscured). Analytical LC/MS (Method 1): Purity: 100%; Observed Mass: 510.30; Retention Time: 0.86 min. (Method 2): Purity: 100%; Observed Mass: 510.20; Retention Time: 1.13 min. TLR9 $IC_{50}$ (nM)=130.

Examples 113 and 114

7-fluoro-6-(1-(1-isopropylazepan-4-yl)piperidin-4-yl)-1-methyl-2-(4-(methylsulfonyl)phenyl)-1H-benzo[d]imidazole (113-114)

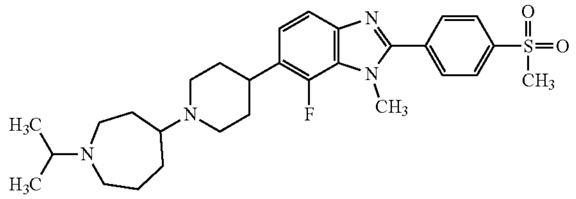

Step A. Intermediate 113A. Preparation of 6-(1-(azepan-4-yl)piperidin-4-yl)-7-fluoro-1-methyl-2-(4-(methylsulfonyl)phenyl)-1H-benzo[d]imidazole dihydrochloride (113A)

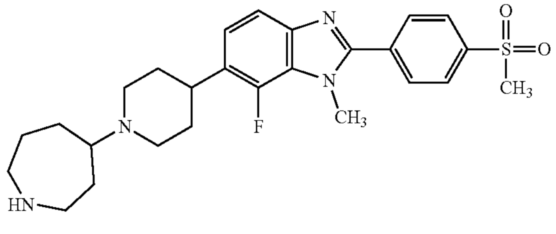

Intermediate 114A was synthesized according to the general procedures described for the preparation of Intermediate 109A, substituting Intermediate 102A (1.4 g, 3.3 mmol) where appropriate to afford the title compound (1.6 g, 2.9 mmol, 87% yield) as a pale yellow solid. Analytical LC/MS (Method 4): Observed Mass: 485.2; Retention Time: 0.887 min.

Step B. Examples 113 and 114

Examples 113 and 114 were synthesized according to the general procedures described for the preparation of Examples 108 and 109 (Step B), using Intermediate 113A (150 mg, 0.27 mmol) as starting material. The crude mixture was purified via preparative HPLC (Prep Method 1). The resultant racemic mixture was further purified by SFC-chiral chromatography with the following conditions: Instrument: Waters 100 Prep SFC; Column: Chiral AD, 30×250 mm. 5 micron; Mobile Phase: 62% $CO_2$/38% IPA w/0.3% DEA/0.2% FA; Flow Conditions: 100 mL/min.; Detector Wavelength: 220 nm; Injection Details: 400 μL, 30 mg dissolved in 2 mL IPA-0.3% DEA/0.2% FA. Fractions corresponding to the respective desired products were combined and dried via centrifugal evaporation.

Example 113 (4.2 mg, 0.0080 mmol, 3% yield) was isolated as the $1^{st}$ eluting enantiomer. $^1$H NMR (500 MHz, DMSO-$d_6$) δ 8.15-8.05 (m, 4H), 7.54-7.48 (m, 1H), 7.23-7.17 (m, 1H), 4.02 (s, 3H), 3.32 (s, 1H), 3.00 (br s, 7H), 2.48-2.32 (m, 3H), 2.04-1.94 (m, 1H), 1.81 (br d, J=1.4 Hz, 10H), 1.33-1.22 (m, 2H), 1.18-1.09 (m, 6H). Analytical LC/MS (Method 1): Purity: 100%; Observed Mass: 527.20; Retention Time: 0.99 min. (Method 2): Purity: 100%; Observed Mass: 527.10; Retention Time: 1.24 min. Chiral analytical (SFC Method 5): Purity: >99%; Retention Time: 15.2 min. TLR9 $IC_{50}$ (nM)=32.

Example 114 (5.8 mg, 0.011 mmol, 4% yield) was isolated as the $2^{nd}$ eluting enantiomer. $^1$H NMR (500 MHz, DMSO-$d_6$) δ 8.41-8.02 (m, 4H), 7.70-7.44 (m, 1H), 7.35-7.07 (m, 1H), 4.03 (br s, 1H), 3.97-3.86 (m, 1H), 3.41-3.27 (m, 1H), 3.25-3.09 (m, 1H), 3.05-2.72 (m, 3H), 2.57-2.39 (m, 12H), 1.99-1.44 (m, 6H), 1.40-0.77 (m, 8H). Analytical LC/MS (Method 1): Purity: 98.6%; Observed Mass: 527.20; Retention Time: 0.91 min. (Method 2): Purity: 97.4%; Observed Mass: 527.30; Retention Time: 1.13 min. Chiral analytical (SFC Method 5): Purity: >95%; Retention Time: 17.13 min. TLR9 $IC_{50}$ (nM)=13.

Example 115

1-cyclopropyl-4-fluoro-6-(1'-isopropyl-[1,4'-bipiperidin]-4-yl)-2-(4-(methylsulfonyl)phenyl)-1H-benzo[d]imidazole (115)

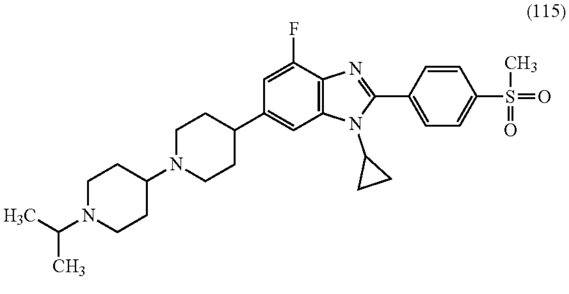 [SMILES: CC(C)N1CCC(N2CCC(c3cc(F)c4nc(-c5ccc(S(C)(=O)=O)cc5)n(C5CC5)c4c3)CC2)CC1]

Step A. Intermediate 115A. Preparation of 5-bromo-N-cyclopropyl-3-fluoro-2-nitroaniline (115A)

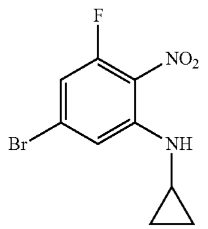

Intermediate 115A was synthesized according to the general procedures described for the preparation of Intermediate 105A, starting with 5-bromo-1,3-difluoro-2-nitrobenzene (8.0 g, 34 mmol), and substituting cyclopropanamine (1.9 g, 34 mmol) where appropriate, to afford the title compound (9.4 g, 34 mmol, 100% yield) as a yellow solid. $^1$H NMR (500 MHz, METHANOL-$d_4$) δ 7.35-7.27 (m, 1H), 6.81-6.75 (m, 1H), 2.61-2.52 (m, 1H), 0.95-0.89 (m, 2H), 0.63 (dt, J=3.4, 1.4 Hz, 2H). Analytical LC/MS (Method): Observed Mass: 276.7; Retention Time: 2.173 min.

Step B. Intermediate 115B. Preparation of 1-cyclopropyl-4-fluoro-2-(4-(methylsulfonyl)phenyl)-6-(piperidin-4-yl)-1H-benzo[d]imidazole hydrochloride (115B)

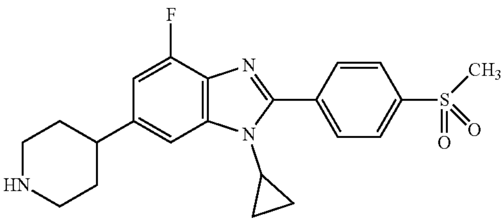

Intermediate 115B was synthesized according to the general procedures described for the preparation of Intermediate 88E (Steps B-E), using Intermediate 115A (3.6 g, 13 mmol) as starting material to afford the title compound (2.2 g, 4.9 mmol, 38% yield over 4 steps) as a pale yellow solid. $^1$H NMR (500 MHz, METHANOL-$d_4$) δ 8.35-8.29 (m, 4H), 7.80-7.78 (m, 1H), 7.48-7.44 (m, 1H), 4.07-3.97 (m, 1H), 3.64-3.57 (m, 3H), 3.29 (s, 3H), 3.28-3.22 (m, 2H), 2.27-2.21 (m, 2H), 2.15-2.08 (m, 2H), 1.38-1.29 (m, 2H), 0.92-0.82 (m, 2H). Analytical LC/MS (Method 4): Observed Mass: 414.1; Retention Time: 1.009 min.

Step C. Example 115

Example 115 was synthesized according to the general procedures described for the preparation of Example 88 (Step F), using Intermediate 115B (75 mg, 0.17 mmol) as starting material. The crude material was purified by preparative HPLC (Prep Method 2) to afford the title compound (33 mg, 0.043 mmol, 25% yield). $^1$H NMR (500 MHz, DMSO-$d_6$) δ 8.29 (d, J=8.5 Hz, 2H), 8.11 (d, J=8.2 Hz, 2H), 7.44-7.34 (m, 1H), 7.06-6.95 (m, 1H), 3.93-3.81 (m, 1H), 3.65-3.37 (m, 2H), 3.33 (s, 1H), 3.06 (br s, 3H), 2.59-2.48 (m, 8H), 2.40-2.30 (m, 2H), 2.21-1.92 (m, 6H), 1.27 (br d, J=6.7 Hz, 6H), 1.16 (br d, J=6.4 Hz, 2H), 0.67 (br s, 2H). Analytical LC/MS (Method 1): Purity: 100%; Observed Mass: 539.20; Retention Time: 0.97 min. (Method 2): Purity: 96.8%; Observed Mass: 539.30; Retention Time: 1.28 min. TLR9 $IC_{50}$ (nM)=24.

Examples 116 and 117

1-cyclopropyl-4-fluoro-6-(1-(8-isopropyl-8-azabicyclo[3.2.1]octan-3-yl)piperidin-4-yl)-2-(4-(methylsulfonyl)phenyl)-1H-benzo[d]imidazole (116-117)

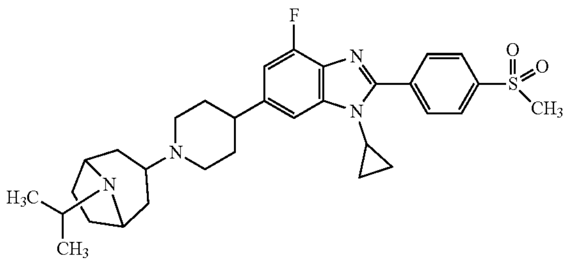

Step A. Intermediate 116A. Preparation of 6-(1-(8-azabicyclo[3.2.1]octan-3-yl) piperidin-4-yl)-1-cyclopropyl-4-fluoro-2-(4-(methylsulfonyl)phenyl)-1H-benzo[d]imidazole dihydrochloride (116A)

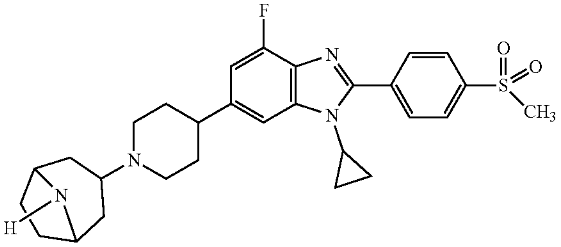

Intermediate 116A was synthesized according to the general procedures described for the preparation of Intermediate 84A, substituting Intermediate 115B (0.68 g, 1.5 mmol) where appropriate to afford the title compound (0.90 g, 1.5 mmol, 100% yield) as a tan solid. $^1$H NMR (500 MHz, METHANOL-$d_4$) δ 8.36-8.27 (m, 4H), 7.85-7.81 (m, 1H), 7.19-7.16 (m, 1H), 4.33-4.26 (m, 1H), 4.25-4.17 (m, 1H), 4.08-3.96 (m, 1H), 3.91-3.79 (m, 3H), 3.72-3.65 (m, 1H), 3.29-3.26 (m, 1H), 3.02-2.90 (m, 1H), 2.52-2.42 (m, 1H), 2.40-2.04 (m, 14H), 1.38-1.30 (m, 2H), 0.93-0.85 (m, 2H). Analytical LC/MS (Method 4): Observed Mass: 523.1; Retention Time: 0.966 min.

Step B. Examples 116 and 117

Examples 116 and 117 were synthesized according to the general procedures described for the preparation of Examples 17 and 18 (Step B), using Intermediate 116A (180 mg, 0.30 mmol) as starting material. The crude isomeric mixture was purified via preparative HPLC with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 3% B, 3-48% B over 20 minutes, then a 0-minute hold at 100% B; Flow Rate: 20 mL/min; Column Temperature: 25° C. Fraction collection was triggered by MS signals. Fractions corresponding to the respective desired products were combined and dried via centrifugal evaporation.

Example 116 (53 mg, 0.094 mmol, 31% yield) was isolated as the $1^{st}$ eluting isomer. $^1$H NMR (500 MHz, DMSO-$d_6$) δ 8.33-8.24 (m, 2H), 8.14-8.06 (m, 2H), 7.38-7.30 (m, 1H), 7.07-6.98 (m, 1H), 3.90-3.80 (m, 1H), 3.33 (s, 1H), 3.05-2.98 (m, 3H), 2.83-2.73 (m, 1H), 2.72-2.57 (m, 2H), 2.18 (br s, 2H), 1.90-1.76 (m, 7H), 1.74-1.60 (m, 4H), 1.54 (br d, J=7.6 Hz, 2H), 1.49-1.39 (m, 2H), 1.16 (br d, J=6.1 Hz, 2H), 1.02 (d, J=5.8 Hz, 6H), 0.65 (br s, 2H). Analytical LC/MS (Method 1): Purity: 97.2%; Observed Mass: 565.60; Retention Time: 1.01 min. (Method 2): Purity: 95.8%; Observed Mass: 565.40; Retention Time: 1.31 min. TLR9 $IC_{50}$ (nM)=51.

Example 117 (26 mg, 0.046 mmol, 15% yield) was isolated as the $2^{nd}$ eluting isomer. $^1$H NMR (500 MHz, DMSO-$d_6$) δ 8.34-8.22 (m, 2H), 8.16-8.05 (m, 2H), 7.41-7.34 (m, 1H), 7.08-7.00 (m, 1H), 4.26-4.05 (m, 2H), 3.93-3.77 (m, 1H), 3.66-3.39 (m, 2H), 3.32 (s, 3H), 3.20-2.91 (m, 1H), 2.72-2.57 (m, 1H), 2.49-2.34 (m, 1H), 2.33-1.90 (m, 10H), 1.32 (br s, 6H), 1.15 (br d, J=6.1 Hz, 3H), 0.66 (br s, 2H) (three protons obscured). Analytical LC/MS (Method 1): Purity: 94.8%; Observed Mass: 565.30; Retention Time: 1.05 min. (Method 2): Purity: 96.2%; Observed Mass: 565.30; Retention Time: 1.53 min. TLR9 $IC_{50}$ (nM)=71.

Example 118

6-(1-(8-isobutyl-8-azabicyclo[3.2.1]octan-3-yl)piperidin-4-yl)-1,4-dimethyl-2-(4-(methylsulfonyl)phenyl)-1H-benzo[d]imidazole (118)

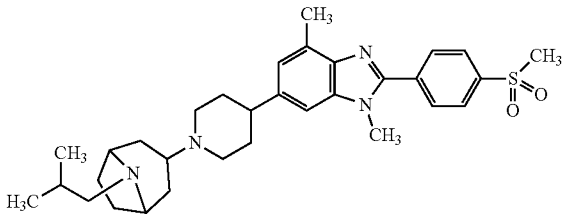

To a solution of $NaBH_3CN$ (50 mg, 0.78 mmol) in methanol (2 mL) was added a solution of $ZnCl_2$ (0.5 M in THF) (0.13 mL, 0.26 mmol), Intermediate 22C (free amine form) (100 mg, 0.26 mmol) and 8-isobutyl-8-azabicyclo[3.2.1]octan-3-one (140 mg, 0.78 mmol) in sequence. The resulting suspension was stirred at 60° C. for 8 hours. The reaction mixture was purified by preparative HPLC (Prep Method 3) to afford the title compound (27 mg, 0.048 mmol, 18% yield) as a white solid. $^1$H NMR (300 MHz, DMSO-$d_6$) δ 8.16-8.04 (m, 4H), 7.30 (s, 1H), 6.97 (s, 1H), 3.88 (s, 3H), 3.31-3.29 (m, 2H), 3.22-3.10 (m, 3H), 3.07-2.95 (m, 2H), 2.59-2.51 (m, 5H), 2.24-2.04 (m, 4H), 1.87-1.44 (m, 13H), 0.87 (d, J=5.4 Hz, 6H). Analytical LC/MS (Method 6):

Purity: 96.5%; Observed Mass: 549.4; Retention Time: 2.368 min. TLR9 $IC_{50}$ (nM)=120.

Example 119

6-(1'-isopropyl-[1,4'-bipiperidin]-4-yl)-1,7-dimethyl-2-(4-(methylsulfonyl)phenyl)-1H-benzo[d]imidazole (119)

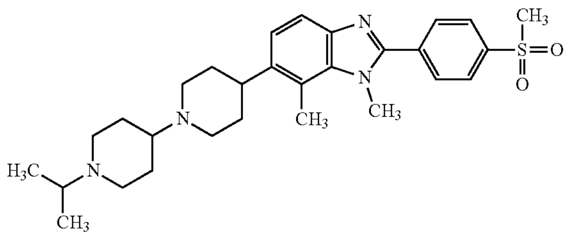

Step A. Intermediate 119A. Preparation of 1,7-dimethyl-2-(4-(methylsulfonyl)phenyl)-6-(piperidin-4-yl)-1H-benzo[d]imidazole (119A)

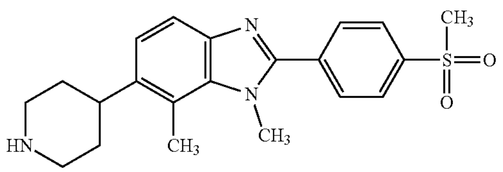

Intermediate 119A was synthesized according to the general procedures described for the preparation of Intermediate 88E (Steps A-E), using 1-bromo-3-fluoro-2-methyl-4-nitrobenzene as starting material. Analytical LC/MS (Method 7): Observed Mass: 384.1; Retention Time: 0.613 min.

Step B. Example 119

To a solution of $ZnCl_2$ (2 M solution in THF) (0.1 mL) in methanol (2 mL) was added $NaBH_3CN$ (50 mg, 0.78 mmol). The resulting mixture was stirred at room temperature for 10 min., then Intermediate 119A (60 mg, 0.16 mmol) and 1-isopropylpiperidin-4-one (110.5 mg, 0.78 mmol) were added. After stirring the mixture at 60° C. for 2 h, the crude material was purified by preparative HPLC (Prep Method 3) to afford the title compound (22 mg, 27% yield) as a white solid. $^1$H NMR (300 MHz, Chloroform-d) δ 8.12 (d, J=6.9 Hz, 2H), 7.95 (d, J=6.9 Hz, 2H), 7.65 (d, J=8.5 Hz, 1H), 7.31 (d, J=8.5 Hz, 1H), 4.08 (s, 3H), 3.19-3.00 (m, 7H), 2.95-2.86 (m, 2H), 2.78 (s, 3H), 2.47 (s, 3H), 2.35-2.10 (m, 2H), 2.01-1.77 (m, 8H), 1.13 (s, 6H). Analytical LC/MS (Method 6): Purity: 97.9%; Observed Mass: 509.2; Retention Time: 0.562 min. TLR9 $IC_{50}$ (nM)=1100.

Example 120

6-(1'-isopropyl-[1,4'-bipiperidin]-4-yl)-1,5-dimethyl-2-(4-(methylsulfonyl)phenyl)-1H-benzo[d]imidazole (120)

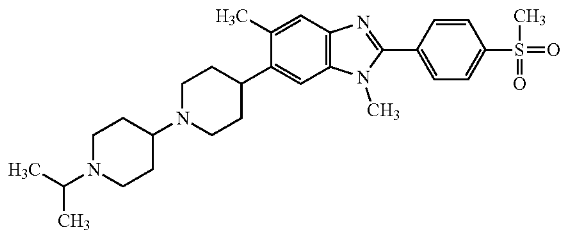

Step A. Intermediate 119A. Preparation of 1,5-dimethyl-2-(4-(methylsulfonyl)phenyl)-6-(piperidin-4-yl)-1H-benzo[d]imidazole (120A)

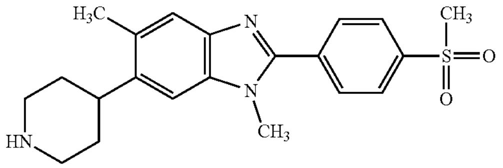

Intermediate 120A was synthesized according to the general procedures described for the preparation of Intermediate 88E (Steps A-E), using 1-bromo-5-fluoro-2-methyl-4-nitrobenzene as starting material. Analytical LC/MS (Method 7): Observed Mass: 384.2; Retention Time: 0.584 min.

Step B. Example 120

Example 120 was synthesized according to the general procedures described for the preparation of Example 119, using Intermediate 120A (100 mg, 0.26 mmol) as starting material. The crude material was purified by preparative HPLC (Prep Method 3) to afford the title compound (51 mg, 37% yield) as a white solid. $^1$H NMR (400 MHz, DMSO-$d_6$) δ 8.15-8.05 (m, 4H), 7.49 (d, J=15.1 Hz, 2H), 3.91 (s, 3H), 3.31 (s, 3H), 3.00 (dd, J=10.7, 3.6 Hz, 2H), 2.82 (dd, J=8.6, 5.9 Hz, 2H), 2.79-2.62 (m, 2H), 2.42 (s, 3H), 2.37-2.15 (m, 3H), 2.08 (t, J=11.5, 2.2 Hz, 2H), 1.85-1.71 (m, 6H), 1.51-1.35 (m, 2H), 0.95 (d, J=6.6 Hz, 6H). Analytical LC/MS (Method 6): Purity: 95.6%; Observed Mass: 509.2; Retention Time: 0.57 min. TLR9 $IC_{50}$ (nM)=180.

Example 121

6-(1-(8-isobutyl-8-azabicyclo[3.2.1]octan-3-yl)piperidin-4-yl)-4-methyl-2-(4-(methylsulfonyl)phenyl)-1H-benzo[d]imidazole (121)

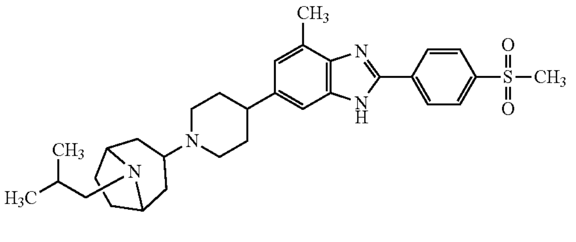

Step A. Intermediate 121A. Preparation of 4-methyl-2-(4-(methylsulfonyl)phenyl)-6-(piperidin-4-yl)-1H-benzo[d]imidazole (121A)

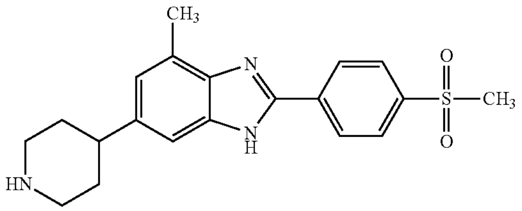

Intermediate 121A was synthesized according to the general procedures described for the preparation of Intermediate 11D (Steps A-E), substituting 4-methylsulfonylbenzaldehyde where appropriate. Analytical LC/MS (Method 8): Observed Mass: 370.1; Retention Time: 0.873 min.

Step B. Example 121

Example 121 was synthesized according to the general procedures described for the preparation of Example 118, using Intermediate 121A (100 mg, 0.27 mmol) as starting material. The crude material was purified by preparative HPLC (Prep Method 3) to afford the title compound (65 mg, 0.11 mmol, 43% yield) as a white solid. $^1H$ NMR (400 MHz, Methanol-$d_4$) δ 8.37 (d, J=8.4 Hz, 1H), 8.13 (d, J=8.4 Hz, 1H), 7.34 (s, 1H), 7.04 (s, 1H), 3.34-3.38 (m, 2H), 3.23-3.14 (m, 5H), 2.72-2.60 (m, 5H), 2.33-2.24 (m, 4H), 2.04-1.69 (m, 11H), 1.68-1.61 (m, 2H), 0.98 (d, J=5.4 Hz, 6H) (two protons obscured). Analytical LC/MS (Method 6): Purity: 96.7%; Observed Mass: 535.2; Retention Time: 2.41 min. TLR9 $IC_{50}$ (nM)=19.

Example 122

2-(3-fluoro-4-(methylsulfonyl)phenyl)-6-(1'-isopropyl-[1,4'-bipiperidin]-4-yl)-1,4-dimethyl-1H-benzo[d]imidazole (122)

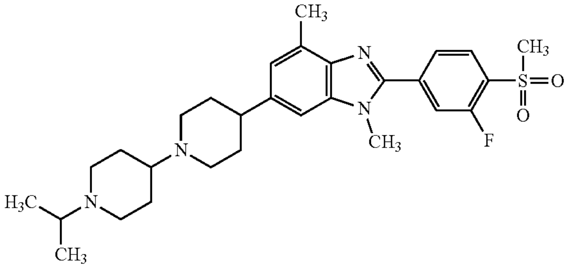

Step A. Intermediate 122A. Preparation of 2-(3-fluoro-4-(methylsulfonyl)phenyl)-1,4-dimethyl-6-(piperidin-4-yl)-1H-benzo[d]imidazole (122A)

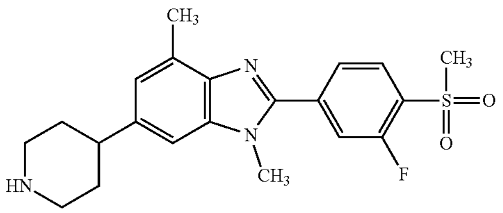

Intermediate 122A was synthesized according to the general procedures described for the preparation of Intermediate 112E (Step D-E), substituting 3-fluoro-4-(methylsulfonyl)benzaldehyde where appropriate. Analytical LC/MS (Method 7): Observed Mass: 402.2; Retention Time: 0.442 min.

Step B. Example 122

Example 121 was synthesized according to the general procedures described for the preparation of Example 119, using Intermediate 122A (100 mg, 0.25 mmol) as starting material. The crude material was purified by preparative HPLC (Prep Method 3) to afford the title compound (19 mg, 0.036, 14% yield) as a white solid. $^1H$ NMR (400 MHz, Methanol-$d_4$) δ 8.19-8.11 (m, 1H), 7.93-7.85 (m, 2H), 7.30 (s, 1H), 7.09 (s, 1H), 3.93 (s, 3H), 3.36 (s, 3H), 3.24-3.12 (m, 4H), 2.95-2.87 (m, 1H), 2.80-2.70 (m, 1H), 2.64 (s, 3H), 2.54-2.38 (m, 5H), 2.06-1.83 (m, 6H), 1.74-1.65 (m, 2H), 1.17 (d, J=6.6 Hz, 6H). Analytical LC/MS (Method 6): Purity: 97.2%; Observed Mass: 527.1; Retention Time: 1.387 min. TLR9 $IC_{50}$ (nM)=140.

Examples 123 and 124

6-(1-(8-cyclobutyl-8-azabicyclo[3.2.1]octan-3-yl) piperidin-4-yl)-2-(3-fluoro-4-(methylsulfonyl)phenyl)-1,4-dimethyl-1H-benzo[d]imidazole (123-124)

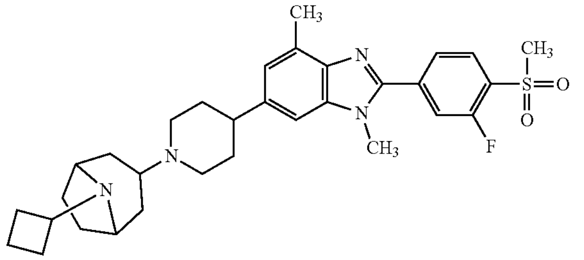

Step A. Intermediate 123A. Preparation of 6-(1-(8-azabicyclo[3.2.1]octan-3-yl) piperidin-4-yl)-2-(3-fluoro-4-(methylsulfonyl)phenyl)-1,4-dimethyl-1H-benzo[d]imidazole (123A)

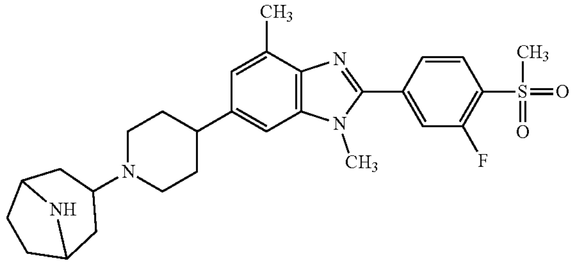

Intermediate 123A was synthesized according to the general procedures described for the preparation of Intermediate 84A, substituting Intermediate 122A to afford the title compound. Analytical LC/MS (Method 8): Observed Mass: 511.3; Retention Time: 0.590 min.

Step B. Examples 123 and 124

To a mixture of Intermediate 123A (100 mg, 0.20 mmol) and cyclobutanone (100 mg, 1.4 mmol) in methanol (5 mL) was added AcOH (0.20 mL, 3.5 mmol). After stirring 0.5 h, $NaBH_3CN$ (150 mg, 2.3 mmol) was added and the reaction mixture was stirred under $N_2$. After 18 h, the crude reaction mixture was purified by preparative HPLC (Prep Method 3) to afford the title compounds.

Example 123 (1.3 mg, 1% yield) was isolated as a white solid and was the 1st eluting isomer. $^1H$ NMR (400 MHz, Methanol-$d_4$) δ 8.03 (dd, J=8.3, 7.2 Hz, 1H), 7.77-7.75 (m, 2H), 7.17 (s, 1H), 6.96 (s, 1H), 3.81 (s, 3H), 3.38 (s, 3H), 3.34-3.20 (m, 4H), 3.06-3.03 (m, 1H), 2.60-2.58 (m, 1H), 2.56 (s, 3H), 2.45-2.43 (m, 1H), 2.05-1.53 (m, 20H). Analytical LC/MS (Method 6): Purity: 92.7%; Observed Mass: 565.3; Retention Time: 0.869 min. TLR9 $IC_{50}$ (nM)=890.

Example 124 (9.1 mg, 8% yield) was isolated as a white solid and was the $2^{nd}$ eluting isomer. $^1H$ NMR (400 MHz, Methanol-$d_4$) δ 8.03 (dd, J=8.3, 7.2 Hz, 1H), 7.78-7.74 (m, 2H), 7.17 (s, 1H), 6.96 (s, 1H), 3.81 (s, 3H), 3.23 (s, 3H), 3.21-3.20 (m, 2H), 3.18-3.12 (m, 1H), 3.02 (d, J=11.3 Hz, 2H), 2.65-2.58 (m, 2H), 2.52 (s, 3H), 2.27-2.22 (m, 2H), 2.00-1.96 (m, 2H), 1.90-1.80 (m, 6H), 1.77-1.54 (m, 10H). Analytical LC/MS (Method 6): Purity: 96.2%; Observed Mass: 565.3; Retention Time: 0.882 min. TLR9 $IC_{50}$ (nM)=580.

Example 125

6-(6-(1'-isopropyl-[1,4'-bipiperidin]-4-yl)-1,4-dimethyl-1H-benzo[d]imidazol-2-yl)-8-methoxy-[1,2,4]triazolo[1,5-a]pyridine (125)

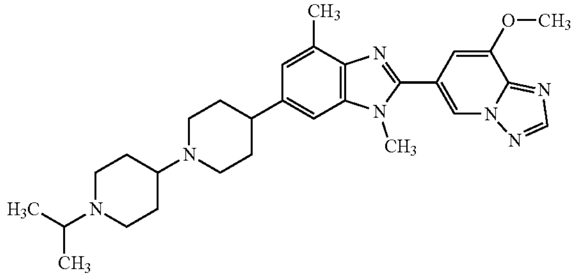

Step A. Intermediate 125A. Preparation of 6-(1,4-dimethyl-6-(piperidin-4-yl)-1H-benzo[d]imidazol-2-yl)-8-methoxy-[1,2,4]triazolo[1,5-a]pyridine (125A)

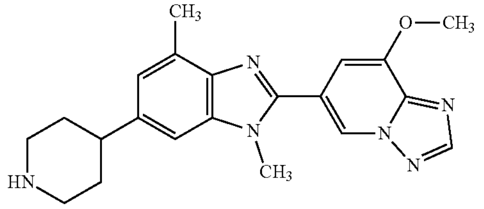

Intermediate 124A was synthesized according to the general procedures described for the preparation of Intermediate 112E (Step D-E), substituting 8-methoxy-[1,2,4]triazolo[1,5-a]pyridine-6-carbaldehyde where appropriate. Analytical LC/MS (Method 8): Observed Mass: 377.2; Retention Time: 0.485 min.

Step B. Example 125

Example 125 was synthesized according to the general procedures described for the preparation of Example 119, using Intermediate 125A (60 mg, 0.16 mmol) as starting material. The crude material was purified by preparative HPLC (Prep Method 3) to afford the title compound (35 mg, 0.069 mmol, 43% yield) as a white solid. $^1H$ NMR (300 MHz, Methanol-$d_4$) δ 8.87 (s, 1H), 8.49 (s, 1H), 7.54 (s, 1H), 7.31 (s, 1H), 7.09 (s, 1H), 4.15 (s, 3H), 3.95 (s, 3H), 3.22-3.12 (m, 2H), 3.10-3.01 (m, 2H), 2.80-2.71 (m, 2H), 2.63 (s, 3H), 2.47-2.37 (m, 3H), 2.30-2.24 (m, 2H), 2.03-1.86 (m, 6H), 1.72-1.62 (m, 2H), 1.11 (d, J=8.4 Hz, 6H).

Analytical LC/MS (Method 6): Purity: 98.2%; Observed Mass: 502.1; Retention Time: 0.909 min. TLR9 $IC_{50}$ (nM)=28.

Example 126

6-(6-(1-(8-isobutyl-8-azabicyclo[3.2.1]octan-3-yl)piperidin-4-yl)-1,4-dimethyl-1H-benzo[d]imidazol-2-yl)-8-methoxy-[1,2,4]triazolo[1,5-a]pyridine (126)

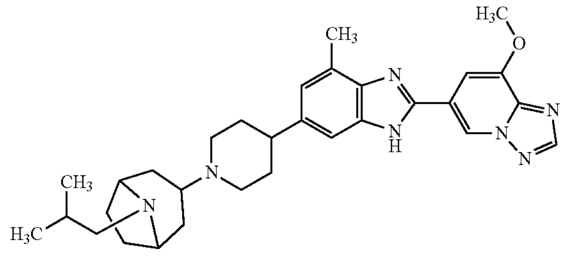

Example 126 was synthesized according to the general procedures described for the preparation of Example 118, using Intermediate 125A (80 mg, 0.21 mmol) as starting material. The crude material was purified by preparative PLC (Prep Method 3) to afford the title compound (21 mg, 0.037 mmol, 17% yield) as a white solid. $^1H$ NMR (300 MHz, Methanol-$d_4$) δ 8.88 (s, 1H), 8.48 (s, 1H), 7.48 (s, 1H), 7.29 (s, 1H), 7.07 (s, 1H), 4.17 (s, 3H), 3.96 (s, 3H), 3.34-3.32 (m, 2H), 3.23-3.14 (m, 2H), 2.78-2.60 (m, 5H), 2.35-2.23 (m, 4H), 2.07-1.56 (m, 13H), 0.96 (d, J=6.9 Hz, 6H). Analytical LC/MS (Method 6): Purity: 97.8%; Observed Mass: 542.3; Retention Time: 0.596 min TLR9 $IC_{50}$ (nM)=590.

The following Examples were prepared according to the general methods described elsewhere herein using appropriate starting materials, reagents and conditions.

| Ex. No. | Structure | Method |
|---|---|---|
| 127 | 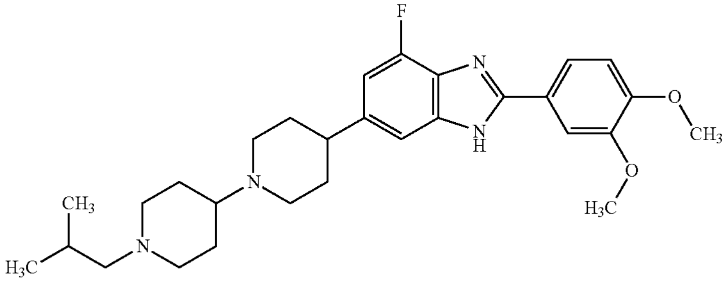 [SMILES: COc1ccc(-c2nc3c(F)cc(C4CCN(C5CCN(CC(C)C)CC5)CC4)cc3[nH]2)cc1OC] | Ex. 83 |
| 128 | 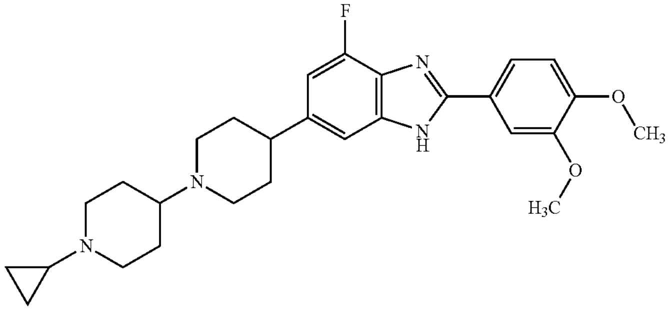 [SMILES: COc1ccc(-c2nc3c(F)cc(C4CCN(C5CCN(C6CC6)CC5)CC4)cc3[nH]2)cc1OC] | Ex. 83 |
| 129 | 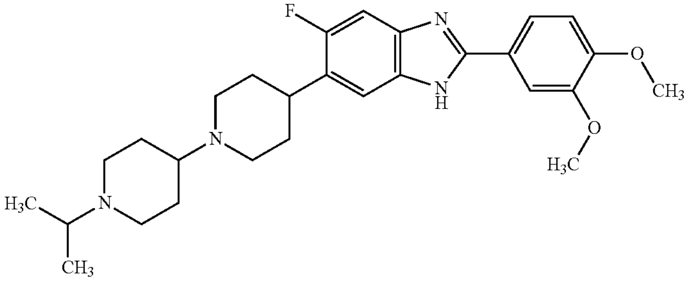 [SMILES: COc1ccc(-c2nc3cc(F)c(C4CCN(C5CCN(C(C)C)CC5)CC4)cc3[nH]2)cc1OC] | Ex. 83 |

-continued
| Ex. No. | Structure | Method |
| --- | --- | --- |
| 130 | 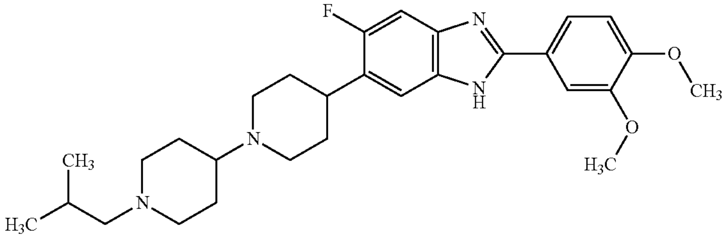 [SMILES: COc1ccc(-c2nc3cc(F)c(C4CCN(C5CCN(CC(C)C)CC5)CC4)cc3[nH]2)cc1OC] | Ex. 83 |
| 131 | 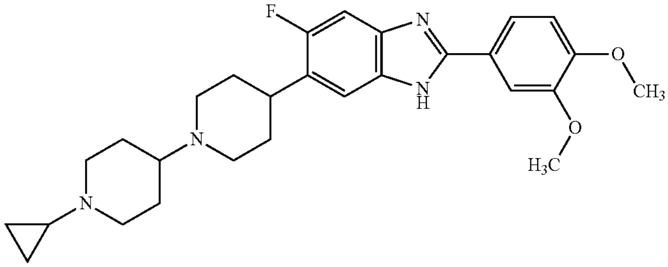 [SMILES: COc1ccc(-c2nc3cc(F)c(C4CCN(C5CCN(C6CC6)CC5)CC4)cc3[nH]2)cc1OC] | Ex. 83 |
| 132 | 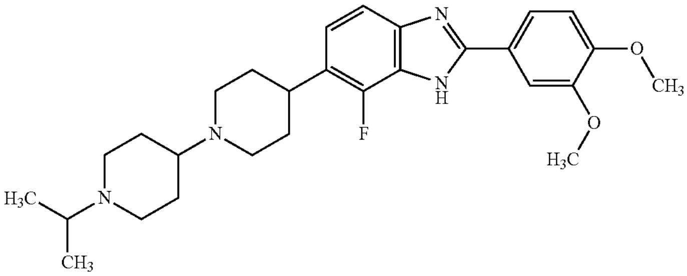 [SMILES: COc1ccc(-c2nc3ccc(C4CCN(C5CCN(C(C)C)CC5)CC4)c(F)c3[nH]2)cc1OC] | Ex. 83 |
| 133 | 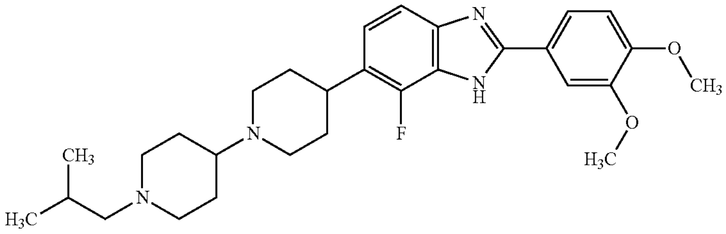 [SMILES: COc1ccc(-c2nc3ccc(C4CCN(C5CCN(CC(C)C)CC5)CC4)c(F)c3[nH]2)cc1OC] | Ex. 83 |
| 134 | 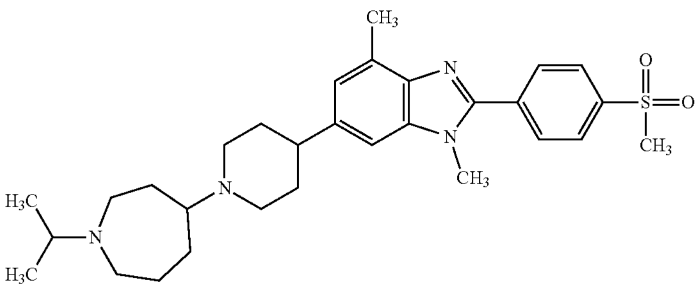 [SMILES: Cc1cc(C2CCN(C3CCCN(C(C)C)CC3)CC2)cc2c1nc(-c1ccc(S(C)(=O)=O)cc1)n2C] | Ex. 22 |

-continued
| Ex. No. | Structure | Method |
|---|---|---|
| 135 | 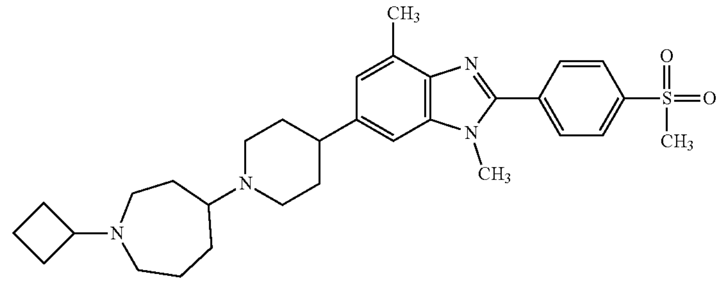 [SMILES: Cc1cc(C2CCN(C3CCCN(C4CCC4)CC3)CC2)cc2c1nc(-c1ccc(S(C)(=O)=O)cc1)n2C] | Ex. 22 |
| 136 | 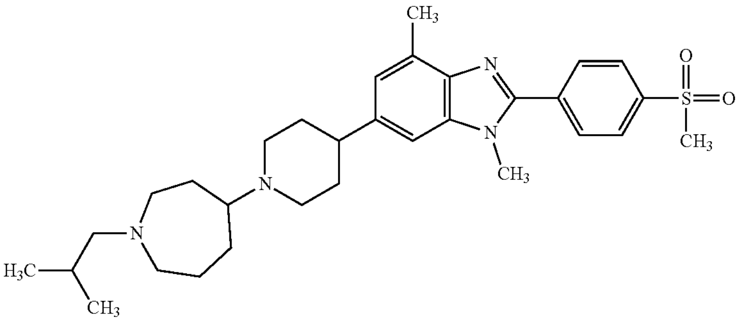 [SMILES: Cc1cc(C2CCN(C3CCCN(CC(C)C)CC3)CC2)cc2c1nc(-c1ccc(S(C)(=O)=O)cc1)n2C] | Ex. 22 |
| 137 | 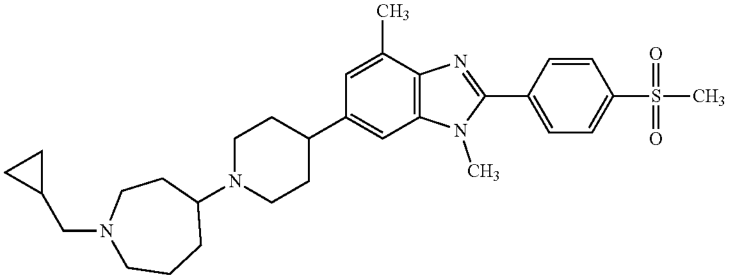 [SMILES: Cc1cc(C2CCN(C3CCCN(CC4CC4)CC3)CC2)cc2c1nc(-c1ccc(S(C)(=O)=O)cc1)n2C] | Ex. 22 |
| 138 | 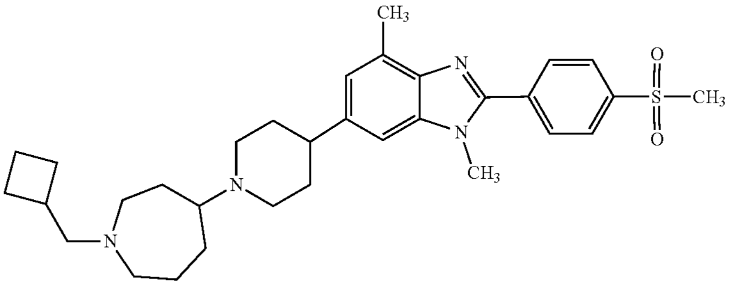 | Ex. 22 |
| 139 | 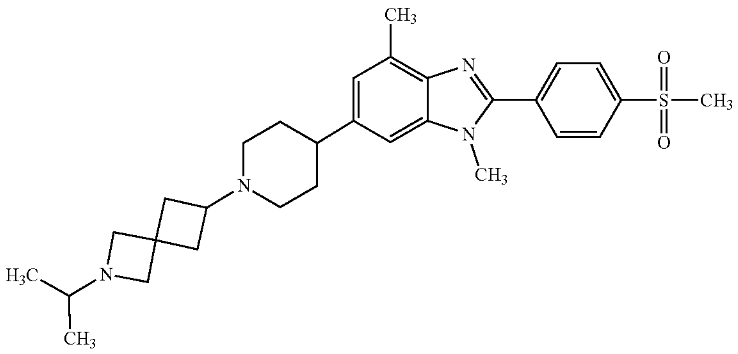 | Ex. 22 |

-continued
| Ex. No. | Structure | Method |
|---|---|---|
| 140 | 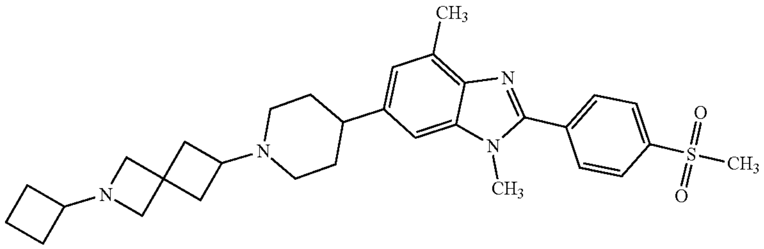 [SMILES: Cc1cc(C2CCN(C3CC4(C3)CN(C3CCC3)C4)CC2)cc2c1nc(-c1ccc(S(C)(=O)=O)cc1)n2C] | Ex. 22 |
| 141 | 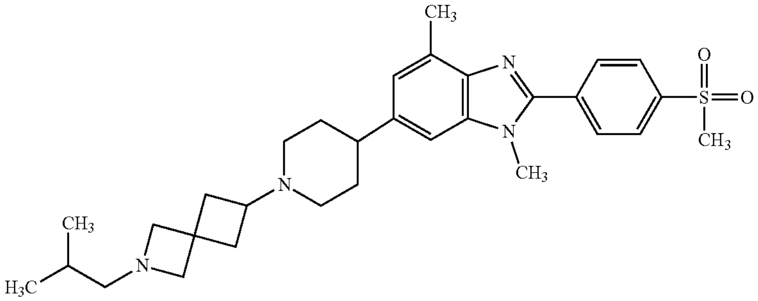 | Ex. 22 |
| 142 | 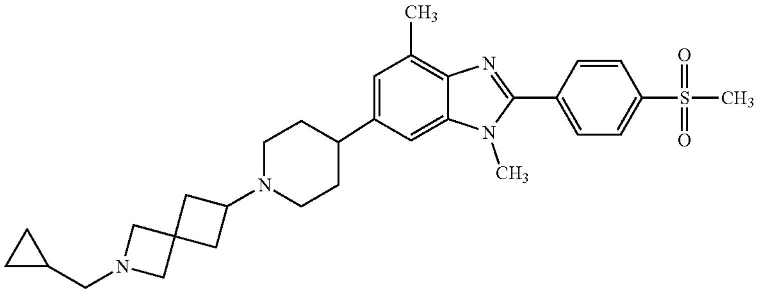 | Ex. 22 |
| 143 | 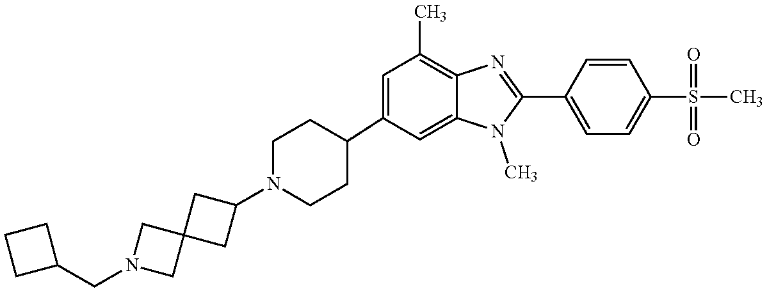 | Ex. 22 |
| 144 | 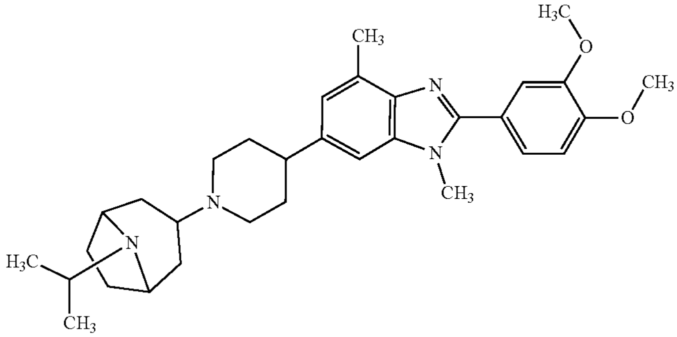 1$^{st}$ eluting isomer | Ex. 17 |

-continued
| Ex. No. | Structure | Method |
|---|---|---|
| 145 | 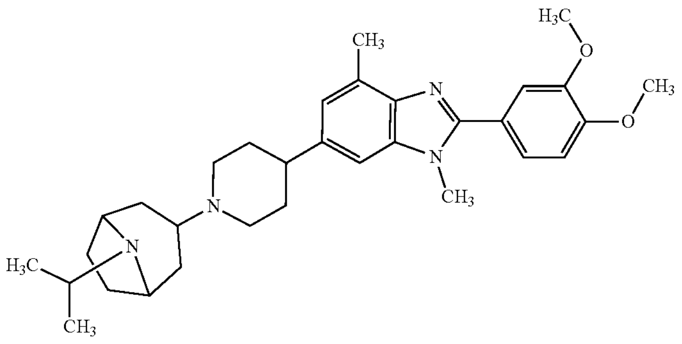 2nd eluting isomer | Ex. 17 |
| 146 | 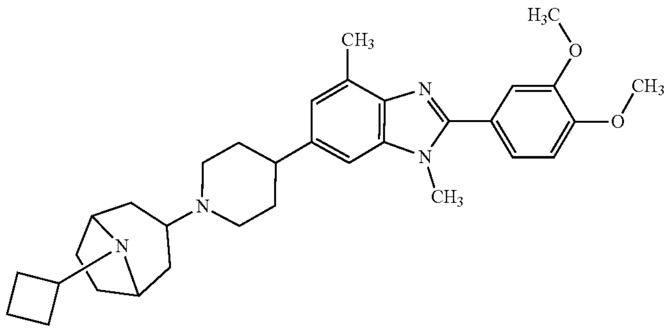 1st eluting isomer | Ex. 17 |
| 147 | 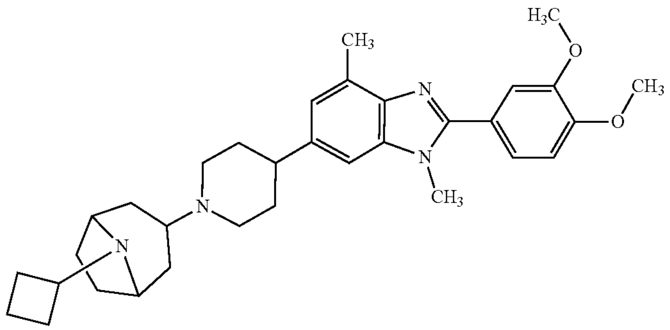 2nd eluting isomer | Ex. 17 |
| 148 | 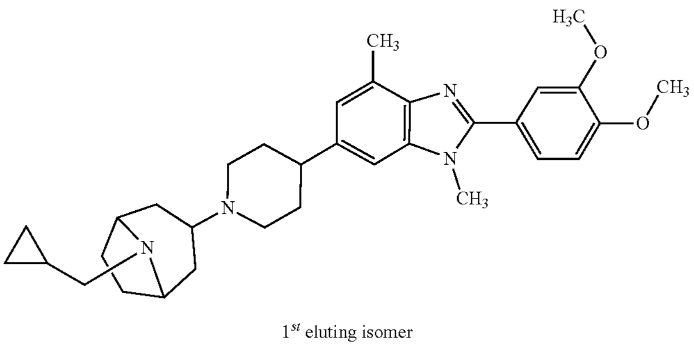 [SMILES: COc1ccc(-c2nc3c(C)cc(C4CCN(C5CC6CCC(C5)N6CC5CC5)CC4)cc3n2C)cc1OC] 1st eluting isomer | Ex. 17 |

-continued
| Ex. No. | Structure | Method |
|---|---|---|
| 149 | 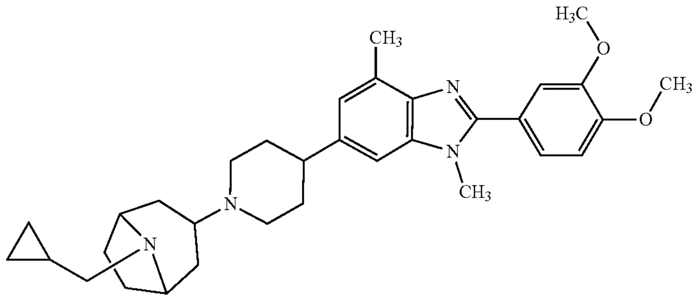 2nd eluting isomer | Ex. 17 |
| 150 | 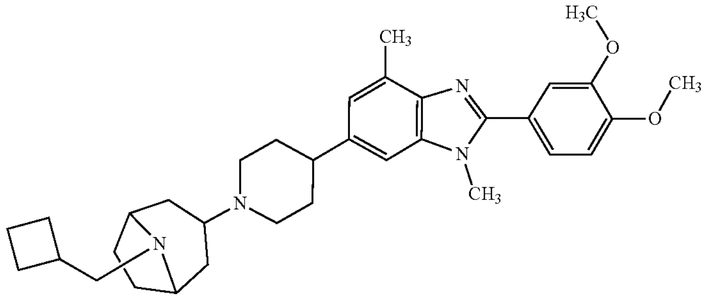 1st eluting isomer | Ex. 17 |
| 151 | 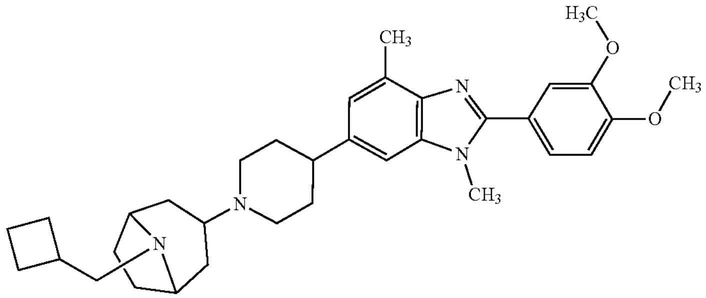 2nd eluting isomer | Ex. 17 |
| 152 | 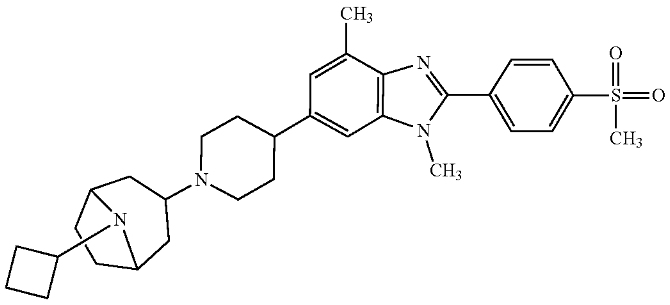 1st eluting isomer | Ex. 84 |

-continued
| Ex. No. | Structure | Method |
| --- | --- | --- |
| 153 | 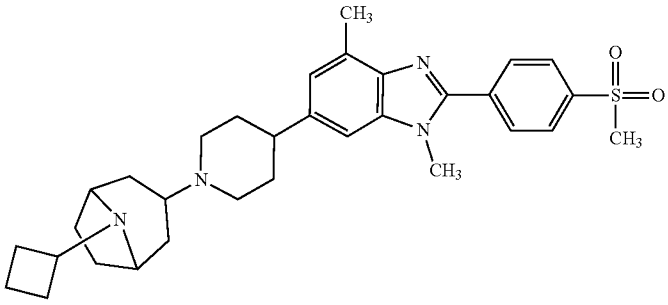 2nd eluting isomer | Ex. 84 |
| 154 | 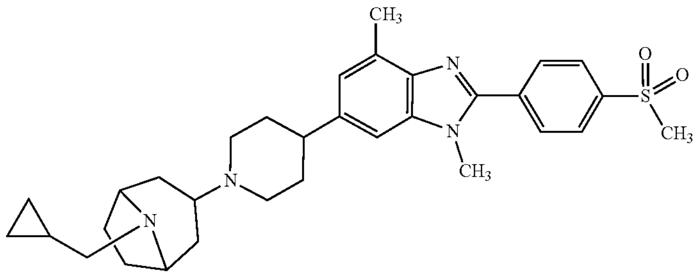 1st eluting isomer | Ex. 84 |
| 155 | 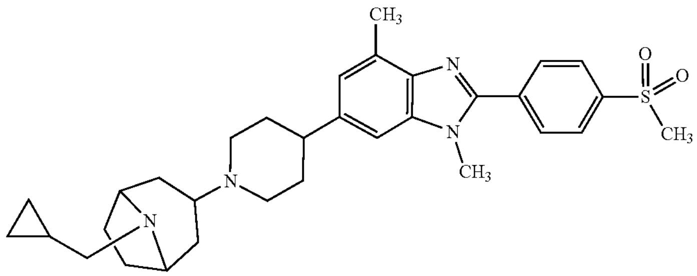 2nd eluting isomer | Ex. 84 |
| 156 | 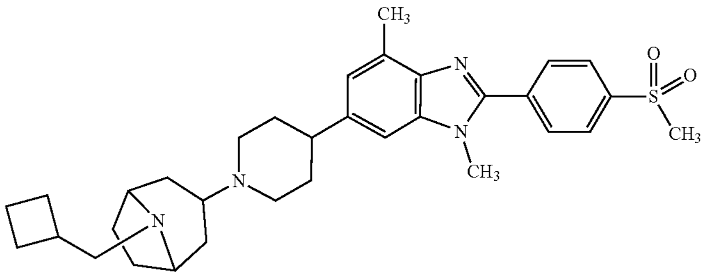 1st eluting isomer | Ex. 84 |

-continued
| Ex. No. | Structure | Method |
|---|---|---|
| 157 | 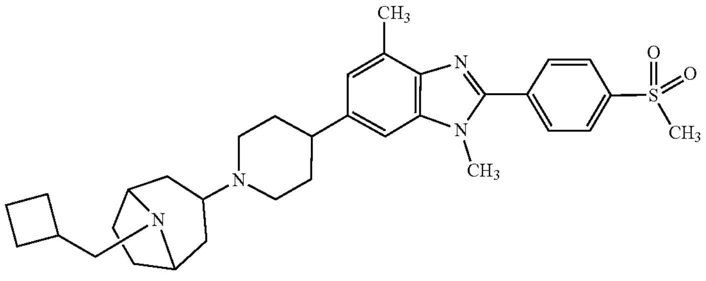 2nd eluting isomer | Ex. 84 |
| 158 | 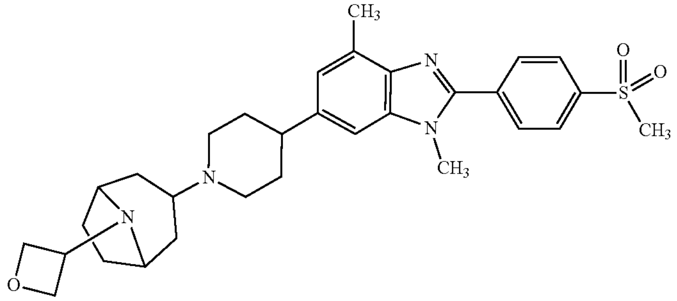 1st eluting isomer | Ex. 84 |
| 159 | 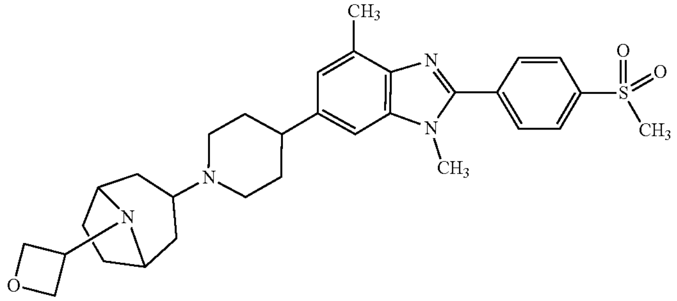 2nd eluting isomer | Ex. 84 |
| 160 | 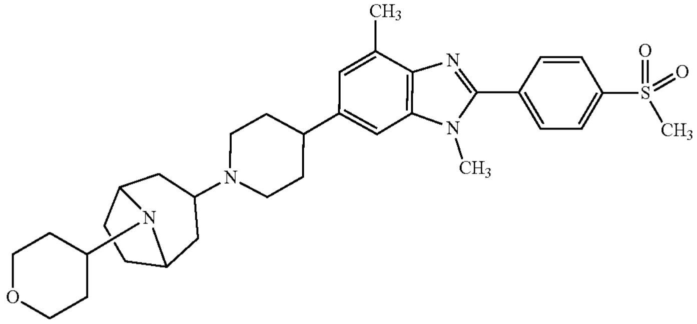 1st eluting isomer | Ex. 84 |

-continued
| Ex. No. | Structure | Method |
|---|---|---|
| 161 | 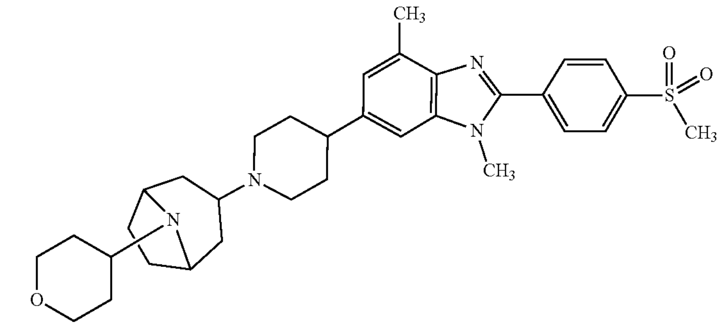 2nd eluting isomer | Ex. 84 |
| 162 | 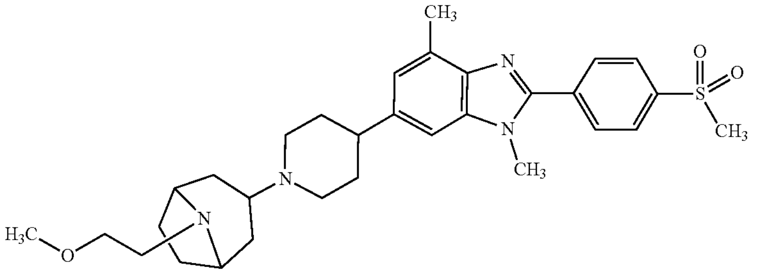 1st eluting isomer | Ex. 84 |
| 163 | 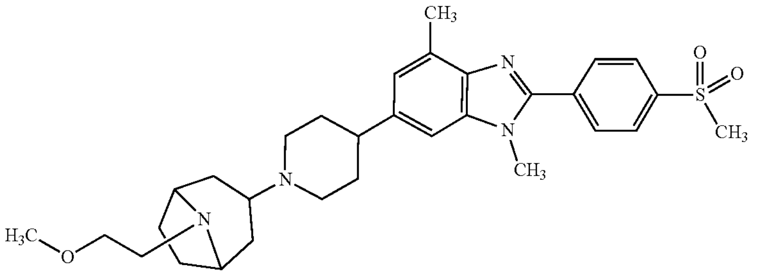 2nd eluting isomer | Ex. 84 |
| 164 | 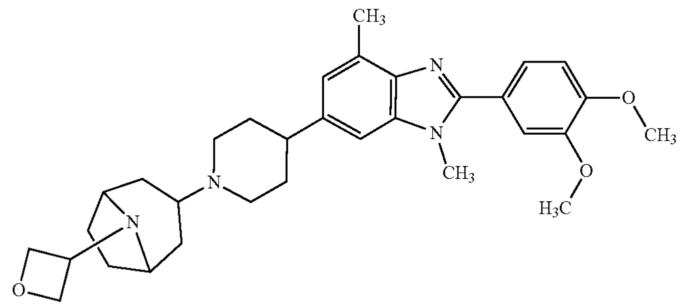 1st eluting isomer | Ex. 17 |

-continued
| Ex. No. | Structure | Method |
|---|---|---|
| 165 | 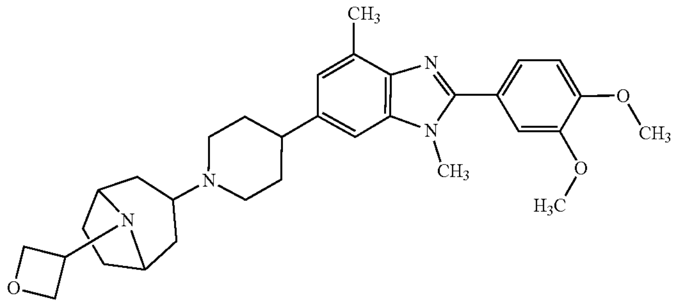<br>2nd eluting isomer | Ex. 17 |
| 166 | 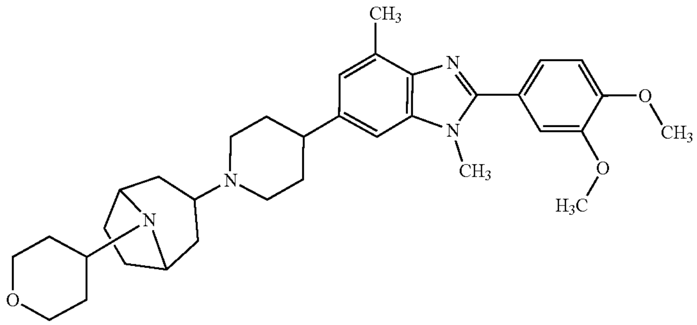<br>1st eluting isomer | Ex. 17 |
| 167 | 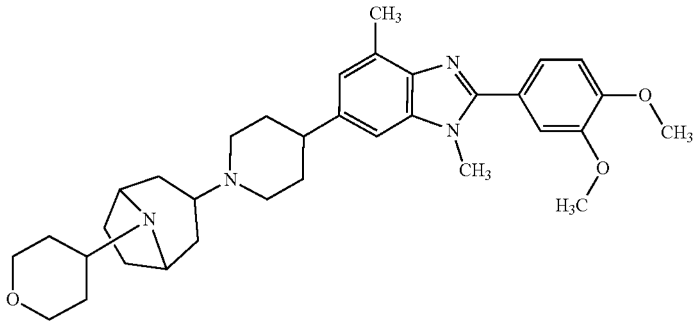<br>2nd eluting isomer | Ex. 17 |
| 168 | 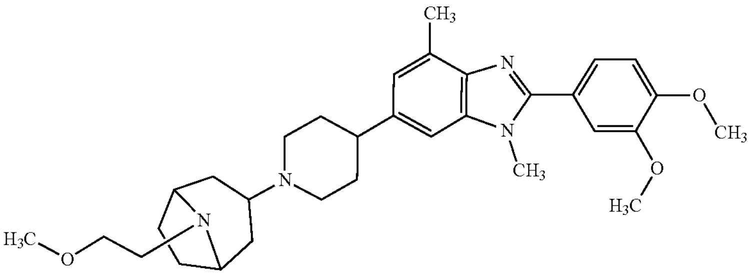<br>1st eluting isomer | Ex. 17 |

-continued
| Ex. No. | Structure | Method |
|---|---|---|
| 169 | 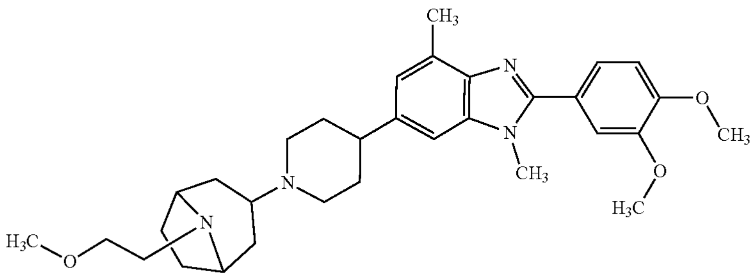 2nd eluting isomer | Ex. 17 |
| 170 | 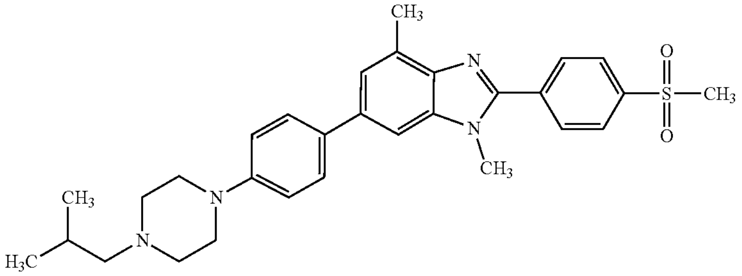 [SMILES: Cc1cc(-c2ccc(N3CCN(CC(C)C)CC3)cc2)cc2c1nc(-c1ccc(S(C)(=O)=O)cc1)n2C] | Ex. 86 |
| 171 | 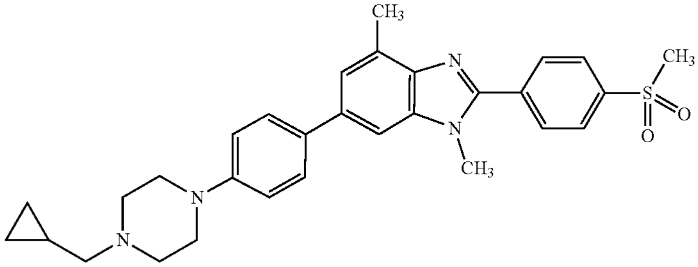 [SMILES: Cc1cc(-c2ccc(N3CCN(CC4CC4)CC3)cc2)cc2c1nc(-c1ccc(S(C)(=O)=O)cc1)n2C] | Ex. 86 |
| 172 | 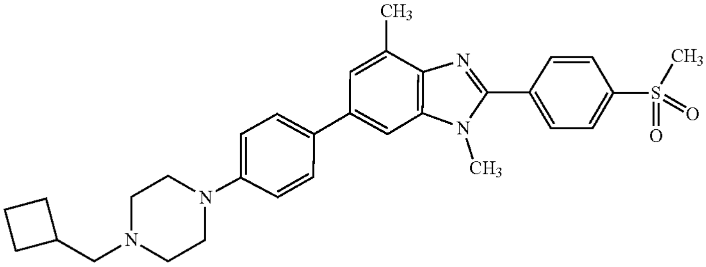 [SMILES: Cc1cc(-c2ccc(N3CCN(CC4CCC4)CC3)cc2)cc2c1nc(-c1ccc(S(C)(=O)=O)cc1)n2C] | Ex. 86 |
| 173 | 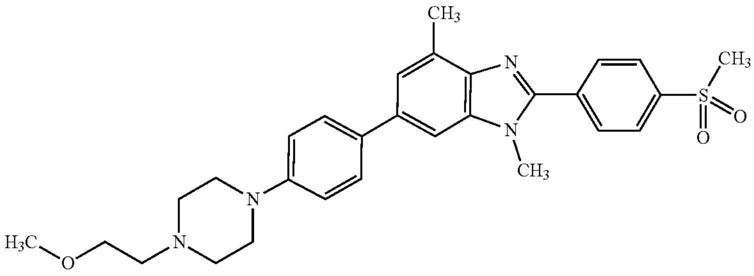 [SMILES: COCCN1CCN(c2ccc(-c3cc(C)c4nc(-c5ccc(S(C)(=O)=O)cc5)n(C)c4c3)cc2)CC1] | Ex. 86 |

-continued
| Ex. No. | Structure | Method |
|---|---|---|
| 174 | 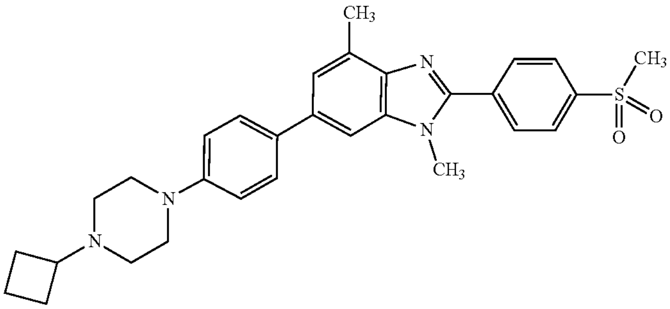 [SMILES: Cc1cc(-c2ccc(N3CCN(C4CCC4)CC3)cc2)cc2c1nc(-c1ccc(S(C)(=O)=O)cc1)n2C] | Ex. 86 |
| 175 | 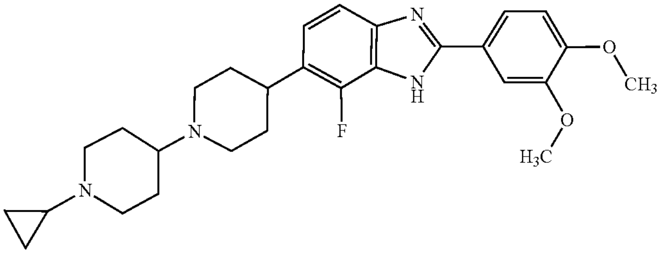 [SMILES: COc1ccc(-c2nc3ccc(C4CCN(C5CCN(C6CC6)CC5)CC4)c(F)c3[nH]2)cc1OC] | Ex. 83 |
| 176 | 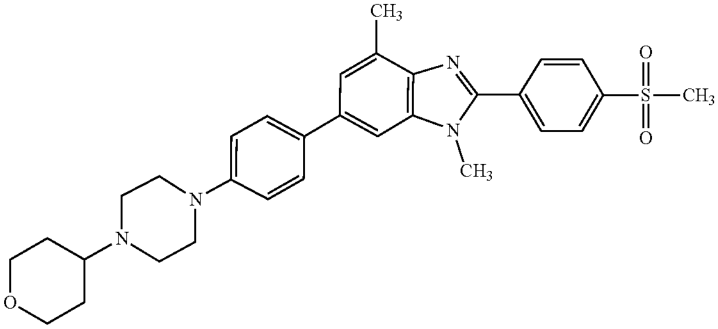 [SMILES: Cc1cc(-c2ccc(N3CCN(C4CCOCC4)CC3)cc2)cc2c1nc(-c1ccc(S(C)(=O)=O)cc1)n2C] | Ex. 86 |
| 177 | 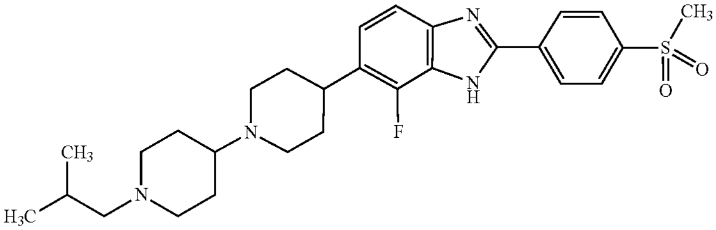 [SMILES: CC(C)CN1CCC(N2CCC(c3ccc4nc(-c5ccc(S(C)(=O)=O)cc5)[nH]c4c3F)CC2)CC1] | Ex. 87 |
| 178 | 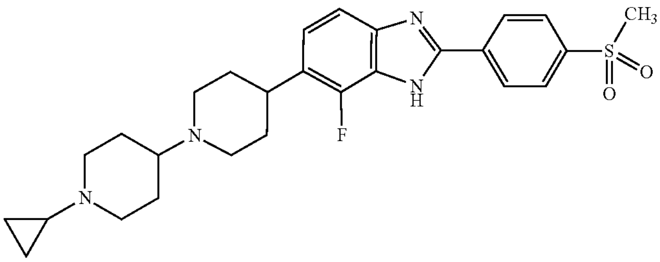 [SMILES: CS(=O)(=O)c1ccc(-c2nc3ccc(C4CCN(C5CCN(C6CC6)CC5)CC4)c(F)c3[nH]2)cc1] | Ex. 87 |

-continued
| Ex. No. | Structure | Method |
|---|---|---|
| 179 | 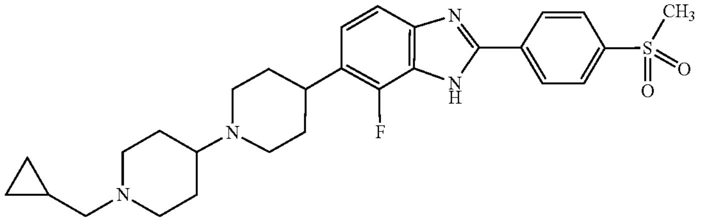 [SMILES: CS(=O)(=O)c1ccc(-c2nc3ccc(C4CCN(C5CCN(CC6CC6)CC5)CC4)c(F)c3[nH]2)cc1] | Ex. 87 |
| 180 | 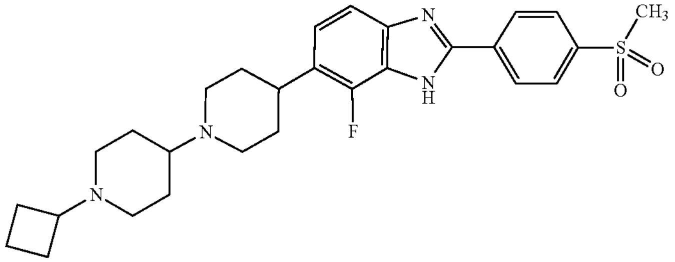 [SMILES: CS(=O)(=O)c1ccc(-c2nc3ccc(C4CCN(C5CCN(C6CCC6)CC5)CC4)c(F)c3[nH]2)cc1] | Ex. 87 |
| 181 | 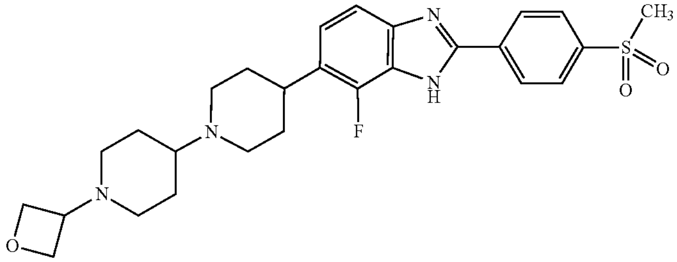 [SMILES: CS(=O)(=O)c1ccc(-c2nc3ccc(C4CCN(C5CCN(C6COC6)CC5)CC4)c(F)c3[nH]2)cc1] | Ex. 87 |
| 182 | 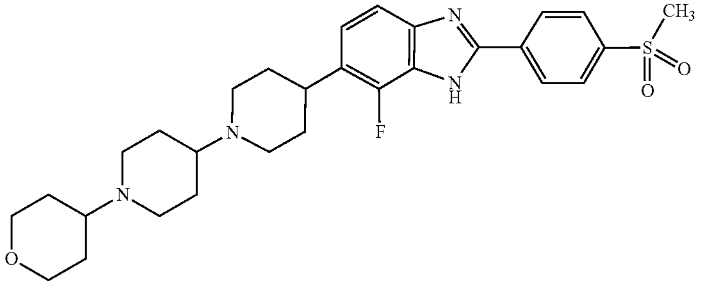 [SMILES: CS(=O)(=O)c1ccc(-c2nc3ccc(C4CCN(C5CCN(C6CCOCC6)CC5)CC4)c(F)c3[nH]2)cc1] | Ex. 87 |
| 183 | 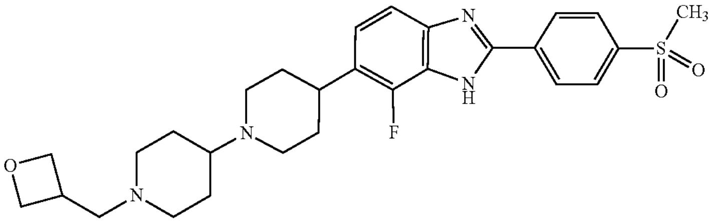 [SMILES: CS(=O)(=O)c1ccc(-c2nc3ccc(C4CCN(C5CCN(CC6COC6)CC5)CC4)c(F)c3[nH]2)cc1] | Ex. 87 |
| 184 | 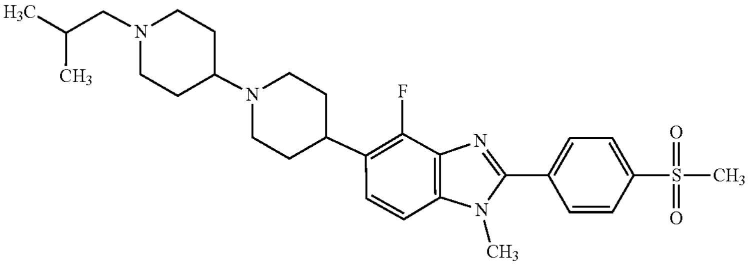 [SMILES: CC(C)CN1CCC(N2CCC(c3ccc4c(nc(-c5ccc(S(C)(=O)=O)cc5)n4C)c3F)CC2)CC1] | Ex. 88 |

-continued
| Ex. No. | Structure | Method |
| --- | --- | --- |
| 185 | 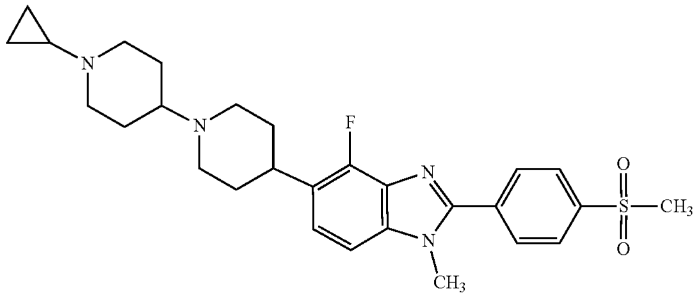 [SMILES: Cn1c(-c2ccc(S(C)(=O)=O)cc2)nc2c(F)c(C3CCN(C4CCN(C5CC5)CC4)CC3)ccc21] | Ex. 88 |
| 186 | 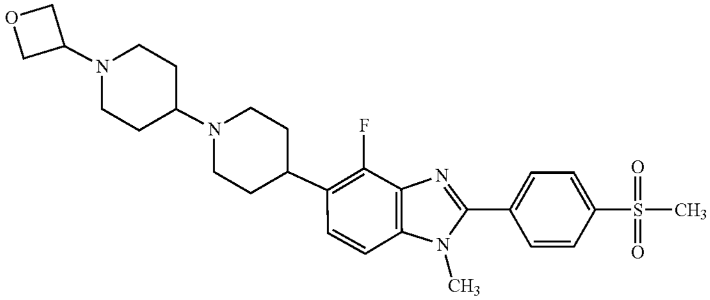 [SMILES: Cn1c(-c2ccc(S(C)(=O)=O)cc2)nc2c(F)c(C3CCN(C4CCN(C5COC5)CC4)CC3)ccc21] | Ex. 88 |
| 187 | 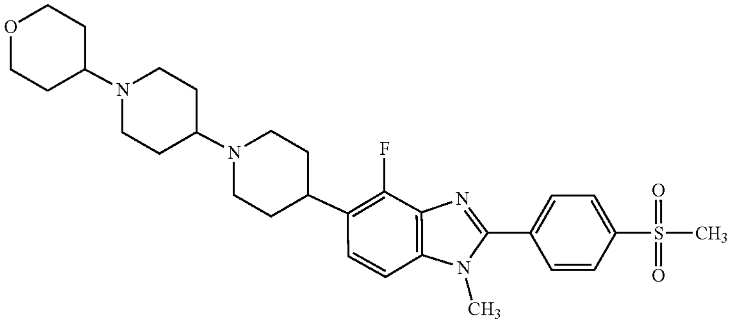 [SMILES: Cn1c(-c2ccc(S(C)(=O)=O)cc2)nc2c(F)c(C3CCN(C4CCN(C5CCOCC5)CC4)CC3)ccc21] | Ex. 88 |
| 188 | 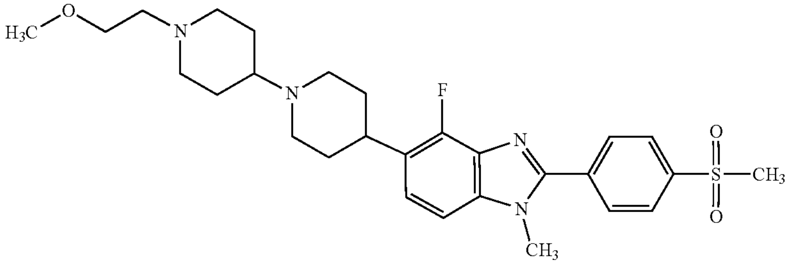 | Ex. 88 |
| 189 | 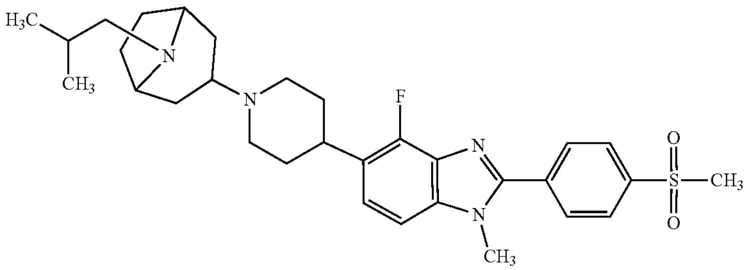 1st eluting isomer | Ex. 89 |

-continued
| Ex. No. | Structure | Method |
|---|---|---|
| 190 | 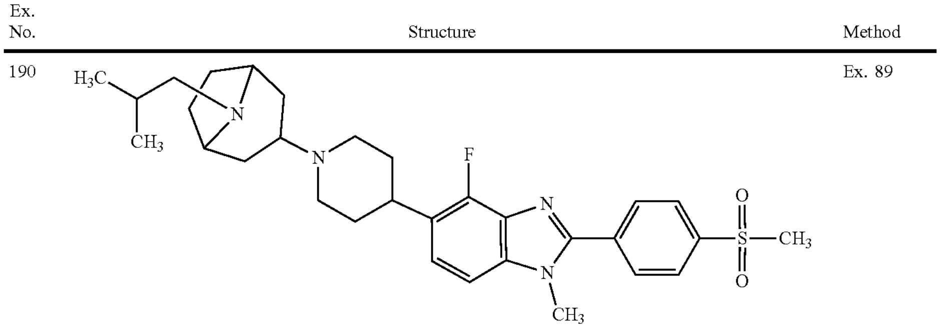 2nd eluting isomer | Ex. 89 |
| 191 | 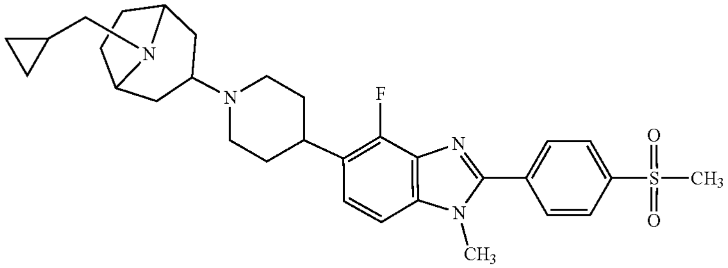 1st eluting isomer | Ex. 89 |
| 192 | 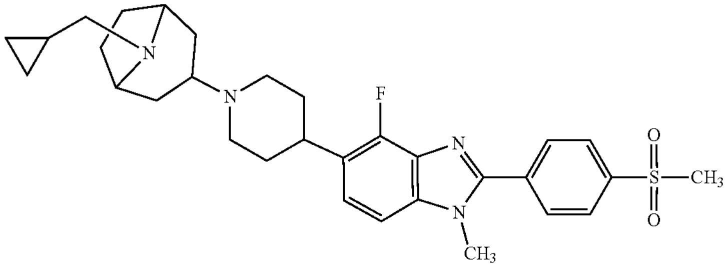 2nd eluting isomer | Ex. 89 |
| 193 | 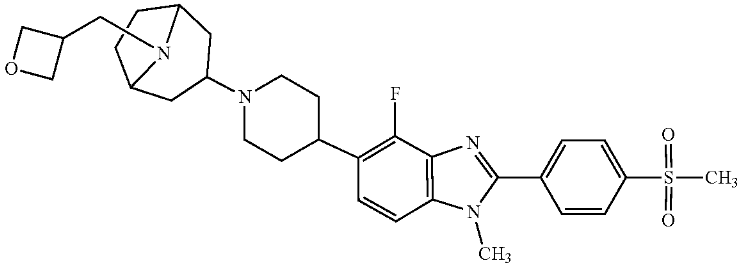 1st eluting isomer | Ex. 89 |
| 194 | 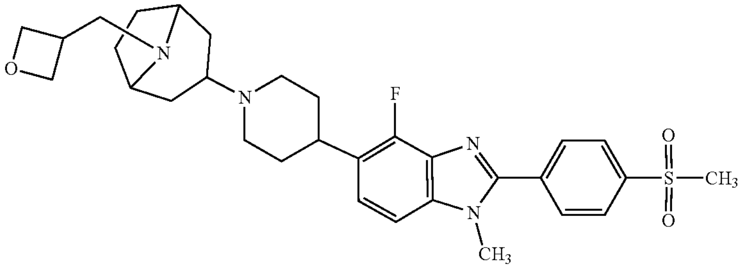 2nd eluting isomer | Ex. 89 |

-continued
| Ex. No. | Structure | Method |
|---|---|---|
| 195 | 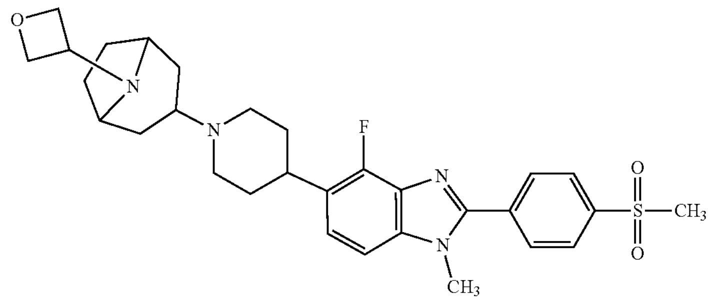 1st eluting isomer | Ex. 89 |
| 196 | 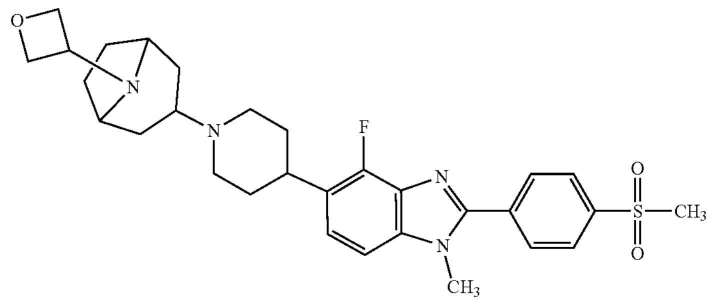 2nd eluting isomer | Ex. 89 |
| 197 | 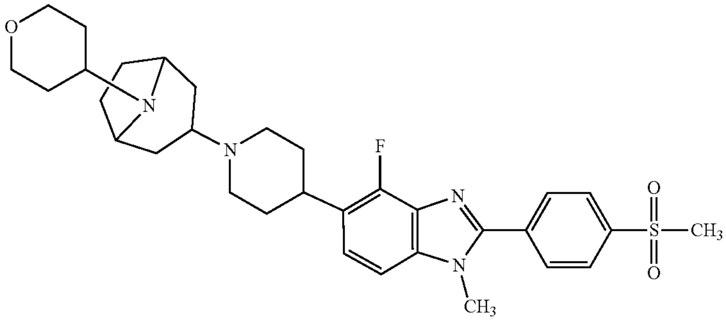 1st eluting isomer | Ex. 89 |
| 198 | 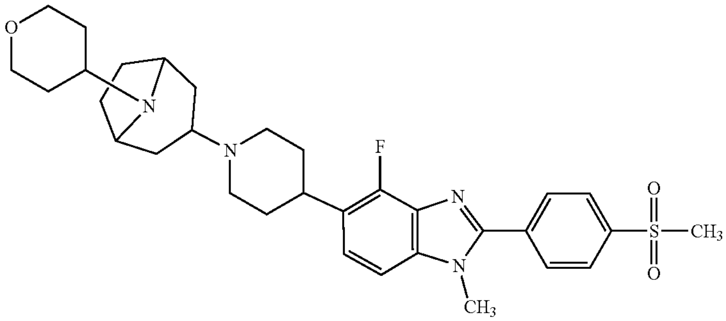 2nd eluting isomer | Ex. 89 |

-continued
| Ex. No. | Structure | Method |
|---|---|---|
| 199 | 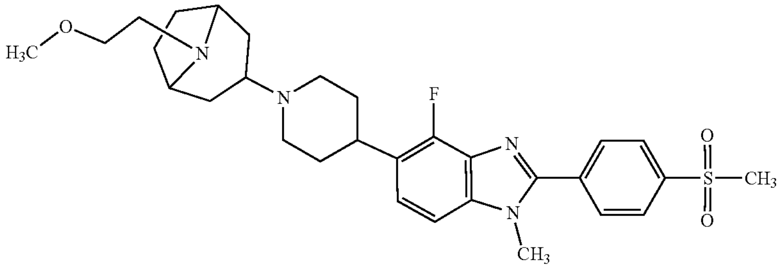 1st eluting isomer | Ex. 89 |
| 200 | 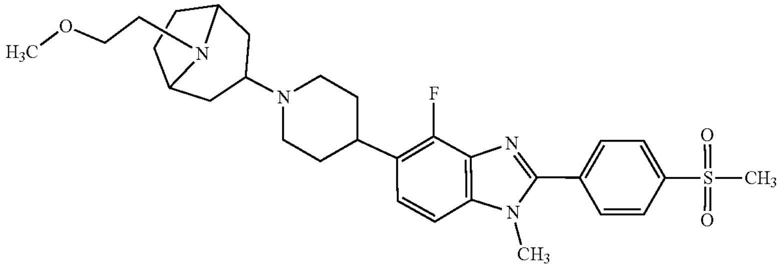 2nd eluting isomer | Ex. 89 |
| 201 | 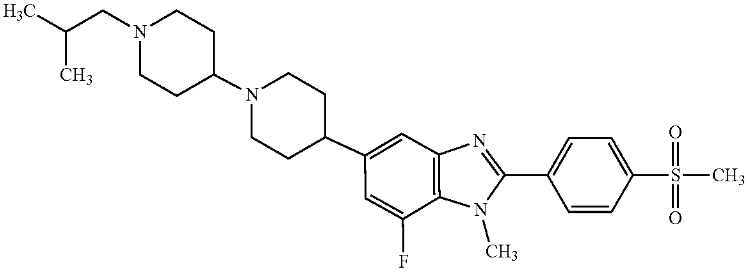 [SMILES: CC(C)CN1CCC(N2CCC(c3cc(F)c4c(c3)nc(-c3ccc(S(C)(=O)=O)cc3)n4C)CC2)CC1] | Ex. 91 |
| 202 | 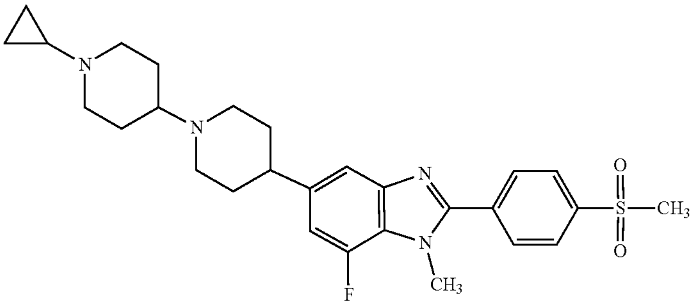 [SMILES: Cn1c(-c2ccc(S(C)(=O)=O)cc2)nc2cc(C3CCN(C4CCN(C5CC5)CC4)CC3)cc(F)c21] | Ex. 91 |
| 203 | 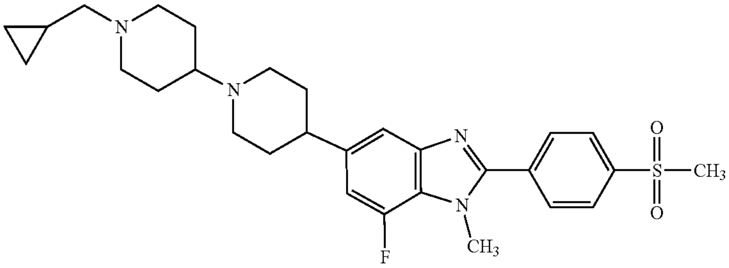 [SMILES: Cn1c(-c2ccc(S(C)(=O)=O)cc2)nc2cc(C3CCN(C4CCN(CC5CC5)CC4)CC3)cc(F)c21] | Ex. 91 |

-continued
| Ex. No. | Structure | Method |
| --- | --- | --- |
| 204 | 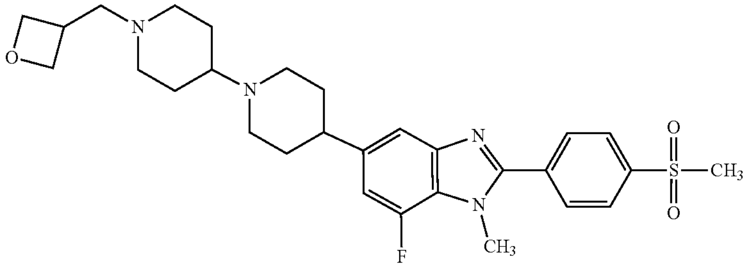 [SMILES: Cn1c(-c2ccc(S(C)(=O)=O)cc2)nc2cc(C3CCN(C4CCN(CC5COC5)CC4)CC3)cc(F)c21] | Ex. 91 |
| 205 | 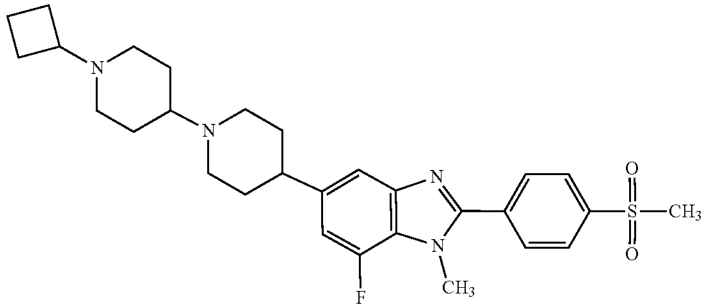 [SMILES: Cn1c(-c2ccc(S(C)(=O)=O)cc2)nc2cc(C3CCN(C4CCN(C5CCC5)CC4)CC3)cc(F)c21] | Ex. 91 |
| 206 | 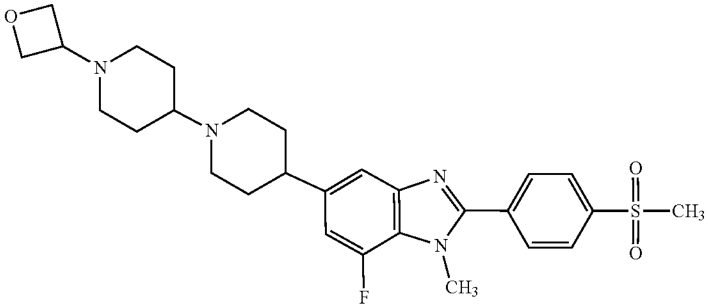 [SMILES: Cn1c(-c2ccc(S(C)(=O)=O)cc2)nc2cc(C3CCN(C4CCN(C5COC5)CC4)CC3)cc(F)c21] | Ex. 91 |
| 207 | 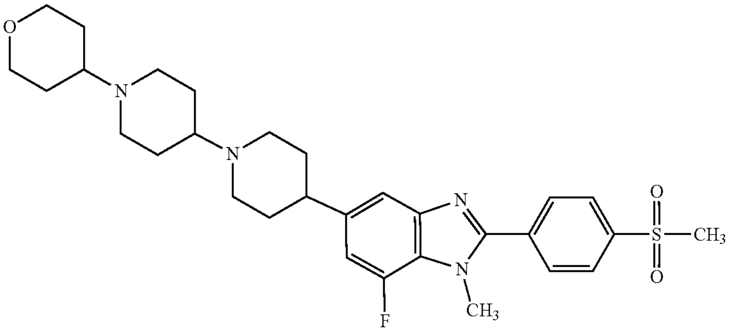 [SMILES: Cn1c(-c2ccc(S(C)(=O)=O)cc2)nc2cc(C3CCN(C4CCN(C5CCOCC5)CC4)CC3)cc(F)c21] | Ex. 91 |
| 208 | 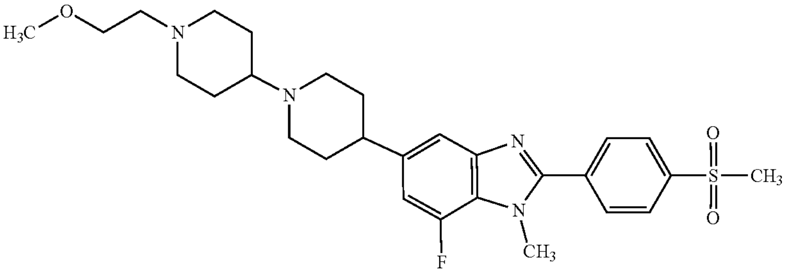 | Ex. 91 |

-continued
| Ex. No. | Structure | Method |
|---|---|---|
| 209 | 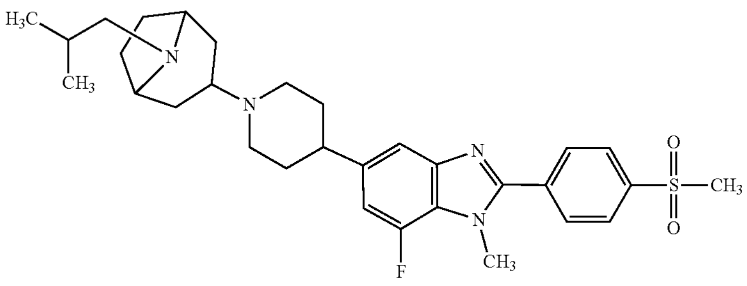 1st eluting isomer | Ex. 92 |
| 210 | 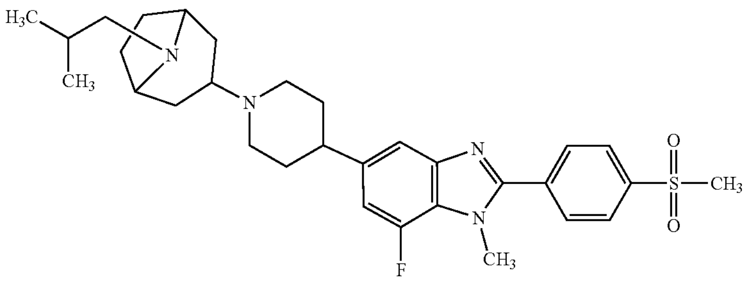 2nd eluting isomer | Ex. 92 |
| 211 | 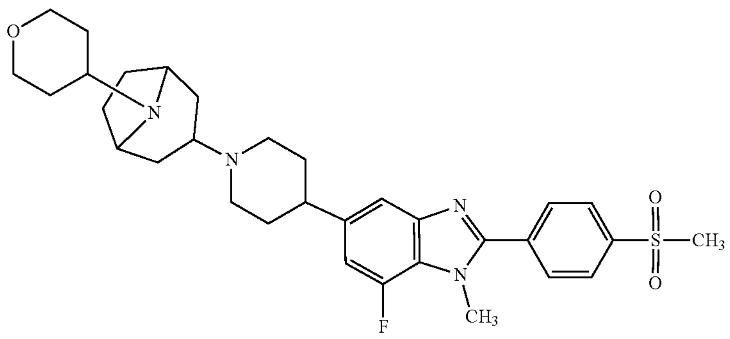 1st eluting isomer | Ex. 92 |
| 212 | 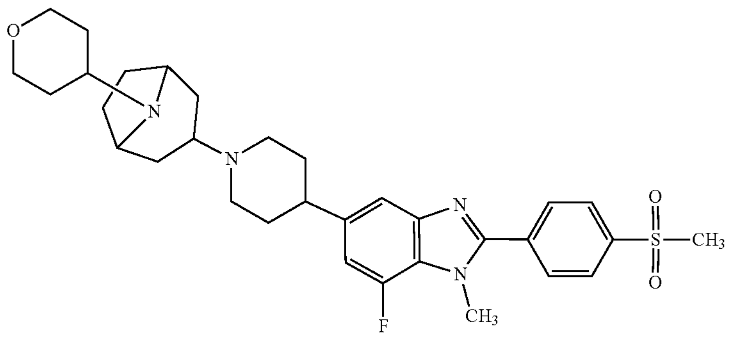 2nd eluting isomer | Ex. 92 |

-continued
| Ex. No. | Structure | Method |
|---|---|---|
| 213 | 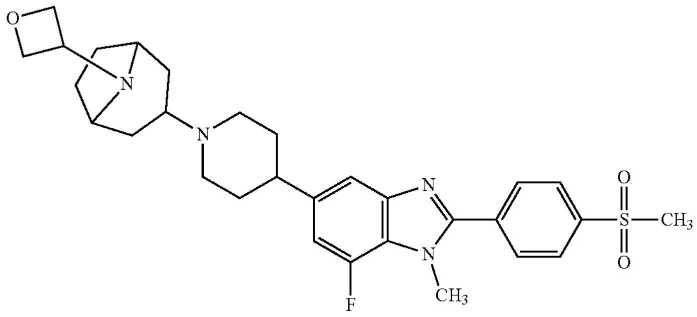 1st eluting isomer | Ex. 92 |
| 214 | 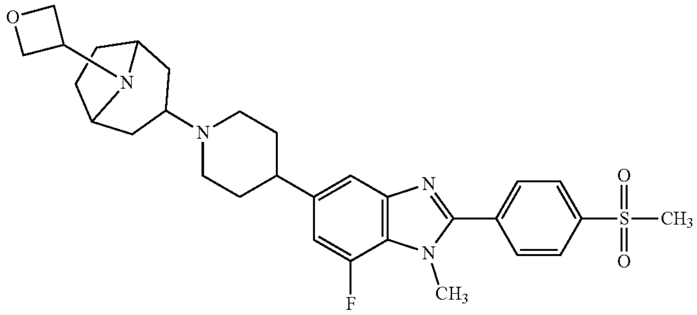 2nd eluting isomer | Ex. 92 |
| 215 | 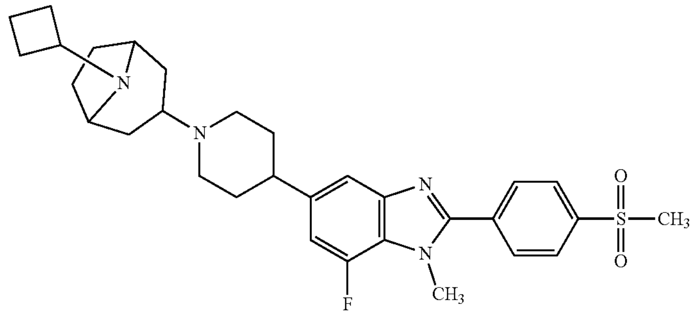 1st eluting isomer | Ex. 92 |
| 216 | 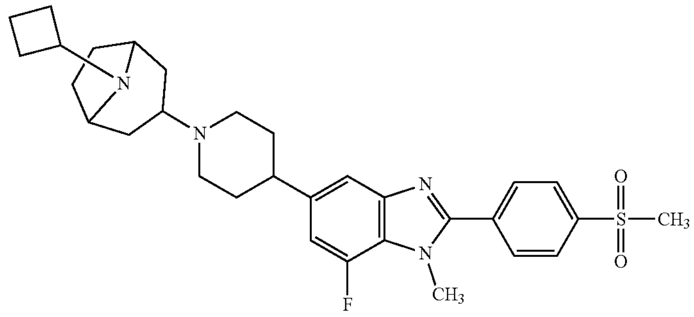 2nd eluting isomer | Ex. 92 |

-continued
| Ex. No. | Structure | Method |
|---|---|---|
| 217 | 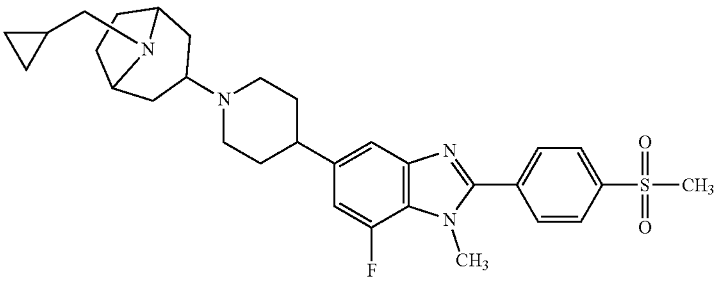 1st eluting isomer | Ex. 92 |
| 218 | 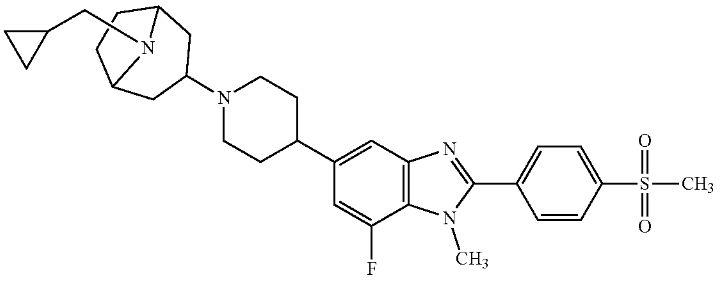 2nd eluting isomer | Ex. 92 |
| 219 | 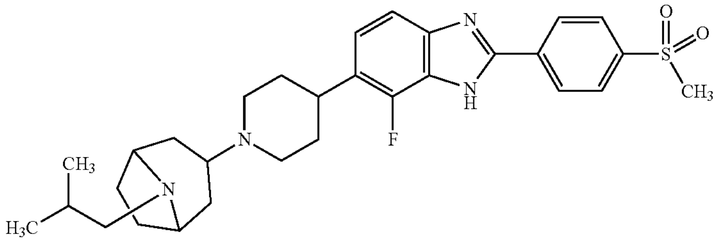 1st eluting isomer | Ex. 94 |
| 220 | 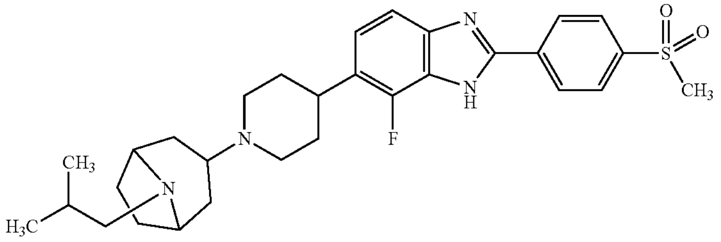 2nd eluting isomer | Ex. 94 |
| 221 | 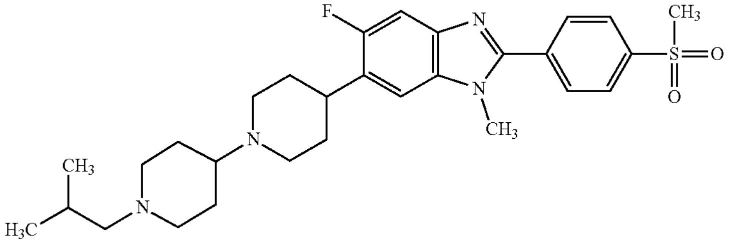 [SMILES: CC(C)CN1CCC(N2CCC(c3cc4c(cc3F)nc(-c3ccc(S(C)(=O)=O)cc3)n4C)CC2)CC1] | Ex. 96 |

-continued
| Ex. No. | Structure | Method |
|---|---|---|
| 222 | 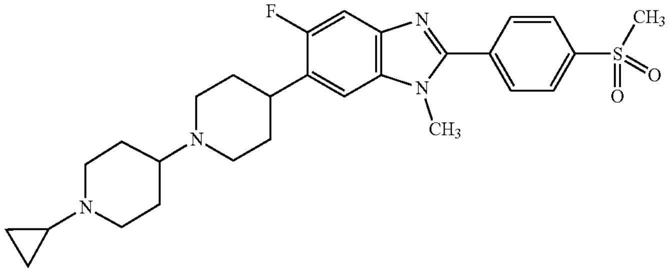 [SMILES: Cn1c(-c2ccc(S(C)(=O)=O)cc2)nc2cc(F)c(C3CCN(C4CCN(C5CC5)CC4)CC3)cc21] | Ex. 96 |
| 223 | 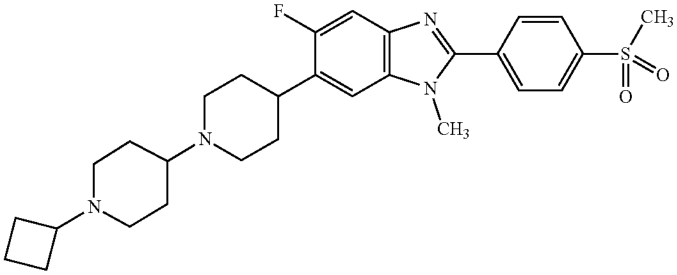 [SMILES: Cn1c(-c2ccc(S(C)(=O)=O)cc2)nc2cc(F)c(C3CCN(C4CCN(C5CCC5)CC4)CC3)cc21] | Ex. 96 |
| 224 | 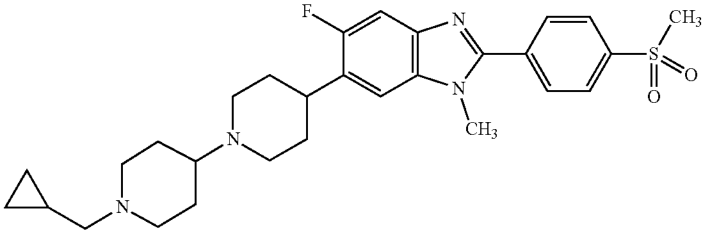 [SMILES: Cn1c(-c2ccc(S(C)(=O)=O)cc2)nc2cc(F)c(C3CCN(C4CCN(CC5CC5)CC4)CC3)cc21] | Ex. 96 |
| 225 | 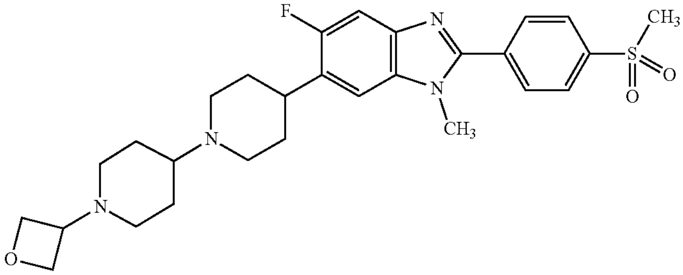 [SMILES: Cn1c(-c2ccc(S(C)(=O)=O)cc2)nc2cc(F)c(C3CCN(C4CCN(C5COC5)CC4)CC3)cc21] | Ex. 96 |
| 226 | 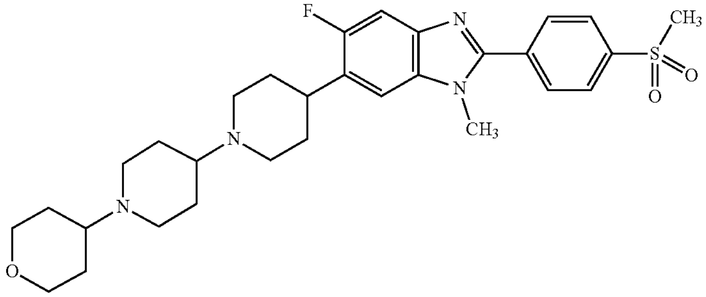 [SMILES: Cn1c(-c2ccc(S(C)(=O)=O)cc2)nc2cc(F)c(C3CCN(C4CCN(C5CCOCC5)CC4)CC3)cc21] | Ex. 96 |

-continued
| Ex. No. | Structure | Method |
|---|---|---|
| 227 | 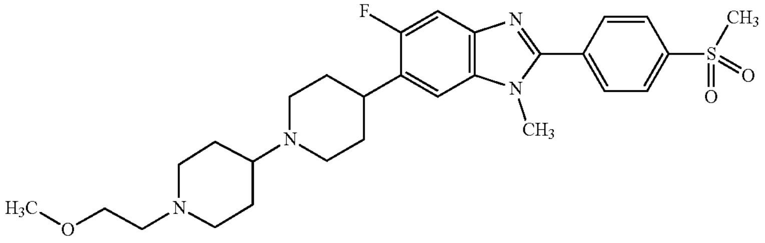 [SMILES: COCCN1CCC(N2CCC(c3cc4c(cc3F)nc(-c3ccc(S(C)(=O)=O)cc3)n4C)CC2)CC1] | Ex. 96 |
| 228 | 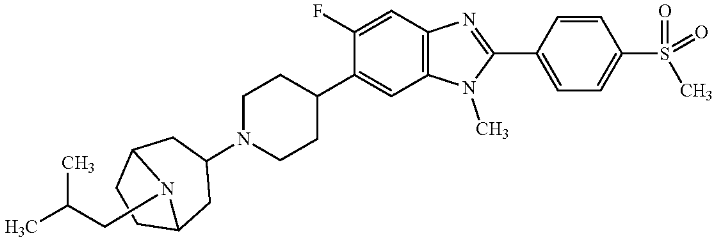<br>1$^{st}$ eluting isomer | Ex. 97 |
| 229 | 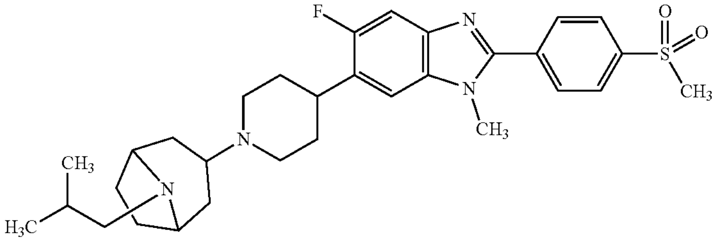<br>2$^{nd}$ eluting isomer | Ex. 97 |
| 230 | 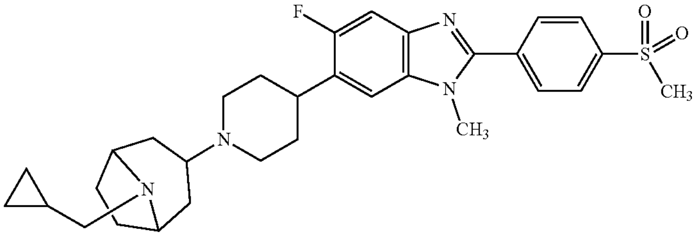<br>1$^{st}$ eluting isomer | Ex. 97 |
| 231 | 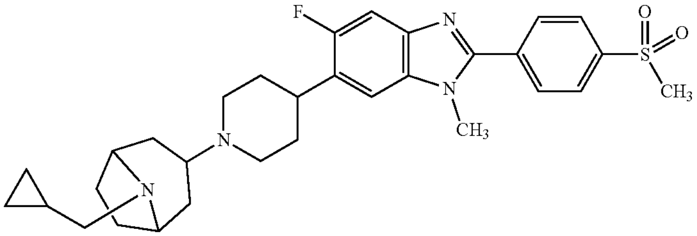<br>2$^{nd}$ eluting isomer | Ex. 97 |

-continued
| Ex. No. | Structure | Method |
|---|---|---|
| 232 | 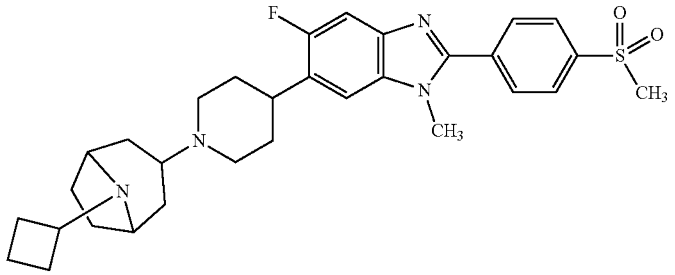 1st eluting isomer | Ex. 97 |
| 233 | 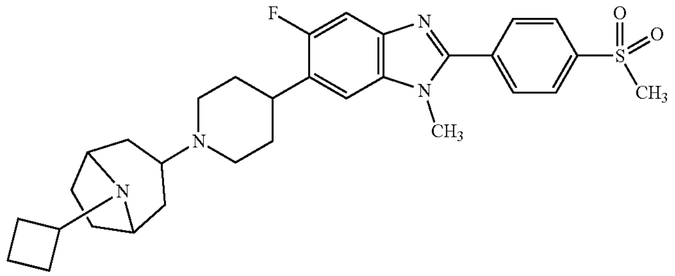 2nd eluting isomer | Ex. 97 |
| 234 | 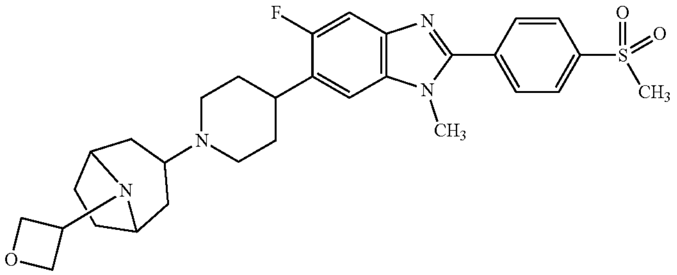 1st eluting isomer | Ex. 97 |
| 235 | 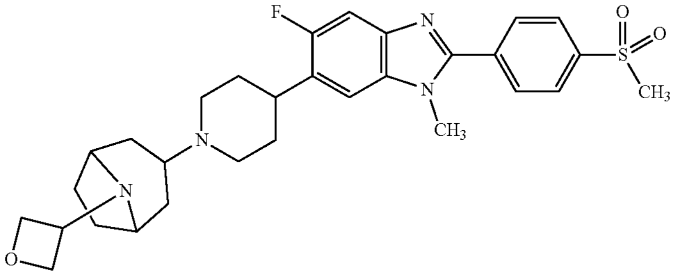 2nd eluting isomer | Ex. 97 |

-continued
| Ex. No. | Structure | Method |
| --- | --- | --- |
| 236 | 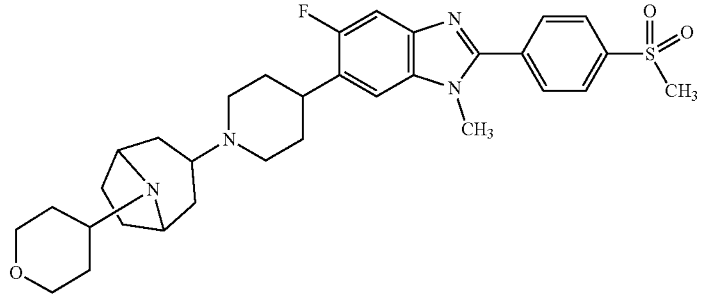 1st eluting isomer | Ex. 97 |
| 237 | 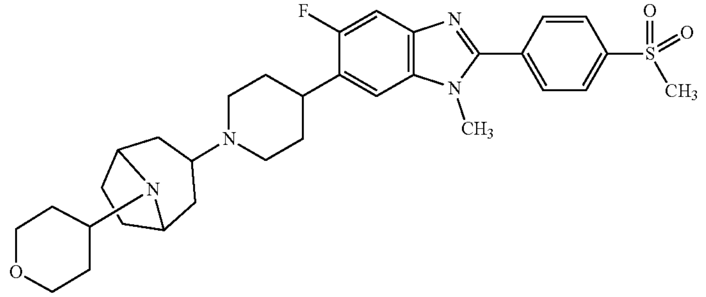 2nd eluting isomer | Ex. 97 |
| 238 | 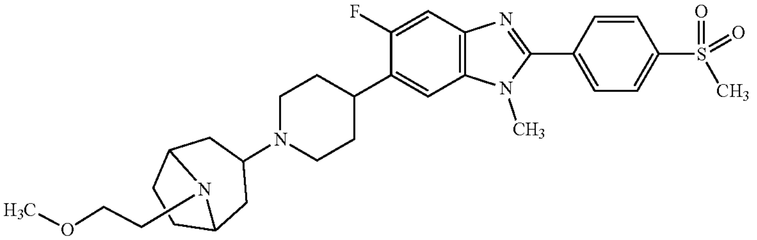 1st eluting isomer | Ex. 97 |
| 239 | 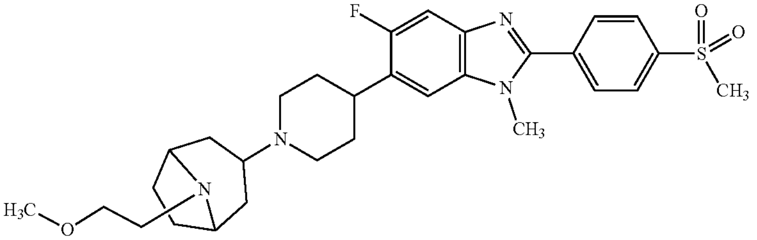 2nd eluting isomer | Ex. 97 |
| 240 | 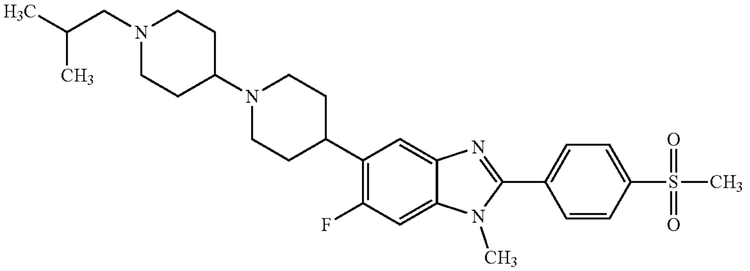 [SMILES: CC(C)CN1CCC(N2CCC(c3cc4nc(-c5ccc(S(C)(=O)=O)cc5)n(C)c4cc3F)CC2)CC1] | Ex. 99 |

-continued
| Ex. No. | Structure | Method |
|---|---|---|
| 241 | 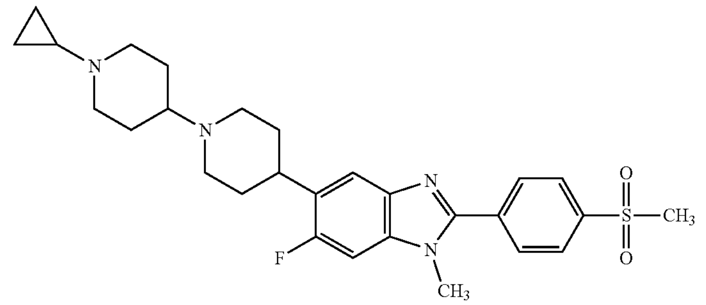 [SMILES: Cn1c(-c2ccc(S(C)(=O)=O)cc2)nc2cc(C3CCN(C4CCN(C5CC5)CC4)CC3)c(F)cc21] | Ex. 99 |
| 242 | 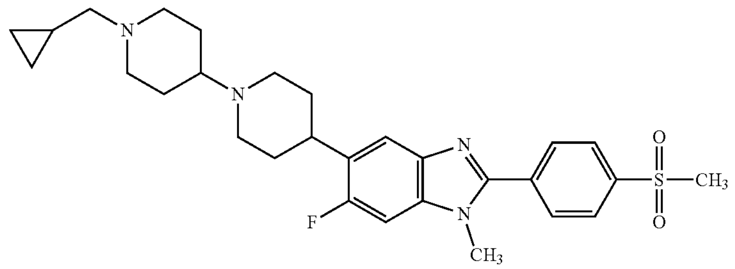 [SMILES: Cn1c(-c2ccc(S(C)(=O)=O)cc2)nc2cc(C3CCN(C4CCN(CC5CC5)CC4)CC3)c(F)cc21] | Ex. 99 |
| 243 | 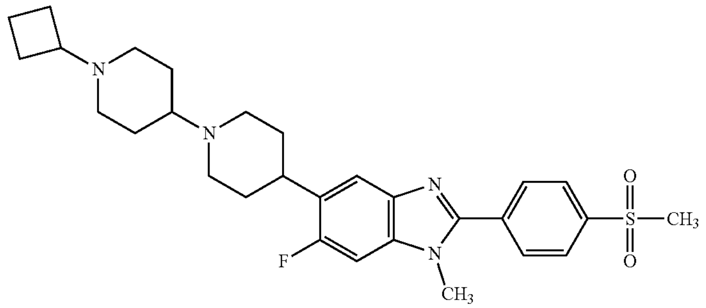 [SMILES: Cn1c(-c2ccc(S(C)(=O)=O)cc2)nc2cc(C3CCN(C4CCN(C5CCC5)CC4)CC3)c(F)cc21] | Ex. 99 |
| 244 | 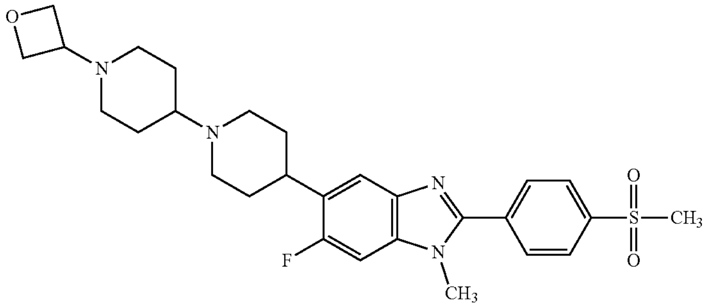 [SMILES: Cn1c(-c2ccc(S(C)(=O)=O)cc2)nc2cc(C3CCN(C4CCN(C5COC5)CC4)CC3)c(F)cc21] | Ex. 99 |
| 245 | 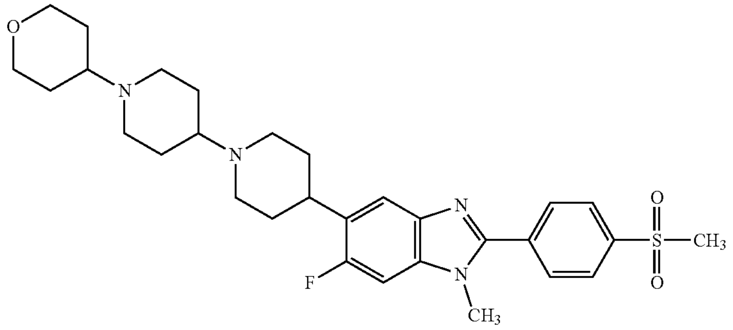 [SMILES: Cn1c(-c2ccc(S(C)(=O)=O)cc2)nc2cc(C3CCN(C4CCN(C5CCOCC5)CC4)CC3)c(F)cc21] | Ex. 99 |

-continued
| Ex. No. | Structure | Method |
|---|---|---|
| 246 | 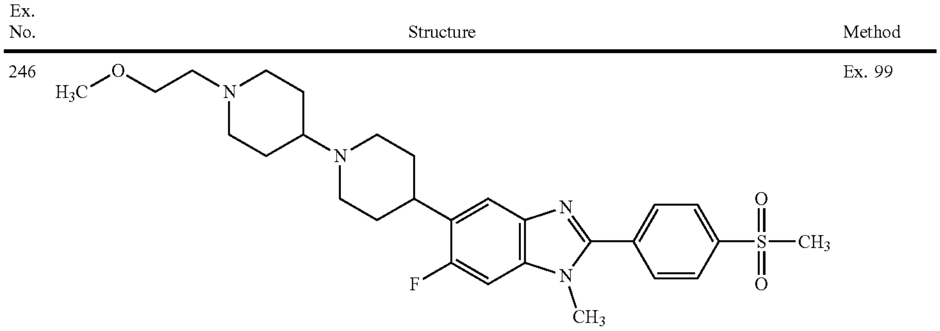 | Ex. 99 |
| 247 | 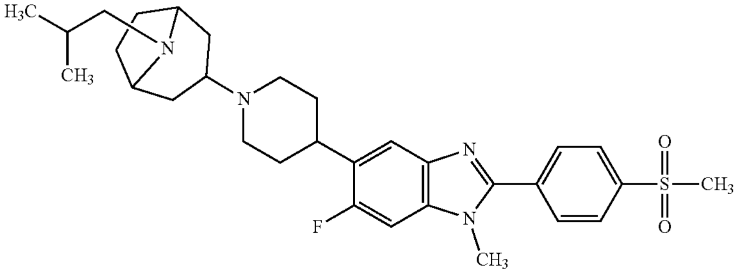<br>1st eluting isomer | Ex. 100 |
| 248 | 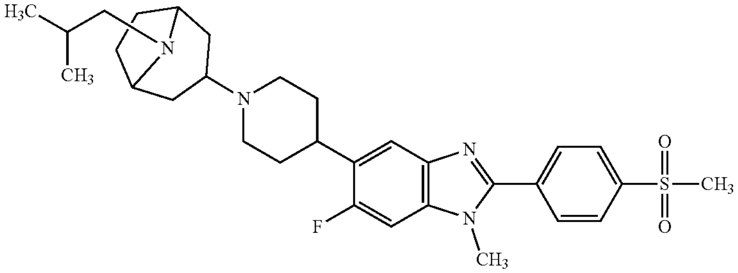<br>2nd eluting isomer | Ex. 100 |
| 249 | 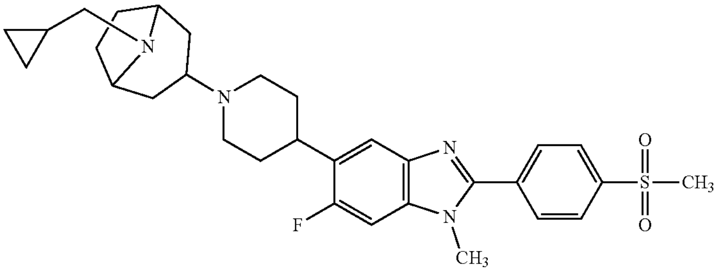<br>1st eluting isomer | Ex. 100 |
| 250 | 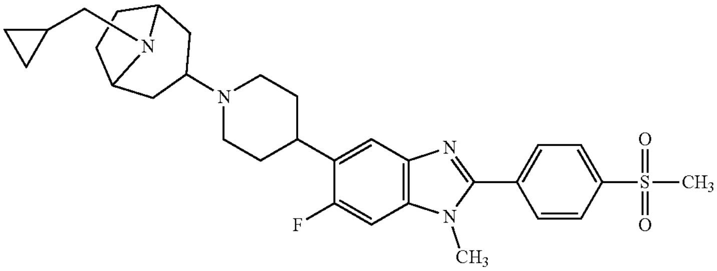<br>2nd eluting isomer | Ex. 100 |

-continued
| Ex. No. | Structure | Method |
|---|---|---|
| 251 | 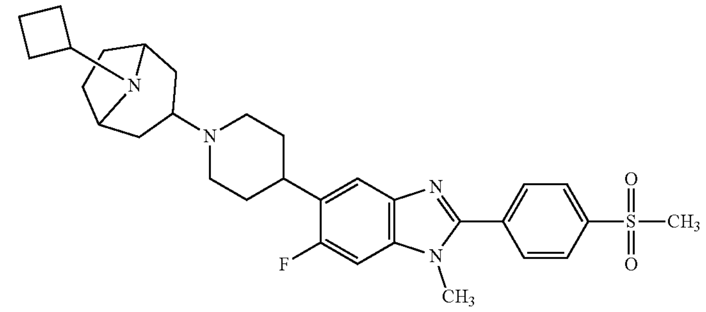 1st eluting isomer | Ex. 100 |
| 252 | 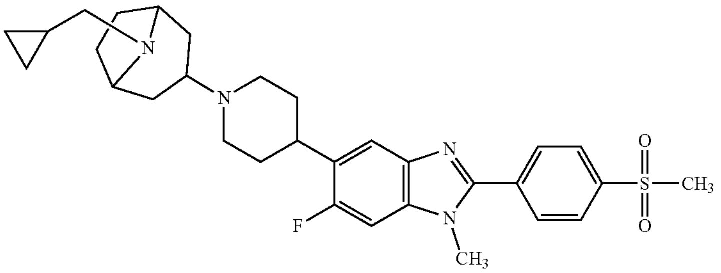 2nd eluting isomer | Ex. 100 |
| 253 | 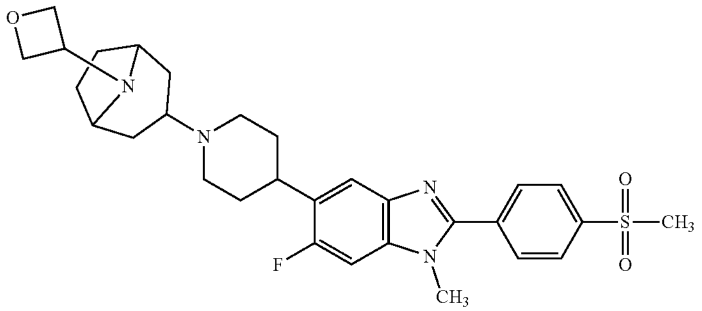 1st eluting isomer | Ex. 100 |
| 254 | 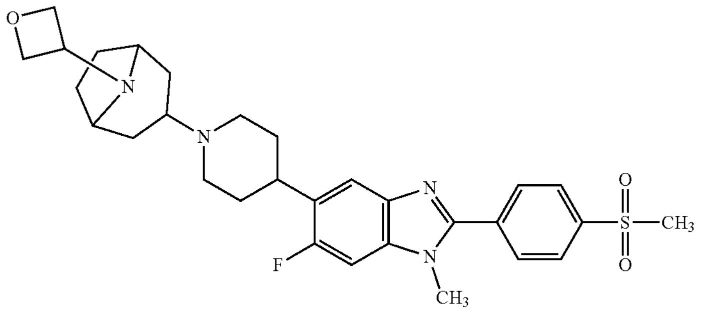 2nd eluting isomer | Ex. 100 |

-continued
| Ex. No. | Structure | Method |
|---|---|---|
| 255 | 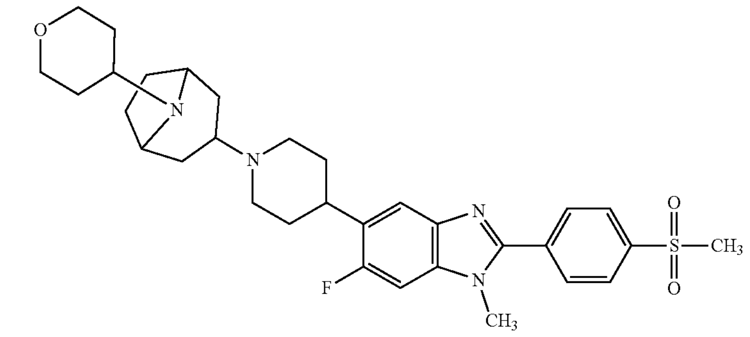 1st eluting isomer | Ex. 100 |
| 256 | 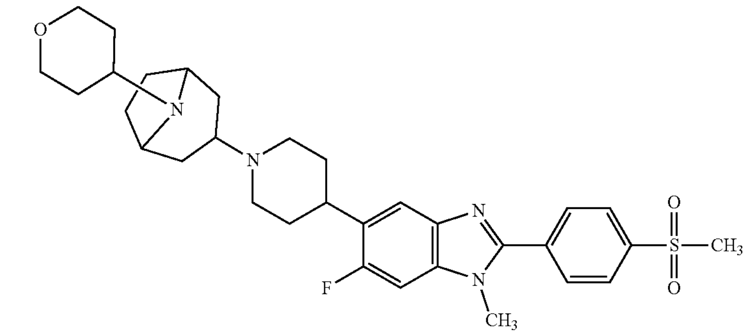 2nd eluting isomer | Ex. 100 |
| 257 | 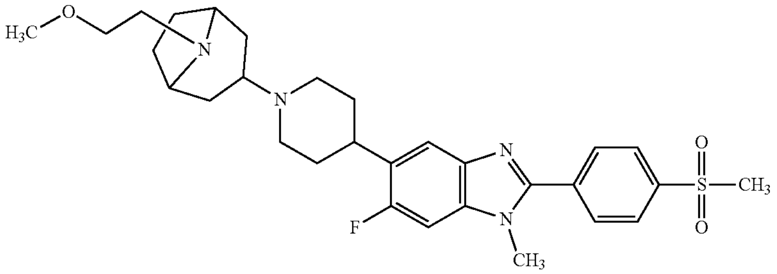 1st eluting isomer | Ex. 100 |
| 258 | 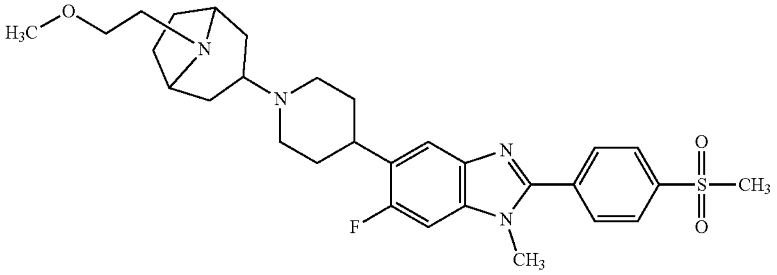 2nd eluting isomer | Ex. 100 |

-continued
| Ex. No. | Structure | Method |
|---|---|---|
| 259 | 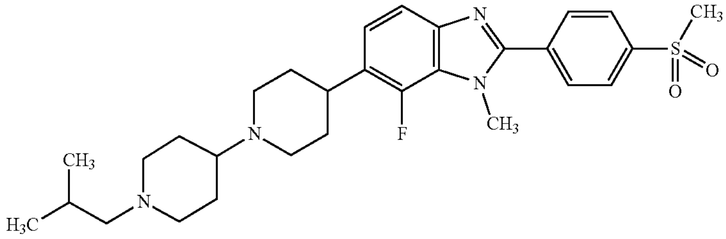 [SMILES: CC(C)CN1CCC(N2CCC(c3ccc4nc(-c5ccc(S(C)(=O)=O)cc5)n(C)c4c3F)CC2)CC1] | Ex. 102 |
| 260 | 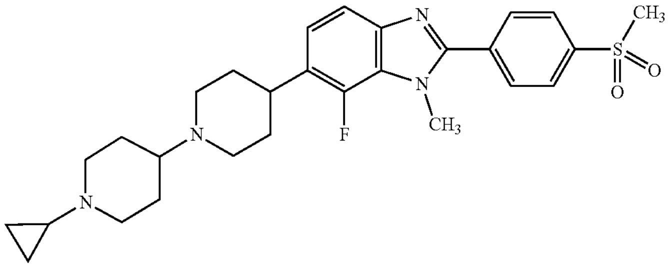 [SMILES: Cn1c(-c2ccc(S(C)(=O)=O)cc2)nc2ccc(C3CCN(C4CCN(C5CC5)CC4)CC3)c(F)c21] | Ex. 102 |
| 261 | 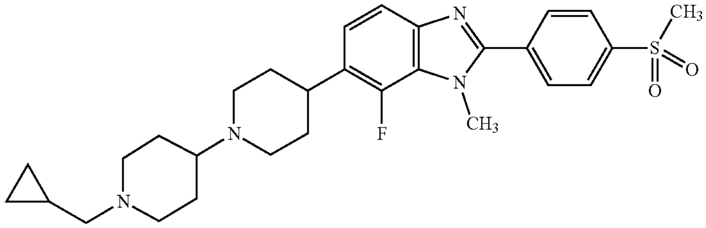 [SMILES: Cn1c(-c2ccc(S(C)(=O)=O)cc2)nc2ccc(C3CCN(C4CCN(CC5CC5)CC4)CC3)c(F)c21] | Ex. 102 |
| 262 | 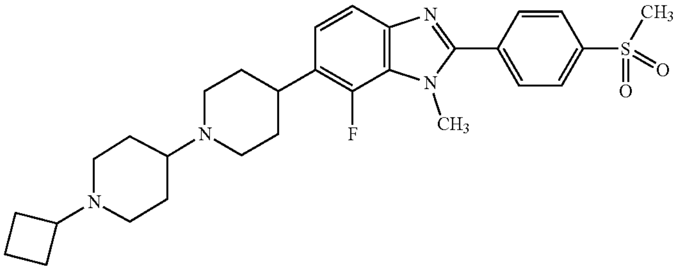 [SMILES: Cn1c(-c2ccc(S(C)(=O)=O)cc2)nc2ccc(C3CCN(C4CCN(C5CCC5)CC4)CC3)c(F)c21] | Ex. 102 |
| 263 | 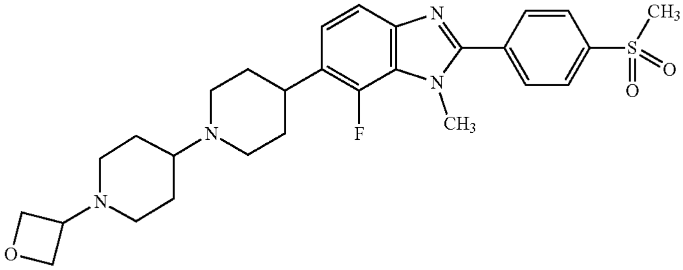 [SMILES: Cn1c(-c2ccc(S(C)(=O)=O)cc2)nc2ccc(C3CCN(C4CCN(C5COC5)CC4)CC3)c(F)c21] | Ex. 102 |

-continued
| Ex. No. | Structure | Method |
|---|---|---|
| 264 | 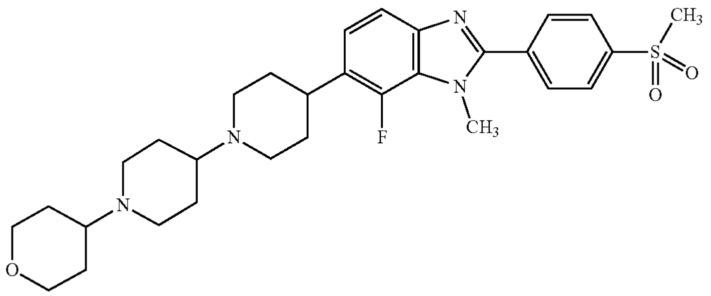 [SMILES: Cn1c(-c2ccc(S(C)(=O)=O)cc2)nc2ccc(C3CCN(C4CCN(C5CCOCC5)CC4)CC3)c(F)c21] | Ex. 102 |
| 265 | 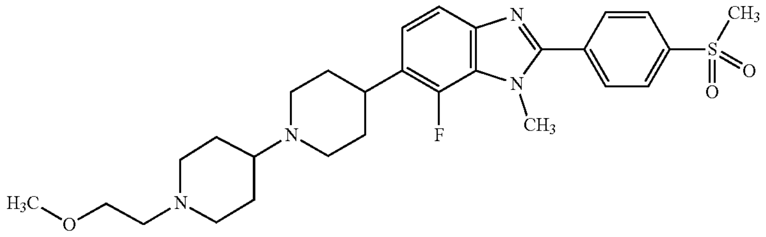 [SMILES: COCCN1CCC(N2CCC(c3ccc4nc(-c5ccc(S(C)(=O)=O)cc5)n(C)c4c3F)CC2)CC1] | Ex. 102 |
| 266 | 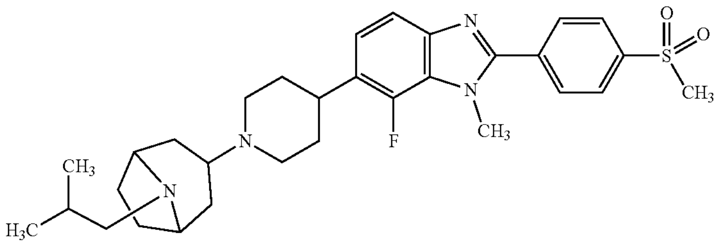 1st eluting isomer | Ex. 103 |
| 267 | 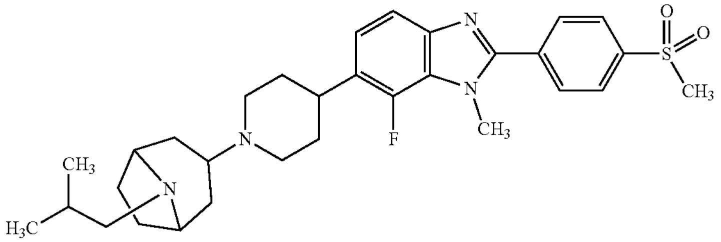 2nd eluting isomer | Ex. 103 |
| 268 | 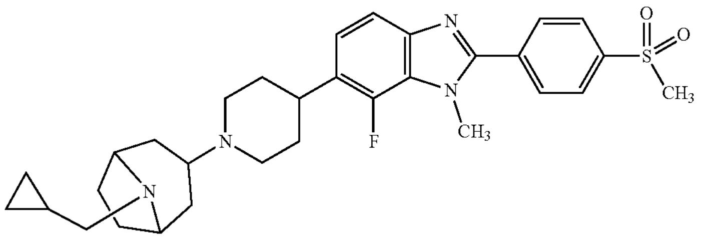 1st eluting isomer | Ex. 103 |

-continued
| Ex. No. | Structure | Method |
|---|---|---|
| 269 | 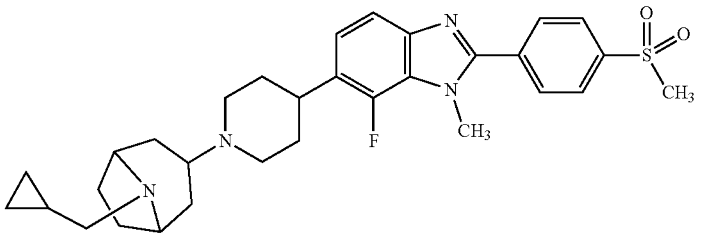<br>2nd eluting isomer | Ex. 103 |
| 270 | 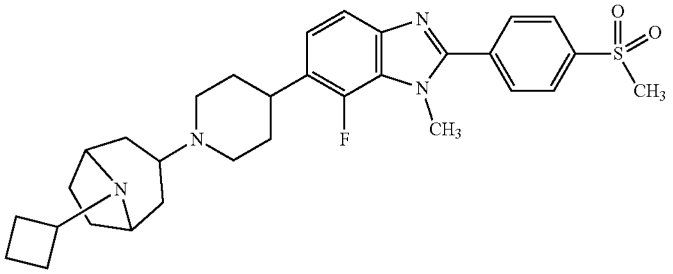<br>1st eluting isomer | Ex. 103 |
| 271 | 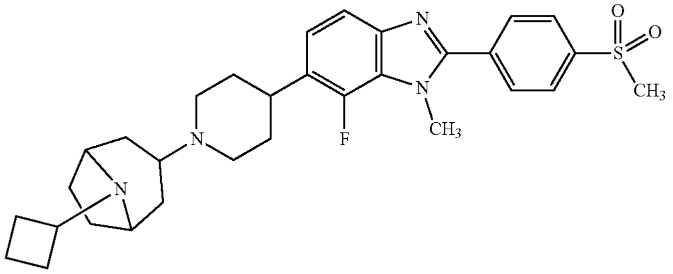<br>2nd eluting isomer | Ex. 103 |
| 272 | 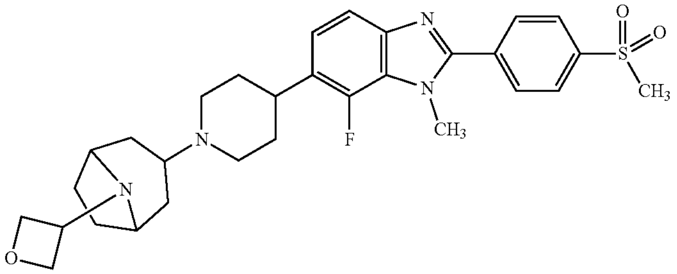<br>1st eluting isomer | Ex. 103 |
| 273 | 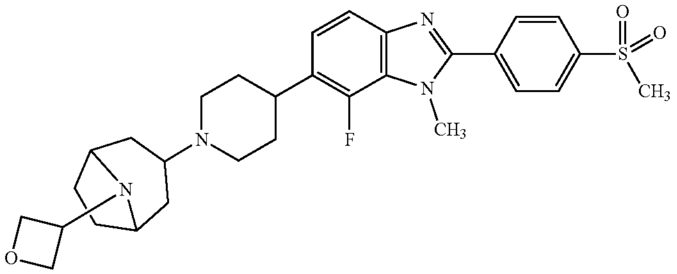<br>2nd eluting isomer | Ex. 103 |

-continued
| Ex. No. | Structure | Method |
| --- | --- | --- |
| 274 | 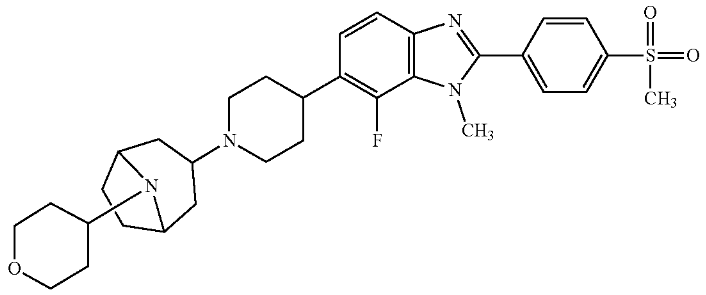 1st eluting isomer | Ex. 103 |
| 275 | 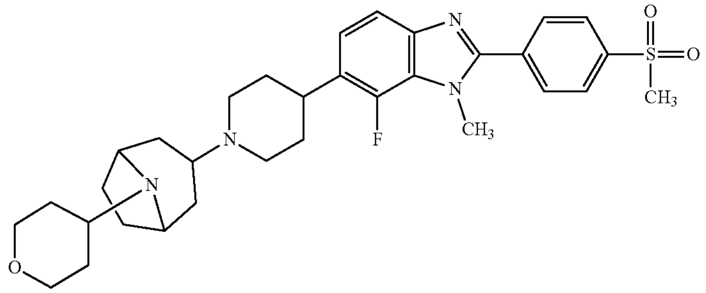 2nd eluting isomer | Ex. 103 |
| 276 | 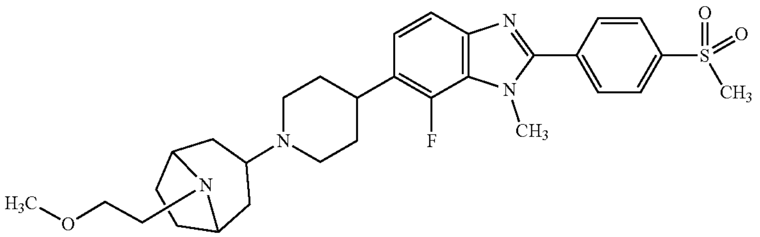 1st eluting isomer | Ex. 103 |
| 277 | 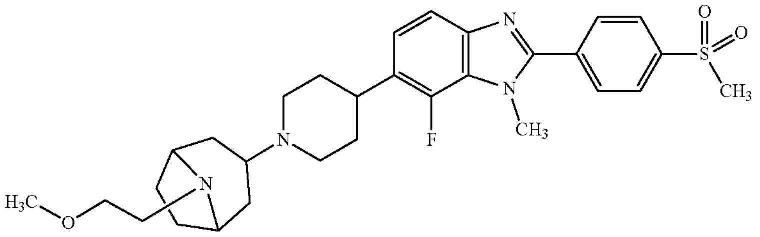 2nd eluting isomer | Ex. 103 |
| 278 | 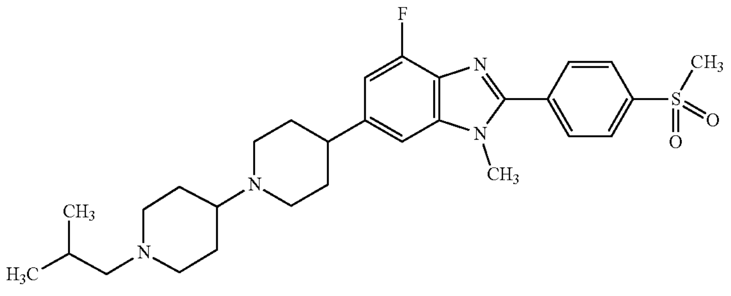 [SMILES: CC(C)CN1CCC(N2CCC(c3cc(F)c4nc(-c5ccc(S(C)(=O)=O)cc5)n(C)c4c3)CC2)CC1] | Ex. 105 |

-continued
| Ex. No. | Structure | Method |
|---|---|---|
| 279 | 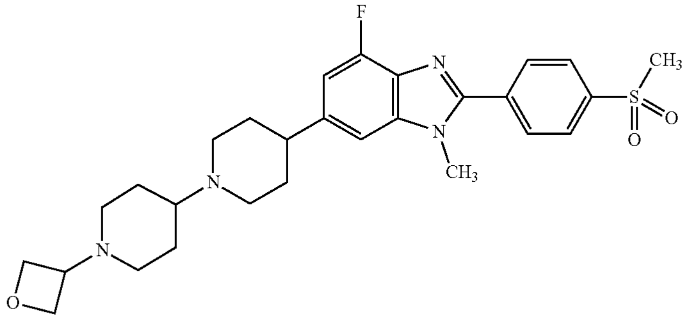 [SMILES: Cn1c(-c2ccc(S(C)(=O)=O)cc2)nc2c(F)cc(C3CCN(C4CCN(C5COC5)CC4)CC3)cc21] | Ex. 105 |
| 280 | 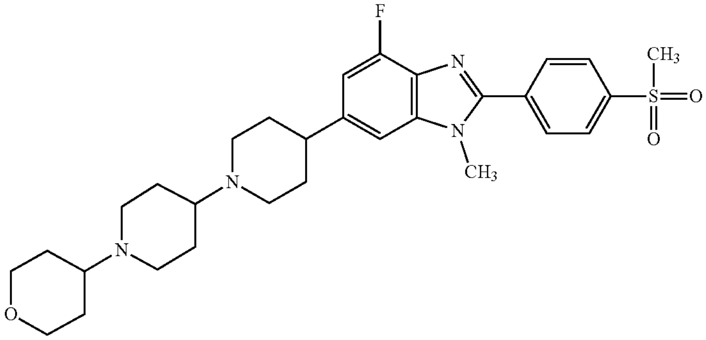 [SMILES: Cn1c(-c2ccc(S(C)(=O)=O)cc2)nc2c(F)cc(C3CCN(C4CCN(C5CCOCC5)CC4)CC3)cc21] | Ex. 105 |
| 281 | 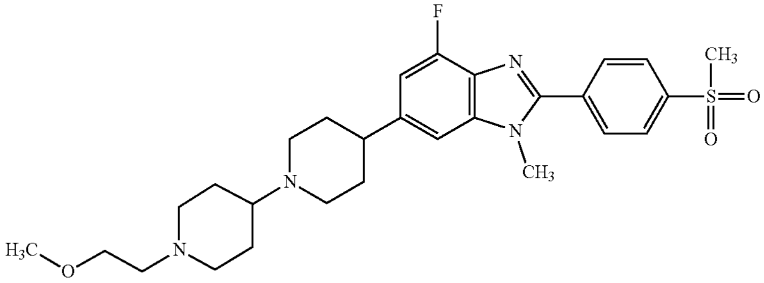 [SMILES: COCCN1CCC(N2CCC(c3cc(F)c4nc(-c5ccc(S(C)(=O)=O)cc5)n(C)c4c3)CC2)CC1] | Ex. 105 |
| 282 | 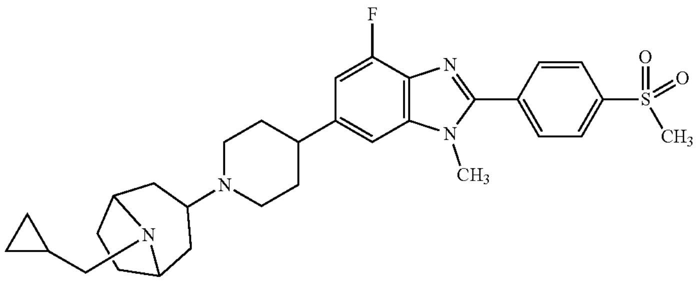 1st eluting isomer | Ex. 106 |

-continued
| Ex. No. | Structure | Method |
|---|---|---|
| 283 | 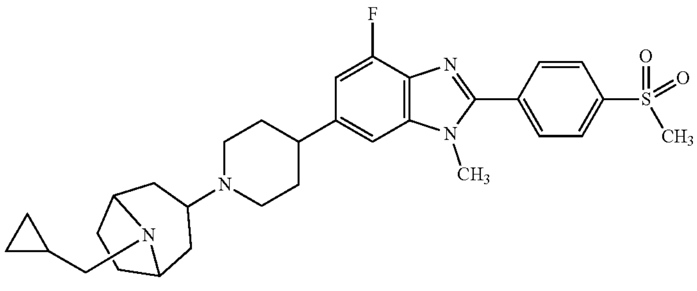 2nd eluting isomer | Ex. 106 |
| 284 | 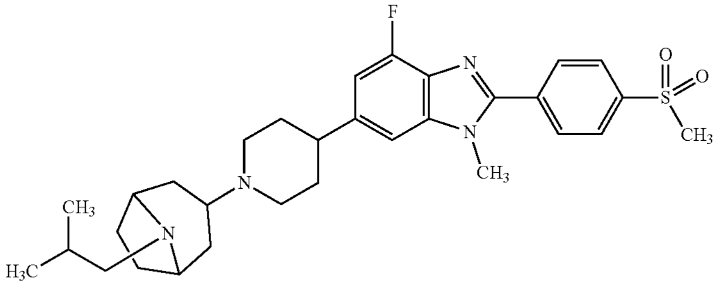 1st eluting isomer | Ex. 106 |
| 285 | 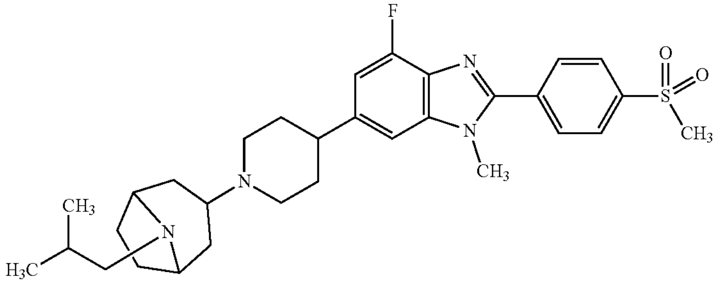 2nd eluting isomer | Ex. 106 |
| 286 | 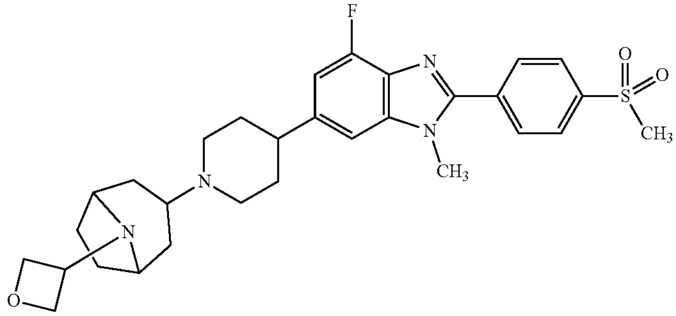 1st eluting isomer | Ex. 106 |

-continued
| Ex. No. | Structure | Method |
|---|---|---|
| 287 | 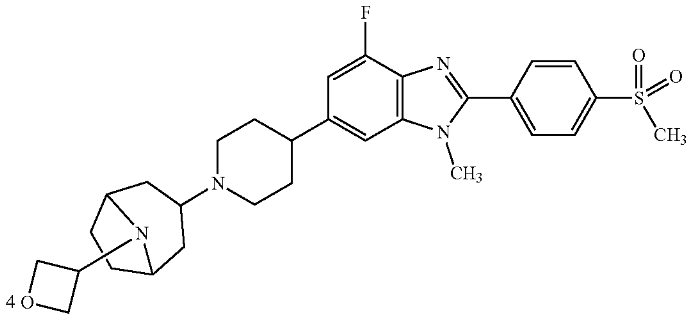<br>$2^{nd}$ eluting isomer | Ex. 106 |
| 288 | 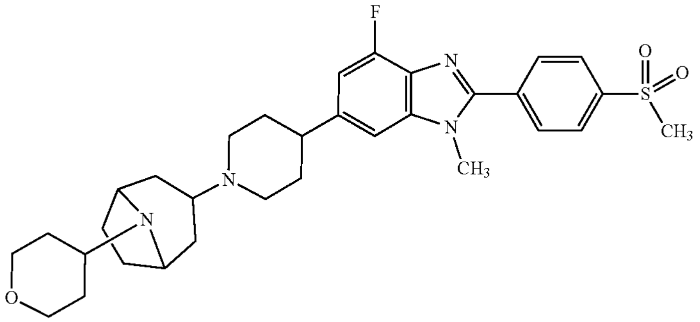<br>$1^{st}$ eluting isomer | Ex. 106 |
| 289 | 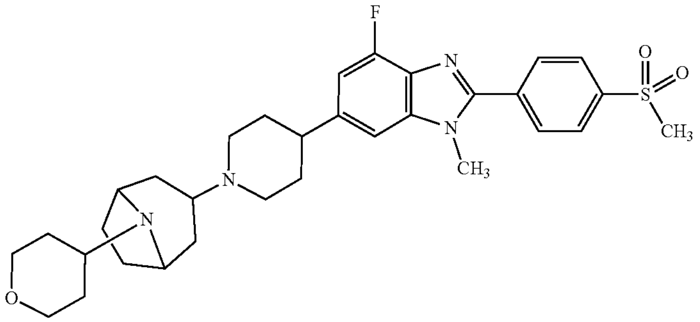<br>$2^{nd}$ eluting isomer | Ex. 106 |
| 290 | 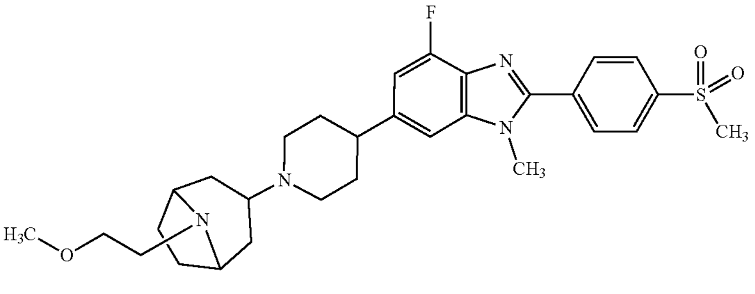<br>$1^{st}$ eluting isomer | Ex. 106 |

-continued
| Ex. No. | Structure | Method |
|---|---|---|
| 291 | 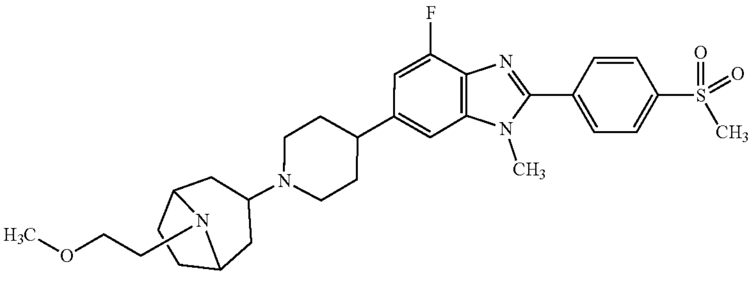 2nd eluting isomer | Ex. 106 |
| 292 | 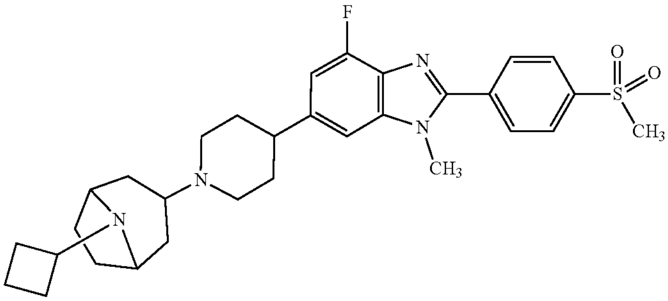 1st eluting isomer | Ex. 106 |
| 293 | 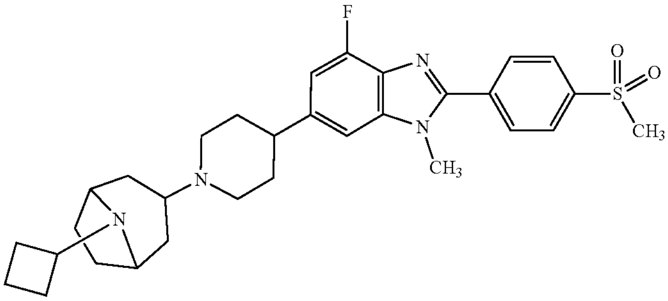 2nd eluting isomer | Ex. 106 |
| 294 | 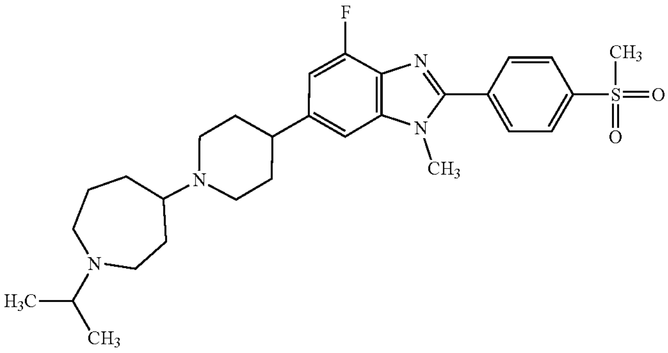 1st eluting enantiomer | Ex. 108 |

-continued
| Ex. No. | Structure | Method |
| --- | --- | --- |
| 295 | 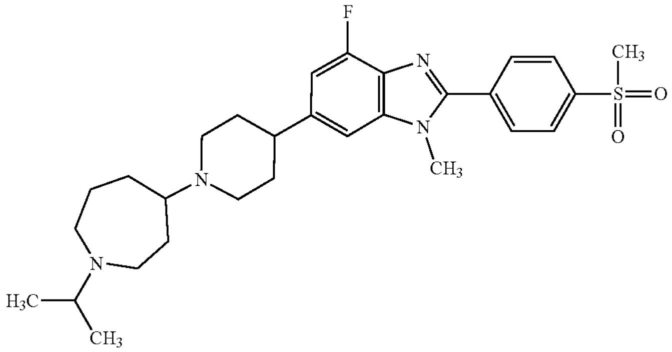 2nd eluting enantiomer | Ex. 108 |
| 296 | 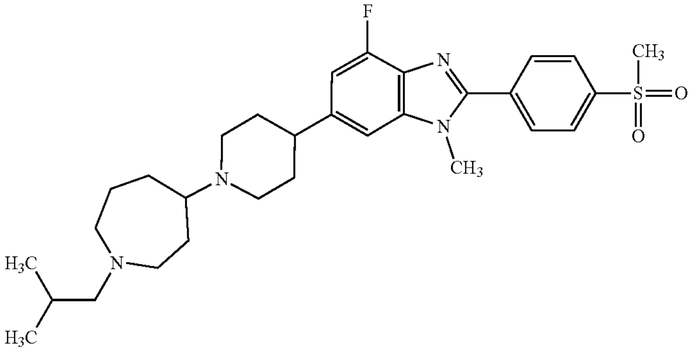 1st eluting enantiomer | Ex. 108 |
| 297 | 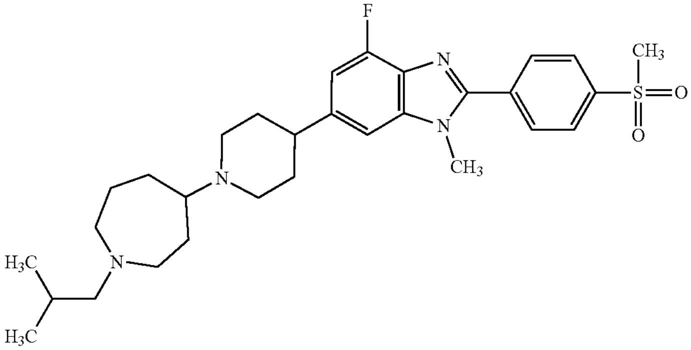 2nd eluting enantiomer | Ex. 108 |
| 298 | 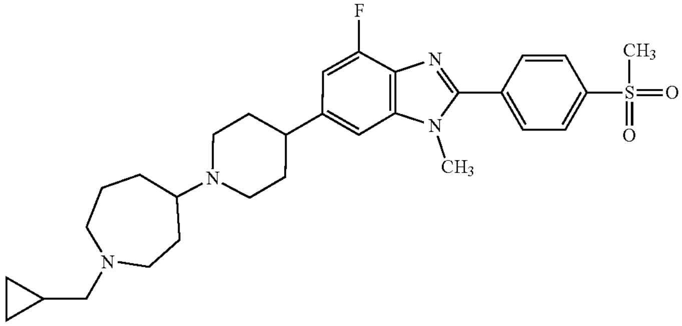 1st eluting enantiomer | Ex. 108 |

-continued
| Ex. No. | Structure | Method |
|---|---|---|
| 299 | 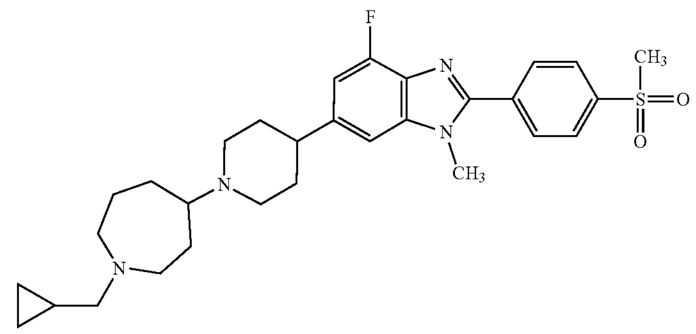 2nd eluting enantiomer | Ex. 108 |
| 300 | 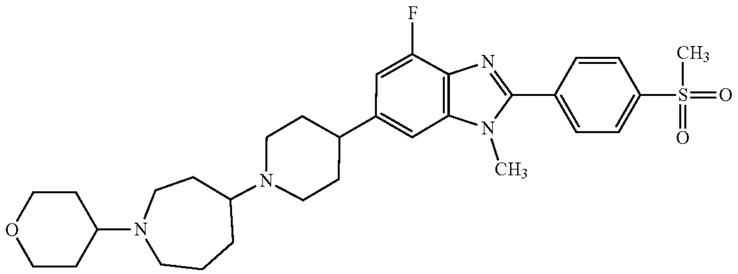 1st eluting enantiomer. | Ex. 108 |
| 301 | 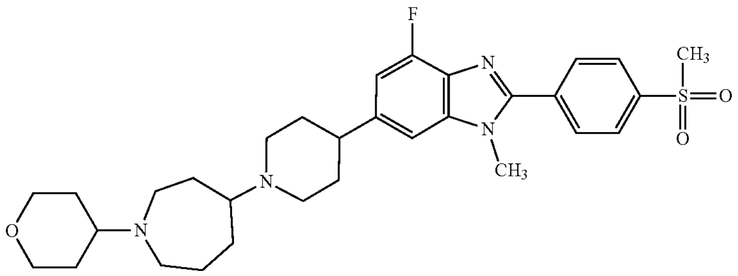 2nd eluting enantiomer | Ex. 108 |
| 302 | 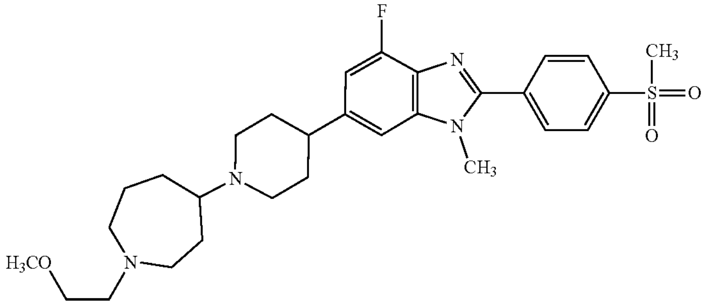 1st eluting enantiomer | Ex. 108 |

-continued
| Ex. No. | Structure | Method |
|---|---|---|
| 303 | 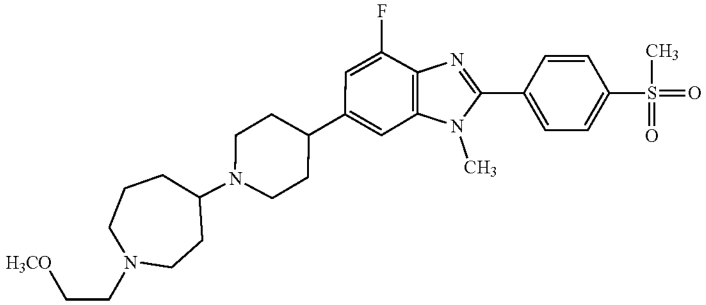 2nd eluting enantiomer | Ex. 108 |
| 304 | 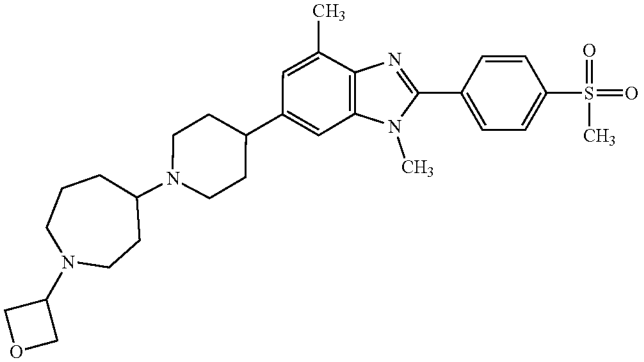 1st eluting enantiomer | Ex. 110 |
| 305 | 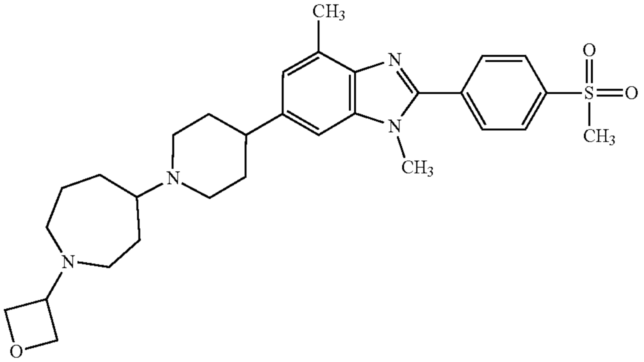 2nd eluting enantiomer | Ex. 110 |
| 306 | 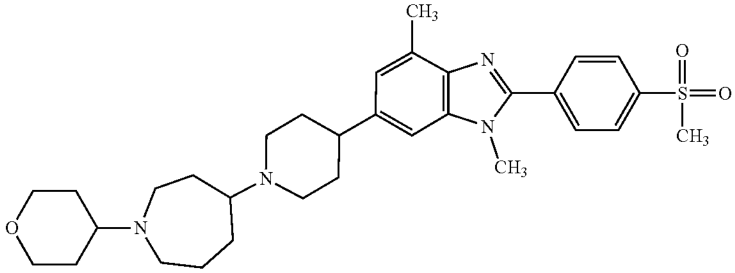 1st eluting enantiomer | Ex. 110 |

-continued
| Ex. No. | Structure | Method |
| --- | --- | --- |
| 307 | 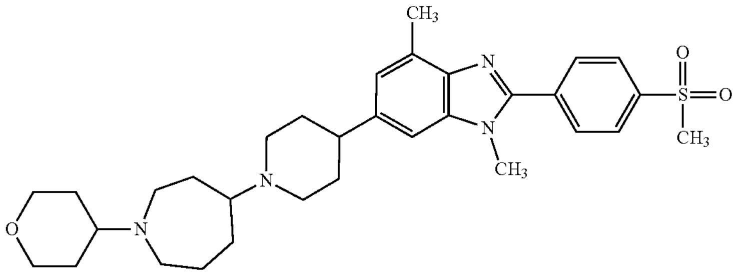 2nd eluting enantiomer | Ex. 110 |
| 308 | 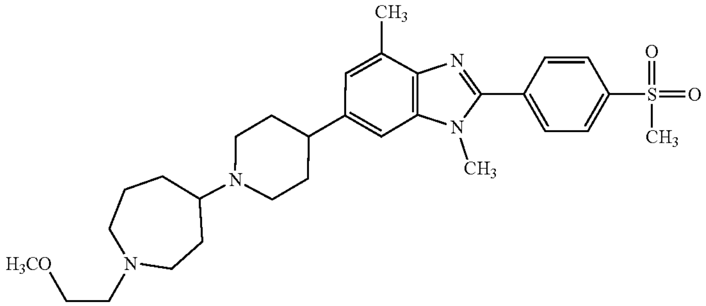 1st eluting enantiomer | Ex. 110 |
| 309 | 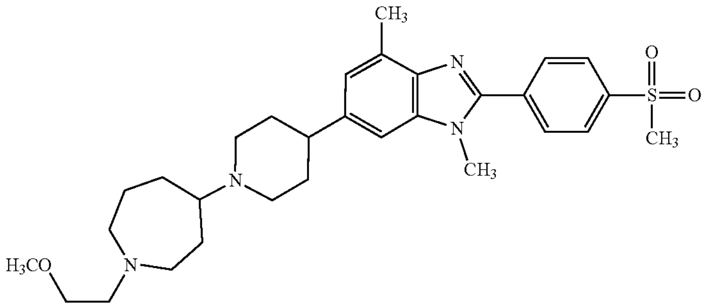 2nd eluting enantiomer | Ex. 110 |
| 310 | 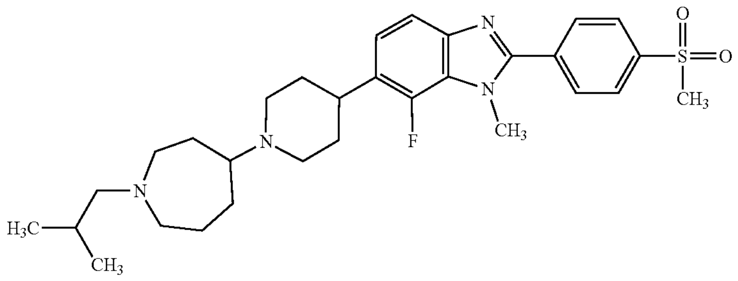 1st eluting enantiomer. | Ex. 113 |

-continued
| Ex. No. | Structure | Method |
| --- | --- | --- |
| 311 | 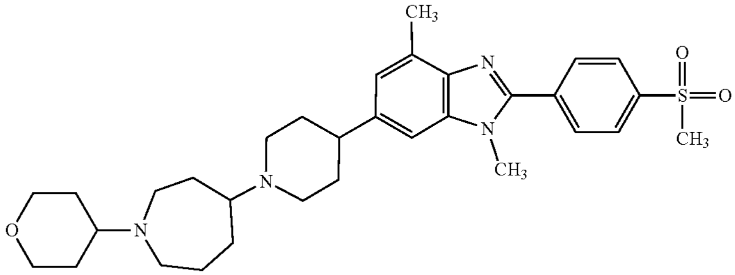 2nd eluting enantiomer | Ex. 113 |
| 312 | 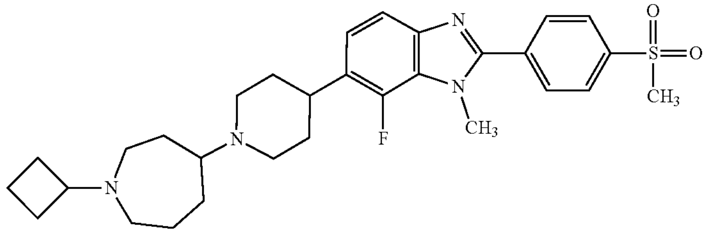 1st eluting enantiomer | Ex. 113 |
| 313 | 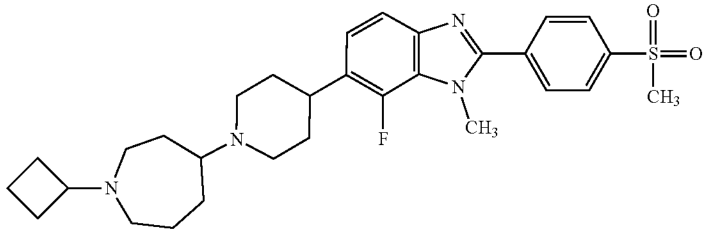 2nd eluting enantiomer | Ex. 113 |
| 314 | 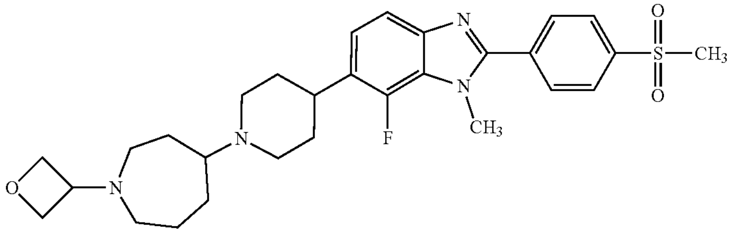 1st eluting enantiomer | Ex. 113 |
| 315 | 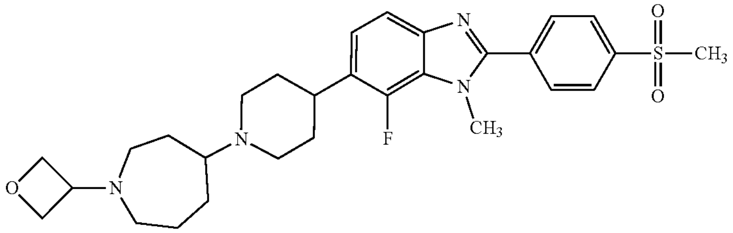 2nd eluting enantiomer | Ex. 113 |

-continued
| Ex. No. | Structure | Method |
|---|---|---|
| 316 | 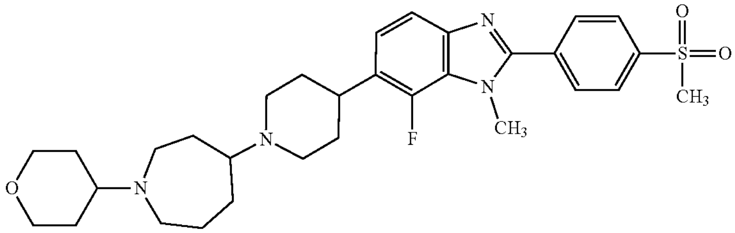 1st eluting enantiomer | Ex. 113 |
| 317 | 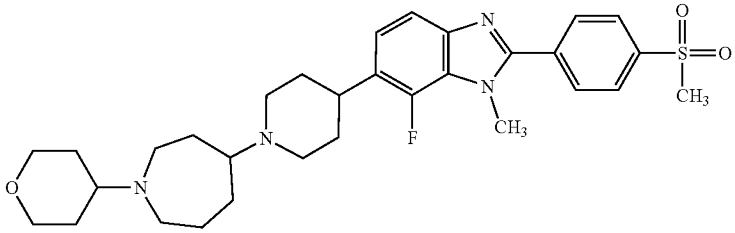 2nd eluting enantiomer | Ex. 113 |
| 318 | 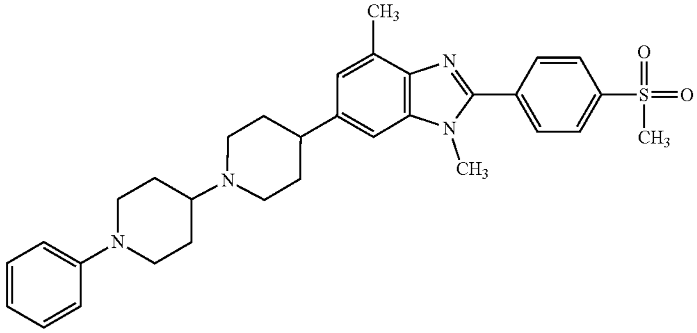 [SMILES: Cc1cc(C2CCN(C3CCN(c4ccccc4)CC3)CC2)cc2c1nc(-c1ccc(S(C)(=O)=O)cc1)n2C] | Ex. 22 |
| 319 | 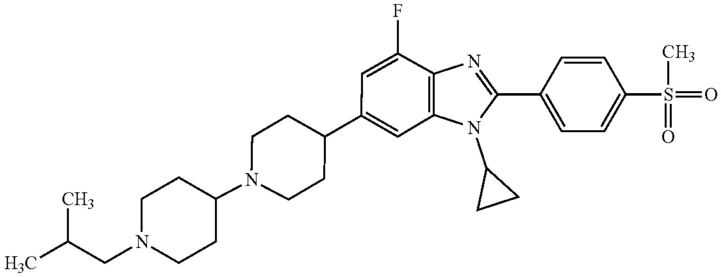 [SMILES: CC(C)CN1CCC(N2CCC(c3cc(F)c4nc(-c5ccc(S(C)(=O)=O)cc5)n(C5CC5)c4c3)CC2)CC1] | Ex. 115 |
| 320 | 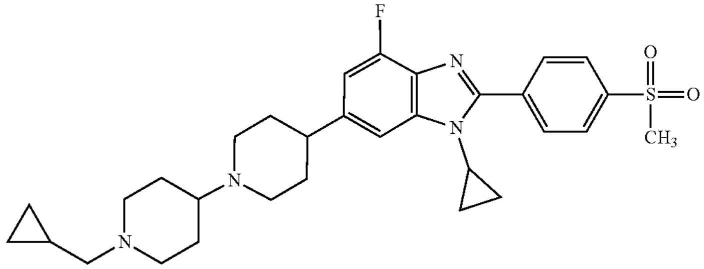 [SMILES: CS(=O)(=O)c1ccc(-c2nc3c(F)cc(C4CCN(C5CCN(CC6CC6)CC5)CC4)cc3n2C2CC2)cc1] | Ex. 115 |

-continued
| Ex. No. | Structure | Method |
|---|---|---|
| 321 | 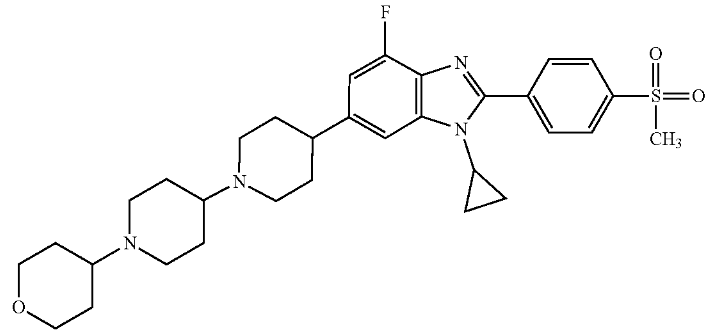 [SMILES: CS(=O)(=O)c1ccc(-c2nc3c(F)cc(C4CCN(C5CCN(C6CCOCC6)CC5)CC4)cc3n2C2CC2)cc1] | Ex. 115 |
| 322 | 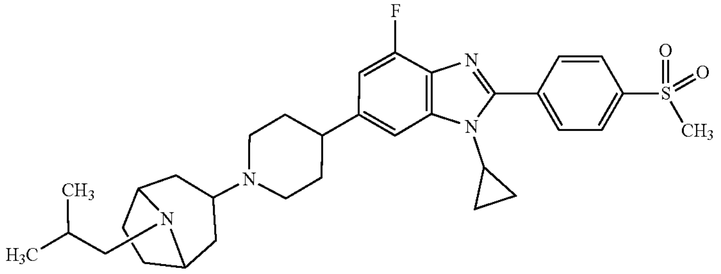<br>1st eluting isomer | Ex. 116 |
| 323 | 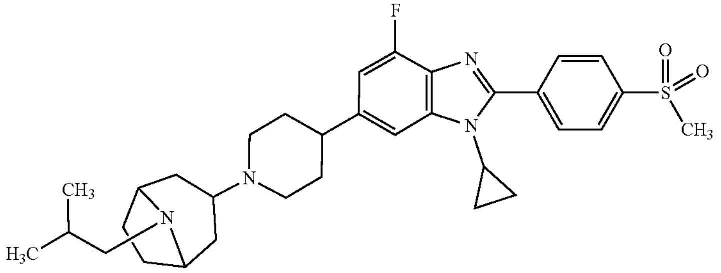<br>2nd eluting isomer | Ex. 116 |
| 324 | 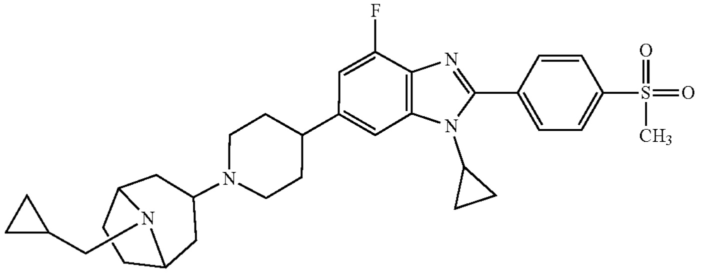<br>1st eluting isomer | Ex. 116 |

-continued
| Ex. No. | Structure | Method |
|---|---|---|
| 325 | 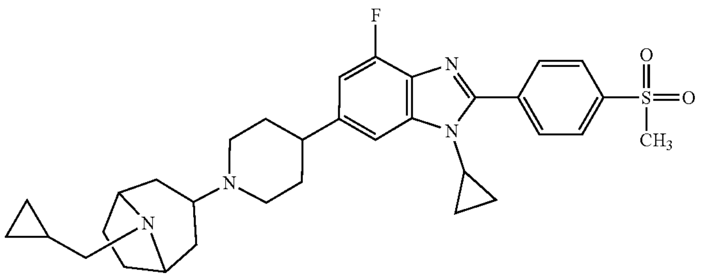<br>2nd eluting isomer | Ex. 116 |
| 326 | 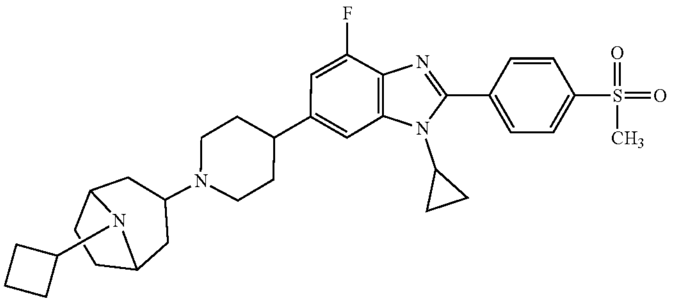<br>1st eluting isomer | Ex. 116 |
| 327 | 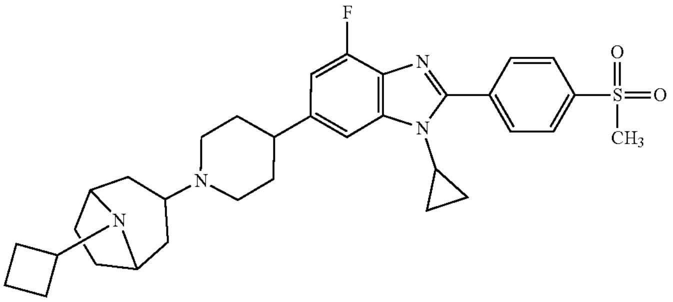<br>2nd eluting isomer | Ex. 116 |
| 328 | 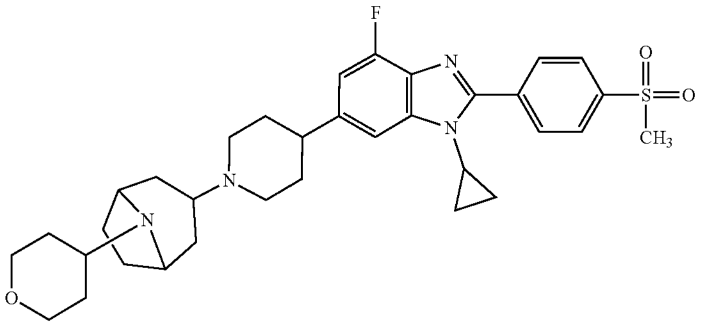<br>1st eluting isomer | Ex. 116 |

-continued
| Ex. No. | Structure | Method |
|---|---|---|
| 329 | 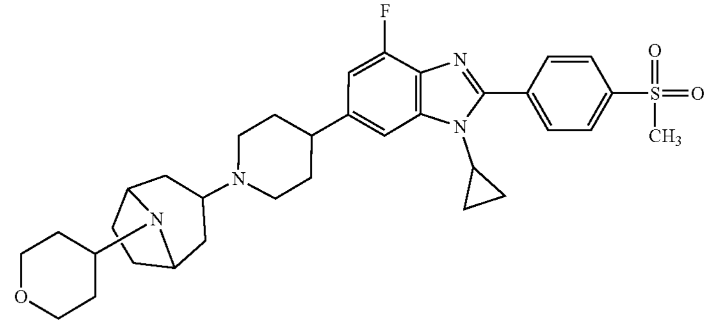 2nd eluting isomer | Ex. 116 |
| 330 | 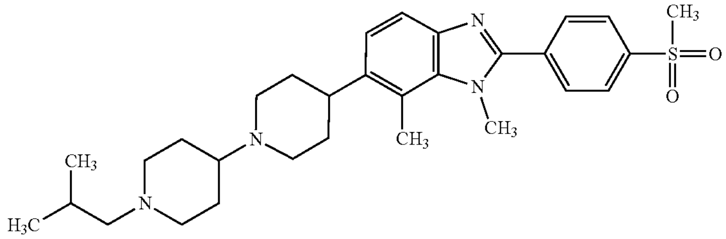 [SMILES: Cc1c(C2CCN(C3CCN(CC(C)C)CC3)CC2)ccc2nc(-c3ccc(S(C)(=O)=O)cc3)n(C)c12] | Ex. 119 |
| 331 | 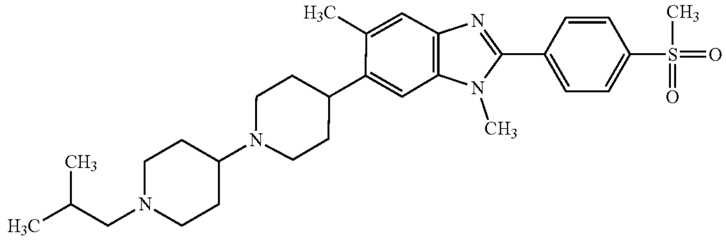 [SMILES: Cc1cc2nc(-c3ccc(S(C)(=O)=O)cc3)n(C)c2cc1C1CCN(C2CCN(CC(C)C)CC2)CC1] | Ex. 120 |
| 332 | 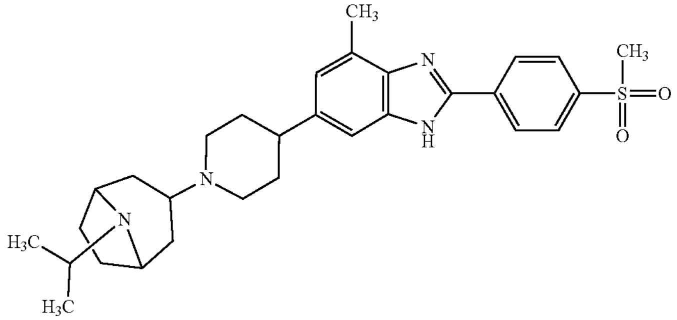 1st eluting isomer | Ex. 121 |

-continued
| Ex. No. | Structure | Method |
| --- | --- | --- |
| 333 | 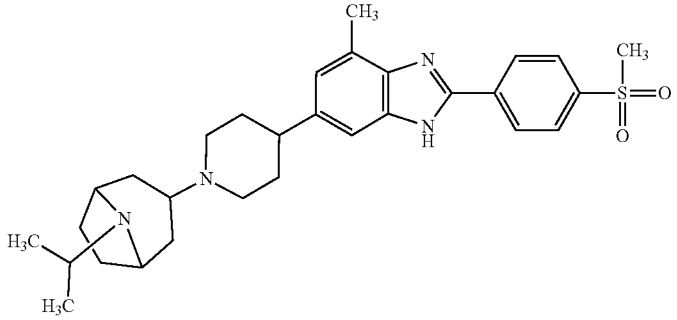 2nd eluting isomer | Ex. 121 |
| 334 | 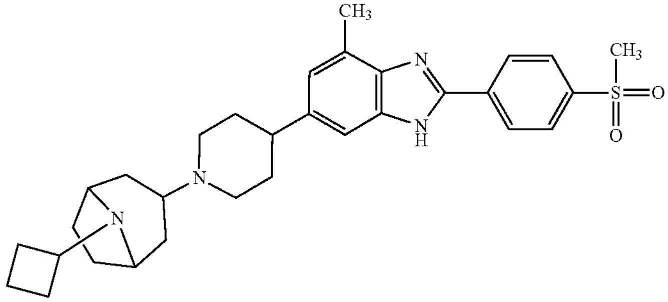 single isomer | Ex. 121 |
| 335 | 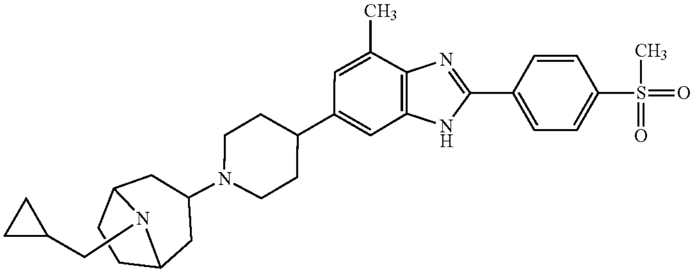 1st eluting isomer | Ex. 121 |
| 336 | 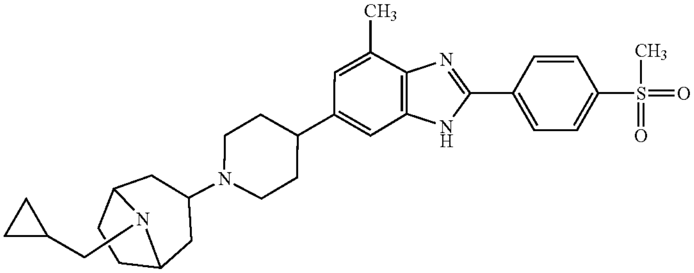 2nd eluting isomer | Ex. 121 |

-continued
| Ex. No. | Structure | Method |
|---|---|---|
| 337 | 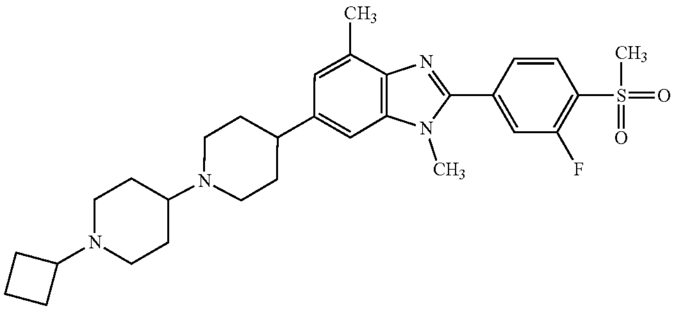 [SMILES: Cc1cc(C2CCN(C3CCN(C4CCC4)CC3)CC2)cc2c1nc(-c1ccc(S(C)(=O)=O)c(F)c1)n2C] | Ex. 122 |
| 338 | 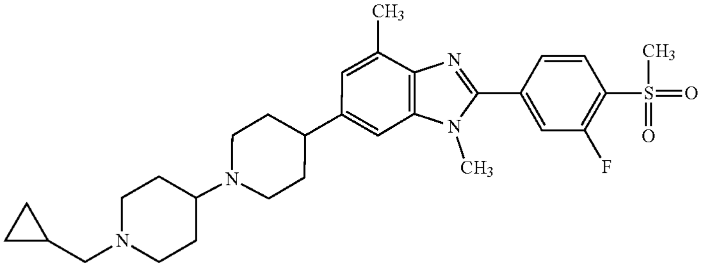 [SMILES: Cc1cc(C2CCN(C3CCN(CC4CC4)CC3)CC2)cc2c1nc(-c1ccc(S(C)(=O)=O)c(F)c1)n2C] | Ex. 122 |
| 339 | 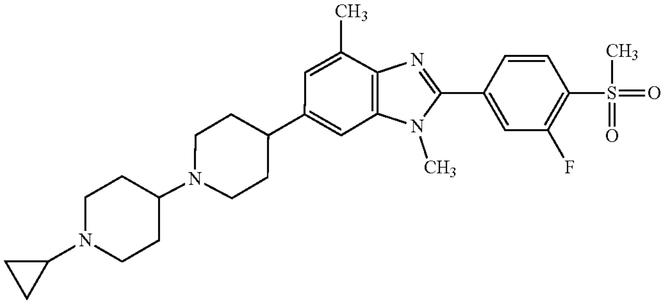 [SMILES: Cc1cc(C2CCN(C3CCN(C4CC4)CC3)CC2)cc2c1nc(-c1ccc(S(C)(=O)=O)c(F)c1)n2C] | Ex. 122 |
| 340 | 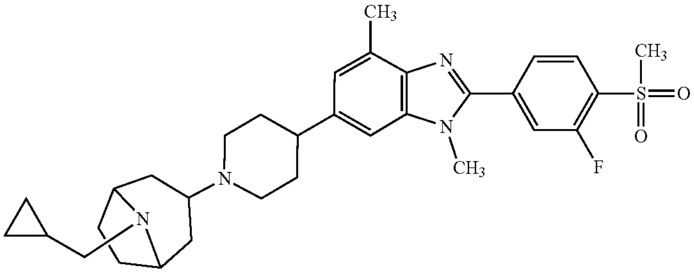<br>1st eluting isomer | Ex. 123 |
| 341 | 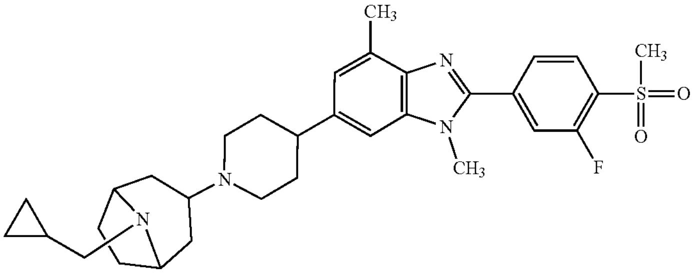<br>2nd eluting isomer | Ex. 123 |

-continued
| Ex. No. | Structure | Method |
|---|---|---|
| 342 | 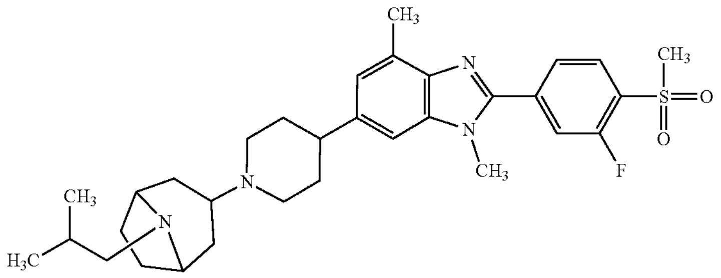 single isomer | Ex. 123 |
| 343 | 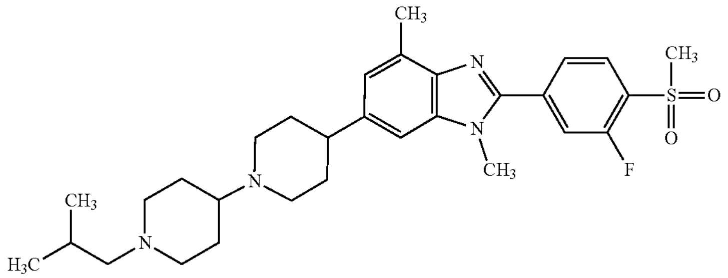 [SMILES: Cc1cc(C2CCN(C3CCN(CC(C)C)CC3)CC2)cc2c1nc(-c1ccc(S(C)(=O)=O)c(F)c1)n2C] | Ex. 122 |
| 344 | 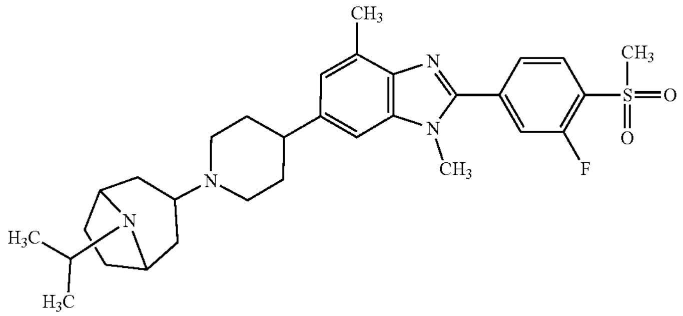 single isomer | Ex. 123 |
| 345 | 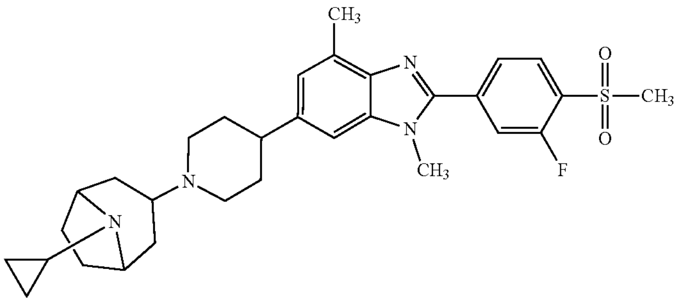 single isomer | Ex. 123 |

-continued
| Ex. No. | Structure | Method |
| --- | --- | --- |
| 346 | 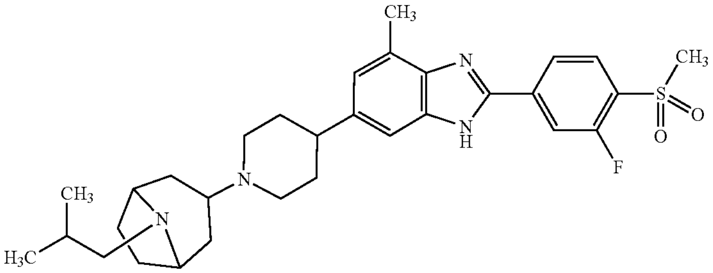 single isomer | Ex. 123 |
| 347 | 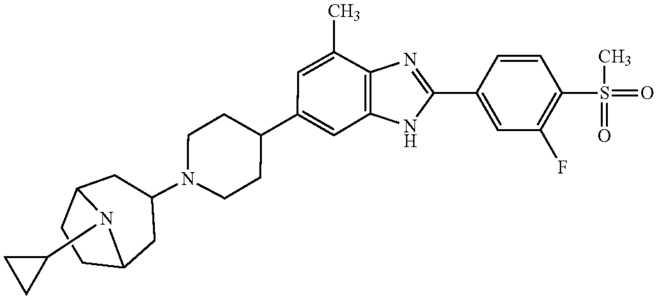 single isomer | Ex. 123 |
| 348 | 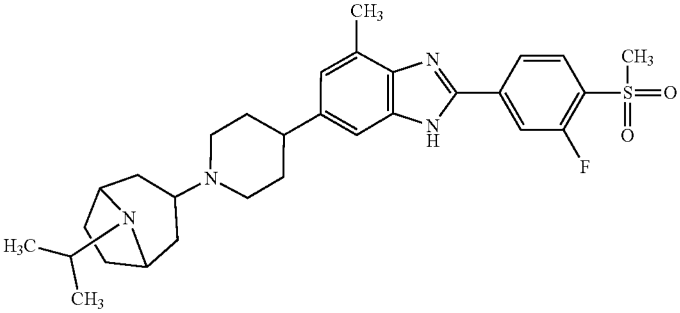 single isomer | Ex. 123 |
| 349 | 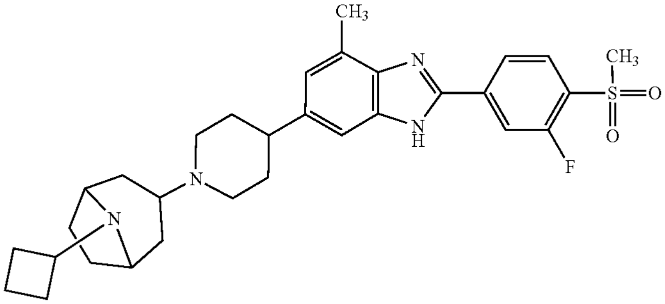 1st eluting isomer | Ex. 123 |

-continued
| Ex. No. | Structure | Method |
|---|---|---|
| 350 | 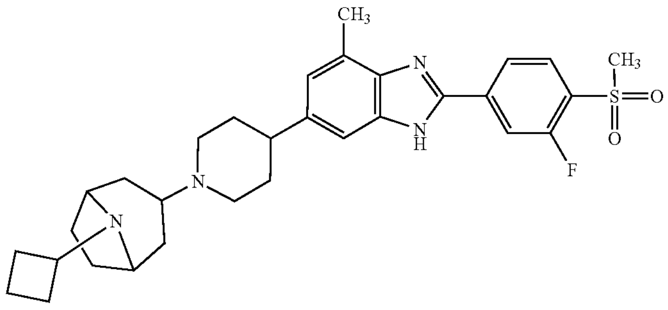<br>2nd eluting isomer | Ex. 123 |
| 351 | 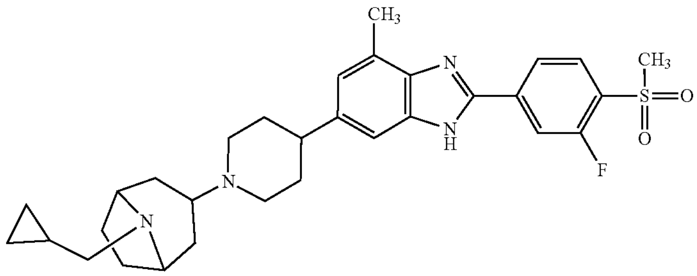<br>1st eluting isomer | Ex. 123 |
| 352 | 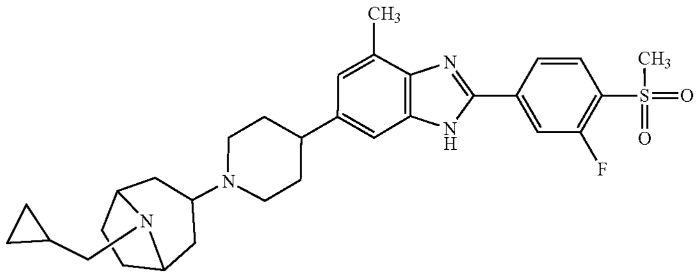<br>2nd eluting isomer | Ex. 123 |
| 353 | 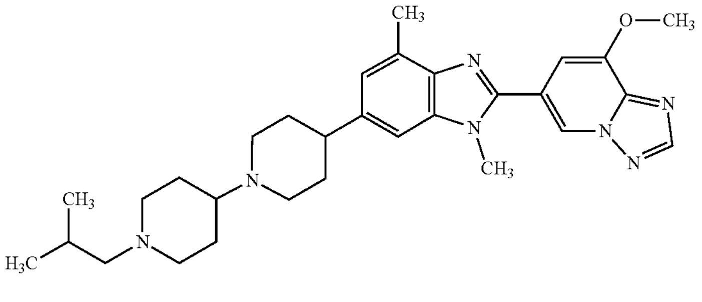 [SMILES: COc1cc(-c2nc3c(C)cc(C4CCN(C5CCN(CC(C)C)CC5)CC4)cc3n2C)cn2ncnc12] | Ex. 124 |

-continued
| Ex. No. | Structure | Method |
|---|---|---|
| 354 | 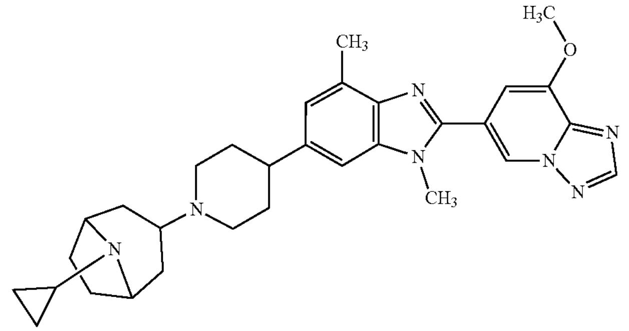 single isomer | Ex. 125 |
| 355 | 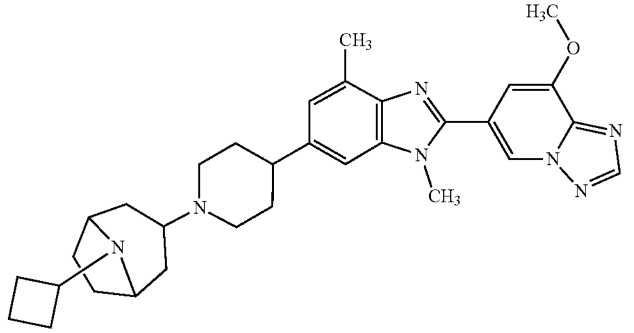 1st eluting isomer | Ex. 125 |
| 356 | 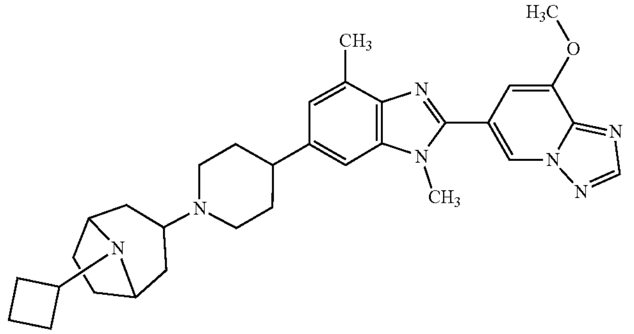 2nd eluting isomer | Ex. 125 |
| 357 | 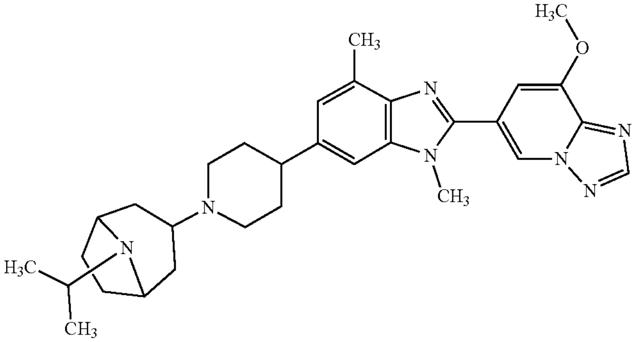 single isomer | Ex. 125 |

-continued
| Ex. No. | Structure | Method |
|---|---|---|
| 358 | 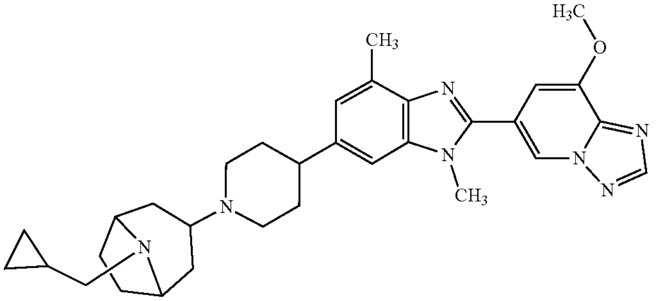<br>single isomer | Ex. 125 |
| 359 | 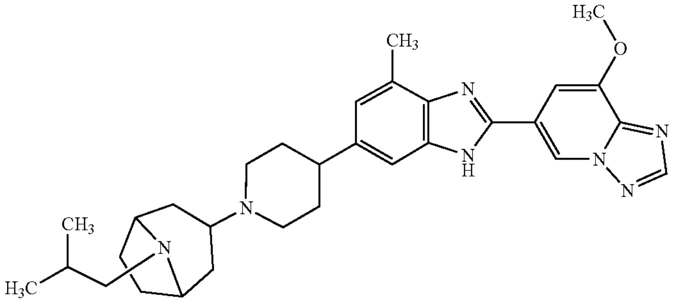<br>single isomer | Ex. 125 |
| 360 | 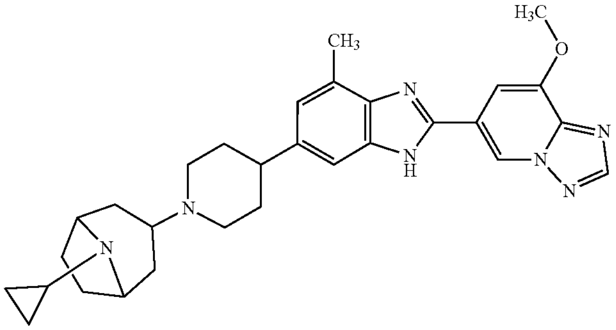<br>single isomer | Ex. 125 |
| 361 | 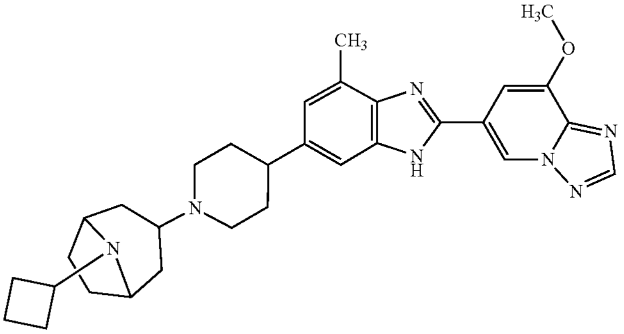<br>single isomer | Ex. 125 |

-continued

| Ex. No. | Structure | Method |
|---|---|---|
| 362 | 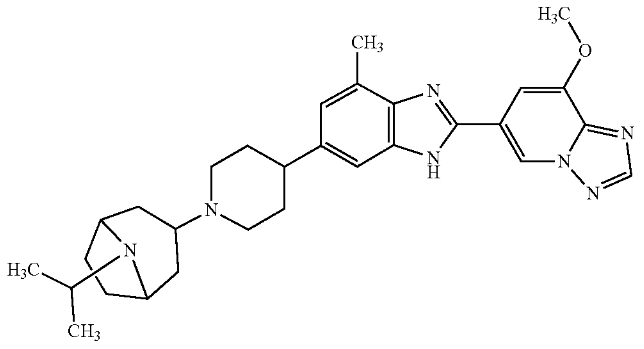<br>single isomer | Ex. 125 |

| Ex. No. | Analytical LC/MS, Preparative HPLC method, yield, and $^1$H NMR |
|---|---|
| 127 | Analytical LC/MS (Method 1): Purity: 100%; Observed Mass: 494.95; Retention Time: 0.99 min. (Method 2): Purity: 100%; Observed Mass: 495.00; Retention Time: 1.46 min. Prep Method 2: 17 mg, 17% yield; $^1$H NMR (500 MHz, DMSO-$d_6$) δ 7.79 (s, 2H), 7.25 (s, 1H), 7.16 (br d, J = 8.9 Hz, 1H), 6.99-6.89 (m, 1H), 3.90 (s, 3H), 3.86 (s, 3H), 3.74-3.53 (m, 1H), 3.25-3.12 (m, 2H), 3.07-2.91 (m, 4H), 2.51 (br s, 3H), 2.36-2.24 (m, 2H), 2.21-1.94 (m, 8H), 0.98 (br d, J = 6.7 Hz, 6H) (two protons obscured). TLR9 $IC_{50}$ (nM) = 31 |
| 128 | Analytical LC/MS (Method 1): Purity: 100%; Observed Mass: 479.23; Retention Time: 1.0 min. (Method 1): Purity: 94%; Observed Mass: 479.22; Retention Time: 1.39 min. Prep Method 2: 7.8 mg, 11% yield; $^1$H NMR (500 MHz, DMSO-$d_6$) δ 7.74 (br s, 2H), 7.22-7.16 (m, 1H), 7.13 (d, J = 8.2 Hz, 1H), 6.94-6.84 (m, 1H), 3.88 (s, 3H), 3.84 (s, 3H), 3.02-2.91 (m, 4H), 2.65-2.56 (m, 1H), 2.32-2.19 (m, 3H), 2.17-2.04 (m, 2H), 1.85-1.77 (m, 2H), 1.75-1.59 (m, 4H), 1.58-1.50 (m, 1H), 1.46-1.31 (m, 2H), 0.45-0.34 (m, 2H), 0.32-0.23 (m, 2H). TLR9 $IC_{50}$ (nM) = 270 |
| 129 | Analytical LC/MS (Method 1): Purity: 95.5%; Observed Mass: 481.25; Retention Time: 0.97 min. (Method 2): Purity: 96.1%; Observed Mass: 481.16; Retention Time: 1.34 min. Prep Method 1: 61 mg, 88% yield; $^1$H NMR (500 MHz, DMSO-$d_6$) δ 7.74-7.66 (m, 2H), 7.47-7.37 (m, 1H), 7.35-7.27 (m, 1H), 7.15-7.08 (m, 1H), 3.87 (s, 3H), 3.83 (s, 3H), 3.03-2.95 (m, 2H), 2.90-2.77 (m, 3H), 2.75-2.63 (m, 1H), 2.33-2.18 (m, 3H), 2.15-2.07 (m, 2H), 1.83-1.66 (m, 6H), 1.52-1.39 (m, 2H), 0.97 (d, J = 6.4 Hz, 6H) (one proton obscured). TLR9 $IC_{50}$ (nM) = 190 |
| 130 | Analytical LC/MS (Method 1): Purity: 100%; Observed Mass: 495.28; Retention Time: 1.0 min. (Method 1): Purity: 100%; Observed Mass: 495.22; Retention Time: 1.68 min. Prep Method 2: 16 mg, 34% yield; $^1$H NMR (500 MHz, DMSO-$d_6$) δ 7.75-7.63 (m, 2H), 7.49-7.38 (m, 1H), 7.35-7.26 (m, 1H), 7.16-7.07 (m, 1H), 3.87 (s, 3H), 3.83 (s, 3H), 3.66-3.49 (m, 3H), 3.05-2.97 (m, 2H), 2.92-2.78 (m, 4H), 2.36-2.20 (m, 3H), 2.04-1.98 (m, 2H), 1.87-1.66 (m, 6H), 1.55-1.42 (m, 2H), 0.84 (br d, J = 6.7 Hz, 6H). TLR9 $IC_{50}$ (nM) = 22 |
| 131 | Analytical LC/MS (Method 1): Purity: 97.2%; Observed Mass: 479.22; Retention Time: 0.98 min. (Method 2): Purity: 100%; Observed Mass: 479.22; Retention Time: 1.4 min. Prep Method 1: 19 mg, 29% yield; $^1$H NMR (500 MHz, DMSO-$d_6$) δ 7.73 (s, 2H), 7.54-7.23 (m, 2H), 7.14-7.09 (m, 1H), 3.87 (s, 3H), 3.83 (s, 3H), 3.03-2.93 (m, 4H), 2.86-2.76 (m, 1H), 2.35-2.25 (m, 3H), 2.17-2.05 (m, 2H), 1.84-1.65 (m, 6H), 1.60-1.50 (m, 1H), 1.45-1.34 (m, 2H), 0.43-0.36 (m, 2H), 0.32-0.21 (m, 2H) (one proton obscured). TLR9 $IC_{50}$ (nM) = 59 |
| 132 | Analytical LC/MS (Method 1): Purity: 93.4%; Observed Mass: 480.98; Retention Time: 1.01 min. (Method 2): Purity: 92.7%; Observed Mass: 480.91; Retention Time: 1.24 min. Prep Method 1: 43 mg, 59% yield; $^1$H NMR (500 MHz, DMSO-$d_6$) δ 7.76 (br s, 2H), 7.35-7.27 (m, 1H), 7.19-7.05 (m, 2H), 3.89 (s, 3H), 3.84 (s, 3H), 3.02-2.94 (m, 2H), 2.93-2.79 (m, 3H), 2.73-2.62 (m, 1H), 2.34-2.17 (m, 3H), 2.15-2.05 (m, 2H), 1.79-1.71 (m, 6H), 1.49-1.38 (m, 2H), 0.96 (d, J = 6.4 Hz, 6H) (one proton obscured. TLR9 $IC_{50}$ (nM) = 200 |
| 133 | Analytical LC/MS (Method 1): Purity: 95%; Observed Mass: 494.94; Retention Time: 1.01 min. (Method 2): Purity: 97.9%; Observed Mass: 495.26; Retention Time: 1.45 min. Prep Method 1: 24 mg, 32% yield; 1H NMR (500 MHz, DMSO-d6) δ 7.87-7.72 (m, 2H), 7.36-7.26 (m, 1H), 7.25- |

-continued

| Ex. No. | Analytical LC/MS, Preparative HPLC method, yield, and $^1$H NMR |
|---|---|
| | 7.10 (m, 2H), 3.88 (s, 3H), 3.86-3.80 (m, 3H), 3.06-2.96 (m, 2H), 2.95-2.80 (m, 3H), 2.33-2.16 (m, 3H), 2.03-1.97 (m, 2H), 1.89-1.69 (m, 8H), 1.57-1.40 (m, 3H), 0.84 (br d, J = 6.4 Hz, 6H) (one proton obscured). TLR9 $IC_{50}$ (nM) = 2200 |
| 134 | Analytical LC/MS (Method 1): Purity: 100%; Observed Mass: 522.98; Retention Time: 0.91 min. (Method 2): Purity: 99.2%; Observed Mass: 523.25; Retention Time: 1.18 min. Prep Method 1: 45 mg, 80% yield; $^1$H NMR (500 MHz, DMSO-$d_6$) δ 8.17-8.01 (m, 4H), 7.35-7.19 (m, 1H), 7.06-6.91 (m, 1H), 3.88 (s, 2H), 3.30 (s, 2H), 2.92-2.78 (m, 3H), 2.74-2.59 (m, 3H), 2.55 (s, 8H), 2.44-2.27 (m, 2H), 1.88-1.67 (m, 7H), 1.66-1.40 (m, 3H), 0.96 (br d, J = 2.7 Hz, 6H). TLR9 $IC_{50}$ (nM) = 21 |
| 135 | Analytical LC/MS (Method 1): Purity: 100%; Observed Mass: 535.19; Retention Time: 1.08 min. (Method 2): Purity: 100%; Observed Mass: 535.23; Retention Time: 1.23 min. Prep Method 1: 51 mg, 88% yield; $^1$H NMR (500 MHz, DMSO-$d_6$) δ 8.11 (s, 4H), 7.30 (s, 1H), 6.99 (s, 1H), 3.49-3.41 (m, 1H), 2.91-2.81 (m, 3H), 2.75-2.66 (m, 1H), 2.53 (br d, J = 18.9 Hz, 8H), 2.43-2.26 (m, 5H), 2.02-1.92 (m, 2H), 1.85-1.66 (m, 9H), 1.65-1.39 (m, 5H) (two protons obscured). TLR9 $IC_{50}$ (nM) = 23 |
| 136 | Analytical LC/MS (Method 1): Purity: 100%; Observed Mass: 536.95; Retention Time: 0.94 min. (Method 2): Purity: 100%; Observed Mass: 537.27; Retention Time: 1.35 min. Prep Method 2: 57 mg, 70% yield; $^1$H NMR (500 MHz, DMSO-$d_6$) δ 8.13 (s, 4H), 7.35-7.28 (m, 1H), 7.12-7.03 (m, 1H), 3.66-3.39 (m, 1H), 3.29-3.15 (m, 1H), 3.12-2.92 (m, 3H), 2.60-2.49 (m, 14H), 2.39-1.96 (m, 9H), 1.96-1.70 (m, 2H), 0.98 (dd, J = 6.4, 2.7 Hz, 6H) (two protons obscured). TLR9 $IC_{50}$ (nM) = 140 |
| 137 | Analytical LC/MS (Method 1): Purity: 97.5%; Observed Mass: 535.19; Retention Time: 1.09 min. (Method 2): Purity: 100%; Observed Mass: 534.97; Retention Time: 1.22 min. Prep Method 1: 47 mg, 79% yield; $^1$H NMR (500 MHz, DMSO-$d_6$) δ 8.03 (s, 4H), 7.22 (s, 1H), 6.91 (s, 1H), 3.80 (s, 3H), 3.46-3.29 (m, 2H), 3.22 (s, 2H), 2.85-2.68 (m, 3H), 2.67-2.55 (m, 3H), 2.45 (br d, J = 19.5 Hz, 3H), 2.33-2.23 (m, 4H), 1.80-1.58 (m, 8H), 1.56-1.38 (m, 3H), 0.80-0.70 (m, 1H), 0.41-0.33 (m, 2H), 0.06--0.07 (m, 2H). TLR9 $IC_{50}$ (nM) = 19 |
| 138 | Analytical LC/MS (Method 1): Purity: 100%; Observed Mass: 548.97; Retention Time: 0.97 min. (Method 2): Purity: 100%; Observed Mass: 549.00; Retention Time: 1.34 min. Prep Method 2: 58 mg, 70% yield; $^1$H NMR (500 MHz, DMSO-$d_6$) δ 8.15 (s, 4H), 7.36 (s, 1H), 7.10-7.01 (m, 1H), 3.97-3.88 (m, 3H), 3.66-3.40 (m, 1H), 3.34-3.29 (m, 3H), 3.30-3.14 (m, 3H), 3.14-2.96 (m, 2H), 2.80-2.66 (m, 1H), 2.61-2.57 (m, 3H), 2.53-2.49 (m, 3H), 2.40-2.28 (m, 2H), 2.27-2.00 (m, 8H), 1.98-1.77 (m, 6H), 1.75-1.61 (m, 1H) (two protons obscured). TLR9 $IC_{50}$ (nM) = 62 |
| 139 | Analytical LC/MS (Method 1): Purity: 100%; Observed Mass: 521.23; Retention Time: 0.92 min. (Method 2): Purity: 100%; Observed Mass: 521.22; Retention Time: 1.18 min. Prep Method 1: 40 mg, 62% yield; $^1$H NMR (500 MHz, DMSO-$d_6$) δ 8.12 (s, 4H), 7.31 (s, 1H), 6.99 (s, 1H), 3.89 (s, 3H), 3.50-3.37 (m, 1H), 3.31 (s, 2H), 3.17-3.09 (m, 1H), 3.05-2.98 (m, 2H), 2.93-2.85 (m, 2H), 2.55 (s, 5H), 2.27-2.13 (m, 3H), 1.94-1.67 (m, 8H), 0.83 (d, J = 6.1 Hz, 6H) (one proton obscured). TLR9 $IC_{50}$ (nM) = 210 |
| 140 | Analytical LC/MS (Method 1): Purity: 100%; Observed Mass: 532.96; Retention Time: 0.93 min. (Method 2): Purity: 97.9%; Observed Mass: 533.18; Retention Time: 1.3 min. Prep Method 1: 33 mg, 49% yield; $^1$H NMR (500 MHz, DMSO-$d_6$) δ 8.16-8.08 (m, 4H), 7.35-7.28 (m, 1H), 7.02-6.94 (m, 1H), 3.89 (s, 3H), 3.49-3.39 (m, 3H), 3.35-3.28 (m, 2H), 3.23-3.13 (m, 1H), 2.97-2.85 (m, 2H), 2.73-2.56 (m, 4H), 2.29-2.18 (m, 2H), 2.16-2.00 (m, 3H), 1.98-1.52 (m, 14H). TLR9 $IC_{50}$ (nM) = 290 |
| 141 | Analytical LC/MS (Method 1): Purity: 99.3%; Observed Mass: 535.02; Retention Time: 0.98 min. (Method 2): Purity: 100%; Observed Mass: 535.02; Retention Time: 0.98 min. Prep Method 1: 35 mg, 54% yield; $^1$H NMR (500 MHz, DMSO-$d_6$) δ 8.16-8.05 (m, 4H), 7.35-7.25 (m, 1H), 7.03-6.96 (m, 1H), 3.96-3.75 (m, 4H), 3.63-3.40 (m, 6H), 3.34-3.25 (m, 3H), 2.96-2.86 (m, 2H), 2.82-2.71 (m, 1H), 2.55 (s, 5H), 2.41-2.30 (m, 2H), 2.29-2.17 (m, 2H), 2.16-2.03 (m, 3H), 2.00-1.90 (m, 2H), 1.88-1.54 (m, 6H). TLR9 $IC_{50}$ (nM) = 250 |
| 142 | Analytical LC/MS (Method 1): Purity: 97.5%; Observed Mass: 532.97; Retention Time: 0.94 min. (Method 2): Purity: 96.2%; Observed Mass: 533.2; Retention Time: 1.21 min. Prep Method 1: 39 mg, 57% yield; $^1$H NMR (500 MHz, DMSO-$d_6$) δ 8.11-8.03 (m, 4H), 7.30-7.24 (m, 1H), 6.98-6.92 (m, 1H), 3.84 (s, 3H), 3.43-3.32 (m, 1H), 3.29-3.22 (m, 2H), 3.17-3.09 (m, 1H), 3.06-3.00 (m, 1H), 2.89-2.80 (m, 2H), 2.50 (s, 5H), 2.20-2.10 (m, 4H), 2.09-1.99 (m, 1H), 1.87-1.80 (m, 3H), 1.79-1.62 (m, 6H), 0.68-0.60 (m, 1H), 0.35-0.28 (m, 2H), 0.01 (br d, J = 4.3 Hz, 2H). TLR9 $IC_{50}$ (nM) = 68 |
| 143 | Analytical LC/MS (Method 1): Purity: 100%; Observed Mass: 547.35; Retention Time: 1.01 min. (Method 2): Purity: 100%; Observed Mass: 546.97; Retention Time: 1.26 min. Prep Method 1: 37 mg, 55% yield; $^1$H NMR (500 MHz, DMSO-$d_6$) δ 8.11 (s, 4H), 7.34-7.28 (m, 1H), 7.02-6.96 |

-continued

| Ex. No. | Analytical LC/MS, Preparative HPLC method, yield, and $^1$H NMR |
|---|---|
| | (m, 1H), 3.89 (s, 3H), 3.49-3.37 (m, 1H), 3.33-3.23 (m, 2H), 3.21-3.10 (m, 1H), 2.94-2.83 (m, 2H), 2.53 (br d, J = 19.2 Hz, 8H), 2.31-2.17 (m, 3H), 2.16-2.03 (m, 1H), 2.00-1.85 (m, 5H), 1.85-1.68 (m, 8H), 1.67-1.56 (m, 2H). TLR9 $IC_{50}$ (nM) = 85 |
| 144 | Analytical LC/MS (Method 1): Purity: 95.1%; Observed Mass: 517.3; Retention Time: 0.99 min. (Method 2): Purity: 95.8%; Observed Mass: 517.02; Retention Time: 1.37 min. Prep Method 1: 41 mg, 45% yield; $^1$H NMR (500 MHz, DMSO-$d_6$) δ 7.38-7.31 (m, 2H), 7.25-7.21 (m, 1H), 7.16-7.11 (m, 1H), 6.95-6.91 (m, 1H), 3.88-3.83 (m, 6H), 3.05-2.98 (m, 2H), 2.83-2.73 (m, 1H), 2.70-2.59 (m, 1H), 2.56-2.49 (m, 7H), 2.23-2.15 (m, 2H), 1.95-1.87 (m, 2H), 1.86-1.76 (m, 4H), 1.76-1.62 (m, 4H), 1.60-1.51 (m, 2H), 1.50-1.42 (m, 2H), 1.03 (d, J = 6.1 Hz, 6H). TLR9 $IC_{50}$ (nM) = 62 |
| 145 | Analytical LC/MS (Method 1): Purity: 94.3%; Observed Mass: 516.9; Retention Time: 0.99 min. (Method 2): Purity: 98.1%; Observed Mass: 517.00; Retention Time: 1.58 min. Prep Method 1: 51 mg, 57% yield; $^1$H NMR (500 MHz, DMSO-$d_6$) δ 7.35 (s, 2H), 7.22 (s, 1H), 7.13 (d, J = 8.2 Hz, 1H), 6.94 (s, 1H), 3.85 (s, 6H), 3.35-3.26 (m, 1H), 2.71-2.57 (m, 2H), 2.53 (br d, J = 19.5 Hz, 7H), 2.41-2.32 (m, 1H), 1.96-1.67 (m, 16H), 1.07-0.99 (m, 6H). TLR9 $IC_{50}$ (nM) = 24 |
| 146 | Analytical LC/MS (Method 1): Purity: 95.8%; Observed Mass: 528.99; Retention Time: 0.98 min. (Method 2): Purity: 95.6%; Observed Mass: 529.29; Retention Time: 1.46 min. Prep Method 1: 47 mg, 52% yield; $^1$H NMR (500 MHz, DMSO-$d_6$) δ 7.38-7.30 (m, 2H), 7.23-7.18 (m, 1H), 7.15-7.10 (m, 1H), 6.96-6.92 (m, 1H), 3.84 (s, 3H), 3.64 (br s, 5H), 3.33-3.27 (m, 2H), 3.16-3.07 (m, 1H), 3.04-2.97 (m, 2H), 2.69-2.56 (m, 2H), 2.55 (s, 3H), 2.24-2.14 (m, 2H), 2.06-1.95 (m, 2H), 1.92-1.77 (m, 7H), 1.76-1.52 (m, 10H). TLR9 $IC_{50}$ (nM) = 70 |
| 147 | Analytical LC/MS (Method 1): Purity: 100%; Observed Mass: 528.97; Retention Time: 0.99 min. (Method 2): Purity: 98.9%; Observed Mass: 529.11; Retention Time: 1.64 min. Prep Method 1: 32 mg, 37% yield; $^1$H NMR (500 MHz, DMSO-$d_6$) δ 7.39-7.30 (m, 2H), 7.25-7.20 (m, 1H), 7.17-7.09 (m, 1H), 6.97-6.90 (m, 1H), 3.85 (s, 6H), 3.29-3.22 (m, 1H), 3.19-3.11 (m, 1H), 3.04-2.94 (m, 1H), 2.59-2.48 (m, 8H), 2.42-2.30 (m, 1H), 2.02-1.53 (m, 21H). TLR9 $IC_{50}$ (nM) = 200 |
| 148 | Analytical LC/MS (Method 1): Purity: 97.8%; Observed Mass: 528.98; Retention Time: 1.06 min. (Method 2): Purity: 96%; Observed Mass: 528.96; Retention Time: 1.39 min. Prep Method 1: 27 mg, 30% yield; $^1$H NMR (500 MHz, DMSO-$d_6$) δ 7.25-7.17 (m, 2H), 7.10-7.05 (m, 1H), 7.02-6.97 (m, 1H), 6.83-6.77 (m, 1H), 3.71 (s, 5H), 3.49-3.33 (m, 2H), 2.92-2.83 (m, 2H), 2.55-2.47 (m, 1H), 2.45-2.42 (m, 2H), 2.22 (br d, J = 6.1 Hz, 2H), 2.13-2.02 (m, 2H), 1.74 (br s, 4H), 1.70-1.63 (m, 2H), 1.62-1.41 (m, 8H), 0.79-0.69 (m, 1H), 0.34 (br d, J = 6.7 Hz, 2H), 0.01 (br d, J = 4.0 Hz, 2H) (four protons obscured). TLR9 $IC_{50}$ (nM) = 34 |
| 149 | Analytical LC/MS (Method 1): Purity: 99.5%; Observed Mass: 528.99; Retention Time: 1.02 min. (Method 2): Purity: 99.3%; Observed Mass: 529.03; Retention Time: 1.65 min. Prep Method 1: 15 mg, 17% yield; $^1$H NMR (500 MHz, DMSO-$d_6$) δ 7.25-7.15 (m, 2H), 7.06 (s, 1H), 6.98 (br d, J = 8.5 Hz, 1H), 6.79 (s, 1H), 3.69 (s, 4H), 3.55-3.37 (m, 3H), 3.36-3.26 (m, 1H), 3.20-3.08 (m, 2H), 2.47-2.41 (m, 2H), 2.20 (br d, J = 4.9 Hz, 3H), 1.90-1.62 (m, 13H), 1.62-1.50 (m, 2H), 0.78-0.70 (m, 1H), 0.33 (br d, J = 8.2 Hz, 2H), 0.01 (br d, J = 4.6 Hz, 2H) (four protons obscured). TLR9 $IC_{50}$ (nM) = 47 |
| 150 | Analytical LC/MS (Method 1): Purity: 100%; Observed Mass: 542.98; Retention Time: 1.04 min. (Method 2): Purity: 100%; Observed Mass: 542.99; Retention Time: 1.52 min. Prep Method 1: 38 mg, 43% yield; $^1$H NMR (500 MHz, DMSO-$d_6$) δ 7.38-7.29 (m, 2H), 7.25-7.19 (m, 1H), 7.17-7.10 (m, 1H), 6.96-6.89 (m, 1H), 3.85 (s, 5H), 3.25-3.15 (m, 2H), 3.04-2.93 (m, 2H), 2.58-2.55 (m, 3H), 2.43-2.37 (m, 3H), 2.35-2.27 (m, 1H), 2.23-2.12 (m, 2H), 2.08-1.95 (m, 3H), 1.95-1.56 (m, 16H), 1.55-1.47 (m, 4H). TLR9 $IC_{50}$ (nM) = 32 |
| 151 | Analytical LC/MS (Method 1): Purity: 100%; Observed Mass: 542.99; Retention Time: 1.01 min. (Method 2): Purity: 96.8%; Observed Mass: 543.01; Retention Time: 1.77 min. Prep Method 1: 31 mg, 34% yield; $^1$H NMR (500 MHz, DMSO-$d_6$) δ 7.38-7.30 (m, 2H), 7.22-7.18 (m, 1H), 7.15-7.10 (m, 1H), 6.97-6.89 (m, 1H), 3.84 (s, 4H), 3.82-3.79 (m, 2H), 3.67-3.56 (m, 1H), 3.27-3.15 (m, 4H), 2.53 (s, 3H), 2.46-2.37 (m, 3H), 2.36-2.30 (m, 1H), 2.04-1.90 (m, 4H), 1.84 (br s, 11H), 1.78-1.61 (m, 8H). TLR9 $IC_{50}$ (nM) = 170 |
| 152 | Analytical LC/MS (Method 1): Purity: 97.4%; Observed Mass: 547.25; Retention Time: 0.94 min. (Method 2): Purity: 97.4%; Observed Mass: 546.94; Retention Time: 1.26 min. Prep Method 1: 33 mg, 33% yield; $^1$H NMR (500 MHz, DMSO-$d_6$) δ 8.10 (s, 4H), 7.29 (s, 1H), 6.98 (s, 1H), 3.92-3.83 (m, 3H), 3.59-3.54 (m, 3H), 3.32-3.22 (m, 4H), 3.15-3.05 (m, 1H), 3.03-2.95 (m, 2H), 2.67-2.56 (m, 2H), 2.27-2.16 (m, 2H), 2.04-1.94 (m, 2H), 1.92-1.76 (m, 8H), 1.75-1.49 (m, 9H). TLR9 $IC_{50}$ (nM) = 84 |
| 153 | Analytical LC/MS (Method 1): Purity: 100%; Observed Mass: 546.95; Retention Time: 0.94 min. (Method 2): Purity: 100%; Observed Mass: 547.26; Retention Time: 1.46 min. Prep Method 1: 14 mg, 14% yield; $^1$H |

-continued

| Ex. No. | Analytical LC/MS, Preparative HPLC method, yield, and $^1$H NMR |
|---|---|
| | NMR (500 MHz, DMSO-$d_6$) δ 8.10 (s, 4H), 7.28 (s, 1H), 6.99 (s, 1H), 3.87 (s, 2H), 3.69-3.54 (m, 3H), 3.25-3.18 (m, 2H), 3.13-2.99 (m, 1H), 2.55 (d, J = 2.7 Hz, 4H), 2.52 (br s, 5H), 2.41-2.32 (m, 1H), 2.03-1.89 (m, 4H), 1.89-1.78 (m, 9H), 1.77-1.55 (m, 5H). TLR9 $IC_{50}$ (nM) = 120 |
| 154 | Analytical LC/MS (Method 1): Purity: 99.1%; Observed Mass: 546.98; Retention Time: 0.89 min. (Method 2): Purity: 99.3%; Observed Mass: 546.99; Retention Time: 1.33 min. Prep Method 1: 32 mg, 33% yield; $^1$H NMR (500 MHz, DMSO-$d_6$) δ 7.98 (s, 4H), 7.16 (s, 1H), 6.91-6.84 (m, 1H), 3.75 (s, 3H), 3.49-3.30 (m, 2H), 3.17 (s, 2H), 2.94-2.81 (m, 2H), 2.56-2.43 (m, 3H), 2.28-2.18 (m, 2H), 2.13-2.03 (m, 2H), 1.76 (br s, 7H), 1.63-1.41 (m, 8H), 0.79-0.69 (m, 1H), 0.38-0.29 (m, 2H), 0.05--0.04 (m, 2H). TLR9 $IC_{50}$ (nM) = 30 |
| 155 | Analytical LC/MS (Method 1): Purity: 99.2%; Observed Mass: 546.99; Retention Time: 0.89 min. (Method 2): Purity: 98%; Observed Mass: 546.99; Retention Time: 1.52 min. Prep Method 1: 32 mg, 33% yield; $^1$H NMR (500 MHz, DMSO-$d_6$) δ 8.00 (s, 4H), 7.19 (s, 1H), 6.88 (s, 1H), 3.78 (s, 3H), 3.27-3.22 (m, 1H), 3.19 (s, 3H), 2.52-2.45 (m, 2H), 2.40 (br s, 4H), 2.30-2.21 (m, 1H), 2.19-2.09 (m, 2H), 1.90-1.81 (m, 2H), 1.74 (br d, J = 7.9 Hz, 13H), 0.77-0.69 (m, 1H), 0.39-0.27 (m, 2H), 0.04--0.03 (m, 2H). TLR9 $IC_{50}$ (nM) = 160 |
| 156 | Analytical LC/MS (Method 1): Purity: 99.2%; Observed Mass: 560.99; Retention Time: 0.98 min. (Method 2): Purity: 100%; Observed Mass: 560.97; Retention Time: 1.42 min. Prep Method 1: 34 mg, 34% yield; $^1$H NMR (500 MHz, DMSO-$d_6$) δ 8.11 (s, 4H), 7.29 (s, 1H), 7.01-6.96 (m, 1H), 3.88 (s, 2H), 3.30 (s, 2H), 3.24-3.16 (m, 2H), 3.04-2.94 (m, 2H), 2.60-2.57 (m, 1H), 2.51 (br s, 5H), 2.44-2.38 (m, 3H), 2.22-2.13 (m, 2H), 2.06-1.95 (m, 3H), 1.91-1.58 (m, 12H), 1.52 (br s, 4H). TLR9 $IC_{50}$ (nM) = 31 |
| 157 | Analytical LC/MS (Method 1): Purity: 96.9%; Observed Mass: 561.03; Retention Time: 0.92 min. (Method 2): Purity: 96.8%; Observed Mass: 561.32; Retention Time: 1.64 min. Prep Method 1: 21 mg, 21% yield; $^1$H NMR (500 MHz, DMSO-$d_6$) δ 8.10 (s, 4H), 7.29 (s, 1H), 6.99 (s, 1H), 3.88 (s, 2H), 3.63-3.52 (m, 4H), 3.29 (s, 4H), 3.23-3.14 (m, 2H), 2.61-2.57 (m, 1H), 2.45-2.39 (m, 3H), 2.38-2.30 (m, 1H), 2.04-1.90 (m, 5H), 1.86 (br s, 8H), 1.80-1.62 (m, 8H). TLR9 $IC_{50}$ (nM) = 340 |
| 158 | Analytical LC/MS (Method 1): Purity: 97%; Observed Mass: 548.96; Retention Time: 0.89 min. (Method 2): Purity: 100%; Observed Mass: 549.25; Retention Time: 1.21 min. Prep Method 1: 13 mg, 16% yield; $^1$H NMR (500 MHz, DMSO-$d_6$) δ 8.14-8.07 (m, 4H), 7.30 (s, 1H), 7.00 (s, 1H), 4.59-4.53 (m, 2H), 4.38-4.28 (m, 2H), 3.88 (s, 2H), 3.59-3.47 (m, 2H), 3.30 (s, 3H), 3.17-3.08 (m, 3H), 2.80-2.61 (m, 3H), 2.55 (s, 3H), 2.43-2.30 (m, 2H), 1.90-1.72 (m, 6H), 1.65 (br s, 4H), 1.56-1.50 (m, 2H). TLR9 $IC_{50}$ (nM) = 160 |
| 159 | Analytical LC/MS (Method 1): Purity: 100%; Observed Mass: 548.94; Retention Time: 0.90 min. (Method 2): Purity: 95.9%; Observed Mass: 549.26; Retention Time: 1.26 min. Prep Method 1: 9.1 mg, 11% yield; $^1$H NMR (500 MHz, DMSO-$d_6$) δ 8.14-8.06 (m, 4H), 7.32-7.25 (m, 1H), 7.03-6.96 (m, 1H), 4.53 (s, 2H), 4.31 (s, 2H), 3.87 (s, 2H), 3.71-3.52 (m, 3H), 3.28 (s, 3H), 3.24-3.18 (m, 1H), 3.02 (br s, 2H), 2.63-2.53 (m, 2H), 2.49-2.43 (m, 1H), 2.27-2.17 (m, 1H), 2.04-1.79 (m, 8H), 1.78-1.62 (m, 7H). TLR9 $IC_{50}$ (nM) = 930 |
| 160 | Analytical LC/MS (Method 1): Purity: 98.1%; Observed Mass: 576.95; Retention Time: 0.91 min. (Method 2): Purity: 100%; Observed Mass: 576.98; Retention Time: 1.24 min. Prep Method 1: 30 mg, 34% yield; $^1$H NMR (500 MHz, DMSO-$d_6$) δ 8.11 (s, 4H), 7.30 (s, 1H), 7.03-6.92 (m, 1H), 3.88 (s, 4H), 3.60-3.49 (m, 1H), 3.30 (s, 4H), 3.13-3.00 (m, 2H), 2.72-2.57 (m, 3H), 2.55 (s, 4H), 2.53-2.50 (m, 3H), 2.27-2.16 (m, 2H), 1.86-1.70 (m, 7H), 1.69-1.62 (m, 2H), 1.60-1.47 (m, 4H), 1.39-1.22 (m, 2H). TLR9 $IC_{50}$ (nM) = 52 |
| 161 | Analytical LC/MS (Method 1): Purity: 100%; Observed Mass: 576.93; Retention Time: 0.92 min. (Method 2): Purity: 97.4%; Observed Mass: 576.96; Retention Time: 1.40 min. Prep Method 1: 15 mg, 17% yield; $^1$H NMR (500 MHz, DMSO-$d_6$) δ 8.12 (s, 4H), 7.31 (s, 1H), 7.00 (s, 1H), 3.89 (s, 4H), 3.51-3.34 (m, 3H), 3.31 (s, 3H), 2.61-2.54 (m, 5H), 2.51 (br s, 6H), 2.47-2.33 (m, 2H), 1.93-1.80 (m, 7H), 1.78-1.65 (m, 6H), 1.33-1.19 (m, 2H). TLR9 $IC_{50}$ (nM) = 210 |
| 162 | Analytical LC/MS (Method 1): Purity: 100%; Observed Mass: 551.24; Retention Time: 0.90 min. (Method 2): Purity: 99.2%; Observed Mass: 551.29; Retention Time: 1.26 min. Prep Method 1: 13 mg, 15% yield; $^1$H NMR (500 MHz, DMSO-$d_6$) δ 8.11 (s, 4H), 7.30 (s, 1H), 6.99 (s, 1H), 3.88 (s, 2H), 3.54-3.38 (m, 2H), 3.30 (s, 2H), 3.25 (s, 3H), 3.03-2.94 (m, 2H), 2.55 (s, 6H), 2.52 (br s, 5H), 2.23-2.11 (m, 2H), 1.86 (s, 5H), 1.76-1.65 (m, 2H), 1.60 (br s, 2H), 1.56-1.46 (m, 3H). TLR9 $IC_{50}$ (nM) = 61 |
| 163 | Analytical LC/MS (Method 1): Purity: 100%; Observed Mass: 550.98; Retention Time: 0.88 min. (Method 2): Purity: 100%; Observed Mass: 551.32; Retention Time: 1.39 min. Prep Method 1: 6.7 mg, 8% yield; $^1$H NMR (500 MHz, DMSO-$d_6$) δ 8.17-8.05 (m, 4H), 7.30 (s, 1H), 6.99 (s, 1H), 3.89 (s, 3H), 3.48-3.36 (m, 1H), 3.31 (s, 2H), 3.24 (s, 3H), 3.20-3.11 |

-continued

| Ex. No. | Analytical LC/MS, Preparative HPLC method, yield, and $^1H$ NMR |
|---|---|
| | (m, 2H), 2.56 (s, 4H), 2.52 (br s, 2H), 2.39 (s, 2H), 2.36-2.30 (m, 1H), 1.95-1.63 (m, 13H) (three protons obscured). TLR9 $IC_{50}$ (nM) = 600 |
| 164 | Analytical LC/MS (Method 1): Purity: 100%; Observed Mass: 531.03; Retention Time: 0.93 min. (Method 2): Purity: 98.9%; Observed Mass: 531.04; Retention Time: 1.23 min. Prep Method 1: 8.3 mg, 14% yield; $^1H$ NMR (500 MHz, DMSO-$d_6$) δ 7.39-7.33 (m, 2H), 7.26-7.22 (m, 1H), 7.17-7.11 (m, 1H), 6.97-6.89 (m, 1H), 4.56 (s, 2H), 4.36-4.26 (m, 2H), 3.88-3.81 (m, 7H), 3.72-3.62 (m, 1H), 3.44-3.26 (m, 2H), 3.16-3.07 (m, 2H), 3.05-2.99 (m, 1H), 2.54 (br d, J = 8.2 Hz, 6H), 2.33-2.21 (m, 2H), 1.81 (br s, 6H), 1.66-1.48 (m, 6H). TLR9 $IC_{50}$ (nM) = 110 |
| 165 | Analytical LC/MS (Method 1): Purity: 100%; Observed Mass: 530.96; Retention Time: 0.96 min. (Method 2): Purity: 100%; Observed Mass: 531.00; Retention Time: 1.37 min. Prep Method 1: 19 mg, 33% yield; $^1H$ NMR (500 MHz, DMSO-$d_6$) δ 7.38-7.31 (m, 2H), 7.24-7.20 (m, 1H), 7.16-7.10 (m, 1H), 6.96-6.90 (m, 1H), 4.53 (s, 2H), 4.31 (s, 2H), 3.88-3.80 (m, 7H), 3.59-3.43 (m, 1H), 3.29-3.19 (m, 2H), 3.01 (br s, 2H), 2.58-2.55 (m, 3H), 2.47-2.37 (m, 1H), 2.00-1.65 (m, 17H). TLR9 $IC_{50}$ (nM) = 1300 |
| 166 | Analytical LC/MS (Method 1): Purity: 100%; Observed Mass: 559.04; Retention Time: 0.94 min. (Method 2): Purity: 100%; Observed Mass: 559.06; Retention Time: 1.24 min. Prep Method 2: 34 mg, 39% yield; $^1H$ NMR (500 MHz, DMSO-$d_6$) δ 7.64-7.56 (m, 1H), 7.54-7.46 (m, 2H), 7.33-7.25 (m, 2H), 4.45-4.37 (m, 1H), 4.34-4.21 (m, 1H), 3.98 (s, 4H), 3.90 (d, J = 13.4 Hz, 6H), 3.85-3.71 (m, 1H), 3.40-3.27 (m, 1H), 3.18 (s, 2H), 2.62 (s, 3H), 2.55 (s, 5H), 2.53-2.51 (m, 2H), 2.32-1.96 (m, 13H), 1.75-1.58 (m, 2H). TLR9 $IC_{50}$ (nM) = 40 |
| 167 | Analytical LC/MS (Method 1): Purity: 100%; Observed Mass: 559.0; Retention Time: 0.96 min. (Method 2): Purity: 100%; Observed Mass: 559.02; Retention Time: 1.52 min. Prep Method 1: 25 mg, 41% yield; $^1H$ NMR (500 MHz, DMSO-$d_6$) δ 7.37-7.32 (m, 2H), 7.26-7.21 (m, 1H), 7.17-7.11 (m, 1H), 6.96-6.92 (m, 1H), 3.91-3.82 (m, 8H), 3.49-3.25 (m, 5H), 2.57-2.53 (m, 6H), 2.46-2.33 (m, 2H), 2.11-1.66 (m, 16H), 1.46-1.26 (m, 4H). TLR9 $IC_{50}$ (nM) = 790 |
| 168 | Analytical LC/MS (Method 1): Purity: 100%; Observed Mass: 533.04; Retention Time: 0.97 min. (Method 2): Purity: 100%; Observed Mass: 533.02; Retention Time: 1.36 min. Prep Method 1: 13 mg, 22% yield; $^1H$ NMR (500 MHz, DMSO-$d_6$) δ 7.38-7.31 (m, 2H), 7.23-7.20 (m, 1H), 7.16-7.11 (m, 1H), 6.97-6.89 (m, 1H), 3.85 (s, 5H), 3.81 (s, 2H), 3.58-3.45 (m, 1H), 3.44-3.38 (m, 1H), 3.33-3.28 (m, 1H), 3.25 (s, 2H), 3.05-2.98 (m, 2H), 2.69-2.53 (m, 8H), 2.28-2.18 (m, 2H), 1.93-1.77 (m, 6H), 1.64 (br s, 5H), 1.59-1.48 (m, 4H). TLR9 $IC_{50}$ (nM) = 51 |
| 169 | Analytical LC/MS (Method 1): Purity: 99.4%; Observed Mass: 532.96; Retention Time: 0.97 min. (Method 2): Purity: 100%; Observed Mass: 533.01; Retention Time: 1.54 min. Prep Method 1: 16 mg, 28% yield; $^1H$ NMR (500 MHz, DMSO-$d_6$) δ 7.39-7.30 (m, 2H), 7.24-7.18 (m, 1H), 7.17-7.10 (m, 1H), 6.96-6.90 (m, 1H), 3.84 (s, 4H), 3.81 (s, 2H), 3.69-3.54 (m, 3H), 3.42 (s, 1H), 3.24 (s, 6H), 2.55 (s, 5H), 2.47 (s, 2H), 2.36 (br s, 1H), 2.02-1.92 (m, 2H), 1.92-1.78 (m, 9H), 1.71 (br d, J = 12.5 Hz, 4H). TLR9 $IC_{50}$ (nM) = 200 |
| 170 | Analytical LC/MS (Method 1): Purity: 99.2%; Observed Mass: 517.26; Retention Time: 1.18 min. (Method 2): Purity: 100%; Observed Mass: 517.20; Retention Time: 2.32 min. Prep Method 1: 18 mg, 26% yield; $^1H$ NMR (500 MHz, DMSO-$d_6$) δ 8.22-8.06 (m, 4H), 7.70-7.35 (m, 4H), 7.09-7.00 (m, 2H), 3.96 (s, 3H), 3.49 (br d, J = 4.9 Hz, 4H), 3.31 (s, 2H), 3.26-3.12 (m, 1H), 2.63 (s, 3H), 2.55 (s, 2H), 2.28-2.06 (m, 2H), 1.96-1.72 (m, 2H), 1.32-1.19 (m, 1H), 0.90 (br d, J = 6.4 Hz, 6H). TLR9 $IC_{50}$ (nM) = 4400 |
| 171 | Analytical LC/MS (Method 1): Purity: 100%; Observed Mass: 515.00; Retention Time: 1.17 min. (Method 2): Purity: 100%; Observed Mass: 515.25; Retention Time: 1.84 min. Prep Method 1: 28 mg, 41% yield; $^1H$ NMR (500 MHz, DMSO-$d_6$) δ 8.06-7.97 (m, 4H), 7.56-7.49 (m, 3H), 7.28-7.23 (m, 1H), 6.97-6.88 (m, 2H), 3.84 (s, 3H), 3.42-3.26 (m, 3H), 3.19 (s, 2H), 3.16-3.07 (m, 2H), 2.55-2.52 (m, 2H), 2.39 (br s, 5H), 2.21-2.08 (m, 2H), 0.82-0.71 (m, 1H), 0.44-0.36 (m, 2H), 0.05--0.04 (m, 2H). TLR9 $IC_{50}$ (nM) = 650 |
| 172 | Analytical LC/MS (Method 4): Purity: 97.9%; Observed Mass: 529.1; Retention Time: 1.182 min. (Method 2): Purity: 91.3%; Observed Mass: 529.1; Retention Time: 1.728 min. Prep Method 1: 26 mg, 37% yield; $^1H$ NMR (500 MHz, DMSO-$d_6$) δ 8.22-8.08 (m, 4H), 7.69-7.63 (m, 3H), 7.40-7.35 (m, 1H), 7.06-7.00 (m, 2H), 3.97 (s, 3H), 3.23-3.15 (m, 3H), 2.65-2.60 (m, 3H), 2.42-2.36 (m, 4H), 2.10-2.01 (m, 8H), 1.93-1.77 (m, 3H), 1.72-1.64 (m, 2H). TLR9 $IC_{50}$ (nM) = 1800 |
| 173 | Analytical LC/MS (Method 1): Purity: 95.3%; Observed Mass: 519.19; Retention Time: 1.07 min. (Method 2): Purity: 97.8%; Observed Mass: 519.16; Retention Time: 1.70 min. Prep Method 1: 37 mg, 51% yield; $^1H$ NMR (500 MHz, DMSO-$d_6$) δ 8.20-8.08 (m, 4H), 7.70-7.62 (m, 3H), 7.41-7.35 (m, 1H), 7.08-7.00 (m, 2H), 3.96 (br s, 3H), 3.53-3.42 (m, 2H), 3.31 (br s, 2H), 3.29-3.26 (m, 1H), 3.24-3.17 (m, 2H), 2.63 (br s, 7H), 2.57-2.55 (m, 1H), 2.52 (br s, 5H) (one proton obscured). TLR9 $IC_{50}$ (nM) = 1100 |

-continued

| Ex. No. | Analytical LC/MS, Preparative HPLC method, yield, and $^1$H NMR |
|---|---|
| 174 | Analytical LC/MS (Method 4): Purity: 98.7%; Observed Mass: 515.1; Retention Time: 1.080 min. (Method 5): Purity: 92%; Observed Mass: 515.3; Retention Time: 1.775 min. Prep Method 1: 44 mg, 64% yield; $^1$H NMR (500 MHz, DMSO-$d_6$) δ 8.20-8.10 (m, 4H), 7.69-7.61 (m, 3H), 7.41-7.36 (m, 1H), 7.07-7.00 (m, 2H), 3.9-3.95 (m, 3H), 3.22-3.17 (m, 6H), 2.81-2.72 (m, 1H), 2.63 (s, 3H), 2.44-2.40 (m, 5H), 2.05-1.97 (m, 2H), 1.89-1.79 (m, 2H), 1.71-1.63 (m, 2H). TLR9 $IC_{50}$ (nM) = 480 |
| 175 | Analytical LC/MS (Method 1): Purity: 95.5%; Observed Mass: 479.2; Retention Time: 1.01 min. (Method 2): Purity: 98.5%; Observed Mass: 478.94; Retention Time: 1.35 min. Prep Method 1: 9.2 mg, 13% yield; 1H NMR (500 MHz, DMSO-d6) δ 7.86-7.69 (m, 2H), 7.45-7.23 (m, 1H), 7.17-7.06 (m, 2H), 3.89 (s, 3H), 3.84 (s, 3H), 2.97 (br d, J = 10.7 Hz, 3H), 2.93-2.83 (m, 1H), 2.52 (br s, 3H), 2.33-2.23 (m, 2H), 2.18-2.07 (m, 2H), 1.97-1.85 (m, 1H), 1.74 (br s, 5H), 1.60-1.49 (m, 1H), 1.46-1.31 (m, 2H), 0.45-0.36 (m, 2H), 0.33-0.24 (m, 2H). TLR9 $IC_{50}$ (nM) = 530 |
| 176 | Analytical LC/MS (Method 4): Purity: 98.4%; Observed Mass: 545.1; Retention Time: 1.019 min. (Method 5): Purity: 95%; Observed Mass: 545.1; Retention Time: 1.574 min. Prep Method 1: 27 mg, 37% yield; $^1$H NMR (500 MHz, DMSO-$d_6$) δ 8.20-8.07 (m, 4H), 7.70-7.62 (m, 3H), 7.40-7.35 (m, 1H), 7.07-7.01 (m, 2H), 4.13-4.06 (m, 1H), 3.97 (s, 3H), 3.94-3.89 (m, 2H), 3.22-3.16 (m, 8H), 2.68-2.62 (m, 7H), 2.47-2.36 (m, 4H) (one proton obscured). TLR9 $IC_{50}$ (nM) = 680 |
| 177 | Analytical LC/MS (Method 1): Purity: 95.8%; Observed Mass: 512.91; Retention Time: 1.03 min. (Method 2): Purity: 100%; Observed Mass: 513.23; Retention Time: 1.40 min. Prep Method 1: 8.2 mg, 10% yield; $^1$H NMR (500 MHz, DMSO-$d_6$) δ 8.45-8.37 (m, 2H), 8.10 (br d, J = 8.5 Hz, 2H), 7.45-7.36 (m, 1H), 7.26-7.16 (m, 1H), 3.30-3.26 (m, 2H), 3.07-3.00 (m, 2H), 3.00-2.80 (m, 4H), 2.42-2.23 (m, 4H), 2.12-1.96 (m, 5H), 1.76 (br d, J = 7.2 Hz, 5H), 1.56-1.44 (m, 3H), 0.91-0.80 (m, 6H). TLR9 $IC_{50}$ (nM) = 120 |
| 178 | Analytical LC/MS (Method 1): Purity: 97.5%; Observed Mass: 496.93; Retention Time: 0.94 min. (Method 2): Purity: 95.3%; Observed Mass: 497.00; Retention Time: 1.28 min. Prep Method 1: 35 mg, 43% yield; $^1$H NMR (500 MHz, DMSO-$d_6$) δ 8.49-8.37 (m, 2H), 8.15-8.08 (m, 2H), 7.46-7.31 (m, 1H), 7.26-7.14 (m, 1H), 3.54-3.50 (m, 3H), 3.29 (s, 2H), 3.14-3.05 (m, 1H), 3.04-2.95 (m, 2H), 2.55 (s, 3H), 2.49-2.39 (m, 2H), 2.21-2.10 (m, 2H), 1.80 (br s, 5H), 1.63-1.55 (m, 1H), 1.50-1.39 (m, 2H), 0.43-0.37 (m, 2H), 0.29 (br d, J = 2.4 Hz, 2H). TLR9 $IC_{50}$ (nM) = 240 |
| 179 | Analytical LC/MS (Method 1): Purity: 98.7%; Observed Mass: 511.23; Retention Time: 0.96 min. (Method 2): Purity: 98.3%; Observed Mass: 511.24; Retention Time: 1.23 min. Prep Method 1: 22 mg, 33% yield; $^1$H NMR (500 MHz, DMSO-$d_6$) δ 8.40-8.30 (m, 2H), 8.07-7.99 (m, 2H), 7.37-7.29 (m, 1H), 7.20-7.11 (m, 1H), 3.54 (br s, 3H), 3.21 (s, 2H), 3.02-2.91 (m, 4H), 2.89-2.79 (m, 1H), 2.45 (s, 4H), 2.28-2.16 (m, 3H), 2.12 (br d, J = 6.5 Hz, 2H), 1.93-1.80 (m, 3H), 1.45 (br d, J = 2.0 Hz, 2H), 0.82-0.72 (m, 1H), 0.39 (br d, J = 7.6 Hz, 2H), 0.01 (br d, J = 4.6 Hz, 2H). TLR9 $IC_{50}$ (nM) = 180 |
| 180 | Analytical LC/MS (Method 1): Purity: 98.1%; Observed Mass: 510.89; Retention Time: 1.01 min. (Method 2): Purity: 100%; Observed Mass: 510.92; Retention Time: 1.31 min. Prep Method 1: 14 mg, 21% yield; $^1$H NMR (500 MHz, DMSO-$d_6$) δ 8.49-8.35 (m, 2H), 8.10 (br d, J = 8.3 Hz, 2H), 7.45-7.35 (m, 1H), 7.21 (s, 1H), 3.53 (br s, 3H), 3.28 (s, 2H), 3.05-2.97 (m, 2H), 2.97-2.89 (m, 1H), 2.88-2.81 (m, 2H), 2.75-2.61 (m, 1H), 2.39-2.23 (m, 3H), 2.02-1.90 (m, 2H), 1.76 (br s, 9H), 1.65-1.55 (m, 2H), 1.50-1.39 (m, 2H). TLR9 $IC_{50}$ (nM) = 25 |
| 181 | Analytical LC/MS (Method 1): Purity: 96.6%; Observed Mass: 513.40; Retention Time: 0.90 min. (Method 2): Purity: 100%; Observed Mass: 513.40; Retention Time: 1.01 min. Prep Method 1: 27 mg, 39% yield. $^1$H NMR (500 MHz, DMSO-$d_6$) δ 8.20-8.05 (m, 4H), 7.62-7.55 (m, 1H), 7.20-7.13 (m, 1H), 4.78-4.67 (m, 4H), 4.32-4.16 (m, 1H), 4.04 (s, 3H), 3.67-3.57 (m, 1H), 3.33 (s, 2H), 3.29-3.21 (m, 1H), 2.86-2.67 (m, 1H), 2.55 (s, 5H), 2.41-2.29 (m, 2H), 2.07 (br s, 6H) (one proton obscured). TLR9 $IC_{50}$ (nM) = 640 |
| 182 | Analytical LC/MS (Method 1): Purity: 95.1%; Observed Mass: 541.01; Retention Time: 0.98 min. (Method 2): Purity: 97.8%; Observed Mass: 541.14; Retention Time: 1.06 min. Prep Method 1: 8.4 mg, 11% yield; $^1$H NMR (500 MHz, DMSO-$d_6$) δ 8.48-8.37 (m, 2H), 8.15-8.07 (m, 2H), 7.44-7.35 (m, 1H), 7.26-7.18 (m, 1H), 3.92-3.83 (m, 2H), 3.56-3.54 (m, 3H), 3.05-2.89 (m, 4H), 2.51 (br s, 5H), 2.44-2.35 (m, 1H), 2.34-2.18 (m, 3H), 2.13-2.03 (m, 2H), 1.75 (br s, 5H), 1.70-1.62 (m, 2H), 1.49-1.34 (m, 4H). TLR9 $IC_{50}$ (nM) = 320 |
| 183 | Analytical LC/MS (Method 1): Purity: 94.9%; Observed Mass: 527.23; Retention Time: 0.93 min. (Method 2): Purity: 98.4%; Observed Mass: 527.15; Retention Time: 1.12 min. Prep Method 1: 8.3 mg, 11% yield; $^1$H NMR (500 MHz, DMSO-$d_6$) δ 8.42 (br d, J = 7.9 Hz, 2H), 8.11 (br d, J = 8.2 Hz, 2H), 7.40 (br d, J = 4.6 Hz, 1H), 7.21 (br t, J = 7.3 Hz, 1H), 4.64 (s, 2H), 4.25 (s, 2H), 3.57-3.35 (m, 3H), 3.22-3.09 (m, 2H), 3.08-2.89 (m, 3H), 2.80 (br d, J = 11.0 Hz, 2H), 2.63-2.58 (m, 2H), 2.41-2.24 (m, 3H), 1.95-1.91 (m, 2H), 1.76 (br d, J = 5.5 Hz, 6H), 1.52-1.38 (m, 2H). TLR9 $IC_{50}$ (nM) = 110 |

-continued

| Ex. No. | Analytical LC/MS, Preparative HPLC method, yield, and $^1$H NMR |
|---|---|
| 184 | Analytical LC/MS (Method 1): Purity: 97.5%; Observed Mass: 526.94; Retention Time: 1.04 min. (Method 2): Purity: 98.4%; Observed Mass: 526.94; Retention Time: 1.43 min. Prep Method 1: 17 mg, 21% yield; $^1$H NMR (500 MHz, DMSO-$d_6$) δ 8.20-8.08 (m, 4H), 7.46 (d, J = 8.5 Hz, 1H), 7.33-7.23 (m, 1H), 3.91 (s, 3H), 3.48 (br s, 7H), 3.12-3.04 (m, 1H), 3.03-2.87 (m, 2H), 2.47-2.31 (m, 2H), 2.15-2.01 (m, 2H), 1.98-1.86 (m, 2H), 1.85-1.71 (m, 6H), 1.59-1.46 (m, 2H), 0.85 (d, J = 6.6 Hz, 6H). TLR9 $IC_{50}$ (nM) = 850 |
| 185 | Analytical LC/MS (Method 1): Purity: 98.2%; Observed Mass: 511.15; Retention Time: 1.01 min. (Method 2): Purity: 100%; Observed Mass: 511.22; Retention Time: 1.35 min. Prep Method 1: 36 mg, 45% yield; $^1$H NMR (500 MHz, DMSO-$d_6$) δ 8.19-8.08 (m, 4H), 7.44 (d, J = 8.5 Hz, 1H), 7.33-7.23 (m, 1H), 3.91 (s, 3H), 3.52-3.47 (m, 2H), 3.07-2.91 (m, 4H), 2.55-2.48 (m, 2H), 2.42-2.31 (m, 3H), 2.19-2.08 (m, 2H), 1.76 (br s, 6H), 1.61-1.53 (m, 1H), 1.47-1.34 (m, 2H), 0.46-0.36 (m, 2H), 0.28 (br d, J = 2.1 Hz, 2H). TLR9 $IC_{50}$ (nM) = 700 |
| 186 | Analytical LC/MS (Method 1): Purity: 98.2%; Observed Mass: 526.96; Retention Time: 1.16 min. (Method 2): Purity: 100%; Observed Mass: 526.94; Retention Time: 1.16 min. Prep Method 1: 20 mg, 37% yield; $^1$H NMR (500 MHz, DMSO-$d_6$) δ 8.13 (d, J = 2.5 Hz, 4H), 7.45 (br d, J = 8.5 Hz, 1H), 7.31-7.25 (m, 1H), 4.56-4.48 (m, 2H), 4.45-4.37 (m, 2H), 3.90 (s, 2H), 3.53 (br s, 6H), 3.47-3.34 (m, 1H), 3.16-2.97 (m, 2H), 2.80-2.72 (m, 2H), 2.56-2.53 (m, 3H), 1.88-1.71 (m, 7H), 1.60-1.46 (m, 2H). TLR9 $IC_{50}$ (nM) = 7300 |
| 187 | Analytical LC/MS (Method 1): Purity: 98.5%; Observed Mass: 555.25; Retention Time: 0.93 min. (Method 2): Purity: 98.9%; Observed Mass: 555.26; Retention Time: 1.08 min. Prep Method 1: 12 mg, 22% yield; $^1$H NMR (500 MHz, DMSO-$d_6$) δ 8.24-8.06 (m, 4H), 7.52-7.44 (m, 1H), 7.34-7.24 (m, 1H), 3.92 (s, 4H), 3.52-3.35 (m, 3H), 3.32 (s, 1H), 3.30-3.23 (m, 1H), 3.19-2.97 (m, 4H), 2.55-2.51 (m, 6H), 2.49-2.42 (m, 1H), 2.30-2.12 (m, 2H), 1.91-1.76 (m, 5H), 1.76-1.67 (m, 2H), 1.58-1.38 (m, 4H). TLR9 $IC_{50}$ (nM) = 520 |
| 188 | Analytical LC/MS (Method 1): Purity: 100%; Observed Mass: 529.27; Retention Time: 0.93 min. (Method 2): Purity: 98.9%; Observed Mass: 529.44; Retention Time: 1.09 min. Prep Method 1: 28 mg, 52% yield; $^1$H NMR (500 MHz, DMSO-$d_6$) δ 8.12 (s, 4H), 7.47-7.40 (m, 1H), 7.32-7.24 (m, 1H), 3.77-3.72 (m, 6H), 3.45-3.39 (m, 1H), 3.29 (s, 3H), 3.21 (s, 2H), 3.02-2.96 (m, 2H), 2.95-2.87 (m, 2H), 2.46-2.41 (m, 2H), 2.32-2.18 (m, 3H), 1.99-1.89 (m, 2H), 1.84-1.68 (m, 6H), 1.52-1.41 (m, 2H). TLR9 $IC_{50}$ (nM) = 440 |
| 189 | Analytical LC/MS (Method 1): Purity: 97.6%; Observed Mass: 553.31; Retention Time: 1.07 min. (Method 2): Purity: 100%; Observed Mass: 553.22; Retention Time: 1.42 min. Prep Method 1: 16 mg, 21% yield; $^1$H NMR (500 MHz, DMSO-$d_6$) δ 8.11 (s, 4H), 7.46-7.42 (m, 1H), 7.29-7.25 (m, 1H), 3.28 (s, 3H), 3.09-3.00 (m, 2H), 2.99-2.90 (m, 1H), 2.31-2.16 (m, 5H), 1.91-1.83 (m, 4H), 1.81-1.72 (m, 5H), 1.72-1.61 (m, 6H), 1.59-1.51 (m, 3H), 0.89-0.85 (m, 6H). TLR9 $IC_{50}$ (nM) = 150 |
| 190 | Analytical LC/MS (Method 1): Purity: 95.3%; Observed Mass: 553.30; Retention Time: 0.99 min. (Method 2): Purity: 95.6%; Observed Mass: 553.28; Retention Time: 1.51 min. Prep Method 1: 6.7 mg, 9% yield; $^1$H NMR (500 MHz, DMSO-$d_6$) δ 8.17-8.08 (m, 4H), 7.46-7.42 (m, 1H), 7.30-7.25 (m, 1H), 4.07-4.02 (m, 4H), 3.60-3.48 (m, 3H), 3.31-3.14 (m, 5H), 3.02-2.90 (m, 2H), 2.61-2.56 (m, 2H), 2.09-1.98 (m, 3H), 1.84 (br s, 3H), 1.81-1.62 (m, 7H), 0.91-0.82 (m, 6H). TLR9 $IC_{50}$ (nM) = 2600 |
| 191 | Analytical LC/MS (Method 1): Purity: 96.8%; Observed Mass: 550.95; Retention Time: 0.97 min. (Method 2): Purity: 99%; Observed Mass: 551.26; Retention Time: 1.19 min. Prep Method 1: 19 mg, 25% yield; $^1$H NMR (500 MHz, DMSO-$d_6$) δ 8.06-7.94 (m, 4H), 7.32 (br d, J = 8.5 Hz, 1H), 7.15 (br s, 1H), 3.79 (s, 2H), 3.44-3.25 (m, 2H), 3.19 (s, 2H), 2.90-2.84 (m, 2H), 2.84-2.76 (m, 1H), 2.56-2.46 (m, 1H), 2.21 (br d, J = 6.1 Hz, 2H), 2.16-2.05 (m, 2H), 1.77 (s, 4H), 1.62 (br s, 6H), 1.50-1.36 (m, 4H), 0.81-0.67 (m, 1H), 0.37-0.31 (m, 2H), 0.03--0.05 (m, 2H). TLR9 $IC_{50}$ (nM) = 96 |
| 192 | Analytical LC/MS (Method 1): Purity: 98.4%; Observed Mass: 551.26; Retention Time: 1.43 min. (Method 2): Purity: 97.4%; Observed Mass: 551.26; Retention Time: 1.43 min. Prep Method 1: 11 mg, 14%; $^1$H NMR (500 MHz, DMSO-$d_6$) δ 8.05-7.96 (m, 4H), 7.36-7.28 (m, 1H), 7.19-7.11 (m, 1H), 3.78 (s, 3H), 3.44-3.24 (m, 2H), 3.18 (s, 3H), 2.89-2.75 (m, 1H), 2.29-2.22 (m, 1H), 2.16 (br d, J = 6.1 Hz, 2H), 1.93-1.80 (m, 2H), 1.74 (br s, 7H), 1.69-1.54 (m, 5H), 0.81-0.67 (m, 1H), 0.34 (br d, J = 6.7 Hz, 2H), 0.01 (br d, J = 3.7 Hz, 2H) (two protons obscured). TLR9 $IC_{50}$ (nM) = 190 |
| 193 | Analytical LC/MS (Method 1): Purity: 100%; Observed Mass: 567.01; Retention Time: 1.0 min. (Method 2): Purity: 98.7%; Observed Mass: 567.02; Retention Time: 1.25 min. Prep Method 1: 13 mg, 17% yield; $^1$H NMR (500 MHz, DMSO-$d_6$) δ 8.18-8.08 (m, 4H), 7.44 (d, J = 8.5 Hz, 1H), 7.27 (s, 1H), 4.62 (br d, J = 7.5 Hz, 2H), 4.27 (t, J = 6.1 Hz, 2H), 3.91 (s, 3H), 3.45 (br s, 5H), 3.19-3.12 (m, 1H), 3.10-2.86 (m, 3H), 2.66 (br d, J = 7.1 Hz, 3H), 2.29-2.16 (m, 2H), 1.89-1.80 (m, 2H), 1.74 (br s, 4H), 1.63-1.47 (m, 6H). TLR9 $IC_{50}$ (nM) = 82 |

-continued

| Ex. No. | Analytical LC/MS, Preparative HPLC method, yield, and $^1H$ NMR |
|---|---|
| 194 | Analytical LC/MS (Method 1): Purity: 100%; Observed Mass: 567.00; Retention Time: 0.99 min. (Method 2): Purity: 100%; Observed Mass: 566.99; Retention Time: 1.38 min. Prep Method 1: 12 mg, 16% yield; $^1H$ NMR (500 MHz, DMSO-$d_6$) δ 8.18-8.09 (m, 4H), 7.45 (d, J = 8.5 Hz, 1H), 7.27 (s, 1H), 4.62 (dd, J = 7.6, 5.8 Hz, 2H), 4.26 (t, J = 6.0 Hz, 2H), 3.92 (s, 3H), 3.47-3.42 (m, 6H), 3.28-3.19 (m, 1H), 3.04 (br d, J = 7.0 Hz, 2H), 2.97-2.85 (m, 1H), 2.57-2.52 (m, 2H), 2.34 (br s, 1H), 1.93-1.63 (m, 13H). TLR9 $IC_{50}$ (nM) = 630 |
| 195 | Analytical LC/MS (Method 1): Purity: 95.5%; Observed Mass: 553.23; Retention Time: 0.92 min. (Method 2): Purity: 86.9%; Observed Mass: 553.24; Retention Time: 1.11 min. Prep Method 1: 6.1 mg, 7% yield; $^1H$ NMR (500 MHz, DMSO-$d_6$) δ 8.13 (br d, J = 4.8 Hz, 4H), 7.44 (br d, J = 8.6 Hz, 1H), 7.31-7.24 (m, 1H), 4.57-4.49 (m, 2H), 4.35-4.26 (m, 2H), 3.91 (s, 3H), 3.70-3.59 (m, 2H), 3.31 (s, 2H), 3.11-3.07 (m, 1H), 3.02-2.86 (m, 3H), 2.66-2.57 (m, 1H), 2.55 (s, 2H), 2.32-2.18 (m, 2H), 1.92-1.87 (m, 1H), 1.83-1.70 (m, 6H), 1.61-1.55 (m, 2H), 1.54-1.48 (m, 2H). TLR9 $IC_{50}$ (nM) = 490 |
| 196 | Analytical LC/MS (Method 1): Purity: 91.8%; Observed Mass: 552.94; Retention Time: 0.93 min. (Method 2): Purity: 95.1%; Observed Mass: 553.22; Retention Time: 1.17 min. Prep Method 1: 6.7 mg, 7% yield; $^1H$ NMR (500 MHz, DMSO-$d_6$) δ 8.13 (br d, J = 4.8 Hz, 4H), 7.49-7.42 (m, 1H), 7.31-7.25 (m, 1H), 4.61-4.50 (m, 2H), 4.37-4.24 (m, 2H), 3.91 (s, 3H), 3.70-3.58 (m, 2H), 3.31 (s, 2H), 3.13-3.05 (m, 1H), 3.02-2.86 (m, 3H), 2.68-2.56 (m, 1H), 2.56-2.52 (m, 2H), 2.34-2.18 (m, 2H), 1.93-1.89 (m, 1H), 1.84-1.69 (m, 6H), 1.62-1.47 (m, 4H). TLR9 $IC_{50}$ (nM) = 580 |
| 197 | Analytical LC/MS (Method 1): Purity: 93.7%; Observed Mass: 580.99; Retention Time: 1.01 min. (Method 2): Purity: 88.7%; Observed Mass: 581.31; Retention Time: 1.28 min. Prep Method 1: 11 mg, 13% yield; $^1H$ NMR (500 MHz, DMSO-$d_6$) δ 8.13 (br d, J = 5.1 Hz, 4H), 7.50-7.41 (m, 1H), 7.31-7.23 (m, 1H), 3.96-3.89 (m, 3H), 3.88-3.81 (m, 2H), 3.47-3.41 (m, 2H), 3.36-3.28 (m, 2H), 3.08-3.02 (m, 1H), 2.99-2.86 (m, 1H), 2.72-2.58 (m, 2H), 2.51 (br s, 5H), 2.28-2.15 (m, 2H), 1.84-1.71 (m, 7H), 1.69. 1.59 (m, 2H), 1.59-1.52 (m, 2H), 1.52-1.43 (m, 2H), 1.35-1.19 (m, 2H). TLR9 $IC_{50}$ (nM) = 160 |
| 198 | Analytical LC/MS (Method 1): Purity: 100%; Observed Mass: 581.04; Retention Time: 1.02 min. (Method 2): Purity: 100%; Observed Mass: 581.05; Retention Time: 1.44 min. Prep Method 1: 5.7 mg, 8% yield; $^1H$ NMR (500 MHz, DMSO-$d_6$) δ 8.19-8.05 (m, 4H), 7.51-7.42 (m, 1H), 7.34-7.23 (m, 1H), 3.92 (s, 3H), 3.88-3.81 (m, 2H), 3.46-3.39 (m, 4H), 3.32 (s, 2H), 3.01-2.88 (m, 1H), 2.55 (s, 2H), 2.53-2.48 (m, 5H), 2.43-2.34 (m, 1H), 1.96-1.69 (m, 13H), 1.38-1.21 (m, 2H). TLR9 $IC_{50}$ (nM) = 57 |
| 199 | Analytical LC/MS (Method 1): Purity: 98.8%; Observed Mass: 555.00; Retention Time: 0.95 min. (Method 2): Purity: 98.3%; Observed Mass: 555.27; Retention Time: 1.15 min. Prep Method 1: 16 mg, 21% yield; $^1H$ NMR (500 MHz, DMSO-$d_6$) δ 8.15-8.10 (m, 4H), 7.46-7.40 (m, 1H), 7.29-7.22 (m, 1H), 3.88 (s, 3H), 3.44-3.38 (m, 2H), 3.23 (s, 3H), 3.03-2.96 (m, 2H), 2.95-2.87 (m, 1H), 2.61-2.48 (m, 6H), 2.23-2.13 (m, 2H), 1.89-1.67 (m, 8H), 1.66-1.46 (m, 6H). TLR9 $IC_{50}$ (nM) = 75 |
| 200 | Analytical LC/MS (Method 1): Purity: 95.3%; Observed Mass: 555.0; Retention Time: 1.02 min. (Method 2): Purity: 99.3%; Observed Mass: 555.0; Retention Time: 1.47 min. Prep Method 1: 10 mg, 13% yield; $^1H$ NMR (500 MHz, DMSO-$d_6$) δ 8.14-8.09 (m, 4H), 7.43 (d, J = 8.5 Hz, 1H), 7.30-7.23 (m, 1H), 3.40-3.35 (m, 2H), 3.28 (s, 3H), 3.22 (s, 6H), 2.98-2.85 (m, 1H), 2.51 (s, 5H), 2.39 (br s, 3H), 1.74 (br dd, J = 11.7, 5.4 Hz, 11H), 1.63 (br dd, J = 14.1, 1.9 Hz, 2H). TLR9 $IC_{50}$ (nM) = 380 |
| 201 | Analytical LC/MS (Method 1): Purity: 100%; Observed Mass: 527.02; Retention Time: 1.05 min. (Method 2): Purity: 100%; Observed Mass: 527.09; Retention Time: 1.53 min. Prep Method 1: 63 mg, 84% yield; $^1H$ NMR (500 MHz, DMSO-$d_6$) δ 8.17-8.04 (m, 4H), 7.41 (s, 1H), 7.11-7.02 (m, 1H), 4.00 (s, 3H), 3.82-3.67 (m, 2H), 3.60-3.59 (m, 2H), 3.30 (s, 2H), 3.28-3.18 (m, 1H), 3.04-2.98 (m, 1H), 2.83-2.56 (m, 3H), 2.26-1.99 (m, 4H), 1.98-1.84 (m, 4H), 1.84-1.71 (m, 3H), 1.69-1.54 (m, 2H), 0.88-0.83 (m, 6H). TLR9 $IC_{50}$ (nM) = 97 |
| 202 | Analytical LC/MS (Method 1): Purity: 99.5%; Observed Mass: 511.23; Retention Time: 0.95 min. (Method 2): Purity: 98.9%; Observed Mass: 510.92; Retention Time: 1.26 min. Prep Method 1: 62 mg, 85% yield; $^1H$ NMR (500 MHz, DMSO-$d_6$) δ 8.20-8.03 (m, 4H), 7.46-7.36 (m, 1H), 7.10-7.00 (m, 1H), 4.00 (s, 3H), 3.74 (br s, 1H), 3.30 (s, 2H), 3.25-3.14 (m, 1H), 3.05-2.96 (m, 2H), 2.81-2.57 (m, 3H), 2.56-2.52 (m, 2H), 2.25-2.10 (m, 2H), 1.96-1.70 (m, 6H), 1.67-1.56 (m, 1H), 1.54-1.37 (m, 2H), 0.50-0.36 (m, 2H), 0.30 (br s, 2H). TLR9 $IC_{50}$ (nM) = 500 |
| 203 | Analytical LC/MS (Method 1): Purity: 99.4%; Observed Mass: 525.11; Retention Time: 1.15 min. (Method 2): Purity: 98.3%; Observed Mass: 525.21; Retention Time: 1.31 min. Prep Method 1: 29 mg, 48% yield; $^1H$ NMR (500 MHz, DMSO-$d_6$) δ 8.10-7.97 (m, 4H), 7.35-7.30 (m, 1H), 7.04-6.96 (m, 1H), 3.94 (s, 3H), 3.25 (s, 1H), 3.04-2.87 (m, 3H), 2.61-2.51 (m, 1H), 2.44 (br s, 2H), 2.28-2.16 (m, 3H), 2.12 (br d, J = 6.1 Hz, 2H), 1.88 (br |

-continued

| Ex. No. | Analytical LC/MS, Preparative HPLC method, yield, and $^1$H NMR |
|---|---|
| | t, J = 11.0 Hz, 2H), 1.79-1.55 (m, 6H), 1.49-1.38 (m, 2H), 0.83-0.70 (m, 1H), 0.39 (br d, J = 7.6 Hz, 2H), 0.01 (br d, J = 4.3 Hz, 2H) (one proton obscured). TLR9 $IC_{50}$ (nM) = 110 |
| 204 | Analytical LC/MS (Method 1): Purity: 100%; Observed Mass: 540.93; Retention Time: 1.0 min. (Method 2): Purity: 99.2%; Observed Mass: 540.93; Retention Time: 1.24 min. Prep Method 1: 47 mg, 75% yield; $^1$H NMR (500 MHz, DMSO-$d_6$) δ 8.22-7.98 (m, 4H), 7.46-7.36 (m, 1H), 7.13-7.00 (m, 1H), 4.64 (s, 2H), 4.25 (s, 2H), 4.01 (s, 3H), 3.50-3.38 (m, 2H), 3.32 (s, 2H), 3.22-3.13 (m, 1H), 3.12-3.01 (m, 1H), 2.83 (br d, J = 11.0 Hz, 2H), 2.63 (br d, J = 6.7 Hz, 3H), 2.55 (s, 1H), 2.47-2.35 (m, 2H), 1.99-1.82 (m, 4H), 1.81-1.63 (m, 4H), 1.56-1.41 (m, 2H). TLR9 $IC_{50}$ (nM) = 780 |
| 205 | Analytical LC/MS (Method 1): Purity: 100%; Observed Mass: 525.24; Retention Time: 0.96 min. (Method 2): Purity: 99.2%; Observed Mass: 525.26; Retention Time: 1.33 min. Prep Method 2: 19 mg, 22% yield; $^1$H NMR (500 MHz, DMSO-$d_6$) δ 8.18-8.04 (m, 4H), 7.50-7.36 (m, 1H), 7.18-7.00 (m, 1H), 4.03 (s, 3H), 3.67-3.53 (m, 1H), 3.44-3.37 (m, 1H), 3.33 (s, 1H), 3.25-3.10 (m, 1H), 3.09-2.97 (m, 1H), 2.90-2.73 (m, 1H), 2.58-2.54 (m, 1H), 2.51 (br s, 2H), 2.43-2.27 (m, 2H), 2.26-2.09 (m, 6H), 2.08-1.87 (m, 4H), 1.83-1.65 (m, 2H) (five protons obscured). TLR9 $IC_{50}$ (nM) = 110 |
| 206 | Analytical LC/MS (Method 1): Purity: 100%; Observed Mass: 526.93; Retention Time: 0.98 min. (Method 2): Purity: 100%; Observed Mass: 526.94; Retention Time: 1.17 min. Prep Method 2: 31 mg, 36% yield; $^1$H NMR (500 MHz, DMSO-$d_6$) δ 8.16-8.09 (m, 4H), 7.46-7.41 (m, 1H), 7.11-7.04 (m, 1H), 4.78-4.66 (m, 4H), 4.29-4.15 (m, 1H), 4.03 (s, 3H), 3.69-3.57 (m, 1H), 3.33 (s, 2H), 3.22-3.13 (m, 1H), 3.08-2.98 (m, 1H), 2.79-2.65 (m, 1H), 2.55 (s, 5H), 2.52-2.47 (m, 2H), 2.41-2.26 (m, 2H), 2.21-2.10 (m, 2H), 2.07-1.87 (m, 4H). TLR9 $IC_{50}$ (nM) = 840 |
| 207 | Analytical LC/MS (Method 1): Purity: 100%; Observed Mass: 555.28; Retention Time: 0.97 min. (Method 2): Purity: 98.2%; Observed Mass: 554.97; Retention Time: 1.22 min. Prep Method 2: 22 mg, 25% yield; $^1$H NMR (500 MHz, DMSO-$d_6$) δ 8.16-8.09 (m, 4H), 7.45-7.40 (m, 1H), 7.08-7.04 (m, 1H), 4.03 (s, 5H), 3.75-3.57 (m, 2H), 3.33 (s, 1H), 3.25-3.13 (m, 1H), 3.11-2.97 (m, 2H), 2.55 (s, 6H), 2.52-2.49 (m, 2H), 2.44-2.31 (m, 2H), 2.19-2.10 (m, 2H), 2.09-1.91 (m, 6H), 1.77-1.61 (m, 2H) (two protons obscured). TLR9 $IC_{50}$ (nM) = 110 |
| 208 | Analytical LC/MS (Method 1): Purity: 93.1%; Observed Mass: 528.93; Retention Time: 0.99 min. (Method 2): Purity: 93.4%; Observed Mass: 528.93; Retention Time: 1.26 min. Prep Method 1: 54 mg, 83% yield; $^1$H NMR (500 MHz, DMSO-$d_6$) δ 8.19-8.03 (m, 4H), 7.44-7.26 (m, 1H), 7.10-7.03 (m, 1H), 4.00 (s, 3H), 3.55-3.45 (m, 3H), 3.44-3.39 (m, 1H), 3.23 (s, 2H), 3.20-3.16 (m, 1H), 3.01-2.89 (m, 3H), 2.68-2.58 (m, 2H), 2.48-2.39 (m, 2H), 2.31-2.19 (m, 3H), 1.99-1.88 (m, 3H), 1.88-1.78 (m, 2H), 1.77-1.62 (m, 4H), 1.54-1.39 (m, 2H). TLR9 $IC_{50}$ (nM) = 940 |
| 209 | Analytical LC/MS (Method 1): Purity: 100%; Observed Mass: 553.27; Retention Time: 1.40 min. (Method 2): Purity: 98.8%; Observed Mass: 552.99; Retention Time: 1.52 min. Prep Method 1: 7.5 mg, 13% yield; $^1$H NMR (500 MHz, DMSO-$d_6$) δ 8.15-8.06 (m, 4H), 7.39 (s, 1H), 7.11-7.01 (m, 1H), 4.01 (s, 3H), 3.32 (s, 1H), 3.11-3.00 (m, 1H), 2.74-2.59 (m, 2H), 2.58-2.54 (m, 1H), 2.51 (br s, 3H), 2.33-2.09 (m, 4H), 1.85 (br d, J = 12.8 Hz, 4H), 1.76-1.48 (m, 9H), 0.89 (br d, J = 6.4 Hz, 6H) (one proton obscured). TLR9 $IC_{50}$ (nM) = 81 |
| 210 | Analytical LC/MS (Method 1): Purity: 96%; Observed Mass: 552.96; Retention Time: 1.0 min. (Method 2): Purity: 96.1%; Observed Mass: 553.22; Retention Time: 1.74 min. Prep Method 1: 7.3 mg, 12% yield; $^1$H NMR (500 MHz, DMSO-$d_6$) δ 8.16-8.05 (m, 4H), 7.42-7.35 (m, 1H), 7.11-7.01 (m, 1H), 4.00 (s, 3H), 3.59-3.38 (m, 1H), 3.31 (s, 2H), 3.28-3.21 (m, 1H), 2.63 (br s, 1H), 2.55 (s, 1H), 2.51 (br s, 4H), 2.46-2.37 (m, 1H), 2.23-2.09 (m, 2H), 2.08-1.99 (m, 2H), 1.98-1.59 (m, 11H), 0.97-0.84 (m, 6H). TLR9 $IC_{50}$ (nM) = 120 |
| 211 | Analytical LC/MS (Method 1): Purity: 98.7%; Observed Mass: 580.96; Retention Time: 0.96 min. (Method 2): Purity: 100%; Observed Mass: 581.18; Retention Time: 1.39 min. Prep Method 1: 3.9 mg, 7% yield; $^1$H NMR (500 MHz, DMSO-$d_6$) δ 8.15-8.07 (m, 4H), 7.42-7.39 (m, 1H), 7.10-7.05 (m, 1H), 4.04-3.98 (m, 3H), 3.92-3.80 (m, 3H), 3.73-3.60 (m, 3H), 3.58-3.39 (m, 3H), 3.11-2.99 (m, 3H), 2.74-2.61 (m, 4H), 2.27-2.18 (m, 3H), 1.86-1.61 (m, 6H), 1.60-1.48 (m, 4H), 1.35-1.22 (m, 3H). TLR9 $IC_{50}$ (nM) = 270 |
| 212 | Analytical LC/MS (Method 1): Purity: 96%; Observed Mass: 581.29; Retention Time: 0.96 min. (Method 2): Purity: 98%; Observed Mass: 580.95; Retention Time: 1.42 min. Prep Method 1: 12 mg, 20% yield; $^1$H NMR (500 MHz, DMSO-$d_6$) δ 8.12 (q, J = 8.3 Hz, 4H), 7.40 (s, 1H), 7.07 (br d, J = 12.8 Hz, 1H), 4.01 (s, 3H), 3.89-3.80 (m, 2H), 3.32 (s, 3H), 2.68-2.57 (m, 1H), 2.57-2.54 (m, 3H), 2.47-2.34 (m, 2H), 1.94-1.79 (m, 10H), 1.74 (br s, 4H), 1.69 (br s, 4H), 1.31-1.19 (m, 2H) (one proton obscured). TLR9 $IC_{50}$ (nM) = 460 |
| 213 | Analytical LC/MS (Method 1): Purity: 96.5%; Observed Mass: 552.92; Retention Time: 0.95 min. (Method 2): Purity: 97.4%; Observed Mass: |

-continued

| Ex. No. | Analytical LC/MS, Preparative HPLC method, yield, and $^1$H NMR |
|---|---|
| | 553.21; Retention Time: 1.23 min. Prep Method 1: 8.9 mg, 15% yield; $^1$H NMR (500 MHz, DMSO-$d_6$) δ 8.18-8.04 (m, 4H), 7.39 (s, 1H), 7.06 (br d, J = 13.1 Hz, 1H), 4.58-4.51 (m, 2H), 4.35-4.29 (m, 2H), 3.64-3.48 (m, 2H), 3.30 (s, 2H), 3.14-3.07 (m, 2H), 3.03-2.97 (m, 2H), 2.66-2.57 (m, 2H), 2.55 (s, 3H), 2.28-2.16 (m, 2H), 1.89 (br s, 3H), 1.85-1.75 (m, 3H), 1.75-1.56 (m, 3H), 1.56-1.36 (m, 3H). TLR9 $IC_{50}$ (nM) = 340 |
| 214 | Analytical LC/MS (Method 1): Purity: 97.9%; Observed Mass: 553.23; Retention Time: 0.95 min. (Method 2): Purity: 98.1%; Observed Mass: 552.94; Retention Time: 1.28 min. Prep Method 1: 12 mg, 20% yield; $^1$H NMR (500 MHz, DMSO-$d_6$) δ 8.15-8.04 (m, 4H), 7.43-7.36 (m, 1H), 7.11-7.01 (m, 1H), 4.53 (s, 2H), 4.30 (s, 2H), 4.00 (s, 2H), 3.64-3.50 (m, 2H), 3.31-3.29 (m, 2H), 3.23-3.15 (m, 2H), 3.01 (br s, 2H), 2.65-2.57 (m, 1H), 2.48-2.41 (m, 1H), 2.02-1.81 (m, 8H), 1.75-1.71 (m, 3H), 1.70-1.59 (m, 4H). TLR9 $IC_{50}$ (nM) = 4700 |
| 215 | Analytical LC/MS (Method 1): Purity: 100%; Observed Mass: 550.97; Retention Time: 0.99 min. (Method 2): Purity: 96.4%; Observed Mass: 551.26; Retention Time: 1.35 min. Prep Method 1: 9.9 mg, 17% yield; $^1$H NMR (500 MHz, DMSO-$d_6$) δ 8.11 (q, J = 8.4 Hz, 4H), 7.39 (s, 1H), 7.06 (br d, J = 12.8 Hz, 1H), 4.01 (s, 3H), 3.32 (s, 1H), 3.28-3.21 (m, 1H), 3.13-3.04 (m, 1H), 3.02-2.93 (m, 2H), 2.67-2.57 (m, 2H), 2.21 (br s, 2H), 2.05-1.96 (m, 2H), 1.91 (s, 3H), 1.87-1.72 (m, 6H), 1.71-1.49 (m, 9H) (one proton obscured). TLR9 $IC_{50}$ (nM) = 70 |
| 216 | Analytical LC/MS (Method 1): Purity: 95.4%; Observed Mass: 551.24; Retention Time: 0.99 min. (Method 2): Purity: 98.1%; Observed Mass: 550.95; Retention Time: 1.54 min. Prep Method 1: 10 mg, 17% yield; $^1$H NMR (500 MHz, DMSO-$d_6$) δ 8.16-8.05 (m, 4H), 7.41-7.36 (m, 1H), 7.09-7.03 (m, 1H), 4.00 (s, 3H), 3.57-3.46 (m, 1H), 3.31 (s, 2H), 3.27-3.15 (m, 3H), 3.09-2.97 (m, 1H), 2.69-2.56 (m, 2H), 2.47-2.32 (m, 1H), 2.03-1.72 (m, 16H), 1.71-1.55 (m, 4H). TLR9 $IC_{50}$ (nM) = 270 |
| 217 | Analytical LC/MS (Method 1): Purity: 97.8%; Observed Mass: 551.16; Retention Time: 1.04 min. (Method 2): Purity: 95.5%; Observed Mass: 551.16; Retention Time: 1.36 min. Prep Method 1: 13 mg, 22% yield; $^1$H NMR (500 MHz, DMSO-$d_6$) δ 8.07-7.88 (m, 4H), 7.33-7.23 (m, 1H), 7.01-6.89 (m, 1H), 3.87 (s, 2H), 3.53-3.33 (m, 2H), 3.17 (s, 2H), 2.91-2.80 (m, 2H), 2.56-2.44 (m, 2H), 2.26-2.17 (m, 2H), 2.12-2.01 (m, 2H), 1.74 (s, 4H), 1.70-1.64 (m, 2H), 1.58-1.40 (m, 7H), 0.79-0.70 (m, 1H), 0.40-0.27 (m, 2H), 0.01 (br d, J = 4.0 Hz, 2H) (one proton obscured). TLR9 $IC_{50}$ (nM) = 130 |
| 218 | Analytical LC/MS (Method 1): Purity: 100%; Observed Mass: 550.97; Retention Time: 1.05 min. (Method 2): Purity: 100%; Observed Mass: 550.98; Retention Time: 1.60 min. Prep Method 1: 9.4 mg, 17% yield; $^1$H NMR (500 MHz, DMSO-$d_6$) δ 8.13-7.81 (m, 4H), 7.42-7.09 (m, 1H), 7.01-6.83 (m, 1H), 3.87 (s, 3H), 3.50-3.35 (m, 1H), 3.32-3.25 (m, 1H), 3.21-3.09 (m, 4H), 2.52-2.44 (m, 1H), 2.27-2.21 (m, 1H), 2.20-2.13 (m, 2H), 1.91-1.82 (m, 2H), 1.73 (br d, J = 12.5 Hz, 11H), 1.61-1.48 (m, 2H), 0.79-0.69 (m, 1H), 0.38-0.25 (m, 2H), 0.07--0.07 (m, 2H). TLR9 $IC_{50}$ (nM) = 140 |
| 219 | Analytical LC/MS (Method 1): Purity: 96.9%; Observed Mass: 538.95; Retention Time: 1.01 min. (Method 2): Purity: 95.6%; Observed Mass: 538.99; Retention Time: 1.33 min. Prep Method 1: 4.5 mg, 4% yield; $^1$H NMR (500 MHz, DMSO-$d_6$) δ 8.43 (br d, J = 8.5 Hz, 2H), 8.10 (br d, J = 8.2 Hz, 2H), 7.40 (br d, J = 8.5 Hz, 1H), 7.22-7.15 (m, 1H), 3.28 (s, 3H), 3.22-3.17 (m, 2H), 3.05-2.99 (m, 2H), 2.96-2.87 (m, 1H), 2.64-2.57 (m, 1H), 2.29-2.18 (m, 2H), 2.14 (br d, J = 7.0 Hz, 2H), 1.86-1.81 (m, 2H), 1.75 (br s, 5H), 1.66-1.47 (m, 7H), 0.88 (d, J = 6.7 Hz, 6H). TLR9 $IC_{50}$ (nM) = 65 |
| 220 | Analytical LC/MS (Method 1): Purity: 95.5%; Observed Mass: 539.37; Retention Time: 1.14 min. (Method 2): Purity: 97.9%; Observed Mass: 538.93; Retention Time: 1.56 min. Prep Method 2: 5.5 mg, 6% yield; $^1$H NMR (500 MHz, DMSO-$d_6$) δ 8.45 (br d, J = 8.5 Hz, 2H), 8.13 (d, J = 8.5 Hz, 2H), 7.47 (br d, J = 7.9 Hz, 1H), 7.17 (br d, J = 3.4 Hz, 1H), 4.06-3.95 (m, 1H), 3.30 (s, 2H), 2.99-2.86 (m, 1H), 2.85-2.72 (m, 2H), 2.57-2.55 (m, 2H), 2.51 (br s, 6H), 2.34-1.91 (m, 12H), 0.99 (br d, J = 6.1 Hz, 6H) (one proton obscured). TLR9 $IC_{50}$ (nM) = 680 |
| 221 | Analytical LC/MS (Method 1): Purity: 100%; Observed Mass: 526.95; Retention Time: 0.93 min. (Method 2): Purity: 100%; Observed Mass: 526.96; Retention Time: 1.43 min. Prep Method 1: 56 mg, 60% yield; $^1$H NMR (500 MHz, DMSO-$d_6$) δ 8.17-8.09 (m, 4H), 7.64-7.59 (m, 1H), 7.54-7.47 (m, 1H), 3.94 (s, 3H), 3.35-3.28 (m, 1H), 3.02-2.92 (m, 1H), 2.55-2.50 (m, 9H), 2.21-1.95 (m, 3H), 1.94-1.69 (m, 8H), 1.64-1.51 (m, 2H), 0.90-0.85 (m, 6H). TLR9 $IC_{50}$ (nM) = 350 |
| 222 | Analytical LC/MS (Method 1): Purity: 96.5%; Observed Mass: 511.24; Retention Time: 0.87 min. (Method 2): Purity: 93.6%; Observed Mass: 510.88; Retention Time: 1.3 min. Prep Method 2: 78 mg, 60% yield; $^1$H NMR (500 MHz, DMSO-$d_6$) δ 8.16-8.10 (m, 4H), 7.58-7.54 (m, 1H), 7.54-7.49 (m, 1H), 3.94 (s, 3H), 3.60 (br d, J = 11.3 Hz, 1H), 3.32 (s, 2H), 3.28-3.20 (m, 1H), 3.13 (s, 1H), 2.55 (s, 4H), 2.51 (br s, 3H), 2.40-2.23 (m, 2H), 2.21-2.01 (m, 4H), 2.00-1.77 (m, 2H), 0.96-0.70 (m, 5H) (one proton obscured). TLR9 $IC_{50}$ (nM) = 130 |

-continued

| Ex. No. | Analytical LC/MS, Preparative HPLC method, yield, and $^1$H NMR |
|---|---|
| 223 | Analytical LC/MS (Method 1): Purity: 100%; Observed Mass: 524.94; Retention Time: 0.94 min. (Method 2): Purity: 100%; Observed Mass: 524.96; Retention Time: 1.36 min. Prep Method 1: 23 mg, 33% yield; $^1$H NMR (500 MHz, DMSO-$d_6$) δ 8.19-8.08 (m, 4H), 7.64-7.56 (m, 1H), 7.51-7.44 (m, 1H), 3.92 (s, 2H), 3.59-3.44 (m, 4H), 3.30 (s, 2H), 3.21-3.14 (m, 1H), 3.11-3.01 (m, 2H), 2.97-2.87 (m, 2H), 2.84-2.69 (m, 1H), 2.46-2.32 (m, 3H), 2.04-1.94 (m, 2H), 1.83 (br s, 8H), 1.68-1.57 (m, 2H), 1.55-1.44 (m, 2H). TLR9 $IC_{50}$ (nM) = 290 |
| 224 | Analytical LC/MS (Method 1): Purity: 100%; Observed Mass: 525.21; Retention Time: 0.96 min. (Method 2): Purity: 100%; Observed Mass: 525.22; Retention Time: 1.32 min. Prep Method 1: 22 mg, 33% yield; $^1$H NMR (500 MHz, DMSO-$d_6$) δ 8.03 (s, 4H), 7.53 (br d, J = 6.7 Hz, 1H), 7.38 (br d, J = 11.6 Hz, 1H), 3.84 (s, 2H), 3.43-3.29 (m, 1H), 3.22 (s, 2H), 3.05-2.90 (m, 3H), 2.89-2.76 (m, 1H), 2.31-2.10 (m, 5H), 2.02-1.88 (m, 2H), 1.73 (br s, 6H), 1.51-1.35 (m, 2H), 0.81-0.68 (m, 1H), 0.44-0.32 (m, 2H), 0.01 (br d, J = 2.1 Hz, 2H) (two protons obscured). TLR9 $IC_{50}$ (nM) = 190 |
| 225 | Analytical LC/MS (Method 1): Purity: 97.1%; Observed Mass: 527.22; Retention Time: 0.85 min. (Method 2): Purity: 99.2%; Observed Mass: 526.92; Retention Time: 1.17 min. Prep Method 1: 12 mg, 17% yield; $^1$H NMR (500 MHz, DMSO-$d_6$) δ 8.12 (s, 4H), 7.62-7.58 (m, 1H), 7.52-7.46 (m, 1H), 4.58-4.51 (m, 2H), 4.45-4.40 (m, 2H), 3.93 (s, 3H), 3.56-3.45 (m, 5H), 3.31 (s, 2H), 2.81-2.74 (m, 2H), 2.55 (s, 2H), 1.94-1.71 (m, 7H), 1.59-1.46 (m, 4H). TLR9 $IC_{50}$ (nM) = 5400 |
| 226 | Analytical LC/MS (Method 1): Purity: 97.6%; Observed Mass: 554.99; Retention Time: 0.92 min. (Method 2): Purity: 97.1%; Observed Mass: 555.05; Retention Time: 1.24 min. Prep Method 1: 9.8 mg, 13% yield; $^1$H NMR (500 MHz, DMSO-$d_6$) δ 8.17-8.00 (m, 4H), 7.69-7.61 (m, 1H), 7.53-7.45 (m, 1H), 3.94 (s, 2H), 3.92-3.82 (m, 2H), 3.34-3.23 (m, 2H), 3.07-2.85 (m, 4H), 2.55 (s, 1H), 2.46-2.36 (m, 2H), 2.35-2.15 (m, 4H), 2.14-1.99 (m, 3H), 1.92 (s, 1H), 1.86-1.72 (m, 6H), 1.68 (br d, J = 10.7 Hz, 2H), 1.49-1.37 (m, 4H). TLR9 $IC_{50}$ (nM) = 900 |
| 227 | Analytical LC/MS (Method 1): Purity: 96.7%; Observed Mass: 529.22; Retention Time: 0.87 min. (Method 2): Purity: 98.6%; Observed Mass: 529.22; Retention Time: 1.21 min. Prep Method 1: 8.8 mg, 13% yield; $^1$H NMR (500 MHz, DMSO-$d_6$) δ 8.16-8.08 (m, 4H), 7.65-7.59 (m, 1H), 7.50-7.45 (m, 1H), 3.93 (s, 3H), 3.51-3.39 (m, 1H), 3.31 (s, 2H), 3.24 (s, 2H), 3.09-3.01 (m, 2H), 2.99-2.87 (m, 3H), 2.56-2.52 (m, 1H), 2.48 (br s, 2H), 2.40-2.26 (m, 3H), 2.06-1.94 (m, 2H), 1.82 (br s, 6H), 1.58-1.41 (m, 2H) (two protons obscured). TLR9 $IC_{50}$ (nM) = 410 |
| 228 | Analytical LC/MS (Method 1): Purity: 100%; Observed Mass: 553.28; Retention Time: 0.92 min. (Method 2): Purity: 98.2%; Observed Mass: 553.28; Retention Time: 1.29 min. Prep Method 1: 15 mg, 11% yield; $^1$H NMR (500 MHz, DMSO-$d_6$) δ 8.18-8.06 (m, 4H), 7.63-7.57 (m, 1H), 7.52-7.43 (m, 1H), 3.93 (s, 3H), 3.31 (s, 2H), 3.16-3.08 (m, 1H), 2.97-2.87 (m, 1H), 2.85-2.71 (m, 1H), 2.45-2.21 (m, 4H), 1.99-1.55 (m, 14H), 0.96-0.84 (m, 8H) (one proton obscured). TLR9 $IC_{50}$ (nM) = 69 |
| 229 | Analytical LC/MS (Method 1): Purity: 95.5%; Observed Mass: 552.97; Retention Time: 1.62 min. (Method 2): Purity: 95.6%; Observed Mass: 553.32; Retention Time: 1.61 min. Prep Method 1: 5.5 mg, 4% yield; $^1$H NMR (500 MHz, DMSO-$d_6$) δ 8.08 (s, 4H), 7.64-7.57 (m, 1H), 7.47 (d, J = 11.0 Hz, 1H), 3.94 (s, 3H), 3.55-3.39 (m, 1H), 3.31 (s, 2H), 3.28-3.22 (m, 1H), 3.16-3.10 (m, 2H), 2.90-2.82 (m, 1H), 2.47-2.36 (m, 1H), 2.05 (br d, J = 7.3 Hz, 2H), 2.01-1.74 (m, 13H), 1.73-1.57 (m, 3H), 0.88 (d, J = 6.7 Hz, 6H). TLR9 $IC_{50}$ (nM) = 95 |
| 230 | Analytical LC/MS (Method 1): Purity: 100%; Observed Mass: 550.98; Retention Time: 1.37 min. (Method 2): Purity: 100%; Observed Mass: 550.99; Retention Time: 1.36 min. Prep Method 1: 17 mg, 13% yield; $^1$H NMR (500 MHz, DMSO-$d_6$) δ 8.00 (s, 4H), 7.50 (br d, J = 6.4 Hz, 1H), 7.35 (d, J = 11.0 Hz, 1H), 3.81 (s, 3H), 3.20 (s, 2H), 2.95-2.86 (m, 2H), 2.82-2.72 (m, 1H), 2.58-2.47 (m, 1H), 2.20 (br d, J = 6.1 Hz, 2H), 2.15-2.03 (m, 2H), 1.81-1.72 (m, 4H), 1.67 (br s, 4H), 1.53 (br d, J = 11.0 Hz, 2H), 1.48-1.38 (m, 4H), 0.74 (br s, 1H), 0.38-0.30 (m, 2H), 0.01 (br d, J = 4.3 Hz, 2H) (one proton obscured). TLR9 $IC_{50}$ (nM) = 36 |
| 231 | Analytical LC/MS (Method 1): Purity: 99.3%; Observed Mass: 550.98; Retention Time: 1.52 min. (Method 2): Purity: 99.3%; Observed Mass: 550.99; Retention Time: 1.51 min. Prep Method 1: 20 mg, 15% yield; $^1$H NMR (500 MHz, DMSO-$d_6$) δ 7.87 (s, 4H), 7.38-7.31 (m, 1H), 7.22 (s, 1H), 3.68 (s, 2H), 3.49-3.31 (m, 4H), 3.16-3.10 (m, 2H), 3.05 (s, 3H), 2.70-2.61 (m, 1H), 2.19-2.09 (m, 1H), 1.86 (br d, J = 7.0 Hz, 4H), 1.80 (br s, 2H), 1.74-1.68 (m, 2H), 1.66-1.51 (m, 7H), 0.78-0.66 (m, 1H), 0.31 (br d, J = 7.0 Hz, 2H), 0.01 (br d, J = 4.0 Hz, 2H). TLR9 $IC_{50}$ (nM) = 58 |
| 232 | Analytical LC/MS (Method 1): Purity: 96%; Observed Mass: 550.97; Retention Time: 0.96 min. (Method 2): Purity: 98.7%; Observed Mass: 550.96; Retention Time: 1.35 min. Prep Method 1: 14 mg, 11% yield; $^1$H NMR (500 MHz, DMSO-$d_6$) δ 8.14-8.09 (m, 4H), 7.61-7.56 (m, 1H), 7.49-7.43 (m, 1H), 3.92 (s, 3H), 3.67-3.51 (m, 2H), 3.16-3.07 (m, 1H), 3.02 (br |

-continued

| Ex. No. | Analytical LC/MS, Preparative HPLC method, yield, and $^1$H NMR |
|---|---|
| | d, J = 10.7 Hz, 2H), 2.88 (br s, 1H), 2.74-2.60 (m, 1H), 2.32-2.19 (m, 2H), 2.06-1.95 (m, 3H), 1.91-1.74 (m, 11H), 1.70-1.53 (m, 7H). TLR9 $IC_{50}$ (nM) = 45 |
| 233 | Analytical LC/MS (Method 1): Purity: 98.6%; Observed Mass: 550.97; Retention Time: 0.95 min. (Method 2): Purity: 97.6%; Observed Mass: 551.29; Retention Time: 1.50 min. Prep Method 1: 8.9 mg, 7% yield; $^1$H NMR (500 MHz, DMSO-$d_6$) δ 8.17-8.03 (m, 4H), 7.62-7.55 (m, 1H), 7.51-7.43 (m, 1H), 3.98-3.90 (m, 3H), 3.59-3.46 (m, 1H), 3.32-3.27 (m, 4H), 3.26-3.20 (m, 1H), 3.19-3.16 (m, 1H), 3.11-3.00 (m, 1H), 2.93-2.82 (m, 1H), 2.42-2.34 (m, 1H), 2.04-1.73 (m, 18H), 1.72-1.55 (m, 2H). TLR9 $IC_{50}$ (nM) = 58 |
| 234 | Analytical LC/MS (Method 1): Purity: 98.3%; Observed Mass: 553.37; Retention Time: 0.91 min. (Method 2): Purity: 94.9%; Observed Mass: 553.24; Retention Time: 1.14 min. Prep Method 1: 10 mg, 7% yield; $^1$H NMR (500 MHz, DMSO-$d_6$) δ 8.19-8.07 (m, 4H), 7.66-7.60 (m, 1H), 7.51-7.43 (m, 1H), 4.59-4.50 (m, 2H), 4.37-4.26 (m, 2H), 3.94 (s, 3H), 3.72-3.61 (m, 1H), 3.32 (s, 1H), 3.14-3.07 (m, 2H), 3.05-2.98 (m, 2H), 2.92-2.86 (m, 1H), 2.69-2.59 (m, 1H), 2.31-2.19 (m, 2H), 1.91 (s, 3H), 1.80 (br s, 6H), 1.58 (br d, J = 1.2 Hz, 5H). TLR9 $IC_{50}$ (nM) = 150 |
| 235 | Analytical LC/MS (Method 1): Purity: 100%; Observed Mass: 553.27; Retention Time: 1.31 min. (Method 2): Purity: 100%; Observed Mass: 553.04; Retention Time: 1.31 min. Prep Method 1: 7.0 mg, 5% yield; $^1$H NMR (500 MHz, DMSO-$d_6$) δ 8.18-8.09 (m, 4H), 7.64-7.59 (m, 1H), 7.51-7.46 (m, 1H), 4.54 (t, J = 6.1 Hz, 2H), 4.32 (s, 2H), 3.95 (s, 3H), 3.63-3.52 (m, 1H), 3.32 (s, 1H), 3.07-3.00 (m, 1H), 2.95-2.86 (m, 1H), 2.55 (s, 4H), 2.36-2.24 (m, 1H), 1.99 (br d, J = 2.7 Hz, 3H), 1.94-1.68 (m, 11H) (one proton obscured). TLR9 $IC_{50}$ (nM) = 1700 |
| 236 | Analytical LC/MS (Method 1): Purity: 100%; Observed Mass: 580.98; Retention Time: 1.29 min. (Method 2): Purity: 100%; Observed Mass: 580.99; Retention Time: 1.29 min. Prep Method 1: 21 mg, 15% yield; $^1$H NMR (500 MHz, DMSO-$d_6$) δ 8.16-8.08 (m, 4H), 7.61-7.57 (m, 1H), 7.49-7.45 (m, 1H), 3.92 (s, 2H), 3.90-3.84 (m, 2H), 3.63-3.52 (m, 7H), 3.30 (s, 3H), 3.11-3.06 (m, 2H), 2.95-2.88 (m, 2H), 2.73-2.67 (m, 2H), 2.30-2.23 (m, 2H), 1.85-1.79 (m, 6H), 1.71-1.63 (m, 3H), 1.61-1.51 (m, 4H). TLR9 $IC_{50}$ (nM) = 99 |
| 237 | Analytical LC/MS (Method 1): Purity: 97.7%; Observed Mass: 581.04; Retention Time: 1.42 min. (Method 2): Purity: 98.9%; Observed Mass: 580.99; Retention Time: 1.41 min. Prep Method 1: 14 mg, 10% yield; $^1$H NMR (500 MHz, DMSO-$d_6$) δ 8.17-8.08 (m, 4H), 7.64-7.59 (m, 1H), 7.50-7.45 (m, 1H), 3.94 (s, 3H), 3.89-3.82 (m, 2H), 3.31 (s, 4H), 2.92-2.84 (m, 1H), 2.43-2.35 (m, 1H), 1.89 (s, 22H), 1.33-1.23 (m, 2H). TLR9 $IC_{50}$ (nM) = 87 |
| 238 | Analytical LC/MS (Method 1): Purity: 96.1%; Observed Mass: 554.96; Retention Time: 1.32 min. (Method 2): Purity: 96%; Observed Mass: 555.01; Retention Time: 1.31 min. Prep Method 1: 15 mg, 11% yield; $^1$H NMR (500 MHz, DMSO-$d_6$) δ 8.14-8.06 (m, 4H), 7.64-7.56 (m, 1H), 7.46 (d, J = 11.0 Hz, 1H), 3.92 (s, 3H), 3.58-3.48 (m, 1H), 3.44-3.39 (m, 1H), 3.30 (s, 3H), 3.24 (s, 2H), 3.04-2.98 (m, 2H), 2.92-2.83 (m, 1H), 2.60 (br s, 1H), 2.55-2.52 (m, 2H), 2.27-2.18 (m, 2H), 1.92-1.83 (m, 4H), 1.82-1.74 (m, 4H), 1.68-1.58 (m, 2H), 1.58-1.48 (m, 4H) (one proton obscured). TLR9 $IC_{50}$ (nM) = 58 |
| 239 | Analytical LC/MS (Method 1): Purity: 97%; Observed Mass: 554.99; Retention Time: 1.43 min. (Method 2): Purity: 97%; Observed Mass: 555.00; Retention Time: 1.44 min. Prep Method 1: 12 mg, 9% yield; $^1$H NMR (500 MHz, DMSO-$d_6$) δ 8.11 (s, 4H), 7.59 (d, J = 6.4 Hz, 1H), 7.47 (d, J = 11.0 Hz, 1H), 3.93 (s, 3H), 3.58-3.46 (m, 1H), 3.45-3.39 (m, 1H), 3.34-3.21 (m, 7H), 2.92-2.83 (m, 1H), 2.46 (s, 2H), 2.41-2.32 (m, 1H), 1.98-1.70 (m, 17H). TLR9 $IC_{50}$ (nM) = 290 |
| 240 | Analytical LC/MS (Method 1): Purity: 98.1%; Observed Mass: 527.00; Retention Time: 0.99 min. (Method 2): Purity: 96.3%; Observed Mass: 527.38; Retention Time: 1.38 min. Prep Method 1: 51 mg, 54% yield; $^1$H NMR (500 MHz, DMSO-$d_6$) δ 8.11 (s, 4H), 7.65-7.59 (m, 1H), 7.55-7.49 (m, 1H), 3.89-3.86 (m, 2H), 3.29 (s, 3H), 3.19-3.15 (m, 1H), 3.08-3.02 (m, 2H), 2.92-2.83 (m, 3H), 2.41-2.28 (m, 3H), 2.06-2.00 (m, 3H), 1.90-1.71 (m, 8H), 1.54-1.45 (m, 2H), 0.84 (br d, J = 6.4 Hz, 6H). TLR9 $IC_{50}$ (nM) = 120 |
| 241 | Analytical LC/MS (Method 1): Purity: 97.5%; Observed Mass: 511.37; Retention Time: 0.95 min. (Method 2): Purity: 100%; Observed Mass: 511.21; Retention Time: 1.29 min. Prep Method 1: 31 mg, 34% yield; $^1$H NMR (500 MHz, DMSO-$d_6$) δ 8.16-8.09 (m, 4H), 7.64-7.59 (m, 1H), 7.59-7.53 (m, 1H), 3.89 (s, 3H), 3.46-3.39 (m, 1H), 3.31 (s, 1H), 3.11-3.04 (m, 1H), 2.99 (br d, J = 10.4 Hz, 2H), 2.94-2.85 (m, 1H), 2.50-2.34 (m, 2H), 2.15 (br t, J = 11.2 Hz, 2H), 1.88-1.72 (m, 6H), 1.62-1.54 (m, 1H), 1.49-1.38 (m, 2H), 0.44-0.37 (m, 2H), 0.31-0.25 (m, 2H) (three protons obscured). TLR9 $IC_{50}$ (nM) = 1700 |
| 242 | Analytical LC/MS (Method 1): Purity: 97.8%; Observed Mass: 525.15; Retention Time: 0.97 min. (Method 2): Purity: 97.6%; Observed Mass: 524.96; Retention Time: 1.44 min. Prep Method 1: 30 mg, 43% yield; $^1$H NMR (500 MHz, DMSO-$d_6$) δ 8.11-7.98 (m, 4H), 7.58-7.50 (m, 1H), 7.49-7.41 (m, 1H), 3.81 (s, 3H), 3.42-3.32 (m, 1H), 3.23 (s, 2H), 3.01-2.92 (m, |

-continued

| Ex. No. | Analytical LC/MS, Preparative HPLC method, yield, and $^1H$ NMR |
|---|---|
| | 3H), 2.82-2.71 (m, 1H), 2.42 (br s, 2H), 2.23 (br d, J = 11.6 Hz, 3H), 2.13 (br d, J = 6.4 Hz, 2H), 1.90 (br s, 2H), 1.79-1.61 (m, 5H), 1.49-1.39 (m, 2H), 0.82-0.71 (m, 1H), 0.39 (br d, J = 7.9 Hz, 2H), 0.01 (br d, J = 4.3 Hz, 2H). TLR9 $IC_{50}$ (nM) = 160 |
| 243 | Analytical LC/MS (Method 1): Purity: 100%; Observed Mass: 524.95; Retention Time: 0.95 min. (Method 2): Purity: 98.4%; Observed Mass: 525.24; Retention Time: 1.37 min. Prep Method 1: 11 mg, 16% yield; $^1H$ NMR (500 MHz, DMSO-$d_6$) δ 8.15-8.09 (m, 4H), 7.64-7.60 (m, 1H), 7.56-7.51 (m, 1H), 3.88 (s, 2H), 3.49 (br s, 3H), 3.30 (s, 1H), 3.21-3.15 (m, 2H), 3.04-2.97 (m, 2H), 2.87-2.78 (m, 3H), 2.70-2.60 (m, 3H), 2.40-2.13 (m, 5H), 1.90 (br s, 4H), 1.83-1.54 (m, 6H). TLR9 $IC_{50}$ (nM) = 940 |
| 244 | Analytical LC/MS (Method 1): Purity: 100%; Observed Mass: 527.20; Retention Time: 0.97 min. (Method 2): Purity: 100%; Observed Mass: 527.19; Retention Time: 1.25 min. Prep Method 1: 30 mg, 44% yield; $^1H$ NMR (500 MHz, DMSO-$d_6$) δ 8.12 (s, 4H), 7.66-7.60 (m, 1H), 7.59-7.51 (m, 1H), 4.53 (s, 2H), 4.42 (s, 2H), 3.89 (s, 3H), 3.46-3.34 (m, 1H), 3.32 (s, 1H), 3.17-3.04 (m, 1H), 2.98-2.83 (m, 1H), 2.80-2.73 (m, 2H), 2.55 (s, 5H), 2.47-2.33 (m, 2H), 1.87-1.72 (m, 7H), 1.57-1.46 (m, 2H). TLR9 $IC_{50}$ (nM) = 3600 |
| 245 | Analytical LC/MS (Method 1): Purity: 99.3%; Observed Mass: 554.96; Retention Time: 0.98 min. (Method 2): Purity: 100%; Observed Mass: 555.25; Retention Time: 1.30 min. Prep Method 1: 16 mg, 23% yield; $^1H$ NMR (500 MHz, DMSO-$d_6$) δ 8.17-8.07 (m, 4H), 7.65-7.60 (m, 1H), 7.58-7.52 (m, 1H), 3.89 (s, 4H), 3.51-3.41 (m, 2H), 3.31 (s, 3H), 3.12-2.84 (m, 5H), 2.44-2.34 (m, 3H), 2.22-2.10 (m, 2H), 1.82 (br d, J = 2.4 Hz, 8H), 1.54-1.35 (m, 5H) (one proton obscured). TLR9 $IC_{50}$ (nM) = 1100 |
| 246 | Analytical LC/MS (Method 1): Purity: 100%; Observed Mass: 529.35; Retention Time: 0.96 min. (Method 2): Purity: 99.3%; Observed Mass: 529.01; Retention Time: 1.36 min. Prep Method 1: 7.2 mg, 11% yield; $^1H$ NMR (500 MHz, DMSO-$d_6$) δ 8.16-8.05 (m, 4H), 7.64-7.58 (m, 1H), 7.58-7.48 (m, 1H), 3.88 (s, 3H), 3.51-3.38 (m, 1H), 3.31 (s, 2H), 3.23 (s, 2H), 3.00 (br d, J = 11.0 Hz, 2H), 2.92 (br d, J = 11.0 Hz, 2H), 2.84 (br s, 1H), 2.51 (br s, 3H), 2.44 (s, 2H), 2.32-2.20 (m, 3H), 1.94 (br s, 2H), 1.84-1.68 (m, 6H), 1.46 (br d, J = 9.2 Hz, 2H). TLR9 $IC_{50}$ (nM) = 400 |
| 247 | Analytical LC/MS (Method 1): Purity: 100%; Observed Mass: 552.99; Retention Time: 1.50 min. (Method 2): Purity: 100%; Observed Mass: 553.33; Retention Time: 1.49 min. Prep Method 1: 29 mg, 26% yield; $^1H$ NMR (500 MHz, DMSO-$d_6$) δ 8.16-8.07 (m, 4H), 7.63-7.58 (m, 1H), 7.54-7.49 (m, 1H), 3.87 (s, 2H), 3.68-3.56 (m, 6H), 3.29 (s, 3H), 3.26-3.22 (m, 1H), 3.22-3.07 (m, 2H), 3.07-3.02 (m, 2H), 2.91-2.80 (m, 1H), 2.68-2.57 (m, 2H), 2.25 (br s, 2H), 2.17 (br d, J = 7.6 Hz, 2H), 1.92-1.50 (m, 6H), 0.88 (d, J = 6.7 Hz, 6H). TLR9 $IC_{50}$ (nM) = 30 |
| 248 | Analytical LC/MS (Method 1): Purity: 98.2%; Observed Mass: 552.99; Retention Time: 1.67 min. (Method 2): Purity: 98.2%; Observed Mass: 553.01; Retention Time: 1.66 min. Prep Method 1: 30 mg, 26% yield; $^1H$ NMR (500 MHz, DMSO-$d_6$) δ 8.12 (s, 4H), 7.60 (d, J = 6.4 Hz, 1H), 7.55 (d, J = 10.7 Hz, 1H), 3.89 (s, 3H), 3.32 (s, 1H), 3.27-3.20 (m, 1H), 2.89-2.79 (m, 1H), 2.51 (br s, 3H), 2.46-2.37 (m, 1H), 2.11-1.57 (m, 16H), 0.89 (br d, J = 6.4 Hz, 6H) (three protons obscured). TLR9 $IC_{50}$ (nM) = 78 |
| 249 | Analytical LC/MS (Method 1): Purity: 97.6%; Observed Mass: 550.99; Retention Time: 0.98 min. (Method 2): Purity: 97.6%; Observed Mass: 551.38; Retention Time: 1.43 min. Prep Method 1: 21 mg, 19% yield; $^1H$ NMR (500 MHz, DMSO-$d_6$) δ 8.02 (s, 4H), 7.50 (d, J = 6.7 Hz, 1H), 7.44 (d, J = 10.7 Hz, 1H), 3.79 (s, 3H), 3.21 (s, 2H), 2.93-2.85 (m, 2H), 2.77-2.68 (m, 1H), 2.55-2.47 (m, 1H), 2.45 (s, 2H), 2.22-2.16 (m, 2H), 2.15-2.08 (m, 2H), 1.79 (s, 5H), 1.44 (br s, 8H), 0.84-0.66 (m, 1H), 0.40-0.27 (m, 2H), 0.07--0.11 (m, 2H). TLR9 $IC_{50}$ (nM) = 32 |
| 250 | Analytical LC/MS (Method 1): Purity: 98.4%; Observed Mass: 550.98; Retention Time: 1.0 min. (Method 2): Purity: 100%; Observed Mass: 551.02; Retention Time: 1.59 min. Prep Method 1: 20 mg, 18% yield; $^1H$ NMR (500 MHz, DMSO-$d_6$) δ 8.01-7.95 (m, 4H), 7.49-7.45 (m, 1H), 7.43-7.37 (m, 1H), 3.75 (s, 3H), 3.48-3.33 (m, 1H), 3.32-3.26 (m, 1H), 3.17 (s, 4H), 2.77-2.64 (m, 1H), 2.30-2.22 (m, 1H), 2.17 (br d, J = 6.4 Hz, 2H), 1.85 (br s, 2H), 1.79-1.66 (m, 11H), 1.61 (br s, 2H), 0.81-0.69 (m, 1H), 0.33 (br d, J = 6.7 Hz, 2H), 0.01 (br d, J = 4.6 Hz, 2H). TLR9 $IC_{50}$ (nM) = 110 |
| 251 | Analytical LC/MS (Method 1): Purity: 99.1%; Observed Mass: 550.96; Retention Time: 1.44 min. (Method 2): Purity: 99.1%; Observed Mass: 551.00; Retention Time: 1.44 min. Prep Method 1: 23 mg, 20% yield; $^1H$ NMR (500 MHz, DMSO-$d_6$) δ 8.15-8.06 (m, 4H), 7.63-7.58 (m, 1H), 7.56-7.49 (m, 1H), 3.87 (s, 2H), 3.58-3.49 (m, 1H), 3.30 (s, 2H), 3.25 (br s, 2H), 3.13-3.04 (m, 1H), 3.00 (br d, J = 10.1 Hz, 2H), 2.87-2.78 (m, 1H), 2.67-2.57 (m, 1H), 2.23 (br t, J = 11.0 Hz, 2H), 1.99 (br d, J = 5.5 Hz, 2H), 1.88 (s, 1H), 1.86-1.50 (m, 16H). TLR9 $IC_{50}$ (nM) = 71 |
| 252 | Analytical LC/MS (Method 1): Purity: 92.9%; Observed Mass: 551.15; Retention Time: 0.98 min. (Method 2): Purity: 93.5%; Observed Mass: 551.26; Retention Time: 1.49 min. Prep Method 1: 32 mg, 27% yield; $^1H$ NMR (500 MHz, DMSO-$d_6$) δ 8.19-8.07 (m, 4H), 7.64-7.58 (m, 1H), 7.58-7.50 (m, 1H), 3.89 (s, 3H), 3.49-3.41 (m, 1H), 3.31 (s, 1H), 3.28-3.16 (m, |

-continued

| Ex. No. | Analytical LC/MS, Preparative HPLC method, yield, and $^1$H NMR |
|---|---|
| | 1H), 3.00 (s, 1H), 2.91-2.75 (m, 1H), 2.65-2.50 (m, 5H), 2.43-2.34 (m, 1H), 2.03-1.55 (m, 19H). TLR9 $IC_{50}$ (nM) = 59 |
| 253 | Analytical LC/MS (Method 1): Purity: 98.1%; Observed Mass: 552.96; Retention Time: 0.94 min. (Method 2): Purity: 94.9%; Observed Mass: 553.37; Retention Time: 1.33 min. Prep Method 1: 18 mg, 15% yield; $^1$H NMR (500 MHz, DMSO-$d_6$) δ 8.17-8.07 (m, 4H), 7.64-7.59 (m, 1H), 7.57-7.50 (m, 1H), 4.64-4.49 (m, 2H), 4.32 (s, 2H), 3.89 (s, 3H), 3.73-3.60 (m, 1H), 3.54-3.34 (m, 1H), 3.31 (s, 2H), 3.11 (br d, J = 1.2 Hz, 2H), 3.07-2.99 (m, 1H), 2.91-2.79 (m, 1H), 2.74-2.61 (m, 1H), 2.34-2.24 (m, 2H), 1.85-1.67 (m, 6H), 1.65-1.49 (m, 6H) (one proton obscured). TLR9 $IC_{50}$ (nM) = 280 |
| 254 | Analytical LC/MS (Method 1): Purity: 98.3%; Observed Mass: 552.96; Retention Time: 0.95 min. (Method 2): Purity: 98.4%; Observed Mass: 553.37; Retention Time: 1.33 min. Prep Method 1: 14 mg, 12% yield; $^1$H NMR (500 MHz, DMSO-$d_6$) δ 8.18-8.07 (m, 4H), 7.63-7.59 (m, 1H), 7.58-7.52 (m, 1H), 4.54 (t, J = 6.1 Hz, 2H), 4.35-4.27 (m, 2H), 3.89 (s, 3H), 3.62-3.52 (m, 1H), 3.28-3.21 (m, 1H), 3.01 (br s, 2H), 2.90-2.79 (m, 1H), 2.55 (s, 2H), 2.48-2.39 (m, 1H), 1.98-1.67 (m, 15H) (one proton obscured). TLR9 $IC_{50}$ (nM) = 5300 |
| 255 | Analytical LC/MS (Method 1): Purity: 100%; Observed Mass: 580.99; Retention Time: 0.99 min. (Method 2): Purity: 100%; Observed Mass: 581.27; Retention Time: 1.37 min. Prep Method 1: 11 mg, 10% yield; $^1$H NMR (500 MHz, DMSO-$d_6$) δ 8.16-8.08 (m, 4H), 7.61 (br d, J = 6.7 Hz, 1H), 7.57-7.51 (m, 1H), 3.89 (s, 3H), 3.87-3.83 (m, 1H), 3.35-3.29 (m, 1H), 3.07-3.02 (m, 1H), 2.88-2.79 (m, 1H), 2.72-2.57 (m, 2H), 2.51 (br s, 3H), 2.26-2.15 (m, 2H), 1.79 (br s, 8H), 1.67-1.41 (m, 6H), 1.27 (br d, J = 10.7 Hz, 2H) (five protons obscured). TLR9 $IC_{50}$ (nM) = 72 |
| 256 | Analytical LC/MS (Method 1): Purity: 97.3%; Observed Mass: 581.01; Retention Time: 1.47 min. (Method 2): Purity: 97.2%; Observed Mass: 581.01; Retention Time: 1.47 min. Prep Method 1: 31 mg, 26% yield; $^1$H NMR (500 MHz, DMSO-$d_6$) δ 8.17-8.06 (m, 4H), 7.63-7.58 (m, 1H), 7.55-7.48 (m, 1H), 3.87 (s, 3H), 3.73-3.55 (m, 7H), 3.54-3.47 (m, 1H), 3.29 (s, 5H), 2.90-2.80 (m, 1H), 2.62-2.56 (m, 1H), 2.43-2.35 (m, 1H), 1.96-1.70 (m, 14H), 1.38-1.27 (m, 2H). TLR9 $IC_{50}$ (nM) = 320 |
| 257 | Analytical LC/MS (Method 1): Purity: 100%; Observed Mass: 554.97; Retention Time: 1.0 min. (Method 2): Purity: 100%; Observed Mass: 554.96; Retention Time: 1.37 min. Prep Method 1: 22 mg, 20% yield; $^1$H NMR (500 MHz, DMSO-$d_6$) δ 8.15-8.09 (m, 4H), 7.66-7.60 (m, 2H), 4.23-4.12 (m, 2H), 3.90 (s, 2H), 3.84-3.74 (m, 1H), 3.72-3.66 (m, 1H), 3.62-3.51 (m, 1H), 3.33 (d, J = 16.8 Hz, 5H), 3.28-3.15 (m, 2H), 2.58-2.48 (m, 7H), 2.32-1.94 (m, 12H). TLR9 $IC_{50}$ (nM) = 49 |
| 258 | Analytical LC/MS (Method 1): Purity: 95.1%; Observed Mass: 554.99; Retention Time: 1.49 min. (Method 2): Purity: 95.8%; Observed Mass: 555.31; Retention Time: 1.49 min. Prep Method 1: 35 mg, 30% yield; $^1$H NMR (500 MHz, DMSO-$d_6$) δ 8.14-8.05 (m, 4H), 7.59 (d, J = 6.7 Hz, 1H), 7.51 (d, J = 10.7 Hz, 1H), 3.86 (s, 2H), 3.72-3.55 (m, 2H), 3.39 (t, J = 6.1 Hz, 2H), 3.29 (s, 3H), 3.25-3.15 (m, 6H), 2.81 (br s, 1H), 2.42 (br t, J = 6.1 Hz, 2H), 2.36 (br d, J = 5.8 Hz, 1H), 1.99-1.61 (m, 14H). TLR9 $IC_{50}$ (nM) = 100 |
| 259 | Analytical LC/MS (Method 1): Purity: 99.3%; Observed Mass: 526.95; Retention Time: 0.97 min. (Method 2): Purity: 100%; Observed Mass: 527.27; Retention Time: 1.47 min. Prep Method 1: 15 mg, 16% yield; $^1$H NMR (500 MHz, DMSO-$d_6$) δ 8.18-8.02 (m, 4H), 7.58-7.48 (m, 1H), 7.27-7.15 (m, 1H), 4.03 (s, 3H), 3.11-2.88 (m, 1H), 2.76-2.62 (m, 1H), 2.51 (br s, 8H), 2.28-2.04 (m, 2H), 2.03-1.93 (m, 1H), 1.92-1.68 (m, 7H), 1.59 (br d, J = 2.4 Hz, 3H), 1.31-1.19 (m, 1H), 0.88 (br d, J = 6.1 Hz, 6H). TLR9 $IC_{50}$ (nM) = 500 |
| 260 | Analytical LC/MS (Method 1): Purity: 98.6%; Observed Mass: 511.20; Retention Time: 0.93 min. (Method 2): Purity: 100%; Observed Mass: 510.91; Retention Time: 1.42 min. Prep Method 2: 13 mg, 10% yield; $^1$H NMR (500 MHz, DMSO-$d_6$) δ 8.17-8.06 (m, 4H), 7.60-7.54 (m, 1H), 7.20-7.11 (m, 1H), 4.04 (s, 3H), 3.71-3.52 (m, 2H), 3.32 (s, 2H), 3.29-3.14 (m, 1H), 2.87-2.68 (m, 1H), 2.55 (s, 2H), 2.51 (br s, 4H), 2.37-2.28 (m, 2H), 2.19-1.88 (m, 6H), 0.94 (br s, 2H), 0.83 (br d, J = 7.0 Hz, 2H) (two protons obscured). TLR9 $IC_{50}$ (nM) = 660 |
| 261 | Analytical LC/MS (Method 1): Purity: 100%; Observed Mass: 524.95; Retention Time: 0.95 min. (Method 2): Purity: 100%; Observed Mass: 525.24; Retention Time: 1.20 min. Prep Method 2: 56 mg, 43% yield; $^1$H NMR (500 MHz, DMSO-$d_6$) δ 8.16-8.05 (m, 4H), 7.60-7.54 (m, 1H), 7.19-7.14 (m, 1H), 4.04 (s, 3H), 3.78-3.70 (m, 1H), 3.66-3.58 (m, 1H), 3.54-3.41 (m, 1H), 3.32 (s, 3H), 3.01 (br d, J = 6.7 Hz, 3H), 2.55 (s, 3H), 2.51 (br s, 2H), 2.41-2.32 (m, 2H), 2.19-1.96 (m, 6H), 1.14-1.04 (m, 1H), 0.67 (br d, J = 6.7 Hz, 2H), 0.39 (br d, J = 4.0 Hz, 2H) (one proton obscured). TLR9 $IC_{50}$ (nM) = 150 |
| 262 | Analytical LC/MS (Method 1): Purity: 100%; Observed Mass: 524.96; Retention Time: 0.95 min. (Method 2): Purity: 100%; Observed Mass: 524.97; Retention Time: 1.37 min. Prep Method 2: 44 mg, 34% yield; $^1$H NMR (500 MHz, DMSO-$d_6$) δ 8.18-8.06 (m, 4H), 7.63-7.52 (m, 1H), 7.20-7.09 (m, 1H), 4.04 (s, 3H), 3.67-3.52 (m, 1H), 3.33 (s, 1H), 2.91-2.79 (m, |

-continued

| Ex. No. | Analytical LC/MS, Preparative HPLC method, yield, and $^1$H NMR |
|---|---|
| | 1H), 2.55 (s, 3H), 2.53-2.48 (m, 4H), 2.39-2.30 (m, 2H), 2.27-2.01 (m, 8H), 1.95 (br d, J = 10.4 Hz, 2H), 1.85-1.67 (m, 2H) (four protons obscured). TLR9 $IC_{50}$ (nM) = 170 |
| 263 | Analytical LC/MS (Method 1): Purity: 100%; Observed Mass: 526.95; Retention Time: 0.95 min. (Method 2): Purity: 97.4%; Observed Mass: 527.19; Retention Time: 1.21 min. Prep Method 2: 63 mg, 49% yield; $^1$H NMR (500 MHz, DMSO-$d_6$) δ 8.20-8.05 (m, 4H), 7.62-7.55 (m, 1H), 7.20-7.13 (m, 1H), 4.78-4.67 (m, 4H), 4.32-4.16 (m, 1H), 4.04 (s, 3H), 3.67-3.57 (m, 1H), 3.33 (s, 2H), 3.29-3.21 (m, 1H), 2.86-2.67 (m, 1H), 2.55 (s, 7H), 2.41-2.29 (m, 2H), 2.07 (br s, 6H) (one proton obscured). TLR9 $IC_{50}$ (nM) = 1800 |
| 264 | Analytical LC/MS (Method 1): Purity: 100%; Observed Mass: 555.35; Retention Time: 0.94 min. (Method 2): Purity: 95.2%; Observed Mass: 554.96; Retention Time: 1.33 min. Prep Method 2: 94 mg, 71% yield; $^1$H NMR (500 MHz, DMSO-$d_6$) δ 8.19-8.05 (m, 4H), 7.60-7.53 (m, 1H), 7.18-7.14 (m, 1H), 4.06-4.03 (m, 3H), 4.02-3.97 (m, 2H), 3.74-3.68 (m, 1H), 3.65-3.54 (m, 1H), 3.33 (s, 2H), 3.16-2.98 (m, 2H), 2.51 (br s, 6H), 2.45-2.33 (m, 2H), 2.26-2.11 (m, 2H), 2.10-1.94 (m, 5H), 1.80-1.61 (m, 2H) (five protons obscured). TLR9 $IC_{50}$ (nM) = 280 |
| 265 | Analytical LC/MS (Method 1): Purity: 97%; Observed Mass: 529.22; Retention Time: 0.93 min. (Method 2): Purity: 97%; Observed Mass: 528.94; Retention Time: 1.24 min. Prep Method 1: 35 mg, 39% yield; $^1$H NMR (500 MHz, DMSO-$d_6$) δ 8.16-8.04 (m, 4H), 7.53-7.46 (m, 1H), 7.26-7.18 (m, 1H), 4.02 (s, 3H), 3.78-3.62 (m, 1H), 3.46-3.30 (m, 1H), 3.23 (s, 1H), 3.17 (d, J = 5.0 Hz, 3H), 3.07-2.96 (m, 2H), 2.92 (br d, J = 11.5 Hz, 2H), 2.51 (br s, 4H), 2.48-2.42 (m, 2H), 2.36-2.19 (m, 3H), 1.99-1.88 (m, 2H), 1.76 (br d, J = 1.2 Hz, 5H), 1.52-1.40 (m, 2H). TLR9 $IC_{50}$ (nM) = 1000 |
| 266 | Analytical LC/MS (Method 1): Purity: 99.2%; Observed Mass: 553.15; Retention Time: 0.99 min. (Method 2): Purity: 99.2%; Observed Mass: 552.98; Retention Time: 1.32 min. Prep Method 1: 16 mg, 11% yield; $^1$H NMR (500 MHz, DMSO-$d_6$) δ 8.19-8.02 (m, 4H), 7.53-7.47 (m, 1H), 7.27-7.14 (m, 1H), 4.02 (s, 3H), 3.52-3.40 (m, 4H), 3.31 (s, 2H), 3.19-3.16 (m, 1H), 3.14-2.92 (m, 3H), 2.42-2.13 (m, 5H), 1.91 (br s, 3H), 1.78 (br d, J = 4.0 Hz, 8H), 0.90 (br d, J = 6.4 Hz, 6H). TLR9 $IC_{50}$ (nM) = 97 |
| 267 | Analytical LC/MS (Method 1): Purity: 98.1%; Observed Mass: 553.18; Retention Time: 0.99 min. (Method 2): Purity: 98.9%; Observed Mass: 553.07; Retention Time: 1.53 min. Prep Method 1: 16 mg, 11% yield; $^1$H NMR (500 MHz, DMSO-$d_6$) δ 8.19-8.03 (m, 4H), 7.55-7.48 (m, 1H), 7.25-7.18 (m, 1H), 4.02 (s, 3H), 3.52 (br d, J = 4.9 Hz, 4H), 3.31 (s, 3H), 2.67 (s, 3H), 1.91 (s, 3H), 1.87-1.58 (m, 8H), 1.15 (s, 3H), 0.95-0.85 (m, 6H) (two protons obscured). TLR9 $IC_{50}$ (nM) = 350 |
| 268 | Analytical LC/MS (Method 1): Purity: 100%; Observed Mass: 550.97; Retention Time: 1.39 min. (Method 2): Purity: 100%; Observed Mass: 550.99; Retention Time: 1.39 min. Prep Method 1: 18 mg, 12% yield; $^1$H NMR (500 MHz, DMSO-$d_6$) δ 8.03-7.89 (m, 4H), 7.43-7.30 (m, 1H), 7.12-6.97 (m, 1H), 3.88 (s, 3H), 3.18 (s, 1H), 2.87 (br d, J = 10.4 Hz, 2H), 2.83-2.73 (m, 1H), 2.59-2.45 (m, 1H), 2.37 (br s, 4H), 2.28-2.17 (m, 2H), 2.16-2.02 (m, 2H), 1.79-1.71 (m, 2H), 1.67-1.59 (m, 4H), 1.57-1.40 (m, 6H), 0.77-0.66 (m, 1H), 0.33 (br d, J = 6.7 Hz, 2H), 0.01 (br d, J = 3.4 Hz, 2H). TLR9 $IC_{50}$ (nM) = 60 |
| 269 | Analytical LC/MS (Method 1): Purity: 100%; Observed Mass: 551.26; Retention Time: 1.02 min. (Method 2): Purity: 99.3%; Observed Mass: 550.94; Retention Time: 1.56 min. Prep Method 1: 12 mg, 8% yield; $^1$H NMR (500 MHz, DMSO-$d_6$) δ 7.97-7.87 (m, 4H), 7.34-7.28 (m, 1H), 7.05-6.99 (m, 1H), 3.82 (s, 3H), 3.46-3.31 (m, 4H), 3.11 (s, 4H), 2.79-2.71 (m, 1H), 2.26 (br d, J = 7.0 Hz, 2H), 2.21-2.16 (m, 1H), 1.81 (br d, J = 6.4 Hz, 6H), 1.74-1.70 (m, 2H), 1.65-1.54 (m, 5H), 0.78-0.70 (m, 1H), 0.34-0.30 (m, 2H), 0.04--0.03 (m, 2H). TLR9 $IC_{50}$ (nM) = 180 |
| 270 | Analytical LC/MS (Method 1): Purity: 97.9%; Observed Mass: 551.30; Retention Time: 1.4 min. (Method 2): Purity: 97.9%; Observed Mass: 550.99; Retention Time: 1.4 min. Prep Method 1: 22 mg, 15% yield; $^1$H NMR (500 MHz, DMSO-$d_6$) δ 8.18-8.04 (m, 4H), 7.54-7.45 (m, 1H), 7.27-7.16 (m, 1H), 4.02 (s, 3H), 3.52-3.41 (m, 3H), 3.31 (s, 2H), 3.28-3.23 (m, 1H), 3.20-3.16 (m, 1H), 3.14-3.05 (m, 1H), 3.04-2.88 (m, 4H), 2.67-2.59 (m, 2H), 2.22 (br d, J = 9.5 Hz, 2H), 2.04-1.96 (m, 3H), 1.90 (s, 1H), 1.88-1.51 (m, 10H). TLR9 $IC_{50}$ (nM) = 65 |
| 271 | Analytical LC/MS (Method 1): Purity: 95.1%; Observed Mass: 551.08; Retention Time: 0.94 min. (Method 2): Purity: 95%; Observed Mass: 551.27; Retention Time: 1.45 min. Prep Method 1: 17 mg, 11% yield; $^1$H NMR (500 MHz, DMSO-$d_6$) δ 8.18-8.03 (m, 4H), 7.50 (d, J = 8.2 Hz, 1H), 7.20 (br t, J = 7.5 Hz, 1H), 4.02 (s, 3H), 3.32 (s, 2H), 3.18-3.04 (m, 1H), 2.99-2.87 (m, 1H), 2.68-2.61 (m, 1H), 2.55 (s, 1H), 2.43-2.34 (m, 1H), 2.07-1.73 (m, 17H), 1.72-1.48 (m, 4H) (two protons obscured). TLR9 $IC_{50}$ (nM) = 410 |
| 272 | Analytical LC/MS (Method 1): Purity: 95.5%; Observed Mass: 552.95; Retention Time: 0.97 min. (Method 2): Purity: 96.3%; Observed Mass: 553.22; Retention Time: 1.21 min. Prep Method 1: 8.2 mg, 5% yield; $^1$H NMR (500 MHz, DMSO-$d_6$) δ 8.16-8.05 (m, 4H), 7.52-7.44 (m, 1H), 7.24- |

-continued

| Ex. No. | Analytical LC/MS, Preparative HPLC method, yield, and $^1$H NMR |
|---|---|
| | 7.16 (m, 1H), 4.53 (t, J = 6.1 Hz, 2H), 4.30 (t, J = 5.7 Hz, 2H), 4.02 (s, 3H), 3.61-3.50 (m, 1H), 3.32 (s, 1H), 3.28-3.22 (m, 1H), 3.00 (br s, 2H), 2.97-2.88 (m, 1H), 2.55 (s, 1H), 2.43 (br s, 1H), 1.97-1.84 (m, 4H), 1.82-1.68 (m, 9H) (three protons obscured). |
| 273 | Analytical LC/MS (Method 1): Purity: 99.2%; Observed Mass: 553.13; Retention Time: 0.95 min. (Method 2): Purity: 100%; Observed Mass: 553.16; Retention Time: 1.26 min. Prep Method 1: 8.6 mg, 6% yield; $^1$H NMR (500 MHz, DMSO-$d_6$) δ 8.18-8.04 (m, 4H), 7.53-7.45 (m, 1H), 7.25-7.13 (m, 1H), 4.59-4.52 (m, 2H), 4.31 (s, 2H), 4.02 (s, 3H), 3.71-3.62 (m, 1H), 3.52-3.42 (m, 1H), 3.37-3.29 (m, 1H), 3.13-3.06 (m, 2H), 3.03-2.86 (m, 3H), 2.67-2.57 (m, 1H), 2.27-2.18 (m, 2H), 1.82-1.71 (m, 6H), 1.64-1.48 (m, 6H) (one proton obscured). TLR9 $IC_{50}$ (nM) = 300 |
| 274 | Analytical LC/MS (Method 1): Purity: 98.5%; Observed Mass: 580.98; Retention Time: 1.31 min. (Method 2): Purity: 98.4%; Observed Mass: 581.01; Retention Time: 1.31 min. Prep Method 1: 25 mg, 16% yield; $^1$H NMR (500 MHz, DMSO-$d_6$) δ 8.17-8.06 (m, 4H), 7.50 (d, J = 8.5 Hz, 1H), 7.21 (br t, J = 7.5 Hz, 1H), 4.03 (s, 3H), 3.90-3.84 (m, 2H), 3.36-3.29 (m, 2H), 3.13-3.03 (m, 2H), 3.02-2.89 (m, 1H), 2.79-2.62 (m, 2H), 2.55 (s, 2H), 2.29-2.18 (m, 2H), 1.92 (s, 2H), 1.86-1.74 (m, 8H), 1.71-1.63 (m, 2H), 1.62-1.48 (m, 4H), 1.36-1.23 (m, 3H). TLR9 $IC_{50}$ (nM) = 51 |
| 275 | Analytical LC/MS (Method 1): Purity: 96.7%; Observed Mass: 581.01; Retention Time: 1.43 min. (Method 2): Purity: 96..7%; Observed Mass: 580.97; Retention Time: 1.43 min. Prep Method 1: 18 mg, 12% yield; $^1$H NMR (500 MHz, DMSO-$d_6$) δ 8.17-8.06 (m, 4H), 7.52-7.46 (m, 1H), 7.26-7.17 (m, 1H), 4.03 (s, 3H), 3.93-3.83 (m, 2H), 3.32 (s, 4H), 3.04-2.89 (m, 2H), 2.44-2.32 (m, 2H), 2.02-1.73 (m, 14H), 1.47-1.25 (m, 4H) (four protons obscured). TLR9 $IC_{50}$ (nM) = 89 |
| 276 | Analytical LC/MS (Method 1): Purity: 96.2%; Observed Mass: 554.98; Retention Time: 0.95 min. (Method 2): Purity: 96.7%; Observed Mass: 555.38; Retention Time: 1.29 min. Prep Method 1: 25 mg, 16% yield; $^1$H NMR (500 MHz, DMSO-$d_6$) δ 8.16-8.06 (m, 4H), 7.53-7.46 (m, 1H), 7.21 (br d, J = 7.9 Hz, 1H), 4.02 (s, 3H), 3.54-3.38 (m, 5H), 3.31 (s, 2H), 3.25 (s, 3H), 3.19-3.14 (m, 1H), 3.06-2.89 (m, 4H), 2.65 (s, 2H), 2.28-2.20 (m, 2H), 1.91 (s, 4H), 1.79-1.48 (m, 7H). TLR9 $IC_{50}$ (nM) = 170 |
| 277 | Analytical LC/MS (Method 1): Purity: 91.9%; Observed Mass: 554.96; Retention Time: 0.95 min. (Method 2): Purity: 97.5%; Observed Mass: 555.26; Retention Time: 1.39 min. Prep Method 1: 18 mg, 11% yield; $^1$H NMR (500 MHz, DMSO-$d_6$) δ 8.21-7.97 (m, 4H), 7.49 (d, J = 8.5 Hz, 1H), 7.20 (br t, J = 7.3 Hz, 1H), 4.03 (s, 2H), 3.25 (s, 2H), 3.21-3.13 (m, 2H), 2.98-2.86 (m, 2H), 2.58-2.54 (m, 2H), 2.51 (br s, 3H), 2.41 (br t, J = 6.0 Hz, 5H), 1.95-1.64 (m, 12H) (three protons obscured). TLR9 $IC_{50}$ (nM) = 270 |
| 278 | Analytical LC/MS (Method 1): Purity: 96.7%; Observed Mass: 527.03; Retention Time: 0.94 min. (Method 2): Purity: 95.6%; Observed Mass: 527.20; Retention Time: 1.33 min. Prep Method 1: 20 mg, 35% yield; $^1$H NMR (500 MHz, DMSO-$d_6$) δ 8.17-8.10 (m, 4H), 7.43-7.37 (m, 1H), 7.07-6.99 (m, 1H), 3.92 (s, 3H), 3.33-3.30 (m, 2H), 3.12-3.06 (m, 1H), 3.02-2.98 (m, 1H), 2.96-2.89 (m, 2H), 2.71-2.67 (m, 3H), 2.64-2.59 (m, 3H), 2.48-2.33 (m, 2H), 2.12-2.03 (m, 2H), 1.96-1.84 (m, 2H), 1.81-1.72 (m, 4H), 1.58-1.48 (m, 2H), 0.88-0.83 (m, 6H). TLR9 $IC_{50}$ (nM) = 58 |
| 279 | Analytical LC/MS (Method 1): Purity: 100%; Observed Mass: 527.60; Retention Time: 0.88 min. (Method 2): Purity: 100%; Observed Mass: 527.50; Retention Time: 1.06 min. Prep Method 2: 32 mg, 40% yield; $^1$H NMR (500 MHz, DMSO-$d_6$) δ 8.18-8.11 (m, 4H), 7.43-7.36 (m, 1H), 7.06-7.00 (m, 1H), 4.73 (br d, J = 6.1 Hz, 4H), 4.33-4.23 (m, 1H), 3.94 (s, 3H), 3.70-3.59 (m, 1H), 3.33 (s, 2H), 3.23-3.14 (m, 1H), 3.12-3.04 (m, 1H), 2.85-2.72 (m, 1H), 2.53-2.48 (m, 3H), 2.41-2.30 (m, 2H), 2.22-2.13 (m, 2H), 2.07 (br s, 4H) (four protons obscured). TLR9 $IC_{50}$ (nM) = 1200 |
| 280 | Analytical LC/MS (Method 1): Purity: 100%; Observed Mass: 555.60; Retention Time: 0.89 min. (Method 2): Purity: 98.5%; Observed Mass: 555.60; Retention Time: 1.11 min. Prep Method 2: 21 mg, 26% yield; $^1$H NMR (500 MHz, DMSO-$d_6$) δ 8.22-8.07 (m, 4H), 7.44-7.35 (m, 1H), 7.10-6.98 (m, 1H), 4.03-3.97 (m, 2H), 3.94 (s, 3H), 3.73-3.53 (m, 2H), 3.37-3.29 (m, 1H), 3.26-2.94 (m, 2H), 2.55 (s, 5H), 2.51 (s, 4H), 2.42-2.31 (m, 2H), 2.20-1.90 (m, 8H), 1.75-1.62 (m, 2H) (two protons obscured). TLR9 $IC_{50}$ (nM) = 73 |
| 281 | Analytical LC/MS (Method 1): Purity: 96.9%; Observed Mass: 529.50; Retention Time: 0.91 min. (Method 2): Purity: 100%; Observed Mass: 529.20; Retention Time: 1.1 min. Prep Method 1: 12 mg, 21% yield; $^1$H NMR (500 MHz, DMSO-$d_6$) δ 8.21-8.04 (m, 4H), 7.43-7.37 (m, 1H), 7.08-6.99 (m, 1H), 3.92 (s, 3H), 3.32 (s, 1H), 3.24 (s, 2H), 3.09-3.00 (m, 2H), 2.99-2.88 (m, 2H), 2.71-2.62 (m, 1H), 2.55 (s, 2H), 2.50-2.45 (m, 2H), 2.38-2.22 (m, 3H), 1.99 (br d, J = 1.5 Hz, 2H), 1.92 (s, 1H), 1.85 (br d, J = 10.4 Hz, 2H), 1.75 (br d, J = 11.9 Hz, 4H), 1.54-1.42 (m, 2H) (two protons obscured). TLR9 $IC_{50}$ (nM) = 120 |
| 282 | Analytical LC/MS (Method 1): Purity: 99.3%; Observed Mass: 551.20; Retention Time: 1.04 min. (Method 2): Purity: 99.3%; Observed Mass: 551.20; Retention Time: 1.33 min. Prep Method 1: 10 mg, 8% yield; $^1$H |

-continued

| Ex. No. | Analytical LC/MS, Preparative HPLC method, yield, and $^1$H NMR |
|---|---|
| | NMR (500 MHz, DMSO-$d_6$) δ 8.10-7.93 (m, 4H), 7.33-7.27 (m, 1H), 6.97-6.86 (m, 1H), 3.82 (s, 3H), 3.22 (s, 1H), 2.95-2.85 (m, 2H), 2.58-2.46 (m, 2H), 2.45 (s, 2H), 2.18 (br d, J = 6.1 Hz, 2H), 2.14-2.04 (m, 2H), 1.84-1.68 (m, 5H), 1.66-1.38 (m, 8H), 0.77-0.70 (m, 1H), 0.34 (br d, J = 6.7 Hz, 2H), 0.01 (br d, J = 4.3 Hz, 2H) (one proton obscured). TLR9 $IC_{50}$ (nM) = 110 |
| 283 | Analytical LC/MS (Method 1): Purity: 99.2%; Observed Mass: 551.20; Retention Time: 1.0 min. (Method 2): Purity: 98.5%; Observed Mass: 551.20; Retention Time: 1.52 min. Prep Method 1: 14 mg, 10% yield; $^1$H NMR (500 MHz, DMSO-$d_6$) δ 8.15-7.97 (m, 4H), 7.34-7.28 (m, 1H), 6.97-6.88 (m, 1H), 3.83 (s, 3H), 3.22 (s, 3H), 2.63-2.51 (m, 1H), 2.45 (s, 1H), 2.32-2.23 (m, 1H), 2.13 (br d, J = 6.1 Hz, 2H), 1.91-1.82 (m, 2H), 1.82-1.59 (m, 14H), 0.80-0.69 (m, 1H), 0.34 (br d, J = 7.9 Hz, 2H), 0.01 (br d, J = 4.9 Hz, 2H) (one proton obscured). TLR9 $IC_{50}$ (nM) = 16 |
| 284 | Analytical LC/MS (Method 1): Purity: 100%; Observed Mass: 553.20; Retention Time: 1.05 min. (Method 2): Purity: 99.4%; Observed Mass: 553.20; Retention Time: 1.41 min. Prep Method 1: 12 mg, 9% yield; $^1$H NMR (500 MHz, DMSO-$d_6$) δ 8.20-8.06 (m, 4H), 7.43-7.36 (m, 1H), 7.08-6.97 (m, 1H), 3.92 (s, 3H), 3.32 (s, 1H), 3.18 (s, 1H), 3.10-2.98 (m, 1H), 2.73-2.60 (m, 2H), 2.55 (s, 1H), 2.19 (br s, 4H), 1.94-1.81 (m, 4H), 1.81-1.50 (m, 9H), 0.90 (d, J = 6.4 Hz, 6H) (three protons obscured). TLR9 $IC_{50}$ (nM) = 120 |
| 285 | Analytical LC/MS (Method 1): Purity: 96.7%; Observed Mass: 553.20; Retention Time: 1.05 min. (Method 2): Purity: 93.8%; Observed Mass: 553.20; Retention Time: 1.62 min. Prep Method 1: 14 mg, 9% yield; $^1$H NMR (500 MHz, DMSO-$d_6$) δ 8.13 (d, J = 5.8 Hz, 4H), 7.44-7.34 (m, 1H), 7.08-6.98 (m, 1H), 3.93 (s, 3H), 3.76-3.58 (m, 1H), 3.32 (s, 1H), 3.28-3.16 (m, 1H), 3.08-2.92 (m, 1H), 2.70-2.60 (m, 1H), 2.57-2.52 (m, 1H), 2.40 (br s, 1H), 2.14-1.51 (m, 17H), 0.92-0.85 (m, 6H) (two protons obscured). TLR9 $IC_{50}$ (nM) = 250 |
| 286 | Analytical LC/MS (Method 1): Purity: 90%; Observed Mass: 553.20; Retention Time: 0.88 min. (Method 2): Purity: 86.1%; Observed Mass: 553.20; Retention Time: 1.17 min. Prep Method 1: 15 mg, 10% yield; $^1$H NMR (500 MHz, DMSO-$d_6$) δ 8.23-8.01 (m, 4H), 7.44-7.36 (m, 1H), 7.10-6.96 (m, 1H), 4.60-4.50 (m, 1H), 4.34-4.27 (m, 1H), 3.93 (s, 3H), 3.64-3.52 (m, 1H), 3.32 (s, 1H), 3.28-3.21 (m, 1H), 3.04-2.96 (m, 1H), 2.70-2.59 (m, 1H), 2.57-2.48 (m, 3H), 2.47-2.37 (m, 1H), 1.99-1.62 (m, 16H), 1.61-1.49 (m, 1H). TLR9 $IC_{50}$ (nM) = 41 |
| 287 | Analytical LC/MS (Method 1): Purity: 96.6%; Observed Mass: 553.20; Retention Time: 1.0 min. (Method 2): Purity: 94.9%; Observed Mass: 553.10; Retention Time: 1.21 min. Prep Method 1: 9 mg, 6% yield; $^1$H NMR (500 MHz, DMSO-$d_6$) δ 8.20-8.08 (m, 4H), 7.43-7.36 (m, 1H), 7.08-6.99 (m, 1H), 4.61-4.50 (m, 2H), 4.38-4.25 (m, 2H), 3.92 (s, 3H), 3.70-3.56 (m, 1H), 3.32 (s, 1H), 3.13-3.08 (m, 1H), 3.03-2.96 (m, 2H), 2.68-2.58 (m, 2H), 2.26-2.17 (m, 2H), 1.90 (s, 3H), 1.81 (br d, J = 1.5 Hz, 7H), 1.63-1.48 (m, 5H). TLR9 $IC_{50}$ (nM) = 100 |
| 288 | Analytical LC/MS (Method 1): Purity: 100%; Observed Mass: 581.20; Retention Time: 0.97 min. (Method 2): Purity: 97.4%; Observed Mass: 581.20; Retention Time: 1.24 min. Prep Method 1: 20 mg, 14% yield; $^1$H NMR (500 MHz, DMSO-$d_6$) δ 8.22-8.03 (m, 4H), 7.45-7.37 (m, 1H), 7.07-6.98 (m, 1H), 3.93 (s, 3H), 3.89-3.82 (m, 2H), 3.53-3.47 (m, 1H), 3.10-3.01 (m, 1H), 2.69-2.62 (m, 2H), 2.55 (s, 2H), 2.22-2.14 (m, 2H), 1.91 (s, 3H), 1.78 (br s, 10H), 1.59-1.44 (m, 4H), 1.35-1.20 (m, 2H) (three protons obscured). TLR9 $IC_{50}$ (nM) = 110 |
| 289 | Analytical LC/MS (Method 1): Purity: 100%; Observed Mass: 581.20; Retention Time: 1.06 min. (Method 2): Purity: 100%; Observed Mass: 581.20; Retention Time: 1.54 min. Prep Method 1: 15 mg, 10% yield; $^1$H NMR (500 MHz, DMSO-$d_6$) δ 8.20-8.09 (m, 4H), 7.41-7.34 (m, 1H), 7.05-6.99 (m, 1H), 4.29-4.08 (m, 2H), 3.94 (s, 5H), 3.52-3.38 (m, 1H), 3.32 (s, 2H), 3.18 (s, 2H), 2.98-2.87 (m, 1H), 2.78-2.61 (m, 1H), 2.56-2.49 (m, 5H), 2.32-1.93 (m, 12H), 1.74-1.54 (m, 3H), 1.19-1.13 (m, 1H). TLR9 $IC_{50}$ (nM) = 29 |
| 290 | Analytical LC/MS (Method 1): Purity: 100%; Observed Mass: 555.20; Retention Time: 1.02 min. (Method 2): Purity: 99.3%; Observed Mass: 555.20; Retention Time: 1.26 min. Prep Method 1: 11 mg, 8% yield; $^1$H NMR (500 MHz, DMSO-$d_6$) δ 8.18-8.08 (m, 4H), 7.41-7.37 (m, 1H), 7.06-6.96 (m, 1H), 3.92 (s, 3H), 3.32 (s, 1H), 3.31-3.27 (m, 1H), 3.25 (s, 2H), 3.04-2.95 (m, 2H), 2.69-2.57 (m, 2H), 2.54-2.51 (m, 5H), 2.27-2.16 (m, 2H), 1.91 (s, 3H), 1.89-1.79 (m, 4H), 1.78-1.66 (m, 2H), 1.66-1.58 (m, 2H), 1.53 (br d, J = 7.9 Hz, 4H). TLR9 $IC_{50}$ (nM) = 150 |
| 291 | Analytical LC/MS (Method 1): Purity: 95.5%; Observed Mass: 555.20; Retention Time: 1.02 min. (Method 2): Purity: 95.9%; Observed Mass: 555.20; Retention Time: 1.42 min. Prep Method 1: 5 mg, 4% yield; $^1$H NMR (500 MHz, DMSO-$d_6$) δ 8.19-8.08 (m, 4H), 7.44-7.36 (m, 1H), 7.08-6.93 (m, 1H), 3.93 (s, 3H), 3.32 (s, 1H), 3.25 (s, 4H), 2.69-2.59 (m, 1H), 2.53-2.49 (m, 4H), 2.46 (s, 2H), 2.40-2.29 (m, 1H), 1.91 (s, 11H), 1.77-1.64 (m, 4H) (two protons obscured). TLR9 $IC_{50}$ (nM) = 57 |
| 292 | Analytical LC/MS (Method 1): Purity: 94.4%; Observed Mass: 551.20; Retention Time: 1.09 min. (Method 2): Purity: 92.9%; Observed Mass: |

-continued

| Ex. No. | Analytical LC/MS, Preparative HPLC method, yield, and $^1$H NMR |
|---|---|
| | 551.20; Retention Time: 1.48 min. Prep Method 1: 18 mg, 12% yield; $^1$H NMR (500 MHz, DMSO-$d_6$) δ 8.19-8.06 (m, 4H), 7.44-7.37 (m, 1H), 7.01 (br d, J = 11.9 Hz, 1H), 3.92 (s, 3H), 3.34-3.28 (m, 1H), 3.24-3.16 (m, 1H), 3.08-2.95 (m, 3H), 2.66-2.56 (m, 2H), 2.55 (s, 2H), 2.24-2.16 (m, 2H), 2.02-1.95 (m, 2H), 1.92-1.89 (m, 1H), 1.86-1.47 (m, 16H). TLR9 $IC_{50}$ (nM) = 150 |
| 293 | Analytical LC/MS (Method 1): Purity: 94%; Observed Mass: 551.20; Retention Time: 1.08 min. (Method 2): Purity: 95.2%; Observed Mass: 551.10; Retention Time: 1.65 min. Prep Method 1: 11 mg, 8% yield; $^1$H NMR (500 MHz, DMSO-$d_6$) δ 8.17-8.10 (m, 4H), 7.41-7.37 (m, 1H), 7.05-6.94 (m, 1H), 3.92 (s, 3H), 3.33-3.30 (m, 1H), 3.27-3.20 (m, 1H), 3.16-3.10 (m, 1H), 3.00-2.91 (m, 1H), 2.67-2.60 (m, 1H), 2.57-2.54 (m, 1H), 2.41-2.33 (m, 1H), 2.00-1.82 (m, 9H), 1.82-1.53 (m, 14H). TLR9 $IC_{50}$ (nM) = 11 |
| 294 | Analytical LC/MS (Method 1): Purity: 100%; Observed Mass: 527.30; Retention Time: 1.0 min. (Method 2): Purity: 100%; Observed Mass: 527.30; Retention Time: 1.15 min. Prep Method 1: 30 mg, 21% yield; $^1$H NMR (500 MHz, DMSO-$d_6$) δ 8.20-8.05 (m, 4H), 7.44-7.37 (m, 1H), 7.06-6.97 (m, 1H), 3.93 (s, 3H), 3.32 (s, 1H), 2.89 (br d, J = 9.5 Hz, 3H), 2.77-2.56 (m, 6H), 2.38 (br d, J = 11.0 Hz, 2H), 1.89-1.44 (m, 11H), 1.00 (dd, J = 6.4, 4.0 Hz, 6H) (one proton obscured). TLR9 $IC_{50}$ (nM) = 55. Chiral analytical (SFC Method 6): Purity: 99% |
| 295 | Analytical LC/MS (Method 1): Purity: 100%; Observed Mass: 527.30; Retention Time: 0.99 min. (Method 2): Purity: 100%; Observed Mass: 527.40; Retention Time: 1.18 min. Prep Method 1: 9.9 mg, 7% yield; $^1$H NMR (500 MHz, DMSO-$d_6$) δ 8.12-8.03 (m, 4H), 7.36-7.33 (m, 1H), 6.99-6.91 (m, 1H), 3.87 (s, 3H), 3.26 (s, 1H), 2.86-2.76 (m, 2H), 2.73-2.61 (m, 2H), 2.56 (br t, J = 5.2 Hz, 3H), 2.25 (br d, J = 6.1 Hz, 4H), 1.84 (s, 1H), 1.75 (br s, 11H), 0.81-0.73 (m, 1H), 0.43-0.33 (m, 2H), 0.01 (br d, J = 4.3 Hz, 2H) (one proton obscured). TLR9 $IC_{50}$ (nM) = 24. Chiral analytical (SFC Method 6): Purity: 95% |
| 296 | Analytical LC/MS (Method 1): Purity: 100%; Observed Mass: 541.40; Retention Time: 0.94 min. (Method 2): Purity: 96.9%; Observed Mass: 541.30; Retention Time: 1.36 min. Prep Method 1: 10 mg, 7% yield; $^1$H NMR (500 MHz, DMSO-$d_6$) δ 8.21-8.09 (m, 4H), 7.39-7.34 (m, 1H), 7.06-6.99 (m, 1H), 3.93 (s, 3H), 3.67-3.38 (m, 1H), 3.32 (s, 1H), 3.29-3.17 (m, 1H), 3.09-2.89 (m, 4H), 2.54-2.51 (m, 2H), 2.39-2.28 (m, 2H), 2.27-1.68 (m, 11H), 1.17 (s, 2H), 0.97 (dd, J = 6.4, 3.1 Hz, 6H) (two protons obscured). TLR9 $IC_{50}$ (nM) = 22. Chiral analytical (SFC Method 6): Purity: >99%; RT: 39 min. |
| 297 | Analytical LC/MS (Method 1): Purity: 99.1%; Observed Mass: 541.30; Retention Time: 0.94 min. (Method 2): Purity: 98.3%; Observed Mass: 541.20; Retention Time: 1.37 min. Prep Method 1: 10 mg, 7% yield; $^1$H NMR (500 MHz, DMSO-$d_6$) δ 8.21-8.09 (m, 4H), 7.41-7.34 (m, 1H), 7.05-7.00 (m, 1H), 3.94 (s, 3H), 3.71-3.36 (m, 1H), 3.28-2.90 (m, 5H), 2.55-2.52 (m, 2H), 2.41-1.72 (m, 12H), 1.17 (t, J = 7.3 Hz, 2H), 0.98 (dd, J = 6.4, 3.1 Hz, 6H) (four protons obscured). TLR9 $IC_{50}$ (nM) = 23. Chiral analytical (SFC Method 6): Purity: >96%; RT: 45 min. |
| 298 | Analytical LC/MS (Method 1): Purity: 100%; Observed Mass: 539.20; Retention Time: 1.0 min. (Method 2): Purity: 100%; Observed Mass: 539.20; Retention Time: 1.25 min. Prep Method 1: 60 mg, 43% yield; $^1$H NMR (500 MHz, DMSO-$d_6$) δ 8.02-7.93 (m, 4H), 7.27-7.22 (m, 1H), 6.90-6.82 (m, 1H), 3.77 (s, 3H), 3.17 (s, 1H), 2.84-2.72 (m, 3H), 2.66 (br s, 6H), 2.24 (br d, J = 8.9 Hz, 2H), 1.77-1.37 (m, 11H), 1.12-1.04 (m, 1H), 0.74 (br s, 2H), 0.35 (br d, J = 6.7 Hz, 2H), 0.01 (br d, J = 4.3 Hz, 2H). TLR9 $IC_{50}$ (nM) = 58. Chiral analytical (SFC Method 7): Purity: >99%; RT: 15.6 min. |
| 299 | Analytical LC/MS (Method 1): Purity: 100%; Observed Mass: 539.30; Retention Time: 1.01 min. (Method 2): Purity: 100%; Observed Mass: 539.30; Retention Time: 1.26 min. Prep Method 1: 16 mg, 11% yield; $^1$H NMR (500 MHz, DMSO-$d_6$) δ 8.16-8.01 (m, 4H), 7.38-7.30 (m, 1H), 7.00-6.91 (m, 1H), 3.87 (s, 3H), 3.26 (s, 1H), 2.86-2.77 (m, 2H), 2.56 (br t, J = 5.2 Hz, 5H), 2.33-2.21 (m, 4H), 1.84 (s, 1H), 1.80-1.41 (m, 10H), 0.76 (br s, 1H), 0.42-0.34 (m, 2H), 0.03--0.03 (m, 2H) (two protons obscured). TLR9 $IC_{50}$ (nM) = 3.3. Chiral analytical (SFC Method 7): Purity: 94%; RT: 18.8 min. |
| 300 | Analytical LC/MS (Method 1): Purity: 96.9%; Observed Mass: 569.30; Retention Time: 1.04 min. (Method 2): Purity: 97.7%; Observed Mass: 569.30; Retention Time: 1.2 min. Prep Method 1: 12 mg, 8% yield; $^1$H NMR (500 MHz, DMSO-$d_6$) δ 8.22-8.08 (m, 4H), 7.45-7.36 (m, 1H), 7.01 (d, J = 11.6 Hz, 1H), 3.95-3.85 (m, 5H), 3.35-3.30 (m, 1H), 3.30-3.22 (m, 1H), 2.93-2.82 (m, 2H), 2.61 (br s, 6H), 2.46-2.31 (m, 2H), 1.88-1.67 (m, 7H), 1.60 (br d, J = 12.8 Hz, 4H), 1.50-1.37 (m, 3H) (four protons obscured). TLR9 $IC_{50}$ (nM) = 20. Chiral analytical (SFC Method 1): Purity: >95%; RT: 19.86 min. |
| 301 | Analytical LC/MS (Method 1): Purity: 96.7%; Observed Mass: 569.30; Retention Time: 1.03 min. (Method 2): Purity: 96.6%; Observed Mass: 569.30; Retention Time: 1.2 min. Prep Method 1: 12 mg, 8% yield; $^1$H NMR (500 MHz, DMSO-$d_6$) δ 8.20-8.06 (m, 4H), 7.43-7.36 (m, 1H), 7.06- |

-continued

| Ex. No. | Analytical LC/MS, Preparative HPLC method, yield, and $^1$H NMR |
|---|---|
| | 6.96 (m, 1H), 3.93 (s, 3H), 3.90-3.84 (m, 2H), 3.35-3.22 (m, 1H), 2.91-2.83 (m, 2H), 2.74-2.56 (m, 6H), 2.43-2.30 (m, 2H), 1.81 (br s, 7H), 1.65-1.51 (m, 4H), 1.49-1.36 (m, 3H) (five protons obscured). TLR9 $IC_{50}$ (nM) = 48. Chiral analytical (SFC Method 1): Purity: >95%; RT: 25.90 min. |
| 302 | Analytical LC/MS (Method 1): Purity: 100%; Observed Mass: 543.20; Retention Time: 0.93 min. (Method 2): Purity: 100%; Observed Mass: 543.20; Retention Time: 1.14 min. Prep Method 1: 16 mg, 11% yield; $^1$H NMR (500 MHz, DMSO-$d_6$) δ 8.16-8.07 (m, 4H), 7.44-7.34 (m, 1H), 7.07-6.94 (m, 1H), 3.92 (s, 3H), 3.56-3.40 (m, 1H), 3.32 (s, 2H), 3.25 (s, 2H), 2.95 (br d, J = 4.0 Hz, 2H), 2.86-2.75 (m, 2H), 2.74-2.58 (m, 6H), 2.49-2.40 (m, 2H), 1.89-1.46 (m, 10H), 1.21-1.11 (m, 1H) (two protons obscured). TLR9 $IC_{50}$ (nM) = 48. Chiral analytical (SFC Method 8): Purity: >99%; RT: 24.1 min. |
| 303 | Analytical LC/MS (Method 1): Purity: 100%; Observed Mass: 543.20; Retention Time: 0.93 min. (Method 2): Purity: 100%; Observed Mass: 543.20; Retention Time: 1.14 min. Prep Method 1: 16 mg, 11% yield; $^1$H NMR (500 MHz, DMSO-$d_6$) δ 8.18-8.05 (m, 4H), 7.43-7.34 (m, 1H), 7.07-6.97 (m, 1H), 3.92 (s, 2H), 3.55-3.40 (m, 1H), 3.32 (s, 2H), 3.25 (s, 2H), 2.95 (br s, 2H), 2.81 (br s, 2H), 2.74-2.60 (m, 5H), 2.55-2.40 (m, 6H), 1.91-1.46 (m, 9H), 1.31-1.12 (m, 2H). TLR9 $IC_{50}$ (nM) = 14. Chiral analytical (SFC Method 8): Purity: >93%; RT: 27.5 min. |
| 304 | Analytical LC/MS (Method 1): Purity: 100%; Observed Mass: 537.30; Retention Time: 0.89 min. (Method 2): Purity: 100%; Observed Mass: 537.30; Retention Time: 1.2 min. Prep Method 1: 9.7 mg, 7% yield; $^1$H NMR (500 MHz, DMSO-$d_6$) δ 8.16-8.06 (m, 4H), 7.35-7.26 (m, 1H), 7.03-6.96 (m, 1H), 4.52 (t, J = 6.1 Hz, 2H), 4.36 (t, J = 6.0 Hz, 2H), 3.89 (s, 3H), 3.64-3.53 (m, 1H), 3.31 (s, 1H), 2.93-2.85 (m, 2H), 2.79-2.71 (m, 1H), 2.64-2.56 (m, 1H), 2.47-2.27 (m, 6H), 1.89-1.56 (m, 9H), 1.55-1.44 (m, 1H) (five protons obscured). TLR9 $IC_{50}$ (nM) = 180. Chiral analytical (SFC Method 9): Purity: >95%; RT: 22.51 min. |
| 305 | Analytical LC/MS (Method 1): Purity: 100%; Observed Mass: 537.30; Retention Time: 0.88 min. (Method 2): Purity: 100%; Observed Mass: 537.30; Retention Time: 1.2 min. Prep Method 1: 9.2 mg, 6% yield; $^1$H NMR (500 MHz, DMSO-$d_6$) δ 8.15-8.05 (m, 4H), 7.35-7.28 (m, 1H), 7.05-6.94 (m, 1H), 4.52 (s, 2H), 4.36 (s, 2H), 3.89 (s, 3H), 3.65-3.54 (m, 1H), 3.31 (s, 1H), 2.93-2.83 (m, 2H), 2.78-2.67 (m, 1H), 2.62-2.55 (m, 2H), 2.47-2.26 (m, 6H), 1.89-1.44 (m, 10H) (four protons obscured). TLR9 $IC_{50}$ (nM) = 90. Chiral analytical (SFC Method 9): Purity: >95%; RT: 27.11 min. |
| 306 | Analytical LC/MS (Method 1): Purity: 100%; Observed Mass: 565.30; Retention Time: 0.88 min. (Method 2): Purity: 100%; Observed Mass: 565.30; Retention Time: 1.23 min. Prep Method 1: 15 mg, 10% yield; $^1$H NMR (500 MHz, DMSO-$d_6$) δ 8.18-8.06 (m, 4H), 7.35-7.26 (m, 1H), 7.05-6.95 (m, 1H), 3.93-3.81 (m, 4H), 3.31 (s, 2H), 2.94-2.84 (m, 2H), 2.72 (br s, 3H), 2.67-2.55 (m, 5H), 2.46-2.34 (m, 2H), 1.88-1.68 (m, 7H), 1.67-1.52 (m, 4H), 1.51-1.35 (m, 3H) (six protons obscured). TLR9 $IC_{50}$ (nM) = 17. Chiral analytical (SFC Method 3): Purity: >95%; RT: 12.40 min. |
| 307 | Analytical LC/MS (Method 1): Purity: 98.6%; Observed Mass: 565.30; Retention Time: 0.88 min. (Method 2): Purity: 99.4%; Observed Mass: 565.40; Retention Time: 1.23 min. Prep Method 1: 15 mg, 10% yield; $^1$H NMR (500 MHz, DMSO-$d_6$) δ 8.14-8.06 (m, 4H), 7.34-7.28 (m, 1H), 6.99 (s, 1H), 3.89 (s, 5H), 3.36-3.21 (m, 2H), 2.95-2.82 (m, 2H), 2.79-2.66 (m, 3H), 2.65-2.54 (m, 7H), 2.46-2.30 (m, 2H), 1.79 (br s, 7H), 1.66-1.52 (m, 4H), 1.51-1.33 (m, 4H) (two protons obscured). TLR9 $IC_{50}$ (nM) = 3.5. Chiral analytical (SFC Method 3): Purity: >95%; RT: 15.06 min. |
| 308 | Analytical LC/MS (Method 1): Purity: 100%; Observed Mass: 539.30; Retention Time: 0.88 min. (Method 2): Purity: 90%; Observed Mass: 539.30; Retention Time: 1.16 min. Prep Method 1: 13 mg, 8% yield; $^1$H NMR (500 MHz, DMSO-$d_6$) δ 8.18-8.04 (m, 4H), 7.31 (s, 1H), 6.99 (s, 1H), 3.90 (s, 3H), 3.31 (s, 2H), 3.25 (s, 2H), 2.98-2.86 (m, 4H), 2.83-2.72 (m, 2H), 2.66 (br s, 6H), 2.48-2.40 (m, 2H), 1.82 (br s, 10H), 1.32-1.22 (m, 1H), 1.16 (t, J = 7.2 Hz, 4H). TLR9 $IC_{50}$ (nM) = 6.7. Chiral analytical (SFC Method 4): Purity: >95%; RT: 32.2 min. |
| 309 | Analytical LC/MS (Method 1): Purity: 100%; Observed Mass: 539.30; Retention Time: 0.88 min. (Method 2): Purity: 89.2%; Observed Mass: 539.30; Retention Time: 1.16 min. Prep Method 1: 11 mg, 7% yield; $^1$H NMR (500 MHz, DMSO-$d_6$) δ 8.17-8.05 (m, 4H), 7.35-7.28 (m, 1H), 7.03-6.95 (m, 1H), 3.90 (s, 2H), 3.43 (s, 1H), 3.31 (s, 2H), 3.25 (s, 2H), 2.90 (br d, J = 7.3 Hz, 4H), 2.85-2.75 (m, 2H), 2.73-2.59 (m, 6H), 2.47 (br s, 2H), 1.94-1.47 (m, 10H), 1.24 (br s, 1H), 1.17 (br t, J = 7.0 Hz, 3H) (one proton obscured). TLR9 $IC_{50}$ (nM) = 34. Chiral analytical (SFC Method 4): Purity: >95%; RT: 37.5 min. |
| 310 | Analytical LC/MS (Method 1): Purity: 100%; Observed Mass: 541.20; Retention Time: 0.99 min. (Method 2): Purity: 100%; Observed Mass: 541.10; Retention Time: 1.43 min. Prep Method 1: 11 mg, 8% yield; $^1$H NMR (500 MHz, DMSO-$d_6$) δ 8.23-7.99 (m, 4H), 7.58-7.44 (m, 1H), 7.31-7.15 (m, 1H), 4.02 (br s, 3H), 3.54-3.19 (m, 5H), 3.01-2.86 (m, 2H), 2.80-2.62 (m, 2H), 2.51-2.38 (m, 5H), 2.25-2.12 (m, 2H), 1.79 (br d, J = 15.3 Hz, |

-continued

| Ex. No. | Analytical LC/MS, Preparative HPLC method, yield, and $^1$H NMR |
|---|---|
| | 10H), 0.95-0.68 (m, 6H). TLR9 $IC_{50}$ (nM) = 47. Chiral analytical (SFC Method 2): Purity: >99%; RT: 12.49 min. |
| 311 | Analytical LC/MS (Method 1): Purity: 100%; Observed Mass: 541.20; Retention Time: 0.99 min. (Method 2): Purity: 100%; Observed Mass: 541.10; Retention Time: 1.43 min. Prep Method 1: 10 mg, 7% yield; $^1$H NMR (500 MHz, DMSO-$d_6$) δ 8.23-8.03 (m, 4H), 7.57-7.45 (m, 1H), 7.27-7.15 (m, 1H), 4.02 (br s, 3H), 3.55-3.42 (m, 2H), 3.32 (br s, 3H), 2.97 (br d, J = 1.5 Hz, 2H), 2.59 (br s, 4H), 2.23 (br s, 2H), 1.97-1.43 (m, 11H), 0.87 (br s, 6H) (two protons obscured). TLR9 $IC_{50}$ (nM) = 72. Chiral analytical (SFC Method 2): Purity: >98%; RT: 16.62 min. |
| 312 | Analytical LC/MS (Method 1): Purity: 100%; Observed Mass: 539.30; Retention Time: 0.92 min. (Method 2): Purity: 100%; Observed Mass: 539.30; Retention Time: 1.19 min. Prep Method 1: 5.6 mg, 4% yield; $^1$H NMR (500 MHz, DMSO-$d_6$) δ 8.19-8.03 (m, 4H), 7.55-7.47 (m, 1H), 7.22-7.16 (m, 1H), 4.02 (br s, 3H), 3.96-3.89 (m, 2H), 3.22-3.16 (m, 2H), 2.96 (br d, J = 4.9 Hz, 9H), 2.72-2.63 (m, 3H), 2.34-2.26 (m, 1H), 2.10-1.98 (m, 3H), 1.67-1.47 (m, 6H), 1.21-1.15 (m, 1H), 0.90-0.82 (m, 3H). TLR9 $IC_{50}$ (nM) = 64. Chiral analytical (SFC Method 5): Purity: >99%; RT: 16.70 min. |
| 313 | Analytical LC/MS (Method 1): Purity: 100%; Observed Mass: 539.3; Retention Time: 0.92 min. (Method 2): Purity: 100%; Observed Mass: 539.30; Retention Time: 1.18 min. Prep Method 1: 8.2 mg, 7% yield; $^1$H NMR (500 MHz, DMSO-$d_6$) δ 8.15-8.04 (m, 4H), 7.52-7.46 (m, 1H), 7.23-7.17 (m, 1H), 4.01 (s, 3H), 3.19-3.15 (m, 1H), 3.11-2.88 (m, 5H), 2.86-2.60 (m, 4H), 2.48-2.42 (m, 2H), 2.07-1.98 (m, 2H), 1.96-1.68 (m, 7H), 1.67-1.46 (m, 5H), 1.30-1.18 (m, 4H). TLR9 $IC_{50}$ (nM) = 69. Chiral analytical (SFC Method 5): Purity: >90%; RT: 18.45 min. |
| 314 | Analytical LC/MS (Method 1): Purity: 100%; Observed Mass: 541.20; Retention Time: 0.89 min. (Method 2): Purity: 100%; Observed Mass: 541.30; Retention Time: 1.2 min. Prep Method 1: 9 mg, 6% yield; $^1$H NMR (500 MHz, DMSO-$d_6$) δ 8.18-8.03 (m, 4H), 7.57-7.46 (m, 1H), 7.27-7.14 (m, 1H), 4.52 (s, 2H), 4.36 (s, 2H), 4.02 (s, 3H), 3.63-3.53 (m, 1H), 3.53-3.38 (m, 1H), 3.31 (s, 2H), 3.02-2.86 (m, 3H), 2.85-2.73 (m, 1H), 2.44 (br s, 3H), 2.39-2.19 (m, 3H), 1.77 (br s, 10H). TLR9 $IC_{50}$ (nM) = 190. Chiral analytical (SFC Method 9): Purity: >95%; RT: 8.53 min. |
| 315 | Analytical LC/MS (Method 1): Purity: 100%; Observed Mass: 541.20; Retention Time: 0.89 min. (Method 2): Purity: 100%; Observed Mass: 541.30; Retention Time: 1.2 min. Prep Method 1: 9 mg, 6% yield; $^1$H NMR (500 MHz, DMSO-$d_6$) δ 8.17-8.04 (m, 4H), 7.57-7.45 (m, 1H), 7.24-7.10 (m, 1H), 4.59-4.47 (m, 2H), 4.36 (s, 2H), 4.02 (s, 3H), 3.90 (s, 1H), 3.66-3.55 (m, 1H), 3.51-3.40 (m, 2H), 3.31 (s, 2H), 3.18 (s, 2H), 2.96 (br s, 3H), 2.88-2.78 (m, 1H), 2.49-2.41 (m, 2H), 2.38-2.26 (m, 3H), 1.91-1.44 (m, 7H). TLR9 $IC_{50}$ (nM) = 150. Chiral analytical (SFC Method 9): Purity: >95%; RT: 10.98 min. |
| 316 | Analytical LC/MS (Method 1): Purity: 100%; Observed Mass: 569.20; Retention Time: 0.91 min. (Method 2): Purity: 100%; Observed Mass: 569.30; Retention Time: 1.14 min. Prep Method 1: 6.2 mg, 4% yield; $^1$H NMR (500 MHz, DMSO-$d_6$) δ 8.21-8.05 (m, 4H), 7.55-7.48 (m, 1H), 7.26-7.17 (m, 1H), 4.12-4.02 (m, 3H), 3.98-3.85 (m, 4H), 3.43-3.29 (m, 6H), 3.03-2.89 (m, 4H), 2.85-2.71 (m, 4H), 1.84-1.72 (m, 4H), 1.70-1.44 (m, 7H), 1.27-1.19 (m, 3H). TLR9 $IC_{50}$ (nM) = 14. Chiral analytical (SFC Method 5): Purity: >99%; RT: 12.27 min. |
| 317 | Analytical LC/MS (Method 1): Purity: 100%; Observed Mass: 569.30; Retention Time: 0.91 min. (Method 2): Purity: 100%; Observed Mass: 569.30; Retention Time: 1.14 min. Prep Method 1: 10 mg, 7% yield; $^1$H NMR (500 MHz, DMSO-$d_6$) δ 8.19-8.00 (m, 4H), 7.53-7.46 (m, 1H), 7.24-7.16 (m, 1H), 4.02 (br s, 3H), 3.94-3.84 (m, 2H), 3.55-3.46 (m, 3H), 3.02-2.86 (m, 3H), 2.80-2.61 (m, 3H), 1.77 (br d, J = 2.1 Hz, 4H), 1.68-1.56 (m, 4H), 1.53-1.42 (m, 4H), 1.24 (br s, 6H), 0.92-0.81 (m, 3H). TLR9 $IC_{50}$ (nM) = 18. Chiral analytical (SFC Method 5): Purity: >90%; RT: 14.29 min. |
| 318 | Analytical LC/MS (Method 1): Purity: 100%; Observed Mass: 543.3; Retention Time: 1.08 min. (Method 2): Purity: 98.6%; Observed Mass: 543.3; Retention Time: 1.604 min. Prep Method 1: 55 mg, 66% yield; $^1$H NMR (500 MHz, DMSO-$d_6$) δ 8.20-8.02 (m, 4H), 7.38-7.30 (m, 1H), 7.25-7.17 (m, 2H), 7.03-6.99 (m, 1H), 6.98-6.91 (m, 2H), 6.79-6.71 (m, 1H), 3.90 (s, 3H), 3.81-3.73 (m, 2H), 3.16-3.01 (m, 2H), 2.74-2.63 (m, 3H), 2.58-2.54 (m, 7H), 2.45-2.28 (m, 2H), 1.93-1.76 (m, 5H), 1.70-1.54 (m, 2H) (one proton obscured). TLR9 $IC_{50}$ (nM) = 270 |
| 319 | Analytical LC/MS (Method 1): Purity: 100%; Observed Mass: 553.20; Retention Time: 1.14 min. (Method 2): Purity: 95.8%; Observed Mass: 553.60; Retention Time: 1.55 min. Prep Method 1: 35 mg, 36% yield; $^1$H NMR (500 MHz, DMSO-$d_6$) δ 8.29 (d, J = 8.2 Hz, 2H), 8.10 (d, J = 8.2 Hz, 2H), 7.37 (s, 1H), 7.03 (br d, J = 11.9 Hz, 1H), 3.91-3.82 (m, 1H), 3.10-2.99 (m, 1H), 2.93-2.86 (m, 1H), 2.86-2.86 (m, 1H), 2.69 (br s, 1H), 2.54-2.51 (m, 3H), 2.37-2.25 (m, 3H), 2.03 (br d, J = 6.7 Hz, 2H), 1.90-1.82 (m, 4H), 1.75 (br d, J = 13.1 Hz, 5H), 1.56-1.44 (m, 2H), 1.17 (br d, J = 6.1 Hz, 2H), 0.86 (d, J = 6.4 Hz, 6H), 0.66 (br s, 2H) (one proton obscured). TLR9 $IC_{50}$ (nM) = 94 |

-continued

| Ex. No. | Analytical LC/MS, Preparative HPLC method, yield, and $^1$H NMR |
|---|---|
| 320 | Analytical LC/MS (Method 1): Purity: 87.8%; Observed Mass: 551.30; Retention Time: 1.0 min. (Method 2): Purity: 85.9%; Observed Mass: 551.20; Retention Time: 1.24 min. Prep Method 1: 1.2 mg, 1% yield; $^1$H NMR (500 MHz, DMSO-$d_6$) δ 8.29-8.16 (m, 2H), 8.12-7.96 (m, 2H), 7.38-7.27 (m, 1H), 7.04-6.93 (m, 1H), 3.88-3.70 (m, 1H), 3.28 (s, 1H), 2.96 (br s, 3H), 2.69-2.56 (m, 1H), 2.31-2.14 (m, 3H), 2.09 (br d, J = 6.4 Hz, 1H), 1.91-1.76 (m, 3H), 1.75-1.65 (m, 3H), 1.63 (s, 4H), 1.49-1.30 (m, 2H), 1.11 (brs, 2H), 0.84-0.72 (m, 1H), 0.60 (br s, 2H), 0.45-0.32 (m, 2H), 0.01 (br d, J = 4.6 Hz, 2H) (two protons obscured). TLR9 $IC_{50}$ (nM) = 77 |
| 321 | Analytical LC/MS (Method 1): Purity: 100%; Observed Mass: 581.20; Retention Time: 1.03 min. (Method 2): Purity: 100%; Observed Mass: 581.20; Retention Time: 1.35 min. Prep Method 1: 12 mg, 11% yield; $^1$H NMR (500 MHz, DMSO-$d_6$) δ 8.37-8.24 (m, 2H), 8.19-8.04 (m, 2H), 7.41-7.32 (m, 1H), 7.09-6.95 (m, 1H), 3.94-3.81 (m, 3H), 3.33 (s, 1H), 3.29-3.22 (m, 1H), 3.06-2.89 (m, 3H), 2.67 (br s, 1H), 2.55 (s, 1H), 2.40 (br s, 1H), 2.33-2.17 (m, 3H), 2.08 (br t, J = 11.1 Hz, 2H), 1.93-1.54 (m, 9H), 1.52-1.29 (m, 4H), 1.17 (br d, J = 6.1 Hz, 2H), 0.66 (br s, 2H) (two protons obscured). TLR9 $IC_{50}$ (nM) = 36 |
| 322 | Analytical LC/MS (Method 1): Purity: 98.7%; Observed Mass: 579.20; Retention Time: 1.14 min. (Method 2): Purity: 92.5%; Observed Mass: 579.40; Retention Time: 1.51 min. Prep Method 1: 35 mg, 19% yield; $^1$H NMR (500 MHz, DMSO-$d_6$) δ 8.32-8.24 (m, 2H), 8.15-8.04 (m, 2H), 7.42-7.30 (m, 1H), 7.07-6.93 (m, 1H), 3.96-3.79 (m, 1H), 3.26-3.16 (m, 1H), 3.00 (br s, 2H), 2.65 (br s, 1H), 2.59-2.55 (m, 1H), 2.50-2.47 (m, 1H), 2.24-2.08 (m, 4H), 1.93-1.79 (m, 4H), 1.73-1.47 (m, 9H), 1.16 (br d, J = 6.0 Hz, 2H), 0.88 (d, J = 6.5 Hz, 6H), 0.65 (br s, 2H) (three protons obscured). TLR9 $IC_{50}$ (nM) = 12 |
| 323 | Analytical LC/MS (Method 1): Purity: 98.8%; Observed Mass: 579.40; Retention Time: 1.03 min. (Method 2): Purity: 97.8%; Observed Mass: 579.40; Retention Time: 1.71 min. Prep Method 1: 28 mg, 16% yield; $^1$H NMR (500 MHz, DMSO-$d_6$) δ 8.35-8.21 (m, 2H), 8.15-8.03 (m, 2H), 7.43-7.28 (m, 1H), 7.11-6.94 (m, 1H), 3.89-3.76 (m, 1H), 3.32 (s, 2H), 3.26-3.19 (m, 1H), 3.15-3.06 (m, 2H), 2.71-2.61 (m, 1H), 2.46-2.37 (m, 1H), 2.05-1.79 (m, 13H), 1.77-1.59 (m, 6H), 1.16 (br d, J = 6.1 Hz, 2H), 0.88 (d, J = 6.7 Hz, 6H), 0.65 (br s, 2H). TLR9 $IC_{50}$ (nM) = 60 |
| 324 | Analytical LC/MS (Method 1): Purity: 100%; Observed Mass: 577.20; Retention Time: 1.18 min. (Method 2): Purity: 95.9%; Observed Mass: 577.20; Retention Time: 1.48 min. Prep Method 2: 35 mg, 14% yield; $^1$H NMR (500 MHz, DMSO-$d_6$) δ 8.31-8.25 (m, 2H), 8.14-8.04 (m, 2H), 7.45-7.36 (m, 1H), 7.07-6.97 (m, 1H), 4.33-4.13 (m, 2H), 3.96-3.74 (m, 2H), 3.66-3.47 (m, 1H), 3.32 (s, 2H), 3.23-3.02 (m, 2H), 2.91 (br s, 1H), 2.38-1.87 (m, 12H), 1.20-1.03 (m, 3H), 0.70-0.60 (m, 4H), 0.45-0.33 (m, 2H) (four protons obscured). TLR9 $IC_{50}$ (nM) = 42 |
| 325 | Analytical LC/MS (Method 1): Purity: 99.1%; Observed Mass: 557.30; Retention Time: 1.02 min. (Method 2): Purity: 99.5%; Observed Mass: 557.50; Retention Time: 1.46 min. Prep Method 1: 35 mg, 20% yield; $^1$H NMR (500 MHz, DMSO-$d_6$) δ 8.25-8.10 (m, 2H), 8.06-7.94 (m, 2H), 7.31-7.21 (m, 1H), 6.95-6.82 (m, 1H), 3.79-3.67 (m, 1H), 3.58-3.42 (m, 2H), 3.32-3.24 (m, 1H), 3.20 (s, 4H), 2.63-2.50 (m, 1H), 2.31-2.22 (m, 1H), 2.14 (br d, J = 6.1 Hz, 2H), 1.93-1.84 (m, 2H), 1.83-1.52 (m, 12H), 1.05 (br d, J = 6.1 Hz, 2H), 0.80-0.67 (m, 1H), 0.53 (br d, J = 1.8 Hz, 2H), 0.34 (br d, J = 7.9 Hz, 2H), 0.01 (br d, J = 4.6 Hz, 2H). TLR9 $IC_{50}$ (nM) = 15 |
| 326 | Analytical LC/MS (Method 1): Purity: 93.9%; Observed Mass: 577.40; Retention Time: 1.11 min. (Method 2): Purity: 95%; Observed Mass: 577.40; Retention Time: 1.42 min. Prep Method 1: 42 mg, 23% yield; $^1$H NMR (500 MHz, DMSO-$d_6$) δ 8.35-8.22 (m, 2H), 8.16-8.05 (m, 2H), 7.39-7.30 (m, 1H), 7.06-6.95 (m, 1H), 3.91-3.78 (m, 1H), 3.33 (s, 1H), 3.20 (br s, 1H), 2.98 (br d, J = 11.0 Hz, 3H), 2.70-2.57 (m, 2H), 2.20 (br t, J = 11.0 Hz, 2H), 1.98 (br d, J = 7.6 Hz, 2H), 1.90 (s, 1H), 1.86-1.47 (m, 16H), 1.17 (br d, J = 6.1 Hz, 2H), 0.65 (br s, 2H) (two protons obscured). TLR9 $IC_{50}$ (nM) = 23 |
| 327 | Analytical LC/MS (Method 1): Purity: 100%; Observed Mass: 577.20; Retention Time: 1.14 min. (Method 2): Purity: 100%; Observed Mass: 577.20; Retention Time: 1.68 min. Prep Method 2: 27 mg, 11% yield; $^1$H NMR (500 MHz, DMSO-$d_6$) δ 8.35-8.22 (m, 2H), 8.14-8.06 (m, 2H), 7.44-7.33 (m, 1H), 7.07-6.98 (m, 1H), 3.94-3.82 (m, 2H), 3.67-3.47 (m, 1H), 3.33 (s, 2H), 3.16-2.90 (m, 1H), 2.81-2.47 (m, 7H), 2.34-1.86 (m, 13H), 1.85-1.62 (m, 2H), 1.16 (br d, J = 6.7 Hz, 3H), 0.67 (br s, 2H) (two protons obscured). TLR9 $IC_{50}$ (nM) = 110 |
| 328 | Analytical LC/MS (Method 1): Purity: 95.1%; Observed Mass: 607.20; Retention Time: 1.08 min. (Method 2): Purity: 90.4%; Observed Mass: 607.40; Retention Time: 1.34 min. Prep Method 1: 32 mg, 16% yield; $^1$H NMR (500 MHz, DMSO-$d_6$) δ 8.35-8.22 (m, 2H), 8.15-8.04 (m, 2H), 7.41-7.31 (m, 1H), 7.06-6.94 (m, 1H), 3.85 (br dd, J = 7.5, 3.1 Hz, 3H), 3.54-3.42 (m, 1H), 3.32 (s, 2H), 3.10-2.95 (m, 2H), 2.70-2.55 (m, 4H), 2.16 (br s, 2H), 1.90 (s, 2H), 1.87-1.42 (m, 14H), 1.34-1.10 (m, 4H), 0.65 (br s, 2H) (one proton obscured). TLR9 $IC_{50}$ (nM) = 12 |

-continued

| Ex. No. | Analytical LC/MS, Preparative HPLC method, yield, and $^1$H NMR |
|---|---|
| 329 | Analytical LC/MS (Method 1): Purity: 97.9%; Observed Mass: 607.30; Retention Time: 1.04 min. (Method 2): Purity: 100%; Observed Mass: 607.20; Retention Time: 1.52 min. Prep Method 1: 26 mg, 14% yield; $^1$H NMR (500 MHz, DMSO-$d_6$) δ 8.34-8.23 (m, 2H), 8.14-8.06 (m, 2H), 7.38-7.32 (m, 1H), 7.05-6.97 (m, 1H), 3.91-3.81 (m, 2H), 3.51-3.40 (m, 1H), 3.37-3.22 (m, 6H), 2.74-2.62 (m, 1H), 2.44-2.33 (m, 1H), 1.99-1.65 (m, 20H), 1.39-1.26 (m, 2H), 1.17 (br d, J = 6.1 Hz, 2H), 0.66 (br s, 2H). TLR9 $IC_{50}$ (nM) = 28 |
| 330 | Analytical LC/MS (Method 6): Purity: 98.2%; Observed Mass: 523.3; Retention Time: 0.585 min. Prep Method 3: 15 mg, 18% yield; $^1$H NMR (400 MHz, Chloroform-d) o 8.10 (d, J = 6.4 Hz, 2H), 7.93 (d, J = 6.4 Hz, 2H), 7.64 (d, J = 8.5 Hz, 1H), 7.32 (d, J = 8.6 Hz, 1H), 4.06 (s, 3H), 3.28-3.11 (m, 1H), 3.11 (s, 3H), 3.09-2.91 (m, 3H), 2.78 (s, 3H), 2.70-2.30 (m, 3H), 2.22-1.45 (m, 14H), 0.91 (d, J = 6.5 Hz, 6H). TLR9 $IC_{50}$ (nM) = 1400 |
| 331 | Analytical LC/MS (Method 6): Purity: 95.0%; Observed Mass: 523.2; Retention Time: 0.597 min. Prep Method 3: 52 mg, 36% yield; $^1$H NMR (400 MHz, DMSO-$d_6$) δ 8.15-8.05 (m, 4H), 7.49 (d, J = 14.2 Hz, 2H), 3.91 (s, 3H), 3.31 (s, 3H), 3.02 (d, J = 11.2 Hz, 2H), 2.86 (d, J = 11.8 Hz, 2H), 2.81-2.70 (m, 1H), 2.42 (s, 3H), 2.35-2.18 (m, 3H), 2.00 (d, J = 7.4Hz, 2H), 1.87-1.72 (m, 9H), 1.54-1.40 (m, 2H), 0.85 (d, J = 6.5 Hz, 6H). TLR9 $IC_{50}$ (nM) = 140 |
| 332 | Analytical LC/MS (Method 6): Purity: 96.3%; Observed Mass: 521.3; Retention Time: 0.904 min. Prep Method 3: 2.2 mg, 2% yield; $^1$H NMR (400 MHz, Methanol-$d_4$) δ 8.37 (d, J = 6.8 Hz, 2H), 8.13 (d, J = 6.8 Hz, 2H), 7.34 (s, 1H), 7.03 (s, 1H), 3.61 (s, 2H), 3.33-3.32 (m, 2H), 3.21 (s, 3H), 2.82-2.79 (m, 1H), 2.67-2.66 (m, 1H), 2.64 (s, 3H), 2.59-2.54 (m, 1H), 2.16-2.09 (m, 2H), 2.01-1.77 (m, 12H), 1.17 (d, J = 6.3 Hz, 6H). TLR9 $IC_{50}$ (nM) = 170 |
| 333 | Analytical LC/MS (Method 6): Purity: 99%; Observed Mass: 521.3; Retention Time: 0.954 min. Prep Method 3: 6.3 mg, 4% yield; $^1$H NMR (400 MHz, Methanol-$d_4$) δ 8.24 (d, J = 7.2 Hz, 2H), 8.01 (d, J = 6.8 Hz, 2H), 7.21 (s, 1H), 6.90 (s, 1H), 3.49 (s, 2H), 3.08 (s, 3H), 3.06-3.03 (m, 2H), 2.93-2.87 (m, 1H), 2.62-2.55 (m, 1H), 2.52 (s, 3H), 2.49-2.48 (m, 1H), 2.17-2.11 (m, 2H), 1.88-1.50 (m, 12H), 1.04 (d, J = 6.3 Hz, 6H). TLR9 $IC_{50}$ (nM) = 330 |
| 334 | Analytical LC/MS (Method 6): Purity: 96.5%; Observed Mass: 533.3; Retention Time: 0.613 min. Prep Method 3: 6.3 mg, 5% yield; $^1$H NMR (400 MHz, Methanol-$d_4$) δ 8.38 (d, J = 8.4 Hz, 2H), 8.15 (d, J = 7.2 Hz, 2H), 7.37 (s, 1H), 7.05 (s, 1H), 3.95 (s, 2H), 3.80-3.60 (m, 2H), 3.45-3.35 (m, 2H), 3.30-3.25 (m, 1H), 3.20 (s, 3H), 2.90-2.80 (m, 1H), 2.80-2.70 (m, 1H), 2.65 (s, 3H), 2.45-2.15 (m, 9H), 2.15-1.90 (m, 9H). TLR9 $IC_{50}$ (nM) = 300 |
| 335 | Analytical LC/MS (Method 6): Purity: 99.1%; Observed Mass: 533.2; Retention Time: 0.63 min. Prep Method 3: 22 mg, 15% yield; $^1$H NMR (400 MHz, Methanol-$d_4$) δ 8.37-8.36 (m, 2H), 8.14-8.12 (m, 2H), 7.33 (s, 1H), 7.03 (s, 1H), 3.60 (d, J = 4.7 Hz, 2H), 3.21 (s, 3H), 3.15-3.12 (m, 2H), 2.76-2.70 (m, 1H), 2.70-2.65 (m, 1H), 2.64 (s, 3H), 2.45 (d, J = 6.6 Hz, 2H), 2.35-2.30 (m, 2H), 2.03-1.69 (m, 12H), 1.03-0.97 (m, 1H), 0.61-0.56 (m, 2H), 0.24-0.20 (m, 2H). TLR9 $IC_{50}$ (nM) = 130 |
| 336 | Analytical LC/MS (Method 6): Purity: 93.8%; Observed Mass: 533.3; Retention Time: 1.077 min. Prep Method 3: 6.7 mg, 4% yield; $^1$H NMR (400 MHz, Methanol-$d_4$) δ 8.17-8.15 (m, 2H), 7.94-7.91 (m, 2H), 7.13 (s, 1H), 6.82 (s, 1H), 3.31 (s, 2H), 3.12-3.11 (m, 2H), 3.00 (s, 3H), 2.45-2.43 (m, 1H), 2.41 (s, 3H), 2.33-2.31 (m, 1H), 2.15 (d, J = 6.6 Hz, 2H), 2.00-1.93 (m, 2H), 1.84-1.59 (m, 12H), 0.79-0.71 (m, 1H), 0.39-0.34 (m, 2H), 0.03-0.01 (m, 2H). TLR9 $IC_{50}$ (nM) = 77 |
| 337 | Analytical LC/MS (Method 6): Purity: 94.4%; Observed Mass: 539.2; Retention Time: 0.605 min. Prep Method 3: 46 mg, 57% yield; $^1$H NMR (300 MHz, Chloroform-d) δ 8.10 (t, J = 7.2, 7.5 Hz, 1H), 7.78-7.67 (m, 2H), 7.13 (s, 1H), 7.06 (s, 1H), 3.88 (s, 3H), 3.27 (s, 3H), 3.13-2.94 (m, 4H), 2.80-2.58 (m, 5H), 2.52-2.35 (m, 3H), 2.14-2.05 (m, 1H), 2.01-1.82 (m, 8H), 1.73-1.55 (m, 7H). TLR9 $IC_{50}$ (nM) = 53 |
| 338 | Analytical LC/MS (Method 9): Purity: 97.9%; Observed Mass: 539.4; Retention Time: 0.787 min. Prep Method 3: 22 mg, 27% yield; $^1$H NMR (300 MHz, Chloroform-d) δ 8.10 (t, J = 7.8, 7.5 Hz, 1H), 7.78-7.67 (m, 2H), 7.13 (s, 1H), 7.06 (s, 1H), 3.86 (s, 3H), 3.39-3.02 (m, 8H), 2.76-8-2.62 (m, 4H), 2.50-2.31 (m, 3H), 2.26 (d, J = 6.5 Hz, 2H), 2.09-1.85 (m, 9H), 1.01-0.81 (m, 1H), 0.72-0.48 (m, 2H), 0.17-0.04 (m, 2H). TLR9 $IC_{50}$ (nM) = 260 |
| 339 | Analytical LC/MS (Method 6): Purity: 97.7%; Observed Mass: 525.2; Retention Time: 0.589 min. Prep Method 3: 17 mg, 21% yield; $^1$H NMR (300 MHz, Chloroform-d) δ 8.10 (t, J = 7.7 Hz, 1H), 7.72 (t, J = 7.8 Hz, 2H), 7.11 (s, 1H), 7.05 (s, 1H), 3.89 (s, 3H), 3.27 (s, 3H), 3.25-3.01 (m, 4H), 2.79-2.61 (m, 4H), 2.58-2.35 (m, 3H), 2.22 (t, J = 11.7, 10.8 Hz, 2H), 2.01-1.82 (m, 7H), 1.63-1.49 (m, 2H), 0.60-0.36 (m, 4H). TLR9 $IC_{50}$ (nM) = 340 |
| 340 | Analytical LC/MS (Method 6): Purity: 91.9%; Observed Mass: 565.2; Retention Time: 0.88 min. Prep Method 3: 3.1 mg, 4% yield; $^1$H NMR (300 MHz, Chloroform-d) δ 8.13 (dd, J = 8.3, 7.1 Hz, 1H), 7.77-7.73 (m, 2H), 7.12-7.07 (m, 2H), 3.89 (s, 3H), 3.46-3.42 (m, 2H), 3.34-3.29 (m, 2H), |

-continued

| Ex. No. | Analytical LC/MS, Preparative HPLC method, yield, and $^1$H NMR |
|---|---|
| | 3.22 (s, 3H), 2.70 (s, 3H), 2.64-2.61 (m, 2H), 2.33-2.14 (m, 4H), 2.04-1.61 (m, 12H), 0.95-0.92 (m, 1H), 0.56-0.50 (m, 2H), 0.14-0.09 (m, 2H). TLR9 $IC_{50}$ (nM) = 84 |
| 341 | Analytical LC/MS (Method 6): Purity: 95.9%; Observed Mass: 565.3; Retention Time: 0.89 min. Prep Method 3: 9.7 mg, 13% yield; $^1$H NMR (300 MHz, Chloroform-d) δ 8.12 (dd, J = 8.3, 7.1 Hz, 1H), 7.76-7.73 (m, 2H), 7.13-7.07 (m, 2H), 3.87 (s, 3H), 3.55-3.52 (m, 2H), 3.29 (s, 3H), 3.13 (d, J = 11.0Hz, 2H), 2.66 (s, 3H), 2.64-2.59 (m, 2H), 2.38 (d, J = 6.3 Hz, 2H), 2.28-2.25 (m, 2H), 1.95-1.53 (m, 12H), 0.93-0.91 (m, 1H), 0.55-0.49 (m, 2H), 0.16-0.12 (m, 2H). TLR9 $IC_{50}$ (nM) = 37 |
| 342 | Analytical LC/MS (Method 6): Purity: 99.1%; Observed Mass: 567.2; Retention Time: 0.996 min. Prep Method 3: 20 mg, 14% yield; $^1$H NMR (300 MHz, Methanol-$d_4$) δ 8.20-8.09 (m, 1H), 7.92-7.83 (m, 2H), 7.29 (s, 1H), 7.08 (s, 1H), 3.92 (s, 3H), 3.59-3.42 (m, 2H), 3.35 (s, 3H), 3.19-3.12 (m, 2H), 2.88-2.64 (m, 2H), 2.63 (s, 3H), 2.46 (d, J = 10.5 Hz, 4H), 2.19-1.70 (m, 13H), 1.15 (d, J = 6.5Hz, 6H). TLR9 $IC_{50}$ (nM) = 120 |
| 343 | Analytical LC/MS (Method 6): Purity: 95.9%; Observed Mass: 541.1; Retention Time: 0.919 min. Prep Method 3: 16 mg, 23% yield; $^1$H NMR (300 MHz, DMSO-$d_6$) δ 8.10-7.92 (m, 3H), 7.33 (s, 1H), 7.01 (s, 1H), 3.92 (s, 3H), 3.59-3.50 (m, 1H), 3.09 (d, J = 10.9 Hz, 3H), 2.92 (d, J = 11.0 Hz, 2H), 2.70-2.50 (m, 5H), 2.39 (t, J = 11.5 Hz, 3H), 2.06 (d, J = 7.3 Hz, 2H), 1.90-1.68 (m, 9H), 1.60-1.40 (m, 2H), 0.86 (d, J = 6.5 Hz, 6H). TLR9 $IC_{50}$ (nM) = 160 |
| 344 | Analytical LC/MS (Method 6): Purity: 91.2%; Observed Mass: 553.3; Retention Time: 0.611 min. Prep Method 3: 9.7 mg, 13% yield; $^1$H NMR (400 MHz, Methanol-$d_4$) 0 8.03 (dd, J = 8.3, 7.3 Hz, 1H), 7.78-7.74 (m, 2H), 7.17 (s, 1H), 6.96 (d, J = 1.4 Hz, 1H), 3.81 (s, 3H), 3.58-3.53 (m, 2H), 3.22 (s, 3H), 3.09-3.06 (m, 2H), 2.94-2.91 (m, 1H), 2.64-2.60 (m, 2H), 2.52 (s, 3H), 2.22-2.16 (m, 2H), 1.90-1.54 (m, 12H), 1.06 (d, J = 6.2 Hz, 6H). TLR9 $IC_{50}$ (nM) = 120 |
| 345 | Analytical LC/MS (Method 6): Purity: 96.9%; Observed Mass: 551.2; Retention Time: 0.613 min. $^1$H NMR (400 MHz, Methanol-$d_4$) δ 8.02 (dd, J = 8.3, 7.2 Hz, 1H), 7.77-7.73 (m, 2H), 7.16 (d, J = 1.5 Hz, 1H), 6.95 (d, J = 1.3 Hz, 1H), 3.80 (s, 3H), 3.32-3.29 (m, 2H), 3.23 (s, 3H), 3.04 (d, J = 11.3 Hz, 2H), 2.66-2.54 (m, 2H), 2.51 (s, 3H), 2.24-2.19 (m, 2H), 1.97-1.94 (m, 3H), 1.83-1.56 (m, 10H), 0.40-0.36 (m, 4H). TLR9 $IC_{50}$ (nM) = 130 |
| 346 | Analytical LC/MS (Method 6): Purity: 97.2%; Observed Mass: 553.2; Retention Time: 0.640 min. Prep Method 3: 8.7 mg, 6.0% yield; $^1$H NMR (400 MHz, Methanol-$d_4$) δ 8.20-8.09 (m, 3H), 7.35 (s, 1H), 7.06 (s, 1H), 3.42-3.30 (m, 5H), 3.19 (d, J = 11.4 Hz, 2H), 2.73-2.62 (m, 5H), 2.34-2.26 (m, 4H), 2.04-1.95 (m, 2H), 1.95-1.70 (m, 9H), 1.66 (d, J = 8.0 Hz, 2H), 0.98 (d, J = 6.6 Hz, 6H). TLR9 $IC_{50}$ (nM) = 56 |
| 347 | Analytical LC/MS (Method 6): Purity: 95.1%; Observed Mass: 537.2; Retention Time: 1.109 min. $^1$H NMR (400 MHz, Methanol-$d_4$) δ 8.20-8.03 (m, 3H), 7.33 (s, 1H), 7.04 (s, 1H), 3.47-3.38 (m, 2H), 3.31 (s, 3H), 3.22-3.06 (m, 2H), 2.80-2.68 (m, 1H), 2.67-2.58 (m, 4H), 2.32 (t, J = 11.5 Hz, 2H), 2.15-2.00 (m, 3H), 1.98-1.85 (m, 2H), 1.85-1.77 (m, 4H), 1.77-1.64 (m, 4H), 0.57-0.39 (m, 4H). TLR9 $IC_{50}$ (nM) = 44 |
| 348 | Analytical LC/MS (Method 6): Purity: 95.1%; Observed Mass: 539.2; Retention Time: 1.11 min. $^1$H NMR (300 MHz, Methanol-$d_4$) δ 8.21-8.06 (m, 3H), 7.34 (s, 1H), 7.04 (s, 1H), 3.70-3.61 (m, 2H), 3.33 (s, 3H), 3.18 (d, J = 11.0 Hz, 2H), 3.09-3.01 (m, 1H), 2.77-2.69 (m, 2H), 2.64 (s, 3H), 2.31-2.24 (m, 2H), 2.01-1.60 (m, 12H), 1.17 (d, J = 6.0 Hz, 6H). TLR9 $IC_{50}$ (nM) = 180 |
| 349 | Analytical LC/MS (Method 6): Purity: 96.8%; Observed Mass: 551.3; Retention Time: 0.649 min. $^1$H NMR (400 MHz, Methanol-$d_4$) δ 8.22-8.00 (m, 3H), 7.34 (s, 1H), 7.05 (s, 1H), 3.39 (s, 2H), 3.29-3.24 (m, 4H), 3.13 (d, J = 10.4 Hz, 2H), 2.82-2.71 (m, 1H), 2.71-2.58 (m, 4H), 2.42-2.30 (m, 2H), 2.18-2.07 (m, 2H), 2.06-1.88 (m, 7H), 1.88-1.71 (m, 7H), 1.68 (d, J = 8.1 Hz, 2H). TLR9 $IC_{50}$ (nM) = 24 |
| 350 | Analytical LC/MS (Method 6): Purity: 93.0%; Observed Mass: 551.3; Retention Time: 1.013 min. $^1$H NMR (400 MHz, Methanol-$d_4$) δ 8.08-7.91 (m, 3H), 7.21 (s, 1H), 6.92 (s, 1H), 3.21-3.20 (m, 4H), 3.20-3.07 (m, 4H), 3.06-2.93 (m, 1H), 2.59-2.35 (m, 5H), 2.05-1.93 (m, 4H), 1.92-1.74 (m, 10H), 1.71-1.59 (m, 5H). TLR9 $IC_{50}$ (nM) = 55 |
| 351 | Analytical LC/MS (Method 6): Purity: 98.7%; Observed Mass: 551.2; Retention Time: 0.643 min. 1H NMR (400 MHz, Chloroform-d) δ 8.09-7.97 (m, 3H), 7.28 (s, 1H), 7.04 (s, 1H), 3.46 (s, 2H), 3.36-3.18 (m, 5H), 2.68-2.45 (m, 5H), 2.33-2.16 (m, 4H), 2.00-1.71 (m, 12H), 0.99-0.87 (m, 1H), 0.56-0.45 (m, 2H), 0.20-0.06 (m, 2H). TLR9 $IC_{50}$ (nM) = 48 |
| 352 | Analytical LC/MS (Method 6): Purity: 95.1%; Observed Mass: 551.3; Retention Time: 2.283 min. 1H NMR (400 MHz, Methanol-$d_4$) δ 8.19-8.03 (m, 3H), 7.34 (s, 1H), 7.04 (s, 1H), 3.65 (s, 2H), 3.28 (s, 3H), 3.20-3.05 (m, 2H), 2.84-2.70 (m, 1H), 2.64-2.55 (m, 4H), 2.53-2.42 (m, 2H), 2.34 (t, J = 11.6 Hz, 2H), 2.10-1.99 (m, 2H), 1.97-1.61 (m, 10H), 1.04-0.89 (m, 1H), 0.68-0.49 (m, 2H), 0.22-0.15 (m, 2H). TLR9 $IC_{50}$ (nM) = 26 |

-continued

| Ex. No. | Analytical LC/MS, Preparative HPLC method, yield, and $^1$H NMR |
|---|---|
| 353 | Analytical LC/MS (Method 6): Purity: 98.8%; Observed Mass: 516.2; Retention Time: 0.943 min. Prep Method 3: 60 mg, 71% yield; $^1$H NMR (300 MHz, Methanol-$d_4$) δ 8.89 (s, 1H), 8.49 (s, 1H), 7.47 (s, 1H), 7.29 (s, 1H), 7.07 (s, 1H), 4.15 (s, 3H), 3.95 (s, 3H), 3.21-3.13 (m, 2H), 3.05-2.95 (m, 2H), 2.75-2.65 (m, 1H), 2.63 (s, 3H), 2.45-2.32 (m, 3H), 2.16-2.08 (m, 2H), 2.04-1.78 (m, 9H), 1.75-1.60 (m, 2H), 0.92 (d, J = 6.9 Hz, 6H). TLR9 $IC_{50}$ (nM) = 16 |
| 354 | Analytical LC/MS (Method 6): Purity: 98.7%; Observed Mass: 526.2; Retention Time: 0.568 min. $^1$H NMR (400 MHz, Methanol-$d_4$) δ 8.76 (d, J = 1.3 Hz, 1H), 8.36 (s, 1H), 7.36 (d, J = 1.3 Hz, 1H), 7.17 (d, J = 1.5 Hz, 1H), 6.95 (s, 1H), 4.05 (s, 3H), 3.85 (s, 3H), 3.32-3.29 (m, 2H), 3.05-3.02 (m, 2H), 2.64-2.59 (m, 2H), 2.52 (s, 3H), 2.25-2.20 (m, 2H), 1.96-1.93 (m, 3H), 1.84-1.56 (m, 10H), 0.40-0.36 (m, 4H). TLR9 $IC_{50}$ (nM) = 85 |
| 355 | Analytical LC/MS (Method 6): Purity: 98.4%; Observed Mass: 540.3. $^1$H NMR (400 MHz, Methanol-$d_4$) δ 8.89 (s, 1H), 8.47 (s, 1H), 7.48 (s, 1H), 7.28 (s, 1H), 7.06 (s, 1H), 4.16 (s, 3H), 3.95 (s, 3H), 3.35 (s, 3H), 3.28-3.18 (m, 1H), 3.16-3.09 (m, 1H), 2.91-2.67 (m, 2H), 2.63 (s, 3H), 2.41-2.30 (m, 2H), 2.17-1.58 (m, 18H). TLR9 $IC_{50}$ (nM) = 11 |
| 356 | Analytical LC/MS (Method 6): Purity: 93.4%; Observed Mass: 540.3. $^1$H NMR (400 MHz, Methanol-$d_4$) δ 8.89 (s, 1H), 8.47 (s, 1H), 7.47 (s, 1H), 7.28 (s, 1H), 7.06 (s, 1H), 4.16 (s, 3H), 3.95 (s, 3H), 3.30 (s, 4H), 3.13-3.07 (m, 1H), 2.74-2.62 (m, 1H), 2.63 (s, 3H), 2.61-2.48 (m, 1H), 2.22-1.60 (m, 20H). TLR9 $IC_{50}$ (nM) = 41 |
| 357 | Analytical LC/MS (Method 6): Purity: 97.4%; Observed Mass: 528.3; Retention Time: 0.564 min. $^1$H NMR (400 MHz, Methanol-$d_4$) δ 8.89 (s, 1H), 8.49 (s, 1H), 7.47 (s, 1H), 7.28 (s, 1H), 7.07 (s, 1H), 4.16 (s, 3H), 3.95 (s, 3H), 3.63-3.58 (m, 2H), 3.22-3.15 (m, 2H), 3.06-2.95 (m, 1H), 2.80-2.65 (m, 2H), 2.63 (s, 3H), 2.34-2.23 (m, 2H), 2.02-1.89 (m, 4H), 1.90-1.77 (m, 4H), 1.75-1.57 (m, 4H), 1.14 (d, J = 6.0 Hz, 6H). TLR9 $IC_{50}$ (nM) = 32 |
| 358 | Analytical LC/MS (Method 6): Purity: 98.0%; Observed Mass: 540.3; Retention Time: 0.579 min. $^1$H NMR (400 MHz, Methanol-$d_4$) δ 8.89 (s, 1H), 8.47 (s, 1H), 7.47 (s, 1H), 7.28 (s, 1H), 7.06 (s, 1H), 4.16 (s, 3H), 3.94 (s, 3H), 3.58-3.52 (m, 2H), 3.17-3.09 (m, 2H), 2.79-2.65 (m, 2H), 2.63 (s, 3H), 2.42-2.28 (m, 4H), 2.05-1.61 (m, 12H), 1.00-0.88 (m, 1H), 0.60-0.49 (m, 2H), 0.22-0.14 (m, 2H). TLR9 $IC_{50}$ (nM) = 8.1 |
| 359 | Analytical LC/MS (Method 6): Purity: 98.9%; Observed Mass: 528.2; Retention Time: 0.618 min. $^1$H NMR (300 MHz, Methanol-$d_4$) δ 9.16 (s, 1H), 8.44 (s, 1H), 7.85 (s, 1H), 7.32 (s, 1H), 7.02 (s, 1H), 4.21 (s, 3H), 3.39-3.32 (m, 2H), 3.21-3.12 (m, 2H), 2.70-2.59 (m, 5H), 2.33-2.21 (m, 4H), 2.03-1.57 (m, 13H), 0.96 (d, J = 6.6 Hz, 6H). TLR9 $IC_{50}$ (nM) = 76 |
| 360 | Analytical LC/MS (Method 6): Purity: 95.1%; Observed Mass: 512.2; Retention Time: 2.432 min. $^1$H NMR (400 MHz, Methanol-$d_4$) δ 9.03 (d, J = 1.4 Hz, 1H), 8.33 (s, 1H), 7.73 (d, J = 1.4 Hz, 1H), 7.19 (s, 1H), 6.89 (s, 1H), 4.09 (s, 3H), 3.31 (d, J = 4.6 Hz, 2H), 3.03 (d, J = 11.5 Hz, 2H), 2.65-2.62 (m, 1H), 2.55-2.51 (m, 1H), 2.49 (s, 3H), 2.24-2.18 (m, 2H), 1.98-1.93 (m, 3H), 1.82-1.54 (m, 10H), 0.42-0.36 (m, 4H). TLR9 $IC_{50}$ (nM) = 9.7 |
| 361 | Analytical LC/MS (Method 6): Purity: 91.9%; Observed Mass: 526.2; Retention Time: 0.561 min. $^1$H NMR (400 MHz, Methanol-$d_4$) δ 9.02 (d, J = 1.5 Hz, 1H), 8.32 (s, 1H), 7.72 (d, J = 1.6 Hz, 1H), 7.19 (s, 1H), 6.89 (s, 1H), 4.11 (s, 3H), 3.21-3.20 (m, 2H), 3.17-3.11 (m, 1H), 3.00 (d, J = 11.3 Hz, 2H), 2.66-2.61 (m, 1H), 2.58 (s, 3H), 2.51-2.48 (m, 1H), 2.21 (dd, J = 12.9, 10.1 Hz, 2H), 2.01-1.95 (m, 2H), 1.88-1.52 (m, 16H). TLR9 $IC_{50}$ (nM) = 21 |
| 362 | Analytical LC/MS (Method 6): Purity: 95.9%; Observed Mass: 514.2; Retention Time: 0.593 min. $^1$H NMR (300 MHz, Methanol-$d_4$) δ 9.15 (s, 1H), 8.45 (s, 1H), 7.87 (s, 1H), 7.33 (s, 1H), 7.02 (s, 1H), 4.21 (s, 3H), 3.66-3.60 (m, 2H), 3.23-3.14 (m, 2H), 3.11-2.94 (m, 1H), 2.82-2.67 (m, 1H), 2.64 (s, 4H), 2.35-2.21 (m, 2H), 2.08-1.78 (m, 8H), 1.76-1.56 (m, 4H), 1.16 (d, J = 6.3 Hz, 6H). TLR9 $IC_{50}$ (nM) = 150 |

Example 363

1,4-dimethyl-6-(4-(1-methylpiperidin-4-yl)phenyl)-2-(4-(methylsulfonyl)phenyl)-1H-benzo[d]imidazole (363)

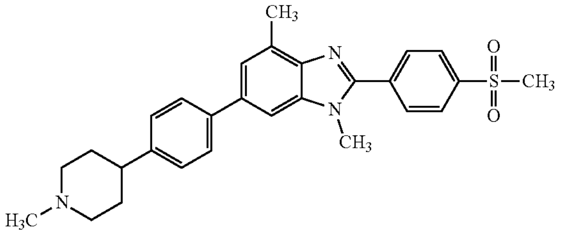

A mixture of Intermediate 22A (40 mg, 0.11 mmol), 1-methyl-4-(4-(4,4,5,5-tetramethyl-1,3,2-dioxaborolan-2-yl)phenyl)piperidine (40 mg, 0.13 mmol), XPhos Pd G3 (8.9 mg, 11 μmol), and potassium phosphate tribasic (0.19 mL, 0.37 mmol) in 1,4-dioxane (2 mL) was degassed and heated in a closed vial at 95° C. for 10 h. Upon cooling to room temperature, the mixture was diluted with MeOH, filtered, and the filtrate was purified by preparative HPLC (Prep Method 4). The obtained product was basified with 1.5 M $K_3PO_4$ solution, and extracted with dichloromethane (4×35 mL). The combined extract was dried over anhydrous $Na_2SO_4$. Removal of the solvent under vacuum provided the title product (26 mg, 0.053 mmol, 50% yield) as a white solid. LCMS $(M+H)^+$=474.2. $^1$H NMR (500 MHz, chloroform-d) δ 8.14 (d, J=8.6 Hz, 2H), 8.04 (d, J=8.6 Hz, 2H), 7.65 (d, J=8.3 Hz, 2H), 7.44 (d, J=0.8 Hz, 1H), 7.41 (dd, J=1.5, 0.8 Hz, 1H), 7.37 (d, J=8.2 Hz, 2H), 3.94 (s, 3H), 3.20-3.10 (m, 2H), 3.13 (s, 3H), 2.78 (s, 3H), 2.68-2.55 (m, 1H), 2.46 (s, 3H), 2.24 (br s, 2H), 2.06-1.93 (m, 4H). TLR9 $IC_{50}$=140 nM.

Example 364

1,4-dimethyl-2-(4-(methylsulfonyl)phenyl)-6-(4-(1-(tetrahydro-2H-pyran-4-yl)piperidin-4-yl)phenyl)-1H-benzo[d]imidazole (364)

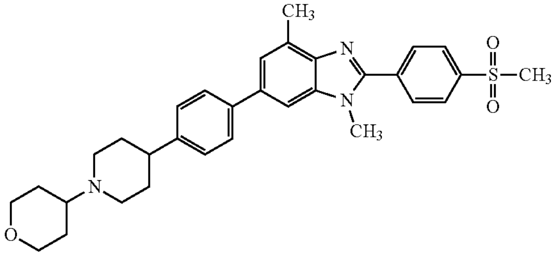

Step A. Intermediate 364A. Preparation of tert-butyl 4-(4-(1,4-dimethyl-2-(4-(methylsulfonyl)phenyl)-1H-benzo[d]imidazol-6-yl)phenyl)piperidine-1-carboxylate (364A)

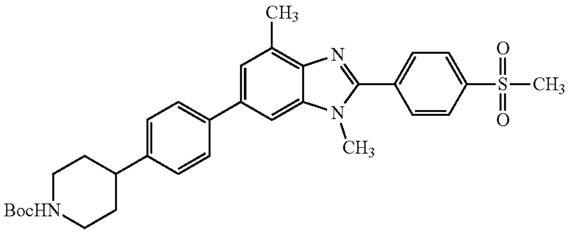

A mixture of Intermediate 22A (400 mg, 1.1 mmol), tert-butyl 4-(4-(4,4,5,5-tetramethyl-1,3,2-dioxaborolan-2-yl)phenyl)piperidine-1-carboxylate (530 mg, 1.4 mmol), XPhos Pd G3 (89 mg, 0.11 mmol), and potassium phosphate tribasic (1.9 mL, 3.7 mmol) in 1,4-dioxane (20 mL) was degassed and heated in a closed vial at 95° C. for 10 h. Upon cooling to room temperature, the mixture was diluted with ethyl acetate (30 mL) and filtered through Celite. The filtrate was further diluted with ethyl acetate (120 mL), washed with brine (25 mL), and dried over anhydrous $MgSO_4$ and concentrated. The crude product was purified by flash column chromatography (80 g silica gel, solid loading, 45-95% ethyl acetate/hexane). Fractions corresponding to product were combined, concentrated and dried in vacuo to afford the title compound (520 mg, 0.93 mmol, 88% yield) as a yellow solid. LCMS $(M+H)^+$=560.1. $^1$H NMR (400 MHz, DMSO-$d_6$) δ 8.20-8.15 (m, 2H), 8.15-8.10 (m, 2H), 7.75 (d, J=1.0 Hz, 1H), 7.71 (d, J=8.2 Hz, 2H), 7.41 (s, 1H), 7.36 (d, J=8.4 Hz, 2H), 4.18-4.06 (m, 2H), 3.98 (s, 3H), 3.33 (s, 3H), 2.92-2.69 (m, 3H), 2.65 (s, 3H), 1.81 (br d, J=12.7 Hz, 2H), 1.55 (qd, J=12.6, 4.0 Hz, 2H), 1.44 (s, 9H).

Step B. Intermediate 364B. Preparation of 1,4-Dimethyl-2-(4-(methylsulfonyl)phenyl)-6-(4-(piperidin-4-yl)phenyl)-1H-benzo[d]imidazole (364B)

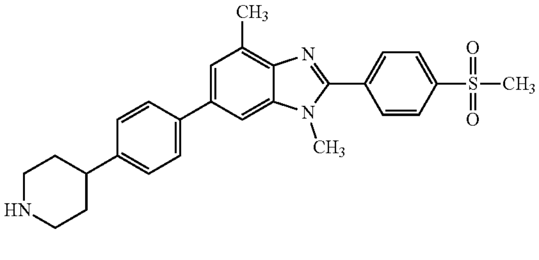

To a solution of Intermediate 364A (520 mg, 0.92 mmol) in dichloromethane (15 mL) at 0° C. was added TFA (15 mL, 200 mmol) over 1 min. The mixture was stirred at 0° C. for 1 h and then concentrated under vacuum to dryness. To the residue was added 1.5 M $K_3PO_4$ solution (10 mL) and the mixture was extracted with 5% MeOH/DCM (4×40 mL). The combined extract was dried over anhydrous $Na_2SO_4$. Removal of the solvent under vacuum provided the title compound (420 mg, 0.92 mmol, 100% yield) as a beige solid. LCMS $(M+H)^+$=460.1. $^1H$ NMR (500 MHz, DMSO-$d_6$) δ 8.20-8.17 (m, 2H), 8.15-8.12 (m, 2H), 7.80-7.74 (m, 3H), 7.42 (s, 1H), 7.35 (d, J=8.2 Hz, 2H), 3.99 (s, 3H), 3.42 (br d, J=11.8 Hz, 2H), 3.33 (s, 3H), 3.05 (q, J=11.8 Hz, 2H), 2.92 (tt, J=12.1, 3.4 Hz, 1H), 2.65 (s, 3H), 2.05-1.97 (m, 2H), 1.90-1.79 (m, 2H).

Step C. Example 364

To a solution of Intermediate 364B (45 mg, 0.098 mmol), tetrahydro-4H-pyran-4-one (39 mg, 0.39 mmol), magnesium sulfate (240 mg, 2.0 mmol), and acetic acid (0.056 mL, 0.98 mmol) in acetonitrile (2 mL) at room temperature was added sodium triacetoxyborohydride (93 mg, 0.44 mmol) in one portion. The mixture was stirred at room temperature for 48 h. The heterogeneous mixture was diluted with ethyl acetate (5 mL) and filtered through Celite. The filtrate was concentrated under vacuum to dryness.

The crude product was purified by preparative HPLC (Prep Method 4). The obtained product was basified with 1.5 M $K_3PO_4$ solution, and extracted with dichloromethane (4×35 mL). The combined extract was dried over anhydrous $Na_2SO_4$. Removal of the solvent under vacuum provided the title compound (15 mg, 0.026 mmol, 27% yield) as a white solid. LCMS $(M+H)^+$=544.1. $^1H$ NMR (500 MHz, DMSO-$d_6$) δ 8.20-8.16 (m, 2H), 8.15-8.11 (m, 2H), 7.77-7.69 (m, 3H), 7.42 (s, 1H), 7.36 (d, J=8.2 Hz, 2H), 3.98 (s, 3H), 3.97-3.88 (m, 2H), 3.33 (s, 3H), 3.14-2.94 (m, 2H), 2.65 (s, 3H), 2.34-2.15 (m, 1H), 1.97-1.44 (m, 8H). TLR9 $IC_{50}$=310 nM.

Example 365

6-(6-(1-isopropylpiperidin-4-yl)pyridin-3-yl)-1,4-dimethyl-2-(4-(methylsulfonyl)phenyl)-1H-benzo[d]imidazole (365)

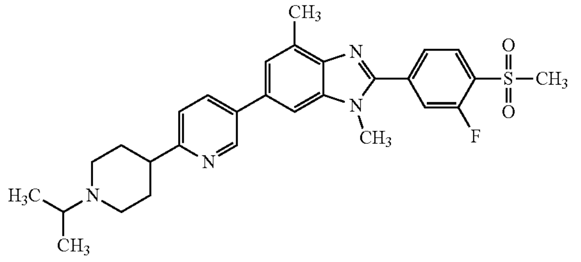

Step A. Intermediate 356A. Preparation of 1,4-dimethyl-2-(4-(methylsulfonyl)phenyl)-6-(4,4,5,5-tetramethyl-1,3,2-dioxaborolan-2-yl)-1H-benzo[d]imidazole (365A)

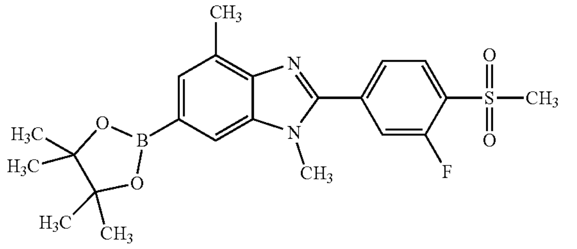

A mixture of Intermediate 22A (200 mg, 0.53 mmol), 4,4,4',4',5,5,5',5'-octamethyl-2,2'-bi(1,3,2-dioxaborolane) (210 mg, 0.84 mmol), $PdCl_2(dppf)-CH_2C_{12}$ adduct (43 mg, 0.053 mmol), and potassium acetate (160 mg, 1.6 mmol) in 1,4-dioxane (8 mL) was heated in a pressure reaction vessel at 100° C. for 15 h. The mixture was then cooled, diluted with ethyl acetate (50 mL) and filtered through Celite. The filtrate was concentrated under vacuum, and the residue was purified by flash column chromatography (40 g silica gel, solid loading, 50-90% ethyl acetate/hexane) to provide the title intermediate (170 mg, 0.39 mmol, 75% yield), as a white solid. LCMS $(M+H)^+$=426.8. $^1H$ NMR (400 MHz, chloroform-d) δ 8.17-8.11 (m, 2H), 8.07-8.00 (m, 2H), 7.79 (s, 1H), 7.65-7.61 (m, 1H), 3.93 (s, 3H), 3.13 (s, 3H), 2.73 (s, 3H), 1.42 (s, 12H).

Step B. Example 365

A mixture of Intermediate 365A (57 mg, 0.13 mmol), 5-bromo-2-(1-isopropylpiperidin-4-yl)pyridine (30 mg, 0.11 mmol), XPhos Pd G3 (9.0 mg, 11 μmol), and potassium phosphate tribasic (0.19 mL, 0.37 mmol) in 1,4-dioxane (3 mL) was degassed and heated in a closed vial at 95° C. for 7 h. Upon cooling to room temperature, the residue was dissolved in MeOH and purified by preparative HPLC (Prep Method 4). The obtained residue was basified with 1.5 M $K_3PO_4$ solution, and extracted with dichloromethane (4×35 mL). The combined extract was dried over anhydrous $Na_2SO_4$. Removal of the solvent under vacuum provided the title compound (25 mg, 0.047 mmol, 44% yield), as a white solid. LCMS $(M+H)^+$=503.1. $^1H$ NMR (500 MHz, chloroform-d) δ 8.85 (d, J=1.8 Hz, 1H), 8.15 (d, J=8.6 Hz, 2H), 8.04 (d, J=8.6 Hz, 2H), 7.93 (dd, J=8.2, 2.4 Hz, 1H), 7.43 (d, J=0.8 Hz, 1H), 7.38 (s, 1H), 7.34 (d, J=8.0 Hz, 1H), 3.95 (s, 3H), 3.24-3.09 (m, 2H), 3.14 (s, 3H), 2.99-2.77 (m, 2H), 2.79 (s, 3H), 2.43 (br s, 2H), 2.19-1.95 (m, 4H), 1.18 (br d, J=5.7 Hz, 6H). TLR9 $IC_{50}$=300 nM.

Example 366

1-(4-(1,4-dimethyl-2-(4-(methylsulfonyl)phenyl)-1H-benzo[d]imidazol-6-yl)phenethyl)-4-methylpiperidin-4-ol (366)

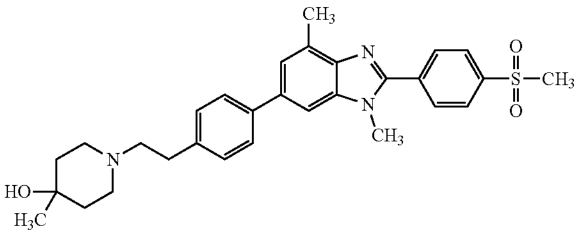

Step A. Intermediate 366A. Preparation of 1-(4-bromophenethyl)-4-methylpiperidin-4-ol (366A)

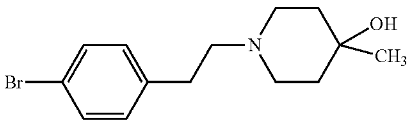

To a solution of 2-(4-bromophenyl)acetaldehyde (380 mg, 1.9 mmol), 4-methylpiperidin-4-ol (650 mg, 5.7 mmol), magnesium sulfate (4500 mg, 38 mmol), and acetic acid (1.1 mL, 19 mmol) in DMF (8 mL) at room temperature was added sodium triacetoxyborohydride (1600 mg, 7.5 mmol) in one portion. The mixture was stirred at room temperature for 20 h. The heterogeneous mixture was diluted with ethyl acetate (10 mL) and filtered through Celite. The filtrate was concentrated under vacuum to dryness. The residue was dissolved in ethyl acetate (120 mL), washed with saturated $NaHCO_3$ solution (2×20 mL), and dried over anhydrous $MgSO_4$. The crude residue was purified by flash column chromatography (40 g silica gel, 0-8% methanol/dichloromethane). Fractions corresponding to product were combined, concentrated and the product was dried in vacuo to afford the title intermediate (200 mg, 0.68 mmol, 36% yield) as a white solid. LCMS $(M+H)^+$=297.9. $^1H$ NMR (400 MHz, CHLOROFORM-d) δ 7.47-7.29 (m, 2H), 7.16-6.96 (m, 2H), 2.81-2.72 (m, 2H), 2.71-2.54 (m, 4H), 2.44 (td, J=11.0, 2.7 Hz, 2H), 1.78-1.58 (m, 4H), 1.26 (s, 3H).

Step B. Intermediate 366B. Preparation of 4-methyl-1-(4-(4,4,5,5-tetramethyl-1,3,2-dioxaborolan-2-yl)phenethyl)piperidin-4-ol (366B)

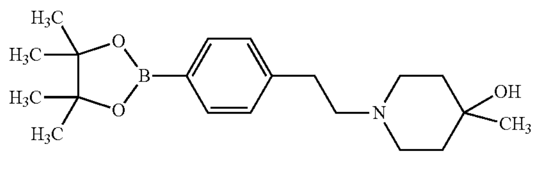

A mixture of Intermediate 366A (0.20 g, 0.67 mmol), 4,4,4',4',5,5,5',5'-octamethyl-2,2'-bi(1,3,2-dioxaborolane) (0.27 g, 1.1 mmol), $PdCl_2(dppf)-CH_2Cl_2$ adduct (0.055 g, 0.067 mmol), and potassium acetate (0.20 g, 2.0 mmol) in 1,4-dioxane (6 mL) was heated in a pressure reaction vessel at 100° C. for 16 h. Upon cooling to room temperature, the mixture was diluted with ethyl acetate (10 mL) and filtered through Celite. The filtrate was further diluted with ethyl acetate (60 mL), washed with brine (15 mL), and dried over anhydrous $MgSO_4$. The crude residue was purified by flash column chromatography (40 g silica gel, 0-10% methanol/dichloromethane). The fractions corresponding to product were combined, concentrated and dried in vacuo to afford the title intermediate (52 mg, 0.15 mmol, 23% yield) as a beige solid. LCMS $(M+H)^+$=346.1. $^1H$ NMR (500 MHz, chloroform-d) δ 7.76 (d, J=7.9 Hz, 2H), 7.24 (d, J=7.9 Hz, 2H), 2.98-2.87 (m, 2H), 2.85-2.69 (m, 4H), 2.57 (br s, 2H), 1.83 (br s, 2H), 1.66 (br d, J=13.2 Hz, 2H), 1.36 (s, 12H), 1.30 (s, 3H).

Step C. Example 366

A mixture of Intermediate 22A (45 mg, 0.12 mmol), Intermediate 366B (51 mg, 0.15 mmol), XPhos Pd G3 (10 mg, 0.012 mmol), and potassium phosphate tribasic (0.21 mL, 0.42 mmol) in 1,4-dioxane (2 mL) was degassed and heated in a closed vial at 95° C. for 10 h. Upon cooling to room temperature, the mixture was diluted with MeOH, filtered, and the filtrate was purified by preparative HPLC (Prep Method 4). The obtained residue was basified with 1.5 M $K_3PO_4$ solution, and extracted with dichloromethane (4×35 mL). The combined extract was dried over anhydrous $Na_2SO_4$. Removal of the solvent under vacuum provided the title compound (25 mg, 0.048 mmol, 41% yield) as a white solid. LCMS $(M+H)^+$=518.1. $^1H$ NMR (500 MHz, DMSO-$d_6$) δ 8.20-8.16 (m, 2H), 8.15-8.11 (m, 2H), 7.78-7.70 (m, 3H), 7.43 (s, 1H), 7.37 (br d, J=7.1 Hz, 2H), 3.99 (s, 3H), 3.33 (s, 2H), 3.45-2.68 (m, 8H), 2.65 (s, 3H), 1.86-1.41 (m, 4H), 1.17 (br s, 3H). TLR9 $IC_{50}$=450 nM.

Example 367

1,4-dimethyl-2-(4-(methylsulfonyl)phenyl)-6-(4-(4-(pyrrolidin-1-yl)piperidin-1-yl) phenyl)-1H-benzo[d]imidazole (367)

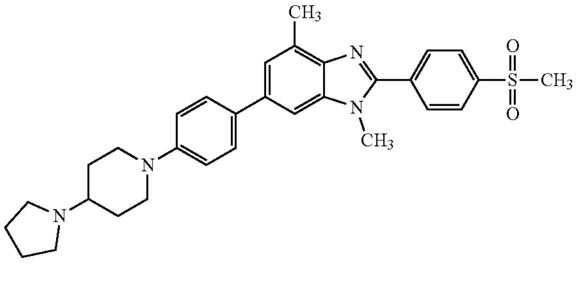

Step A. Intermediate 367A. Preparation of 1-(4-(4,4,5,5-tetramethyl-1,3,2-dioxaborolan-2-yl)phenyl)piperidin-4-one (367A)

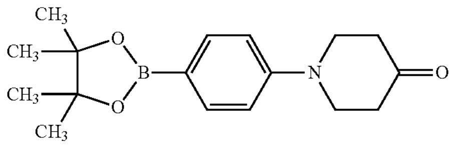

A mixture of 1-(4-bromophenyl)piperidin-4-one (1.0 g, 3.9 mmol), 4,4,4',4',5,5,5',5'-octamethyl-2,2'-bi(1,3,2-dioxaborolane) (1.6 g, 6.3 mmol), $PdCl_2(dppf)$-$CH_2Cl_2$ adduct (0.32 g, 0.39 mmol), and potassium acetate (1.2 g, 12 mmol) in 1,4-dioxane (25 mL) in a pressure reaction vial was heated at 100° C. for 8 h. The mixture then cooled, diluted with ethyl acetate (50 mL) and filtered through Celite. The filtrate was concentrated under vacuum, and the residue was purified by flash column chromatography (120 g silica gel, solid loading, 10-50% ethyl acetate/hexane). Fractions corresponding to product were combined, concentrated and dried in vacuo to provide the title intermediate (0.54 g, 1.8 mmol, 45% yield) as a white solid. LCMS $(M+H)^+$=302.0. $^1H$ NMR (400 MHz, chloroform-d) δ 7.77 (d, J=8.8 Hz, 2H), 6.96 (d, J=8.8 Hz, 2H), 3.72 (t, J=6.1 Hz, 4H), 2.56 (t, J=6.1 Hz, 4H), 1.36 (s, 12H).

Step B. Intermediate 367B. Preparation of 4-(pyrrolidin-1-yl)-1-(4-(4,4,5,5-tetramethyl-1,3,2-dioxaborolan-2-yl)phenyl)piperidine (367B)

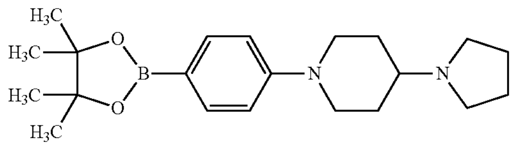

To a solution of Intermediate 367A (200 mg, 0.664 mmol), pyrrolidine (0.17 mL, 2.0 mmol), magnesium sulfate (1600 mg, 13 mmol), and acetic acid (0.38 mL, 6.6 mmol) in DMF (1 mL) was added sodium triacetoxyborohydride (560 mg, 2.7 mmol) in one portion. The mixture was stirred at room temperature for 24 h. The heterogeneous mixture was diluted with ethyl acetate (15 mL) and filtered through Celite. The filtrate was concentrated under vacuum to dryness. To the residue was added 1.5 M $K_3PO_4$ solution (10 mL) and the mixture was extracted with dichloromethane (4×40 mL). The combined extract was dried over anhydrous $Na_2SO_4$ and concentrated. The crude residue was purified by flash column chromatography (40 g silica gel, 5-18% MeOH/$CH_2Cl_2$). The fractions corresponding to product were combined, concentrated and dried in vacuo to provide the title intermediate (40 mg, 0.11 mmol, 17% yield) as a white solid. LCMS $(M+H)^+$=357.1. $^1H$ NMR (500 MHz, chloroform-d) δ 7.70 (d, J=8.6 Hz, 2H), 6.91 (d, J=8.7 Hz, 2H), 3.82 (br d, J=12.9 Hz, 2H), 2.82 (td, J=12.3, 2.4 Hz, 2H), 2.65 (br s, 4H), 2.22 (br s, 1H), 2.06-1.96 (m, 2H), 1.83 (br s, 4H), 1.73-1.66 (m, 2H), 1.35 (s, 12H).

Step C. Example 367

A mixture of Intermediate 22A (34 mg, 0.090 mmol), Intermediate 367B (38 mg, 0.11 mmol), XPhos Pd G3) (7.6 mg, 9.0 μmol), and potassium phosphate tribasic (0.16 mL, 0.31 mmol) in 1,4-dioxane (2 mL) was degassed and heated in a closed vial at 95° C. for 7 h. Upon cooling to room temperature, the mixture was diluted with MeOH, filtered, and the filtrate was purified by preparative HPLC (Prep Method 4). The obtained residue was basified with 1.5 M $K_3PO_4$ solution, and extracted with dichloromethane (4×35 mL). The combined extract was dried over anhydrous $Na_2SO_4$. Removal of the solvent under vacuum provided the title compound (5.0 mg, 9.2 μmol, 10% yield) as a pale yellow solid. LCMS $(M+H)^+$=529.3. $^1H$ NMR (500 MHz, chloroform-d) δ 8.14 (d, J=8.6 Hz, 2H), 8.07-8.00 (m, 2H), 7.60 (d, J=8.7 Hz, 2H), 7.42-7.37 (m, 2H), 7.05 (d, J=8.9 Hz, 2H), 3.93 (s, 3H), 3.82 (br d, J=12.6 Hz, 2H), 3.13 (s, 3H), 2.90-2.72 (m, 8H), 2.10 (br d, J=11.7 Hz, 2H), 1.95-1.59 (m, 8H). TLR9 $IC_{50}$=510 nM.

Example 368

1-(4-(1,4-dimethyl-2-(4-(methylsulfonyl)phenyl)-1H-benzo[d]imidazol-6-yl)phenyl)-N,N-dimethylpiperidin-4-amine (368)

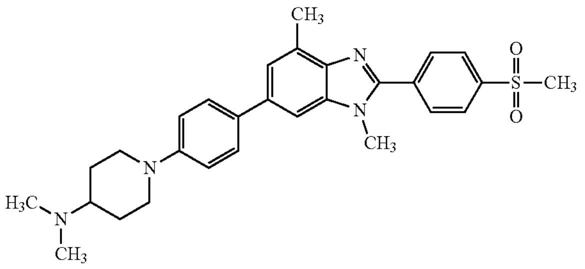

Step A. Intermediate 368A. Preparation of 1-(4-(1,4-dimethyl-2-(4-(methylsulfonyl) phenyl)-1H-benzo[d]imidazol-6-yl)phenyl)piperidin-4-one (368A)

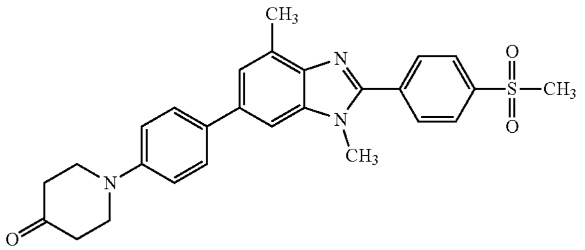

A mixture of Intermediate 22A (140 mg, 0.36 mmol), 1-(4-(4,4,5,5-tetramethyl-1,3,2-dioxaborolan-2-yl)phenyl) piperidin-4-one (130 mg, 0.43 mmol), XPhos Pd G3 (30 mg, 0.036 mmol), and potassium phosphate tribasic (0.62 mL, 1.3 mmol) in 1,4-dioxane (5 mL) was degassed and heated in a closed vial at 85° C. for 16 h. Upon cooling to room temperature, the mixture was diluted with ethyl acetate (60 mL), washed with brine (15 mL), dried over anhydrous $MgSO_4$ and concentrated. The crude residue was purified by flash column chromatography (40 g silica gel, solid loading, 0-5% ethyl acetate). The fractions corresponding to product were combined, concentrated and dried in vacuo to afford the title intermediate (98 mg, 0.21 mmol, 58% yield) as a pale yellow solid. LCMS $(M+H)^+$=474.2. $^1$H NMR (500 MHz, chloroform-d) δ 8.17-8.11 (m, 2H), 8.06-8.01 (m, 2H), 7.68-7.62 (m, 2H), 7.41 (s, 1H), 7.40 (s, 1H), 7.11 (d, J=8.7 Hz, 2H), 3.94 (s, 3H), 3.73-3.70 (m, 4H), 3.13 (s, 3H), 2.78 (s, 3H), 2.63 (t, J=6.0 Hz, 4H).

Step B. Example 368

To a solution of Intermediate 368A (45 mg, 0.095 mmol), dimethylamine in THE (0.17 mL, 0.33 mmol), magnesium sulfate (230 mg, 1.9 mmol), and acetic acid (0.054 mL, 0.95 mmol) in DMF (1 mL) was added sodium triacetoxyborohydride (81 mg, 0.38 mmol) in one portion. The mixture was stirred at room temperature for 24 h. The heterogeneous mixture was diluted with ethyl acetate (5 mL) and filtered through Celite. The filtrate was concentrated under vacuum to dryness. The residue was purified by preparative HPLC (Method 4). The obtained residue was basified with 1 N NaOH solution, and extracted with dichloromethane (4×35 mL). The combined extract was dried over anhydrous $Na_2SO_4$. Removal of the solvent under vacuum provided the title compound (16 mg, 0.031 mmol, 33% yield) as a pale yellow solid. LCMS $(M+H)^+$=503.3. $^1$H NMR (400 MHz, CHLOROFORM-d) δ 8.17-8.11 (m, 2H), 8.07-8.01 (m, 2H), 7.64-7.58 (m, 2H), 7.42-7.38 (m, 2H), 7.06 (d, J=8.8 Hz, 2H), 3.93 (s, 3H), 3.85 (br d, J=12.5 Hz, 2H), 3.13 (s, 3H), 2.88-2.76 (m, 2H), 2.77 (s, 3H), 2.50-2.41 (m. 1H), 2.42 (s, 6H), 2.03 (br d, J=12.1 Hz, 2H), 1.80-1.69 (m, 2H). TLR9 $IC_{50}$=410 nM.

Example 369

1,4-dimethyl-2-(4-(methylsulfonyl)phenyl)-6-(4-((4-(pyrrolidin-1-yl)piperidin-1-yl)methyl)phenyl)-1H-benzo[d]imidazole (369)

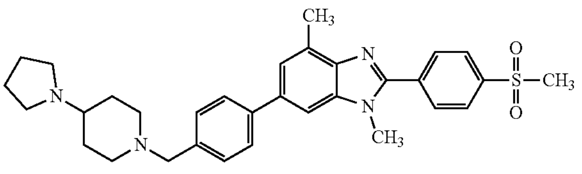

Step A. Intermediate 369A. Preparation of 4-(1,4-dimethyl-2-(4-(methylsulfonyl) phenyl)-1H-benzo [d]imidazol-6-yl)benzaldehyde (369A)

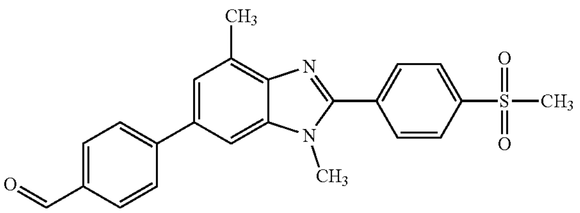

A mixture of Intermediate 22A (400 mg, 1.1 mmol), 4-(4,4,5,5-tetramethyl-1,3,2-dioxaborolan-2-yl)benzaldehyde (310 mg, 1.3 mmol), XPhos Pd G3 (89 mg, 0.11 mmol), and potassium phosphate tribasic (1.9 mL, 3.7 mmol) in 1,4-dioxane (15 mL) was degassed and heated in a closed vial at 95° C. for 7 h. Upon cooling to room temperature, the mixture was diluted with ethyl acetate (30 mL) and filtered through Celite. The filtrate was further diluted with ethyl acetate (120 mL), washed with brine (25 mL), and dried over anhydrous $MgSO_4$ and concentrated. The crude residue was purified by flash column chromatography (80 g silica gel, solid loading, 45-95% ethyl acetate/hexane). Fractions corresponding to product were combined, concentrated and dried in vacuo to afford the title intermediate (360 mg, 0.89 mmol, 84% yield) as a yellow solid. LCMS $(M+H)^+$=405.0. $^1$H NMR (500 MHz, chloroform-d) δ 10.11 (s, 1H), 8.18-8.13 (m, 2H), 8.07-8.03 (m, 2H), 8.03-7.99 (m, 2H), 7.87 (d, J=8.3 Hz, 2H), 7.52 (d, J=1.0 Hz, 1H), 7.47 (s, 1H), 3.98 (s, 3H), 3.14 (s, 3H), 2.81 (s, 3H).

Step B. Example 369

To a solution of Intermediate 369A (40 mg, 0.099 mmol), 4-(pyrrolidin-1-yl) piperidine (46 mg, 0.30 mmol), magnesium sulfate (240 mg, 2.0 mmol), and acetic acid (0.057 mL, 0.99 mmol) in DMF (1 mL) was added sodium triacetoxyborohydride (84 mg, 0.396 mmol) in one portion. The mixture was stirred at room temperature for 18 h. The heterogeneous mixture was diluted with ethyl acetate (5 mL) and filtered through Celite. The filtrate was concentrated under vacuum to dryness. The residue purified by preparative HPLC (Prep Method 4). The obtained residue was basified with 1 N NaOH solution, and extracted with dichloromethane (4×35 mL). The combined extract was dried over anhydrous $Na_2SO_4$. Removal of the solvent under vacuum provided the title compound (13 mg, 0.023 mmol, 24% yield) as a white solid. LCMS $(M+H)^+$=543.3. $^1$H NMR (500 MHz, chloroform-d) δ 8.15 (d, J=8.5 Hz, 2H), 8.07-8.02 (m, 2H), 7.65 (d, J=8.0 Hz, 2H), 7.47-7.41 (m, 4H), 3.95 (s, 3H), 3.60 (br s, 2H), 3.14 (s, 3H), 3.05 (br d, J=11.2 Hz, 2H), 2.79 (s, 3H), 2.18-1.54 (m, 15H). TLR9 $IC_{50}$=120 nM.

Example 370

1,4-dimethyl-6-(4-((6-methyl-2,6-diazaspiro[3.3]heptan-2-yl)methyl)phenyl)-2-(4-(methylsulfonyl)phenyl)-1H-benzo[d]imidazole (370)

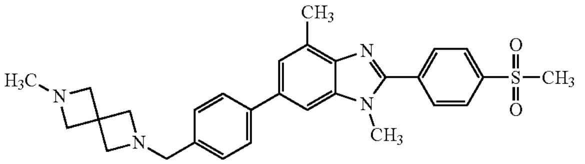

To a solution of Intermediate 369A (35 mg, 0.087 mmol), 2-methyl-2,6-diazaspiro[3.3]heptane dihydrochloride (56 mg, 0.30 mmol), triethylamine (84 μL, 0.61 mmol), magnesium sulfate (210 mg, 1.7 mmol), and acetic acid (59 μL, 1.0 mmol) in DMF (1 mL) was added sodium triacetoxyborohydride (83 mg, 0.389 mmol) in one portion. The mixture was stirred at room temperature for 24 h. The heterogeneous mixture was diluted with ethyl acetate (5 mL) and filtered through Celite. The filtrate was concentrated under vacuum to dryness. The crude residue was purified by preparative HPLC (Prep Method 4). The obtained residue was basified with 1.5 M $K_3PO_4$ solution, and extracted with dichloromethane (4×35 mL). The combined extract was dried over anhydrous $Na_2SO_4$. Removal of the solvent under vacuum provided the title compound (34 mg, 0.065 mmol, 75% yield) as a white solid. LCMS $(M+H)^+$=501.1. $^1H$ NMR (400 MHz, chloroform-d) δ 8.17-8.12 (m, 2H), 8.04 (d, J=8.6 Hz, 2H), 7.64 (d, J=8.2 Hz, 2H), 7.44 (s, 1H), 7.41 (d, J=1.4 Hz, 1H), 7.37 (d, J=8.2 Hz, 2H), 3.94 (s, 3H), 3.66 (s, 2H), 3.54 (br s, 4H), 3.43 (s, 4H), 3.13 (s, 3H), 2.78 (s, 3H), 2.43 (s, 3H). TLR9 $IC_{50}$=56 nM.

Example 371

6-(4-((6-isobutyl-2,6-diazaspiro[3.3]heptan-2-yl)methyl)phenyl)-1,4-dimethyl-2-(4-(methylsulfonyl)phenyl)-1H-benzo[d]imidazole (371)

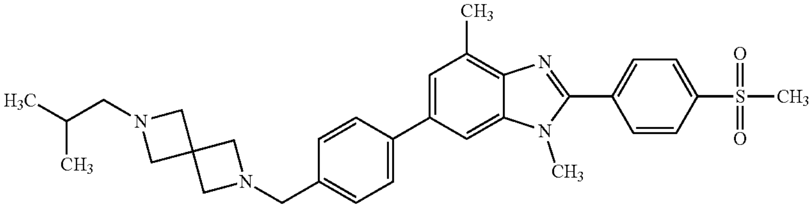

Step A. Intermediate 371A. Preparation of tert-butyl 6-(4-(1,4-dimethyl-2-(4-(methylsulfonyl)phenyl)-1H-benzo[d]imidazol-6-yl)benzyl)-2,6-diazaspiro[3.3]heptane-2-carboxylate (371A)

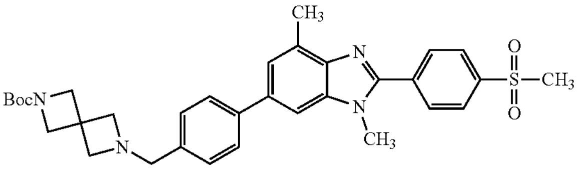

To a solution of Intermediate 369A (150 mg, 0.37 mmol), tert-butyl 2,6-diazaspiro[3.3]heptane-2-carboxylate, oxalic acid salt (370 mg, 1.3 mmol), triethylamine (0.26 mL, 1.9 mmol), magnesium sulfate (890 mg, 7.4 mmol), and acetic acid (59 μL, 1.0 mmol) in DMF (1 mL) was added sodium triacetoxyborohydride (310 mg, 1.5 mmol) in one portion. The mixture was stirred at room temperature for 22 h. The heterogeneous mixture was diluted with ethyl acetate (15 mL) and filtered through Celite. The filtrate was diluted with ethyl acetate (120 mL), washed with 1.5 M $K_3PO_4$ solution (2×15 mL), and dried over anhydrous $Na_2SO_4$. After the solvent was removed under vacuum, the residue was purified by flash column chromatography (40 g silica gel, 0-6% methanol/$CH_2Cl_2$) to provide the title intermediate (170 mg, 0.290 mmol, 78% yield) as a white solid. LCMS $(M+H)^+$=587.3. $^1H$ NMR (400 MHz, chloroform-d) δ 8.17-8.13 (m, 2H), 8.07-8.02 (m, 2H), 7.65 (d, J=8.2 Hz, 2H), 7.44 (s, 1H), 7.42 (s, 1H), 7.37 (d, J=8.2 Hz, 2H), 4.03 (s, 4H), 3.94 (s, 3H), 3.65 (s, 2H), 3.40 (s, 4H), 3.13 (s, 3H), 2.78 (s, 3H), 1.45 (s, 9H).

Step B. Intermediate 371B. Preparation of 6-(4-((2,6-diazaspiro[3.3]heptan-2-yl)methyl)phenyl)-1,4-dimethyl-2-(4-(methylsulfonyl)phenyl)-1H-benzo[d]imidazole (371B)

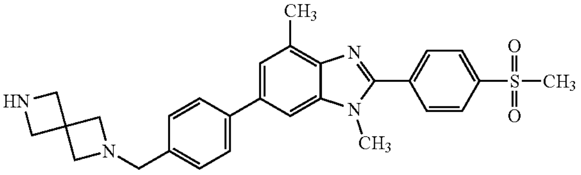

To a solution of Intermediate 371A (170 mg, 0.28 mmol) in dichloromethane (3 mL) at 0° C. was added TFA (3 mL, 38.9 mmol) over 1 min. The mixture was stirred at 0° C. for 1 h and then concentrated under vacuum to dryness. To the residue was added 1.5 M $K_3PO_4$ solution (10 mL) and the mixture was extracted with 5% MeOH/DCM (4×40 mL). The combined extract was dried over anhydrous $Na_2SO_4$. Removal of the solvent under vacuum provided the title intermediate (56 mg, 0.12 mmol, 41% yield) as a beige solid, which was used in the next step without further purification. LCMS $(M+H)^+$=487.2.

Step C. Example 371

To a solution of Intermediate 371B (26 mg, 0.053 mmol), isobutyraldehyde (15 mg, 0.21 mmol), magnesium sulfate (130 mg, 1.1 mmol), and acetic acid (0.031 mL, 0.53 mmol) in acetonitrile (2 mL) was added sodium triacetoxyborohydride (51 mg, 0.24 mmol) in one portion. The mixture was stirred at room temperature for 36 h. The heterogeneous mixture was diluted with ethyl acetate (5 mL) and filtered through Celite. The filtrate was concentrated under vacuum to dryness. The residue was purified by preparative HPLC (Prep Method 1). The obtained residue was basified with 1 N NaOH solution, and extracted with dichloromethane (4×35 mL). The combined extract was dried over anhydrous $Na_2SO_4$. Removal of the solvent under vacuum provided the title compound (15 mg, 0.028 mmol, 52% yield) as a white solid. LCMS $(M+H)^+$=543.2. $^1$H NMR (500 MHz, chloroform-d) δ 8.15 (d, J=8.5 Hz, 2H), 8.04 (d, J=8.3 Hz, 2H), 7.64 (d, J=8.0 Hz, 2H), 7.44 (s, 1H), 7.41 (s, 1H), 7.38 (d, J=8.0 Hz, 2H), 3.95 (s, 3H), 3.66 (s, 2H), 3.52-3.30 (m, 8H), 3.14 (s, 3H), 2.78 (s, 3H), 2.29 (br s, 2H), 1.76-1.58 (m, 1H), 0.91 (d, J=6.7 Hz, 6H). TLR9 $IC_{50}$=55 nM.

Example 372

1-cyclopropyl-4-methyl-2-(4-(methylsulfonyl)phenyl)-6-(4-((4-(pyrrolidin-1-yl)piperidin-1-yl)methyl)phenyl)-1H-benzo[d]imidazole (372)

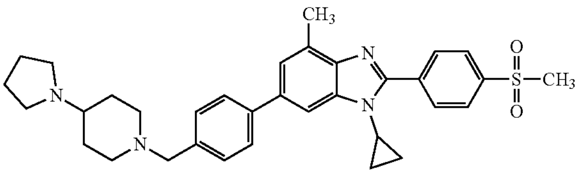

Step A. Intermediate 371A. Preparation of 5-bromo-N-cyclopropyl-3-methyl-2-nitroaniline (372A)

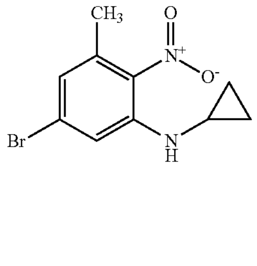

To a mixture of 5-bromo-1-fluoro-3-methyl-2-nitro-benzene (5.0 g, 21 mmol) and cyclopropanamine (1.2 g, 21 mmol) in DMSO (40 mL) was added N,N-diisopropylethylamine (5.7 mL, 65 mmol). The resulting mixture was stirred at 90° C. overnight. Upon cooling to room temperature, the mixture was diluted with ethyl acetate (300 mL), washed with water (3×100 mL), and dried over anhydrous $Na_2SO_4$. After the solvent was removed under vacuum, the residue was purified by flash column chromatography (1:3 ethyl acetate/petroleum ether as eluent). Fractions corresponding to product were combined concentrated and dried in vacuo to afford the title intermediate (5.5 g, 95% yield) as a yellow solid. LCMS $(M+H)^+$=271.1.

Step B. Intermediate 371B. Preparation of 5-bromo-N1-cyclopropyl-3-methyl-benzene-1,2-diamine (372B)

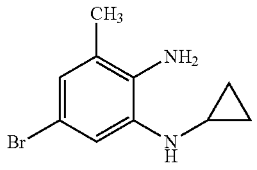

A solution of Intermediate 372A (5.0 g, 18 mmol) in ethanol (30 mL) and water (8 mL) was degassed three times with nitrogen before iron powder (11 g, 190 mmol) was added. The reaction vessel was evacuated and back-filled with nitrogen three times. The mixture was stirred at 70° C. overnight. Upon cooling to room temperature, the insoluble material was removed by filtration. The filtrate was concentrated under vacuum to afford the title intermediate (4.2 g crude) as a light yellow solid. LCMS $(M+H)^+$=242.1.

Step C. Intermediate 371C. Preparation of 6-bromo-1-cyclopropyl-4-methyl-2-(4-methylsulfonylphenyl)benzimidazole (372C)

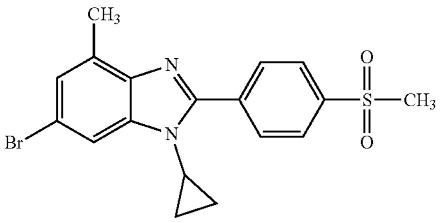

To a mixture of Intermediate 372B (4.2 g, 17 mmol) and 4-methylsulfonylbenzaldehyde (3.3 g, 17.91 mmol) in DMF (30 mL) and water (1 mL) was added Oxone (11 g, 18 mmol). The mixture was stirred at 90° C. overnight. Upon cooling to room temperature, the reaction mixture was diluted with ethyl acetate (300 mL), washed with water (3×100 mL), and dried over anhydrous $Na_2SO_4$. After the solvent was removed under vacuum, the residue was purified with flash column chromatography to afford the title intermediate (2.6 g, 36% yield) as a gray solid. LCMS $(M+H)^+$=405.1. $^1$H NMR (400 MHz, chloroform-d) δ 10.90

(s, 1H), 8.16-8.10 (m, 4H), 7.69 (d, J=1.8 Hz, 1H), 7.36 (s, 1H), 3.63-3.58 (m, 1H), 3.13 (s, 3H), 2.65 (s, 3H), 1.24-1.19 (m, 2H), 0.79-0.75 (m, 2H).

Step D. Intermediate 371D. Preparation of 4-(1-cyclopropyl-4-methyl-2-(4-(methylsulfonyl)phenyl)-1H-benzo[d]imidazol-6-yl)benzaldehyde (372D)

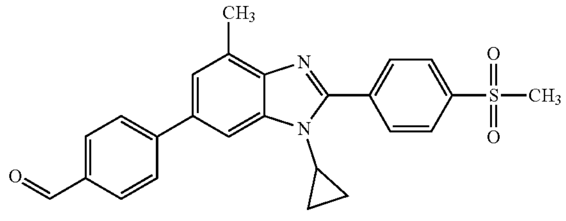

A mixture of Intermediate 372C (300 mg, 0.74 mmol), 4-(4,4,5,5-tetramethyl-1,3,2-dioxaborolan-2-yl)benzaldehyde (220 mg, 0.95 mmol), XPhos Pd G3 (63 mg, 0.074 mmol), and potassium phosphate tribasic (1.3 mL, 2.6 mmol) in 1,4-dioxane (14 mL) was degassed and heated in a closed vial at 95° C. for 8 h. Upon cooling to room temperature, the mixture was diluted with ethyl acetate (120 mL), washed with brine (20 mL), and dried over anhydrous $MgSO_4$ and concentrated. The crude product was purified by flash column chromatography (80 g silica gel, solid loading, 35-90% ethyl acetate/hexane). Fractions corresponding to product were combined, concentrated and dried in vacuo to afford the title intermediate (110 mg, 0.26 mmol, 35% yield) as a yellow solid. LCMS $(M+H)^+$=431.0.

Step E. Example 372

To a solution of Intermediate 372D (30 mg, 0.070 mmol), 4-(pyrrolidin-1-yl) piperidine (38 mg, 0.24 mmol), magnesium sulfate (170 mg, 1.4 mmol), and acetic acid (59 μL, 1.0 mmol) in DMF (1 mL) was added sodium triacetoxyborohydride (67 mg, 0.31 mmol) in one portion. The mixture was stirred at room temperature for 24 h. The heterogeneous mixture was diluted with ethyl acetate (5 mL) and filtered through Celite. The filtrate was concentrated under vacuum to dryness. The residue was purified by preparative HPLC (Prep Method 4). The obtained residue was basified with 1.5 M $K_3PO_4$ solution, and extracted with dichloromethane (4×35 mL). The combined extract was dried over anhydrous $Na_2SO_4$. Removal of the solvent under vacuum provided the title compound (12 mg, 0.019 mmol, 27% yield) as a white solid. LCMS $(M+H)^+$=569.1. $^1$H NMR (400 MHz, chloroform-d) δ 8.26-8.19 (m, 2H), 8.14-8.09 (m, 2H), 7.68-7.63 (m, 3H), 7.44 (br d, J=7.8 Hz, 2H), 7.40 (s, 1H), 3.67-3.57 (m, 3H), 3.14 (s, 3H), 3.09-2.93 (m, 4H), 2.77 (s, 3H), 2.18-1.77 (m, 13H), 1.22-1.16 (m, 2H), 0.89-0.74 (m, 2H). TLR9 $IC_{50}$=54 nM.

The following Examples were prepared according to the general methods described elsewhere herein using appropriate starting materials, reagents and conditions.

| Ex. No. | Structure | Method |
| --- | --- | --- |
| 374 | 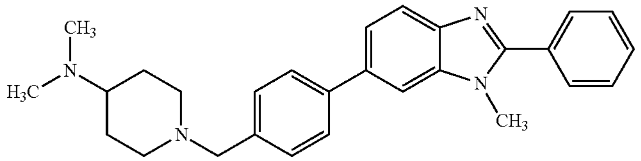 [SMILES: CN(C)C1CCN(Cc2ccc(-c3ccc4nc(-c5ccccc5)n(C)c4c3)cc2)CC1] | Ex. 373 |
| 375 | 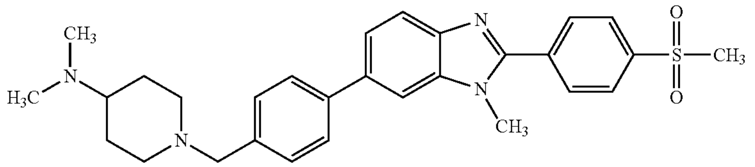 | Ex. 373 |
| 376 | 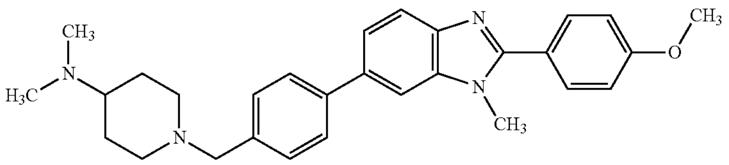 | Ex. 373 |

-continued
| Ex. No. | Structure | Method |
|---|---|---|
| 377 | 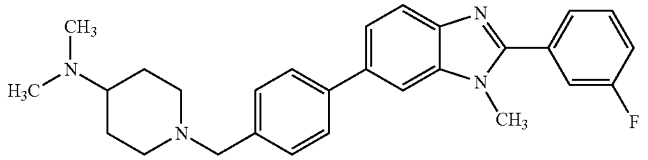 [SMILES: CN(C)C1CCN(Cc2ccc(-c3ccc4nc(-c5cccc(F)c5)n(C)c4c3)cc2)CC1] | Ex. 373 |
| 378 | 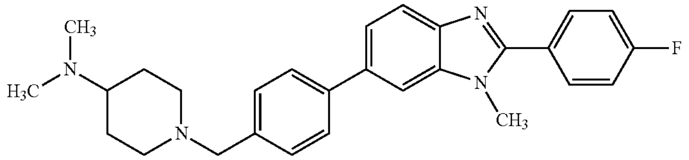 [SMILES: CN(C)C1CCN(Cc2ccc(-c3ccc4nc(-c5ccc(F)cc5)n(C)c4c3)cc2)CC1] | Ex. 373 |
| 379 | 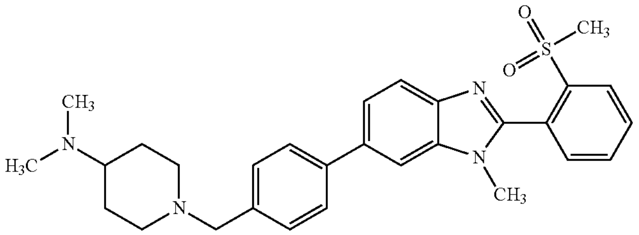 [SMILES: CN(C)C1CCN(Cc2ccc(-c3ccc4nc(-c5ccccc5S(C)(=O)=O)n(C)c4c3)cc2)CC1] | Ex. 373 |
| 380 | 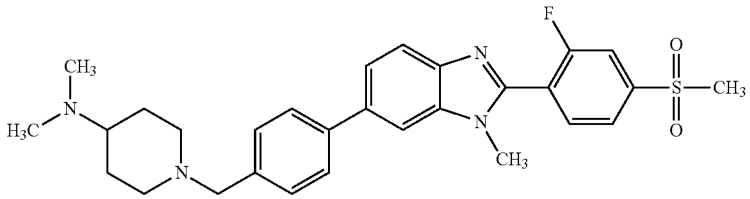 | Ex. 373 |
| 381 | 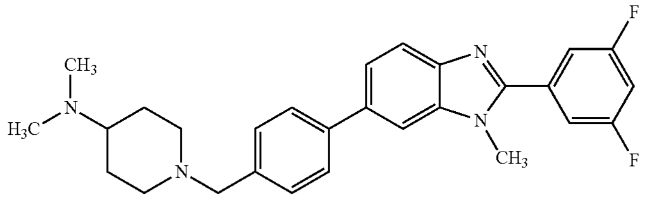 [SMILES: CN(C)C1CCN(Cc2ccc(-c3ccc4nc(-c5cc(F)cc(F)c5)n(C)c4c3)cc2)CC1] | Ex. 373 |
| 382 | 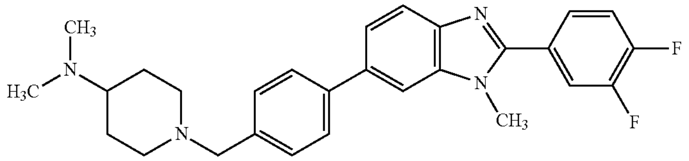 [SMILES: CN(C)C1CCN(Cc2ccc(-c3ccc4nc(-c5ccc(F)c(F)c5)n(C)c4c3)cc2)CC1] | Ex. 373 |
| 383 | 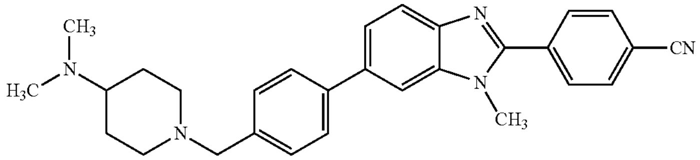 [SMILES: CN(C)C1CCN(Cc2ccc(-c3ccc4nc(-c5ccc(C#N)cc5)n(C)c4c3)cc2)CC1] | Ex. 373 |

-continued
| Ex. No. | Structure | Method |
|---|---|---|
| 384 | 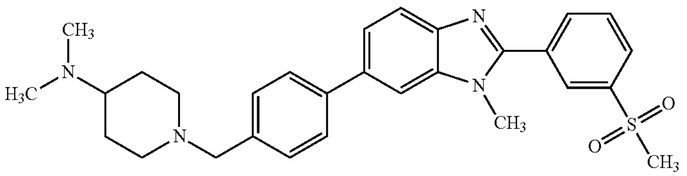 [SMILES: CN(C)C1CCN(Cc2ccc(-c3ccc4nc(-c5cccc(S(C)(=O)=O)c5)n(C)c4c3)cc2)CC1] | Ex. 373 |
| 385 | 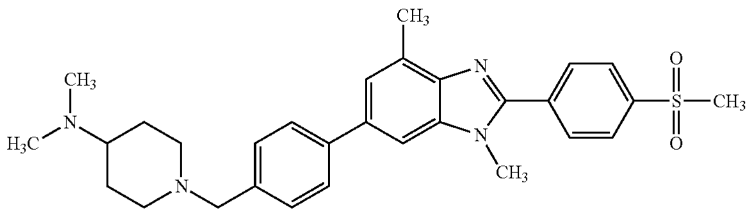 | Ex. 369 |
| 386 | 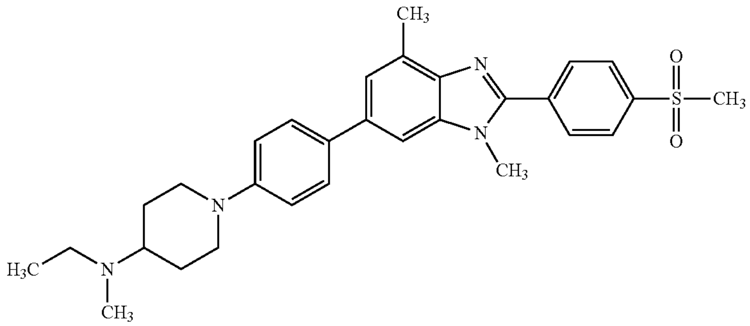 [SMILES: CCN(C)C1CCN(c2ccc(-c3cc(C)c4nc(-c5ccc(S(C)(=O)=O)cc5)n(C)c4c3)cc2)CC1] | Ex. 368 |
| 387 | 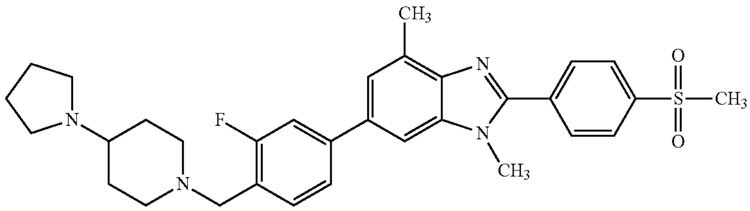 [SMILES: Cc1cc(-c2ccc(CN3CCC(N4CCCC4)CC3)c(F)c2)cc2c1nc(-c1ccc(S(C)(=O)=O)cc1)n2C] | Ex. 369 |
| 388 | 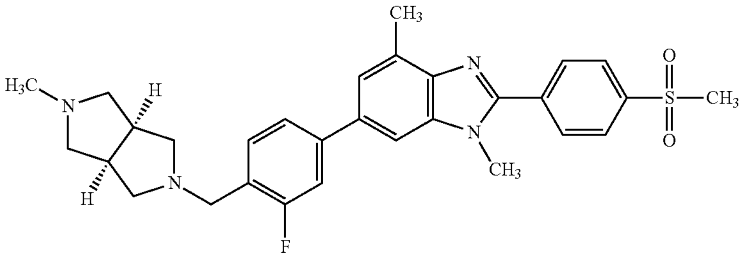 | Ex. 369 |
| 389 | 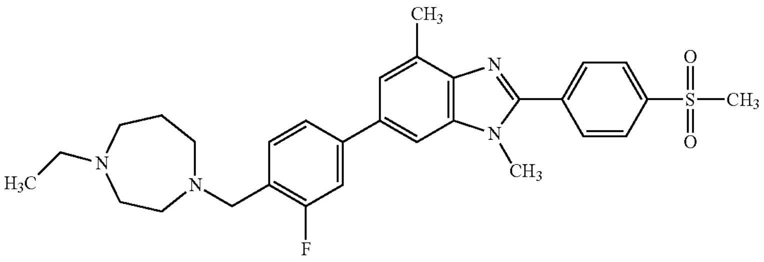 [SMILES: CCN1CCCN(Cc2ccc(-c3cc(C)c4nc(-c5ccc(S(C)(=O)=O)cc5)n(C)c4c3)cc2F)CC1] | Ex. 369 |

-continued
| Ex. No. | Structure | Method |
| --- | --- | --- |
| 390 | 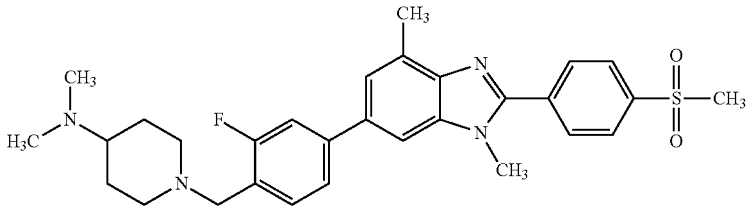 | Ex. 369 |
| 391 | 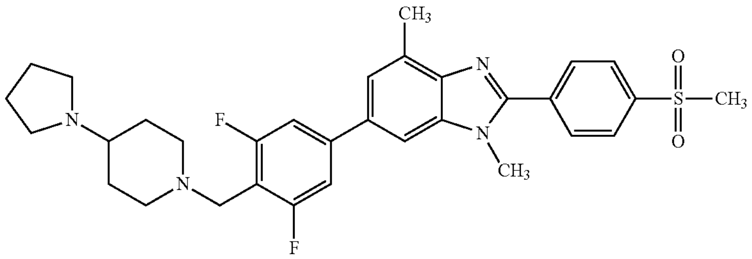 [SMILES: Cc1cc(-c2cc(F)c(CN3CCC(N4CCCC4)CC3)c(F)c2)cc2c1nc(-c1ccc(S(C)(=O)=O)cc1)n2C] | Ex. 369 |
| 392 | 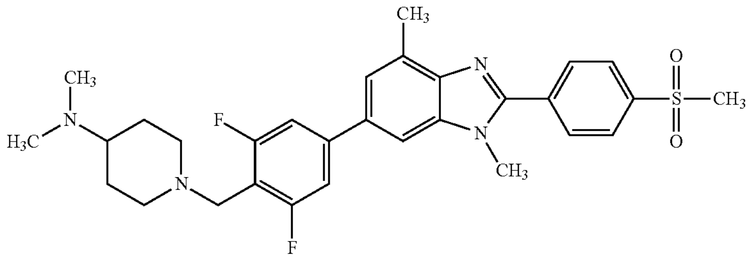 | Ex. 369 |
| 393 | 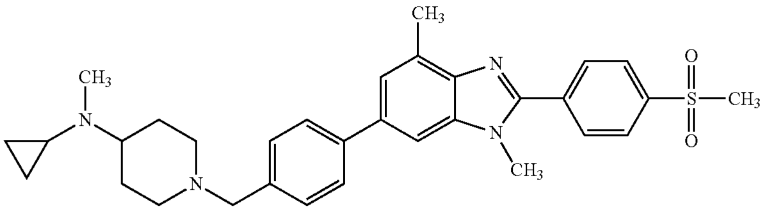 [SMILES: Cc1cc(-c2ccc(CN3CCC(N(C)C4CC4)CC3)cc2)cc2c1nc(-c1ccc(S(C)(=O)=O)cc1)n2C] | Ex. 369 |
| 394 | 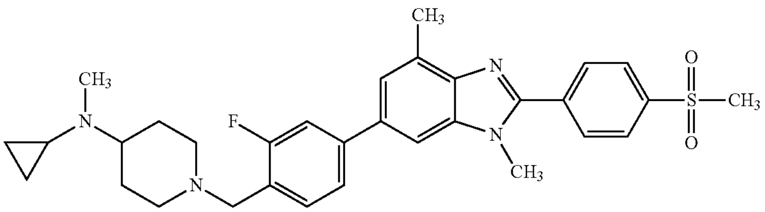 [SMILES: Cc1cc(-c2ccc(CN3CCC(N(C)C4CC4)CC3)c(F)c2)cc2c1nc(-c1ccc(S(C)(=O)=O)cc1)n2C] | Ex. 369 |
| 395 | 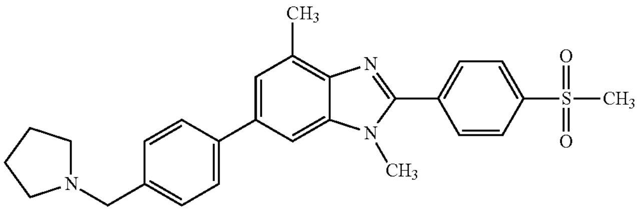 [SMILES: Cc1cc(-c2ccc(CN3CCCC3)cc2)cc2c1nc(-c1ccc(S(C)(=O)=O)cc1)n2C] | Ex. 369 |

-continued
| Ex. No. | Structure | Method |
|---|---|---|
| 396 | 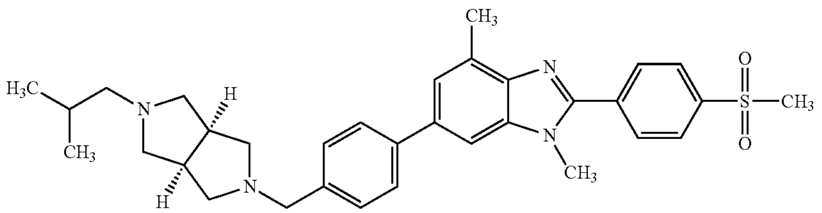 [SMILES: Cc1cc(-c2ccc(CN3C[C@@H]4CN(CC(C)C)C[C@@H]4C3)cc2)cc2c1nc(-c1ccc(S(C)(=O)=O)cc1)n2C] | Ex. 369 |
| 397 | 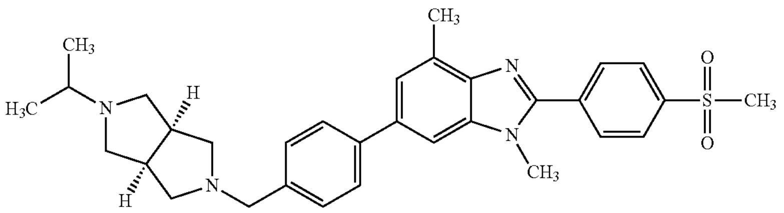 [SMILES: Cc1cc(-c2ccc(CN3C[C@@H]4CN(C(C)C)C[C@@H]4C3)cc2)cc2c1nc(-c1ccc(S(C)(=O)=O)cc1)n2C] | Ex. 369 |
| 398 | 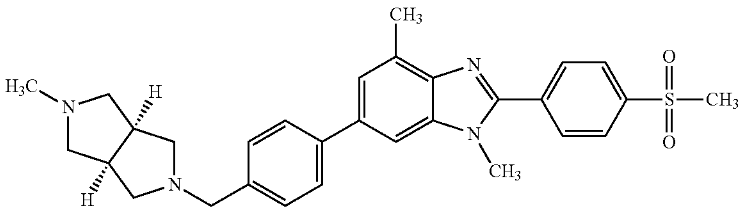 | Ex. 369 |
| 399 | 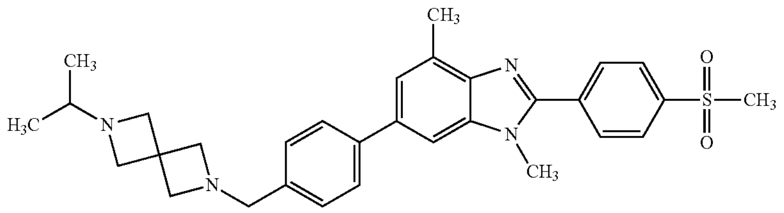 [SMILES: Cc1cc(-c2ccc(CN3CC4(C3)CN(C(C)C)C4)cc2)cc2c1nc(-c1ccc(S(C)(=O)=O)cc1)n2C] | Ex. 369 |
| 400 | 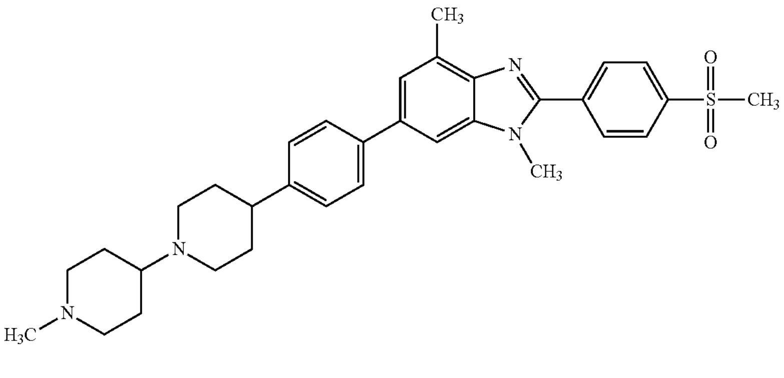 | Ex. 363 |

-continued
| Ex. No. | Structure | Method |
|---|---|---|
| 401 | 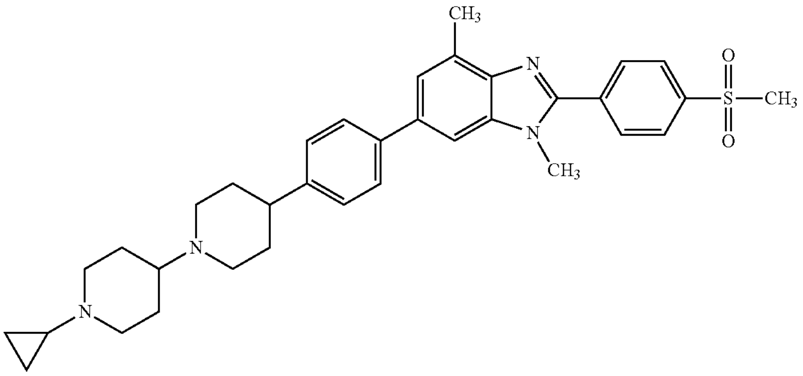 [SMILES: Cc1cc(-c2ccc(C3CCN(C4CCN(C5CC5)CC4)CC3)cc2)cc2c1nc(-c1ccc(S(C)(=O)=O)cc1)n2C] | Ex. 363 |
| 402 | 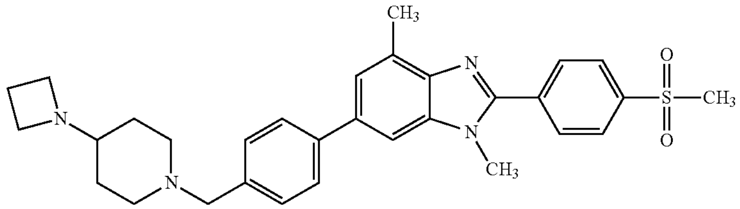 [SMILES: Cc1cc(-c2ccc(CN3CCC(N4CCC4)CC3)cc2)cc2c1nc(-c1ccc(S(C)(=O)=O)cc1)n2C] | Ex. 369 |
| 403 | 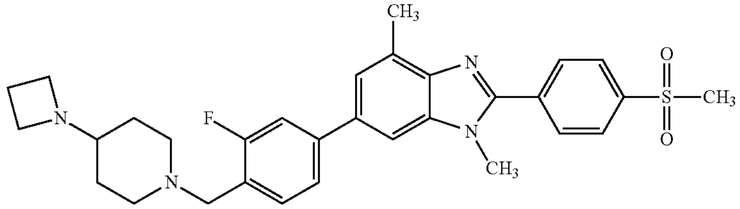 [SMILES: Cc1cc(-c2ccc(CN3CCC(N4CCC4)CC3)c(F)c2)cc2c1nc(-c1ccc(S(C)(=O)=O)cc1)n2C] | Ex. 369 |
| 404 | 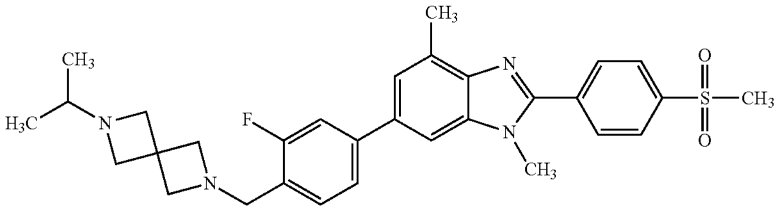 [SMILES: Cc1cc(-c2ccc(CN3CC4(C3)CN(C(C)C)C4)c(F)c2)cc2c1nc(-c1ccc(S(C)(=O)=O)cc1)n2C] | Ex. 369 |
| 405 | 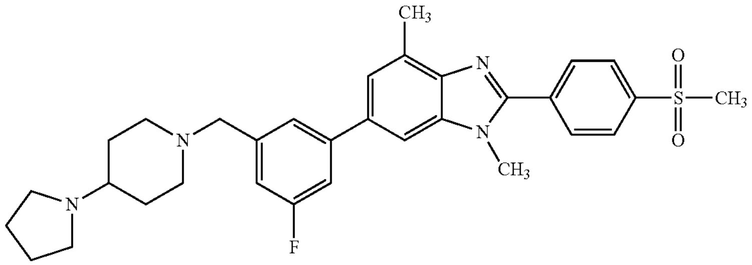 [SMILES: Cc1cc(-c2cc(F)cc(CN3CCC(N4CCCC4)CC3)c2)cc2c1nc(-c1ccc(S(C)(=O)=O)cc1)n2C] | Ex. 369 |

-continued
| Ex. No. | Structure | Method |
| --- | --- | --- |
| 406 | 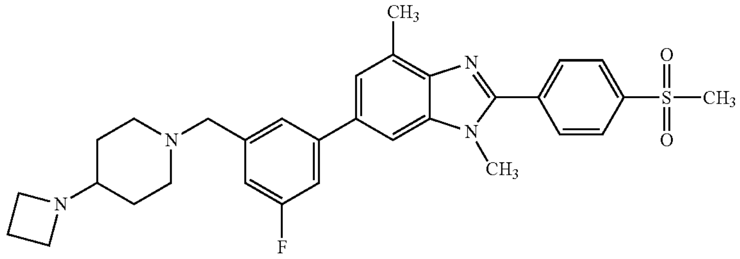 [SMILES: Cc1cc(-c2cc(F)cc(CN3CCC(N4CCC4)CC3)c2)cc2c1nc(-c1ccc(S(C)(=O)=O)cc1)n2C] | Ex. 369 |
| 407 | 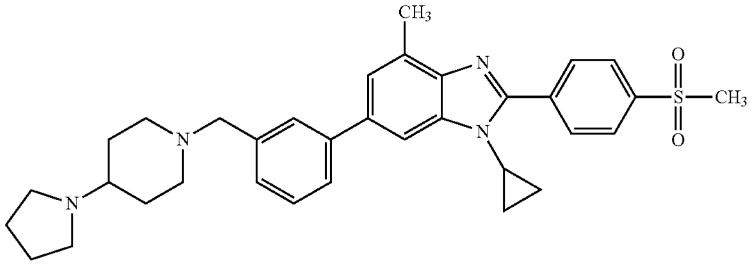 [SMILES: Cc1cc(-c2cccc(CN3CCC(N4CCCC4)CC3)c2)cc2c1nc(-c1ccc(S(C)(=O)=O)cc1)n2C1CC1] | Ex. 372 |
| 408 | 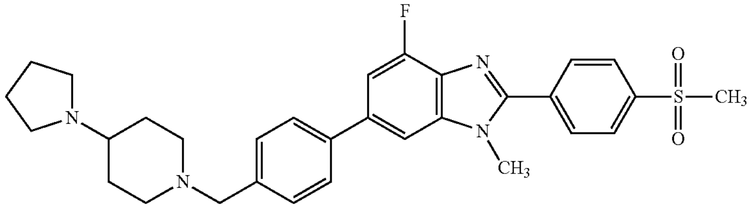 [SMILES: Cn1c(-c2ccc(S(C)(=O)=O)cc2)nc2c(F)cc(-c3ccc(CN4CCC(N5CCCC5)CC4)cc3)cc21] | Ex. 372 |
| 409 | 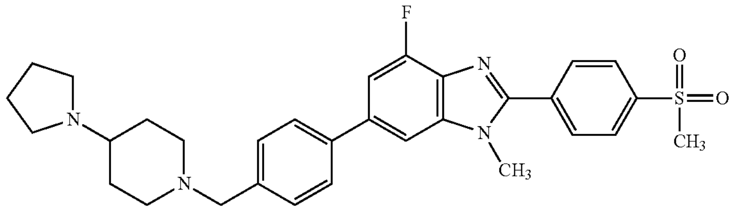 [SMILES: Cn1c(-c2ccc(S(C)(=O)=O)cc2)nc2c(F)cc(-c3ccc(CN4CCC(N5CCCC5)CC4)cc3)cc21] | Ex. 369 |
| 410 | 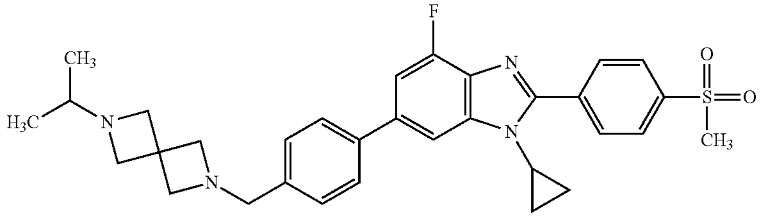 [SMILES: CC(C)N1CC2(CN(Cc3ccc(-c4cc(F)c5nc(-c6ccc(S(C)(=O)=O)cc6)n(C6CC6)c5c4)cc3)C2)C1] | Ex. 372 |
| 411 | 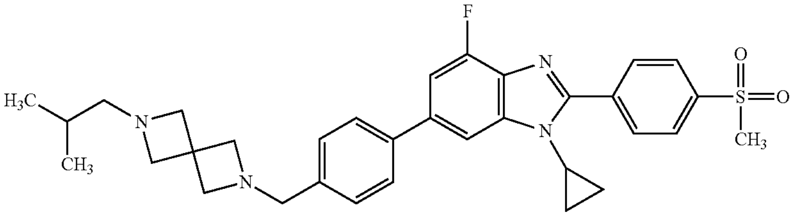 [SMILES: CC(C)CN1CC2(CN(Cc3ccc(-c4cc(F)c5nc(-c6ccc(S(C)(=O)=O)cc6)n(C6CC6)c5c4)cc3)C2)C1] | Ex. 372 |

-continued

| Ex. No. | Structure | Method |
|---|---|---|
| 412 | 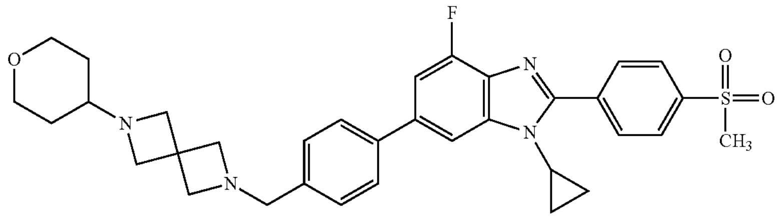 [SMILES: CS(=O)(=O)c1ccc(-c2nc3c(F)cc(-c4ccc(CN5CC6(C5)CN(C5CCOCC5)C6)cc4)cc3n2C2CC2)cc1] | Ex. 372 |
| 413 | 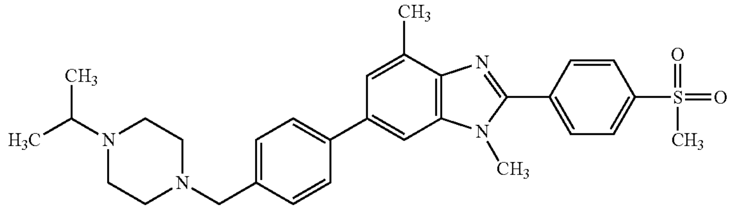 [SMILES: Cc1cc(-c2ccc(CN3CCN(C(C)C)CC3)cc2)cc2c1nc(-c1ccc(S(C)(=O)=O)cc1)n2C] | Ex. 369 |
| 414 | 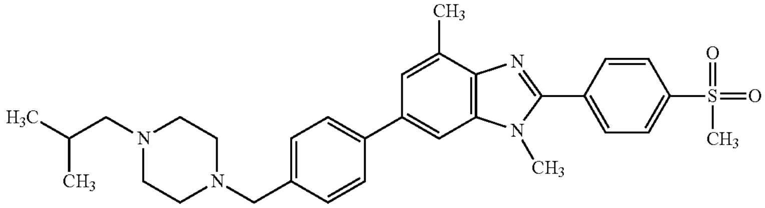 [SMILES: Cc1cc(-c2ccc(CN3CCN(CC(C)C)CC3)cc2)cc2c1nc(-c1ccc(S(C)(=O)=O)cc1)n2C] | Ex. 369 |
| 415 | 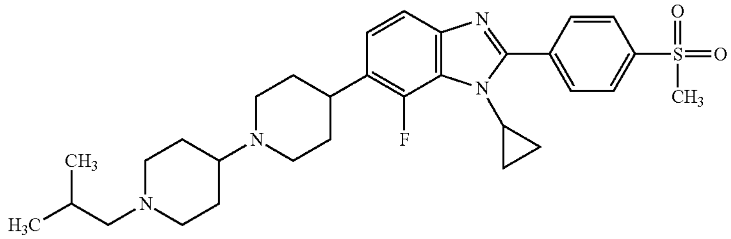 [SMILES: CC(C)CN1CCC(N2CCC(c3ccc4nc(-c5ccc(S(C)(=O)=O)cc5)n(C5CC5)c4c3F)CC2)CC1] | Ex. 115 |

| Ex. No. | Analytical LC/MS, Preparative HPLC method, yield, and $^1$H NMR |
|---|---|
| 374 | Analytical LC/MS (Method 1): Purity: 98.6%; Observed Mass: 425.20; Retention Time: 1.5 min. (Method 2): Purity: 100%; Observed Mass: 425.20; Retention Time: 0.99 min. Prep Method 1: 23.9 mg, 27% yield; $^1$H NMR (500 MHz, DMSO-$d_6$) δ 8.13 (s, 1H), 7.95-7.90 (m, 4H), 7.85 (d, J = 8.5 Hz, 1H), 7.76 (br d, J = 7.9 Hz, 1H), 7.68-7.62 (m, 5H), 4.39 (br s, 2H), 4.01 (s, 3H), 3.08-2.98 (m, 2H), 2.77 (br s, 6H), 2.54-2.53 (m, 3H), 2.30-2.19 (m, 2H), 1.94-1.83 (m, 2H). TLR9 $IC_{50}$ (nM) = 280 |
| 375 | Analytical LC/MS (Method 1): Purity: 100%; Observed Mass: 503.50; Retention Time: 1.06 min. (Method 2): Purity: 100%; Observed Mass: 503.50; Retention Time: 0.74 min. Prep Method 1: 29.5 mg, 39% yield; $^1$H NMR (500 MHZ, DMSO-$d_6$) δ 8.20-8.15 (m, 2H), 8.14-8.08 (m, 2H), 7.94 (s, 1H), 7.78 (d, J = 8.2 Hz, 1H), 7.73 (br d, J = 7.9 Hz, 2H), 7.60 (br d, J = 8.5 Hz, 1H), 7.39 (br d, J = 7.6 Hz, 2H), 3.98 (s, 3H), 3.30 (s, 2H), 2.85 (br d, J = 11.0 Hz, 2H), 2.16 (s, 6H), 2.10-2.01 (m, 1H), 1.93 (br t, J = 11.7 Hz, 2H), 1.87 (s, 3H), 1.71 (br d, J = 11.6 Hz, 2H), 1.38 (q, J = 10.9 Hz, 2H). TLR9 $IC_{50}$ (nM) = 200 |
| 376 | Analytical LC/MS (Method 1): Purity: 98%; Observed Mass: 455.20; Retention Time: 1.52 min. (Method 2): Purity: 98%; Observed Mass: 455.30; Retention Time: 0.97 min. Prep Method 1: 55.1 mg, 70% yield; $^1$H NMR (500 MHz, DMSO-$d_6$) δ 7.84 (s, 1H), 7.80 (d, J = 8.5 Hz, 2H), 7.70 (dd, J = 7.9, 4.3 Hz, 3H), 7.57-7.51 (m, 1H), 7.38 (br d, J = 7.9 Hz, 2H), 7.13 (d, J = 8.5 Hz, 2H), 3.90 (s, 3H), 3.84 (s, 3H), 3.68-3.56 (m, 2H), 2.86 (br d, J = 10.4 Hz, 2H), 2.20 (s, 6H), 2.16-2.10 (m, 1H), 1.93 (br t, J = 11.3 Hz, 2H), 1.73 (br d, J = 11.6 Hz, 2H), 1.46-1.32 (m, 2H). TLR9 $IC_{50}$ (nM) = 210 |

-continued

| Ex. No. | Analytical LC/MS, Preparative HPLC method, yield, and $^1$H NMR |
|---|---|
| 377 | Analytical LC/MS (Method 1): Purity: 95.3%; Observed Mass: 443.40; Retention Time: 1.30 min. (Method 2): Purity: 95.5%; Observed Mass: 443.50; Retention Time: 0.82 min. Prep Method 1: 34.4 mg, 43% yield; $^1$H NMR (500 MHZ, DMSO-$d_6$) δ 7.90 (s, 1H), 7.76-7.69 (m, 4H), 7.68-7.61 (m, 1H), 7.58 (d, J = 9.2 Hz, 1H), 7.44-7.36 (m, 3H), 3.94 (s, 3H), 3.50-3.46 (m, 3H), 2.86 (br d, J = 11.6 Hz, 2H), 2.20 (s, 6H), 2.17-2.09 (m, 1H), 1.93 (br t, J = 11.4 Hz, 2H), 1.73 (br d, J = 12.5 Hz, 2H), 1.44-1.35 (m, 2H). TLR9 $IC_{50}$ (nM) = 350 |
| 378 | Analytical LC/MS (Method 1): Purity: 100%; Observed Mass: 443.20; Retention Time: 1.54 min. (Method 2): Purity: 100%; Observed Mass: 443.30; Retention Time: 0.96 min. Prep Method 1: 40.1 mg, 54% yield; $^1$H NMR (500 MHZ, DMSO-$d_6$) δ 7.93 (dd, J = 8.5, 5.5 Hz, 2H), 7.89 (s, 1H), 7.76-7.68 (m, 3H), 7.56 (br d, J = 7.9 Hz, 1H), 7.46-7.36 (m, 4H), 3.93 (s, 3H), 3.47 (br s, 2H), 2.85 (br d, J = 10.4 Hz, 2H), 2.15 (s, 6H), 2.07-2.00 (m, 1H), 1.93 (br t, J = 11.1 Hz, 2H), 1.71 (br d, J = 12.2 Hz, 2H), 1.43-1.31 (m, 2H). TLR9 $IC_{50}$ (nM) = 350 |
| 379 | Analytical LC/MS (Method 1): Purity: 100%; Observed Mass: 503.20; Retention Time: 1.01 min. (Method 2): Purity: 99.2%; Observed Mass: 503.20; Retention Time: 1.32 min. Prep Method 2: 34.3 mg, 33% yield; $^1$H NMR (500 MHz, DMSO-$d_6$) δ 8.18 (d, J = 6.7 Hz, 1H), 8.00 (s, 1H), 7.96-7.87 (m, 3H), 7.78 (d, J = 8.2 Hz, 2H), 7.66-7.57 (m, 3H), 4.37 (br s, 2H), 3.62 (s, 3H), 3.57-3.49 (m, 4H), 3.41 (br s, 3H), 3.11-2.96 (m, 2H), 2.77 (br s, 6H), 2.24 (br d, J = 9.2 Hz, 2H), 1.98-1.81 (m, 2H). TLR9 $IC_{50}$ (nM) = 98 |
| 380 | Analytical LC/MS (Method 1): Purity: 97.5%; Observed Mass: 521.20; Retention Time: 1.11 min. (Method 2): Purity: 98.3%; Observed Mass: 521.30; Retention Time: 1.34 min. Prep Method 2: 20.2 mg, 26% yield; $^1$H NMR (500 MHZ, DMSO-$d_6$) δ 8.08-7.97 (m, 6H), 7.90 (br d, J = 7.9 Hz, 2H), 7.83 (d, J = 8.5 Hz, 1H), 7.67 (br d, J = 8.5 Hz, 1H), 7.61 (br d, J = 7.9 Hz, 2H), 4.33 (br s, 2H), 3.82 (s, 3H), 3.61-3.51 (m, 1H), 3.37 (s, 3H), 3.05-2.93 (m, 1H), 2.76 (s, 7H), 2.22 (br d, J = 12.2 Hz, 2H), 1.98-1.81 (m, 2H). TLR9 $IC_{50}$ (nM) = 174 |
| 381 | Analytical LC/MS (Method 1): Purity: 96%; Observed Mass: 461.20; Retention Time: 1.06 min. (Method 2): Purity: 97.5%; Observed Mass: 461.30; Retention Time: 1.69 min. Prep Method 1: 12.6 mg, 11% yield; $^1$H NMR (500 MHz, DMSO-$d_6$) δ 7.94 (s, 1H), 7.76 (d, J = 8.5 Hz, 1H), 7.73 (br d, J = 7.9 Hz, 2H), 7.64-7.56 (m, 3H), 7.48 (br t, J = 9.2 Hz, 1H), 7.39 (br d, J = 8.2 Hz, 2H), 3.98 (s, 3H), 3.65-3.01 (m, 2H), 2.85 (br d, J = 11.3 Hz, 2H), 2.15 (s, 6H), 2.07-2.01 (m, 1H), 1.93 (br t, J = 11.4 Hz, 2H), 1.76-1.62 (m, 2H), 1.45-1.32 (m, 2H). TLR9 $IC_{50}$ (nM) = 140 |
| 382 | Analytical LC/MS (Method 1): Purity: 100%; Observed Mass: 461.20; Retention Time: 1.06 min. (Method 2): Purity: 100%; Observed Mass: 461.20; Retention Time: 1.54 min. Prep Method 2: 10.4 mg, 10% yield; $^1$H NMR (500 MHZ, DMSO-$d_6$) δ 8.01-7.93 (m, 2H), 7.90 (br d, J = 7.9 Hz, 2H), 7.80-7.73 (m, 2H), 7.70-7.63 (m, 2H), 7.61 (br d, J = 7.9 Hz, 2H), 4.35 (br s, 2H), 3.96 (s, 3H), 3.83-2.83 (m, 5H), 2.77 (s, 6H), 2.23 (br d, J = 12.2 Hz, 2H), 1.94-1.81 (m, 2H). TLR9 $IC_{50}$ (nM) = 3.2 |
| 383 | Analytical LC/MS (Method 1): Purity: 95.3%; Observed Mass: 450.20; Retention Time: 0.98 min. (Method 2): Purity: 98.7%; Observed Mass: 450.30; Retention Time: 1.48 min. Prep Method 1: 6.4 mg, 6% yield; $^1$H NMR (500 MHz, DMSO-$d_6$) δ 8.12-8.06 (m, 4H), 8.04 (s, 1H), 7.92 (br d, J = 8.2 Hz, 2H), 7.83 (d, J = 8.2 Hz, 1H), 7.68 (br d, J = 8.9 Hz, 1H), 7.62 (br d, J = 7.9 Hz, 2H), 4.38 (br s, 2H), 4.00 (s, 3H), 3.33-2.97 (m, 5H), 2.77 (br s, 6H), 2.23 (br d, J = 9.5 Hz, 2H), 1.96-1.82 (m, 2H). TLR9 $IC_{50}$ (nM) = 68 |
| 384 | Analytical LC/MS (Method 1): Purity: 100%; Observed Mass: 503.20; Retention Time: 0.87 min. (Method 2): Purity: 100%; Observed Mass: 503.30; Retention Time: 1.31 min. Prep Method 1: 15.4 mg, 12% yield; $^1$H NMR (500 MHz, DMSO-$d_6$) δ 8.42 (s, 1H), 8.27 (br d, J = 7.6 Hz, 1H), 8.13 (br d, J = 7.9 Hz, 1H), 8.03 (s, 1H), 7.92-7.87 (m, 3H), 7.81 (d, J = 8.5 Hz, 1H), 7.66 (br d, J = 8.5 Hz, 1H), 7.60 (br d, J = 5.2 Hz, 2H), 4.49-4.20 (m, 2H), 4.02 (s, 3H), 3.58-3.44 (m, 2H), 3.34-3.32 (m, 4H), 3.08-2.85 (m, 2H), 2.76 (br s, 6H), 2.27-2.13 (m, 2H), 1.95-1.77 (m, 2H). TLR9 $IC_{50}$ (nM) = 41 |
| 385 | LCMS $(M + H)^+$ = 517.3. $^1$H NMR (500 MHz, chloroform-d) δ 8.17-8.12 (m, 2H), 8.06-8.03 (m, 2H), 7.66 (d, J = 8.2 Hz, 2H), 7.47-7.40 (m, 4H), 3.95 (s, 3H), 3.61 (br s, 2H), 3.14 (s, 3H), 3.07 (br d, J = 11.5 Hz, 2H), 2.79 (s, 3H), 2.66-2.43 (m, 7H), 2.09 (br s, 2H), 1.95 (br d, J = 11.1 Hz, 2H), 1.75-1.70 (m, 2H). TLR9 $IC_{50}$ (nM) = 180 |
| 386 | LCMS $(M + H)^+$ = 517.3. $^1$H NMR (400 MHZ, chloroform-d) δ 8.17-8.10 (m, 2H), 8.07-8.00 (m, 2H), 7.62 (d, J = 8.8 Hz, 2H), 7.40 (s, 1H), 7.39 (d, J = 0.8 Hz, 1H), 7.05 (d, J = 8.8 Hz, 2H), 3.93 (s, 3H), 3.92-3.86 (m, 2H), 3.13 (s, 3H), 3.08-2.95 (m, 2H), 2.86 (td, J = 12.3, 1.9 Hz, 2H), 2.77 (s, 3H), 2.70-2.58 (m, 1H), 2.64 (s, 3H), 2.14 (br d, J = 9.4 Hz, 2H), 1.91 (qd, J = 11.9, 3.0 Hz, 2H), 1.36 (br t, J = 6.7 Hz, 3H). TLR9 $IC_{50}$ (nM) = 270 |

-continued

| Ex. No. | Analytical LC/MS, Preparative HPLC method, yield, and $^1$H NMR |
|---|---|
| 387 | LCMS $(M + H)^+$ = 561.3. $^1$H NMR (500 MHz, chloroform-d) δ 8.18-8.13 (m, 2H), 8.07-8.02 (m, 2H), 7.53-7.48 (m, 1H), 7.47-7.44 (m, 2H), 7.42-7.39 (m, 1H), 7.37 (dd, J = 11.1, 1.7 Hz, 1H), 3.95 (s, 3H), 3.66 (s, 2H), 3.14 (s, 3H), 3.01 (br d, J = 11.8 Hz, 2H), 2.91-2.66 (m, 4H), 2.79 (s, 3H), 2.41-2.20 (m, 1H), 2.14 (br t, J = 11.4 Hz, 2H), 2.02-1.86 (m, 6H), 1.76 (br d, J = 9.6 Hz, 2H). TLR9 $IC_{50}$ (nM) = 56 |
| 388 | LCMS $(M + H)^+$ = 533.3. $^1$H NMR (500 MHz, chloroform-d) δ 8.18-8.12 (m, 2H), 8.07-8.02 (m, 2H), 7.51-7.43 (m, 3H), 7.40 (s, 1H), 7.37 (dd, J = 11.1, 1.4 Hz, 1H), 3.95 (s, 3H), 3.77 (s, 2H), 3.14 (s, 3H), 2.89 (br s, 4H), 2.79 (s, 3H), 2.72 (br s, 2H), 2.53 (br d, J = 7.6 Hz, 4H), 2.50 (br s, 3H). TLR9 $IC_{50}$ (nM) = 230 |
| 389 | LCMS $(M + H)^+$ = 535.3. $^1$H NMR (500 MHz, chloroform-d) δ 8.18-8.12 (m, 2H), 8.08-8.01 (m, 2H), 7.57-7.50 (m, 1H), 7.47-7.43 (m, 2H), 7.41 (d, J = 1.4 Hz, 1H), 7.37 (dd, J = 11.2, 1.7 Hz, 1H), 3.95 (s, 3H), 3.80 (s, 2H), 3.14 (s, 3H), 2.89-2.79 (m, 8H), 2.79 (s, 3H), 2.67 (br d, J = 6.5 Hz, 2H), 1.96-1.85 (m, 2H), 1.13 (br t, J = 7.1 Hz, 3H). TLR9 $IC_{50}$ (nM) = 330 |
| 390 | LCMS $(M + H)^+$ = 535.3. $^1$H NMR (500 MHz, chloroform-d) δ 8.17-8.13 (m, 2H), 8.06-8.03 (m, 2H), 7.51-7.43 (m, 3H), 7.41-7.36 (m, 2H), 3.95 (s, 3H), 3.67 (s, 2H), 3.14 (s, 3H), 3.07 (br d, J = 11.8 Hz, 2H), 2.79 (s, 3H), 2.47 (s, 4H), 2.47 (s, 3H), 2.15 (br t, J = 11.4 Hz, 2H), 1.96 (br d, J = 11.7 Hz, 2H), 1.75-1.67 (m, 2H). TLR9 $IC_{50}$ (nM) = 91 |
| 391 | LCMS $(M + H)^+$ = 579.3. $^1$H NMR (500 MHz, chloroform-d) δ 8.19-8.13 (m, 2H), 8.08-8.01 (m, 2H), 7.44 (d, J = 1.0 Hz, 1H), 7.38 (s, 1H), 7.23 (d, J = 8.3 Hz, 2H), 3.96 (s, 3H), 3.78 (s, 2H), 3.14 (s, 3H), 3.04 (br d, J = 11.7 Hz, 2H), 2.94-2.63 (m, 4H), 2.79 (s, 3H), 2.42-2.23 (m, 1H), 2.18 (br t, J = 11.5 Hz, 2H), 2.02-1.85 (m, 6H), 1.78-1.66 (m, 2H). TLR9 $IC_{50}$ (nM) = 180 |
| 392 | LCMS $(M + H)^+$ = 553.2. $^1$H NMR (500 MHz, chloroform-d) δ 8.16 (d, J = 8.5 Hz, 2H), 8.05 (d, J = 8.5 Hz, 2H), 7.43 (d, J = 1.0 Hz, 1H), 7.40-7.36 (m, 1H), 7.23 (d, J = 8.3 Hz, 2H), 3.96 (s, 3H), 3.78 (s, 2H), 3.14 (s, 3H), 3.07 (br d, J = 11.7 Hz, 2H), 2.79 (s, 3H), 2.36 (s, 6H), 2.32-2.24 (m, 1H), 2.16 (br t, J = 11.4 Hz, 2H), 1.87 (br d, J = 12.1 Hz, 2H), 1.68-1.59 (m, 2H). TLR9 $IC_{50}$ (nM) = 470 |
| 393 | LCMS $(M + H)^+$ = 543.3. $^1$H NMR (500 MHz, chloroform-d) δ 8.18-8.12 (m, 2H), 8.07-8.01 (m, 2H), 7.66 (br d, J = 8.0 Hz, 2H), 7.51-7.40 (m, 4H), 3.95 (s, 3H), 3.64 (br s, 2H), 3.14 (s, 3H), 3.11-3.01 (m, 2H), 2.79 (s, 3H), 2.66-2.51 (m, 1H), 2.42 (br s, 2H), 2.19-1.69 (m, 8H), 0.65-0.35 (m, 4H). TLR9 $IC_{50}$ (nM) = 330 |
| 394 | LCMS $(M + H)^+$ = 561.3. $^1$H NMR (500 MHZ, chloroform-d) δ 8.18-8.12 (m, 2H), 8.07-8.02 (m, 2H), 7.55-7.43 (m, 3H), 7.42-7.35 (m, 2H), 3.95 (s, 3H), 3.71 (br s, 2H), 3.14 (s, 3H), 3.12-3.04 (m, 2H), 2.79 (s, 3H), 2.66-2.49 (m, 1H), 2.42 (br s, 2H), 2.25-2.05 (m, 2H), 2.01-1.67 (m, 6H), 0.69-0.38 (m, 4H). TLR9 $IC_{50}$ (nM) = 560 |
| 395 | LCMS $(M + H)^+$ = 460.2. $^1$H NMR (500 MHz, DMSO-$d_6$) δ 8.20-8.16 (m, 2H), 8.15-8.11 (m, 2H), 7.76 (s, 1H), 7.73 (d, J = 8.0 Hz, 2H), 7.45-7.39 (m, 3H), 3.98 (s, 3H), 3.64 (s, 2H), 3.18 (s, 3H), 2.65 (s, 3H), 2.48 (br s, 4H), 1.72 (br s, 4H). TLR9 $IC_{50}$ (nM) = 1400 |
| 396 | LCMS $(M + H)^+$ = 557.3. $^1$H NMR (500 MHz, chloroform-d) δ 8.15 (d, J = 8.6 Hz, 2H), 8.07-8.02 (m, 2H), 7.66 (d, J = 8.2 Hz, 2H), 7.50-7.44 (m, 3H), 7.42 (d, J = 0.8 Hz, 1H), 3.95 (s, 3H), 3.72 (br s, 2H), 3.14 (s, 3H), 2.92-2.69 (m, 4H), 2.79 (s, 3H), 2.57-2.29 (m, 6H), 1.92-1.69 (m, 3H), 0.99 (br d, J = 6.2 Hz, 6H). TLR9 $IC_{50}$ (nM) = 200 |
| 397 | LCMS $(M + H)^+$ = 543.3. $^1$H NMR (500 MHz, chloroform-d) δ 8.17-8.12 (m, 2H), 8.07-8.01 (m, 2H), 7.65 (d, J = 8.2 Hz, 2H), 7.48-7.40 (m, 4H), 3.95 (s, 3H), 3.71 (s, 2H), 3.50-3.22 (m, 2H), 3.14 (s, 3H), 2.95 (br s, 2H), 2.82-2.74 (m, 1H), 2.79 (s, 3H), 2.65 (br d, J = 8.7 Hz, 2H), 2.47 (br s, 4H), 1.30 (br s, 6H). TLR9 $IC_{50}$ (nM) = 86 |
| 398 | LCMS $(M + H)^+$ = 515.2. $^1$H NMR (500 MHZ, chloroform-d) δ 8.17-8.12 (m, 2H), 8.07-8.01 (m, 2H), 7.65 (d, J = 8.2 Hz, 2H), 7.47-7.42 (m, 4H), 3.95 (s, 3H), 3.72 (s, 2H), 3.14 (s, 3H), 2.93-2.80 (m, 4H), 2.79 (s, 3H), 2.71 (br s, 2H), 2.59-2.45 (m, 4H), 2.49 (s, 3H). TLR9 $IC_{50}$ (nM) = 130 |
| 399 | LCMS $(M + H)^+$ = 529.1. $^1$H NMR (500 MHz, chloroform-d) δ 8.15 (d, J = 8.3 Hz, 2H), 8.06-8.02 (m, 2H), 7.64 (d, J = 8.2 Hz, 2H), 7.44 (s, 1H), 7.42 (s, 1H), 7.37 (d, J = 8.0 Hz, 2H), 3.95 (s, 3H), 3.66 (s, 2H), 3.49-3.31 (m, 8H), 3.13 (s, 3H), 2.78 (s, 3H), 2.43-2.26 (m, 1H), 0.99 (br d, J = 4.9 Hz, 6H). TLR9 $IC_{50}$ (nM) = 97 |
| 400 | LCMS $(M + H)^+$ = 557.2. $^1$H NMR (500 MHz, DMSO-$d_6$) δ 8.15 (br d, J = 1.8 Hz, 4H), 7.77 (s, 3H), 7.51-7.44 (m, 1H), 7.41-7.34 (m, 2H), 3.97 (s, 2H), 3.89 (s, 2H), 3.71-3.55 (m, 3H), 3.31 (s, 2H), 3.17 (s, 5H), 2.80 (br s, 2H), 2.65 (s, 3H), 2.55 (s, 2H), 2.41-2.26 (m, 2H), 2.17-1.86 (m, 6H) (one proton obscured). TLR9 $IC_{50}$ (nM) = 76 |
| 401 | LCMS $(M + H)^+$ = 583.3. $^1$H NMR (500 MHZ, DMSO-$d_6$) δ 8.25-8.10 (m, 4H), 7.77 (s, 3H), 7.48 (s, 1H), 7.40-7.32 (m, 2H), 3.99 (s, 3H), 3.77-3.55 (m, 2H), 3.33 (s, 2H), 3.26-3.13 (m, 2H), 3.06-2.86 (m, 2H), 2.85-2.76 (m, 1H), 2.66 (s, 3H), 2.57-2.53 (m, 1H), 2.42-2.24 (m, 2H), 2.15-1.87 (m, 6H), 1.26-1.12 (m, 1H), 1.02-0.91 (m, 2H), 0.91-0.76 (m, 2H) (three protons obscured). TLR9 $IC_{50}$ (nM) = 100 |

-continued

| Ex. No. | Analytical LC/MS, Preparative HPLC method, yield, and $^1$H NMR |
|---|---|
| 402 | LCMS $(M + H)^+$ = 529.3. $^1$H NMR (500 MHZ, chloroform-d) δ 8.17-8.12 (m, 2H), 8.07-8.01 (m, 2H), 7.65 (d, J = 8.2 Hz, 2H), 7.48-7.40 (m, 4H), 3.95 (s, 3H), 3.64-3.55 (m, 2H), 3.37 (br d, J = 3.6 Hz, 2H), 3.14 (s, 3H), 2.97-2.88 (m, 2H), 2.85-2.76 (m, 1H), 2.79 (s, 3H), 2.30-2.02 (m, 4H), 1.84-1.61 (m, 6H). TLR9 $IC_{50}$ (nM) = 3.9 |
| 403 | LCMS $(M + H)^+$ = 547.3. $^1$H NMR (500 MHZ, CHLOROFORM-d) δ 8.17-8.12 (m, 2H), 8.07-8.02 (m, 2H), 7.54-7.43 (m, 3H), 7.40 (s, 1H), 7.36 (dd, J = 11.2, 1.6 Hz, 1H), 3.95 (s, 3H), 3.67 (br s, 2H), 3.34 (br s, 2H), 3.14 (s, 3H), 2.94 (br d, J = 11.4 Hz, 2H), 2.81-2.75 (m, 1H), 2.79 (s, 3H), 2.15 (br s, 4H), 1.85-1.43 (m, 6H). TLR9 $IC_{50}$ (nM) = 81 |
| 404 | LCMS $(M + H)^+$ = 547.2. $^1$H NMR (500 MHz, CHLOROFORM-d) δ 8.17-8.12 (m, 2H), 8.07-8.02 (m, 2H), 7.46-7.39 (m, 4H), 7.37 (dd, J = 11.2, 1.5 Hz, 1H), 3.95 (s, 3H), 3.70 (s, 2H), 3.63-3.32 (m, 7H), 3.14 (s, 3H), 2.78 (s, 3H), 2.61-2.37 (m, 1H), 1.11-0.98 (m, 6H). TLR9 $IC_{50}$ (nM) = 69 |
| 405 | LCMS $(M + H)^+$ = 561.1. $^1$H NMR (500 MHz, chloroform-d) δ 8.15 (d, J = 8.6 Hz, 2H), 8.08-8.02 (m, 2H), 7.47-7.38 (m, 3H), 7.27 (br d, J = 9.4 Hz, 1H), 7.06 (br d, J = 9.4 Hz, 1H), 3.96 (s, 3H), 3.60 (s, 2H), 3.14 (s, 3H), 2.99 (br d, J = 10.8 Hz, 2H), 2.87-2.54 (m, 4H), 2.79 (s, 3H), 2.37-2.16 (m, 1H), 2.09 (br t, J = 11.3 Hz, 2H), 2.01-1.75 (m, 8H). TLR9 $IC_{50}$ (nM) = 21 |
| 406 | LCMS $(M + H)^+$ = 547.3. $^1$H NMR (500 MHZ, CHLOROFORM-d) δ 8.18-8.12 (m, 2H), 8.08-8.02 (m, 2H), 7.47-7.38 (m, 3H), 7.28-7.26 (m, 1H), 7.06 (br d, J = 9.3 Hz, 1H), 3.96 (s, 3H), 3.60 (s, 2H), 3.35 (br s, 2H), 3.14 (s, 3H), 2.92 (br d, J = 10.7 Hz, 2H), 2.84-2.72 (m, 1H), 2.79 (s, 3H), 2.24-2.04 (m, 4H), 1.84-1.53 (m, 6H). TLR9 $IC_{50}$ (nM) = 130 |
| 407 | LCMS $(M + H)^+$ = 569.1. $^1$H NMR (500 MHZ, CHLOROFORM-d) δ 8.23 (d, J = 8.5 Hz, 2H), 8.12 (d, J = 8.3 Hz, 2H), 7.69-7.57 (m, 3H), 7.45 (t, J = 7.6 Hz, 1H), 7.40 (s, 1H), 7.34 (br d, J = 7.4 Hz, 1H), 3.69-3.61 (m, 3H), 3.14 (s, 3H), 3.05 (br d, J = 10.8 Hz, 2H), 2.77 (s, 3H), 3.01-2.49 (m, 3H), 2.17-1.71 (m, 12H), 1.21 (q, J = 6.5 Hz, 2H), 0.84-0.78 (m, 2H). TLR9 $IC_{50}$ (nM) = 46 |
| 408 | Analytical LC/MS (Method 1): Purity: 94.1%; Observed Mass: 573.60; Retention Time: 1.07 min. (Method 2): Purity: 93.7%; Observed Mass: 573.60; Retention Time: 1.28 min. Prep Method 1: 50 mg, 47% yield; $^1$H NMR (500 MHZ, DMSO-$d_6$) δ 8.34 (d, J = 8.5 Hz, 2H), 8.13 (br d, J = 8.2 Hz, 2H), 7.79-7.69 (m, 3H), 7.43 (br d, J = 8.2 Hz, 3H), 3.98-3.86 (m, 1H), 3.57-3.43 (m, 1H), 3.34 (s, 2H), 2.87-2.75 (m, 2H), 2.57-2.56 (m, 1H), 2.49-2.43 (m, 4H), 2.09-1.90 (m, 3H), 1.88-1.76 (m, 3H), 1.66 (br s, 4H), 1.49-1.33 (m, 2H), 1.29-1.11 (m, 2H), 0.72 (br s, 2H). TLR9 $IC_{50}$ (nM) = 140 |
| 409 | Analytical LC/MS (Method 1): Purity: 99%; Observed Mass: 547.20; Retention Time: 1.16 min. (Method 2): Purity: 99.4%; Observed Mass: 547.20; Retention Time: 1.40. Prep Method 1: 83 mg, 88% yield; $^1$H NMR (500 MHZ, DMSO-$d_6$) δ 8.25-8.09 (m, 4H), 7.82 (s, 1H), 7.76 (s, 2H), 7.42 (br d, J = 7.9 Hz, 3H), 3.99 (s, 2H), 3.79-3.59 (m, 3H), 3.50 (s, 1H), 3.31 (s, 3H), 3.19-3.15 (m, 1H), 2.85-2.78 (m, 2H), 2.61 (br s, 2H), 2.19-2.09 (m, 1H), 1.97 (br s, 2H), 1.87 (s, 3H), 1.70 (br s, 3H), 1.54-1.35 (m, 2H). TLR9 $IC_{50}$ (nM) = 5.3 |
| 410 | Analytical LC/MS (Method 1): Purity: 95.4%; Observed Mass: 559.20; Retention Time: 1.23 min. (Method 2): Purity: 100%; Observed Mass: 559.30; Retention Time: 1.49. Prep Method 1: 76 mg, 94% yield; $^1$H NMR (500 MHZ, DMSO-$d_6$) δ 8.33 (d, J = 8.2 Hz, 2H), 8.13 (d, J = 8.2 Hz, 2H), 7.78-7.70 (m, 3H), 7.49-7.41 (m, 1H), 7.38 (br d, J = 7.9 Hz, 2H), 4.03-3.82 (m, 1H), 3.63-3.44 (m, 1H), 3.34 (s, 2H), 3.21 (br d, J = 15.0 Hz, 5H), 2.53-2.49 (m, 4H), 2.32-2.21 (m, 1H), 1.91 (s, 1H), 1.24-1.18 (m, 2H), 0.83 (d, J = 6.1 Hz, 6H), 0.72 (br s, 2H). TLR9 $IC_{50}$ (nM) = 44 |
| 411 | Analytical LC/MS (Method 1): Purity: 100%; Observed Mass: 573.20; Retention Time: 1.13 min. (Method 2): Purity: 97.1%; Observed Mass: 573.20; Retention Time: 1.49. Prep Method 1: 40 mg, 48% yield; $^1$H NMR (500 MHz, DMSO-$d_6$) δ 8.41-8.27 (m, 2H), 8.12 (d, J = 8.2 Hz, 2H), 7.81-7.66 (m, 3H), 7.49-7.41 (m, 1H), 7.38 (br d, J = 7.9 Hz, 2H), 3.97-3.86 (m, 1H), 3.63-3.56 (m, 1H), 3.34 (s, 2H), 3.31-3.23 (m, 3H), 2.55 (s, 3H), 2.25-2.15 (m, 2H), 1.92 (s, 4H), 1.57-1.45 (m, 1H), 1.23-1.17 (m, 2H), 0.82 (d, J = 6.7 Hz, 6H), 0.76-0.69 (m, 2H). TLR9 $IC_{50}$ (nM) = 0.85 |
| 412 | Analytical LC/MS (Method 1): Purity: 98.7%; Observed Mass: 601.30; Retention Time: 1.15 min. (Method 2): Purity: 97.1%; Observed Mass: 601.30; Retention Time: 1.45. Prep Method 1: 85 mg, 98% yield; $^1$H NMR (500 MHZ, DMSO-$d_6$) δ 8.36-8.36 (m, 1H), 8.34 (br d, J = 7.9 Hz, 1H), 8.13 (br d, J = 8.2 Hz, 2H), 7.80-7.65 (m, 3H), 7.45 (br d, J = 11.6 Hz, 1H), 7.39 (br d, J = 7.9 Hz, 2H), 3.98-3.91 (m, 1H), 3.83-3.74 (m, 2H), 3.63-3.52 (m, 1H), 3.35 (s, 2H), 3.30-3.17 (m, 7H), 2.26-2.08 (m, 1H), 1.92 (s, 4H), 1.62-1.49 (m, 2H), 1.21 (br d, J = 6.7 Hz, 4H), 0.73 (br s, 2H) (one proton obscured). TLR9 $IC_{50}$ (nM) = 77 |
| 413 | Analytical LC/MS (Method 1): Purity: 96.3%; Observed Mass: 517.19; Retention Time: 1.03 min. (Method 2): Purity: 94.9%; Observed Mass: 517.19; Retention Time: 1.51. Prep Method 1: 53 mg, 88% yield; $^1$H NMR (500 MHz, DMSO-$d_6$) δ 8.22-8.10 (m, 4H), 7.81-7.67 (m, 3H), 7.47-7.36 (m, 3H), 4.01-3.96 (m, 3H), 3.60-3.48 (m, 1H), 2.70-2.63 (m, 3H), 2.56-2.50 (m, 8H), 2.49-2.35 (m, 3H), 1.09-0.91 (m, 6H) (two protons obscured). TLR9 $IC_{50}$ (nM) = 1900 |

-continued

| Ex. No. | Analytical LC/MS, Preparative HPLC method, yield, and $^1$H NMR |
|---|---|
| 414 | Analytical LC/MS (Method 1): Purity: 96.4%; Observed Mass: 531.37; Retention Time: 1.06 min. (Method 2): Purity: 96.4%; Observed Mass: 531.37; Retention Time: 2.01. Prep Method 1: 23 mg, 38% yield; $^1$H NMR (500 MHZ, DMSO-$d_6$) δ 8.24-8.06 (m, 4H), 7.79-7.65 (m, 3H), 7.49-7.32 (m, 3H), 3.98 (s, 3H), 3.54-3.47 (m, 1H), 3.46-3.38 (m, 1H), 3.32 (s, 1H), 2.65 (s, 3H), 2.55 (s, 2H), 2.48-2.13 (m, 5H), 2.02 (br d, J = 7.4 Hz, 2H), 1.83-1.55 (m, 1H), 0.84 (d, J = 6.5 Hz, 6H) (three protons obscured). TLR9 $IC_{50}$ (nM) = 1800 |
| 415 | Analytical LC/MS (Method 1): Purity: 100%; Observed Mass: 553.30; Retention Time: 0.98 min. (Method 2): Purity: 100%; Observed Mass: 553.30; Retention Time: 1.50 min. Prep Method 2: 52 mg, 35% yield; $^1$H NMR (500 MHZ, DMSO-$d_6$) δ 8.28-8.23 (m, 2H), 8.11 (d, J = 8.2 Hz, 2H), 7.55 (d, J = 8.2 Hz, 1H), 7.17-7.13 (m, 1H), 4.08-3.97 (m, 1H), 3.76-3.54 (m, 1H), 3.34 (s, 1H), 3.33-3.19 (m, 1H), 3.08-2.90 (m, 3H), 2.61-2.49 (m, 4H), 2.38-2.26 (m, 2H), 2.24-1.98 (m, 7H), 1.08 (br d, J = 7.0 Hz, 2H), 0.98 (br d, J = 6.4 Hz, 6H), 0.70 (br s, 2H) (five protons obscured). TLR9 $IC_{50}$ (nM) = 65 |

Example 416

6-(4-((1-isopropylpiperidin-4-yl)oxy)phenyl)-1,4-dimethyl-2-(4-(methylsulfonyl)phenyl)-1H-benzo[d]imidazole (416)

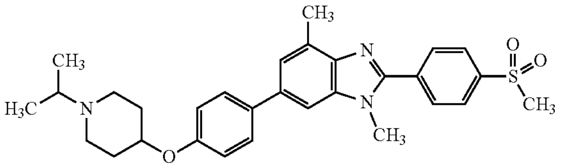

Step A. Intermediate 416A. Preparation of tert-butyl 4-(4-(1,4-dimethyl-2-(4-(methylsulfonyl)phenyl)-1H-benzo[d]imidazol-6-yl)phenoxy)piperidine-1-carboxylate (416A)

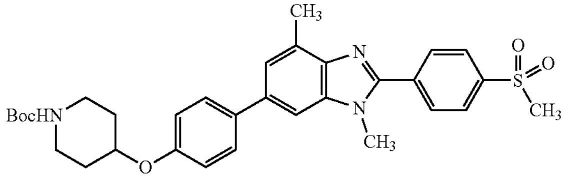

To a 40 mL vial were added Intermediate 22A (230 mg, 0.61 mmol), tert-butyl 4-(4-(4,4,5,5-tetramethyl-1,3,2-dioxaborolan-2-yl)phenoxy)piperidine-1-carboxylate (250 mg, 0.61 mmol), XPhos Pd G3 (26 mg, 0.030 mmol), 1,4-dioxane (10 mL), followed by potassium phosphate tribasic (450 mg, 2.1 mmol) dissolved in water (2 mL). The vessel was flushed with $N_2$ and the reaction mixture was stirred at 85° C. After 18 h, the reaction mixture was cooled, diluted with water (100 mL) and extracted with EtOAc (2×50 mL). The organic phase was combined, washed with brine, dried over $MgSO_4$, filtered and concentrated. The residue was purified by flash column chromatography (80 g silica gel cartridge; A=DCM, B=MeOH; 30 min grad.; 0% B to 15% B; flow rate=60 mL/min). The fractions corresponding to product were combined, concentrated and dried in vacuo to afford the title compound (340 mg, 0.59 mmol, 97% yield) as a pale yellow solid. $^1$H NMR (500 MHz, METHANOL-$d_4$) δ 8.26-8.18 (m, 2H), 8.15-8.06 (m, 2H), 7.70-7.64 (m, 2H), 7.61-7.57 (m, 1H), 7.44-7.39 (m, 1H), 7.14-7.05 (m, 2H), 4.69-4.62 (m, 1H), 4.00-3.94 (m, 3H), 3.82-3.73 (m, 2H), 3.37 (s, 3H), 2.72 (s, 3H), 2.05-1.97 (m, 2H), 1.79-1.71 (m, 3H), 1.22 (s, 9H) (one proton obscured). Analytical LC/MS (Method 4): Observed Mass: 576.3; Retention Time: 1.821 min.

Step B. Intermediate 416B. Preparation of 1,4-dimethyl-2-(4-(methylsulfonyl)phenyl)-6-(4-(piperidin-4-yloxy)phenyl)-1H-benzo[d]imidazole hydrochloride (416B)

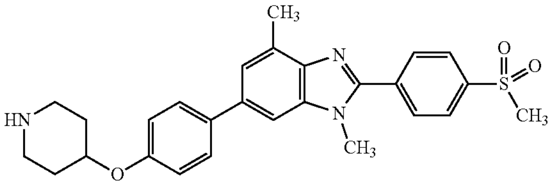

To a 100 mL pear shaped flask were added Intermediate 416A (340 mg, 0.59 mmol), MeOH (20 mL), and 4 M HCl in dioxane (10 mL). After 30 min, the solvent was concentrated and the residue was co-evaporated with toluene (2×), and the product was dried in vacuo to afford the title compound (300 mg, 0.59 mmol, 100% yield) as a tan solid. $^1$H NMR (500 MHz, METHANOL-$d_4$) δ 8.37-8.31 (m, 2H), 8.23-8.19 (m, 2H), 7.94-7.91 (m, 1H), 7.80-7.74 (m, 2H), 7.73-7.70 (m, 1H), 7.20-7.16 (m, 2H), 4.13 (s, 3H), 3.63-3.60 (m, 1H), 3.50-3.43 (m, 3H), 3.36-3.34 (m, 1H), 3.32-3.29 (m, 3H), 3.28-3.18 (m, 3H), 2.77 (s, 3H) (one proton obscured). Analytical LC/MS (Method 4): Observed Mass: 476.2; Retention Time: 1.025 min.

Step C. Example 416

To a 40 mL vial were added Intermediate 416B (60 mg, 0.12 mmol), propan-2-one (34 mg, 0.59 mmol), AcOH (7.4

μL, 0.13 mmol), magnesium sulfate (210 mg, 1.8 mmol), and DMF (2 mL). The reaction mixture was stirred for 20 min, then sodium triacetoxyborohydride (120 mg, 0.59 mmol) was added and the reaction mixture was stirred. After 18 h, the reaction mixture was diluted with 10% IPA/$CHCl_3$ (40 mL) and filtered. The filtrate was partitioned into 10% KOH (sat. with solid NaCl) (20 mL) and the layers were separated. The aqueous phase was extracted with 10% IPA/$CHCl_3$ (10 mL), the organic phase was combined, washed with brine, dried over $MgSO_4$, filtered and concentrated. The crude material was purified by preparative HPLC (Prep Method 1) to afford the title compound (49 mg, 0.095 mmol, 79% yield). $^1$H NMR (500 MHz, DMSO-$d_6$) δ 8.19-8.11 (m, 4H), 7.73-7.65 (m, 3H), 7.41-7.36 (m, 1H), 7.11-7.04 (m, 2H), 4.55-4.46 (m, 1H), 3.96 (s, 3H), 3.31 (s, 2H), 3.02-2.87 (m, 2H), 2.64 (s, 5H), 2.09-2.01 (m, 2H), 1.91 (s, 2H), 1.81-1.67 (m, 2H), 1.08 (br d, J=6.4 Hz, 6H). Analytical LC/MS (Method 1): Purity: 97.3%; Observed Mass: 518.22; Retention Time: 1.14 min. (Method 2): Purity: 97.1%; Observed Mass: 518.12; Retention Time: 1.50 min. TLR9 $IC_{50}$ (nM)=1200.

The following Examples were prepared according to the general methods described hereinabove using appropriate starting materials, reagents and conditions.

| | | |
|---|---|---|
| 417 | 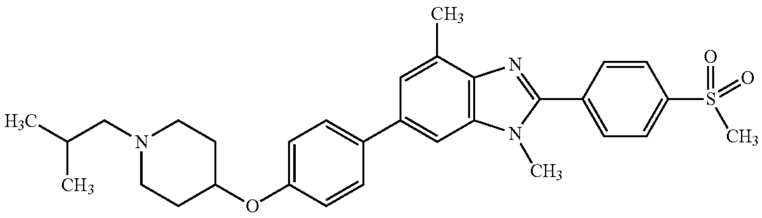 [SMILES: Cc1cc(-c2ccc(OC3CCN(CC(C)C)CC3)cc2)cc2c1nc(-c1ccc(S(C)(=O)=O)cc1)n2C] | Ex. 416 |
| 418 | 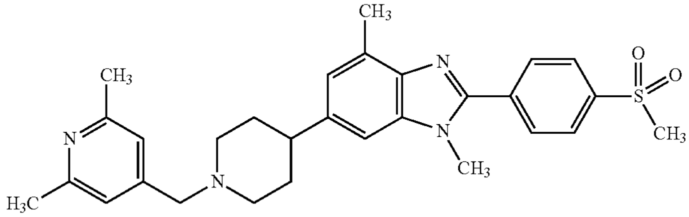 [SMILES: Cc1cc(CN2CCC(c3cc(C)c4nc(-c5ccc(S(C)(=O)=O)cc5)n(C)c4c3)CC2)cc(C)n1] | Ex. 22 |
| 419 | 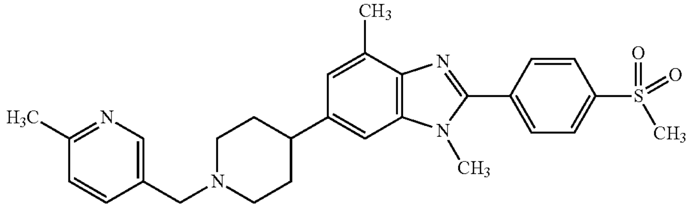 [SMILES: Cc1ccc(CN2CCC(c3cc(C)c4nc(-c5ccc(S(C)(=O)=O)cc5)n(C)c4c3)CC2)cn1] | Ex. 22 |
| 420 | 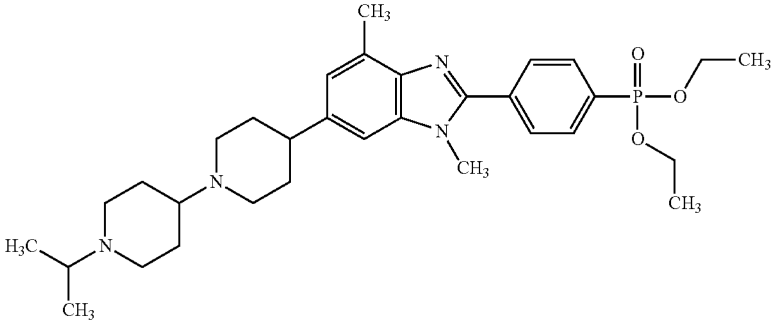 [SMILES: CCOP(=O)(OCC)c1ccc(-c2nc3c(C)cc(C4CCN(C5CCN(C(C)C)CC5)CC4)cc3n2C)cc1] | Ex. 22 |
| 421 | 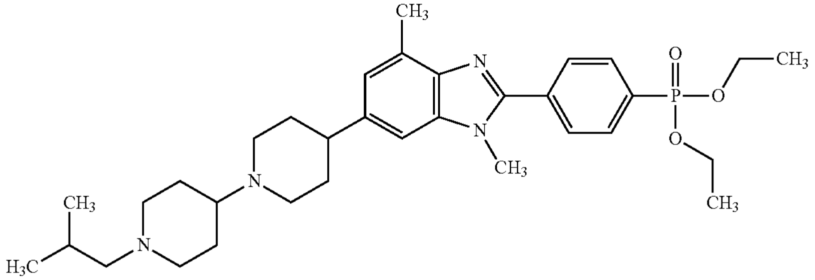 [SMILES: CCOP(=O)(OCC)c1ccc(-c2nc3c(C)cc(C4CCN(C5CCN(CC(C)C)CC5)CC4)cc3n2C)cc1] | Ex. 22 |

-continued

422

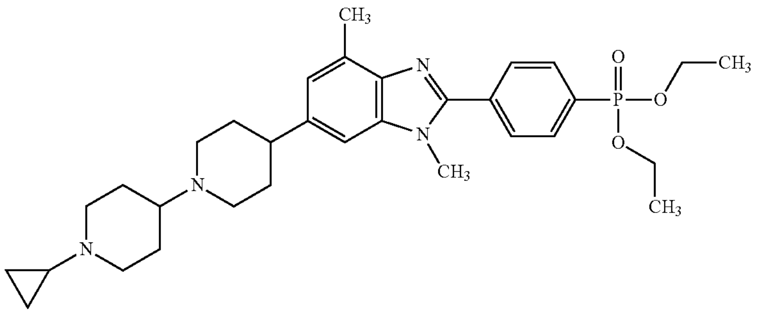 [SMILES: CCOP(=O)(OCC)c1ccc(-c2nc3c(C)cc(C4CCN(C5CCN(C6CC6)CC5)CC4)cc3n2C)cc1]

Ex. 22

| Ex. No. | LC/MS, Preparative HPLC method, yield, and $^1$H NMR |
|---|---|
| 417 | Analytical LC/MS (Method 1): Purity: 100%; Observed Mass: 531.92; Retention Time: 1.27 min. (Method 2): Purity: 100%; Observed Mass: 531.95; Retention Time: 1.66 min. Prep Method 1: 21 mg, 33% yield; $^1$H NMR (500 MHZ, DMSO-$d_6$) δ 8.20-8.08 (m, 4H), 7.73-7.65 (m, 3H), 7.41-7.35 (m, 1H), 7.11-6.99 (m, 2H), 4.50-4.38 (m, 1H), 3.97 (s, 3H), 3.32 (s, 1H), 2.63 (s, 4H), 2.57-2.53 (m, 1H), 2.19 (br s, 2H), 2.06 (d, J = 7.4 Hz, 2H), 2.00-1.93 (m, 2H), 1.82-1.71 (m, 1H), 1.70-1.58 (m, 2H), 0.87 (d, J = 6.6 Hz, 6H) (two protons obscured). TLR9 $IC_{50}$ (nM) = 800 |
| 418 | Analytical LC/MS (Method 1): Purity: 100%; Observed Mass: 503.20; Retention Time: 0.88 min. (Method 2): Purity: 98.4%; Observed Mass: 503.30; Retention Time: 1.68 min. Prep Method 1: 67 mg, 87% yield; $^1$H NMR (500 MHZ, DMSO-$d_6$) δ 8.18-8.05 (m, 4H), 7.38-7.30 (m, 1H), 7.02 (s, 3H), 3.90 (s, 3H), 3.35-3.27 (m, 1H), 2.97-2.88 (m, 2H), 2.67-2.59 (m, 1H), 2.54-2.50 (m, 5H), 2.42 (s, 5H), 2.17-2.06 (m, 2H), 1.94-1.88 (m, 2H), 1.85-1.76 (m, 4H) (one proton obscured). TLR9 $IC_{50}$ (nM) = 2500 |
| 419 | Analytical LC/MS (Method 1): Purity: 98.5%; Observed Mass: 489.20; Retention Time: 0.93 min. (Method 2): Purity: 92.2%; Observed Mass: 489.00; Retention Time: 1.48 min. Prep Method 1: 45 mg, 56% yield; $^1$H NMR (500 MHz, DMSO-$d_6$) δ 8.42-8.35 (m, 1H), 8.17-8.06 (m, 4H), 7.66-7.59 (m, 1H), 7.38-7.30 (m, 1H), 7.26-7.19 (m, 1H), 7.04-6.97 (m, 1H), 3.89 (s, 3H), 3.55-3.49 (m, 1H), 3.31 (s, 1H), 2.97-2.89 (m, 2H), 2.65-2.58 (m, 1H), 2.55-2.50 (m, 3H), 2.46 (s, 3H), 2.09 (br d, J = 3.1 Hz, 2H), 1.79 (br d, J = 5.8 Hz, 4H) (three protons obscured). TLR9 $IC_{50}$ (nM) = 2100 |
| 420 | Analytical LC/MS (Method 1): Purity: 91.6%; Observed Mass: 567.30; Retention Time: 1.09 min. (Method 2): Purity: 97.1%; Observed Mass: 567.30; Retention Time: 1.49 min. Prep Method 1: 56 mg, 72% yield; $^1$H NMR (500 MHz, DMSO-$d_6$) δ 8.08-7.96 (m, 2H), 7.96-7.84 (m, 2H), 7.38-7.22 (m, 1H), 7.07-6.90 (m, 1H), 4.15-4.02 (m, 4H), 3.87 (s, 3H), 3.07-2.98 (m, 1H), 2.96-2.88 (m, 1H), 2.86-2.69 (m, 1H), 2.53 (br d, J = 19.3 Hz, 8H), 2.31 (br s, 4H), 1.86-1.62 (m, 5H), 1.55-1.35 (m, 2H), 1.28 (t, J = 7.0 Hz, 5H), 1.00 (br d, J = 6.4 Hz, 6H) (one proton obscured). TLR9 $IC_{50}$ (nM) = 140 |
| 421 | Analytical LC/MS (Method 1): Purity: 93.4%; Observed Mass: 581.20; Retention Time: 1.13 min. (Method 2): Purity: 96.7%; Observed Mass: 581.40; Retention Time: 1.69 min. Prep Method 1: 41 mg, 53% yield; $^1$H NMR (500 MHZ, DMSO-$d_6$) δ 8.01 (br dd, J = 7.8, 3.5 Hz, 2H), 7.89 (dd, J = 12.7, 8.1 Hz, 2H), 7.31 (s, 1H), 6.98 (s, 1H), 4.17-4.01 (m, 4H), 3.88 (s, 3H), 3.06-2.99 (m, 1H), 2.94-2.80 (m, 2H), 2.66-2.58 (m, 1H), 2.55 (s, 5H), 2.39-2.21 (m, 3H), 2.02 (br s, 2H), 1.89-1.61 (m, 8H), 1.53-1.43 (m, 2H), 1.28 (t, J = 7.0 Hz, 6H), 0.86 (d, J = 6.4 Hz, 6H). TLR9 $IC_{50}$ (nM) = 140 |
| 422 | Analytical LC/MS (Method 1): Purity: 100%; Observed Mass: 565.30; Retention Time: 0.93 min. (Method 2): Purity: 100%; Observed Mass: 565.40; Retention Time: 1.48 min. Prep Method 2: 36 mg, 51% yield; $^1$H NMR (500 MHz, DMSO-$d_6$) δ 8.09-8.00 (m, 2H), 7.98-7.89 (m, 2H), 7.46-7.28 (m, 1H), 7.11-6.95 (m, 1H), 4.18-4.00 (m, 4H), 3.91 (s, 3H), 3.73-3.52 (m, 1H), 3.29-2.95 (m, 2H), 2.62-2.47 (m, 9H), 2.40-2.24 (m, 2H), 2.11 (br s, 6H), 1.28 (t, J = 7.0 Hz, 6H), 1.04-0.87 (m, 2H), 0.86-0.71 (m, 2H) (two protons obscured). TLR9 $IC_{50}$ (nM) = 180 |

The following Examples were prepared according to the general methods described elsewhere herein using appropriate starting materials, reagents and conditions.

| Ex. No. | Structure |
|---|---|
| 423 | 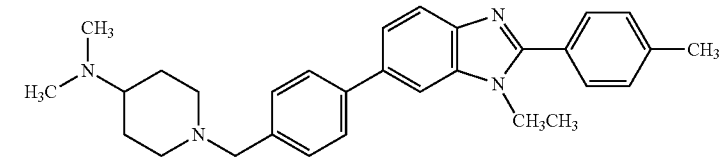 |
| 424 | 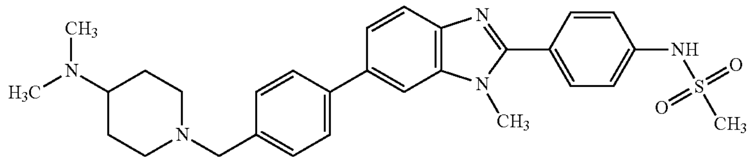 [SMILES: CN(C)C1CCN(Cc2ccc(-c3ccc4nc(-c5ccc(NS(C)(=O)=O)cc5)n(C)c4c3)cc2)CC1] |
| 425 | 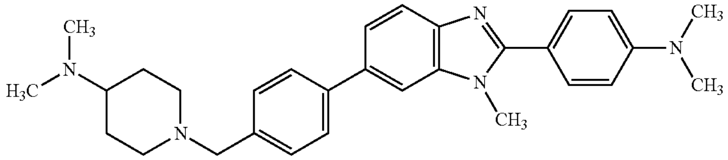 |
| 426 | 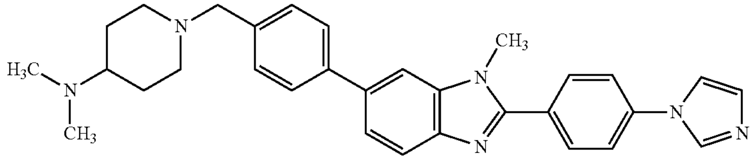 [SMILES: CN(C)C1CCN(Cc2ccc(-c3ccc4nc(-c5ccc(-n6ccnc6)cc5)n(C)c4c3)cc2)CC1] |
| 427 | 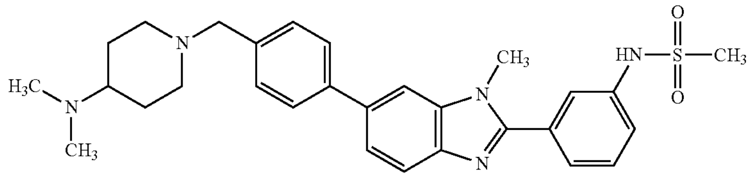 |

| Ex. No. | Analytical LC/MS, Preparative HPLC method, yield, and 1H NMR |
|---|---|
| 425 | Analytical LC/MS (Method 2): Purity: 93.4%; Observed Mass: 417.3; Retention Time: 1.5 min.; Prep method 1: 2.7 mg, 8% yield; $^{1}$H NMR (500 MHz, DMSO-$d_6$) δ 7.75 (s, 1H), 7.67 (br d, J = 7.9 Hz, 2H), 7.59 (br d, J = 7.9 Hz, 1H), 7.44 (br d, J = 8.5 Hz, 1H), 7.36 (br d, J = 7.9 Hz, 2H), 3.81 (s, 3H), 2.87 (br d, J = 11.6 Hz, 2H), 2.27 (br s, 6H), 2.14-2.04 (m, 3H), 2.01-1.87 (m, 5H), 1.83-1.64 (m, 7H), 1.48-1.35 (m, 3H); TLR9 $IC_{50}$ (nM) = 61 |
| 426 | Analytical LC/MS (Method 1): Purity: 100%; Observed Mass: 493.2; Retention Time: 1.18 min; Analytical LC/MS (Method 2): Purity: 97.8%; Observed Mass: 493.2; Retention Time: 1.71 min. Prep method 1: 1.3 mg, 3% yield; $^{1}$H NMR $^{1}$H NMR (500 MHZ, DMSO-$d_6$) δ 8.14 (br d, J = 7.6 Hz, 2H), 8.03 (s, 1H), 7.96 (br d, J = 8.2 Hz, 2H), 7.91 (br d, J = 7.9 Hz, 2H), 7.81 (d, J = 8.5 Hz, 1H), 7.70-7.60 (m, 3H), 4.45-4.24 (m, 2H), 4.00 (s, 3H), 3.10-2.84 (m, 2H), 2.76 (br s, 6H), 2.26-2.18 (m, 2H), 2.02-1.84 (m, 3H) (two protons obscured); TLR9 $IC_{50}$ (nM) = nd |
| 427 | Analytical LC/MS (Method 1): Purity: 100%; Observed Mass: 349.1; Retention Time: 0.67 min; Analytical LC/MS (Method 2): Purity: 90.5%; Observed Mass: 349.1; Retention Time: 0.67 min. Prep method 1: 1.6 mg, 7% yield; $^{1}$H NMR (500 MHz, DMSO-$d_6$) δ 8.20 (s, 1H), 7.84 (s, 1H), 7.73-7.68 (m, 3H), 7.52 (br d, J = 7.9 Hz, 1H), 7.39 (br d, J = 7.9 Hz, 2H), 3.89 |

-continued

| Ex. No. | Analytical LC/MS, Preparative HPLC method, yield, and 1H NMR |
|---|---|
| | (s, 3H), 3.53 (s, 1H), 2.93 (br d, J = 10.4 Hz, 2H), 2.59-2.50 (m, 6H), 1.99 (br t, J = 11.7 Hz, 2H), 1.85 (br d, J = 11.0 Hz, 2H), 1.60-1.47 (m, 2H); TLR9 $IC_{50}$ (nM) = nd |

Biological Assays

The pharmacological properties of the compounds of this invention may be confirmed by a number of biological assays. The exemplified biological assays, which follow, have been carried out with compounds of the invention.

TLR7/8/9 Inhibition Reporter Assays

HEK-Blue™-cells (Invivogen) overexpressing human TLR7, TLR8 or TLR9 receptors were used for screening inhibitors of these receptors using an inducible SLAP (secreted embryonic alkaline phosphatase) reporter gene under the control of the IFN-03 minimal promoter fused to five NF-κB and AP-1-binding sites. Briefly, cells are seeded into Greiner 384 well plates (15000 cells per well for TLR7, 20,000 for TLR8 and 25,000 for TLR9) and then treated with test compounds in DMSO to yield a final dose response concentration range of 0.05 nM-50 μM. After a 30 minute compound pre-treatment at room temperature, the cells are then stimulated with a TLR7 ligand (gardiquimod at a final concentration of 7.5 μM), TLR8 ligand (R848 at a final concentration of 15.9 μM) or TLR9 ligand (ODN2006 at a final concentration of 5 nM) to activate NF-κB and AP-1 which induce the production of SLAP. After a 22 hour incubation at 37° C., 500 $C_{02}$, SLAP levels are determined with the addition of HEK-Blue™ Detection reagent (Invivogen), a cell culture medium that allows for detection of SLAP, according to manufacturer's specifications. The percent inhibition is determined as the 00 reduction in the HEK-Blue signal present in wells treated with agonist plus DMSO alone compared to wells treated with a known inhibitor.

TABLE 1

| Ex. No. | TLR 9 $IC_{50}$ (μM) | TLR 7 $IC_{50}$ (μM) | TLR 8 $IC_{50}$ (μM) |
|---|---|---|---|
| 1 | 0.056 | 5.9 | 1.1 |
| 2 | 0.123 | 16 | >50 |
| 3 | 0.169 | 0.28 | >50 |
| 4 | 0.253 | 4.7 | >50 |
| 5 | 0.250 | 6.8 | 0.84 |
| 6 | 0.191 | 2.9 | 29 |
| 7 | 0.283 | 5.7 | >50 |
| 8 | 0.210 | 2.5 | >50 |
| 9 | 0.249 | 2.7 | 1.3 |
| 10 | 0.244 | >50 | >50 |
| 11 | 0.033 | 5.0 | >50 |
| 12 | 0.060 | 22 | >50 |
| 13 | 0.617 | >50 | >50 |
| 14 | 0.509 | >50 | >50 |
| 15 | 0.019 | 7.1 | >50 |
| 16 | 0.0104 | 10 | >50 |
| 17 | 0.025 | 6.5 | >50 |
| 18 | 0.029 | 7.7 | >50 |
| 19 | 0.028 | 2.5 | >50 |
| 20 | 0.069 | 4.1 | >50 |
| 21 | 0.024 | 2.6 | >50 |
| 22 | 0.0076 | 24 | >50 |
| 23 | 0.159 | 8.8 | >50 |
| 24 | 0.048 | 3.0 | >50 |
| 25 | 0.164 | 3.0 | >50 |
| 26 | 0.132 | 32 | >50 |
| 27 | 0.106 | 2.4 | >50 |
| 28 | 0.019 | 2.7 | >50 |
| 29 | 0.0112 | 6.6 | >50 |

TABLE 1-continued

| Ex. No. | TLR 9 $IC_{50}$ (μM) | TLR 7 $IC_{50}$ (μM) | TLR 8 $IC_{50}$ (μM) |
|---|---|---|---|
| 30 | 0.254 | 9.8 | >50 |
| 31 | 0.749 | >50 | >50 |
| 32 | 0.212 | 5.7 | >50 |
| 33 | 0.681 | 8.1 | 35.0 |
| 34 | 0.173 | 16 | >50 |
| 35 | 0.852 | 25 | >50 |
| 36 | 0.357 | 6.6 | 4.6 |
| 37 | 0.388 | 7.5 | >50 |
| 38 | 0.208 | 3.4 | >50 |
| 39 | 0.590 | 6.4 | 30 |
| 40 | 0.149 | 2.3 | 46 |
| 41 | 0.404 | 3.7 | 1.6 |
| 42 | 0.255 | 32 | >50 |
| 43 | 0.0098 | 0.65 | 31.0 |
| 44 | 0.052 | 9.1 | 5.5 |
| 45 | 0.020 | 11 | >50 |
| 46 | 0.610 | 18 | >50 |
| 47 | 0.013 | 7.2 | >50 |
| 48 | 0.019 | >50 | >50 |
| 49 | 0.065 | 5.8 | >50 |
| 50 | 0.023 | 2.9 | >50 |
| 51 | 0.130 | 20 | >50 |
| 52 | 0.129 | 4.8 | >50 |
| 53 | 0.421 | 24 | >50 |
| 54 | 0.131 | 7.7 | >50 |
| 55 | 0.140 | 9.3 | >50 |
| 56 | 0.050 | 3.2 | >50 |
| 57 | 0.171 | 16 | >50 |
| 58 | 0.047 | 3.1 | >50 |
| 59 | 0.100 | 3.8 | >50 |
| 60 | 0.045 | 1.5 | >50 |
| 61 | 0.049 | n.d. | n.d. |
| 62 | 0.345 | 0.74 | >50 |
| 63 | 0.196 | n.d. | n.d. |
| 64 | 0.091 | n.d. | n.d. |
| 65 | 0.297 | n.d. | n.d. |
| 66 | 0.069 | n.d. | n.d. |
| 67 | 0.044 | n.d. | n.d. |
| 68 | 0.085 | n.d. | n.d. |
| 69 | 0.241 | n.d. | n.d. |
| 70 | 0.208 | n.d. | n.d. |
| 71 | 1.77 | n.d. | n.d. |
| 72 | 0.088 | n.d. | n.d. |
| 73 | 0.270 | n.d. | n.d. |
| 74 | 0.037 | n.d. | n.d. |
| 75 | 0.063 | n.d. | n.d. |
| 76 | 0.257 | n.d. | n.d. |
| 77 | 0.031 | n.d. | n.d. |
| 78 | 0.267 | n.d. | n.d. |
| 79 | 0.111 | n.d. | n.d. |
| 80 | 0.358 | n.d. | n.d. |
| 81 | 0.049 | n.d. | n.d. |
| 82 | 0.032 | n.d. | n.d. |
| 83 | 0.210 | n.d. | n.d. |
| 84 | 0.072 | 18.6 | >25 |
| 85 | 0.106 | 5.7 | >25 |
| 86 | 0.300 | 5.2 | >50 |
| 87 | 0.950 | >50 | >50 |
| 88 | 0.363 | >50 | >50 |
| 89 | 0.162 | >50 | >50 |
| 90 | 0.231 | >50 | >50 |
| 91 | 0.104 | 19.4 | >50 |
| 92 | 0.105 | >50 | >50 |
| 93 | 0.650 | >50 | >50 |
| 94 | 0.073 | >50 | >50 |
| 95 | 0.029 | >50 | >50 |
| 96 | 0.073 | 7.3 | >50 |

TABLE 1-continued

| Ex. No. | TLR 9 $IC_{50}$ (μM) | TLR 7 $IC_{50}$ (μM) | TLR 8 $IC_{50}$ (μM) |
|---|---|---|---|
| 97 | 0.079 | 47.0 | >50 |
| 98 | 0.010 | 23.8 | >50 |
| 99 | 0.358 | 38.3 | >50 |
| 100 | 0.062 | 39.9 | >50 |
| 101 | 0.075 | 19.5 | >50 |
| 102 | 0.030 | 9.8 | >50 |
| 103 | 0.054 | 25.9 | >50 |
| 104 | 0.140 | 39.2 | >50 |
| 105 | 0.095 | 25.5 | >50 |
| 106 | 0.387 | 35.1 | >50 |
| 107 | 0.269 | 5.8 | >50 |
| 108 | 0.0258 | 24.0 | >50 |
| 109 | 0.090 | 17.2 | >50 |
| 110 | 0.083 | 1.2 | >50 |
| 111 | 0.024 | 1.5 | >50 |
| 112 | 0.127 | >50 | >50 |
| 113 | 0.032 | >50 | >50 |
| 114 | 0.013 | >50 | 16.7 |
| 115 | 0.024 | 1.9 | n.d. |
| 116 | 0.051 | 3.5 | >50 |
| 117 | 0.071 | 2.2 | >50 |
| 118 | 0.116 | 19.2 | >25 |
| 119 | 1.09 | n.d. | n.d. |
| 120 | 0.178 | n.d. | n.d. |
| 121 | 0.019 | 14.5 | >25 |
| 122 | 0.139 | 8.9 | >25 |
| 123 | 0.889 | n.d. | n.d. |
| 124 | 0.577 | 3.1 | >50 |
| 125 | 0.028 | 0.6 | 2.1 |
| 126 | 0.588 | n.d. | 4.5 |
| 127 | 0.031 | n.d. | n.d. |
| 128 | 0.268 | n.d. | n.d. |
| 129 | 0.185 | n.d. | n.d. |
| 130 | 0.022 | n.d. | n.d. |
| 131 | 0.059 | n.d. | n.d. |
| 132 | 0.202 | n.d. | n.d. |
| 133 | 2.20 | n.d. | n.d. |
| 134 | 0.020 | n.d. | n.d. |
| 135 | 0.023 | n.d. | n.d. |
| 136 | 0.136 | n.d. | n.d. |
| 137 | 0.019 | n.d. | n.d. |
| 138 | 0.062 | n.d. | n.d. |
| 139 | 0.211 | n.d. | n.d. |
| 140 | 0.290 | n.d. | n.d. |
| 141 | 0.248 | n.d. | n.d. |
| 142 | 0.068 | n.d. | n.d. |
| 143 | 0.085 | n.d. | n.d. |
| 144 | 0.062 | n.d. | n.d. |
| 145 | 0.024 | n.d. | n.d. |
| 146 | 0.070 | n.d. | n.d. |
| 147 | 0.199 | n.d. | n.d. |
| 148 | 0.034 | n.d. | n.d. |
| 149 | 0.047 | n.d. | n.d. |
| 150 | 0.032 | n.d. | n.d. |
| 151 | 0.172 | n.d. | n.d. |
| 152 | 0.084 | 14.7 | >25 |
| 153 | 0.0123 | 14.3 | >25 |
| 154 | 0.030 | 9.0 | >25 |
| 155 | 0.163 | n.d. | n.d. |
| 156 | 0.031 | 8.9 | >25 |
| 157 | 0.339 | n.d. | n.d. |
| 158 | 1.61 | >25 | >25 |
| 159 | 0.934 | >25 | >25 |
| 160 | 0.052 | 23.5 | >25 |
| 161 | 0.211 | >25 | >25 |
| 162 | 0.061 | 19.9 | >25 |
| 163 | 0.599 | 6.2 | >25 |
| 164 | 0.109 | >25 | >25 |
| 165 | 1.30 | >25 | >25 |
| 166 | 0.040 | 4.7 | >25 |
| 167 | 0.788 | >25 | >25 |
| 168 | 0.051 | 14.0 | >25 |
| 169 | 0.204 | 10.5 | 23.7 |
| 170 | 4.44 | n.d. | n.d. |
| 171 | 0.653 | n.d. | n.d. |
| 172 | 1.78 | n.d. | n.d. |
| 173 | 1.11 | n.d. | n.d. |
| 174 | 0.480 | >50 | >50 |

TABLE 1-continued

| Ex. No. | TLR 9 $IC_{50}$ (μM) | TLR 7 $IC_{50}$ (μM) | TLR 8 $IC_{50}$ (μM) |
|---|---|---|---|
| 175 | 0.527 | n.d. | n.d. |
| 176 | 0.680 | n.d. | n.d. |
| 177 | 0.120 | >50 | >50 |
| 178 | 0.238 | >50 | >50 |
| 179 | 0.184 | >50 | >50 |
| 180 | | >50 | >50 |
| 181 | 0.641 | >50 | >50 |
| 182 | 0.316 | >50 | >50 |
| 183 | 0.110 | >50 | >50 |
| 184 | 0.850 | >50 | >50 |
| 185 | 0.697 | >50 | >50 |
| 186 | 7.30 | >50 | >50 |
| 187 | 0.523 | >50 | >50 |
| 188 | 0.441 | >50 | >50 |
| 189 | 0.154 | >50 | >50 |
| 190 | 2.63 | >50 | >50 |
| 191 | 0.096 | 3.8 | >50 |
| 192 | 0.186 | >50 | >50 |
| 193 | 0.082 | >50 | >50 |
| 194 | 0.631 | 45.6 | >50 |
| 195 | 0.490 | >50 | >50 |
| 196 | 0.578 | >50 | >50 |
| 197 | 0.155 | >50 | >50 |
| 198 | 0.057 | >50 | >50 |
| 199 | 0.075 | 25.6 | >50 |
| 200 | 0.380 | 47.8 | >50 |
| 201 | 0.097 | 14.4 | >50 |
| 202 | 0.502 | >50 | >50 |
| 203 | 0.108 | 15.4 | >50 |
| 204 | 0.781 | >50 | >50 |
| 205 | 0.114 | 21.3 | >50 |
| 206 | 0.840 | >50 | >50 |
| 207 | 0.110 | 18.3 | >50 |
| 208 | 0.937 | >50 | >50 |
| 209 | 0.081 | 16.7 | 16.7 |
| 210 | | >50 | >50 |
| 211 | 0.165 | >50 | >50 |
| 212 | 0.456 | >50 | >50 |
| 213 | 0.335 | >50 | >50 |
| 214 | 4.66 | >50 | >50 |
| 215 | 0.070 | 17.0 | >50 |
| 216 | 0.269 | 23.2 | >50 |
| 217 | 0.125 | 12.9 | >50 |
| 218 | 0.140 | 5.6 | 48.7 |
| 219 | 0.065 | 18.5 | >50 |
| 220 | 0.683 | 41.9 | >50 |
| 221 | 0.354 | 7.8 | >50 |
| 222 | 0.133 | 35.6 | >50 |
| 223 | 0.290 | >50 | >50 |
| 224 | 0.192 | 25.7 | >50 |
| 225 | 5.35 | >50 | >50 |
| 226 | 0.898 | >50 | >50 |
| 227 | 0.407 | 27.4 | >50 |
| 228 | 0.069 | 1.4 | 16.7 |
| 229 | 0.095 | 43.2 | >50 |
| 230 | 0.036 | 32.4 | >50 |
| 231 | 0.058 | >50 | >50 |
| 232 | 0.045 | 22.4 | >50 |
| 233 | 0.058 | 29.0 | >50 |
| 234 | 0.152 | >50 | >50 |
| 235 | 1.73 | >50 | >50 |
| 236 | 0.099 | >50 | >50 |
| 237 | 0.087 | >50 | >50 |
| 238 | 0.058 | 34.6 | >50 |
| 239 | 0.290 | 51.2 | >50 |
| 240 | 0.121 | 6.6 | >50 |
| 241 | 1.71 | >50 | >50 |
| 242 | 0.158 | 14.2 | >50 |
| 243 | 0.943 | >50 | >50 |
| 244 | 3.57 | >50 | >50 |
| 245 | 1.06 | >50 | >50 |
| 246 | 0.398 | 26.2 | >50 |
| 247 | 0.030 | 21.1 | >50 |
| 248 | 0.078 | >50 | >50 |
| 249 | 0.032 | 21.5 | >50 |
| 250 | 0.110 | 36.7 | >50 |
| 251 | 0.071 | 19.5 | >50 |
| 252 | 0.059 | 14.8 | >50 |

TABLE 1-continued

| Ex. No. | TLR 9 $IC_{50}$ (μM) | TLR 7 $IC_{50}$ (μM) | TLR 8 $IC_{50}$ (μM) |
|---|---|---|---|
| 253 | 0.278 | >50 | >50 |
| 254 | 5.31 | >50 | >50 |
| 255 | 0.072 | >50 | >50 |
| 256 | 0.315 | 17.6 | >50 |
| 257 | 0.049 | 30.7 | >50 |
| 258 | 0.100 | 18.8 | >50 |
| 259 | 0.500 | >50 | >50 |
| 260 | 0.660 | 21.5 | >50 |
| 261 | 0.154 | 7.9 | >50 |
| 262 | 0.171 | 14.1 | >50 |
| 263 | 1.77 | 11.9 | n.d. |
| 264 | 0.281 | 2.3 | 20.7 |
| 265 | 1.04 | 7.6 | >50 |
| 266 | 0.097 | 18.6 | >50 |
| 267 | 0.347 | >50 | >50 |
| 268 | 0.060 | 27.6 | >50 |
| 269 | 0.176 | 12.0 | 21.5 |
| 270 | 0.065 | 17.7 | >50 |
| 271 | 0.407 | 31.6 | >50 |
| 272 | 0.600 | 0.0 | >50 |
| 273 | 0.303 | 7.5 | >50 |
| 274 | 0.051 | 26.1 | >50 |
| 275 | 0.089 | >50 | >50 |
| 276 | 0.167 | 1.5 | >50 |
| 277 | 0.269 | 1.0 | 16.3 |
| 278 | 0.058 | 9.0 | >50 |
| 279 | 1.22 | 19.5 | >50 |
| 280 | 0.073 | 0.7 | >50 |
| 281 | 0.124 | 7.0 | >50 |
| 282 | 0.108 | 7.1 | >50 |
| 283 | 0.016 | 4.7 | >50 |
| 284 | 0.118 | 5.3 | >50 |
| 285 | 0.248 | 4.8 | >50 |
| 286 | 0.041 | 29.0 | >50 |
| 287 | 0.104 | 0.0 | >50 |
| 288 | 0.105 | 31.7 | >50 |
| 289 | 0.029 | 3.2 | >50 |
| 290 | 0.144 | 22.2 | >50 |
| 291 | 0.057 | 1.8 | 34.8 |
| 292 | 0.147 | 21.7 | >50 |
| 293 | 0.011 | 8.2 | 44.2 |
| 294 | 0.055 | 2.3 | >50 |
| 295 | 0.024 | 0.7 | >50 |
| 296 | 0.022 | 14.1 | >50 |
| 297 | 0.023 | 12.5 | >50 |
| 298 | 0.058 | 3.0 | >50 |
| 299 | 0.0033 | 2.1 | >50 |
| 300 | 0.020 | 2.9 | >50 |
| 301 | 0.048 | 3.1 | >50 |
| 302 | 0.048 | 1.9 | >50 |
| 303 | 0.014 | 4.2 | >50 |
| 304 | 0.180 | 12.3 | >50 |
| 305 | 0.090 | 8.6 | >50 |
| 306 | 0.017 | 9.5 | >50 |
| 307 | 0.0035 | 20.5 | >50 |
| 308 | 0.0067 | 2.6 | >50 |
| 309 | 0.034 | 1.9 | >50 |
| 310 | 0.046 | >50 | >50 |
| 311 | 0.072 | >50 | >50 |
| 312 | 0.064 | >50 | >50 |
| 313 | 0.069 | >50 | >50 |
| 314 | 0.192 | 6.1 | >50 |
| 315 | 0.147 | 6.2 | >50 |
| 316 | 0.014 | >50 | 16.7 |
| 317 | 0.018 | >50 | 16.7 |
| 318 | 0.269 | 10.2 | >50 |
| 319 | 0.094 | 1.4 | >50 |
| 320 | 0.077 | n.d. | n.d. |
| 321 | 0.036 | 1.9 | >50 |
| 322 | 0.012 | 1.4 | >50 |
| 323 | 0.060 | 2.1 | >50 |
| 324 | 0.042 | 1.5 | >50 |
| 325 | 0.015 | 8.2 | >50 |
| 326 | 0.023 | 1.3 | >50 |
| 327 | 0.111 | 2.0 | 18.4 |
| 328 | 0.012 | 2.3 | >50 |
| 329 | 0.028 | 1.2 | >50 |
| 330 | 1.39 | n.d. | n.d. |

TABLE 1-continued

| Ex. No. | TLR 9 $IC_{50}$ (μM) | TLR 7 $IC_{50}$ (μM) | TLR 8 $IC_{50}$ (μM) |
|---|---|---|---|
| 331 | 0.143 | n.d. | n.d. |
| 332 | 0.172 | >50 | >50 |
| 333 | 0.329 | >50 | >50 |
| 334 | 0.296 | >50 | >50 |
| 335 | 0.130 | >50 | >50 |
| 336 | 0.077 | 25.4 | >50 |
| 337 | 0.053 | 1.2 | >50 |
| 338 | 0.258 | 3.8 | >50 |
| 339 | 0.343 | 12.7 | >25 |
| 340 | 0.084 | n.d. | n.d. |
| 341 | 0.037 | 2.2 | 16.7 |
| 342 | 0.123 | 12.7 | >25 |
| 343 | 0.156 | 12.6 | >25 |
| 344 | 0.0124 | 10.8 | >50 |
| 345 | 0.132 | n.d. | n.d. |
| 346 | 0.056 | 7.6 | >25 |
| 347 | 0.044 | n.d. | n.d. |
| 348 | 0.180 | n.d. | n.d. |
| 349 | 0.024 | n.d. | n.d. |
| 350 | 0.055 | n.d. | n.d. |
| 351 | 0.048 | n.d. | n.d. |
| 352 | 0.026 | n.d. | n.d. |
| 353 | 0.016 | 0.1 | 8.2 |
| 354 | 0.085 | 7.5 | 0.7 |
| 355 | 0.011 | 0.2 | 3.1 |
| 356 | 0.041 | n.d. | n.d |
| 357 | 0.032 | 0.3 | 7.9 |
| 358 | 0.0081 | 0.1 | 2.8 |
| 359 | 0.076 | 2.9 | 14.9 |
| 360 | 0.0097 | 0.7 | 26.3 |
| 361 | 0.020 | n.d. | n.d. |
| 362 | 0.152 | n.d. | n.d. |
| 363 | 0.100 | 4.3 | n.d. |
| 364 | 0.310 | >50 | >50 |
| 365 | 0.300 | 2.1 | 14.2 |
| 366 | 0.446 | n.d. | n.d. |
| 367 | 0.508 | 2.3 | 1.9 |
| 368 | 0.414 | 1.4 | 1.7 |
| 369 | 0.121 | 0.9 | n.d. |
| 370 | 0.056 | 1.8 | 4.5 |
| 371 | 0.055 | 1.8 | 6.8 |
| 372 | 0.054 | 1.4 | 5.1 |
| 374 | 0.279 | 0.8 | >50 |
| 375 | 0.203 | 1.3 | 0.4 |
| 376 | 0.206 | 0.8 | 1.4 |
| 377 | 0.346 | 1.3 | 19.6 |
| 378 | 0.349 | 2.2 | 17.1 |
| 379 | 0.098 | 1.0 | 18.8 |
| 380 | 0.174 | 1.3 | 0.3 |
| 381 | 0.140 | n.d. | n.d. |
| 382 | 3.24 | n.d. | n.d. |
| 383 | 0.068 | 2.2 | 2.3 |
| 384 | 41.0 | n.d. | n.d. |
| 385 | 0.179 | 1.2 | 5.6 |
| 386 | 0.267 | 1.7 | 4.4 |
| 387 | 0.056 | 0.0 | 7.3 |
| 388 | 0.227 | 0.4 | 3.2 |
| 389 | 0.327 | 0.3 | 1.8 |
| 390 | 0.091 | 4.2 | 10.2 |
| 391 | 0.178 | 2.1 | 11.7 |
| 392 | 0.466 | 10.2 | 6.4 |
| 393 | 0.334 | >50 | 9.5 |
| 394 | 0.563 | >50 | 5.7 |
| 395 | 1.36 | 11.2 | n.d. |
| 396 | 0.203 | 6.7 | n.d. |
| 397 | 0.086 | 2.6 | n.d. |
| 398 | 0.128 | 1.7 | n.d. |
| 399 | 0.097 | 1.0 | 2.7 |
| 400 | 0.076 | 1.5 | 1.3 |
| 401 | 0.104 | 2.7 | 1.2 |
| 402 | 0.0039 | 0.6 | 5.8 |
| 403 | 0.094 | 0.3 | 15.8 |
| 404 | 0.069 | 0.1 | 7.2 |
| 405 | 0.021 | 0.3 | 0.9 |
| 406 | 0.133 | 0.6 | 2.0 |
| 407 | 0.046 | 0.8 | 5.0 |
| 408 | 0.136 | 1.6 | 0.9 |
| 409 | 0.0053 | 1.5 | 1.0 |

TABLE 1-continued

| Ex. No. | TLR 9 $IC_{50}$ (μM) | TLR 7 $IC_{50}$ (μM) | TLR 8 $IC_{50}$ (μM) |
|---|---|---|---|
| 410 | 0.044 | n.d. | n.d. |
| 411 | 0.0009 | n.d. | n.d. |
| 412 | 0.077 | n.d. | n.d. |
| 413 | 1.88 | >50 | 5.4 |
| 414 | 177 | n.d. | n.d. |
| 415 | 0.065 | n.d. | n.d. |
| 416 | 1.19 | n.d. | n.d. |
| 417 | 0.800 | n.d. | n.d. |
| 418 | 2.51 | n.d. | n.d. |
| 419 | 2.14 | 2.3 | 8.4 |
| 420 | 0.136 | >50 | 42.2 |
| 421 | 0.139 | 0.7 | >50 |
| 422 | 0.180 | 4.0 | 27.3 |

n.d.: not determined

What is claimed is:

1. A compound of Formula (I):

(I)

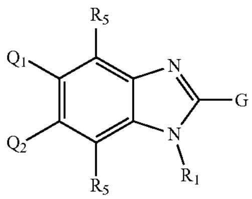

or a stereoisomer, a tautomer, a solvate, or a salt thereof, wherein:

one of $Q_1$ and $Q_2$ is A and the other of $Q_1$ and $Q_2$ is $R_5$;

G is:

(i) phenyl substituted with 1 to 2 substituents independently selected from F, Cl, Br, —CN, $C_{1-3}$ alkyl, $C_{1-2}$ fluoroalkyl, $C_{1-3}$ alkoxy, $C_{1-2}$ fluoroalkoxy, $C_{3-6}$ cycloalkyl, —$NR_xR_x$, —$C(O)NR_yR_y$, —$S(O)_2(C_{1-3}$ alkyl), —$S(O)_2$(phenyl), —$S(O)_2NR_xR_x$, —$NR_xS(O)_2$($C_{1-3}$ alkyl), —$S(O)(NH)NR_xR_x$, and —$P(O)(OCH_2CH_3)_2$;

(ii)

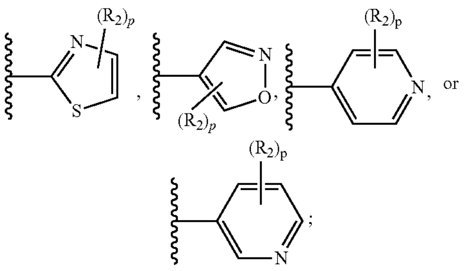

(iii)

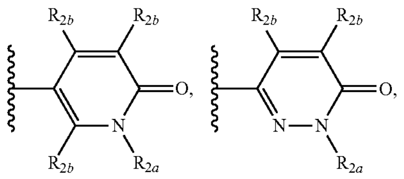

-continued

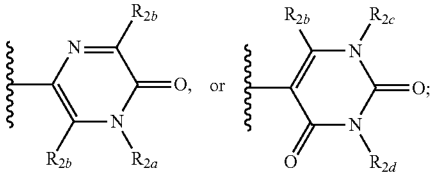

(iv)

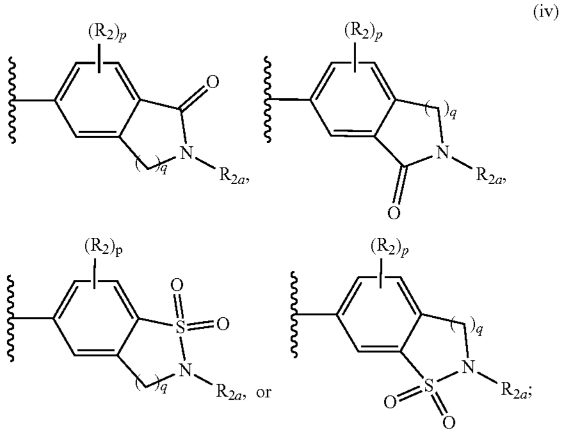

(v) a 9-membered heterocyclic ring selected from:

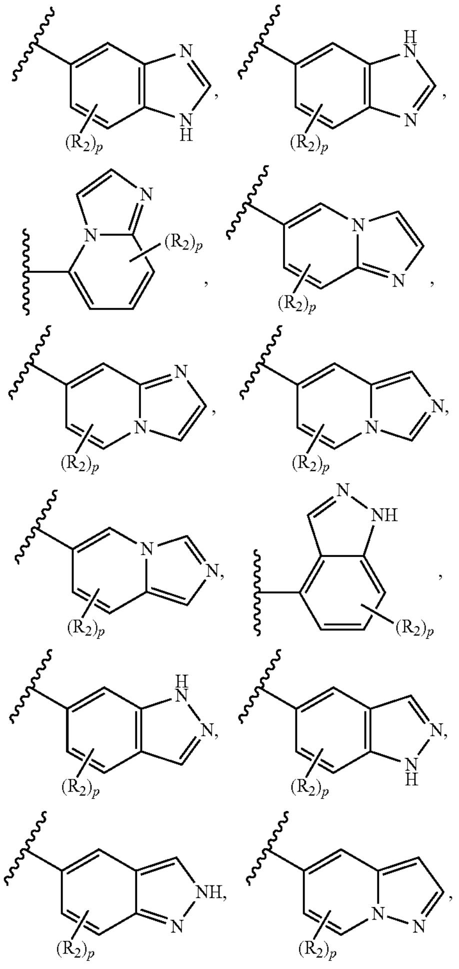

-continued
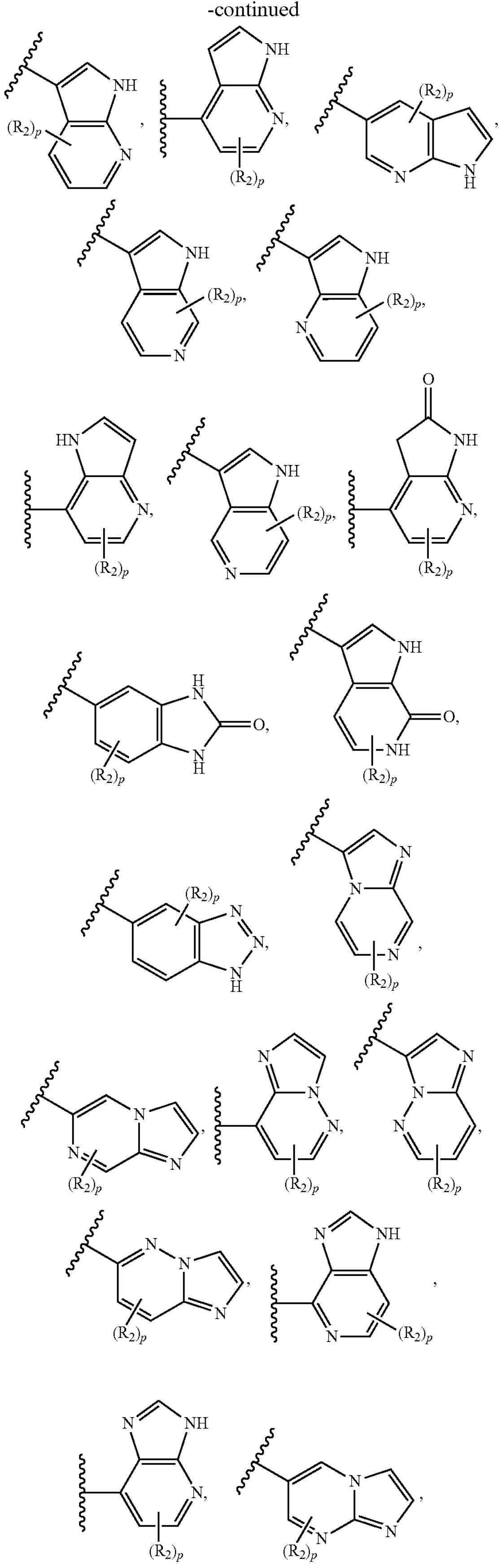
-continued
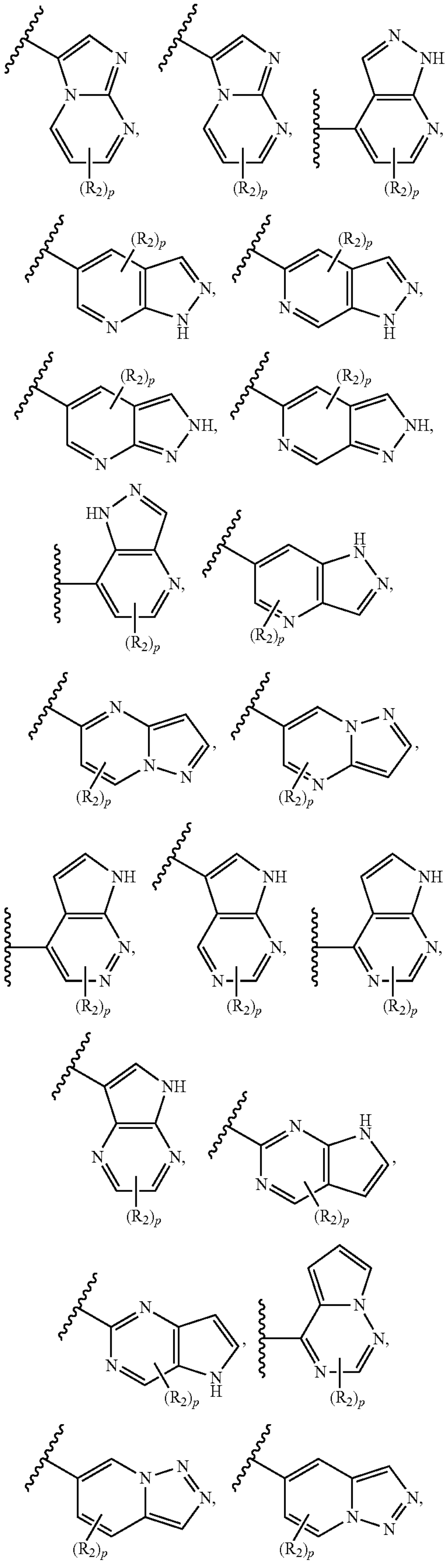

-continued
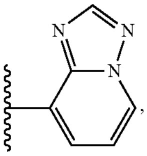, 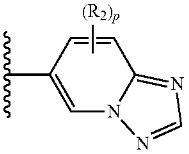
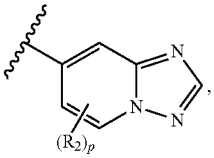 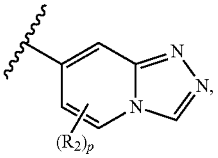
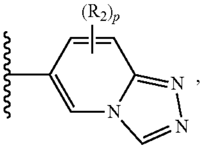, 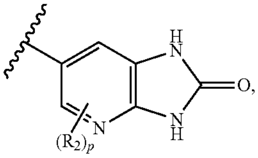
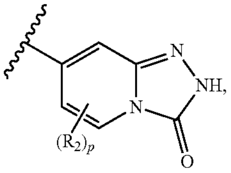 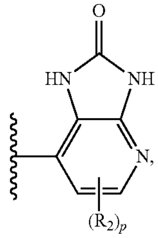
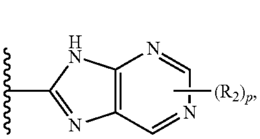 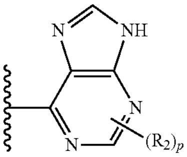,
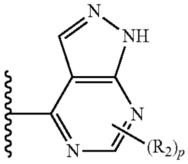, 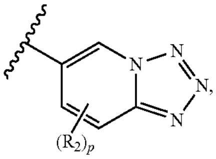
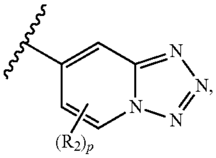 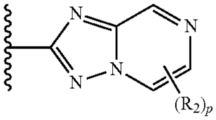,
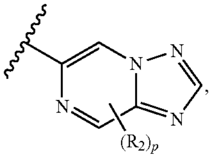 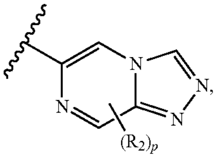
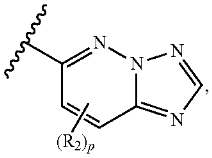 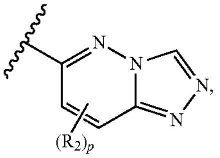
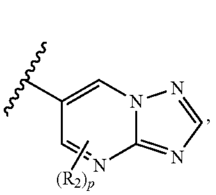 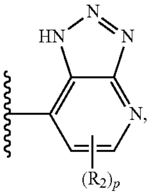
-continued
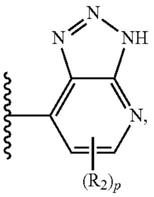 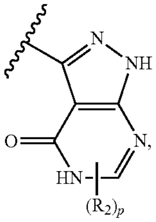 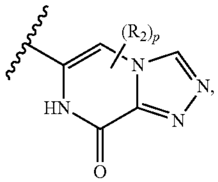
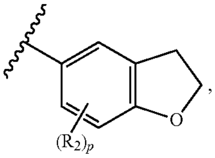 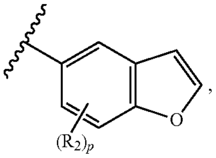
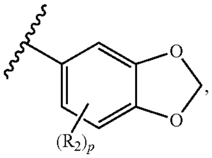 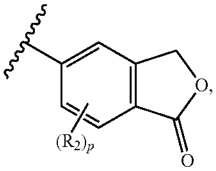
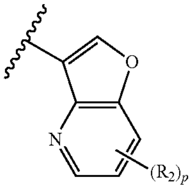, 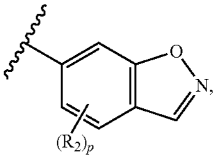
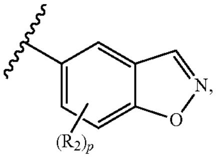 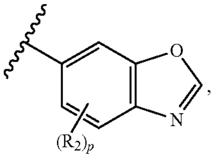
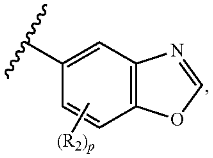 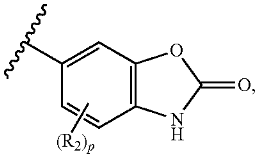
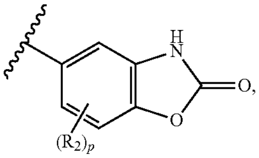 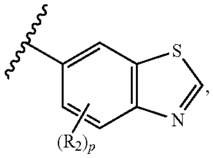
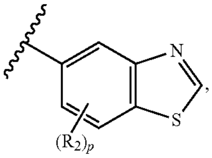 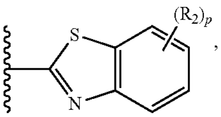,
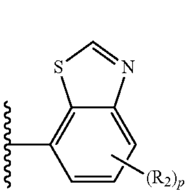, 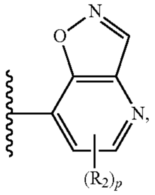

-continued

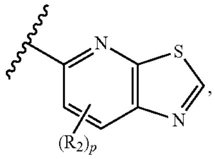, 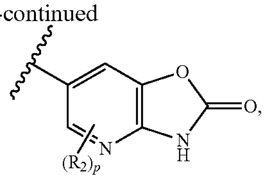, and

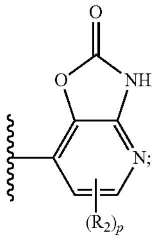;

or (vi) 10-membered heterocyclic ring selected from:

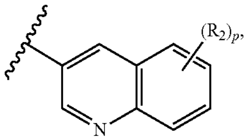, 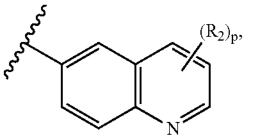,

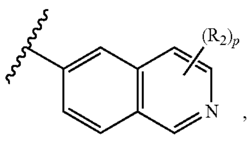, 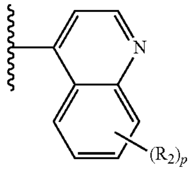,

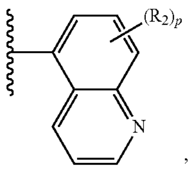, 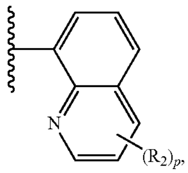, 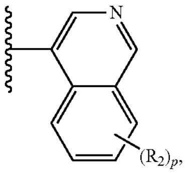,

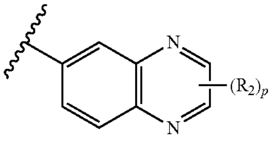, 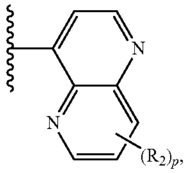,

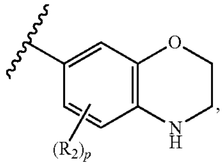, 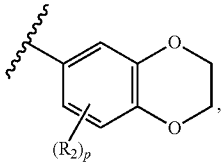, and

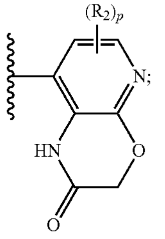;

A is piperidinyl, phenyl, pyridinyl, pyrimidinyl, 6-azabicyclo[3.2.1]octanyl, or azabicyclo[3.2.1]octanyl, each substituted with -L-$R_4$ and zero to 3 $R_{4b}$;

L is a bond, $—(CR_xR_x)_{1-2}—$, —O—, or $—C(O)(CR_xR_x)_{0-2}—$;

$R_1$ is hydrogen, $C_{1-3}$ alkyl, $C_{1-2}$ fluoroalkyl, or $C_{3-4}$ cycloalkyl;

each $R_2$ is independently halo, —CN, —OH, $—NO_2$, $C_{1-4}$ alkyl, $C_{1-2}$ fluoroalkyl, $C_{1-2}$ cyanoalkyl, $C_{1-3}$ hydroxyalkyl, $C_{1-3}$ aminoalkyl, $—O(CH_2)_{1-2}OH$, $—(CH_2)_{0-4}O(C_{1-4}$ alkyl), $C_{1-3}$ fluoroalkoxy, $—(CH_2)_{1-4}O(C_{1-3}$ alkyl), $—O(CH_2)_{1-2}OC(O)(C_{1-3}$ alkyl), $—O(CH_2)_{1-2}NR_xR_x$, $—C(O)O(C_{1-3}$ alkyl), $—(CH_2)_{0-2}C(O)NR_yR_y$, $—C(O)NR_x(C_{1-5}$ hydroxyalkyl), $—C(O)NR_x(C_{2-6}$ alkoxyalkyl), $—C(O)NR_x(C_{3-6}$ cycloalkyl), $—NR_yR_y$, $—NR_y(C_{1-3}$ fluoroalkyl), $—NR_y(C_{1-4}$ hydroxyalkyl), $—NR_xCH_2$(phenyl), $—NR_xS(O)_2(C_{3-6}$ cycloalkyl), $—NR_xC(O)(C_{1-3}$ alkyl), $—NR_xCH_2(C_{3-6}$ cycloalkyl), $—S(O)_2(C_{1-3}$ alkyl), $—S(O)_2N(C_{1-3}$ alkyl$)_2$, $—S(O)(NH)N(C_{1-3}$ alkyl$)_2$, $—(CH_2)_{0-2}(C_{3-6}$ cycloalkyl), $—(CH_2)_{0-2}$(phenyl), morpholinyl, dioxothiomorpholinyl, dimethyl pyrazolyl, methylpiperidinyl, methylpiperazinyl, amino-oxadiazolyl, imidazolyl, triazolyl, or —C(O)(thiazolyl);

$R_{2a}$ is $C_{1-6}$ alkyl, $C_{1-3}$ fluoroalkyl, $C_{1-6}$ hydroxyalkyl, $C_{1-3}$ aminoalkyl, $—(CH_2)_{0-4}O(C_{1-3}$ alkyl), $C_{3-6}$ cycloalkyl, $—(CH_2)_{1-3}C(O)NR_xR_x$, $—CH_2(C_{3-6}$ cycloalkyl), $—CH_2$(phenyl), tetrahydrofuranyl, tetrahydropyranyl, or phenyl;

each $R_{2b}$ is independently hydrogen, halo, —CN, $—NR_xR_x$, $C_{1-6}$ alkyl, $C_{1-3}$ fluoroalkyl, $C_{1-3}$ hydroxyalkyl, $C_{1-3}$ fluoroalkoxy, $—(CH_2)_{0-2}O(C_{1-3}$ alkyl), $—(CH_2)_{0-3}C(O)NR_xR_x$, $—(CH_2)_{1-3}(C_{3-6}$ cycloalkyl), $—C(O)O(C_{1-3}$ alkyl), $—C(O)NR_x(C_{1-3}$ alkyl), $—CR_x{=}CR_xR_x$, or $—CR_x{=}CH(C_{3-6}$ cycloalkyl);

$R_{2}$, is $R_{2a}$ or $R_{2b}$;

$R_{2d}$ is $R_{2a}$ or $R_{2b}$; provided that one of $R_{2c}$ and $R_{2d}$ is $R_{2a}$, and the other of $R_{2c}$ and $R_{2d}$ is $R_{2b}$;

$R_4$ is:

(i) $—N(CH_3)_2$;

(ii) $R_4$ is pyrrolidinyl, piperidinyl, piperazinyl, azepanyl, diazepanyl, pyridinyl, azaspiro[3.3]heptanyl, azabicyclo[3.2.1]octanyl, diazaspiro[3.3]heptanyl, or hexahydropyrrolo[3,4-c]pyrrolyl, each substituted with zero to 2 $R_{4a}$; or (iii)

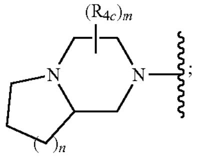;

each $R_{4a}$ is independently $C_{1-6}$ alkyl, $C_{1-3}$ fluoroalkyl, $—(CH_2)_{1-2}O(C_{1-2}$ alkyl), $C_{3-6}$ cycloalkyl, $—CH_2(C_{3-6}$ cycloalkyl), $—CH_2$(oxetanyl), $—C(O)(C_{1-4}$ alkyl), $—C(O)(C_{3-6}$ cycloalkyl), —C(O)(phenyl), $—C(O)CH_2(C_{3-6}$ cycloalkyl), $—C(O)CH_2$(phenyl), $—C(O)O(C_{1-4}$ alkyl), $—NR_x(C_{1-3}$ alkyl), $—NR_x(C_{3-6}$ cycloalkyl), azetidinyl, oxetanyl, tetrahydropyranyl, pyrrolidinyl, phenyl, or piperidinyl substituted with zero to 2 substituents selected from —OH and $—CH_3$;

$R_{4b}$ is F, Cl, or $—CH_3$;

each $R_{4c}$ is independently $C_{1-6}$ alkyl, $C_{1-3}$ fluoroalkyl, $—CH_2(C_{3-6}$ cycloalkyl), $—C(O)(C_{1-4}$ alkyl), —C(O)(phenyl), $—C(O)CH_2$(phenyl), $—C(O)OCH_2CH_3$, or $C_{3-6}$ cycloalkyl;

each $R_5$ is independently hydrogen, F, Cl, $C_{1-2}$ alkyl, $C_{1-2}$ fluoroalkyl, or cyclopropyl;

each $R_x$ is independently hydrogen or —$CH_3$;

each $R_y$ is independently hydrogen or $C_{1-6}$ alkyl;

m is zero, 1, or 2;

n is zero, 1, or 2;

p is zero, 1, 2, 3, or 4; and q is 1 or 2.

2. The compound according to claim 1 or a stereoisomer, a tautomer, a solvate, or a salt thereof, wherein $Q_1$ is $R_5$ and $Q_2$ is A.

3. The compound according to claim 1 or a stereoisomer, a tautomer, a solvate, or a salt thereof, wherein $Q_1$ is A and $Q_2$ is $R_5$.

4. The compound according to claim 1 or a stereoisomer, a tautomer, a solvate, or a salt thereof, wherein:

G is:

(i) phenyl substituted with 1 to 2 substituents independently selected from F, Cl, Br, —CN, —$CH_3$, —$OCH_3$, —$OCHF_2$, —$OCF_3$, cyclopropyl, —C(O)$NR_yR_y$, —$N(CH_3)_2$, —$S(O)_2CH_3$, —$S(O)_2$(phenyl), —$S(O)_2NR_xR_x$, —$NHS(O)_2CH_3$, —S(O)(NH)$NR_xR_x$, and —$P(O)(OCH_2CH_3)_2$;

(ii)

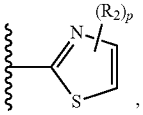
,
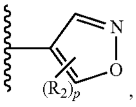
, or
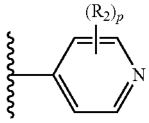
;

(iii)

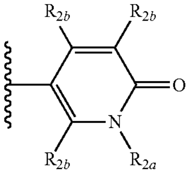
or
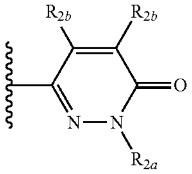
;

(iv)

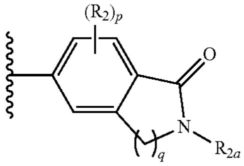
,
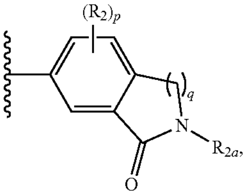

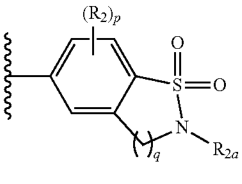
, or
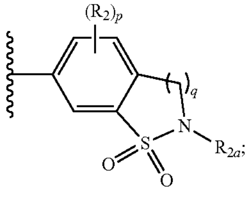

(v) a 9-membered heterocyclic ring selected from:

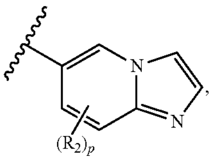
,
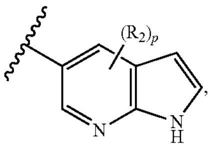
,

-continued

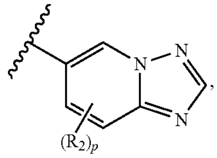
,
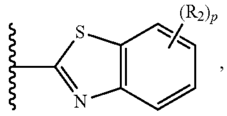
,

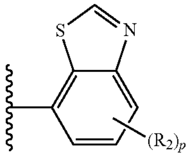
, and
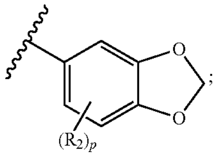
;

or (vi) 10-membered heterocyclic ring selected from:

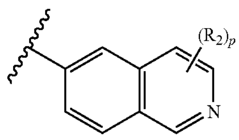
,
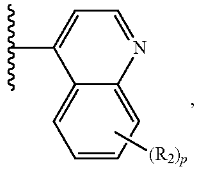
,

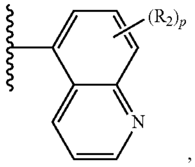

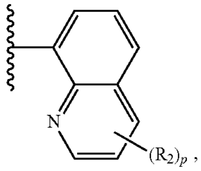
, and

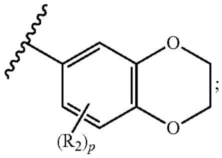
;

A is piperidinyl, phenyl, pyridinyl, pyrimidinyl, or azabicyclo[3.2.1]octanyl, each substituted with -L-$R_4$ and zero to 2 $R_{4b}$;

L is a bond, —$CH_2$—, —$CH_2CH_2$—, —O—, or —C(O)$(CH_2)_{0-2}$—;

$R_1$ is hydrogen, $C_{1-3}$ alkyl, or $C_{1-2}$ fluoroalkyl;

each $R_2$ is independently F, Cl, —CN, —OH, $C_{1-3}$ alkyl, $C_{1-2}$ fluoroalkyl, $C_{1-2}$ cyanoalkyl, $C_{1-3}$ hydroxyalkyl, $C_{1-2}$ aminoalkyl, —$(CH_2)_{0-2}O(C_{1-3}$ alkyl), $C_{3-6}$ cycloalkyl, —$NR_xR_x$, —$(CH_2)_{0-2}C(O)NR_xR_x$, —$CH_2(C_{3-6}$ cycloalkyl), —$CH_2$(phenyl), or phenyl;

$R_{2a}$ is $C_{1-4}$ alkyl, $C_{1-2}$ fluoroalkyl, $C_{1-4}$ hydroxyalkyl, —$(CH_2)_{1-3}OCH_3$, $C_{3-6}$ cycloalkyl, —$CH_2C(O)NR_xR_x$, —$CH_2(C_{3-6}$ cycloalkyl), —$CH_2$(phenyl), tetrahydrofuranyl, or phenyl;

each $R_{2b}$ is independently hydrogen, F, Cl, —CN, —$NR_xR_x$, $C_{1-6}$ alkyl, $C_{1-2}$ fluoroalkyl, $C_{1-3}$ hydroxyalkyl, —$(CH_2)_{0-2}O(C_{1-2}$ alkyl), —$(CH_2)_{0-2}C(O)NR_xR_x$, —$(CH_2)_{1-3}$(cyclopropyl), —C(O)O($C_{1-2}$ alkyl), —C(O)$NR_x(C_{1-3}$ alkyl), —$CR_x$=$CH_2$, or —CH=CH($C_{3-6}$ cycloalkyl);

$R_4$ is:

(i) pyrrolidinyl, piperidinyl, piperazinyl, pyridinyl, azaspiro[3.3]heptanyl, or azabicyclo[3.2.1]octanyl, each substituted with zero to 2 $R_{4a}$; or (ii)

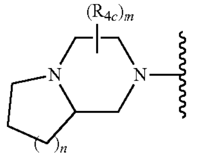

each $R_{4a}$ is independently $C_{1-6}$ alkyl, $C_{1-3}$ fluoroalkyl, $-(CH_2)_{1-2}OCH_3$, $C_{3-6}$ cycloalkyl, $-CH_2(C_{3-6}$ cycloalkyl), $-CH_2$(oxetanyl), $-C(O)(C_{1-4}$ alkyl), $-C(O)(C_{3-6}$ cycloalkyl), $-C(O)$(phenyl), $-C(O)CH_2(C_{3-6}$ cycloalkyl), $-C(O)CH_2$(phenyl), $-C(O)O(C_{1-4}$ alkyl), $-NR_x(C_{1-3}$ alkyl), $-NR_x$(cyclopropyl), azetidinyl, oxetanyl, tetrahydropyranyl, pyrrolidinyl, phenyl, or piperidinyl substituted with zero to 2 substituents selected from —OH and $-CH_3$;

$R_{4b}$ is F or $-CH_3$;

each $R_{4c}$ is independently $C_{1-6}$ alkyl, $C_{1-3}$ fluoroalkyl, $-CH_2(C_{3-6}$ cycloalkyl), $-C(O)(C_{1-4}$ alkyl), $-C(O)$(phenyl), $-C(O)CH_2$(phenyl), $-C(O)OCH_2CH_3$, or $C_{3-6}$ cycloalkyl; and each $R_5$ is independently hydrogen, F, Cl, $C_{1-2}$ alkyl, $C_{1-2}$ fluoroalkyl, or cyclopropyl.

5. The compound according to claim 1 or a stereoisomer, a tautomer, a solvate, or a salt sat thereof, wherein:

G is:

(i) phenyl substituted with 1 to 2 substituents independently selected from F, Cl, Br, —CN, $-CH_3$, $-OCH_3$, $-OCHF_2$, $-OCF_3$, cyclopropyl, $-N(CH_3)_2$, $-S(O)_2CH_3$, $-S(O)_2$(phenyl), $-NHS(O)_2CH_3$, and $-P(O)(OCH_2CH_3)_2$;

(ii)

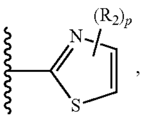 , 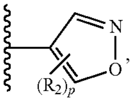 , or 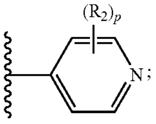 ;

(iii) a 9-membered heterocyclic ring selected from:

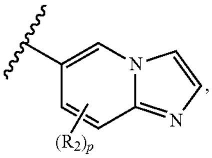 , 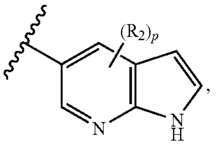 , 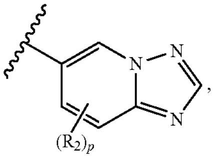 , 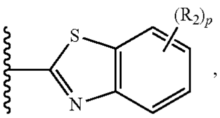 , 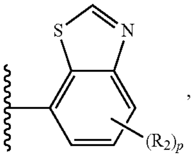 , and 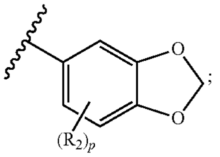 ;

or (iv) 10-membered heterocyclic ring selected from:

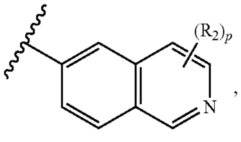 , 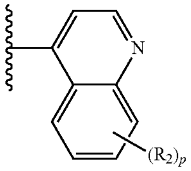 , 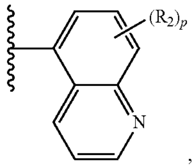 , 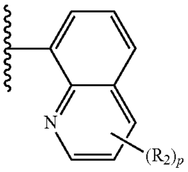 , and 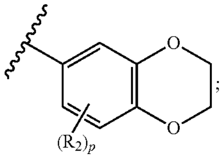 ;

A is piperidinyl, phenyl, pyridinyl, or azabicyclo[3.2.1]octanyl, each substituted with -L-$R_4$ and zero to 2 $R_{4b}$;

L is a bond, $-CH_2-$, $-CH_2CH_2-$, or —O—;

$R_1$ is hydrogen, $-CH_3$, $-CH_2CH_3$, $-CH(CH_3)_2$, $-CH_2CHF_2$, or cyclopropyl;

each $R_2$ is independently F, $-CH_3$, or $-OCH_3$;

$R_4$ is pyrrolidinyl, piperidinyl, piperazinyl, azepanyl, diazepanyl, pyridinyl, azaspiro[3.3]heptanyl, azabicyclo[3.2.1]octanyl, diazaspiro[3.3]heptanyl, or hexahydropyrrolo[3,4-c]pyrrolyl, each substituted with zero to 2 $R_{4a}$;

$R_{4a}$ is independently $-CH_3$, $-CH_2CH_3$, $-CH(CH_3)_2$, $-CH_2CH(CH_3)_2$, $-CH_2CH_2OCH_3$, $-C(O)CH(CH_3)_2$, cyclopropyl, cyclobutyl, $-CH_2$(cyclopropyl), $-CH_2$(cyclobutyl), $-CH_2$(oxetanyl), $-N(CH_3)_2$, $-N(CH_3)(CH_2CH_3)$, $-N(CH_3)$(cyclopropyl), azetidinyl, oxetanyl, tetrahydropyranyl, pyrrolidinyl, phenyl, or piperidinyl substituted with zero to 2 substituents selected from —OH and $-CH_3$; and each $R_5$ is independently hydrogen, $-CH_3$, or $-CF_3$.

6. The compound according to claim 5 or a stereoisomer, a tautomer, a solvate, or a salt thereof, wherein:

$Q_1$ is $R_5$;

$Q_2$ is A.

7. The compound according to claim 1 or a stereoisomer, a tautomer, a solvate, or a salt thereof, wherein:

$Q_1$ is A;

$Q_2$ is $R_5$;

G is dimethoxyphenyl;

A is piperidinyl substituted with -L-$R_4$;

L is a bond;

$R_1$ is hydrogen, $-CH_3$, $-CH_2CH_3$, $-CH(CH_3)_2$, or $-CH_2CHF_2$;

each $R_2$ is independently F, $-CH_3$, or $-OCH_3$;

$R_4$ is piperidinyl substituted with $R_{4a}$;

$R_{4a}$ is independently $-CH(CH_3)_2$, $-CH_2CH(CH_3)_2$, or cyclopropyl; and each $R_5$ is independently hydrogen or $-CF_3$.

8. The compound according to claim 1 or a stereoisomer, a tautomer, a solvate, or a salt thereof, wherein said compound is:

2-(3,4-dimethoxyphenyl)-6-(1'-isobutyl-[1,4'-bipiperidin]-4-yl)-1-methyl-1H-benzo[d]imidazole (26);

6-(1'-cyclopropyl-[1,4'-bipiperidin]-4-yl)-2-(3,4-dimethoxyphenyl)-1-methyl-1H-benzo[d]imidazole (27);

2-(3,4-dimethoxyphenyl)-6-(1'-isobutyl-[1,4'-bipiperidin]-4-yl)-1H-benzo[d]imidazole (28);
6-(1'-cyclopropyl-[1,4'-bipiperidin]-4-yl)-2-(3,4-dimethoxyphenyl)-1H-benzo[d]imidazole (29);
2-(3,4-dimethoxyphenyl)-6-(1'-isobutyl-[1,4'-bipiperidin]-4-yl)-1-isopropyl-1H-benzo[d]imidazole (30);
6-(1'-cyclopropyl-[1,4'-bipiperidin]-4-yl)-2-(3,4-dimethoxyphenyl)-1-isopropyl-1H-benzo[d]imidazole (31);
1-(2,2-difluoroethyl)-2-(3,4-dimethoxyphenyl)-6-(1'-isobutyl-[1,4'-bipiperidin]-4-yl)-1H-benzo[d]imidazole (32);
6-(1'-cyclopropyl-[1,4'-bipiperidin]-4-yl)-1-(2,2-difluoroethyl)-2-(3,4-dimethoxyphenyl)-1H-benzo[d]imidazole (33);
2-(3,4-dimethoxyphenyl)-5-(1'-isobutyl-[1,4'-bipiperidin]-4-yl)-1-methyl-1H-benzo[d]imidazole (34);
5-(1'-cyclopropyl-[1,4'-bipiperidin]-4-yl)-2-(3,4-dimethoxyphenyl)-1-methyl-1H-benzo[d]imidazole (35);
2-(3,4-dimethoxyphenyl)-5-(1'-isobutyl-[1,4'-bipiperidin]-4-yl)-1-isopropyl-1H-benzo[d]imidazole (36);
5-(1'-cyclopropyl-[1,4'-bipiperidin]-4-yl)-2-(3,4-dimethoxyphenyl)-1-isopropyl-1H-benzo[d]imidazole (37);
1-(2,2-difluoroethyl)-2-(3,4-dimethoxyphenyl)-5-(1'-isobutyl-[1,4'-bipiperidin]-4-yl)-1H-benzo[d]imidazole (38);
5-(1'-cyclopropyl-[1,4'-bipiperidin]-4-yl)-1-(2,2-difluoroethyl)-2-(3,4-dimethoxyphenyl)-1H-benzo[d]imidazole (39);
2-(3,4-dimethoxyphenyl)-1-ethyl-6-(1'-isobutyl-[1,4'-bipiperidin]-4-yl)-1H-benzo[d]imidazole (40);
2-(3,4-dimethoxyphenyl)-1-ethyl-5-(1'-isobutyl-[1,4'-bipiperidin]-4-yl)-1H-benzo[d]imidazole (41);
2-(3,4-dimethoxyphenyl)-5-(1'-isobutyl-[1,4'-bipiperidin]-4-yl)-6-(trifluoromethyl)-1H-benzo[d]imidazole (42);
2-(3,4-dimethoxyphenyl)-6-(1'-isobutyl-[1,4'-bipiperidin]-4-yl)-4-methyl-1H-benzo[d]imidazole (43);
6-(1'-cyclopropyl-[1,4'-bipiperidin]-4-yl)-2-(3,4-dimethoxyphenyl)-4-methyl-1H-benzo[d]imidazole (44);
2-(3,4-dimethoxyphenyl)-6-(1'-isopropyl-[1,4'-bipiperidin]-4-yl)-1,4-dimethyl-1H-benzo[d]imidazole (45);
6-(1'-cyclopropyl-[1,4'-bipiperidin]-4-yl)-2-(3,4-dimethoxyphenyl)-1,4-dimethyl-1H-benzo[d]imidazole (46);
2-(3,4-dimethoxyphenyl)-6-(1-(2-isobutyl-2-azaspiro[3.3]heptan-6-yl)piperidin-4-yl)-1,4-dimethyl-1H-benzo[d]imidazole (47);
6-(1-(2-(cyclopropylmethyl)-2-azaspiro[3.3]heptan-6-yl)piperidin-4-yl)-2-(3,4-dimethoxyphenyl)-1,4-dimethyl-1H-benzo[d]imidazole (48);
6-(1-(2-cyclobutyl-2-azaspiro[3.3]heptan-6-yl)piperidin-4-yl)-2-(3,4-dimethoxyphenyl)-1,4-dimethyl-1H-benzo[d]imidazole (49);
2-(3,4-dimethoxyphenyl)-6-(8-(1-isobutylpiperidin-4-yl)-8-azabicyclo[3.2.1]octan-3-yl)-1,4-dimethyl-1H-benzo[d]imidazole (50);
6-(8-(1-cyclopropylpiperidin-4-yl)-8-azabicyclo[3.2.1]octan-3-yl)-2-(3,4-dimethoxyphenyl)-1,4-dimethyl-1H-benzo[d]imidazole (51);
6-(1'-isobutyl-[1,4'-bipiperidin]-4-yl)-1,4-dimethyl-2-(4-(methylsulfonyl)phenyl)-1H-benzo[d]imidazole (52);
6-(1'-cyclopropyl-[1,4'-bipiperidin]-4-yl)-1,4-dimethyl-2-(4-(methylsulfonyl)phenyl)-1H-benzo[d]imidazole (53);
2-(3-fluoro-4-methoxyphenyl)-6-(1'-isobutyl-[1,4'-bipiperidin]-4-yl)-1,4-dimethyl-1H-benzo[d]imidazole (54);
6-(1'-cyclopropyl-[1,4'-bipiperidin]-4-yl)-2-(3-fluoro-4-methoxyphenyl)-1,4-dimethyl-1H-benzo[d]imidazole (55);
2-(3-fluoro-4-methoxyphenyl)-6-(1'-isobutyl-[1,4'-bipiperidin]-4-yl)-4-methyl-1H-benzo[d]imidazole (56);
6-(1'-cyclopropyl-[1,4'-bipiperidin]-4-yl)-2-(3-fluoro-4-methoxyphenyl)-4-methyl-1H-benzo[d]imidazole (57);
6-(1'-isobutyl-[1,4'-bipiperidin]-4-yl)-4-methyl-2-(4-(methylsulfonyl)phenyl)-1H-benzo[d]imidazole (58);
4-(6-(1'-isobutyl-[1,4'-bipiperidin]-4-yl)-4-methyl-1H-benzo[d]imidazol-2-yl) quinoline (59);
2-(2,6-dimethylpyridin-4-yl)-6-(1'-isobutyl-[1,4'-bipiperidin]-4-yl)-4-methyl-1H-benzo[d]imidazole (60);
6-(6-(1'-isobutyl-[1,4'-bipiperidin]-4-yl)-4-methyl-1H-benzo[d]imidazol-2-yl)-8-methoxy-[1,2,4]triazolo[1,5-a]pyridine (61);
2-(2,3-dihydrobenzo[b][1,4]dioxin-6-yl)-6-(1'-isobutyl-[1,4'-bipiperidin]-4-yl)-4-methyl-1H-benzo[d]imidazole (62);
6-(1'-isobutyl-[1,4'-bipiperidin]-4-yl)-4-methyl-2-(4-(trifluoromethoxy)phenyl)-1H-benzo[d]imidazole (63);
2-(3-chloro-4-methoxyphenyl)-6-(1'-isobutyl-[1,4'-bipiperidin]-4-yl)-4-methyl-1H-benzo[d]imidazole (64);
2-(2,2-difluorobenzo[d][1,3]dioxol-5-yl)-6-(1'-isobutyl-[1,4'-bipiperidin]-4-yl)-4-methyl-1H-benzo[d]imidazole (65);
2-(3-fluoro-4-(methylsulfonyl)phenyl)-6-(1'-isobutyl-[1,4'-bipiperidin]-4-yl)-4-methyl-1H-benzo[d]imidazole (66);
2-(3-bromo-4-(methylsulfonyl)phenyl)-6-(1'-isobutyl-[1,4'-bipiperidin]-4-yl)-4-methyl-1H-benzo[d]imidazole (67);
2-(4-cyclopropylphenyl)-6-(1'-isobutyl-[1,4'-bipiperidin]-4-yl)-4-methyl-1H-benzo[d]imidazole (68);
2-(4-(difluoromethoxy)-3-fluorophenyl)-6-(1'-isobutyl-[1,4'-bipiperidin]-4-yl)-4-methyl-1H-benzo[d]imidazole (69);
2-(6-(1'-isobutyl-[1,4'-bipiperidin]-4-yl)-4-methyl-1H-benzo[d]imidazol-2-yl) benzo[d]thiazole (70);
4-(6-(1'-isobutyl-[1,4'-bipiperidin]-4-yl)-4-methyl-1H-benzo[d]imidazol-2-yl)-3,5-dimethylisoxazole (71);
5-(6-(1'-isobutyl-[1,4'-bipiperidin]-4-yl)-4-methyl-1H-benzo[d]imidazol-2-yl) quinoline (72);
2-(3-chloro-4-(trifluoromethoxy)phenyl)-6-(1'-isobutyl-[1,4'-bipiperidin]-4-yl)-4-methyl-1H-benzo[d]imidazole (73);
6-(6-(1'-isobutyl-[1,4'-bipiperidin]-4-yl)-4-methyl-1H-benzo[d]imidazol-2-yl) isoquinoline (74);
6-(1'-isobutyl-[1,4'-bipiperidin]-4-yl)-4-methyl-2-(4-(phenylsulfonyl)phenyl)-1H-benzo[d]imidazole (75);
2-(3-(difluoromethoxy)phenyl)-6-(1'-isobutyl-[1,4'-bipiperidin]-4-yl)-4-methyl-1H-benzo[d]imidazole (76);
7-(6-(1'-isobutyl-[1,4'-bipiperidin]-4-yl)-4-methyl-1H-benzo[d]imidazol-2-yl) benzo[d]thiazole (77);
2-(4-(difluoromethoxy)phenyl)-6-(1'-isobutyl-[1,4'-bipiperidin]-4-yl)-4-methyl-1H-benzo[d]imidazole (78);
2-(6-(1'-isobutyl-[1,4'-bipiperidin]-4-yl)-4-methyl-1H-benzo[d]imidazol-2-yl)thiazole (79);
6-(1'-isobutyl-[1,4'-bipiperidin]-4-yl)-4-methyl-2-(2-(trifluoromethoxy)phenyl)-1H-benzo[d]imidazole (80);
6-(1'-isobutyl-[1,4'-bipiperidin]-4-yl)-4-methyl-2-(1H-pyrrolo[2,3-b]pyridin-5-yl)-1H-benzo[d]imidazole (81);
8-(6-(1'-isobutyl-[1,4'-bipiperidin]-4-yl)-4-methyl-1H-benzo[d]imidazol-2-yl) quinoline (82);

2-(3,4-dimethoxyphenyl)-4-fluoro-6-(1'-isopropyl-[1,4'-bipiperidin]-4-yl)-1H-benzo[d]imidazole (83);

6-(1-(8-isopropyl-8-azabicyclo[3.2.1]octan-3-yl)piperidin-4-yl)-1,4-dimethyl-2-(4-(methylsulfonyl)phenyl)-1H-benzo[d]imidazole (84-85);

6-(4-(4-isopropylpiperazin-1-yl)phenyl)-1,4-dimethyl-2-(4-(methylsulfonyl)phenyl)-1H-benzo[d]imidazole (86);

7-fluoro-6-(1'-isopropyl-[1,4'-bipiperidin]-4-yl)-2-(4-(methylsulfonyl)phenyl)-1H-benzo[d]imidazole (87);

4-fluoro-5-(1'-isopropyl-[1,4'-bipiperidin]-4-yl)-1-methyl-2-(4-(methylsulfonyl)phenyl)-1H-benzo[d]imidazole (88);

4-fluoro-5-(1-(8-isopropyl-8-azabicyclo[3.2.1]octan-3-yl)piperidin-4-yl)-1-methyl-2-(4-(methylsulfonyl)phenyl)-1H-benzo[d]imidazole (89-90);

7-fluoro-5-(1'-isopropyl-[1,4'-bipiperidin]-4-yl)-1-methyl-2-(4-(methylsulfonyl)phenyl)-1H-benzo[d]imidazole (91);

7-fluoro-5-(1-(8-isopropyl-8-azabicyclo[3.2.1]octan-3-yl)piperidin-4-yl)-1-methyl-2-(4-(methylsulfonyl)phenyl)-1H-benzo[d]imidazole (92-93);

7-fluoro-6-(1-(8-isopropyl-8-azabicyclo[3.2.1]octan-3-yl)piperidin-4-yl)-2-(4-(methylsulfonyl)phenyl)-1H-benzo[d]imidazole (94-95);

5-fluoro-6-(1'-isopropyl-[1,4'-bipiperidin]-4-yl)-1-methyl-2-(4-(methylsulfonyl)phenyl)-1H-benzo[d]imidazole (96);

5-fluoro-6-(1-(8-isopropyl-8-azabicyclo[3.2.1]octan-3-yl)piperidin-4-yl)-1-methyl-2-(4-(methylsulfonyl)phenyl)-1H-benzo[d]imidazole (97-98);

6-fluoro-5-(1'-isopropyl-[1,4'-bipiperidin]-4-yl)-1-methyl-2-(4-(methylsulfonyl)phenyl)-1H-benzo[d]imidazole (99);

6-fluoro-5-(1-(8-isopropyl-8-azabicyclo[3.2.1]octan-3-yl)piperidin-4-yl)-1-methyl-2-(4-(methylsulfonyl)phenyl)-1H-benzo[d]imidazole (100-101);

7-fluoro-6-(1'-isopropyl-[1,4'-bipiperidin]-4-yl)-1-methyl-2-(4-(methylsulfonyl)phenyl)-1H-benzo[d]imidazole (102);

7-fluoro-6-(1-(8-isopropyl-8-azabicyclo[3.2.1]octan-3-yl)piperidin-4-yl)-1-methyl-2-(4-(methylsulfonyl)phenyl)-1H-benzo[d]imidazole (103-104);

4-fluoro-6-(1'-isopropyl-[1,4'-bipiperidin]-4-yl)-1-methyl-2-(4-(methylsulfonyl)phenyl)-1H-benzo[d]imidazole (105);

4-fluoro-6-(1-(8-isopropyl-8-azabicyclo[3.2.1]octan-3-yl)piperidin-4-yl)-1-methyl-2-(4-(methylsulfonyl)phenyl)-1H-benzo[d]imidazole (106-107);

4-fluoro-1-methyl-2-(4-(methylsulfonyl)phenyl)-6-(1-(1-(oxetan-3-yl)azepan-4-yl) piperidin-4-yl)-1H-benzo[d]imidazole (108-109);

6-(1-(1-cyclobutylazepan-4-yl)piperidin-4-yl)-1,4-dimethyl-2-(4-(methylsulfonyl)phenyl)-1H-benzo[d]imidazole (110-111);

4-(6-(1'-isopropyl-[1,4'-bipiperidin]-4-yl)-1,4-dimethyl-1H-benzo[d]imidazol-2-yl) benzenesulfonamide (112);

7-fluoro-6-(1-(1-isopropylazepan-4-yl)piperidin-4-yl)-1-methyl-2-(4-(methylsulfonyl)phenyl)-1H-benzo[d]imidazole (113-114);

1-cyclopropyl-4-fluoro-6-(1'-isopropyl-[1,4'-bipiperidin]-4-yl)-2-(4-(methylsulfonyl)phenyl)-1H-benzo[d]imidazole (115);

1-cyclopropyl-4-fluoro-6-(1-(8-isopropyl-8-azabicyclo[3.2.1]octan-3-yl)piperidin-4-yl)-2-(4-(methylsulfonyl)phenyl)-1H-benzo[d]imidazole (116-117);

6-(1-(8-isobutyl-8-azabicyclo[3.2.1]octan-3-yl)piperidin-4-yl)-1,4-dimethyl-2-(4-(methylsulfonyl)phenyl)-1H-benzo[d]imidazole (118);

6-(1'-isopropyl-[1,4'-bipiperidin]-4-yl)-1,7-dimethyl-2-(4-(methylsulfonyl)phenyl)-1H-benzo[d]imidazole (119);

6-(1'-isopropyl-[1,4'-bipiperidin]-4-yl)-1,5-dimethyl-2-(4-(methylsulfonyl)phenyl)-1H-benzo[d]imidazole (120);

6-(1-(8-isobutyl-8-azabicyclo[3.2.1]octan-3-yl)piperidin-4-yl)-4-methyl-2-(4-(methylsulfonyl)phenyl)-1H-benzo[d]imidazole (121);

2-(3-fluoro-4-(methylsulfonyl)phenyl)-6-(1'-isopropyl-[1,4'-bipiperidin]-4-yl)-1,4-dimethyl-1H-benzo[d]imidazole (122);

6-(1-(8-cyclobutyl-8-azabicyclo[3.2.1]octan-3-yl)piperidin-4-yl)-2-(3-fluoro-4-(methylsulfonyl)phenyl)-1,4-dimethyl-1H-benzo[d]imidazole (123-124);

6-(6-(1'-isopropyl-[1,4'-bipiperidin]-4-yl)-1,4-dimethyl-1H-benzo[d]imidazol-2-yl)-8-methoxy-[1,2,4]triazolo[1,5-a]pyridine (125);

6-(6-(1-(8-isobutyl-8-azabicyclo[3.2.1]octan-3-yl)piperidin-4-yl)-1,4-dimethyl-1H-benzo[d]imidazol-2-yl)-8-methoxy-[1,2,4]triazolo[1,5-a]pyridine (126);

2-(3,4-dimethoxyphenyl)-4-fluoro-6-(1'-isobutyl-[1,4'-bipiperidin]-4-yl)-1H-benzo[d]imidazole (127);

6-(1'-cyclopropyl-[1,4'-bipiperidin]-4-yl)-2-(3,4-dimethoxyphenyl)-4-fluoro-1H-benzo[d]imidazole (128);

2-(3,4-dimethoxyphenyl)-5-fluoro-6-(1'-isopropyl-[1,4'-bipiperidin]-4-yl)-1H-benzo[d]imidazole (129);

2-(3,4-dimethoxyphenyl)-5-fluoro-6-(1'-isobutyl-[1,4'-bipiperidin]-4-yl)-1H-benzo[d]imidazole (130);

6-(1'-cyclopropyl-[1,4'-bipiperidin]-4-yl)-2-(3,4-dimethoxyphenyl)-5-fluoro-1H-benzo[d]imidazole (131);

2-(3,4-dimethoxyphenyl)-7-fluoro-6-(1'-isopropyl-[1,4'-bipiperidin]-4-yl)-1H-benzo[d]imidazole (132);

2-(3,4-dimethoxyphenyl)-7-fluoro-6-(1'-isobutyl-[1,4'-bipiperidin]-4-yl)-1H-benzo[d]imidazole (133);

6-(1-(1-isopropylazepan-4-yl)piperidin-4-yl)-1,4-dimethyl-2-(4-(methylsulfonyl)phenyl)-1H-benzo[d]imidazole (134);

6-(1-(1-cyclobutylazepan-4-yl)piperidin-4-yl)-1,4-dimethyl-2-(4-(methylsulfonyl)phenyl)-1H-benzo[d]imidazole (135);

6-(1-(1-isobutylazepan-4-yl)piperidin-4-yl)-1,4-dimethyl-2-(4-(methylsulfonyl)phenyl)-1H-benzo[d]imidazole (136);

6-(1-(1-(cyclopropylmethyl)azepan-4-yl)piperidin-4-yl)-1,4-dimethyl-2-(4-(methylsulfonyl)phenyl)-1H-benzo[d]imidazole (137);

6-(1-(1-(cyclobutylmethyl)azepan-4-yl)piperidin-4-yl)-1,4-dimethyl-2-(4-(methylsulfonyl)phenyl)-1H-benzo[d]imidazole (138);

6-(1-(2-isopropyl-2-azaspiro[3.3]heptan-6-yl)piperidin-4-yl)-1,4-dimethyl-2-(4-(methylsulfonyl)phenyl)-1H-benzo[d]imidazole (139);

6-(1-(2-cyclobutyl-2-azaspiro[3.3]heptan-6-yl)piperidin-4-yl)-1,4-dimethyl-2-(4-(methylsulfonyl)phenyl)-1H-benzo[d]imidazole (140);

6-(1-(2-isobutyl-2-azaspiro[3.3]heptan-6-yl)piperidin-4-yl)-1,4-dimethyl-2-(4-(methylsulfonyl)phenyl)-1H-benzo[d]imidazole (141);

6-(1-(2-(cyclopropylmethyl)-2-azaspiro[3.3]heptan-6-yl) piperidin-4-yl)-1,4-dimethyl-2-(4-(methylsulfonyl) phenyl)-1H-benzo[d]imidazole (142);

6-(1-(2-(cyclobutylmethyl)-2-azaspiro[3.3]heptan-6-yl)piperidin-4-yl)-1,4-dimethyl-2-(4-(methylsulfonyl)phenyl)-1H-benzo[d]imidazole (143);

2-(3,4-dimethoxyphenyl)-6-(1-(8-isopropyl-8-azabicyclo[3.2.1]octan-3-yl)piperidin-4-yl)-1,4-dimethyl-1H-benzo[d]imidazole (144-145);

6-(1-(8-cyclobutyl-8-azabicyclo[3.2.1]octan-3-yl)piperidin-4-yl)-2-(3,4-dimethoxyphenyl)-1,4-dimethyl-1H-benzo[d]imidazole (146-147);

6-(1-(8-(cyclopropylmethyl)-8-azabicyclo[3.2.1]octan-3-yl)piperidin-4-yl)-2-(3,4-dimethoxyphenyl)-1,4-dimethyl-1H-benzo[d]imidazole (148-149);

6-(1-(8-(cyclobutylmethyl)-8-azabicyclo[3.2.1]octan-3-yl)piperidin-4-yl)-2-(3,4-dimethoxyphenyl)-1,4-dimethyl-1H-benzo[d]imidazole (150-151);

6-(1-(8-cyclobutyl-8-azabicyclo[3.2.1]octan-3-yl)piperidin-4-yl)-1,4-dimethyl-2-(4-(methylsulfonyl)phenyl)-1H-benzo[d]imidazole (152-153);

6-(1-(8-(cyclopropylmethyl)-8-azabicyclo[3.2.1]octan-3-yl)piperidin-4-yl)-1,4-dimethyl-2-(4-(methylsulfonyl)phenyl)-1H-benzo[d]imidazole (154-155);

6-(1-(8-(cyclobutylmethyl)-8-azabicyclo[3.2.1]octan-3-yl)piperidin-4-yl)-1,4-dimethyl-2-(4-(methylsulfonyl)phenyl)-1H-benzo[d]imidazole (156-157);

1,4-dimethyl-2-(4-(methylsulfonyl)phenyl)-6-(1-(8-(oxetan-3-yl)-8-azabicyclo[3.2.1]octan-3-yl)piperidin-4-yl)-1H-benzo[d]imidazole (158-159);

1,4-dimethyl-2-(4-(methylsulfonyl)phenyl)-6-(1-(8-(tetrahydro-2H-pyran-4-yl)-8-azabicyclo[3.2.1]octan-3-yl)piperidin-4-yl)-1H-benzo[d]imidazole (160-161);

6-(1-(8-(2-methoxyethyl)-8-azabicyclo[3.2.1]octan-3-yl)piperidin-4-yl)-1,4-dimethyl-2-(4-(methylsulfonyl)phenyl)-1H-benzo[d]imidazole (162-163);

2-(3,4-dimethoxyphenyl)-1,4-dimethyl-6-(1-(8-(oxetan-3-yl)-8-azabicyclo[3.2.1]octan-3-yl)piperidin-4-yl)-1H-benzo[d]imidazole (164-165);

2-(3,4-dimethoxyphenyl)-1,4-dimethyl-6-(1-(8-(tetrahydro-2H-pyran-4-yl)-8-azabicyclo[3.2.1]octan-3-yl)piperidin-4-yl)-1H-benzo[d]imidazole (166-167);

2-(3,4-dimethoxyphenyl)-6-(1-(8-(2-methoxyethyl)-8-azabicyclo[3.2.1]octan-3-yl)piperidin-4-yl)-1,4-dimethyl-1H-benzo[d]imidazole (168-169);

6-(4-(4-isobutylpiperazin-1-yl)phenyl)-1,4-dimethyl-2-(4-(methylsulfonyl)phenyl)-1H-benzo[d]imidazole (170);

6-(4-(4-(cyclopropylmethyl)piperazin-1-yl)phenyl)-1,4-dimethyl-2-(4-(methylsulfonyl)phenyl)-1H-benzo[d]imidazole (171);

6-(4-(4-(cyclobutylmethyl)piperazin-1-yl)phenyl)-1,4-dimethyl-2-(4-(methylsulfonyl)phenyl)-1H-benzo[d]imidazole (172);

6-(4-(4-(2-methoxyethyl)piperazin-1-yl)phenyl)-1,4-dimethyl-2-(4-(methylsulfonyl)phenyl)-1H-benzo[d]imidazole (173);

6-(4-(4-cyclobutylpiperazin-1-yl)phenyl)-1,4-dimethyl-2-(4-(methylsulfonyl)phenyl)-1H-benzo[d]imidazole (174);

6-(1'-cyclopropyl-[1,4'-bipiperidin]-4-yl)-2-(3,4-dimethoxyphenyl)-7-fluoro-1H-benzo[d]imidazole (175);

1,4-dimethyl-2-(4-(methylsulfonyl)phenyl)-6-(4-(4-(tetrahydro-2H-pyran-4-yl)piperazin-1-yl)phenyl)-1H-benzo[d]imidazole (176);

7-fluoro-6-(1'-isobutyl-[1,4'-bipiperidin]-4-yl)-2-(4-(methylsulfonyl)phenyl)-1H-benzo[d]imidazole (177);

6-(1'-cyclopropyl-[1,4'-bipiperidin]-4-yl)-7-fluoro-2-(4-(methylsulfonyl)phenyl)-1H-benzo[d]imidazole (178);

6-(1'-(cyclopropylmethyl)-[1,4'-bipiperidin]-4-yl)-7-fluoro-2-(4-(methylsulfonyl)phenyl)-1H-benzo[d]imidazole (179);

6-(1'-cyclobutyl-[1,4'-bipiperidin]-4-yl)-7-fluoro-2-(4-(methylsulfonyl)phenyl)-1H-benzo[d]imidazole (180);

7-fluoro-2-(4-(methylsulfonyl)phenyl)-6-(1'-(oxetan-3-yl)-[1,4'-bipiperidin]-4-yl)-1H-benzo[d]imidazole (181);

7-fluoro-2-(4-(methylsulfonyl)phenyl)-6-(1'-(tetrahydro-2H-pyran-4-yl)-[1,4'-bipiperidin]-4-yl)-1H-benzo[d]imidazole (182);

7-fluoro-2-(4-(methylsulfonyl)phenyl)-6-(1'-(oxetan-3-ylmethyl)-[1,4'-bipiperidin]-4-yl)-1H-benzo[d]imidazole (183);

4-fluoro-5-(1'-isobutyl-[1,4'-bipiperidin]-4-yl)-1-methyl-2-(4-(methylsulfonyl)phenyl)-1H-benzo[d]imidazole (184);

5-(1'-cyclopropyl-[1,4'-bipiperidin]-4-yl)-4-fluoro-1-methyl-2-(4-(methylsulfonyl)phenyl)-1H-benzo[d]imidazole (185);

4-fluoro-1-methyl-2-(4-(methylsulfonyl)phenyl)-5-(1'-(oxetan-3-yl)-[1,4'-bipiperidin]-4-yl)-1H-benzo[d]imidazole (186);

4-fluoro-1-methyl-2-(4-(methylsulfonyl)phenyl)-5-(1'-(tetrahydro-2H-pyran-4-yl)-[1,4'-bipiperidin]-4-yl)-1H-benzo[d]imidazole (187);

4-fluoro-5-(1'-(2-methoxyethyl)-[1,4'-bipiperidin]-4-yl)-1-methyl-2-(4-(methylsulfonyl)phenyl)-1H-benzo[d]imidazole (188);

4-fluoro-5-(1-(8-isobutyl-8-azabicyclo[3.2.1]octan-3-yl)piperidin-4-yl)-1-methyl-2-(4-(methylsulfonyl)phenyl)-1H-benzo[d]imidazole (189-190);

5-(1-(8-(cyclopropylmethyl)-8-azabicyclo[3.2.1]octan-3-yl) piperidin-4-yl)-4-fluoro-1-methyl-2-(4-(methylsulfonyl)phenyl)-1H-benzo[d]imidazole (191-192);

4-fluoro-1-methyl-2-(4-(methylsulfonyl)phenyl)-5-(1-(8-(oxetan-3-ylmethyl)-8-azabicyclo[3.2.1]octan-3-yl)piperidin-4-yl)-1H-benzo[d]imidazole (193-194);

4-fluoro-1-methyl-2-(4-(methylsulfonyl)phenyl)-5-(1-(8-(oxetan-3-yl)-8-azabicyclo[3.2.1]octan-3-yl)piperidin-4-yl)-1H-benzo[d]imidazole (195-196);

4-fluoro-1-methyl-2-(4-(methylsulfonyl)phenyl)-5-(1-(8-(tetrahydro-2H-pyran-4-yl)-8-azabicyclo[3.2.1]octan-3-yl)piperidin-4-yl)-1H-benzo[d]imidazole (197-198);

4-fluoro-5-(1-(8-(2-methoxyethyl)-8-azabicyclo[3.2.1]octan-3-yl)piperidin-4-yl)-1-methyl-2-(4-(methylsulfonyl)phenyl)-1H-benzo[d]imidazole (199-200);

7-fluoro-5-(1'-isobutyl-[1,4'-bipiperidin]-4-yl)-1-methyl-2-(4-(methylsulfonyl)phenyl)-1H-benzo[d]imidazole (201);

5-(1'-cyclopropyl-[1,4'-bipiperidin]-4-yl)-7-fluoro-1-methyl-2-(4-(methylsulfonyl)phenyl)-1H-benzo[d]imidazole (202);

5-(1'-(cyclopropylmethyl)-[1,4'-bipiperidin]-4-yl)-7-fluoro-1-methyl-2-(4-(methylsulfonyl)phenyl)-1H-benzo[d]imidazole (203);

7-fluoro-1-methyl-2-(4-(methylsulfonyl)phenyl)-5-(1'-(oxetan-3-ylmethyl)-[1,4'-bipiperidin]-4-yl)-1H-benzo[d]imidazole (204);

5-(1'-cyclobutyl-[1,4'-bipiperidin]-4-yl)-7-fluoro-1-methyl-2-(4-(methylsulfonyl)phenyl)-1H-benzo[d]imidazole (205);

7-fluoro-1-methyl-2-(4-(methylsulfonyl)phenyl)-5-(1'-(oxetan-3-yl)-[1,4'-bipiperidin]-4-yl)-1H-benzo[d]imidazole (206);

7-fluoro-1-methyl-2-(4-(methylsulfonyl)phenyl)-5-(1'-(tetrahydro-2H-pyran-4-yl)-[1,4'-bipiperidin]-4-yl)-1H-benzo[d]imidazole (207);

7-fluoro-5-(1'-(2-methoxyethyl)-[1,4'-bipiperidin]-4-yl)-1-methyl-2-(4-(methylsulfonyl)phenyl)-1H-benzo[d]imidazole (208);

7-fluoro-5-(1-(8-isobutyl-8-azabicyclo[3.2.1]octan-3-yl)piperidin-4-yl)-1-methyl-2-(4-(methylsulfonyl)phenyl)-1H-benzo[d]imidazole (209-210);

7-fluoro-1-methyl-2-(4-(methylsulfonyl)phenyl)-5-(1-(8-(tetrahydro-2H-pyran-4-yl)-8-azabicyclo[3.2.1]octan-3-yl) piperidin-4-yl)-1H-benzo[d]imidazole (211-212);

7-fluoro-1-methyl-2-(4-(methylsulfonyl)phenyl)-5-(1-(8-(oxetan-3-yl)-8-azabicyclo[3.2.1]octan-3-yl)piperidin-4-yl)-1H-benzo[d]imidazole (213-214);

5-(1-(8-cyclobutyl-8-azabicyclo[3.2.1]octan-3-yl)piperidin-4-yl)-7-fluoro-1-methyl-2-(4-(methylsulfonyl)phenyl)-1H-benzo[d]imidazole (215-216);

5-(1-(8-(cyclopropylmethyl)-8-azabicyclo[3.2.1]octan-3-yl) piperidin-4-yl)-7-fluoro-1-methyl-2-(4-(methylsulfonyl)phenyl)-1H-benzo[d]imidazole (217-218);

7-fluoro-6-(1-(8-isobutyl-8-azabicyclo[3.2.1]octan-3-yl)piperidin-4-yl)-2-(4-(methylsulfonyl)phenyl)-1H-benzo[d]imidazole (219-220);

5-fluoro-6-(1'-isobutyl-[1,4'-bipiperidin]-4-yl)-1-methyl-2-(4-(methylsulfonyl)phenyl)-1H-benzo[d]imidazole (221);

6-(1'-cyclopropyl-[1,4'-bipiperidin]-4-yl)-5-fluoro-1-methyl-2-(4-(methylsulfonyl)phenyl)-1H-benzo[d]imidazole (222);

6-(1'-cyclobutyl-[1,4'-bipiperidin]-4-yl)-5-fluoro-1-methyl-2-(4-(methylsulfonyl)phenyl)-1H-benzo[d]imidazole (223);

6-(1'-(cyclopropylmethyl)-[1,4'-bipiperidin]-4-yl)-5-fluoro-1-methyl-2-(4-(methylsulfonyl)phenyl)-1H-benzo[d]imidazole (224);

5-fluoro-1-methyl-2-(4-(methylsulfonyl)phenyl)-6-(1'-(oxetan-3-yl)-[1,4'-bipiperidin]-4-yl)-1H-benzo[d]imidazole (225);

5-fluoro-1-methyl-2-(4-(methylsulfonyl)phenyl)-6-(1'-(tetrahydro-2H-pyran-4-yl)-[1,4'-bipiperidin]-4-yl)-1H-benzo[d]imidazole (226);

5-fluoro-6-(1'-(2-methoxyethyl)-[1,4'-bipiperidin]-4-yl)-1-methyl-2-(4-(methylsulfonyl)phenyl)-1H-benzo[d]imidazole (227);

5-fluoro-6-(1-(8-isobutyl-8-azabicyclo[3.2.1]octan-3-yl)piperidin-4-yl)-1-methyl-2-(4-(methylsulfonyl)phenyl)-1H-benzo[d]imidazole (228-229);

6-(1-(8-(cyclopropylmethyl)-8-azabicyclo[3.2.1]octan-3-yl)piperidin-4-yl)-5-fluoro-1-methyl-2-(4-(methylsulfonyl)phenyl)-1H-benzo[d]imidazole (230-231);

6-(1-(8-cyclobutyl-8-azabicyclo[3.2.1]octan-3-yl)piperidin-4-yl)-5-fluoro-1-methyl-2-(4-(methylsulfonyl)phenyl)-1H-benzo[d]imidazole (232-233);

5-fluoro-1-methyl-2-(4-(methylsulfonyl)phenyl)-6-(1-(8-(oxetan-3-yl)-8-azabicyclo[3.2.1]octan-3-yl)piperidin-4-yl)-1H-benzo[d]imidazole (234-235);

5-fluoro-1-methyl-2-(4-(methylsulfonyl)phenyl)-6-(1-(8-(tetrahydro-2H-pyran-4-yl)-8-azabicyclo[3.2.1]octan-3-yl) piperidin-4-yl)-1H-benzo[d]imidazole (236-237);

5-fluoro-6-(1-(8-(2-methoxyethyl)-8-azabicyclo[3.2.1]octan-3-yl) piperidin-4-yl)-1-methyl-2-(4-(methylsulfonyl)phenyl)-1H-benzo[d]imidazole (238-239);

6-fluoro-5-(1'-isobutyl-[1,4'-bipiperidin]-4-yl)-1-methyl-2-(4-(methylsulfonyl)phenyl)-1H-benzo[d]imidazole (240);

5-(1'-cyclopropyl-[1,4'-bipiperidin]-4-yl)-6-fluoro-1-methyl-2-(4-(methylsulfonyl)phenyl)-1H-benzo[d]imidazole (241);

5-(1'-(cyclopropylmethyl)-[1,4'-bipiperidin]-4-yl)-6-fluoro-1-methyl-2-(4-(methylsulfonyl)phenyl)-1H-benzo[d]imidazole (242);

5-(1'-cyclobutyl-[1,4'-bipiperidin]-4-yl)-6-fluoro-1-methyl-2-(4-(methylsulfonyl)phenyl)-1H-benzo[d]imidazole (243);

6-fluoro-1-methyl-2-(4-(methylsulfonyl)phenyl)-5-(1'-(oxetan-3-yl)-[1,4'-bipiperidin]-4-yl)-1H-benzo[d]imidazole (244);

6-fluoro-1-methyl-2-(4-(methylsulfonyl)phenyl)-5-(1'-(tetrahydro-2H-pyran-4-yl)-[1,4'-bipiperidin]-4-yl)-1H-benzo[d]imidazole (245);

6-fluoro-5-(1'-(2-methoxyethyl)-[1,4'-bipiperidin]-4-yl)-1-methyl-2-(4-(methylsulfonyl)phenyl)-1H-benzo[d]imidazole (246);

6-fluoro-5-(1-(8-isobutyl-8-azabicyclo[3.2.1]octan-3-yl)piperidin-4-yl)-1-methyl-2-(4-(methylsulfonyl)phenyl)-1H-benzo[d]imidazole (247-248);

5-(1-(8-(cyclopropylmethyl)-8-azabicyclo[3.2.1]octan-3-yl) piperidin-4-yl)-6-fluoro-1-methyl-2-(4-(methylsulfonyl)phenyl)-1H-benzo[d]imidazole (249-250);

5-(1-(8-cyclobutyl-8-azabicyclo[3.2.1]octan-3-yl)piperidin-4-yl)-6-fluoro-1-methyl-2-(4-(methylsulfonyl)phenyl)-1H-benzo[d]imidazole (251-252);

6-fluoro-1-methyl-2-(4-(methylsulfonyl)phenyl)-5-(1-(8-(oxetan-3-yl)-8-azabicyclo[3.2.1]octan-3-yl)piperidin-4-yl)-1H-benzo[d]imidazole (253-254);

6-fluoro-1-methyl-2-(4-(methylsulfonyl)phenyl)-5-(1-(8-(tetrahydro-2H-pyran-4-yl)-8-azabicyclo[3.2.1]octan-3-yl) piperidin-4-yl)-1H-benzo[d]imidazole (255-256);

6-fluoro-5-(1-(8-(2-methoxyethyl)-8-azabicyclo[3.2.1]octan-3-yl) piperidin-4-yl)-1-methyl-2-(4-(methylsulfonyl)phenyl)-1H-benzo[d]imidazole (257-258);

7-fluoro-6-(1'-isobutyl-[1,4'-bipiperidin]-4-yl)-1-methyl-2-(4-(methylsulfonyl)phenyl)-1H-benzo[d]imidazole (259);

6-(1'-cyclopropyl-[1,4'-bipiperidin]-4-yl)-7-fluoro-1-methyl-2-(4-(methylsulfonyl)phenyl)-1H-benzo[d]imidazole (260);

6-(1'-(cyclopropylmethyl)-[1,4'-bipiperidin]-4-yl)-7-fluoro-1-methyl-2-(4-(methylsulfonyl)phenyl)-1H-benzo[d]imidazole (261);

6-(1'-cyclobutyl-[1,4'-bipiperidin]-4-yl)-7-fluoro-1-methyl-2-(4-(methylsulfonyl)phenyl)-1H-benzo[d]imidazole (262);

7-fluoro-1-methyl-2-(4-(methylsulfonyl)phenyl)-6-(1'-(oxetan-3-yl)-[1,4'-bipiperidin]-4-yl)-1H-benzo[d]imidazole (263);

7-fluoro-1-methyl-2-(4-(methylsulfonyl)phenyl)-6-(1'-(tetrahydro-2H-pyran-4-yl)-[1,4'-bipiperidin]-4-yl)-1H-benzo[d]imidazole (264);

7-fluoro-6-(1'-(2-methoxyethyl)-[1,4'-bipiperidin]-4-yl)-1-methyl-2-(4-(methylsulfonyl)phenyl)-1H-benzo[d]imidazole (265);

7-fluoro-6-(1-(8-isobutyl-8-azabicyclo[3.2.1]octan-3-yl)piperidin-4-yl)-1-methyl-2-(4-(methylsulfonyl)phenyl)-1H-benzo[d]imidazole (266-267);

6-(1-(8-(cyclopropylmethyl)-8-azabicyclo[3.2.1]octan-3-yl) piperidin-4-yl)-7-fluoro-1-methyl-2-(4-(methylsulfonyl)phenyl)-1H-benzo[d]imidazole (268-269);

6-(1-(8-cyclobutyl-8-azabicyclo[3.2.1]octan-3-yl)piperidin-4-yl)-7-fluoro-1-methyl-2-(4-(methylsulfonyl)phenyl)-1H-benzo[d]imidazole (270-271);

7-fluoro-1-methyl-2-(4-(methylsulfonyl)phenyl)-6-(1-(8-(oxetan-3-yl)-8-azabicyclo[3.2.1]octan-3-yl)piperidin-4-yl)-1H-benzo[d]imidazole (272-273);

7-fluoro-1-methyl-2-(4-(methylsulfonyl)phenyl)-6-(1-(8-(tetrahydro-2H-pyran-4-yl)-8-azabicyclo[3.2.1]octan-3-yl) piperidin-4-yl)-1H-benzo[d]imidazole (274-275);

7-fluoro-6-(1-(8-(2-methoxyethyl)-8-azabicyclo[3.2.1]octan-3-yl)piperidin-4-yl)-1-methyl-2-(4-(methylsulfonyl)phenyl)-1H-benzo[d]imidazole (276-277);

4-fluoro-6-(1'-isobutyl-[1,4'-bipiperidin]-4-yl)-1-methyl-2-(4-(methylsulfonyl)phenyl)-1H-benzo[d]imidazole (278);

4-fluoro-1-methyl-2-(4-(methylsulfonyl)phenyl)-6-(1'-(oxetan-3-yl)-[1,4'-bipiperidin]-4-yl)-1H-benzo[d]imidazole (279);

4-fluoro-1-methyl-2-(4-(methylsulfonyl)phenyl)-6-(1'-(tetrahydro-2H-pyran-4-yl)-[1,4'-bipiperidin]-4-yl)-1H-benzo[d]imidazole (280);

4-fluoro-6-(1'-(2-methoxyethyl)-[1,4'-bipiperidin]-4-yl)-1-methyl-2-(4-(methylsulfonyl)phenyl)-1H-benzo[d]imidazole (281);

6-(1-(8-(cyclopropylmethyl)-8-azabicyclo[3.2.1]octan-3-yl) piperidin-4-yl)-4-fluoro-1-methyl-2-(4-(methylsulfonyl)phenyl)-1H-benzo[d]imidazole (282-283);

4-fluoro-6-(1-(8-isobutyl-8-azabicyclo[3.2.1]octan-3-yl) piperidin-4-yl)-1-methyl-2-(4-(methylsulfonyl)phenyl)-1H-benzo[d]imidazole (284-285);

4-fluoro-1-methyl-2-(4-(methylsulfonyl)phenyl)-6-(1-(8-(oxetan-3-yl)-8-azabicyclo[3.2.1]octan-3-yl)piperidin-4-yl)-1H-benzo[d]imidazole (286-287);

4-fluoro-1-methyl-2-(4-(methylsulfonyl)phenyl)-6-(1-(8-(tetrahydro-2H-pyran-4-yl)-8-azabicyclo[3.2.1]octan-3-yl) piperidin-4-yl)-1H-benzo[d]imidazole (288-289);

4-fluoro-6-(1-(8-(2-methoxyethyl)-8-azabicyclo[3.2.1]octan-3-yl) piperidin-4-yl)-1-methyl-2-(4-(methylsulfonyl)phenyl)-1H-benzo[d]imidazole (290-291);

6-(1-(8-cyclobutyl-8-azabicyclo[3.2.1]octan-3-yl)piperidin-4-yl)-4-fluoro-1-methyl-2-(4-(methylsulfonyl)phenyl)-1H-benzo[d]imidazole (292-293);

4-fluoro-6-(1-(1-isopropylazepan-4-yl)piperidin-4-yl)-1-methyl-2-(4-(methylsulfonyl) phenyl)-1H-benzo[d]imidazole (294-295);

4-fluoro-6-(1-(1-isobutylazepan-4-yl)piperidin-4-yl)-1-methyl-2-(4-(methylsulfonyl) phenyl)-1H-benzo[d]imidazole (296-297);

6-(1-(1-(cyclopropylmethyl)azepan-4-yl)piperidin-4-yl)-4-fluoro-1-methyl-2-(4-(methylsulfonyl)phenyl)-1H-benzo[d]imidazole (298-299);

4-fluoro-1-methyl-2-(4-(methylsulfonyl)phenyl)-6-(1-(1-(tetrahydro-2H-pyran-4-yl) azepan-4-yl)piperidin-4-yl)-1H-benzo[d]imidazole (300-301);

4-fluoro-6-(1-(1-(2-methoxyethyl)azepan-4-yl)piperidin-4-yl)-1-methyl-2-(4-(methylsulfonyl)phenyl)-1H-benzo[d]imidazole (302-303);

1,4-dimethyl-2-(4-(methylsulfonyl)phenyl)-6-(1-(1-(oxetan-3-yl) azepan-4-yl) piperidin-4-yl)-1H-benzo[d]imidazole (304-305);

1,4-dimethyl-2-(4-(methylsulfonyl)phenyl)-6-(1-(1-(tetrahydro-2H-pyran-4-yl) azepan-4-yl)piperidin-4-yl)-1H-benzo[d]imidazole (306-307);

6-(1-(1-(2-methoxyethyl)azepan-4-yl)piperidin-4-yl)-1,4-dimethyl-2-(4-(methylsulfonyl)phenyl)-1H-benzo[d]imidazole (308-309);

7-fluoro-6-(1-(1-isobutylazepan-4-yl)piperidin-4-yl)-1-methyl-2-(4-(methylsulfonyl) phenyl)-1H-benzo[d]imidazole (310-311);

6-(1-(1-cyclobutylazepan-4-yl)piperidin-4-yl)-7-fluoro-1-methyl-2-(4-(methylsulfonyl)phenyl)-1H-benzo[d]imidazole (312-313);

7-fluoro-1-methyl-2-(4-(methylsulfonyl)phenyl)-6-(1-(1-(oxetan-3-yl)azepan-4-yl)piperidin-4-yl)-1H-benzo[d]imidazole (314-315);

7-fluoro-1-methyl-2-(4-(methylsulfonyl)phenyl)-6-(1-(1-(tetrahydro-2H-pyran-4-yl) azepan-4-yl)piperidin-4-yl)-1H-benzo[d]imidazole (316-317);

1,4-dimethyl-2-(4-(methylsulfonyl)phenyl)-6-(1'-phenyl-[1,4'-bipiperidin]-4-yl)-1H-benzo[d]imidazole (318);

1-cyclopropyl-4-fluoro-6-(1'-isobutyl-[1,4'-bipiperidin]-4-yl)-2-(4-(methylsulfonyl) phenyl)-1H-benzo[d]imidazole (319);

1-cyclopropyl-6-(1'-(cyclopropylmethyl)-[1,4'-bipiperidin]-4-yl)-4-fluoro-2-(4-(methylsulfonyl)phenyl)-1H-benzo[d]imidazole (320);

1-cyclopropyl-4-fluoro-2-(4-(methylsulfonyl)phenyl)-6-(1'-(tetrahydro-2H-pyran-4-yl)-[1,4'-bipiperidin]-4-yl)-1H-benzo[d]imidazole (321);

1-cyclopropyl-4-fluoro-6-(1-(8-isobutyl-8-azabicyclo[3.2.1]octan-3-yl)piperidin-4-yl)-2-(4-(methylsulfonyl)phenyl)-1H-benzo[d]imidazole (322-323);

1-cyclopropyl-6-(1-(8-(cyclopropylmethyl)-8-azabicyclo[3.2.1]octan-3-yl)piperidin-4-yl)-4-fluoro-2-(4-(methylsulfonyl)phenyl)-1H-benzo[d]imidazole (324-325);

6-(1-(8-cyclobutyl-8-azabicyclo[3.2.1]octan-3-yl)piperidin-4-yl)-1-cyclopropyl-4-fluoro-2-(4-(methylsulfonyl)phenyl)-1H-benzo[d]imidazole (326-327);

1-cyclopropyl-4-fluoro-2-(4-(methylsulfonyl)phenyl)-6-(1-(8-(tetrahydro-2H-pyran-4-yl)-8-azabicyclo[3.2.1]octan-3-yl) piperidin-4-yl)-1H-benzo[d]imidazole (328-329);

6-(1'-isobutyl-[1,4'-bipiperidin]-4-yl)-1,7-dimethyl-2-(4-(methylsulfonyl)phenyl)-1H-benzo[d]imidazole (330);

6-(1'-isobutyl-[1,4'-bipiperidin]-4-yl)-1,5-dimethyl-2-(4-(methylsulfonyl)phenyl)-1H-benzo[d]imidazole (331);

6-(1-(8-isopropyl-8-azabicyclo[3.2.1]octan-3-yl)piperidin-4-yl)-4-methyl-2-(4-(methylsulfonyl)phenyl)-1H-benzo[d]imidazole (332-333);

6-(1-(8-cyclobutyl-8-azabicyclo[3.2.1]octan-3-yl)piperidin-4-yl)-4-methyl-2-(4-(methylsulfonyl)phenyl)-1H-benzo[d]imidazole (334);

6-(1-(8-(cyclopropylmethyl)-8-azabicyclo[3.2.1]octan-3-yl) piperidin-4-yl)-4-methyl-2-(4-(methylsulfonyl)phenyl)-1H-benzo[d]imidazole (335-336);

6-(1'-cyclobutyl-[1,4'-bipiperidin]-4-yl)-2-(3-fluoro-4-(methylsulfonyl)phenyl)-1,4-dimethyl-1H-benzo[d]imidazole (337);

6-(1'-(cyclopropylmethyl)-[1,4'-bipiperidin]-4-yl)-2-(3-fluoro-4-(methylsulfonyl) phenyl)-1,4-dimethyl-1H-benzo[d]imidazole (338);

6-(1'-cyclopropyl-[1,4'-bipiperidin]-4-yl)-2-(3-fluoro-4-(methylsulfonyl)phenyl)-1,4-dimethyl-1H-benzo[d]imidazole (339);

6-(1-(8-(cyclopropylmethyl)-8-azabicyclo[3.2.1]octan-3-yl)piperidin-4-yl)-2-(3-fluoro-4-(methylsulfonyl)phenyl)-1,4-dimethyl-1H-benzo[d]imidazole (340-341);

2-(3-fluoro-4-(methylsulfonyl)phenyl)-6-(1-(8-isobutyl-8-azabicyclo[3.2.1]octan-3-yl)piperidin-4-yl)-1,4-dimethyl-1H-benzo[d]imidazole (342);

2-(3-fluoro-4-(methylsulfonyl)phenyl)-6-(1'-isobutyl-[1,4'-bipiperidin]-4-yl)-1,4-dimethyl-1H-benzo[d]imidazole (343);

2-(3-fluoro-4-(methylsulfonyl)phenyl)-6-(1-(8-isopropyl-8-azabicyclo[3.2.1]octan-3-yl)piperidin-4-yl)-1,4-dimethyl-1H-benzo[d]imidazole (344);

6-(1-(8-cyclopropyl-8-azabicyclo[3.2.1]octan-3-yl)piperidin-4-yl)-2-(3-fluoro-4-(methylsulfonyl)phenyl)-1,4-dimethyl-1H-benzo[d]imidazole (345);

2-(3-fluoro-4-(methylsulfonyl)phenyl)-6-(1-(8-isobutyl-8-azabicyclo[3.2.1]octan-3-yl)piperidin-4-yl)-4-methyl-1H-benzo[d]imidazole (346);

6-(1-(8-cyclopropyl-8-azabicyclo[3.2.1]octan-3-yl)piperidin-4-yl)-2-(3-fluoro-4-(methylsulfonyl)phenyl)-4-methyl-1H-benzo[d]imidazole (347);

2-(3-fluoro-4-(methylsulfonyl)phenyl)-6-(1-(8-isopropyl-8-azabicyclo[3.2.1]octan-3-yl)piperidin-4-yl)-4-methyl-1H-benzo[d]imidazole (348);

6-(1-(8-cyclobutyl-8-azabicyclo[3.2.1]octan-3-yl)piperidin-4-yl)-2-(3-fluoro-4-(methylsulfonyl)phenyl)-4-methyl-1H-benzo[d]imidazole (349-350);

6-(1-(8-(cyclopropylmethyl)-8-azabicyclo[3.2.1]octan-3-yl)piperidin-4-yl)-2-(3-fluoro-4-(methylsulfonyl)phenyl)-4-methyl-1H-benzo[d]imidazole (351-352);

6-(6-(1'-isobutyl-[1,4'-bipiperidin]-4-yl)-1,4-dimethyl-1H-benzo[d]imidazol-2-yl)-8-methoxy-[1,2,4]triazolo[1,5-a]pyridine (353);

6-(6-(1-(8-cyclopropyl-8-azabicyclo[3.2.1]octan-3-yl)piperidin-4-yl)-1,4-dimethyl-1H-benzo[d]imidazol-2-yl)-8-methoxy-[1,2,4]triazolo[1,5-a]pyridine (354);

6-(6-(1-(8-cyclobutyl-8-azabicyclo[3.2.1]octan-3-yl)piperidin-4-yl)-1,4-dimethyl-1H-benzo[d]imidazol-2-yl)-8-methoxy-[1,2,4]triazolo[1,5-a]pyridine (355-356);

6-(6-(1-(8-isopropyl-8-azabicyclo[3.2.1]octan-3-yl)piperidin-4-yl)-1,4-dimethyl-1H-benzo[d]imidazol-2-yl)-8-methoxy-[1,2,4]triazolo[1,5-a]pyridine (357);

6-(6-(1-(8-(cyclopropylmethyl)-8-azabicyclo[3.2.1]octan-3-yl)piperidin-4-yl)-1,4-dimethyl-1H-benzo[d]imidazol-2-yl)-8-methoxy-[1,2,4]triazolo[1,5-a]pyridine (358);

6-(6-(1-(8-isobutyl-8-azabicyclo[3.2.1]octan-3-yl)piperidin-4-yl)-4-methyl-1H-benzo[d]imidazol-2-yl)-8-methoxy-[1,2,4]triazolo[1,5-a]pyridine (359);

6-(6-(1-(8-cyclopropyl-8-azabicyclo[3.2.1]octan-3-yl)piperidin-4-yl)-4-methyl-1H-benzo[d]imidazol-2-yl)-8-methoxy-[1,2,4]triazolo[1,5-a]pyridine (360);

6-(6-(1-(8-cyclobutyl-8-azabicyclo[3.2.1]octan-3-yl)piperidin-4-yl)-4-methyl-1H-benzo[d]imidazol-2-yl)-8-methoxy-[1,2,4]triazolo[1,5-a]pyridine (361);

6-(6-(1-(8-isopropyl-8-azabicyclo[3.2.1]octan-3-yl)piperidin-4-yl)-4-methyl-1H-benzo[d]imidazol-2-yl)-8-methoxy-[1,2,4]triazolo[1,5-a]pyridine (362);

1,4-dimethyl-6-(4-(1-methylpiperidin-4-yl)phenyl)-2-(4-(methylsulfonyl)phenyl)-1H-benzo[d]imidazole (363);

1,4-dimethyl-2-(4-(methylsulfonyl)phenyl)-6-(4-(1-(tetrahydro-2H-pyran-4-yl) piperidin-4-yl)phenyl)-1H-benzo[d]imidazole (364);

6-(6-(1-isopropylpiperidin-4-yl)pyridin-3-yl)-1,4-dimethyl-2-(4-(methylsulfonyl) phenyl)-1H-benzo[d]imidazole (365);

1-(4-(1,4-dimethyl-2-(4-(methylsulfonyl)phenyl)-1H-benzo[d]imidazol-6-yl) phenethyl)-4-methylpiperidin-4-ol (366);

1,4-dimethyl-2-(4-(methylsulfonyl)phenyl)-6-(4-(4-(pyrrolidin-1-yl)piperidin-1-yl) phenyl)-1H-benzo[d]imidazole (367);

1-(4-(1,4-dimethyl-2-(4-(methylsulfonyl)phenyl)-1H-benzo[d]imidazol-6-yl)phenyl)-N,N-dimethylpiperidin-4-amine (368);

1,4-dimethyl-2-(4-(methylsulfonyl)phenyl)-6-(4-((4-(pyrrolidin-1-yl)piperidin-1-yl) methyl)phenyl)-1H-benzo[d]imidazole (369);

1,4-dimethyl-6-(4-((6-methyl-2,6-diazaspiro[3.3]heptan-2-yl)methyl)phenyl)-2-(4-(methylsulfonyl)phenyl)-1H-benzo[d]imidazole (370);

6-(4-((6-isobutyl-2,6-diazaspiro[3.3]heptan-2-yl)methyl) phenyl)-1,4-dimethyl-2-(4-(methylsulfonyl)phenyl)-1H-benzo[d]imidazole (371);

1-cyclopropyl-4-methyl-2-(4-(methylsulfonyl)phenyl)-6-(4-((4-(pyrrolidin-1-yl) piperidin-1-yl)methyl)phenyl)-1H-benzo[d]imidazole (372);

N,N-dimethyl-1-(4-(1-methyl-2-phenyl-1H-benzo[d]imidazol-6-yl)benzyl)piperidin-4-amine (374);

N,N-dimethyl-1-(4-(1-methyl-2-(4-(methylsulfonyl)phenyl)-1H-benzo[d]imidazol-6-yl)benzyl)piperidin-4-amine (375);

1-(4-(2-(4-methoxyphenyl)-1-methyl-1H-benzo[d]imidazol-6-yl)benzyl)-N,N-dimethylpiperidin-4-amine (376);

1-(4-(2-(3-fluorophenyl)-1-methyl-1H-benzo[d]imidazol-6-yl)benzyl)-N,N-dimethylpiperidin-4-amine (377);

1-(4-(2-(4-fluorophenyl)-1-methyl-1H-benzo[d]imidazol-6-yl)benzyl)-N,N-dimethylpiperidin-4-amine (378);

N,N-dimethyl-1-(4-(1-methyl-2-(2-(methylsulfonyl)phenyl)-1H-benzo[d]imidazol-6-yl)benzyl)piperidin-4-amine (379);

1-(4-(2-(2-fluoro-4-(methylsulfonyl)phenyl)-1-methyl-1H-benzo[d]imidazol-6-yl) benzyl)-N,N-dimethylpiperidin-4-amine (380);

1-(4-(2-(3,5-difluorophenyl)-1-methyl-1H-benzo[d]imidazol-6-yl)benzyl)-N,N-dimethylpiperidin-4-amine (381);

1-(4-(2-(3,4-difluorophenyl)-1-methyl-1H-benzo[d]imidazol-6-yl)benzyl)-N,N-dimethylpiperidin-4-amine (382);

4-(6-(4-((4-(dimethylamino)piperidin-1-yl)methyl)phenyl)-1-methyl-1H-benzo[d]imidazol-2-yl)benzonitrile (383);

N,N-dimethyl-1-(4-(1-methyl-2-(3-(methylsulfonyl)phenyl)-1H-benzo[d]imidazol-6-yl)benzyl)piperidin-4-amine (384);

1-(4-(1,4-dimethyl-2-(4-(methylsulfonyl)phenyl)-1H-benzo[d]imidazol-6-yl)benzyl)-N,N-dimethylpiperidin-4-amine (385);

1-(4-(1,4-dimethyl-2-(4-(methylsulfonyl)phenyl)-1H-benzo[d]imidazol-6-yl)phenyl)-N-ethyl-N-methylpiperidin-4-amine (386);

6-(3-fluoro-4-((4-(pyrrolidin-1-yl)piperidin-1-yl)methyl) phenyl)-1,4-dimethyl-2-(4-(methylsulfonyl)phenyl)-1H-benzo[d]imidazole (387);

6-(3-fluoro-4-((cis-5-methylhexahydropyrrolo[3,4-c]pyrrol-2(1H)-yl)methyl)phenyl)-1,4-dimethyl-2-(4-(methylsulfonyl)phenyl)-1H-benzo[d]imidazole (388);

6-(4-((4-ethyl-1,4-diazepan-1-yl)methyl)-3-fluorophenyl)-1,4-dimethyl-2-(4-(methylsulfonyl)phenyl)-1H-benzo[d]imidazole (389);

1-(4-(1,4-dimethyl-2-(4-(methylsulfonyl)phenyl)-1H-benzo[d]imidazol-6-yl)-2-fluorobenzyl)-N,N-dimethylpiperidin-4-amine (390);

6-(3,5-difluoro-4-((4-(pyrrolidin-1-yl)piperidin-1-yl) methyl)phenyl)-1,4-dimethyl-2-(4-(methylsulfonyl) phenyl)-1H-benzo[d]imidazole (391);

1-(4-(1,4-dimethyl-2-(4-(methylsulfonyl)phenyl)-1H-benzo[d]imidazol-6-yl)-2,6-difluorobenzyl)-N,N-dimethylpiperidin-4-amine (392);

N-cyclopropyl-1-(4-(1,4-dimethyl-2-(4-(methylsulfonyl) phenyl)-1H-benzo[d]imidazol-6-yl)benzyl)-N-methylpiperidin-4-amine (393);

N-cyclopropyl-1-(4-(1,4-dimethyl-2-(4-(methylsulfonyl) phenyl)-1H-benzo[d]imidazol-6-yl)-2-fluorobenzyl)-N-methylpiperidin-4-amine (394);

1,4-dimethyl-2-(4-(methylsulfonyl)phenyl)-6-(4-(pyrrolidin-1-ylmethyl)phenyl)-1H-benzo[d]imidazole (395);

6-(4-((cis-5-isobutylhexahydropyrrolo[3,4-c]pyrrol-2 (1H)-yl)methyl)phenyl)-1,4-dimethyl-2-(4-(methylsulfonyl)phenyl)-1H-benzo[d]imidazole (396);

6-(4-((cis-5-isopropylhexahydropyrrolo[3,4-c]pyrrol-2 (1H)-yl)methyl)phenyl)-1,4-dimethyl-2-(4-(methylsulfonyl)phenyl)-1H-benzo[d]imidazole (397);

1,4-dimethyl-6-(4-((cis-5-methylhexahydropyrrolo[3,4-c]pyrrol-2(1H)-yl) methyl)phenyl)-2-(4-(methylsulfonyl)phenyl)-1H-benzo[d]imidazole (398);

6-(4-((6-isopropyl-2,6-diazaspiro[3.3]heptan-2-yl) methyl)phenyl)-1,4-dimethyl-2-(4-(methylsulfonyl) phenyl)-1H-benzo[d]imidazole (399);

1,4-dimethyl-6-(4-(1'-methyl-[1,4'-bipiperidin]-4-yl)phenyl)-2-(4-(methylsulfonyl) phenyl)-1H-benzo[d]imidazole (400);

6-(4-(1'-cyclopropyl-[1,4'-bipiperidin]-4-yl)phenyl)-1,4-dimethyl-2-(4-(methylsulfonyl)phenyl)-1H-benzo[d] imidazole (401);

6-(4-((4-(azetidin-1-yl)piperidin-1-yl)methyl)phenyl)-1, 4-dimethyl-2-(4-(methylsulfonyl)phenyl)-1H-benzo[d] imidazole (402);

6-(4-((4-(azetidin-1-yl)piperidin-1-yl)methyl)-3-fluorophenyl)-1,4-dimethyl-2-(4-(methylsulfonyl)phenyl)-1H-benzo[d]imidazole (403);

6-(3-fluoro-4-((6-isopropyl-2,6-diazaspiro[3.3]heptan-2-yl)methyl)phenyl)-1,4-dimethyl-2-(4-(methylsulfonyl) phenyl)-1H-benzo[d]imidazole (404);

6-(3-fluoro-5-((4-(pyrrolidin-1-yl)piperidin-1-yl)methyl) phenyl)-1,4-dimethyl-2-(4-(methylsulfonyl)phenyl)-1H-benzo[d]imidazole (405);

6-(3-((4-(azetidin-1-yl)piperidin-1-yl)methyl)-5-fluorophenyl)-1,4-dimethyl-2-(4-(methylsulfonyl)phenyl)-1H-benzo[d]imidazole (405);

1-cyclopropyl-4-methyl-2-(4-(methylsulfonyl)phenyl)-6-(3-((4-(pyrrolidin-1-yl) piperidin-1-yl)methyl)phenyl)-1H-benzo[d]imidazole (407);

1-cyclopropyl-4-fluoro-2-(4-(methylsulfonyl)phenyl)-6-(4-((4-(pyrrolidin-1-yl) piperidin-1-yl)methyl)phenyl)-1H-benzo[d]imidazole (408);

4-fluoro-1-methyl-2-(4-(methylsulfonyl)phenyl)-6-(4-((4-(pyrrolidin-1-yl)piperidin-1-yl)methyl)phenyl)-1H-benzo[d]imidazole (409);

1-cyclopropyl-4-fluoro-6-(4-((6-isopropyl-2,6-diazaspiro [3.3]heptan-2-yl)methyl) phenyl)-2-(4-(methylsulfonyl)phenyl)-1H-benzo[d]imidazole (410);

1-cyclopropyl-4-fluoro-6-(4-((6-isobutyl-2,6-diazaspiro [3.3]heptan-2-yl)methyl) phenyl)-2-(4-(methylsulfonyl)phenyl)-1H-benzo[d]imidazole (411);

1-cyclopropyl-4-fluoro-2-(4-(methylsulfonyl)phenyl)-6-(4-((6-(tetrahydro-2H-pyran-4-yl)-2,6-diazaspiro[3.3] heptan-2-yl)methyl)phenyl)-1H-benzo[d]imidazole (412);

6-(4-((4-isopropylpiperazin-1-yl)methyl)phenyl)-1,4-dimethyl-2-(4-(methylsulfonyl) phenyl)-1H-benzo[d] imidazole (413);

6-(4-((4-isobutylpiperazin-1-yl)methyl)phenyl)-1,4-dimethyl-2-(4-(methylsulfonyl) phenyl)-1H-benzo[d]imidazole (414);

1-cyclopropyl-7-fluoro-6-(1'-isobutyl-[1,4'-bipiperidin]-4-yl)-2-(4-(methylsulfonyl) phenyl)-1H-benzo[d]imidazole (415);

6-(4-((1-isopropylpiperidin-4-yl)oxy)phenyl)-1,4-dimethyl-2-(4-(methylsulfonyl) phenyl)-1H-benzo[d]imidazole (416);

6-(4-((1-isobutylpiperidin-4-yl)oxy)phenyl)-1,4-dimethyl-2-(4-(methylsulfonyl) phenyl)-1H-benzo[d]imidazole (417);

6-(1-((2,6-dimethylpyridin-4-yl)methyl)piperidin-4-yl)-1,4-dimethyl-2-(4-(methylsulfonyl)phenyl)-1H-benzo [d]imidazole (418);

1,4-dimethyl-6-(1-((6-methylpyridin-3-yl)methyl)piperidin-4-yl)-2-(4-(methylsulfonyl)phenyl)-1H-benzo[d] imidazole (419);

diethyl (4-(6-(1'-isopropyl-[1,4'-bipiperidin]-4-yl)-1,4-dimethyl-1H-benzo[d]imidazol-2-yl)phenyl)phosphonate (420);

diethyl (4-(6-(1'-isobutyl-[1,4'-bipiperidin]-4-yl)-1,4-dimethyl-1H-benzo[d]imidazol-2-yl)phenyl)phosphonate (421);

diethyl (4-(6-(1'-cyclopropyl-[1,4'-bipiperidin]-4-yl)-1,4-dimethyl-1H-benzo[d]imidazol-2-yl)phenyl)phosphonate (422);

1-((4-(1-(115-ethyl)-2-(p-tolyl)-1H-benzo[d]imidazol-6-yl)phenyl)methyl)-N,N-dimethylpiperidin-4-amine (423);

N-(4-(6-(4-((4-(dimethylamino)piperidin-1-yl)methyl) phenyl)-1-methyl-1H-benzo[d]imidazol-2-yl)phenyl) methanesulfonamide (424);

1-(4-(2-(4-(dimethylamino)phenyl)-1-methyl-1H-benzo [d]imidazol-6-yl)benzyl)-N,N-dimethylpiperidin-4-amine (425);

1-(4-(2-(4-(1H-imidazol-1-yl)phenyl)-1-methyl-1H-benzo[d]imidazol-6-yl)benzyl)-N,N-dimethylpiperidin-4-amine (426); or N-(3-(6-(4-((4-(dimethylamino)piperidin-1-yl)methyl) phenyl)-1-methyl-1H-benzo[d]imidazol-2-yl)phenyl) methanesulfonamide (427).

9. A pharmaceutical composition comprising a compound of Formula (I) according claim 1 or a stereoisomer, a tautomer, a solvate, or a pharmaceutically-acceptable salt thereof, and a pharmaceutically acceptable carrier.

10. A method of treating a disease or disorder, comprising administering to a mammalian patient a compound according to claim 1 or a pharmaceutically acceptable salt thereof, wherein said disease or disorder is pathological fibrosis, wherein said pathological fibrosis is liver fibrosis, renal fibrosis, biliary fibrosis, or pancreatic fibrosis.

11. A method of treating a disease or disorder, comprising administering to a mammalian patient a compound according to claim 1 or a pharmaceutically acceptable salt thereof, wherein said disease or disorder is nonalcoholic steatohepatitis (NASH), non-alcoholic fatty liver disease (NAFLD), chronic kidney disease, diabetic kidney disease, primary sclerosing cholangitis (PSC), or primary biliary cirrhosis (PBC).

12. A method of treating a disease or of disorder, comprising administering to a mammalian patient a compound according to claim 1 or a pharmaceutically acceptable salt thereof, wherein said disease or disorder is idiopathic pulmonary fibrosis (IPF).

* * * * *